(12) United States Patent
Fukumoto et al.

(10) Patent No.: US 9,527,807 B2
(45) Date of Patent: Dec. 27, 2016

(54) SULFONAMIDE DERIVATIVE AND USE THEREOF

(75) Inventors: Shoji Fukumoto, Kanagawa (JP);
Osamu Ujikawa, Kanagawa (JP);
Shinji Morimoto, Kanagawa (JP);
Yasutomi Asano, Kanagawa (JP);
Satoshi Mikami, Kanagawa (JP);
Norihito Tokunaga, Kanagawa (JP);
Masakuni Kori, Osaka (JP); Toshihiro Imaeda, Kanagawa (JP); Koichiro Fukuda, Kanagawa (JP); Shinji Nakamura, Kanagawa (JP); Kouichi Iwanaga, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 114 days.

(21) Appl. No.: 14/009,456

(22) PCT Filed: Apr. 5, 2012

(86) PCT No.: PCT/JP2012/059949
§ 371 (c)(1),
(2), (4) Date: Oct. 2, 2013

(87) PCT Pub. No.: WO2012/137982
PCT Pub. Date: Oct. 11, 2012

(65) Prior Publication Data
US 2014/0024650 A1    Jan. 23, 2014

(30) Foreign Application Priority Data

Apr. 5, 2011   (JP) .................................. 2011-084100

(51) Int. Cl.
| | | |
|---|---|---|
| *C07C 311/07* | (2006.01) | |
| *C07D 401/12* | (2006.01) | |
| *C07D 309/14* | (2006.01) | |
| *C07D 295/092* | (2006.01) | |
| *C07D 333/16* | (2006.01) | |

(Continued)

(52) U.S. Cl.
CPC ............ *C07C 311/07* (2013.01); *C07C 311/09* (2013.01); *C07C 311/14* (2013.01); *C07C 317/28* (2013.01); *C07C 323/26* (2013.01); *C07D 207/27* (2013.01); *C07D 207/273* (2013.01); *C07D 209/04* (2013.01); *C07D 211/56* (2013.01); *C07D 211/58* (2013.01); *C07D 211/76* (2013.01); *C07D 213/61* (2013.01); *C07D 213/64* (2013.01); *C07D 213/85* (2013.01); *C07D 231/12* (2013.01); *C07D 231/14* (2013.01); *C07D 233/56* (2013.01); *C07D 233/68* (2013.01); *C07D 237/04* (2013.01); *C07D 239/28* (2013.01); *C07D 261/08* (2013.01); *C07D 263/32* (2013.01); *C07D 277/24* (2013.01); *C07D 277/32* (2013.01); *C07D 277/62* (2013.01); *C07D 295/092* (2013.01); *C07D 295/192* (2013.01); *C07D 305/06* (2013.01); *C07D 307/22* (2013.01); *C07D 309/06* (2013.01); *C07D 309/14* (2013.01); *C07D 333/16* (2013.01); *C07D 401/04* (2013.01); *C07D 401/12* (2013.01); *C07D 405/12* (2013.01); *C07D 405/14* (2013.01); *C07D 409/12* (2013.01); *C07D 413/12* (2013.01); *C07D 417/12* (2013.01); *C07D 493/08* (2013.01); *C07C 2101/02* (2013.01);

(Continued)

(58) Field of Classification Search
None
See application file for complete search history.

(56) References Cited

U.S. PATENT DOCUMENTS

| 5,315,013 A | 5/1994 | Carini et al. |
|---|---|---|
| 6,548,449 B1 | 4/2003 | Andree et al. |

(Continued)

FOREIGN PATENT DOCUMENTS

| JP | 2003-238538 | 8/2003 |
|---|---|---|
| JP | 2005-060385 | 3/2005 |

(Continued)

OTHER PUBLICATIONS

Ward, et al., "Recent Advances in Discovery of Selective AMPA Receptor Positive Allosteric Modulators", Current Medicinal Chemistry, vol. 17, 2010, pp. 3503-3513.

(Continued)

*Primary Examiner* — Kamal Saeed
(74) *Attorney, Agent, or Firm* — Hamre, Schumann, Mueller & Larson, P.C.

(57) ABSTRACT

Provided is a compound having an AMPA receptor function enhancing action, and useful as a prophylactic or therapeutic drug for depression, Alzheimer's disease, schizophrenia, attention deficit hyperactivity disorder (ADHD) and the like. A compound represented by the formula (I):

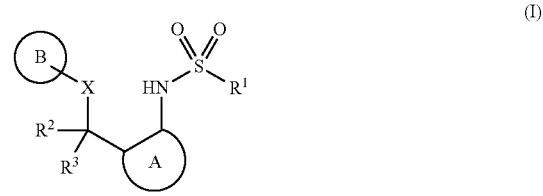

wherein each symbol is as defined in the present specification,
or a salt thereof.

11 Claims, 1 Drawing Sheet

(51) Int. Cl.

| | | |
|---|---|---|
| *C07D 231/12* | (2006.01) | |
| *C07D 211/58* | (2006.01) | |
| *C07C 311/09* | (2006.01) | |
| *C07C 311/14* | (2006.01) | |
| *C07C 317/28* | (2006.01) | |
| *C07C 323/26* | (2006.01) | |
| *C07D 209/04* | (2006.01) | |
| *C07D 213/64* | (2006.01) | |
| *C07D 231/14* | (2006.01) | |
| *C07D 233/68* | (2006.01) | |
| *C07D 261/08* | (2006.01) | |
| *C07D 263/32* | (2006.01) | |
| *C07D 277/24* | (2006.01) | |
| *C07D 277/62* | (2006.01) | |
| *C07D 307/22* | (2006.01) | |
| *C07D 405/12* | (2006.01) | |
| *C07D 413/12* | (2006.01) | |
| *C07D 417/12* | (2006.01) | |
| *C07D 405/14* | (2006.01) | |
| *C07D 309/06* | (2006.01) | |
| *C07D 213/85* | (2006.01) | |
| *C07D 401/04* | (2006.01) | |
| *C07D 237/04* | (2006.01) | |
| *C07D 239/28* | (2006.01) | |
| *C07D 409/12* | (2006.01) | |
| *C07D 493/08* | (2006.01) | |
| *C07D 207/27* | (2006.01) | |
| *C07D 207/273* | (2006.01) | |
| *C07D 277/32* | (2006.01) | |
| *C07D 211/56* | (2006.01) | |
| *C07D 211/76* | (2006.01) | |
| *C07D 295/192* | (2006.01) | |
| *C07D 213/61* | (2006.01) | |
| *C07D 305/06* | (2006.01) | |
| *C07D 233/56* | (2006.01) | |

(52) U.S. Cl.
CPC ....... *C07C 2101/08* (2013.01); *C07C 2101/14* (2013.01); *C07C 2103/74* (2013.01)

(56) References Cited

U.S. PATENT DOCUMENTS

| | | | |
|---|---|---|---|
| 6,649,656 B1* | 11/2003 | Tsuchiya | C07C 235/38 514/535 |
| 6,890,932 B2* | 5/2005 | Tsuchiya | C07C 235/38 514/277 |
| 6,902,847 B1 | 6/2005 | Yata et al. | |
| 6,951,699 B2 | 10/2005 | Yata et al. | |
| 7,074,836 B1 | 7/2006 | Kawada et al. | |
| 7,101,915 B1 | 9/2006 | Kawada et al. | |
| 7,220,783 B2 | 5/2007 | Kawada et al. | |
| 7,514,452 B2 | 4/2009 | Fujii et al. | |
| 7,642,001 B2 | 1/2010 | Yata et al. | |
| 8,110,303 B2 | 2/2012 | Yata et al. | |
| 2004/0048152 A1 | 3/2004 | Yata et al. | |
| 2004/0127495 A1 | 7/2004 | Kawada et al. | |
| 2005/0118500 A1 | 6/2005 | Yata et al. | |
| 2005/0171196 A1 | 8/2005 | Fujii et al. | |
| 2005/0233204 A1 | 10/2005 | Yata et al. | |
| 2006/0251955 A1 | 11/2006 | Yata et al. | |
| 2006/0276532 A1 | 12/2006 | Dominguez-Manzanares | |
| 2006/0281004 A1 | 12/2006 | Yata et al. | |
| 2007/0142441 A1 | 6/2007 | Castano Mansanet et al. | |
| 2010/0130737 A1 | 5/2010 | Itoh et al. | |

FOREIGN PATENT DOCUMENTS

| | | |
|---|---|---|
| WO | 2006/015827 | 2/2006 |
| WO | 2006/015828 | 2/2006 |
| WO | 2006/015829 | 2/2006 |
| WO | 2006/117368 | 11/2006 |
| WO | 2007/005845 | 1/2007 |
| WO | 2007/090840 | 8/2007 |
| WO | 2007/090841 | 8/2007 |
| WO | 2008/073789 | 6/2008 |
| WO | 2008/113795 | 9/2008 |
| WO | 2008/120093 | 10/2008 |
| WO | 2009/080637 | 7/2009 |
| WO | 2009/092712 | 7/2009 |
| WO | 2009/092713 | 7/2009 |
| WO | 2009/119088 | 10/2009 |
| WO | 2009/147167 | 12/2009 |
| WO | 2010/041162 | 4/2010 |
| WO | 2010/115952 | 10/2010 |
| WO | 2010/150192 | 12/2010 |
| WO | 01/00206 | 1/2011 |
| WO | 2011/009951 | 1/2011 |
| WO | 2012/020848 | 2/2012 |

OTHER PUBLICATIONS

Attal, et al., "Synthesis and Antiinflammatory Activity of Aryl Sulphonanilides Structurally Related to Nimesulide", Indian Journal of Pharmaceutical Sciences, vol. 65, No. 2, 2003, pp. 135-138.

Mori, et al., "New Trifluoromethanesulfonanilide Compunds Having High Miticidal Activity against House Dust Mites", Biosci. Biotechnol. Biochem., vol. 68, No. 2, 2004, pp. 425-427.

Menger, et al., "Intramolecular Catalysis in the Hydrolysis of *p*-Nitrophenyl *o*-Methanesulfonamidobenzoate", Tetrahedron, vol. 23, No. 1, 1967, pp. 19-27.

Dingledine, et al., "The Glutamate Receptor Ion Channels", Pharmacological Reviews, vol. 51, No. 1, 1999, pp. 7-61.

Fowler, et al., "The AMPA Receptor Potentiator LY404187 Increases Cerebral Glucose Utilization and c-fos Expression in the Rat", Journal of Cerebral Blood flow & Metabolism, vol. 24, 2004, pp. 1098-1109.

\* cited by examiner

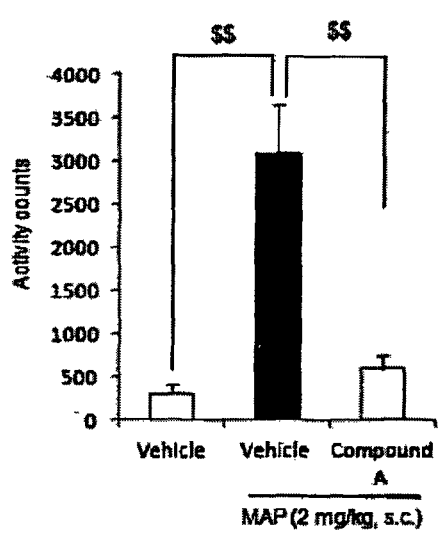
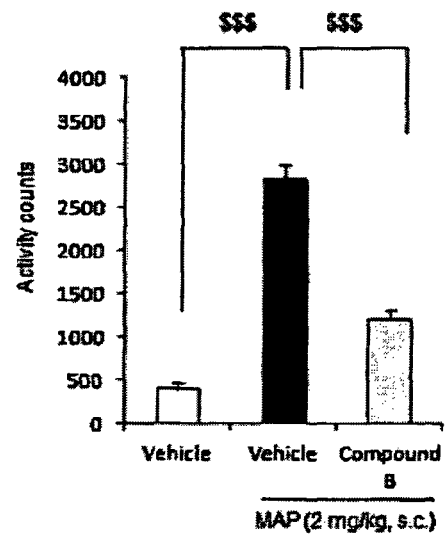

SULFONAMIDE DERIVATIVE AND USE THEREOF

TECHNICAL FIELD OF THE INVENTION

The present invention relates to a sulfonamide derivative, particularly a sulfonamide derivative having an AMPA (α-amino-3-hydroxy-5-methyl-4-isoxazolepropionic acid) receptor function enhancing action.

BACKGROUND OF THE INVENTION

Glutamic acid is an excitatory neurotransmitter most abundantly present in the central nervous system of mammals. Glutamic acid plays an important role in the cognition, mood and control of motor function, and these processes become unstable in mental diseases and neuropathy. Glutamic acid receptors are classified into ion channel-type receptor and G protein conjugated-type receptor, and the ion channel-type receptor is further classified into α-amino-3-hydroxy-5-methyl-4-isoxazolepropionic acid (AMPA) receptor, N-methyl-D-aspartic acid (NMDA) receptor and kainic acid (KA) receptor. (non-patent document 1)

AMPA receptor is one kind of receptor for excitatory neurotransmitter glutamic acid, and was named based on selective activation of the receptor by AMPA. AMPA receptor consists of 4 subunits (GluR1, GluR2, GluR3, GluR4). It includes homomeric receptor constituted, with the same kind of subunits and heteromeric receptor constituted with heterogeneous subunits. It has been reported that the physiological property of AMPA receptor varies depending on the subunits constituting the receptor. (non-patent document 1, 2, 3)

Activation of AMPA receptor is known to cause various intracerebral actions (neural activation, enhancement of neural plasticity, enhancement of neurogenesis, enhancement of BDNF production and the like) (non-patent documents 4, 5, 6, 7). Therefore, a compound having an AMPA receptor function enhancing action is expected to be useful as a drug for the prophylaxis or treatment of mental diseases, neurodegenerative disease, memory disorders, sleep disorder and the like. (non-patent documents 8, 9)

As a compound having an AMPA receptor function enhancing action, patent document 1 discloses a sulfonamide derivative having an AMPA receptor function enhancing action, which is represented by the formula

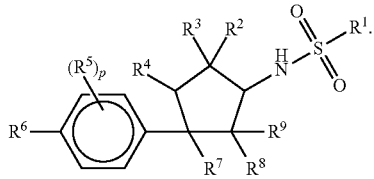

Patent document 2 discloses a sulfonamide derivative having an AMPA receptor function enhancing action, which is represented by the formula

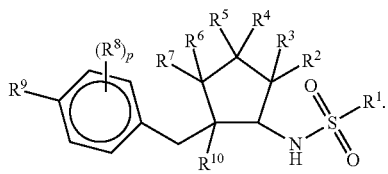

Patent document 3 discloses a sulfonamide derivative having an AMPA receptor function enhancing action, which is represented by the formula

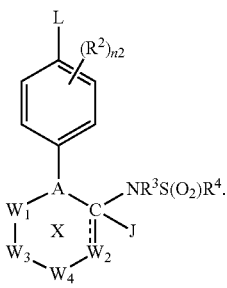

Patent document 4 discloses a sulfonamide derivative having an AMPA receptor function enhancing action; which is represented by the formula

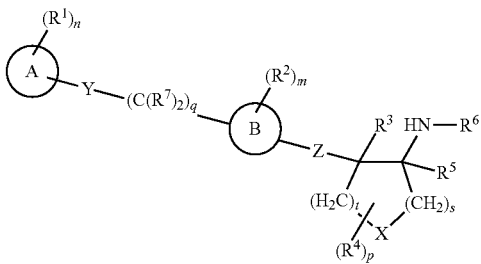

Patent document 5 discloses an indazole derivative having an AMPA receptor function enhancing action, which is represented by the formula

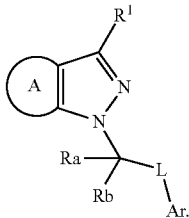

Patent document 6 discloses a sulfonamide derivative having an AMPA receptor function enhancing action, which is represented by the formula

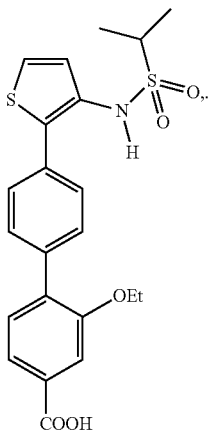 [SMILES: CCOc1cc(C(=O)O)ccc1-c1ccc(-c2sccc2NS(=O)(=O)C(C)C)cc1]

Patent document 7 discloses a sulfonamide derivative having an AMPA receptor function enhancing action, which is represented by the formula

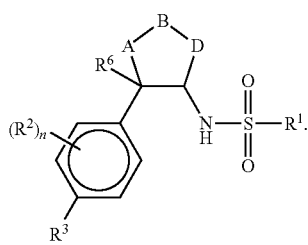

Patent document 8 discloses a sulfonamide derivative having an AMPA receptor function enhancing action, which is represented by the formula

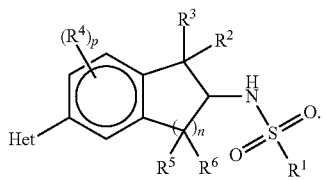

Patent document 9 discloses a sulfonamide derivative having an AMPA receptor function enhancing action, which is represented by the formula

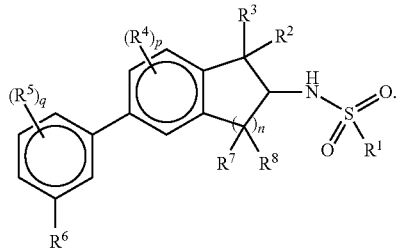

Patent document 10 discloses a sulfonamide derivative having an AMPA receptor function enhancing action, which is represented by the formula

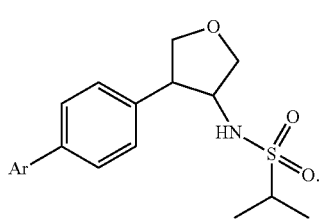

Patent document 11 discloses a sulfonamide derivative having an AMPA receptor function enhancing action, which is represented by the formula

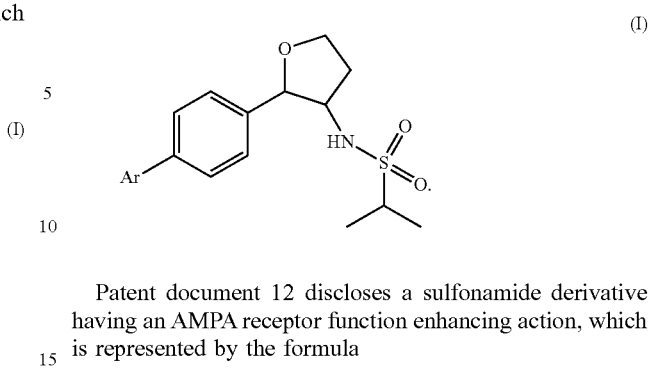

Patent document 12 discloses a sulfonamide derivative having an AMPA receptor function enhancing action, which is represented by the formula

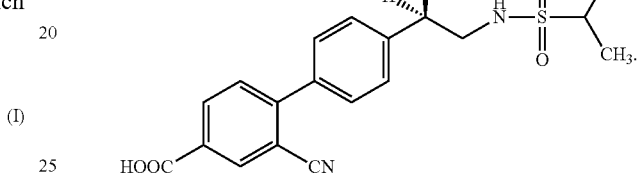

Patent document 13 discloses a sulfonamide derivative having an AMPA receptor function enhancing action, which is represented by the formula

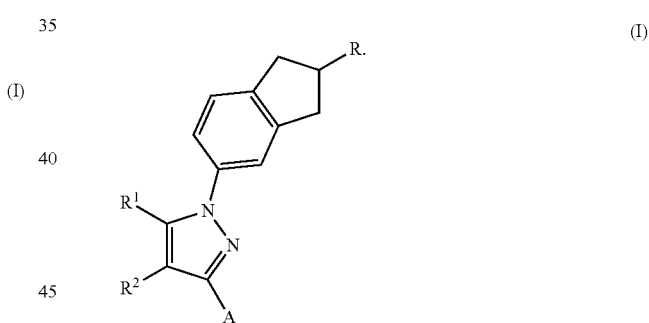

Patent document 14 discloses a sulfonamide derivative having an AMPA receptor function enhancing-action, which is represented by the formula

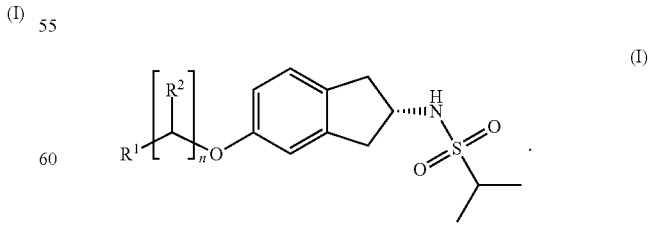

Patent document 15 discloses a sulfonamide derivative having an AMPA receptor function enhancing action, which is represented by the formula

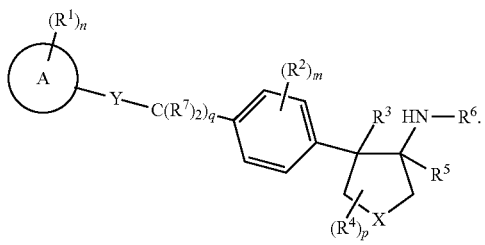
(I)

However, there is still a demand for the development of a sulfonamide derivative having an AMPA receptor function enhancing action.

DOCUMENT LIST

[Patent Documents]
patent document 1: WO2009/092712
patent document 2: WO2009/092713
patent document 3: WO2008/120093
patent document 4: WO2010/150192
patent document 5: WO2009/119088
patent document 6: US-B-2006/2765322
patent document 7: WO2006/015827
patent document 8: WO2006/015828
patent document 9: WO2006/015829
patent document 10: WO2007/090840
patent document 11: WO2007/090841
patent document 12: WO2008/073789
patent document 13: WO2008/113795
patent document 14: WO2009/080637
patent document 15: WO2010/041162
[Non-Patent Documents]
non-patent document 1: Pharmacological Reviews, Vol. 51, 7-61, 1999
non-patent document 2: Neuropharmacology, Vol. 34, 123-139, 1995
non-patent document 3: Ann. Rev. Neurosci., Vol. 25, 103-126, 2002
non-patent document 4: Journal of Cerebral Blood Flow & Metabolism 24:1098-1109
non-patent document 5: Neuroscience 123 (2004) 1011-1024
non-patent document 6: Neuropharmacology 44 (2003) 1013-1021
non-patent document 7: Neuropharmacology 43 (2002) 1-10
non-patent document 8: CNS & Neurological Disorders- Drug Targets, Vol. 7, 129-143, 2008
non-patent document 9: Current Opinion in Drug Discovery and Development, Vol. 9, 571-579, 2006

SUMMARY OF THE INVENTION

Problems to be Solved by the Invention

The present invention aims to provide a sulfonamide derivative having an AMPA receptor function enhancing action (AMPA receptor function enhancing agent (AMPA receptor potentiator); AMPA receptor function enhancing agent is sometimes also referred to as AMPA receptor positive modulator, AMPAkine, AMPA receptor allosteric modulator, AMPA receptor positive allosteric modulator or positive allosteric activator of AMPA receptor).

Means of Solving the Problems

The present inventors have found that a compound represented by the following formula (I) or a salt thereof (sometimes to be referred to as compound (I) in the present specification) has an AMPA receptor function enhancing action, and conducted further studies, which resulted in the completion of the present invention.

Accordingly, the present invention provides the following.
[1] A compound represented by the formula (I)

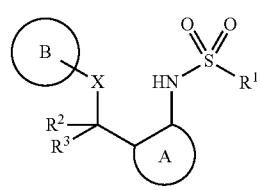
(I)

wherein
$R^1$ is
a $C_{1-6}$ alkyl group optionally substituted by substituent(s) selected from a halogen atom, a $C_{1-3}$ alkoxy group and a $C_{3-6}$ cycloalkyl group;
a $C_{3-6}$ cycloalkyl group optionally substituted by substituent(s) selected from a halogen atom and a $C_{1-3}$ alkoxy group; or an amino group optionally substituted by a $C_{1-6}$ alkyl group optionally substituted by substituent(s) selected from a halogen atom and a $C_{1-3}$ alkoxy group (the substituents on the amino group may be bonded to each other to form a cyclic amino group),
$R^2$ and $R^3$ are the same or different and each is a hydrogen atom or a $C_{1-6}$ alkyl group,
X is —O— or —S—,
ring A is a 3- to 8-membered monocyclic nonaromatic ring optionally substituted by substituent(s) selected from a halogen atom, a $C_{1-6}$ alkyl group optionally substituted by substituent(s) selected from a halogen atom and a phenyl group, an acyl group, an oxo group and a hydroxyl group; or a bicyclic 7- or 8-membered saturated ring optionally substituted by substituent(s) selected from a halogen atom, a $C_{1-6}$ alkyl group optionally substituted by a halogen atom, an acyl group, an oxo group and a hydroxyl group, and
ring B is an optionally substituted 3- to 10-membered ring, or a salt thereof.
[2] The compound of [1], wherein ring A is
optionally further substituted $C_{3-6}$ cycloalkane,
an optionally further substituted tetrahydrofuran ring,
an optionally further substituted tetrahydropyran ring,
an optionally further substituted piperidine ring,
an optionally further substituted tetrahydrothiopyran ring or
an optionally further substituted 8-oxabicyclo[3.2.1]octane ring,
or a salt thereof.
[3] The compound of [1] or [2], wherein the substituent(s) on the ring A is(are) selected from
(1) 1 to 3 halogen atoms,
(2) a $C_{1-6}$ alkyl group optionally-substituted by one phenyl group,
(3) a carbamoyl group substituted by a $C_{1-6}$ alkyl group,
(4) a $C_{1-6}$ alkyl-carbonyl group,
(5) a $C_{1-6}$ alkoxy-carbonyl group,
(6) an oxo group,
(7) a hydroxyl group and
(8) a $C_{1-6}$ alkylsulfonyl group,
or a salt thereof.

[4] The compound of any one of [1]-[3], wherein ring B is
(1) an optionally further substituted benzene ring,
(2) an optionally further substituted pyridine ring,
(3) optionally further substituted $C_{3-6}$ cycloalkane,
(4) an optionally further substituted dihydroindene ring,
(5) an optionally further substituted naphthalene ring,
(6) an optionally further substituted chromene ring,
(7) an optionally further substituted indole ring or
(8) an optionally further substituted benzothiazole ring,
or a salt thereof.

[5] The compound of any one of [1]-[3], wherein ring B is a benzene ring, or a salt thereof.

[6] The compound of any one of [1]-[5], wherein the substituent on the ring B is selected from
(1) a halogen atom;
(2) a cyano group;
(3) a $C_{1-6}$ alkyl group optionally substituted by 1 to 3 substituents selected from a halogen atom and a cyano group;
(4) a hydroxyl group optionally substituted by a $C_{1-6}$ alkyl group optionally substituted by 1 to 3 halogen atoms or a phenyl group (including alkoxy);
(5) an amino group optionally substituted by 1 or 2 substituents selected from a $C_{1-6}$ alkyl group, a $C_{1-6}$ alkyl-carbonyl and a phenyl group;
(6) a $C_{3-6}$ cycloalkyl group;
(7) a tricyclo[3.3.1.1.3.7]decyl group;
(8) phenyl optionally substituted by 1 to 3 substituents selected from a halogen atom and a cyano group;
(9) pyridyl optionally substituted by 1 to 3 substituents selected from a halogen atom, a cyano group and a $C_{1-6}$ alkyl group optionally substituted by 1 to 3 halogen atoms;
(10) pyrazolyl optionally substituted by 1 to 3 substituents selected from a halogen atom, a cyano group, a $C_{1-6}$ alkyl group optionally substituted by 1 to 3 halogen atoms and a $C_{1-6}$ alkoxy group optionally substituted by 1 to 3 halogen atoms;
(11) imidazolyl optionally substituted by a $C_{1-6}$ alkyl group;
(12) thienyl optionally substituted by a cyano group;
(13) pyrimidinyl optionally substituted by 1 to 3 substituents selected from a halogen atom and a cyano group;
(14) isoxazolyl substituted by a $C_{1-6}$ alkyl group;
(15) oxazolyl optionally substituted by a $C_{1-5}$ alkyl group optionally substituted by 1 to 3 halogen atoms;
(16) thiazolyl optionally substituted by 1 to 3 substituents selected from a halogen atom and a $C_{1-6}$ alkyl group optionally substituted by 1 to 3 halogen atoms;
(17) piperidyl optionally substituted by 1 to 3 substituents selected from a $C_{1-6}$ alkyl group optionally substituted by 1 to 3 halogen atoms and an oxo group;
(18) pyrrolidyl optionally substituted by 1 to 3 substituents selected from a halogen atom and an oxo group;
(19) dihydropyridyl optionally substituted by 1 to 3 substituents selected from a $C_{1-6}$ alkyl group and an oxo group;
(20) tetrahydropyridazinyl optionally substituted by 1 to 3 substituents selected from a $C_{1-6}$ alkyl group and an oxo group;
(21) oxetanyl;
(22) morpholinyl;
(23) tetrahydropyranyl;
(24) a sulfanyl group optionally substituted by a $C_{1-6}$ alkyl group substituted by 1 to 3 halogen atoms;
(25) a $C_{1-6}$ alkyl-carbonyl group;
(26) a $C_{1-6}$ alkoxy-carbonyl group; and
(27) an oxo group,
or a salt thereof.

[7] The compound of any one of [1]-[6], wherein $R^1$ is
a $C_{1-6}$ alkyl group optionally substituted by 1 to 3 substituents selected from a halogen atom and a $C_{1-3}$ alkoxy group;
a $C_{3-6}$ cycloalkyl group; or
an amino group substituted by a $C_{1-6}$ alkyl group,
$R^2$ and $R^3$ are hydrogen atoms,
X is —O—,
ring A is
$C_{3-6}$ cycloalkane,
a tetrahydrofuran ring,
a tetrahydropyran ring,
a piperidine ring,
a tetrahydrothiopyran ring or
a 8-oxabicyclo[3.2.1]octane ring, each optionally substituted by 1 to 3 substituents selected from
(1) 1 to 3 halogen atoms;
(2) a $C_{1-6}$ alkyl group optionally substituted by one phenyl group;
(3) a carbamoyl group substituted by a $C_{1-6}$ alkyl group;
(4) a $C_{1-6}$ alkyl-carbonyl group;
(5) a $C_{1-6}$ alkoxy-carbonyl group;
(6) an oxo group;
(7) a hydroxyl group; and
(8) a $C_{1-6}$ alkylsulfonyl group, and
ring B ring is
a benzene ring
$C_{3-6}$ cycloalkane,
a dihydroindene ring,
a naphthalene ring,
a pyridine ring,
a chromene ring,
an indole ring or
a benzothiazole ring, each optionally having 1 to 3 substituent(s) selected from
(1) a halogen atom;
(2) a cyano group;
(3) a $C_{1-6}$ alkyl group optionally substituted by 1 to 3 substituents selected from a halogen atom and a cyano group;
(4) a hydroxyl group optionally substituted by a $C_{1-6}$ alkyl group optionally substituted by 1 to 3 halogen atoms or a phenyl group;
(5) an amino group optionally substituted by 1 or 2 substituents selected from a $C_{1-6}$ alkyl group, a $C_{1-6}$ alkyl-carbonyl and a phenyl group;
(6) a $C_{3-6}$ cycloalkyl group;
(7) a tricyclo[3.3.1.1.3.7]decyl group;
(8) phenyl optionally substituted by 1 to 3 substituents selected from a halogen atom and a cyano group;
(9) pyridyl optionally substituted by 1 to 3 substituents selected from a halogen atom, a cyano group and a $C_{1-6}$ alkyl group optionally substituted by 1 to 3 halogen atoms;
(10) pyrazolyl optionally substituted by 1 to 3 substituents selected from a halogen atom, a cyano group, a $C_{1-6}$ alkyl group optionally substituted by 1 to 3 halogen atoms and a $C_{1-6}$ alkoxy group optionally substituted by 1 to 3 halogen atoms;
(11) imidazolyl optionally substituted by a $C_{1-6}$ alkyl group;
(12) thienyl optionally substituted by a cyano group;
(13) pyrimidinyl optionally substituted by 1 to 3 substituents selected from a halogen atom and a cyano group;
(14) isoxazolyl substituted by a $C_{1-6}$ alkyl group;
(15) oxazolyl optionally substituted by a $C_{1-6}$ alkyl group optionally substituted by 1 to 3 halogen atoms;

(16) thiazolyl optionally substituted by 1 to 3 substituents selected from a halogen atom and a $C_{1-6}$ alkyl group optionally substituted by 1 to 3 halogen atoms;
(17) piperidyl optionally substituted by 1 to 3 substituents selected from a $C_{1-6}$ alkyl group optionally substituted by 1 to 3 halogen atoms and an oxo group;
(18) pyrrolidyl optionally substituted by 1 to 3 substituents selected from a halogen atom and an oxo group;
(19) dihydropyridyl optionally substituted by 1 to 3 substituents selected from a $C_{1-6}$ alkyl group and an oxo group;
(20) tetrahydropyridazinyl optionally substituted by 1 to 3 substituents selected from a $C_{1-6}$ alkyl group and an oxo group;
(21) oxetanyl;
(22) morpholinyl;
(23) tetrahydropyranyl;
(24) a sulfanyl group optionally substituted by a $C_{1-6}$ alkyl group substituted by 1 to 3 halogen atoms;
(25) a $C_{1-6}$ alkyl-carbonyl group;
(26) a $C_{1-6}$ alkoxy-carbonyl group; and
(27) an oxo group,
or a salt thereof.
[8] The compound of any one of [1]-[7], wherein $R^1$ is
a $C_{1-6}$ alkyl group optionally substituted by 1 to 3 halogen atoms;
a $C_{3-6}$ cycloalkyl group; or
an amino group substituted by a $C_{1-6}$ alkyl group,
$R^2$ and $R^3$ are hydrogen atoms,
X is —O—,
ring A is
$C_{3-6}$ cycloalkane,
a tetrahydropyran ring,
a piperidine ring,
a tetrahydrothiopyran ring or
a 8-oxabicyclo[3.2.1]octane ring, each optionally substituted by 1 to 3 substituents selected from
(1) 1 to 3 halogen atoms,
(2) a $C_{1-6}$ alkyl-carbonyl group and
(3) an oxo group, and
ring B is a benzene ring optionally having 1 to 3 substituent(s) selected from
(1) a halogen atom;
(2) a $C_{1-6}$ alkyl group optionally substituted by one cyano group;
(3) a hydroxyl group substituted by a $C_{1-6}$ alkyl group substituted by 1 to 3 halogen atoms;
(4) a $C_{3-6}$ cycloalkyl group;
(5) pyridyl optionally substituted by 1 to 3 substituents selected from a halogen atom, a cyano group and a $C_{1-6}$ alkyl group optionally substituted by 1 to 3 halogen atoms;
(6) pyrazolyl optionally substituted by 1 to 3 substituents selected from a halogen atom, a cyano group and a $C_{1-6}$ alkyl group optionally substituted by 1 to 3 halogen atoms;
(7) imidazolyl substituted by 1 to 3 $C_{1-6}$ alkyl groups;
(8) pyrimidinyl substituted by 1 to 3 halogen atoms;
(9) isoxazolyl substituted by one $C_{1-6}$ alkyl group;
(10) thiazolyl optionally substituted by 1 to 3 substituents selected from a halogen atom and a $C_{1-6}$ alkyl group;
(11) pyrrolidyl substituted by one oxo group;
(12) dihydropyridyl optionally substituted by 1 to 3 substituents selected from a $C_{1-6}$ alkyl group and an oxo group;
(13) oxetanyl;
(14) tetrahydropyranyl; and
(15) a $C_{1-6}$ alkyl-carbonyl group,
or a salt thereof.

[9] N-[(3R,4S)-3-{[4-(4-chloro-1H-pyrazol-1-yl)phenoxy]methyl}tetrahydro-2H-pyran-4-yl]methanesulfonamide or a salt thereof.
[10] N-[(3RS,4SR)-3-({4-[5-(trifluoromethyl)pyridin-2-yl]phenoxy}methyl)tetrahydro-2H-pyran-4-yl]ethanesulfonamide or a salt thereof.
[11] N-[(3R,4S)-4-{[4-(5-chloro-3-fluoropyridin-2-yl)phenoxy]methyl}tetrahydro-2H-pyran-3-yl]cyclopropanesulfonamide or a salt thereof.
[12] A medicament comprising the compound of any one of [1]-[11], or a salt thereof.
[13] The medicament of [12], which is an AMPA receptor function enhancer.
[14] The medicament of [12], which is a prophylactic or therapeutic drug for depression, Alzheimer's disease, schizophrenia or attention deficit hyperactivity disorder.
[15] A method of enhancing AMPA receptor function of a mammal, comprising administering an effective amount of the compound of any one of [1]-[11] or a salt thereof to the mammal.
[16] A method of preventing or treating depression, Alzheimer's disease, schizophrenia or attention deficit hyperactivity disorder in a mammal, comprising administering an effective amount of the compound of any one of [1]-[11] or a salt thereof to the mammal.
[16A] A method of preventing or treating depression in a mammal, comprising administering an effective amount of
N-[(3R,4S)-3-{[4-(4-chloro-1H-pyrazol-1-yl)phenoxy]methyl}tetrahydro-2H-pyran-4-yl]methanesulfonamide,
N-[(3RS,4SR)-3-({4-[5-(trifluoromethyl)pyridin-2-yl]phenoxy}methyl)tetrahydro-2H-pyran-4-yl]ethanesulfonamide, or
N-[(3R,4S)-4-{[4-(5-chloro-3-fluoropyridin-2-yl)phenoxy]methyl}tetrahydro-2H-pyran-3-yl]cyclopropanesulfonamide
or a salt thereof to the mammal.
[16B] A method of preventing or treating Alzheimer's disease in a mammal, comprising administering an effective amount of
N-[(3R,4S)-3-{[4-(4-chloro-1H-pyrazol-1-yl)phenoxy]methyl}tetrahydro-2H-pyran-4-yl]methanesulfonamide,
N-[(3RS,4SR)-3-({4-[5-(trifluoromethyl)pyridin-2-yl]phenoxy}methyl)tetrahydro-2H-pyran-4-yl]ethanesulfonamide, or
N-[(3R,4S)-4-{[4-(5-chloro-3-fluoropyridin-2-yl)phenoxy]methyl}tetrahydro-2H-pyran-3-yl]cyclopropanesulfonamide
or a salt thereof to the mammal.
[16C] A method of preventing or treating schizophrenia in a mammal, comprising administering an effective amount of
N-[(3R,4S)-3-{[4-(4-chloro-1H-pyrazol-1-yl)phenoxy]methyl}tetrahydro-2H-pyran-4-yl]methanesulfonamide,
N-[(3RS,4SR)-3-({4-[5-(trifluoromethyl)pyridin-2-yl]phenoxy}methyl)tetrahydro-2H-pyran-4-yl]ethanesulfonamide, or
N-[(3R,4S)-4-{[4-(5-chloro-3-fluoropyridin-2-yl)phenoxy]methyl}tetrahydro-2H-pyran-3-yl]cyclopropanesulfonamide
or a salt thereof to the mammal.
[16C'] A method of preventing or treating positive symptom of schizophrenia in a mammal, comprising administering an effective amount of
N-[(3R,4S)-3-{[4-(4-chloro-1H-pyrazol-1-yl)phenoxy]methyl}tetrahydro-2H-pyran-4-yl]methanesulfonamide,
N-[(3RS,4SR)-3-({4-[5-(trifluoromethyl)pyridin-2-yl]phenoxy}methyl)tetrahydro-2H-pyran-4-yl]ethanesulfonamide, or N-[(3R,4S)-4-{[4-(5-chloro-3-fluoropyridin-2-yl)phenoxy]
methyl}tetrahydro-2H-pyran-3-yl]cyclopropanesulfona-
mide or a salt thereof to the mammal.

[16C''] A method of preventing or treating negative symptom of schizophrenia in a mammal, comprising administering an effective amount of N-[(3R,4S)-3-{[4-(4-chloro-1H-pyrazol-1-yl)phenoxy]
methyl}tetrahydro-2H-pyran-4-yl]methanesulfonamide, N-[(3RS,4SR)-3-({4-[5-(trifluoromethyl)pyridin-2-yl]
phenoxy}methyl)tetrahydro-2H-pyran-4-yl]ethanesulfonamide, or N-[(3R,4S)-4-{[4-(5-chloro-3-fluoropyridin-2-yl)phenoxy]
methyl}tetrahydro-2H-pyran-3-yl]cyclopropanesulfona-
mide or a salt thereof to the mammal.

[16C'''] A method of preventing or treating cognitive impairment in schizophrenia in a mammal, comprising administering an effective amount of N-[(3R,4S)-3-{[4-(4-chloro-1H-pyrazol-1-yl)phenoxy]
methyl}tetrahydro-2H-pyran-4-yl]methanesulfonamide, N-[(3RS,4SR)-3-({4-[5-(trifluoromethyl)pyridin-2-yl]
phenoxy}methyl)tetrahydro-2H-pyran-4-yl]ethanesulfonamide, or N-[(3R,4S)-4-{[4-(5-chloro-3-fluoropyridin-2-yl)phenoxy]
methyl}tetrahydro-2H-pyran-3-yl]cyclopropanesulfona-
mide or a salt thereof to the mammal.

[16D] A method of preventing or treating attention deficit hyperactivity disorder in a mammal, comprising administering an effective amount of N-[(3R,4S)-3-{[4-(4-chloro-1H-pyrazol-1-yl)phenoxy]
methyl}tetrahydro-2H-pyran-4-yl]methanesulfonamide, N-[(3RS,4SR)-3-({4-[5-(trifluoromethyl)pyridin-2-yl]
phenoxy}methyl)tetrahydro-2H-pyran-4-yl]ethanesulfonamide, or N-[(3R,4S)-4-{[4-(5-chloro-3-fluoropyridin-2-yl)phenoxy]
methyl}tetrahydro-2H-pyran-3-yl]cyclopropanesulfona-
mide or a salt thereof to the mammal.

[17] Use of the compound of any one of [1]-[11] or a salt thereof for the production of an AMPA receptor function enhancer.

[18] Use of the compound of any one of [1]-[11] or a salt thereof for the production of a prophylactic or therapeutic drug for depression, Alzheimer's disease, schizophrenia or attention deficit hyperactivity disorder.

[19] The compound of any one of [1]-[11] or a salt thereof for use for the prophylaxis or treatment of depression, Alzheimer's disease, schizophrenia or attention deficit hyperactivity disorder.

Effect of the Invention

According to the present invention, a compound having an AMPA receptor function enhancing action, which is useful as a prophylactic or therapeutic drug for depression, Alzheimer's disease, schizophrenia, attention deficit hyperactivity disorder (ADHD) and the like can be provided.

BRIEF DESCRIPTION OF THE DRAWINGS

FIG. 1 shows inhibition of methamphetamine (MAP)-induced hyperlocomotion by compound A and B.

DETAILED DESCRIPTION OF THE INVENTION

The present invention is explained in detail in the following.

In the present specification, indication of hydrogen atom in the chemical structural formulas may be sometimes omitted according to the conventional practice in the chemical field.

In the present specification, unless otherwise specified, the "halogen atom" is, for example, fluorine, chlorine, bromine or iodine.

In the present specification, unless otherwise specified, "optionally halogenated" or "halogeno" means optionally having one or more (e.g., 1-3) halogen atoms as substituent (s).

In the present specification, unless otherwise specified, the "$C_{1-6}$ alkyl group" is, for example, methyl, ethyl, propyl, isopropyl, butyl, isobutyl, sec-butyl, tert-butyl, pentyl, isopentyl, neopentyl or hexyl.

In the present specification, unless otherwise specified, the "$C_{3-6}$ cycloalkyl group" is, for example, cyclopropyl, cyclobutyl, cyclopentyl or cyclohexyl.

In the present specification, unless otherwise specified, the "$C_{1-3}$ alkoxy group" is, for example, methoxy, ethoxy, propoxy or isopropoxy.

In the present specification, unless otherwise specified, the "acyl group" is, for example, (1) formyl,
(2) alkyl-carbonyl optionally having substituent(s),
(3) alkenyl-carbonyl optionally having substituent(s),
(4) alkynyl-carbonyl optionally having substituent(s),
(5) cycloalkyl-carbonyl optionally having substituent(s),
(6) cycloalkenyl-carbonyl optionally having substituent(s),
(7) aryl-carbonyl optionally having substituent(s),
(8) heterocyclyl-carbonyl optionally having substituent(s),
(9) carboxyl,
(10) alkoxy-carbonyl optionally having substituent(s),
(11) alkenyloxy-carbonyl optionally having substituent(s),
(12) alkynyloxy-carbonyl optionally having substituent(s),
(13) cycloalkyloxy-carbonyl optionally having substituent (s),
(14) cycloalkenyloxy-carbonyl optionally having substituent(s),
(15) cycloalkynyloxy-carbonyl optionally having substituent(s),
(16) aryloxy-carbonyl optionally having substituent(s),
(17) heterocyclyl-oxy-carbonyl optionally having substituent(s),
(18) carbamoyl optionally having substituent(s),
(19) alkyl-sulfonyl optionally having substituent(s),
(20) cycloalkyl-sulfonyl optionally having substituent(s),
(21) aryl-sulfonyl optionally having substituent(s),
(22) heterocyclyl-sulfonyl optionally having substituent(s),
(23) alkyl-sulfinyl optionally having substituent(s),
(24) cycloalkyl-sulfinyl optionally having substituent(s),
(25) aryl-sulfinyl optionally having substituent(s),
(26) heterocyclyl-sulfinyl optionally having substituent(s)

or the like.

In the present specification, unless otherwise specified, the "3- to 8-membered monocyclic nonaromatic ring" is, for example, a "3- to 8-membered monocyclic nonaromatic hydrocarbon ring" or a "3- to 8-membered monocyclic non-aromatic heterocycle".

In the present specification, unless otherwise specified, the "3- to 8-membered monocyclic nonaromatic hydrocarbon ring" is, for example, a nonaromatic hydrocarbon ring having a carbon number of 3-8 such as $C_{3-8}$ cycloalkane, $C_{5-8}$ cycloalkene, $C_{5-8}$ cycloalkadiene, bridged ring hydrocarbon having a carbon number of 5-8 or the like.

In the present specification, unless otherwise specified, the "$C_{3-8}$ cycloalkane" is, for example, cyclopropane, cyclobutane, cyclopentane, cyclohexane, cycloheptane or cyclooctane.

In the present specification, unless otherwise specified, the "$C_{5-8}$ cycloalkene" is, for example, cyclopentene, cyclohexene, cycloheptene or cyclooctene.

In the present specification, unless otherwise specified, the "$C_{5-8}$ cycloalkadiene" is, for example, cyclopentadiene, cyclohexadiene, cycloheptadiene or cyclooctadiene.

In the present specification, unless otherwise specified, the "bridged ring hydrocarbon having a carbon number of 5-8" is, for example, bicyclo[2.1.0]pentane, bicyclo[2.2.1]heptane, bicyclo[3.2.1]octane, bicyclo[2.2.1]hept-2-ene or tricyclo[2.2.1.0]heptane.

In the present specification, unless otherwise specified, the "aromatic hydrocarbon ring" is, for example, an aromatic hydrocarbon ring having a carbon number of 6-14, as concrete examples thereof include benzene ring, indene ring, naphthalene ring, anthracene ring, and phenanthrene ring.

In the present specification, unless otherwise specified, the "aromatic hydrocarbon ring" may be monocyclic, bicyclic or tricyclic. In addition, the bicyclic or tricyclic "aromatic hydrocarbon ring" may be partially saturated (e.g., dihydroindene ring).

In the present specification, unless otherwise specified, the "heterocycle" is, for example, a 3- to 14-membered heterocycle containing 1-4 hetero atoms selected from a nitrogen atom (N), a sulfur atom (S) or an oxygen atom (O).

In the present specification, unless otherwise specified, the "heterocycle" is, for example, non-aromatic heterocycle or aromatic heterocycle.

In the present specification, unless otherwise specified, the "non-aromatic heterocycle" is, for example, monocyclic non-aromatic heterocycle or fused non-aromatic heterocycle.

In the present specification, unless otherwise specified, the "3-8-membered monocyclic non-aromatic heterocycle" is, for example, non-aromatic heterocycle such as an oxirane ring, an azetidine ring, an oxetane ring, a thietane ring, a pyrrolidine ring, a dihydrofuran ring, a tetrahydrofuran ring, a tetrahydrothiophene ring, an imidazolidine ring, an oxazolidine ring, an isooxazoline ring, a piperidine ring, a dihydropyran ring, a tetrahydropyran ring, a tetrahydrothiopyran ring, a morpholine ring, a thiomorpholine ring, a piperazine ring, a dihydrooxazine ring, a tetrahydrooxazine ring, a dihydropyrimidine ring, a tetrahydropyrimidine ring, an azepane ring, an oxepane ring, a thiepane ring, an oxazepane ring, a thiazepane ring, an azocane ring, an oxocane ring, a thiocane ring, an oxazocane ring, a thiazocane ring and the like.

In the present specification, unless otherwise specified, the "fused non-aromatic heterocycle" is, for example, monocyclic non-aromatic heterocycle fused with one or two rings selected from a nonaromatic hydrocarbon ring having a carbon number of 3-8, a benzene ring, a monocyclic non-aromatic heterocycle or a 5- or 6-membered aromatic heterocycle. Specific examples thereof include bicyclic fused non-aromatic heterocycle such as dihydroindole, dihydroisoindole, dihydrobenzofuran, dihydrobenzodioxine, dihydrobenzodioxepine, chromene, dihydroquinoline, tetrahydroquinoline, dihydroisoquinoline, tetrahydroisoquinoline, dihydrophthalazine, tetrahydrobenzoazepine and the like.

In the present specification, unless otherwise specified, the "bicyclic 7- or 8-membered saturated ring" is, for example, a bicyclic 7- or 8-membered ring obtained by condensation of two rings selected from the above-mentioned "3- to 8-membered monocyclic nonaromatic hydrocarbon ring" and "3- to 8-membered monocyclic nonaromatic heterocycle". Specific examples thereof include a bicyclo[2.2.1]heptane ring, a 7-oxabicyclo[2.2.1]heptane ring, a 7-azabicyclo[2.2.1]heptane ring, a bicyclo[3.2.1]octane ring, a 8-oxabicyclo[3.2.1]octane ring, a 8-azabicyclo[3.2.1]octane ring and the like.

In the present specification, unless otherwise specified, the "aromatic heterocycle" is, for example, monocyclic aromatic heterocycle or fused aromatic heterocycle.

In the present specification, unless otherwise specified, the "monocyclic aromatic heterocycle" is, for example, 5- or 6-membered aromatic heterocycle such as a furan ring, a thiophene ring, a pyrrole ring, an oxazole ring, an isoxazole ring, a thiazole ring, an isothiazole ring, an imidazole ring, a pyrazole ring, a 1,2,3-oxadiazole ring, a 1,2,4-oxadiazole ring, a 1,3,4-oxadiazole ring, a furazan ring, a 1,2,3-thiadiazole ring, a 1,2,4-thiadiazole ring, a 1,3,4-thiadiazole ring, a 1,2,3-triazole ring, a 1,2,4-triazole ring, a tetrazole ring, a pyridine ring, a pyridazine ring, a pyrimidine ring, a pyrazine ring, a triazine ring and the like.

In the present specification, unless otherwise specified, the "fused aromatic heterocycle" is, for example, monocyclic aromatic heterocycle fused with 1 or 2 rings selected from a benzene ring and 5- or 6-membered aromatic heterocycle. Specific examples thereof include bicyclic fused aromatic heterocycle such as quinoline, isoquinoline, quinazoline, quinoxaline, benzofuran, benzothiophene, benzoxazole, benzisoxazole, benzothiazole, benzimidazole, benzotriazole, indole, indolizine, indazole, pyrrolopyrazine (e.g., 1H-pyrrolo[2,3-b]pyrazine, 1H-pyrrolo[2,3-b]pyrazine, pyrrolo[1,2-a]pyrazine), pyrazolopyridine (e.g., pyrazolo[1,5-a]pyridine), imidazopyridine (e.g., 1H-imidazo[4,5-b]pyridine, 1H-imidazo[4,5-c]pyridine, 2H-imidazo[1,2-a]pyridine, imidazo[1,2-a]pyridine, imidazo[1,5-a]pyridine), triazolopyridine (e.g., 1H-[1,2,3]triazolo[4,5-b]pyridine, 1H-[1,2,3]triazolo[4,5-c]pyridine, [1,2,4]triazolo[4,3-a]pyridine, [1,2,4]triazolo[1,5-a]pyridine), imidazopyrazine (e.g., 1H-imidazo[4,5-b]pyrazine, imidazo[1,2-a]pyrazine, imidazo[1,5-a]pyrazine), triazolopyrazine (e.g., [1,2,4]triazolo[1,5-a]pyrazine), pyrazolopyridine (e.g., 1H-pyrazolo[4,3-c]pyridine), pyrazolothiophene (e.g., 2H-pyrazolo[3,4-b]thiophene), pyrazolotriazine (e.g., pyrazolo[5,1-c][1,2,4]triazine) and the like.

In the present specification, unless otherwise specified, the "alkenyl (group)" is, for example, $C_{2-6}$ alkenyl (group).

In the present specification, unless otherwise specified, the "$C_{2-6}$ alkenyl (group)" is, for example, vinyl, 1-propen-1-yl, 2-propen-1-yl, isopropenyl, 2-buten-1-yl, 4-penten-1-yl or 5-hexen-1-yl.

In the present specification, unless otherwise specified, the "alkynyl (group)" is, for example, a $C_{2-6}$ alkynyl group. Examples of the "$C_{2-6}$ alkynyl (group)" include ethynyl, 1-propyn-1-yl, 2-propyn-1-yl, 4-pentyn-1-yl and 5-hexyn-1-yl.

In the present specification, unless otherwise specified, the "$C_{3-7}$ cycloalkyl-$C_{2-6}$ alkynyl (group)" is, for example, cyclopropylethynyl.

In the present specification, unless otherwise specified, the "nonaromatic cyclic hydrocarbon group" is, for example, $C_{3-7}$ cycloalkyl (group), $C_{3-7}$ cycloalkenyl (group), $C_{4-10}$ cycloalkadienyl (group) or a bridged cyclic hydrocarbon group having a carbon number of 5-10 (e.g., tricyclo[3.3.1.1$^{3,7}$]decyl), each of which is optionally fused with one or more (preferably 1 or 2) hydrocarbon rings.

Examples of the "hydrocarbon ring" include the aforementioned "3- to 8-membered monocyclic nonaromatic hydrocarbon ring" and the aforementioned "aromatic hydrocarbon ring".

In the present specification, unless otherwise specified, the "$C_{3-7}$ cycloalkenyl (group)" is, for example, cyclopropenyl, cyclobutenyl, cyclopentenyl, cyclohexenyl or cycloheptenyl.

In the present specification, unless otherwise specified, the "$C_{4-10}$ cycloalkadienyl (group)" is, for example, cyclobutadienyl, cyclopentadienyl, cyclohexadienyl, cycloheptadienyl, cyclooctadienyl, cyclononadienyl or cyclodecadienyl.

In the present specification, unless otherwise specified, the "aromatic cyclic hydrocarbon group" may be monocyclic, bicyclic or tricyclic.

In the present specification, unless otherwise specified, the "aromatic cyclic hydrocarbon group" is, for example, $C_{6-14}$ aryl (group) or the like. Specific examples thereof include phenyl, 1-naphthyl, 2-naphthyl, 2-biphenylyl, 3-biphenylyl, 4-biphenylyl and 2-anthryl.

In the present specification, unless otherwise specified, the "$C_{7-16}$ aralkyl (group)" is, for example, benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl or 4-biphenylylmethyl.

In the present specification, unless otherwise specified, the "$C_{6-14}$ aryl-$C_{2-6}$ alkenyl (group)" is, for example, styryl.

In the present specification, unless otherwise specified, the "$C_{1-7}$ alkylene (group)" (that is, $C_{1-6}$ alkanediyl group) is, for example, methylene, ethylene, trimethylene, tetramethylene, 2-butenylene, 2-methyltetramethylene, pentamethylene or hexamethylene.

In the present specification, unless otherwise specified, the "$C_{2-7}$ alkylene (group)" is, for example, alkylene (group) having a carbon number of 2-7 from the aforementioned "$C_{1-7}$ alkylene (group)". Examples of the "$C_{1-3}$ alkylene (group)" include alkylene (group) having a carbon number of 1-3 from the aforementioned "$C_{1-7}$ alkylene (group)".

In the present specification, unless otherwise specified, the "$C_{2-6}$ alkenylene (group)" is, for example, —CH=CH—, —CH=C(CH$_3$)—, —C(CH$_3$)=CH—, —CH=CH—CH$_2$—, —CH$_2$—CH=CH—, —C(CH$_3$)$_2$—CH=CH—, —CH=CH—CH=CH—CH$_2$—, —CH$_2$—CH$_2$—CH=CH—, —CH=CH—CH=CH—, —CH=CH—CH$_2$—CH$_2$—CH$_2$— or —CH=C(C$_2$H$_5$)—.

In the present specification, unless otherwise specified, the "$C_{2-3}$ alkenylene (group)" is, for example, alkenylene (group) having a carbon number of 2 or 3 from the aforementioned "$C_{2-6}$ alkenylene (group)".

In the present specification, unless otherwise specified, the "$C_{2-6}$ alkynylene (group)" is, for example, —C≡C—, —CH$_2$—C≡C—, —CH$_2$—C≡C—CH(CH$_3$)— or —CH$_2$—C≡C—CH$_2$—CH$_2$—.

In the present specification, unless otherwise specified, the "heterocyclic group" (and heterocyclic moiety in substituent) is, for example, a nonaromatic heterocyclic group or an aromatic heterocyclic group (that is, a heteroaryl group).

In the present specification, unless otherwise specified, the "heterocyclic group" may be monocyclic, bicyclic or tricyclic.

In the present specification, unless otherwise specified, the "heterocyclic group" is, for example, a 3- to 14-membered heterocyclic group containing 1 to 4 hetero atoms selected from an oxygen atom, a sulfur atom and a nitrogen atom, and the like.

In the present specification, unless otherwise specified, the "nonaromatic heterocyclic group" may be saturated or unsaturated.

In the present specification, unless otherwise specified, the "nonaromatic heterocyclic group" is, for example, a 3- to 14-membered nonaromatic heterocyclic group.

In the present specification, unless otherwise specified, examples of the "3-14-membered nonaromatic heterocyclic group" is, for example, a 3- to 6-membered nonaromatic heterocyclic group containing 1 to 4 hetero atoms selected from an oxygen atom, a sulfur atom and a nitrogen atom, which may be fused with a 5- or 6-membered ring.

In the present specification, unless otherwise specified, the "3- to 6-membered nonaromatic heterocyclic group containing 1 to 4 hetero atoms selected from an oxygen atom, a sulfur atom and a nitrogen atom" is, for example, tetrahydrofuryl, oxazolidinyl, imidazolinyl (e.g., 1-imidazolinyl, 2-imidazolinyl, 4-imidazolinyl), aziridinyl (e.g., 1-aziridinyl, 2-aziridinyl), azetidinyl (e.g., 1-azetidinyl, 2-azetidinyl), pyrrolidinyl (e.g., 1-pyrrolidinyl, 2-pyrrolidinyl, 3-pyrrolidinyl), piperidinyl (e.g., 1-piperidinyl, 2-piperidinyl, 3-piperidinyl), azepanyl (e.g., 1-azepanyl, 2-azepanyl, 3-azepanyl, 4-azepanyl), azocanyl (e.g., 1-azocanyl, 2-azocanyl, 3-azocanyl, 4-azocanyl), piperazinyl (e.g., 1,4-piperazin-1-yl, 1,4-piperazin-2-yl), diazepinyl (e.g., 1,4-diazepin-1-yl, 1,4-diazepin-2-yl, 1,4-diazepin-5-yl, 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, 1,5-diazocan-3-yl), tetrahydropyranyl (e.g., tetrahydropyran-4-yl), morpholinyl (e.g., 4-morpholinyl), thiomorpholinyl (e.g., 4-thiomorpholinyl), 2-oxazolidinyl, dihydrofuryl, dihydropyranyl, dihydroquinolyl or 2,3-dihydro-1H-imidazo[1,2-a]imidazol-1-yl.

In the present specification, unless otherwise specified, the "5- or 6-membered ring" is, for example, a hydrocarbon ring having a carbon number of 5 or 6 (e.g., cyclopentane, cyclohexane, cyclopentene, cyclohexene, cyclopentadiene, cyclohexadiene, benzene) or 5- or 6-membered heterocycle.

In the present specification, unless otherwise specified, the "5- or 6-membered heterocycle" is, for example, the aforementioned "heterocycle" which is 5- or 6-membered.

In the present specification, unless otherwise specified, the "3- to 6-membered nonaromatic heterocyclic group containing 1 to 4 hetero atoms selected from an oxygen atom, a sulfur atom and a nitrogen atom, which is fused with a 5- or 6-membered ring" is, for example, 2,3-dihydro-1H-imidazo[1,2-a]benzimidazol-1-yl.

In the present specification, unless otherwise specified, the "aromatic heterocyclic group" is, for example, a 5- or 6-membered monocyclic aromatic heterocyclic group or a 5- to 10-membered aromatic fused heterocyclic group.

In the present specification, unless otherwise specified, the "5- or 6-membered monocyclic aromatic heterocyclic group" is, for example, a 5- or 6-membered monocyclic aromatic heterocyclic group containing 1 to 4 hetero atoms selected from an oxygen atom, a sulfur atom and a nitrogen atom, such as pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), pyrazolyl (e.g., 1-pyrazolyl, 3-pyrazolyl, 4-pyrazolyl), imidazolyl (e.g., 1-imidazolyl, 2-imidazolyl, 4-imidazolyl), isoxazolyl (e.g., 3-isoxazolyl, 4-isoxazolyl, 5-isoxazolyl), oxazolyl (e.g., 2-oxazolyl, 4-oxazolyl, 5-oxazolyl), isothiazolyl (e.g., 3-isothiazolyl, 4-isothiazolyl, 5-isothiazolyl), thiazolyl (e.g., 2-thiazolyl, 4-thiazolyl, 5-thiazolyl), triazolyl (e.g., 1,2,3-triazol-4-yl, 1,2,4-triazol-3-yl), oxadiazolyl (e.g., 1,2,4-oxadiazol-3-yl, 1,2,4-oxadiazol-5-yl), thiadiazolyl (e.g., 1,2,4-thiadiazol-3-yl, 1,2,4-thiadiazol-5-yl), tetrazolyl, pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), pyrazinyl and the like.

In the present specification, unless otherwise specified, the "5- to 10-membered aromatic fused heterocyclic group" is, for example, a 5- to 10-membered aromatic fused heterocyclic group containing 1 to 4 hetero atoms selected from an oxygen atom, a sulfur atom and a nitrogen atom, such as isoindolyl (e.g., 1-isoindolyl, 2-isoindolyl, 3-isoindolyl, 4-isoindolyl, 5-isoindolyl, 6-isoindolyl, 7-isoindolyl), indolyl (e.g., 1-indolyl, 2-indolyl, 3-indolyl, 4-indolyl, 5-indolyl, 6-indolyl, 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, 7-benzo[b]furanyl), benzo[c]furanyl (e.g., 1-benzo[c]furanyl, 4-benzo[c]furanyl, 5-benzo[c]furanyl), benzo[b]thienyl, (e.g., 2-benzo[b]thienyl, 3-benzo[b]thienyl, benzo[b]thienyl, 5-benzo[b]thienyl, 6-benzo[b]thienyl, 7-benzo[b]thienyl), benzo[c]thienyl (e.g., 1-benzo[c]thienyl, 4-benzo[c]thienyl, 5-benzo[c]thienyl), indazolyl (e.g., 1-indazolyl, 2-indazolyl, 3-indazolyl, 4-indazolyl, 5-indazolyl, 6-indazolyl, 7-indazolyl), benzimidazolyl (e.g., 1-benzimidazolyl, 2-benzimidazolyl, 4-benzimidazolyl, 5-benzimidazolyl), 1,2-benzoisoxazolyl (e.g., 1,2-benzoisoxazol-3-yl, 1,2-benzoisoxazol-4-yl, 1,2-benzoisoxazol-5-yl, 1,2-benzoisoxazol-6-yl, 1,2-benzoisoxazol-7-yl), benzoxazolyl (e.g., 2-benzoxazolyl, 4-benzoxazolyl, 5-benzoxazolyl, 6-benzoxazolyl, 7-benzoxazolyl), 1,2-benzoisothiazolyl (e.g., 1,2-benzoisothiazol-3-yl, 1,2-benzoisothiazol-4-yl, 1,2-benzoisothiazol-5-yl, 1,2-benzoisothiazol-6-yl, 1,2-benzoisothiazol-7-yl), benzothiazolyl (e.g., 2-benzothiazolyl, 4-benzothiazolyl, 5-benzothiazolyl, 6-benzothiazolyl, 7-benzothiazolyl), isoquinolyl (e.g., 1-isoquinolyl, 3-isoquinolyl, 4-isoquinolyl, 5-isoquinolyl), quinolyl (e.g., 2-quinolyl, 3-quinolyl, 4-quinolyl, 5-quinolyl, 8-quinolyl), cinnolinyl (e.g., 3-cinnolinyl, 4-cinnolinyl, 5-cinnolinyl, 6-cinnolinyl, 7-cinnolinyl, 8-cinnolinyl), phthalazinyl (e.g., 1-phthalazinyl, 4-phthalazinyl, 5-phthalazinyl, 6-phthalazinyl, 7-phthalazinyl, 8-phthalazinyl), quinazolinyl (e.g., 2-quinazolinyl, 4-quinazolinyl, 5-quinazolinyl, 6-quinazolinyl, 7-quinazolinyl, 8-quinazolinyl), quinoxalinyl (e.g., 2-quinoxalinyl, 3-quinoxalinyl, 5-quinoxalinyl, 6-quinoxalinyl, 7-quinoxalinyl, 8-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, pyrazolo[1,5-a]pyridin-7-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, imidazo[1,2-a]pyridin-8-yl) and the like.

In the present specification, unless otherwise specified, the "$C_{3-7}$ cycloalkyloxy (group)" is, for example, cyclopropyloxy, cyclobutyloxy, cyclopentyloxy or cyclohexyloxy.

In the present specification, unless otherwise specified, the "$C_{6-14}$ aryloxy (group)" is, for example, phenyloxy, 1-naphthyloxy or 2-naphthyloxy.

In the present specification, unless otherwise specified, the "$C_{7-16}$ aralkyloxy (group)" is, for example, benzyloxy or phenethyloxy.

In the present specification, unless otherwise specified, the "alkyl-carbonyloxy (group)" is, for example, $C_{1-6}$ alkyl-carbonyloxy (group).

In the present specification, unless otherwise specified, the "$C_{1-6}$ alkyl-carbonyloxy (group)" is, for example, acetoxy or propionyloxy.

In the present specification, unless otherwise specified, the "alkoxy-carbonyloxy (group)" is, for example, $C_{1-6}$ alkoxy-carbonyloxy (group).

In the present specification, unless otherwise specified, the "$C_{1-6}$ alkoxy-carbonyloxy (group)" is, for example, methoxycarbonyloxy, ethoxycarbonyloxy, propoxycarbonyloxy or but oxycarbonyloxy.

In the present specification, unless otherwise specified, the "mono-alkyl-carbamoyloxy (group)" is, for example, mono-$C_{1-6}$ alkyl-carbamoyloxy (group).

In the present specification, unless otherwise specified, the "mono-$C_{1-6}$ alkyl-carbamoyloxy (group)" is, for example, methylcarbamoyloxy or ethylcarbamoyloxy.

In the present specification, unless otherwise specified, the "di-alkyl-carbamoyloxy (group)" is, for example, di-$C_{1-6}$ alkyl-carbamoyloxy (group).

In the present specification, unless otherwise specified, the "di-$C_{1-6}$ alkyl-carbamoyloxy (group)" is, for example, dimethylcarbamoyloxy or diethylcarbamoyloxy.

In the present specification, unless otherwise specified, the "$C_{6-14}$ aryl-carbonyloxy (group)" is, for example, benzoyloxy or naphthylcarbonyloxy.

In the present specification, unless otherwise specified, the "mono- or di-$C_{6-14}$ aryl-carbamoyloxy (group)" is, for example, phenylcarbamoyloxy or naphthylcarbamoyloxy.

In the present specification, unless otherwise specified, the heterocyclic moiety of the "heterocyclyl-oxy (group)" is, for example, one similar to the aforementioned "heterocyclic group". Specific examples of the "heterocyclyl-oxy (group)" include a 3- to 14-membered heterocyclyl-oxy (group) containing 1 to 5 hetero atoms selected from a nitrogen atom, a sulfur atom and an oxygen atom.

In the present specification, unless otherwise specified, the aromatic heterocyclic moiety of the "aromatic heterocyclyl-oxy (group)" is, for example, one similar to the "aromatic heterocyclic group" exemplified as the aforementioned "heterocyclic group". Specific examples of the "aromatic heterocyclyl-oxy (group)" include a 5- to 14-membered aromatic heterocyclyl-oxy containing 1 to 5 hetero atoms selected from a nitrogen atom, a sulfur atom and an oxygen atom.

In the present specification, unless otherwise specified, the "$C_{1-6}$ alkylsulfonyloxy group" is, for example, methylsulfonyloxy or ethylsulfonyloxy.

In the present specification, unless otherwise specified, the "halogeno $C_{1-6}$ alkylsulfonyloxy group" is, for example, halogenomethylsulfonyloxy or halogenoethylsulfonyloxy.

In the present specification, unless otherwise specified, the "alkylsulfanyl (group)" is, for example, $C_{1-6}$ alkylsulfanyl (group).

In the present specification, unless otherwise specified, the "$C_{1-6}$ alkylsulfanyl (group)" is, for example, methylsulfanyl, ethylsulfanyl, propylsulfanyl, isopropylsulfanyl, butylsulfanyl, sec-butylsulfanyl or tert-butylsulfanyl.

In the present specification, unless otherwise specified, the "$C_{3-7}$ cycloalkylsulfanyl (group)" is, for example, cyclopropylsulfanyl, cyclobutylsulfanyl, cyclopentylsulfanyl or cyclohexylsulfanyl.

In the present specification, unless otherwise specified, to the "$C_{6-14}$ arylsulfanyl (group)" is, for example, phenylsulfanyl, 1-naphthylsulfanyl or 2-naphthylsulfanyl.

In the present specification, unless otherwise specified, the "$C_{7-16}$ aralkylsulfanyl (group)" is, for example, benzylsulfanyl or phenethylsulfanyl.

In the present specification, unless otherwise specified, the heterocyclic moiety of the "heterocyclyl-sulfanyl (group)" is, for example, one similar to the aforementioned "heterocyclic group". Specific examples of the "heterocyclyl-sulfanyl (group)" include 3- to 14-membered heterocyclyl-sulfanyl (group) containing 1 to 5 hetero atoms selected from a nitrogen atom, a sulfur atom and an oxygen atom.

In the present specification, unless otherwise specified, the "alkyl-carbonyl (group)" is, for example, $C_{1-6}$ alkyl-carbonyl.

In the present specification, unless otherwise specified, the "$C_{1-6}$ alkyl-carbonyl (group)" is, for example, acetyl, propionyl or pivaloyl.

In the present specification, unless otherwise specified, the "$C_{3-7}$ cycloalkyl-carbonyl (group)" is, for example, cyclopropylcarbonyl, cyclopentylcarbonyl or cyclohexylcarbonyl.

In the present specification, unless otherwise specified, the "$C_{6-14}$ aryl-carbonyl (group)" is, for example, benzoyl, 1-naphthoyl or 2-naphthoyl.

In the present specification, unless otherwise specified, the "$C_{7-16}$ aralkyl-carbonyl (group)" is, for example, phenylacetyl or 3-phenylpropionyl.

In the present specification, unless otherwise specified, the heterocyclic moiety of the "heterocyclyl-carbonyl (group)" is, for example, one similar to the aforementioned "heterocyclic group". Specific examples thereof include 3- to 14-membered heterocyclyl-carbonyl (group) containing 1 to 5 hetero atoms selected from a nitrogen atom, a sulfur atom and an oxygen atom. More specific examples thereof include picolinoyl, nicotinoyl, isonicotinoyl, 2-thenoyl, 3-thenoyl, 2-furoyl, 3-furoyl, 1-morpholinylcarbonyl, 4-thiomorpholinylcarbonyl, aziridin-1-ylcarbonyl, aziridin-2-ylcarbonyl, azetidin-1-ylcarbonyl, azetidin-2-ylcarbonyl, pyrrolidin-1-ylcarbonyl, pyrrolidin-2-ylcarbonyl, pyrrolidin-3-ylcarbonyl, piperidin-1-ylcarbonyl, piperidin-2-ylcarbonyl, piperidin-3-ylcarbonyl, azepan-1-ylcarbonyl, azepan-2-ylcarbonyl, azepan-3-ylcarbonyl, azepan-4-ylcarbonyl, azocan-1-ylcarbonyl, azocan-2-ylcarbonyl, azocan-3-ylcarbonyl, azocan-4-ylcarbonyl, 1,4-piperazin-1-ylcarbonyl, 1,4-piperazin-2-ylcarbonyl, 1,4-diazepan-1-ylcarbonyl, 1,4-diazepan-2-ylcarbonyl, 1,4-diazepan-5-ylcarbonyl, 1,4-diazepan-6-ylcarbonyl, 1,4-diazocan-1-ylcarbonyl, 1,4-diazocan-2-ylcarbonyl, 1,4-diazocan-5-ylcarbonyl, 1,4-diazocan-6-ylcarbonyl, 1,5-diazocan-1-ylcarbonyl, 1,5-diazocan-2-ylcarbonyl and 1,5-diazocan-3-ylcarbonyl.

In the present specification, unless otherwise specified, the "optionally esterified carboxy (group)" is, for example, carboxy, optionally substituted alkoxy-carbonyl, optionally substituted $C_{6-14}$ aryloxy-carbonyl, optionally substituted $C_{7-16}$ aralkyloxy-carbonyl, optionally substituted silyloxycarbonyl (e.g., TMS-O—CO—, TES-O—CO—, TBS-O—CO—, TIPS-O—CO—, TBDPS-O—CO—) and the like.

In the present specification, unless otherwise specified, the "alkoxy-carbonyl (group)" is, for example, "$C_{1-6}$ alkoxy-carbonyl (group)".

In the present specification, unless otherwise specified, the "$C_{1-6}$ alkoxy-carbonyl (group)" is for example, methoxycarbonyl, ethoxycarbonyl, propoxycarbonyl or tert-butoxycarbonyl.

In the present specification, unless otherwise specified, the "$C_{6-14}$ aryloxy-carbonyl (group)" is, for example, phenoxycarbonyl.

In the present specification, unless otherwise specified, the "$C_{7-16}$ aralkyloxy-carbonyl (group)" is, for example, benzyloxycarbonyl or phenethyloxycarbonyl.

In the present specification, unless otherwise specified, the "alkylsulfonyl (group)" is, for example, $C_{1-6}$ alkylsulfonyl (group).

In the present specification, unless otherwise specified, the "$C_{1-6}$ alkylsulfonyl (group)" is, for example, methylsulfonyl or ethylsulfonyl.

In the present specification, unless otherwise specified, the "$C_{3-7}$ cycloalkylsulfonyl (group)" is, for example, cyclopropylsulfonyl, cyclobutylsulfonyl, cyclopentylsulfonyl or cyclohexylsulfonyl.

In the present specification, unless otherwise specified, the "$C_{6-14}$ arylsulfonyl (group)" is, for example, phenylsulfonyl, 1-naphthylsulfonyl or 2-naphthylsulfonyl.

In the present specification, unless otherwise specified, the heterocyclic moiety of the "heterocyclyl-sulfonyl (group)" is, for example, one similar to the aforementioned "heterocyclic group". Specific examples of the "heterocyclyl-sulfonyl (group)" include 3- to 14-membered heterocyclyl-sulfonyl (group) containing 1 to 5 hetero atoms selected from a nitrogen atom, a sulfur atom and an oxygen atom.

In the present specification, unless otherwise specified, the "alkylsulfinyl (group)" is, for example, $C_{1-6}$ alkylsulfinyl (group).

In the present specification, unless otherwise specified, the "$C_{1-6}$ alkylsulfinyl (group)" is, for example, methylsulfinyl or ethylsulfinyl.

In the present specification, unless otherwise specified, the "$C_{3-7}$ cycloalkylsulfinyl (group)" is, for example, cyclopropylsulfinyl, cyclobutylsulfinyl, cyclopentylsulfinyl or cyclohexylsulfinyl.

In the present specification, unless otherwise specified, the "$C_{6-14}$ arylsulfinyl (group)" is, for example, phenylsulfinyl, 1-naphthylsulfinyl or 2-naphthylsulfinyl.

In the present specification, unless otherwise specified, the heterocyclic moiety of the "heterocyclyl-sulfinyl (group)" is, for example, one similar to the aforementioned "heterocyclic group". Specific examples of the "heterocyclyl-sulfinyl (group)" include 3- to 14-membered heterocyclyl-sulfinyl (group) containing 1 to 5 hetero atoms selected from a nitrogen atom, a sulfur atom and an oxygen atom.

In the present specification, unless otherwise specified, the "alkyl-carbamoyl (group)" is, for example, mono- or di-$C_{1-6}$ alkyl-carbamoyl (group).

In the present specification, unless otherwise specified, the "mono- or di-$C_{1-6}$ alkyl-carbamoyl (group)" is, for example, methylcarbamoyl, dimethylcarbamoyl, ethylcarbamoyl or propylcarbamoyl.

In the present specification, unless otherwise specified, the "mono- or di-alkylamino (group)" is, for example, mono- or alkylamino (group).

In the present specification, unless otherwise specified, the "mono- or di-$C_{1-6}$ alkylamino (group)" is, for example, methylamino, ethylamino, propylamino, dimethylamino or diethylamino.

In the present specification, unless otherwise specified, the "cyclic amino group" is, for example, a 4- to 9-membered cyclic amino group containing 1 or 2 nitrogen atoms. Specific examples thereof include azetidinyl, pyrrolidinyl, piperidinyl, piperazinyl, morpholinyl, thiomorpholinyl, pyrazolidinyl, imidazolidinyl, oxazolidinyl, thiazolidinyl, isoxazolidinyl, isothiazolidinyl, oxadiazolidinyl, thiadiazolidinyl, 7-azabicyclo[2.2.1]heptyl, 8-azabicyclo[3.2.1]octyl and the like.

In the present specification, unless otherwise specified, the "alkyl-carbonylamino (group)" is, for example, $C_{1-6}$ alkyl-carbonylamino.

In the present specification, unless otherwise specified, the "$C_{1-6}$ alkyl-carbonylamino (group)" is, for example, acetylamino, propionylamino or pivaloylamino.

In the present specification, unless otherwise specified, the "heterocycle (group)" of the "heterocyclyl-amino (group)" is, for example, one similar to the aforementioned "heterocyclic group". Example of the "heterocyclyl-amino (group)" include 2-pyridyl-amino.

In the present specification, unless otherwise specified, the "heterocyclyl-carbonyl" of the "heterocyclyl-carbonylamino (group)" is, for example, one similar to the aforementioned "heterocyclyl-carbonyl". Examples of the "heterocyclyl-carbonylamino (group)" include pyridyl-carbonylamino.

In the present specification, unless otherwise specified, the "heterocycle (group)" of the "heterocyclyl-oxycarbonylamino (group)" is, for example, one similar to the aforementioned "heterocyclic group". Examples of the "heterocyclyl-oxycarbonylamino (group)" include 2-pyridyl-oxycarbonylamino.

In the present specification, unless otherwise specified, the "heterocycle (group)" of the "heterocyclyl-sulfonylamino is (group)" is, for example, one similar to the aforementioned "heterocyclic group". Examples of the "heterocyclyl-sulfonylamino (group)" include 2-pyridyl-sulfonylamino.

In the present specification, unless otherwise specified, the "alkoxy-carbonylamino (group)" is, for example, $C_{1-6}$ alkoxy-carbonylamino (group).

In the present specification, unless otherwise specified, the "$C_{1-6}$ alkoxy-carbonylamino (group)" is, for example, methoxycarbonylamino, ethoxycarbonylamino, propoxycarbonylamino or butoxycarbonylamino.

In the present specification, unless otherwise specified, the "alkylsulfonylamino (group)" is, for example, $C_{1-6}$ alkylsulfonylamino (group).

In the present specification, unless otherwise specified, the "$C_{1-6}$ alkylsulfonylamino (group)" is, for example, methylsulfonylamino or ethylsulfonylamino.

In the present specification, unless otherwise specified, the "mono- or di-$C_{3-7}$ cycloalkylamino (group)" is, for example, cyclopropylamino, cyclopentylamino or cyclohexylamino.

In the present specification, unless otherwise specified, the "$C_{3-7}$ cycloalkyl-carbonylamino (group)" is, for example, cyclopropylcarbonylamino, cyclopentylcarbonylamino or cyclohexylcarbonylamino.

In the present specification, unless otherwise specified, the "$C_{3-7}$ cycloalkyloxy-carbonylamino (group)" is, for example, cyclopropoxycarbonylamino, cyclopentyloxycarbonylamino or cyclohexyloxycarbonylamino.

In the present specification, unless otherwise specified, the "$C_{3-7}$ cycloalkylsulfonylamino (group)" is, for example, cyclopropylsulfonylamino, cyclopentylsulfonylamino or cyclohexylsulfonylamino.

In the present specification, unless otherwise specified, the "mono- or di-$C_{6-14}$ arylamino (group)" is, for example, phenylamino or diphenylamino.

In the present specification, unless otherwise specified, the "mono- or di-$C_{7-16}$ aralkylamino (group)" is, for example, benzylamino.

In the present specification, unless otherwise specified, the "$C_{6-14}$ aryl-carbonylamino (group)" is, for example, benzoylamino or naphthoylamino.

In the present specification, unless otherwise specified, the "$C_{6-14}$ arylsulfonylamino (group)" is, for example, phenylsulfonylamino, 2-naphthylsulfonylamino or 1-naphthylsulfonylamino.

In the present specification, unless otherwise specified, the "optionally substituted hydroxyl group" is a hydroxyl group optionally substituted by alkyl ($C_{1-6}$ alkyl) optionally having substituent(s), alkenyl ($C_{2-6}$ alkenyl) optionally having substituent(s), alkynyl ($C_{2-6}$ alkynyl) optionally having substituent(s), cycloalkyl ($C_{3-9}$ cycloalkyl) optionally having substituent(s), cycloalkenyl ($C_{3-8}$ cycloalkenyl) optionally having substituent(s) or aryl ($C_{6-10}$ aryl) optionally having substituent(s).

In the present specification, unless otherwise specified, the "carbamoyl optionally having substituent(s)" is carbamoyl optionally having 1 or 2 substituents selected from alkyl ($C_{1-6}$ alkyl) optionally having substituent(s), alkenyl ($C_{2-6}$ alkenyl) optionally having substituent(s), alkynyl ($C_{2-6}$ alkynyl) optionally having substituent(s), cycloalkyl ($C_{3-8}$ cycloalkyl) optionally having substituent(s), cycloalkenyl ($C_{3-8}$ cycloalkenyl) optionally having substituent(s) and aryl ($C_{6-10}$ aryl) optionally having substituent(s).

In the present specification, unless otherwise specified, the "3- to 10-membered ring" is, for example, 3- to 10-membered one from the above-mentioned "hydrocarbon ring" and "heterocycle".

In the present specification, unless otherwise specified, the "cyclic group" of the "optionally substituted cyclic group" is, for example, the above-mentioned "hydrocarbon ring" or "heterocycle".

[Substituent Group A]

In the present specification, substituent group A includes substituents of the following (1)-(52).

(1) a halogen atom
(2) a nitro group
(3) a cyano group
(4) an optionally esterified carboxy group
(5) an optionally substituted alkyl group
(6) an optionally substituted alkenyl group
(7) an optionally substituted alkynyl group (e.g., an optionally substituted $C_{3-7}$ cycloalkyl-$C_{2-6}$ alkynyl group)
(8) an optionally substituted $C_{3-7}$ cycloalkyl group
(9) an optionally substituted $C_{6-14}$ aryl group
(10) an optionally substituted $C_{7-16}$ aralkyl group
(11) an optionally substituted $C_{6-14}$ aryl-$C_{2-6}$ alkenyl group
(12) an optionally substituted heterocyclic group
(13) a hydroxy group
(14) an optionally substituted alkoxy group
(15) an optionally substituted $C_{3-7}$ cycloalkyloxy group
(16) an optionally substituted $C_{6-14}$ aryloxy group
(17) an optionally substituted $C_{7-16}$ aralkyloxy group
(18) an optionally substituted alkyl-carbonyloxy group
(19) an optionally substituted alkoxy-carbonyloxy group
(20) an optionally substituted mono-alkyl-carbamoyloxy group
(21) an optionally substituted di-alkyl-carbamoyloxy group
(22) an optionally substituted $C_{6-14}$ aryl-carbonyloxy group
(23) an optionally substituted mono- or di-$C_{6-14}$ aryl-carbamoyloxy group
(24) an optionally substituted heterocyclyl-oxy group (e.g., an optionally substituted aromatic heterocyclyl-oxy group)
(25) an optionally substituted $C_{1-6}$ alkylsulfonyloxy group (e.g., an optionally substituted halogeno $C_{1-6}$ alkylsulfonyloxy group)
(26) a sulfanyl (mercapto) group
(27) an optionally substituted alkylsulfanyl group
(28) an optionally substituted $C_{3-7}$ cycloalkylsulfanyl group
(29) an optionally substituted $C_{6-14}$ arylsulfanyl group
(30) an optionally substituted $C_{7-16}$ aralkylsulfanyl group
(31) an optionally substituted heterocyclyl-sulfanyl group
(32) a formyl group
(33) an optionally substituted alkyl-carbonyl group

(34) an optionally substituted $C_{3-7}$ cycloalkyl-carbonyl group
(35) an optionally substituted $C_{6-14}$ aryl-carbonyl group
(36) an optionally substituted $C_{7-16}$ aralkyl-carbonyl group
(37) an optionally substituted heterocyclyl-carbonyl group
(38) an optionally substituted alkylsulfonyl group
(39) an optionally substituted $C_{3-7}$ cycloalkylsulfonyl group
(40) an optionally substituted $C_{6-14}$ arylsulfonyl group
(41) an optionally substituted heterocyclyl-sulfonyl group
(42) an optionally substituted alkylsulfinyl group
(43) an optionally substituted $C_{3-7}$ cycloalkylsulfinyl group
(44) an optionally substituted $C_{6-14}$ arylsulfinyl group
(45) an optionally substituted heterocyclyl-sulfinyl group
(46) a sulfo group
(47) a sulfamoyl group
(48) a sulfinamoyl group
(49) a sulfenamoyl group
(50) a thiocarbamoyl group
(51) an optionally substituted carbamoyl group [e.g., optionally substituted alkyl-carbamoyl and the like]
(52) an optionally substituted amino group
[e.g.,
amino,
an optionally substituted mono- or di-alkylamino group,
an optionally substituted mono- or di-$C_{3-7}$ cycloalkylamino group,
an optionally substituted mono- or di-$C_{6-14}$ arylamino group,
an optionally substituted mono- or di-$C_{7-16}$ aralkylamino group,
an optionally substituted heterocyclyl-amino group,
an optionally substituted $C_{6-14}$ aryl-carbonylamino group,
a formylamino group,
an optionally substituted alkyl-carbonylamino group (e.g., a mono-($C_{1-6}$ alkyl-carbonyl)-amino group),
an optionally substituted $C_{3-7}$ cycloalkyl-carbonylamino group,
an optionally substituted heterocyclyl-carbonylamino group,
an optionally substituted alkoxy-carbonylamino group,
an optionally substituted $C_{3-7}$ cycloalkyloxy-carbonylamino group,
an optionally substituted heterocyclyl-oxycarbonylamino group,
an optionally substituted carbamoylamino group,
an optionally substituted alkylsulfonylamino group,
an optionally substituted $C_{3-7}$ cycloalkylsulfonylamino group,
an optionally substituted heterocyclyl-sulfonylamino group,
an optionally substituted $C_{6-14}$ arylsulfonylamino group]
As respective substituents of the
"optionally substituted alkoxy-carbonyl group",
"optionally substituted alkyl group",
"optionally substituted alkenyl group",
"optionally substituted alkynyl group",
"optionally substituted alkoxy group",
"optionally substituted alkyl-carbonyloxy group",
"optionally substituted alkoxy-carbonyloxy group",
"optionally substituted mono-alkyl-carbamoyloxy group",
"optionally substituted di-alkyl-carbamoyloxy group",
"optionally substituted alkylsulfanyl group",
"optionally substituted alkyl-carbonyl group",
"optionally substituted alkylsulfonyl group",
"optionally substituted alkylsulfinyl group",
"optionally substituted alkyl-carbamoyl group",
"optionally substituted mono- or di-alkylamino group",
"optionally substituted alkyl-carbonylamino group",
"optionally substituted mono-($C_{1-6}$ alkyl-carbonyl)-amino group",
"optionally substituted alkoxy-carbonylamino group" and "optionally substituted alkylsulfonylamino group" in substituent group A, substituents selected from the following substituent group B can be mentioned. The number of the substituents is one to maximum substitutable number, more preferably 1-3, further preferably 1.

In addition, as respective substituents of the
"optionally substituted $C_{6-14}$ aryloxy-carbonyl group",
"optionally substituted $C_{7-16}$ aralkyloxy-carbonyl group",
"optionally substituted $C_{3-7}$ cycloalkyl-$C_{2-6}$ alkynyl group",
"optionally substituted $C_{3-7}$ cycloalkyl group",
"optionally substituted $C_{6-14}$ aryl group",
"optionally substituted $C_{7-16}$ aralkyl group",
"optionally substituted $C_{6-14}$ aryl-$C_{2-6}$ alkenyl group",
"optionally substituted heterocyclic group",
"optionally substituted $C_{3-7}$ cycloalkyloxy group",
"optionally substituted $C_{6-14}$ aryloxy group",
"optionally substituted $C_{7-16}$ aralkyloxy group",
"optionally substituted $C_{6-14}$ aryl-carbonyloxy group",
"optionally substituted mono- or di-$C_{6-14}$ aryl-carbamoyloxy group",
"optionally substituted heterocyclyl-oxy group",
"optionally substituted aromatic heterocyclyl-oxy group",
"optionally substituted $C_{3-7}$ cycloalkylsulfanyl group",
"optionally substituted $C_{6-14}$ arylsulfanyl group",
"optionally substituted $C_{7-16}$ aralkylsulfanyl group",
"optionally substituted heterocyclyl-sulfanyl group",
"optionally substituted $C_{3-7}$ cycloalkyl-carbonyl group",
"optionally substituted $C_{6-14}$ aryl-carbonyl group",
"optionally substituted $C_{7-16}$ aralkyl-carbonyl group",
"optionally substituted heterocyclyl-carbonyl group",
"optionally substituted $C_{3-7}$ cycloalkylsulfonyl group",
"optionally substituted $C_{6-14}$ arylsulfonyl group",
"optionally substituted heterocyclyl-sulfonyl group",
"optionally substituted $C_{3-7}$ cycloalkylsulfinyl group",
"optionally substituted $C_{6-14}$ arylsulfinyl group",
"optionally substituted heterocyclyl-sulfinyl group",
"optionally substituted carbamoyl group",
"optionally substituted amino group",
"optionally substituted mono- or di-$C_{3-8}$ cycloalkylamino group",
"optionally substituted mono- or di-$C_{6-14}$ arylamino group",
"optionally substituted mono- or di-$C_{7-16}$ aralkylamino group",
"optionally substituted heterocyclyl-amino group",
"optionally substituted $C_{6-14}$ aryl-carbonylamino group",
"optionally substituted $C_{3-8}$ cycloalkyl-carbonylamino group",
"optionally substituted heterocyclyl-carbonylamino group",
"optionally substituted $C_{3-8}$ cycloalkoxy-carbonylamino group",
"optionally substituted heterocyclyl-oxycarbonylamino group",
"optionally substituted carbamoylamino group",
"optionally substituted alkylsulfonylamino group",
"optionally substituted $C_{3-8}$ cycloalkylsulfonylamino group",
"optionally substituted heterocyclyl-sulfonylamino group" and
"optionally substituted $C_{6-14}$ arylsulfonylamino group" in substituent group A, for example, substituents selected from the following substituent group B and the following substituent group B' can be mentioned. The number of the substituents is one to maximum substitutable number, more preferably 1-3, further preferably 1.

[Substituent Group B]

In the present specification, substituent group B includes substituents of the following (a)-(bb).

(a) a halogen atom
(b) a hydroxy group
(c) a nitro group
(d) a cyano group
(e) an optionally substituted $C_{6-14}$ aryl group [e.g., a $C_{6-14}$ aryl group optionally substituted by one or more (e.g., 1-5) substituents selected from the group consisting of a halogen atom, hydroxy, cyano, amino, optionally halogenated $C_{1-6}$ alkyl, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like]
(f) an optionally substituted $C_{6-14}$ aryloxy group [e.g., $C_{6-14}$ aryloxy group optionally substituted by one or more (e.g., 1-5) substituents selected from the group consisting of a halogen atom, hydroxy, cyano, amino, optionally halogenated $C_{1-6}$ alkyl, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like]
(g) an optionally substituted $C_{7-16}$ aralkyloxy group [e.g., a $C_{7-16}$ aralkyloxy group optionally substituted by one or more (e.g., 1-5) substituents selected from the group consisting of a halogen atom, hydroxy, cyano, amino, optionally halogenated $C_{1-6}$ alkyl, mono- or di-$C_{1-6}$ alkylamino, mono- or di-$C_{6-14}$ arylamino, mono- or di-$C_{7-16}$ aralkylamino, $C_{3-7}$ cycloalkyl, alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like]
(h) an optionally substituted 5- to 10-membered heterocyclic group containing 1 to 4 hetero atoms selected from a nitrogen atom, a sulfur atom and an oxygen atom [e.g., a 5- to 10-membered heterocyclic group containing 1 to 4 hetero atoms selected from a nitrogen atom, a sulfur atom and an oxygen atom (e.g., pyrazolyl, pyrrolidon-1-yl, furyl, pyridyl, thienyl, pyrrolidino, 1-piperidinyl, 4-piperidyl, piperazinyl, 1-morpholinyl, 4-thiomorpholinyl, azepan-1-yl, azocan-1-yl, azonan-1-yl, 3,4-dihydroisoquinolin-2-yl) optionally substituted by one or more (e.g., 1-5) substituents selected from the group consisting of a halogen atom, hydroxy, cyano, amino, optionally halogenated $C_{1-6}$ alkyl, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like]
(i) an optionally substituted amino group [e.g., an amino group optionally substituted by 1 or 2 substituents selected from, the group consisting of $C_{1-6}$ alkyl, $C_{2-6}$ alkenyl, $C_{6-14}$ aryl, $C_{7-16}$ aralkyl, a heterocyclic group and heterocyclyl-alkyl, each being optionally substituted (examples of the substituent of the "$C_{1-6}$ alkyl, $C_{2-6}$ alkenyl, $C_{6-14}$ aryl, $C_{7-16}$ aralkyl, heterocyclic group and heterocyclyl-alkyl, each being optionally substituted" include a halogen atom, hydroxy, cyano, amino, optionally halogenated $C_{1-6}$ alkyl (excluding substituents of alkyl and alkenyl), mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{3-7}$ cycloalkyloxy-carbonyl, $C_{6-14}$ aryloxy-carbonyl, $C_{7-16}$ aralkyloxy-carbonyl, $C_{1-6}$ alkylsulfanyl, $C_{3-7}$ cycloalkylsulfanyl, $C_{1-6}$ alkylsulfinyl, $C_{3-7}$ cycloalkylsulfinyl, $C_{1-6}$ alkylsulfonyl, $C_{3-7}$ cycloalkylsulfonyl, carbamoyl, thiocarbamoyl, mono- or di-$C_{1-6}$ alkyl-carbamoyl, mono- or di-$C_{6-14}$ aryl-carbamoyl and the like. The number of the substituents is one or more (e.g., 1-5). The "heterocyclic group" and "heterocyclyl-" of "heterocyclyl-alkyl" are exemplified by those similar to the aforementioned "heterocyclic group".)
(j) $C_{3-7}$ cycloalkyl
(k) an optionally substituted $C_{1-6}$ alkoxy group [e.g., a $C_{1-6}$ alkoxy group optionally substituted by one or more (e.g., 1-5) substituents selected from the group consisting of a halogen atom, hydroxy, amino, mono- or di-$C_{1-6}$ alkylamino, mono- or di-$C_{6-14}$ arylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl, trimethylsilyl (TMS) and the like]
(l) a formyl group
(m) a $C_{1-6}$ alkyl-carbonyl group (e.g., acetyl and the like)
(n) a $C_{3-7}$ cycloalkyl-carbonyl group
(o) a $C_{6-14}$ aryl-carbonyl group
(p) a $C_{7-16}$ aralkyl-carbonyl group
(q) a $C_{1-6}$ alkoxy-carbonyl group
(r) a $C_{6-14}$ aryloxy-carbonyl group
(s) a $C_{7-16}$ aralkyloxy-carbonyl group
(t) a $C_{1-6}$ alkylsulfanyl group
(u) a $C_{1-6}$ alkylsulfinyl group
(v) a $C_{1-6}$ alkylsulfonyl group
(w) a carbamoyl group
(x) a thiocarbamoyl group
(y) a mono-$C_{1-6}$ alkyl-carbamoyl group (e.g., methylcarbamoyl, ethylcarbamoyl and the like)
(z) a di-$C_{1-6}$ alkyl-carbamoyl group (e.g., dimethylcarbamoyl, diethylcarbamoyl, ethylmethylcarbamoyl and the like)
(aa) a mono- or di-$C_{6-14}$ aryl-carbamoyl group (e.g., phenylcarbamoyl, 1-naphthylcarbamoyl, 2-naphthylcarbamoyl and the like)
(bb) a mono- or di-5- to 7-membered heterocyclyl-carbamoyl group containing 1 to 4 hetero atoms selected from a nitrogen atom, a sulfur atom and an oxygen atom (e.g., 2-pyridylcarbamoyl, 3-pyridylcarbamoyl, 4-pyridylcarbamoyl, 2-thienylcarbamoyl, 3-thienylcarbamoyl and the like)

[Substituent Group B']

In the present specification, substituent group B' comprises substituents in the following (a)-(c).
(a) an optionally substituted $C_{1-6}$ alkyl group [e.g., a $C_{1-6}$ alkyl group optionally substituted by one or more (e.g., 1-9) substituents selected from the group consisting of a halogen atom, hydroxy, cyano, amino, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkylcarbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like]

(b) an optionally substituted $C_{2-6}$ alkenyl group [e.g., a $C_{2-6}$ alkenyl group optionally substituted by one or more (e.g., 1-5) substituents selected from the group consisting of a halogen atom, hydroxy, cyano, amino, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, and mono- or di-$C_{6-14}$ aryl-carbamoyl and the like]

(c) an optionally substituted $C_{2-6}$ alkynyl group [e.g., a $C_{2-6}$ alkynyl group optionally substituted by one or more (e.g., 1-5) substituents selected from the group consisting of a halogen atom, hydroxy, cyano, amino, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like]

[Substituent Group C]

In the present specification, substituent group C includes substituents of the following (1)-(6).
(1) an oxo group
(2) an imino group
(3) an imino group optionally substituted by one substituent selected from an optionally substituted alkyl group, an optionally substituted $C_{3-7}$ cycloalkyl group, an optionally substituted $C_{6-14}$ aryl group, an optionally substituted $C_{7-16}$ aralkyl group, an optionally substituted heterocyclic group, a hydroxy group, an optionally substituted alkoxy group, an optionally substituted $C_{3-7}$ cycloalkyloxy group, an optionally substituted $C_{6-14}$ aryloxy group, an optionally substituted $C_{7-16}$ aralkyloxy group and an optionally substituted heterocyclyl-oxy group
(4) a methylidene group optionally substituted by 1 or 2 substituents selected from an optionally substituted alkyl group, an optionally substituted $C_{3-7}$ cycloalkyl group, an optionally substituted $C_{6-14}$ aryl group, an optionally substituted $C_{7-16}$ aralkyl group and an optionally substituted heterocyclic group
(5) an optionally substituted $C_{3-7}$ cycloalkylidene group
(6) a $C_{2-7}$ alkylene group optionally substituted by one or more (e.g., 1-3) substituents selected from an optionally substituted alkyl group, an optionally substituted $C_{3-7}$ cycloalkyl group, an optionally substituted $C_{6-14}$ aryl group, an optionally substituted $C_{7-16}$ aralkyl group and an optionally substituted heterocyclic group (when the $C_{2-7}$ alkylene group is present as a divalent group on one carbon atom, in other words, when the $C_{2-7}$ alkylene group substitutes two hydrogen atoms on the aforementioned carbon atom, the $C_{2-7}$ alkylene group forms $C_{3-8}$ cycloalkane together with the aforementioned carbon atom)

Examples of the "optionally substituted alkyl group", "optionally substituted $C_{3-7}$ cycloalkyl group", "optionally substituted $C_{6-14}$ aryl group", "optionally substituted $C_{7-16}$ aralkyl group", "optionally substituted heterocyclic group", "optionally substituted alkoxy group", "optionally substituted $C_{3-7}$ cycloalkyloxy group", "optionally substituted $C_{6-14}$ aryloxy group", "optionally substituted $C_{7-16}$ aralkyloxy group" and "optionally substituted heterocyclyl-oxy group", as the substituents of the substituents constituting substituent group C, include those similar to the substituents described as the substituent constituting substituent group A.

In addition, examples of the substituent of the "optionally substituted $C_{3-7}$ cycloalkylidene group" include substituents selected from the above-mentioned substituent group B and the above-mentioned substituent group B'. The number of the substituents is one-maximum substitutable number, more preferably 1-3, more preferably 1.

The definition of each symbol in the formula (I) is described in detail in the following.

$R^1$ is
(1) a $C_{1-6}$ alkyl group optionally substituted by substituent(s) selected from a halogen atom, a $C_{1-3}$ alkoxy group and a $C_{3-6}$ cycloalkyl group;
(2) a $C_{3-6}$ cycloalkyl group optionally substituted by substituent(s) selected from a halogen atom and a $C_{1-3}$ alkoxy group; or
(3) an amino group optionally substituted by a $C_{1-6}$ alkyl group optionally substituted by substituent(s) selected from a halogen atom and a $C_{1-3}$ alkoxy group (the substituents on the amino group may be bonded to each other to form a cyclic amino group).

The "$C_{1-6}$ alkyl group" for $R^1$ is preferably methyl, ethyl or isopropyl.

The "$C_{1-6}$ alkyl group" for $R^1$ may be substituted by 1-6 (preferably 1-3, more preferably 1 or 2) substituents selected from a halogen atom, a $C_{1-3}$ alkoxy group and a $C_{3-6}$ cycloalkyl group, preferably, a $C_{1-6}$ alkyl group (e.g., methyl, ethyl, isopropyl) optionally substituted by 1 to 3 (particularly 1 or 2) substituents selected from a halogen atom (e.g., a fluorine atom, a chlorine atom) and a $C_{1-3}$ alkoxy group (e.g., methoxy). When the number of the substituents is two or more, the respective substituents may be the same or different.

The "$C_{3-6}$ cycloalkyl group" for $R^1$ is preferably cyclopropyl or cyclobutyl.

The "$C_{3-6}$ cycloalkyl group" for $R^1$ may be substituted by 1-5 (preferably 1-3, more preferably 1-2) substituents selected from a halogen atom and a $C_{1-3}$ alkoxy group, and is preferably an unsubstituted $C_{3-6}$ cycloalkyl group (e.g., cyclopropyl). When the number of the substituents is two or more, the respective substituents may be the same or different.

The "amino group" for $R^1$ may be mono- or di-substituted by a $C_{1-6}$ alkyl group optionally substituted by 1-6 (preferably 1-3, more preferably 1-2) substituents selected from a halogen atom and a $C_{1-3}$ alkoxy group (when the number of the substituents is two or more, the respective substituents may be the same or different), and is preferably an amino group optionally mono- or -di-substituted by a $C_{1-6}$ alkyl group (e.g., methyl, ethyl, propyl). When the amino group is di-substituted by $C_{1-6}$ alkyl groups, the $C_{1-6}$ alkyl groups may be the same or different.

Alternatively, the "amino group" for $R^1$ may be a cyclic amino group (e.g., azetidinyl, pyrrolidinyl, piperidinyl, piperazinyl, morpholinyl, thiomorpholinyl, pyrazolidinyl, imidazolidinyl, oxazolidinyl, thiazolidinyl, isoxazolidinyl, isothiazolidinyl, oxadiazolidinyl, thiadiazolidinyl, 7-azabicyclo[2.2.1]heptyl, 8-azabicyclo[3.2.1]octyl etc.) wherein the substituents on the amino group (that is, $C_{1-6}$ alkyl groups) are bonded.

$R^1$ is preferably
(1) a $C_{1-6}$ alkyl group (e.g., methyl, ethyl, isopropyl) optionally substituted by 1-6 (particularly, 1-3) substituents selected from a halogen atom (e.g., a fluorine atom) and a $C_{1-3}$ alkoxy group (e.g., methoxy);
(2) a $C_{3-6}$ cycloalkyl group (e.g., cyclopropyl, cyclobutyl); or
(3) an amino group optionally mono- or di-substituted by a $C_{1-6}$ alkyl group (e.g., methyl, ethyl, propyl), more preferably
(1) methyl, ethyl, isopropyl, chloromethyl, trifluoromethyl, trifluoroethyl, methoxyethyl;
(2) cyclopropyl; or
(3) methylamino, ethylamino, propylamino, dimethylamino.

$R^2$ and $R^3$ are the same or different and each is a hydrogen atom or a $C_{1-6}$ alkyl group.

$R^2$ and $R^3$ are each preferably a hydrogen atom.

X is —O— or —S—.

As X, —O— is preferable.

Ring A is
(1) a 3- to 8-membered monocyclic nonaromatic ring optionally substituted by substituent(s) selected from a halogen atom, a $C_{1-6}$ alkyl group optionally substituted by substituent(s) selected from a halogen atom and a phenyl group, an acyl group, an oxo group and a hydroxyl group; or
(2) a bicyclic 7- or 8-membered saturated ring optionally substituted by substituent(s) selected from a halogen atom, a $C_{1-6}$ alkyl group optionally substituted by a halogen atom, an acyl group, an oxo group and a hydroxyl group.

Preferred as ring A is (1) a 3- to 8-membered monocyclic nonaromatic ring optionally substituted by substituent(s) selected from a halogen atom, a $C_{1-6}$ alkyl group optionally substituted by substituent(s) selected from a halogen atom and a phenyl group, an acyl group, an oxo group and a hydroxyl group.

Examples of the "3- to 8-membered monocyclic nonaromatic ring" for ring A include "3- to 8-membered monocyclic nonaromatic hydrocarbon ring" and "3- to 8-membered monocyclic non-aromatic heterocycle". As the "3- to 8-membered monocyclic nonaromatic hydrocarbon ring", $C_{3-8}$ cycloalkane is preferable, and $C_{3-6}$ cycloalkane (e.g., cyclopropane, cyclobutane, cyclopentane and cyclohexane) is more preferable. As the "3- to 8-membered monocyclic non-aromatic heterocycle", an azetidine ring, an oxetane ring, a thietane ring, a pyrrolidine ring, a dihydrofuran ring, a tetrahydrofuran ring, a tetrahydrothiophene ring, an imidazolidine ring, an oxazolidine ring, an isooxazoline ring, a piperidine ring, a dihydropyran ring, a tetrahydropyran ring, a tetrahydrothiopyran ring, a morpholine ring, a thiomorpholine ring, a piperazine ring, a dihydrooxazine ring, a tetrahydrooxazine ring, a dihydropyrimidine ring, a tetrahydropyrimidine ring, an azepane ring, an oxepane ring, a thiepane ring, an oxazepane ring, a thiazepane ring, an azocane ring, an oxocane ring, a thiocane ring, an oxazocane ring and a thiazocane ring are preferable, and a tetrahydrofuran ring, a tetrahydropyran ring and a piperidine ring are more preferable.

The "3- to 8-membered monocyclic nonaromatic ring" for ring A may be substituted by 1-5 (preferably 1-3, more preferably 1-2) substituents selected from a halogen atom (e.g., a fluorine atom), a $C_{1-6}$ alkyl group (e.g., methyl, ethyl) optionally substituted by 1-6 (preferably 1-3, more preferably 1-2) substituents selected from a halogen atom and a phenyl group, an acyl group (e.g., alkylcarbonyl, alkoxycarbonyl, alkylcarbamoyl, alkylsulfonyl), an oxo group and a hydroxyl group, and is preferably a 3- to 8-membered monocyclic nonaromatic hydrocarbon ring (particularly, cyclopropane, cyclobutane, cyclopentane and cyclohexane) optionally substituted by 1-3 (particularly, 1 or 2) substituents selected from a halogen atom (e.g., a fluorine atom), an oxo group and a hydroxyl group or a 3- to 8-membered monocyclic non-aromatic heterocycle (particularly, a tetrahydrofuran ring, a tetrahydropyran ring and a piperidine ring) optionally substituted by 1-3 (particularly, 1 or 2) substituents selected from a $C_{1-6}$ alkyl group (e.g., methyl, ethyl) optionally substituted by a phenyl group, alkylcarbonyl (e.g., methylcarbonyl), alkoxycarbonyl (e.g., methoxycarbonyl), alkylcarbamoyl (e.g., ethylcarbamoyl), alkylsulfonyl (e.g., methylsulfonyl) and an oxo group. When the number of the substituents is two or more, the respective substituents may be the same or different.

As the "3- to 8-membered monocyclic nonaromatic ring optionally substituted by substituent(s) selected from a halogen atom, a $C_{1-6}$ alkyl group optionally substituted by substituent(s) selected from a halogen atom and a phenyl group, an acyl group, an oxo group and a hydroxyl group" for ring A, the following rings are particularly preferable.

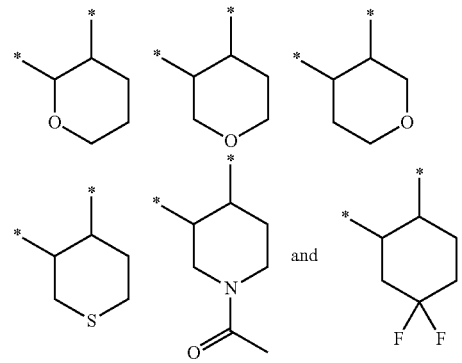

Preferred as the "bicyclic 7- or 8-membered saturated ring" for ring A are the following rings.

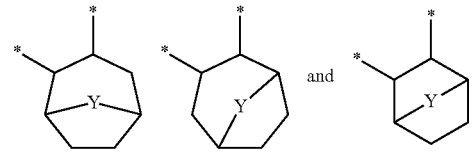

wherein Y is —CH$_2$—, —NH— or —O—.

The "bicyclic 7- or 8-membered saturated ring" for ring A may be substituted by 1-5 (preferably 1-3, more preferably 1-2) substituents selected from a halogen atom (e.g., a fluorine atom, a chlorine atom), a $C_{1-6}$ alkyl group (e.g., methyl, ethyl, isopropyl) optionally substituted by a halogen atom (e.g., a fluorine atom, a chlorine atom), an acyl group (e.g., formyl, acetyl, propionyl), an oxo group and a hydroxyl group, and is preferably the above-mentioned three rings (particularly, a bicyclo[2.2.1]heptane ring, a 7-oxabicyclo[2.2.1]heptane ring, a 7-azabicyclo[2.2.1]heptane ring, a bicyclo[3.2.1]octane ring, a 8-oxabicyclo[3.2.1]octane ring, a 8-azabicyclo[3.2.1]octane ring) optionally substituted by 1-3 (particularly, 1 or 2) substituents selected from a halogen atom and an optionally substituted $C_{1-6}$ alkyl group. When the number of the substituents is two or more, the respective substituents may be the same or different.

As the stereo chemistry (relative configuration) of the substituents on ring A,

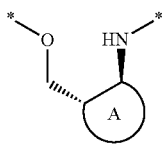

is preferable.

Ring B is an optionally substituted 3- to 10-membered ring.

Examples of the "3- to 10-membered ring" of the "optionally substituted 3- to 10-membered ring" for ring B include "$C_{3-8}$ cycloalkane", a 6- to 10-membered "aromatic hydrocarbon ring", 3- to 10-membered "non-aromatic heterocycle", 5- to 10-membered "aromatic heterocycle", 6- to 10-membered "fused non-aromatic heterocycle" and 8- to 10-membered "fused aromatic heterocycle". Preferred as the "$C_{3-8}$ cycloalkane" are cyclopropane, cyclobutane, cyclopentane, cyclohexane, cycloheptane and cyclooctane, and $C_{3-6}$ cycloalkane (e.g., cyclopropane, cyclobutane, cyclopentane and cyclohexane) is more preferable. As the "aromatic hydrocarbon ring", a benzene ring, a dihydroindene ring and a naphthalene ring are preferable. As the "non-aromatic heterocycle", a piperazine ring, a piperidine ring and a pyrrolidine ring are preferable. As the "aromatic heterocycle", a pyridine ring and a pyrazole ring are preferable. As the "fused non-aromatic heterocycle", a chromene ring is preferable. As the "fused aromatic heterocycle", an indole ring, a benzothiazole ring and a benzoimidazole ring are preferable.

As ring B, a benzene ring or a pyridine ring is more preferable, and a benzene ring is particularly preferable.

The "3- to 10-membered ring" may have 1-5 (preferably 1-3, more preferably 1 or 2) substituents at substitutable position(s).

Examples of such substituent include
(1) a halogen atom (e.g., a fluorine atom, a chlorine atom);
(2) a cyano group;
(3) an optionally substituted $C_{1-6}$ alkyl group (e.g., methyl, ethyl, isopropyl, tert-butyl); preferably, a $C_{1-6}$ alkyl group (e.g., methyl, ethyl, isopropyl, tert-butyl) optionally substituted by 1 to 6 substituents selected from a halogen atom (e.g., a fluorine atom), a cyano group, an acyl group [e.g., formyl, alkyl-carbonyl optionally having substituent(s), alkenyl-carbonyl optionally having substituent(s), alkynyl-carbonyl optionally having substituent(s), cycloalkyl-carbonyl optionally having substituent(s), cycloalkenyl-carbonyl optionally having substituent(s), aryl-carbonyl optionally having substituent(s), heterocyclyl-carbonyl optionally having substituent(s), carboxyl, alkoxy-carbonyl optionally having substituent(s), alkenyloxy-carbonyl optionally having substituent(s), alkynyloxy-carbonyl optionally having substituent(s), cycloalkyloxy-carbonyl optionally having substituent(s), cycloalkenyloxy-carbonyl optionally having substituent(s), cycloalkynyloxy-carbonyl optionally having substituent(s), aryloxy-carbonyl optionally having substituent(s), heterocyclyl-oxy-carbonyl optionally having substituent(s), carbamoyl optionally having substituent(s), alkyl-sulfonyl optionally having substituent(s), cycloalkyl-sulfonyl optionally having substituent(s), aryl-sulfonyl optionally having substituent(s), heterocyclyl-sulfonyl optionally having substituent(s), alkyl-sulfinyl optionally having substituent(s), cycloalkyl-sulfinyl optionally having substituent(s), aryl-sulfinyl optionally having substituent(s), heterocyclyl-sulfinyl optionally having substituent(s)], an optionally substituted hydroxy group, an optionally substituted an amino group and an optionally substituted cyclic group;
(4) an optionally substituted hydroxyl group; preferably, a hydroxyl group optionally substituted by an optionally substituted $C_{1-6}$ alkyl group (e.g., methyl) or an optionally substituted phenyl group;
(5) an optionally substituted amino group; preferably, an amino group optionally substituted by 1 or 2 substituents selected from an optionally substituted $C_{1-6}$ alkyl group (e.g., methyl), an acyl group [e.g., formyl, alkyl-carbonyl (e.g., methylcarbonyl) optionally having substituent(s), alkenyl-carbonyl optionally having substituent(s), alkynyl-carbonyl optionally having substituent(s), cycloalkyl-carbonyl optionally having substituent(s), cycloalkenyl-carbonyl optionally having substituent(s), aryl-carbonyl optionally having substituent(s), heterocyclyl-carbonyl optionally having substituent(s), carboxyl, alkoxy-carbonyl optionally having substituent(s), alkenyloxy-carbonyl optionally having substituent(s), alkynyloxy-carbonyl optionally having substituent(s), cycloalkyloxy-carbonyl optionally having substituent(s), cycloalkenyloxy-carbonyl optionally having substituent(s), cycloalkynyloxy-carbonyl optionally having substituent(s), aryloxy-carbonyl optionally having substituent(s), heterocyclyl-oxy-carbonyl optionally having substituent(s), carbamoyl optionally having substituent(s), alkyl-sulfonyl optionally having substituent(s), cycloalkyl-sulfonyl optionally having substituent(s), aryl-sulfonyl optionally having substituent(s), heterocyclyl-sulfonyl optionally having substituent(s), alkyl-sulfinyl optionally having substituent(s), cycloalkyl-sulfinyl optionally having substituent(s), aryl-sulfinyl optionally having substituent(s), heterocyclyl-sulfinyl optionally having substituent(s)] and an optionally substituted phenyl group;
(6) an optionally substituted 3- to 10-membered hydrocarbon ring group (e.g., a $C_{3-6}$ cycloalkyl group, a nonaromatic cyclic hydrocarbon group, an aromatic cyclic hydrocarbon group); preferably, a 3- to 10-membered hydrocarbon ring group optionally substituted by 1 to 4 substituents selected from a halogen atom, a cyano group, an optionally substituted $C_{1-6}$ alkyl group, an acyl group [e.g., formyl, alkyl-carbonyl optionally having substituent(s), alkenyl-carbonyl optionally having substituent(s), alkynyl-carbonyl optionally having substituent(s), cycloalkyl-carbonyl optionally having substituent(s), cycloalkenyl-carbonyl optionally having substituent(s), aryl-carbonyl optionally having substituent(s), heterocyclyl-carbonyl optionally having substituent(s), carboxyl, alkoxy-carbonyl optionally having substituent(s), alkenyloxy-carbonyl optionally having substituent(s), alkynyloxy-carbonyl optionally having substituent(s), cycloalkyloxy-carbonyl optionally having substituent(s), cycloalkenyloxy-carbonyl optionally having substituent(s), cycloalkynyloxy-carbonyl optionally having substituent(s), aryloxy-carbonyl optionally having substituent(s), heterocyclyl-oxy-carbonyl optionally having substituent(s), carbamoyl optionally having substituent(s), alkyl-sulfonyl optionally having substituent(s), cycloalkyl-sulfonyl optionally having substituent(s), aryl-sulfonyl optionally having substituent(s), heterocyclyl-sulfonyl optionally having substituent(s), alkyl-sulfinyl optionally having substituent(s), cycloalkyl-sulfinyl optionally having substituent(s), aryl-sulfinyl optionally having substituent(s), heterocyclyl-sulfinyl optionally having substituent(s)], an optionally substituted hydroxyl group, an optionally substituted amino group and an optionally substituted cyclic group;

(7) an optionally substituted 4- to 10-membered heterocyclic group (e.g., a nonaromatic heterocyclic group, an aromatic heterocyclic group); preferably, a 4- to 10-membered heterocyclic group optionally substituted by 1 to 4 substituents selected from a halogen atom (e.g., a fluorine atom, a chlorine atom), a cyano group, an optionally substituted $C_{1-6}$ alkyl group (e.g., methyl, ethyl, isopropyl), an acyl group [e.g., formyl, alkyl-carbonyl optionally having substituent(s), alkenyl-carbonyl optionally having substituent(s), alkynyl-carbonyl optionally having substituent(s), cycloalkyl-carbonyl optionally having substituent(s), cycloalkenyl-carbonyl optionally having substituent(s), aryl-carbonyl optionally having substituent(s), heterocyclyl-carbonyl optionally having substituent(s), carboxyl, alkoxy-carbonyl optionally having substituent(s), alkenyloxy-carbonyl optionally having substituent(s), alkynyloxy-carbonyl optionally having substituent(s), cycloalkyloxy-carbonyl optionally having substituent(s), cycloalkenyloxy-carbonyl optionally having substituent(s), cycloalkynyloxy-carbonyl optionally having substituent(s), aryloxy-carbonyl optionally having substituent(s), heterocyclyl-oxy-carbonyl optionally having substituent(s), carbamoyl optionally having substituent(s), alkyl-sulfonyl optionally having substituent(s), cycloalkyl-sulfonyl optionally having substituent(s), aryl-sulfonyl optionally having substituent(s), heterocyclyl-sulfonyl optionally having substituent(s), alkyl-sulfinyl optionally having substituent(s), cycloalkyl-sulfinyl optionally having substituent(s), aryl-sulfinyl optionally having substituent(s), heterocyclyl-sulfinyl optionally having substituent(s)], an optionally substituted hydroxyl group [e.g., a hydroxyl group optionally substituted by an optionally substituted $C_{1-6}$ alkyl is group (e.g., methyl)], an optionally substituted amino group, an optionally substituted cyclic group and an oxo group;

(8) an optionally substituted sulfanyl group; preferably, a sulfanyl group optionally substituted by a $C_{1-6}$ alkyl group (e.g., methyl) substituted by a halogen atom (e.g., a fluorine atom);

(9) an acyl group [e.g., formyl, alkyl-carbonyl (e.g., methylcarbonyl) optionally having substituent(s), alkenyl-carbonyl optionally having substituent(s), alkynyl-carbonyl optionally having substituent(s), cycloalkyl-carbonyl optionally having substituent(s), cycloalkenyl-carbonyl optionally having substituent(s), aryl-carbonyl optionally having substituent(s), heterocyclyl-carbonyl (e.g., piperidinocarbonyl) optionally having substituent(s), carboxyl, alkoxy-carbonyl (e.g., ethoxycarbonyl) optionally having substituent(s), alkenyloxy-carbonyl optionally having substituent(s), alkynyloxy-carbonyl optionally having substituent(s), cycloalkyloxy-carbonyl optionally having substituent(s), cycloalkenyloxy-carbonyl optionally having substituent(s), cycloalkynyloxy-carbonyl optionally having substituent(s), aryloxy-carbonyl optionally having substituent(s), heterocyclyl-oxy-carbonyl optionally having substituent(s), carbamoyl optionally having substituent(s), alkyl-sulfonyl optionally having substituent(s), cycloalkyl-sulfonyl optionally having substituent(s), aryl-sulfonyl optionally having substituent(s), heterocyclyl-sulfonyl optionally having substituent(s), alkyl-sulfinyl optionally having substituent(s), cycloalkyl-sulfinyl optionally having substituent(s), aryl-sulfinyl optionally having substituent(s), heterocyclyl-sulfinyl optionally having substituent(s)];

(10) an oxo group;
and the like. When the number of the substituents is two or more, the respective substituents may be the same or different.

Preferred as the substituent of the "3- to 10-membered ring" are
(1) a halogen atom (e.g., a fluorine atom, a chlorine atom);
(2) a cyano group;
(3) a $C_{1-6}$ alkyl group (e.g., methyl, ethyl, isopropyl, tert-butyl) optionally substituted by 1-6 (preferably 1-3) substituents selected from a halogen atom (e.g., a fluorine atom), a cyano group, an acyl group [e.g., formyl, $C_{1-6}$ alkyl-carbonyl optionally substituted by 1-6 (preferably 1-3) halogen atoms, carboxyl, $C_{1-6}$ alkoxy-carbonyl optionally substituted by 1-6 (preferably 1-3) halogen atoms, carbamoyl optionally mono- or di-substituted by a $C_{1-6}$ alkyl group optionally substituted by 1-6 (preferably 1-3) halogen atoms, $C_{1-6}$ alkyl-sulfonyl optionally substituted by 1-6 (preferably 1-3) halogen atoms, $C_{1-6}$ alkyl-sulfinyl optionally substituted by 1-6 (preferably 1-3) halogen atoms], an optionally substituted hydroxyl group, an optionally substituted amino group and an optionally substituted cyclic group;
(4) a hydroxyl group optionally substituted by an optionally substituted $C_{1-6}$ alkyl group (e.g., methyl) or an optionally substituted phenyl group;
(5) an amino group optionally substituted by 1 or 2 substituents selected from an optionally substituted $C_{1-6}$ alkyl group (e.g., methyl), an acyl group [e.g., formyl, $C_{1-6}$ alkyl-carbonyl optionally substituted by 1-6 (preferably 1-3) halogen atoms, carboxyl, $C_{1-6}$ alkoxy-carbonyl optionally substituted by 1-6 (preferably 1-3) halogen atoms, carbamoyl optionally mono- or di-substituted by a $C_{1-6}$ alkyl group optionally substituted by 1-6 (preferably 1-3) halogen atoms, $C_{1-6}$ alkyl-sulfonyl optionally substituted by 1-6 (preferably 1-3) halogen atoms, $C_{1-6}$ alkyl-sulfinyl optionally substituted by 1-6 (preferably 1-3) halogen atoms] and an optionally substituted phenyl group;
(6) a $C_{3-6}$ cycloalkyl group (e.g., cyclopropyl), a nonaromatic cyclic hydrocarbon group (e.g., tricyclo[3.3.1.1.3.7]decyl) or an aromatic cyclic hydrocarbon group (e.g., phenyl), each of which may be substituted by 1-6 (preferably 1-3) substituents selected from a halogen atom (e.g., a fluorine atom), a cyano group, an optionally substituted $C_{1-6}$ alkyl group, an acyl group [e.g., formyl, $C_{1-6}$ alkyl-carbonyl optionally substituted by 1-6 (preferably 1-3) halogen atoms, carboxyl, $C_{1-6}$ alkoxy-carbonyl optionally substituted by 1-6 (preferably 1-3) halogen atoms, carbamoyl optionally mono- or di-substituted by a $C_{1-6}$ alkyl group optionally substituted by 1-6 (preferably 1-3) halogen atoms, $C_{1-6}$ alkyl-sulfonyl optionally substituted by 1-6 (preferably 1-3) halogen atoms, $C_{1-6}$ alkyl-sulfinyl optionally substituted by 1-6 (preferably 1-3) halogen atoms], an optionally substituted hydroxyl group, an optionally substituted amino group and an optionally substituted cyclic group;
(7) a nonaromatic heterocyclic group (e.g., oxetanyl, morpholinyl, pyrrolidinyl, piperidinyl, tetrahydropyranyl, dihydropyridyl, tetrahydropyridazinyl) or an aromatic heterocyclic group (e.g., pyrazolyl, imidazolyl, oxazolyl, isoxazolyl, thiazolyl, thienyl, pyridyl, pyrimidinyl), each of which may be substituted by 1-6 (preferably 1-3) substituents selected from a halogen atom (e.g., a fluorine atom, a chlorine atom), a cyano group, an optionally substituted $C_{1-6}$ alkyl group (e.g., methyl, ethyl, isopropyl), an acyl group [e.g., formyl, $C_{1-6}$ alkyl-carbonyl optionally substituted by 1-6 (preferably 1-3) halogen atoms, carboxyl, $C_{1-6}$ alkoxy-carbonyl optionally substituted by 1-6 (preferably 1-3) halogen atoms, carbamoyl optionally mono- or di-substituted by a $C_{1-6}$ alkyl group optionally substituted by 1-6 (preferably 1-3) halogen atoms, C$_{1-6}$ alkyl-sulfonyl optionally substituted by 1-6 (preferably 1-3) halogen atoms, C$_{1-6}$ alkyl-sulfinyl optionally substituted by 1-6 (preferably 1-3) halogen atoms], an optionally substituted hydroxyl group [e.g., a hydroxyl group optionally substituted by a C$_{1-6}$ alkyl group (e.g., methyl) optionally substituted by 1-6 (preferably 1-3) halogen atoms (e.g., fluorine atoms)], an optionally substituted amino group, an optionally substituted cyclic group and an oxo group;
(8) a sulfanyl group optionally substituted by a C$_{1-6}$ alkyl group (e.g., methyl) substituted by 1-6 (preferably 1-3) halogen atoms (e.g., fluorine atoms);
(9) an acyl group [e.g., formyl, C$_{1-6}$ alkyl-carbonyl (e.g., methylcarbonyl) optionally substituted by 1-6 (preferably 1-3) halogen atoms (e.g., fluorine atoms), carboxyl, heterocyclyl-carbonyl (e.g., piperidinocarbonyl), C$_{1-6}$ alkoxy-carbonyl (e.g., ethoxycarbonyl) optionally substituted by 1-6 (preferably 1-3) halogen atoms, carbamoyl optionally mono- or di-substituted by a C$_{1-6}$ alkyl group (e.g., ethyl) optionally substituted by 1-6 (preferably 1-3) halogen atoms, C$_{1-6}$ alkyl-sulfonyl optionally substituted by 1-6 (preferably 1-3) halogen atoms, C$_{1-6}$ alkyl-sulfinyl optionally substituted by 1-6 (preferably 1-3) halogen atoms]; and
(10) an oxo group.

As ring B, an aromatic hydrocarbon ring (e.g., benzene ring, dihydroindene ring, naphthalene ring), aromatic heterocycle (e.g., pyridine ring), fused non-aromatic heterocycle (e.g., chromene ring) or fused aromatic heterocycle (e.g., indole ring, benzothiazole ring), each of which optionally has 1-5 (preferably 1-3, more preferably 1 or 2) substituents selected from
(1) a halogen atom (e.g., fluorine atom, chlorine atom);
(2) a cyano group;
(3) a C$_{1-6}$ alkyl group (e.g., methyl, ethyl, isopropyl, tert-butyl) optionally substituted by 1-6 (preferably 1-3) substituents selected from (i) a halogen atom (e.g., fluorine atom), (ii) a cyano group and (iii) a cyclic group (e.g., pyrazolyl) optionally substituted by 1-6 (preferably 1-3) halogen atoms (e.g., chlorine atom);
(4) a hydroxyl group optionally substituted by a C$_{1-6}$ alkyl group (e.g., methyl) optionally substituted by 1-6 (preferably 1-3) halogen atoms (e.g., fluorine atom) or a phenyl group;
(5) an amino group optionally substituted by 1 or 2 substituents selected from a C$_{1-6}$ alkyl group (e.g., methyl), alkyl-carbonyl (e.g., methylcarbonyl) and a phenyl group;
(6) a C$_{3-6}$ cycloalkyl group (e.g., cyclopropyl), a nonaromatic cyclic hydrocarbon group (e.g., tricyclo[3.3.1.1.3.7] decyl) or an aromatic cyclic hydrocarbon group (e.g., phenyl), each of which is optionally substituted by 1-6 (preferably 1-3) substituents selected from a halogen atom (e.g., fluorine atom) and a cyano group;
(7) a nonaromatic heterocyclic group (e.g., oxetanyl, morpholinyl, pyrrolidinyl, piperidinyl, tetrahydropyranyl, dihydropyridyl, tetrahydropyridazinyl) or an aromatic heterocyclic group (e.g., pyrazolyl, imidazolyl, oxazolyl, isoxazolyl, thiazolyl, thienyl, pyridyl, pyrimidinyl), each of which is optionally substituted by 1-6 (preferably 1-3) substituents selected from
(i) a halogen atom (e.g., fluorine atom, chlorine atom), (ii) a cyano group, (iii) a C$_{1-6}$ alkyl group (e.g., methyl, ethyl, isopropyl) optionally substituted by 1-6 (preferably 1-3) halogen atoms (e.g., fluorine atom), (iv) a C$_{1-3}$ alkoxy group (e.g., methoxy) optionally substituted by 1-6 (preferably 1-3) halogen atoms (e.g., fluorine atom), and (v) an oxo group;
(8) a sulfanyl group optionally substituted by a C$_{1-6}$ alkyl group (e.g., methyl) substituted by 1-6 (preferably 1-3) halogen atoms (e.g., fluorine atom);
(9) a C$_{1-6}$ alkyl-carbonyl (e.g., methylcarbonyl) optionally substituted by 1-6 (preferably 1-3) halogen atoms (e.g., fluorine atom);
(10) C$_{1-6}$ alkoxy-carbonyl (e.g., ethoxycarbonyl);
(11) di-C$_{1-6}$ alkyl-carbamoyl (e.g., diethylcarbamoyl);
(12) heterocyclyl-carbonyl (e.g., piperidinocarbonyl); and
(13) an oxo group;
is preferable.

Preferable examples of the substituents, moieties, rings and the like explained in the present specification are more preferably used in combination.

As a compound represented by the formula (I), a compound wherein
R$^1$ is
(1) a C$_{1-6}$ alkyl group (e.g., methyl, ethyl, isopropyl) optionally substituted by 1-6 (particularly, 1-3) substituents selected from a halogen atom (e.g., fluorine atom) and a C$_{1-3}$ alkoxy group (e.g., methoxy);
(2) a C$_{3-6}$ cycloalkyl group (e.g., cyclopropyl, cyclobutyl); or
(3) an amino group optionally substituted by 1 or 2 C$_{1-6}$ alkyl groups (e.g., methyl, ethyl, propyl);
R$^2$ and R$^3$ are both hydrogen atoms;
X is —O— or —S— (particularly, —O—);
ring A is
(1) a 3- to 8-membered monocyclic nonaromatic hydrocarbon ring (particularly, cyclopropane, cyclobutane, cyclopentane or cyclohexane) optionally substituted by 1-3 (particularly, 1-2) substituents selected from a halogen atom (e.g., fluorine atom), an oxo group and a hydroxyl group, (2) 3- to 8-membered monocyclic non-aromatic heterocycle (particularly, tetrahydrofuran ring, tetrahydropyran ring or piperidine ring) optionally substituted by 1-3 (particularly, 1-2) substituents selected from a C$_{1-6}$ alkyl group (e.g., methyl, ethyl) optionally substituted by a phenyl group, alkylcarbonyl (e.g., methylcarbonyl), alkoxycarbonyl (e.g., methoxycarbonyl), alkylcarbamoyl (e.g., ethylcarbamoyl), alkylsulfonyl (e.g., methylsulfonyl) and an oxo group, or (3) a bicyclic 7-8-membered saturated ring represented by the following formula

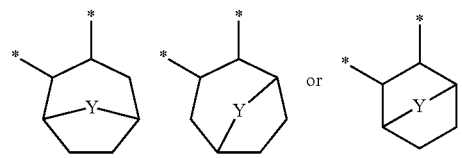

wherein Y is —CH$_2$—, —NH— or —O—, which is selected from a bicyclo[2.2.1]heptane ring, a 7-oxabicyclo[2.2.1]heptane ring, a 7-azabicyclo[2.2.1]heptane ring, a bicyclo[3.2.1]octane ring, a 8-oxabicyclo[3.2.1]octane ring and a 8-azabicyclo[3.2.1]octane ring, each of which is optionally substituted by 1-3 (particularly, 1-2) substituents; and
ring B is C$_{3-8}$ cycloalkane, a 6- to 10-membered aromatic hydrocarbon ring, 3- to 10-membered non-aromatic heterocycle, 5- to 10-membered aromatic heterocycle, 6- to 10-membered fused non-aromatic heterocycle or 8- to 10-membered fused aromatic heterocycle, each of which optionally has 1-5 (preferably 1-3, more preferably 1 or 2) substituents selected from (1) a halogen atom (e.g., fluorine atom, chlorine atom);
(2) a cyano group;
(3) optionally substituted $C_{1-6}$ alkyl group (e.g., methyl, ethyl, isopropyl, tert-butyl); preferably, a $C_{1-6}$ alkyl group (e.g., methyl, ethyl, isopropyl, tert-butyl) optionally substituted 1-6 substituents selected from a halogen atom (e.g., fluorine atom), a cyano group, an acyl group [e.g., formyl, alkyl-carbonyl optionally having substituent(s), alkenyl-carbonyl optionally having substituent(s), alkynyl-carbonyl optionally having substituent(s), cycloalkyl-carbonyl optionally having substituent(s), cycloalkenyl-carbonyl optionally having substituent(s), aryl-carbonyl optionally having substituent(s), heterocyclyl-carbonyl optionally having substituent(s), carboxyl, alkoxy-carbonyl optionally having substituent(s), alkenyloxy-carbonyl optionally having substituent(s), alkynyloxy-carbonyl optionally having substituent(s), cycloalkyloxy-carbonyl optionally having substituent(s), cycloalkenyloxy-carbonyl optionally having substituent(s), cycloalkynyloxy-carbonyl optionally having substituent(s), aryloxy-carbonyl optionally having substituent(s), heterocyclyl-oxy-carbonyl optionally having substituent(s), carbamoyl optionally having substituent(s), alkyl-sulfonyl optionally having substituent(s), cycloalkyl-sulfonyl optionally having substituent(s), aryl-sulfonyl optionally having substituent(s), heterocyclyl-sulfonyl optionally having substituent(s), alkyl-sulfinyl optionally having substituent(s), cycloalkyl-sulfinyl optionally having substituent(s), aryl-sulfinyl optionally having substituent(s), heterocyclyl-sulfinyl optionally having substituent(s)], an optionally substituted hydroxyl group, an optionally substituted amino group and an optionally substituted cyclic group;
(4) an optionally substituted hydroxyl group; preferably, hydroxyl group optionally substituted by an optionally substituted $C_{1-6}$ alkyl group (e.g., methyl) or an optionally substituted phenyl group;
(5) an optionally substituted amino group; preferably, an amino group optionally substituted by 1 or 2 substituents selected from an optionally substituted $C_{1-6}$ alkyl group (e.g., methyl), an acyl group [e.g., formyl, alkyl-carbonyl (e.g., methylcarbonyl) optionally having substituent(s), alkenyl-carbonyl optionally having substituent(s), alkynyl-carbonyl optionally having substituent(s), cycloalkyl-carbonyl optionally having substituent(s), cycloalkenyl-carbonyl optionally having substituent(s), aryl-carbonyl optionally having substituent(s), heterocyclyl-carbonyl optionally having substituent(s), carboxyl, alkoxy-carbonyl optionally having substituent(s), alkenyloxy-carbonyl optionally having substituent(s), alkynyloxy-carbonyl optionally having substituent(s), cycloalkyloxy-carbonyl optionally having substituent(s), cycloalkenyloxy-carbonyl optionally having substituent(s), cycloalkynyloxy-carbonyl optionally having substituent(s), aryloxy-carbonyl optionally having substituent(s), heterocyclyl-oxy-carbonyl optionally having substituent(s), carbamoyl optionally having substituent(s), alkyl-sulfonyl optionally having substituent(s), cycloalkyl-sulfonyl optionally having substituent(s), aryl-sulfonyl optionally having substituent(s), heterocyclyl-sulfonyl optionally having substituent(s), alkyl-sulfinyl optionally having substituent(s), cycloalkyl-sulfinyl optionally having substituent(s), aryl-sulfinyl optionally having substituent(s), heterocyclyl-sulfinyl optionally having substituent(s)] and an optionally substituted phenyl group;
(6) an optionally substituted 3- to 10-membered hydrocarbon ring group (e.g., $C_{3-6}$ cycloalkyl group, nonaromatic cyclic hydrocarbon group, aromatic cyclic hydrocarbon group); preferably, a 3- to 10-membered hydrocarbon ring group optionally substituted by 1-4 substituents selected from a halogen atom, a cyano group, an optionally substituted $C_{1-6}$ alkyl group, an acyl group [e.g., formyl, alkyl-carbonyl optionally having substituent(s), alkenyl-carbonyl optionally having substituent(s), alkynyl-carbonyl optionally having substituent(s), cycloalkyl-carbonyl optionally having substituent(s), cycloalkenyl-carbonyl optionally having substituent(s), aryl-carbonyl optionally having substituent(s), heterocyclyl-carbonyl optionally having substituent(s), carboxyl, alkoxy-carbonyl optionally having substituent(s), alkenyloxy-carbonyl optionally having substituent(s), alkynyloxy-carbonyl optionally having substituent(s), cycloalkyloxy-carbonyl optionally having substituent(s), cycloalkenyloxy-carbonyl optionally having substituent(s), cycloalkynyloxy-carbonyl optionally having substituent(s), aryloxy-carbonyl optionally having substituent(s), heterocyclyl-oxy-carbonyl optionally having substituent(s), carbamoyl optionally having substituent(s), alkyl-sulfonyl optionally having substituent(s), cycloalkyl-sulfonyl optionally having substituent(s), aryl-sulfonyl optionally having substituent(s), heterocyclyl-sulfonyl optionally having substituent(s), alkyl-sulfinyl optionally having substituent(s), cycloalkyl-sulfinyl optionally having substituent(s), aryl-sulfinyl optionally having substituent(s), heterocyclyl-sulfinyl optionally having substituent(s)], an optionally substituted hydroxyl group, an optionally substituted amino group and an optionally substituted cyclic group;
(7) an optionally substituted 4- to 10-membered heterocyclic group (e.g., nonaromatic heterocyclic group, aromatic heterocyclic group); preferably, a 4- to 10-membered heterocyclic group optionally substituted by 1-4 substituents selected from a halogen atom (e.g., fluorine atom, chlorine atom), a cyano group, an optionally substituted $C_{1-6}$ alkyl group (e.g., methyl, ethyl, isopropyl), an acyl group [e.g., formyl, alkyl-carbonyl optionally having substituent(s), alkenyl-carbonyl optionally having substituent(s), alkynyl-carbonyl optionally having substituent(s), cycloalkyl-carbonyl optionally having substituent(s), cycloalkenyl-carbonyl optionally having substituent(s), aryl-carbonyl optionally having substituent(s), heterocyclyl-carbonyl optionally having substituent(s), carboxyl, alkoxy-carbonyl optionally having substituent(s), alkenyloxy-carbonyl optionally having substituent(s), alkynyloxy-carbonyl optionally having substituent(s), cycloalkyloxy-carbonyl optionally having substituent(s), cycloalkenyloxy-carbonyl optionally having substituent(s), cycloalkynyloxy-carbonyl optionally having substituent(s), aryloxy-carbonyl optionally having substituent(s), heterocyclyl-oxy-carbonyl optionally having substituent(s), carbamoyl optionally having substituent(s), alkyl-sulfonyl optionally having substituent(s), cycloalkyl-sulfonyl optionally having substituent(s), aryl-sulfonyl optionally having substituent(s), heterocyclyl-sulfonyl optionally having substituent(s), alkyl-sulfinyl optionally having substituent(s), cycloalkyl-sulfinyl optionally having substituent(s), aryl-sulfinyl optionally having substituent(s), heterocyclyl-sulfinyl optionally having substituent(s)], an optionally substituted hydroxyl group [e.g., a hydroxyl group optionally substituted by an optionally substituted $C_{1-6}$ alkyl group (e.g., methyl)], an optionally substituted amino group, an optionally substituted cyclic group and an oxo group;
(8) an optionally substituted sulfanyl group; preferably, a sulfanyl group optionally substituted by a $C_{1-6}$ alkyl group (e.g., methyl) substituted by a halogen atom (e.g., fluorine atom);
(9) an acyl group [e.g., formyl, alkyl-carbonyl (e.g., methylcarbonyl) optionally having substituent(s), alkenyl-carbonyl optionally having substituent(s), alkynyl-carbonyl optionally having substituent(s), cycloalkyl-carbonyl optionally having substituent(s), cycloalkenyl-carbonyl optionally having substituent(s), aryl-carbonyl optionally having substituent(s), heterocyclyl-carbonyl (e.g., piperidinocarbonyl) optionally having substituent(s), carboxyl, alkoxy-carbonyl (e.g., ethoxycarbonyl) optionally having substituent(s), alkenyloxy-carbonyl optionally having substituent(s), alkynyloxy-carbonyl optionally having substituent(s), cycloalkyloxy-carbonyl optionally having substituent(s), cycloalkenyloxy-carbonyl optionally having substituent(s), cycloalkynyloxy-carbonyl optionally having substituent(s), aryloxy-carbonyl optionally having substituent(s), heterocyclyl-oxy-carbonyl optionally having substituent(s), carbamoyl optionally having substituent(s), alkyl-sulfonyl optionally having substituent(s), cycloalkyl-sulfonyl optionally having substituent(s), aryl-sulfonyl optionally having substituent(s), heterocyclyl-sulfonyl optionally having, substituent(s), alkyl-sulfinyl optionally having substituent(s), cycloalkyl-sulfinyl optionally having substituent(s), aryl-sulfinyl optionally having substituent(s), heterocyclyl-sulfinyl optionally having substituent(s)]; and

(10) an oxo group;
is preferable.

In addition, as a compound represented by the formula (I), a compound wherein $R^1$ is
(1) a $C_{1-6}$ alkyl group (e.g., methyl, ethyl, isopropyl) optionally substituted by 1-6 (particularly, 1-3) substituents selected from a halogen atom (e.g., fluorine atom) and a $C_{1-3}$ alkoxy group (e.g., methoxy);
(2) a $C_{3-6}$ cycloalkyl group (e.g., cyclopropyl, cyclobutyl); or
(3) an amino group optionally substituted by 1 or 2 $C_{1-6}$ alkyl groups (e.g., methyl, ethyl, propyl);

$R^2$ and $R^3$ are both hydrogen atoms;

X is —O— or —S-(particularly, —O—);

ring A is
(1) a 3- to 8-membered monocyclic nonaromatic hydrocarbon ring (particularly, cyclopropane, cyclobutane, cyclopentane or cyclohexane) optionally substituted by 1-5 (particularly, 1-3) substituents selected from a halogen atom (e.g., fluorine atom), an oxo group and a hydroxyl group, (2) 3- to 8-membered monocyclic non-aromatic heterocycle (particularly, tetrahydrofuran ring, tetrahydropyran ring or piperidine ring) optionally substituted by 1-3 (particularly, 1-2) substituents selected from a $C_{1-6}$ alkyl group (e.g., methyl, ethyl) optionally substituted by a phenyl group, alkylcarbonyl (e.g., methylcarbonyl), alkoxycarbonyl (e.g., methoxycarbonyl), alkylcarbamoyl (e.g., ethylcarbamoyl), alkylsulfonyl (e.g., methylsulfonyl) and an oxo group, or (3) a bicyclic 7-8-membered saturated ring selected from a bicyclo[2.2.1]heptane ring, a 7-oxabicyclo[2.2.1]heptane ring, a 7-azabicyclo[2.2.1]heptane ring, a bicyclo[3.2.1]octane ring, a 8-oxabicyclo[3.2.1]octane ring and a 8-azabicyclo[3.2.1]octane ring; and ring B is $C_{3-8}$ cycloalkane, a 6- to 10-membered aromatic hydrocarbon ring, 3- to 10-membered non-aromatic heterocycle, 5- to 10-membered aromatic heterocycle, 6- to 10-membered fused non-aromatic heterocycle or 8- to 10-membered fused aromatic heterocycle, each of which optionally has 1-5 (preferably 1-3, more preferably 1 or 2) substituents selected from
(1) a halogen atom (e.g., fluorine atom, chlorine atom);
(2) a cyano group;
(3) a $C_{1-6}$ alkyl group (e.g., methyl, ethyl, isopropyl, tert-butyl) optionally substituted 1-6 (preferably 1-3) substituents selected from a halogen atom (e.g., fluorine atom), a cyano group, an acyl group [e.g., formyl, $C_{1-6}$ alkyl-carbonyl optionally substituted by 1-6 (preferably 1-3) halogen atoms, carboxyl, $C_{1-6}$ alkoxy-carbonyl optionally substituted by 1-6 (preferably 1-3) halogen atoms, carbamoyl optionally mono- or di-substituted by a $C_{1-6}$ alkyl group optionally substituted by 1-6 (preferably 1-3) halogen atoms, $C_{1-6}$ alkyl-sulfonyl optionally substituted by 1-6 (preferably 1-3) halogen atoms, $C_{1-6}$ alkyl-sulfinyl optionally substituted by 1-6 (preferably 1-3) halogen atoms], an optionally substituted hydroxyl group, an optionally substituted amino group and an optionally substituted cyclic group;
(4) a hydroxyl group optionally substituted by an optionally substituted $C_{1-6}$ alkyl group (e.g., methyl) or an optionally substituted phenyl group;
(5) an amino group optionally substituted by 1 or 2 substituents selected from an optionally substituted $C_{1-6}$ alkyl group (e.g., methyl), an acyl group [e.g., formyl, a $C_{1-6}$ alkyl-carbonyl optionally substituted by 1-6 (preferably 1-3) halogen atoms, carboxyl, $C_{1-6}$ alkoxy-carbonyl optionally substituted by 1-6 (preferably 1-3) halogen atoms, carbamoyl optionally mono- or di-substituted by a $C_{1-6}$ alkyl group optionally substituted by 1-6 (preferably 1-3) halogen atoms, $C_{1-6}$ alkyl-sulfonyl optionally substituted by 1-6 (preferably 1-3) halogen atoms, $C_{1-6}$ alkyl-sulfinyl optionally substituted by 1-6 (preferably 1-3) halogen atoms] and an optionally substituted phenyl group;
(6) a $C_{3-6}$ cycloalkyl group (e.g., cyclopropyl), a nonaromatic cyclic hydrocarbon group (e.g., tricyclo[3.3.1.1.3.7]decyl) or an aromatic cyclic hydrocarbon group (e.g., phenyl), each of which is optionally substituted by 1-6 (preferably 1-3) substituents selected from a halogen atom (e.g., fluorine atom), a cyano group, an optionally substituted $C_{1-6}$ alkyl group, an acyl group [e.g., formyl, $C_{1-6}$ alkyl-carbonyl optionally substituted by 1-6 (preferably 1-3) halogen atoms, carboxyl, $C_{1-6}$ alkoxy-carbonyl optionally substituted by 1-6 (preferably 1-halogen atoms, carbamoyl optionally mono- or di-substituted by a $C_{1-6}$ alkyl group optionally substituted by 1-6 (preferably 1-3) halogen atoms, $C_{1-6}$ alkyl-sulfonyl optionally substituted by 1-6 (preferably 1-3) halogen atoms, $C_{1-6}$ alkyl-sulfinyl optionally substituted by 1-6 (preferably 1-3) halogen atoms], an optionally substituted hydroxyl group, an optionally substituted amino group and an optionally substituted cyclic group;
(7) a nonaromatic heterocyclic group (e.g., oxetanyl, morpholinyl, pyrrolidinyl, piperidinyl, tetrahydropyranyl, dihydropyridyl, tetrahydropyridazinyl) or an aromatic heterocyclic group (e.g., pyrazolyl, imidazolyl, oxazolyl, isoxazolyl, thiazolyl, thienyl, pyridyl, pyrimidinyl), each of which is optionally substituted by 1-6 (preferably 1-3) substituents selected from a halogen atom (e.g., fluorine atom, chlorine atom), a cyano group, an optionally substituted $C_{1-6}$ alkyl group (e.g., methyl, ethyl, isopropyl), an acyl group [e.g., formyl, $C_{1-6}$ alkyl-carbonyl optionally substituted by 1-6 (preferably 1-3) halogen atoms, carboxyl, $C_{1-6}$ alkoxy-carbonyl optionally substituted by 1-6 (preferably 1-3) halogen atoms, carbamoyl optionally mono- or di-substituted by a $C_{1-6}$ alkyl group optionally substituted by 1-6 (preferably 1-3) halogen atoms, $C_{1-6}$ alkyl-sulfonyl optionally substituted by 1-6 (preferably 1-3) halogen atoms, $C_{1-6}$ alkyl-sulfinyl optionally substituted by 1-6 (preferably 1-3) halogen atoms], an optionally substituted hydroxyl group [e.g., a hydroxyl group optionally substituted by a $C_{1-6}$ alkyl group (e.g., methyl) optionally substituted by 1-6 (preferably 1-3) halogen atoms (e.g., fluorine atom)], an optionally substituted amino group, an optionally substituted cyclic group and an oxo group;
(8) a sulfanyl group optionally substituted by a $C_{1-6}$ alkyl group (e.g., methyl) substituted by 1-6 (preferably 1-3) halogen atoms (e.g., fluorine atom);
(9) an acyl group [e.g., formyl, $C_{1-6}$ alkyl-carbonyl (e.g., methylcarbonyl) optionally substituted by 1-6 (preferably 1-3) halogen atoms (e.g., fluorine atom), carboxyl, heterocyclyl-carbonyl (e.g., piperidinocarbonyl), $C_{1-6}$ alkoxy-carbonyl (e.g., ethoxycarbonyl) optionally substituted by 1-6 (preferably 1-3) halogen atoms, carbamoyl optionally mono- or di-substituted by a $C_{1-6}$ alkyl group (e.g., ethyl) optionally substituted by 1-6 (preferably 1-3) halogen atoms, $C_{1-6}$ alkyl-sulfonyl optionally substituted by 1-6 (preferably 1-3) halogen atoms, $C_{1-6}$ alkyl-sulfinyl optionally substituted by 1-6 (preferably 1-3) halogen atoms]; and
(10) an oxo group;
is more preferable.

Furthermore, as a compound represented by the formula (I), a compound wherein
$R^1$ is
(1) methyl, ethyl, isopropyl, chloromethyl, trifluoromethyl, trifluoroethyl, methoxyethyl;
(2) cyclopropyl, cyclobutyl; or
(3) methylamino, ethylamino, propylamino, dimethylamino;
$R^2$ and $R^3$ are both hydrogen atoms;
X is —O—;
ring A is a 3- to 8-membered monocyclic nonaromatic ring represented by the following formula:

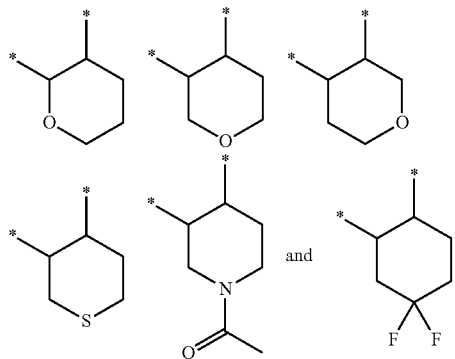

or a bicyclic 7- or 8-membered saturated ring represented by the following formula; and

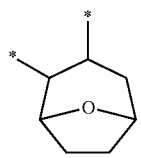 [SMILES: *C1CC2CCC(O2)C1*]

ring B is an aromatic hydrocarbon ring (e.g., benzene ring, dihydroindene ring, naphthalene ring), aromatic heterocycle (e.g., pyridine ring), fused non-aromatic heterocycle (e.g., chromene ring) or fused aromatic heterocycle (e.g., indole ring, benzothiazole ring), each of which optionally has 1-5 (preferably 1-3, more preferably 1 or 2) substituents selected from (1) a halogen atom (e.g., fluorine atom, chlorine atom);
(2) a cyano group;
(3) a $C_{1-6}$ alkyl group (e.g., methyl, ethyl, isopropyl, tert-butyl) optionally substituted by 1-6 (preferably 1-3) substituents selected from (i) a halogen atom (e.g., fluorine atom), (ii) a cyano group and (iii) a cyclic group (e.g., pyrazolyl) optionally substituted by 1-6 (preferably 1-3) halogen atoms (e.g., chlorine atom);
(4) a hydroxyl group optionally substituted by a $C_{1-6}$ alkyl group (e.g., methyl) optionally substituted by 1-6 (preferably 1-3) halogen atoms (e.g., fluorine atom) or a phenyl group;
(5) an amino group optionally substituted by 1 or 2 substituents selected from a $C_{1-6}$ alkyl group (e.g., methyl), alkyl-carbonyl (e.g., methylcarbonyl) and a phenyl group;
(6) a $C_{3-6}$ cycloalkyl group (e.g., cyclopropyl), a nonaromatic cyclic hydrocarbon group (e.g., tricyclo[3.3.1.1$^{3,7}$] decyl) or an aromatic cyclic hydrocarbon group (e.g., phenyl), which is optionally substituted by 1-6 (preferably 1-3) substituents selected from a halogen atom (e.g., fluorine atom) and a cyano group;
(7) a nonaromatic heterocyclic group (e.g., oxetanyl, morpholinyl, pyrrolidinyl, piperidinyl, tetrahydropyranyl, dihydropyridyl, tetrahydropyridazinyl) or an aromatic heterocyclic group (e.g., pyrazolyl, imidazolyl, oxazolyl, isoxazolyl, thiazolyl, thienyl, pyridyl, pyrimidinyl), each of which is optionally substituted by 1-6 (preferably 1-3) substituents selected from (i) a halogen atom (e.g., fluorine atom, chlorine atom), (ii) a cyano group, (iii) a $C_{1-6}$ alkyl group (e.g., methyl, ethyl, isopropyl) optionally substituted by 1-6 (preferably 1-3) halogen atoms (e.g., fluorine atom), (iv) a alkoxy group (e.g., methoxy) optionally substituted by 1-6 (preferably 1-3) halogen atoms (e.g., fluorine atom), and (v) an oxo group;
(8) a sulfanyl group optionally substituted by a $C_{1-6}$ alkyl group (e.g., methyl) substituted by 1-6 (preferably 1-3) halogen atoms (e.g., fluorine atom);
(9) $C_{1-6}$ alkyl-carbonyl (e.g., methylcarbonyl) optionally substituted by 1-6 (preferably 1-3) halogen atoms (e.g., fluorine atom);
(10) $C_{1-6}$ alkoxy-carbonyl (e.g., ethoxycarbonyl);
(11) di-$C_{1-6}$ alkyl-carbamoyl (e.g., diethylcarbamoyl);
(12) heterocyclyl-carbonyl (e.g., piperidinocarbonyl); and
(13) an oxo group;
is particularly preferable.

In another embodiment of the present invention, of the compound (I), a compound wherein
$R^1$ is
a $C_{1-6}$ alkyl group optionally substituted by 1 to 3 substituents selected from a halogen atom and a $C_{1-3}$ alkoxy group;
a $C_{3-6}$ cycloalkyl group; or
an amino group substituted by a $C_{1-6}$ alkyl group
is preferable.

Of the compound (I), a compound wherein $R^2$ and $R^3$ are each a hydrogen atom is preferable.

Of the compound (I), a compound wherein X is —O— is preferable.

Of the compound (I), a compound wherein ring A is optionally further substituted $C_{3-6}$ cycloalkane,
an optionally further substituted tetrahydrofuran ring,
an optionally further substituted tetrahydropyran ring,
an optionally further substituted piperidine ring,
an optionally further substituted tetrahydrothiopyran ring, or
an optionally further substituted 8-oxabicyclo[3.2.1]octane ring
is preferable.

Of the compound. (I), a compound wherein the substituent(s) on ring A is(are) selected from
(1) 1 to 3 halogen atoms,
(2) a $C_{1-6}$ alkyl group optionally substituted by one phenyl group,
(3) a carbamoyl group substituted by a $C_{1-6}$ alkyl group,
(4) a $C_{1-6}$ alkyl-carbonyl group,
(5) a $C_{1-6}$ alkoxy-carbonyl group,
(6) an oxo group,
(7) a hydroxyl group, and
(8) a $C_{1-6}$ alkylsulfonyl group
is preferable.

Of the compound (I), a compound wherein ring A is
$C_{3-6}$ cycloalkane,
tetrahydrofuran ring,
tetrahydropyran ring,
piperidine ring,
tetrahydrothiopyran ring, or
8-oxabicyclo[3.2.1]octane ring, each of which is optionally substituted by 1 to 3 substituents selected from
(1) 1 to 3 halogen atoms,
(2) a $C_{1-6}$ alkyl group, optionally substituted by one phenyl group,
(3) a carbamoyl group substituted by a $C_{1-6}$ alkyl group,
(4) a $C_{1-6}$ alkyl-carbonyl group,
(5) a $C_{1-6}$ alkoxy-carbonyl group,
(6) an oxo group,
(7) a hydroxyl group, and
(8) a $C_{1-6}$ alkylsulfonyl group
is preferable.

Of the compound (I), a compound wherein the ring B is
(1) an optionally further substituted benzene ring,
(2) an optionally further substituted pyridine ring,
(3) optionally further substituted $C_{3-6}$ cycloalkane,
(4) an optionally further substituted dihydroindene ring,
(5) an optionally further substituted naphthalene ring,
(6) an optionally further substituted chromene ring,
(7) an optionally further substituted indole ring or
(8) an optionally further substituted benzothiazole ring
is preferable.

Of the compound (I), a compound wherein the ring B is a benzene ring is preferable.

Of the compound (I), a compound wherein the substituent on the ring B is selected from
(1) a halogen atom;
(2) a cyano group;
(3) a $C_{1-6}$ alkyl group optionally substituted by 1 to 3 substituents selected from a halogen atom and a cyano group;
(4) a hydroxyl group optionally substituted by a $C_{1-6}$ alkyl group optionally substituted by 1 to 3 halogen atoms or a phenyl group (including alkoxy);
(5) an amino group optionally substituted by 1 or 2 substituents selected from a $C_{1-6}$ alkyl group, a $C_{1-6}$ alkyl-carbonyl and a phenyl group;
(6) a $C_{3-6}$ cycloalkyl group;
(7) a tricyclo[3.3.1.1.3.7]decyl group;
(8) phenyl optionally substituted by 1 to 3 substituents selected from a halogen atom and a cyano group;
(9) pyridyl optionally substituted by 1 to 3 substituents selected from a halogen atom, a cyano group and a $C_{1-6}$ alkyl group optionally substituted by 1 to 3 halogen atoms;
(10) pyrazolyl optionally substituted by 1 to 3 substituents selected from a halogen atom, a cyano group, a $C_{1-6}$ alkyl group optionally substituted by 1 to 3 halogen atoms and a $C_{1-6}$ alkoxy group optionally substituted by 1 to 3 halogen atoms;
(11) imidazolyl optionally substituted by a $C_{1-6}$ alkyl group;
(12) thienyl optionally substituted by a cyano group;
(13) pyrimidinyl optionally substituted by 1 to 3 substituents selected from a halogen atom and a cyano group;
(14) isoxazolyl substituted by a $C_{1-6}$ alkyl group;
(15) oxazolyl optionally substituted by a $C_{1-6}$ alkyl group optionally substituted by 1 to 3 halogen atoms;
(16) thiazolyl optionally substituted by 1 to 3 substituents selected from a halogen atom and a $C_{1-6}$ alkyl group optionally substituted by 1 to 3 halogen atoms;
(17) piperidyl optionally substituted by 1 to 3 substituents selected from a $C_{1-6}$ alkyl group optionally substituted by 1 to 3 halogen atoms and an oxo group;
(18) pyrrolidyl optionally substituted by 1 to 3 substituents selected from a halogen atom and an oxo group;
(19) dihydropyridyl optionally substituted by 1 to 3 substituents selected from a $C_{1-6}$ alkyl group and an oxo group;
(20) tetrahydropyridazinyl optionally substituted by 1 to 3 substituents selected from a $C_{1-6}$ alkyl group and an oxo group;
(21) oxetanyl;
(22) morpholinyl;
(23) tetrahydropyranyl;
(24) a sulfanyl group optionally substituted by a $C_{1-6}$ alkyl group substituted by 1 to 3 halogen atoms;
(25) a $C_{1-6}$ alkyl-carbonyl group;
(26) a $C_{1-6}$ alkoxy-carbonyl group; and
(27) an oxo group
is preferable.

In addition, of the compound (I), a compound wherein the ring B is
a benzene ring,
$C_{3-6}$ cycloalkane,
a dihydroindene ring,
a naphthalene ring,
a pyridine ring,
a chromene ring,
an indole ring or
a benzothiazole ring, which optionally has 1 to 3 substituents selected from
(1) a halogen atom;
(2) a cyano group;
(3) a $C_{1-6}$ alkyl group optionally substituted by 1 to 3 substituents selected from a halogen atom and a cyano group;
(4) a hydroxyl group optionally substituted by a $C_{1-6}$ alkyl group optionally substituted by 1 to 3 halogen atoms or a phenyl group;
(5) an amino group optionally substituted by 1 or 2 substituents selected from a $C_{1-6}$ alkyl group, a $C_{1-6}$ alkyl-carbonyl and a phenyl group;
(6) a $C_{3-6}$ cycloalkyl group;
(7) a tricyclo[3.3.1.1.3.7]decyl group;
(8) phenyl optionally substituted by 1 to 3 substituents selected from a halogen atom and a cyano group;
(9) pyridyl optionally substituted by 1 to 3 substituents selected from a halogen atom, a cyano group and a $C_{1-6}$ alkyl group optionally substituted by 1 to 3 halogen atoms;
(10) pyrazolyl optionally substituted by 1 to 3 substituents selected from a halogen atom, a cyano group, a $C_{1-6}$ alkyl group optionally substituted by 1 to 3 halogen atoms and a $C_{1-6}$ alkoxy group optionally substituted by 1 to 3 halogen atoms;
(11) imidazolyl optionally substituted by a $C_{1-6}$ alkyl group;
(12) thienyl optionally substituted by a cyano group;
(13) pyrimidinyl optionally substituted by 1 to 3 substituents selected from a halogen atom and a cyano group;

(14) isoxazolyl substituted by a $C_{1-6}$ alkyl group;
(15) oxazolyl optionally substituted by a $C_{1-6}$ alkyl group optionally substituted by 1 to 3 halogen atoms;
(16) thiazolyl optionally substituted by 1 to 3 substituents selected from a halogen atom and a $C_{1-6}$ alkyl group optionally substituted by 1 to 3 halogen atoms;
(17) piperidyl optionally substituted by 1 to 3 substituents selected from a $C_{1-6}$ alkyl group optionally substituted by 1 to 3 halogen atoms and an oxo group;
(18) pyrrolidyl optionally substituted by 1 to 3 substituents selected from a halogen atom and an oxo group;
(19) dihydropyridyl optionally substituted by 1 to 3 substituents selected from a $C_{1-6}$ alkyl group and an oxo group;
(20) tetrahydropyridazinyl optionally substituted by 1 to 3 substituents selected from a $C_{1-6}$ alkyl group and an oxo group;
(21) oxetanyl;
(22) morpholinyl;
(23) tetrahydropyranyl;
(24) a sulfanyl group optionally substituted by a $C_{1-6}$ alkyl group substituted by 1 to 3 halogen atoms;
(25) a $C_{1-6}$ alkyl-carbonyl group;
(26) a $C_{1-6}$ alkoxy-carbonyl group; and
(27) an oxo group
is preferable.
  Of the compound (I), a compound wherein
    $R^1$ is
a $C_{1-6}$ alkyl group optionally substituted by 1 to 3 substituents selected from a halogen atom and a $C_{1-3}$ alkoxy group;
a $C_{3-6}$ cycloalkyl group; or
an amino group substituted by a $C_{1-6}$ alkyl group,
    $R^2$ and $R^3$ are each a hydrogen atom,
    X is —O—,
    ring A is
$C_{3-6}$ cycloalkane,
tetrahydrofuran ring,
tetrahydropyran ring,
piperidine ring,
tetrahydrothiopyran ring, or
8-oxabicyclo[3.2.1]octane ring, each of which is optionally substituted by 1 to 3 substituents selected from
(1) 1 to 3 halogen atoms,
(2) a $C_{1-6}$ alkyl group optionally substituted by one phenyl group,
(3) a carbamoyl group substituted by a $C_{1-6}$ alkyl group,
(4) a $C_{1-6}$ alkyl-carbonyl group,
(5) a $C_{1-6}$ alkoxy-carbonyl group,
(6) an oxo group,
(7) a hydroxyl group, and
(8) a $C_{1-6}$ alkylsulfonyl group, and
    ring B is a benzene ring,
$C_{3-6}$ cycloalkane,
a dihydroindene ring,
a naphthalene ring,
a pyridine ring,
a chromene ring,
an indole ring or
a benzothiazole ring, which optionally has 1 to 3 substituents selected from
(1) a halogen atom;
(2) a cyano group;
(3) a $C_{1-6}$ alkyl group optionally substituted by 1 to 3 substituents selected from a halogen atom and a cyano group;
(4) a hydroxyl group optionally substituted by a $C_{1-6}$ alkyl group optionally substituted by 1 to 3 halogen atoms or a phenyl group;

(5) an amino group optionally substituted by 1 or 2 substituents selected from a $C_{1-6}$ alkyl group, a $C_{1-6}$ alkyl-carbonyl and a phenyl group;
(6) a $C_{3-6}$ cycloalkyl group;
(7) a tricyclo[3.3.1.1.3.7]decyl group;
(8) phenyl optionally substituted by 1 to 3 substituents selected from a halogen atom and a cyano group;
(9) pyridyl optionally substituted by 1 to 3 substituents selected from a halogen atom, a cyano group and a $C_{1-6}$ alkyl group optionally substituted by 1 to 3 halogen atoms;
(10) pyrazolyl optionally substituted by 1 to 3 substituents selected from a halogen atom, a cyano group, a $C_{1-6}$ alkyl group optionally substituted by 1 to 3 halogen atoms and a $C_{1-6}$ alkoxy group optionally substituted by 1 to 3 halogen atoms;
(11) imidazolyl optionally substituted by a $C_{1-6}$ alkyl group;
(12) thienyl optionally substituted by a cyano group;
(13) pyrimidinyl optionally substituted by 1 to 3 substituents selected from a halogen atom and a cyano group;
(14) isoxazolyl substituted by a $C_{1-6}$ alkyl group;
(15) oxazolyl optionally substituted by a $C_{1-6}$ alkyl group optionally substituted by 1 to 3 halogen atoms;
(16) thiazolyl optionally substituted by 1 to 3 substituents selected from a halogen atom and a $C_{1-6}$ alkyl group optionally substituted by 1 to 3 halogen atoms;
(17) piperidyl optionally substituted by 1 to 3 substituents selected from a $C_{1-6}$ alkyl group optionally substituted by 1 to 3 halogen atoms and an oxo group;
(18) pyrrolidyl optionally substituted by 1 to 0.3 substituents selected from a halogen atom and an oxo group;
(19) dihydropyridyl optionally substituted by 1 to 3 substituents selected from a $C_{1-6}$ alkyl group and an oxo group;
(20) tetrahydropyridazinyl optionally substituted by 1 to 3 substituents selected from a $C_{1-6}$ alkyl group and an oxo group;
(21) oxetanyl;
(22) morpholinyl;
(23) tetrahydropyranyl;
(24) a sulfanyl group optionally substituted by a $C_{1-6}$ alkyl group substituted by 1 to 3 halogen atoms;
(25) a $C_{1-6}$ alkyl-carbonyl group;
(26) a $C_{1-6}$ alkoxy-carbonyl group; and
(27) an oxo group
is preferable.
  Of the compound (I), a compound wherein
    $R^1$ is
a $C_{1-6}$ alkyl group optionally substituted by 1 to 3 halogen atoms;
a $C_{3-6}$ cycloalkyl group; or
an amino group substituted by a $C_{1-6}$ alkyl group,
    $R^2$ and $R^3$ are each a hydrogen atom,
    X is —O—,
    ring A is
$C_{3-6}$ cycloalkane,
tetrahydropyran ring,
piperidine ring,
tetrahydrothiopyran ring, or
8-oxabicyclo[3.2.1]octane ring, each of which is optionally substituted by 1 to 3 substituents selected from
(1) 1 to 3 halogen atoms,
(2) a $C_{1-6}$ alkyl-carbonyl group, and
(3) an oxo group, and
    ring B is a benzene ring optionally having 1 to 3 substituents selected from
(1) a halogen atom;
(2) a $C_{1-6}$ alkyl group optionally substituted by one cyano group;

(3) a hydroxyl group substituted by a $C_{1-6}$ alkyl group substituted by 1 to 3 halogen atoms;
(4) a $C_{3-6}$ cycloalkyl group;
(5) pyridyl optionally substituted by 1 to 3 substituents selected from a halogen atom, a cyano group and a $C_{1-6}$ alkyl group optionally substituted by 1 to 3 halogen atoms;
(6) pyrazolyl optionally substituted by 1 to 3 substituents selected from a halogen atom, a cyano group, and a $C_{1-6}$ alkyl group optionally substituted by 1 to 3 halogen atoms;
(7) imidazolyl substituted by 1 to 3 $C_{1-6}$ alkyl groups;
(8) pyrimidinyl substituted by 1 to 3 halogen atoms;
(9) isoxazolyl substituted by one $C_{1-6}$ alkyl group;
(10) thiazolyl optionally substituted by 1 to 3 substituents selected from a halogen atom and a $C_{1-6}$ alkyl group;
(11) pyrrolidyl substituted by one oxo group;
(12) dihydropyridyl substituted by 1 to 3 substituents selected from a $C_{1-6}$ alkyl group and an oxo group;
(13) oxetanyl;
(14) tetrahydropyranyl; and
(15) a $C_{1-6}$ alkyl-carbonyl group
is preferable.

Of the compound (I), a compound wherein
$R^1$ is
a $C_{1-6}$ alkyl group optionally substituted by 1 to 3 halogen atoms;
a $C_{3-6}$ cycloalkyl group; or
an amino group substituted by a $C_{1-6}$ alkyl group,
$R^2$ and $R^3$ are each a hydrogen atom,
X is —O—,
ring A is
$C_{3-6}$ cycloalkane,
tetrahydropyran ring, or
8-oxabicyclo[3.2.1]octane ring, each of which is optionally substituted by 1 to 3 halogen atoms, and
ring B is a benzene ring optionally having 1 to 3 substituents selected from
(1) a halogen atom;
(2) a $C_{3-6}$ cycloalkyl group;
(3) phenyl substituted by 1 to 3 halogen atoms;
(4) pyridyl optionally substituted by 1 to 3 substituents selected from a halogen atom and a cyano group;
(5) pyrazolyl optionally substituted by 1 to 3 substituents selected from a halogen atom and a $C_{1-6}$ alkyl group optionally substituted by 1 to 3 halogen atoms;
(6) pyrimidinyl optionally substituted by 1 to 3 substituents selected from a halogen atom and a cyano group;
(7) isoxazolyl substituted by a $C_{1-6}$ alkyl group;
(8) thiazolyl optionally substituted by 1 to 3 substituents selected from a halogen atom and a $C_{1-6}$ alkyl group;
(9) pyrrolidyl; and
(10) dihydropyridyl optionally substituted by 1 to 3 substituents selected from a $C_{1-6}$ alkyl group and an oxo group;
is preferable.

Of the compound (I), a compound wherein
$R^1$ is a $C_{1-6}$ alkyl group or a $C_{3-6}$ cycloalkyl group,
$R^2$ and $R^3$ are each a hydrogen atom,
X is —O—,
ring A is
$C_{3-6}$ cycloalkane optionally substituted by 1 to 3 halogen atoms, or
a tetrahydropyran ring, and
ring B is a benzene ring optionally having 1 to 3 substituents selected from
(1) pyridyl optionally substituted by 1 to 3 substituents selected from a halogen atom and a $C_{1-6}$ alkyl group optionally substituted by 1 to 3 halogen atoms; and
(2) pyrrolidyl substituted by one oxo group
is preferable.

Of the compound (I), a compound wherein
$R^1$ is a $C_{1-6}$ alkyl group or a $C_{3-6}$ cycloalkyl group,
$R^2$ and $R^3$ are each a hydrogen atom,
X is —O—,
A ring is a tetrahydropyran ring, and
ring B is a benzene ring substituted by pyridyl optionally substituted by 1 to 3 substituents selected from a halogen atom and a $C_{1-6}$ alkyl group optionally substituted by 1 to 3 halogen atoms
is preferable.

As a compound represented by the formula (I), the compounds of Examples 1-529 can be specifically recited.

Of the compounds of Examples 1-529,
N-[(3R,4S)-3-{[4-(4-chloro-1H-pyrazol-1-yl)phenoxy]methyl}tetrahydro-2H-pyran-4-yl]methanesulfonamide,
N-[(3RS,4SR)-3-{[4-(4-chloro-1H-pyrazol-1-yl)phenoxy]methyl}tetrahydro-2H-pyran-4-yl]methanesulfonamide,
N-[(3RS,4SR)-3-({4-[5-(trifluoromethyl)pyridin-2-yl]phenoxy}methyl)tetrahydro-2H-pyran-4-yl]ethanesulfonamide,
N-[(3RS,4SR)-3-({4-[5-(trifluoromethyl)pyridin-2-yl]phenoxy}methyl)tetrahydro-2H-pyran-4-yl]ethanesulfonamide,
N-[(3R,4S)-4-{[4-(5-chloro-3-fluoropyridin-2-yl)phenoxy]methyl}tetrahydro-2H-pyran-3-yl]cyclopropanesulfonamide,
N-[(1S,2S)-4,4-difluoro-2-{[4-(2-oxopyrrolidin-1-yl)phenoxy]methyl}cyclohexyl]ethanesulfonamide, or
N-[(3R,4S)-3-{[4-(4-chloro-1H-pyrazol-1-yl)-2-fluorophenoxy]methyl}tetrahydro-2H-pyran-4-yl]ethanesulfonamide or a salt thereof is preferable, and
N-[(3R,4S)-3-{[4-(4-chloro-1H-pyrazol-1-yl)phenoxy]methyl}tetrahydro-2H-pyran-4-yl]methanesulfonamide,
N-[(3RS,4SR)-3-({4-[5-(trifluoromethyl)pyridin-2-yl]phenoxy}methyl)tetrahydro-2H-pyran-4-yl]ethanesulfonamide, or
N-[(3R,4S)-4-{[4-(5-chloro-3-fluoropyridin-2-yl)phenoxy]methyl}tetrahydro-2H-pyran-3-yl]cyclopropanesulfonamide
or a salt thereof is more preferable.

When compound (I) is a salt, examples thereof include metal salts, ammonium salts, salts with organic bases, salts with inorganic acids, salts with organic acids, salts with basic or acidic amino acids and the like. Preferable examples of the metal salt include alkali metal salts such as sodium salt, potassium salt and the like; alkaline earth metal salts such as calcium salt, magnesium salt, barium salt and the like; aluminum salt and the like. Preferable examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salts with inorganic acids include salts with hydrochloric acid, hydrobromic acid, nitric acid, sulfuric acid, phosphoric acid and the like. Preferable examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salts with basic amino acids include salts with arginine, lysine, ornithine and the like can be mentioned. Preferable examples of the salts with acidic amino acids include salts with aspartic acid, glutamic acid and the like. Of those, pharmaceutically acceptable salts are preferable. For example, when a compound has an acidic functional group therein, inorganic salts such as alkali metal salts (e.g., sodium salt, potassium salt and the like), alkaline earth metal salts (e.g., calcium salt, magnesium salt, barium salt and the like) and the like, ammonium salt and the like can be mentioned. When a compound has a basic functional group therein, salts with inorganic acids such as hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, p-toluenesulfonic acid and the like can be mentioned.

When compound (I) contains an isomer such as a tautomer, an optical isomer, a stereoisomer, a positional isomer, or a rotational isomer, an isomer present alone or in combination is encompassed in the compound of the present invention. Furthermore, when compound (I) contains an optical isomer, an optical isomer isolated from a racemate is also encompassed in compound (I).

The production methods of the compound of the present invention are explained below.

As examples of the production methods of compounds (I), (I'), (I") and (Ia-h), representative production methods are shown below, by which the production methods are not limited. Compounds (I), (I'), (I") and (Ia-h) can also be produced by the methods shown in the following Reaction Schemes 1-5 or a method analogous thereto and the like. Compounds (I'), (I") and (Ia-h) are all encompassed in compound (I).

Each starting compound can form a salt as long as the reaction is not inhibited and, as such salt, those exemplified as the salts of the aforementioned compound represented by the formula (I) can be used.

A starting material compound without any specific production method may be an easily available commercially product, or can also be produced by a method known per se, or a method analogous thereto.

A product resulting from each reaction in the form of a reaction mixture or a crude product can also be used for the next reaction, or can be isolated from the reaction mixture according to a conventional method and purified by a separation means such as recrystallization, distillation, chromatography, HPLC and the like. For example, the methods described in the Examples or a method analogous thereto and the like can be utilized therefor.

The reagents and reactants used for each reaction may be an easily available commercially product, or can also be produced by a method known per se, or a method analogous thereto, or the methods described in the Examples. For example, the reagents and reactants described in the Examples can be used.

Unless particularly indicated, the solvent used in each reaction is not particularly limited as long as the reaction proceeds, and the reaction may be performed in a solvent inert to the reaction, or without solvent, where two or more kinds of solvents may be used by mixing them at an appropriate ratio. For example, the solvents described in the Examples can be used.

Unless particularly indicated, the equivalent amount of the reagents and reactants used for each reaction is 0.001 equivalent-100 equivalents relative to the substrate of each reaction. For example, the equivalent amounts of the reagents and reactants described in the Examples can be used.

Unless particularly indicated, the reaction time of each reaction is generally 5 min-72 hr. For example, the reaction time described in the Examples can be employed.

Unless particularly indicated, the reaction temperature of each reaction is from −78° C. to heating under reflux. For example, the reaction can be performed at a reaction temperature described in the Examples.

In the following Reaction Schemes, alkylation reaction, hydrolysis, amination reaction, amidation reaction, esterification reaction, etherification reaction, oxidation reaction, reduction reaction and the like are carried out according to a method known per se. Examples of the method include the methods described in ORGANIC FUNCTIONAL GROUP PREPARATIONS, 2nd edition, Academic Press Inc., 1989, or Comprehensive Organic Transformations: A Guide to Functional Group Preparations, 2nd edition, Wiley-VCH, 1999, and the like, and the like.

In the following Reaction Schemes, when the starting material compound has an amino, carboxy, hydroxy, carbonyl or sulfanyl group, a protecting group generally used in the peptide chemistry etc. may be introduced into these functional groups, and the object compound can be obtained by removing the protecting group as necessary after the reaction. A reaction to introduce a protecting group into these functional groups is indicated as "protection reaction" and a reaction to remove the protecting group is indicated as "deprotection reaction". The introduction method of a protecting group (protection reaction) and a removal method of a protecting group (deprotection reaction) can be a method known per se, for example, the method described in Greene's PROTECTIVE GROUPS in ORGANIC SYNTHESIS, 4th Edition, Wiley-Interscience, 2006, or the like, or the method described in the Examples or the like.

<Reaction Scheme 1>

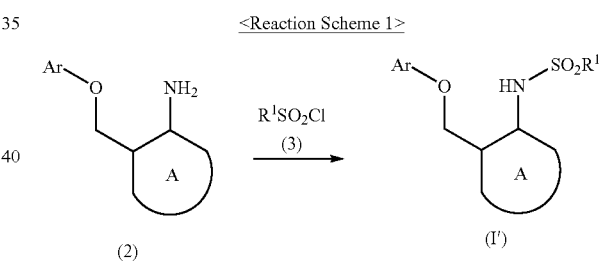

wherein Ar is an optionally substituted 3- to 10-membered aromatic ring, and the other symbols are as defined above.

Compound (2) can be produced, for example, according to the method described in Examples or Reference Examples or a method described in Reaction Schemes 6 to 9 or a method known per se or a method analogous thereto.

Compound (I') can be produced, for example, by subjecting compound (2) to a sulfonylation reaction with compound (3).

This reaction is carried out, for example, by reacting compound (2) with compound (3) in the presence of a base (e.g., potassium carbonate, sodium hydride, sodium hydroxide, triethylamine, 1,8-diazabicyclo[5.4.0]undec-7-ene etc.) in an inert solvent (e.g., N,N-dimethylformamide, acetonitrile, tetrahydrofuran, toluene, water etc.). Where necessary, a phase-transfer catalyst (e.g., tetrabutylammonium bromide, tetrabutylammonium hydrogensulfate etc.) may be used.

<Reaction Scheme 2>

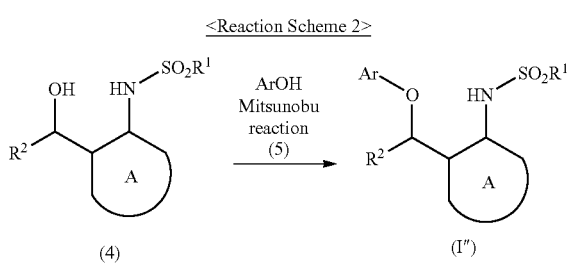

wherein each symbol is as defined above.

Compound (4) can be produced, for example, according to the method described in Reaction Scheme 10 or a method known per se or a method analogous thereto.

Compound (5) may be commercially available product, or can be produced according to a method known per se, the method shown in Reaction Scheme 13 or a method analogous thereto.

Compound (I″) can be produced, for example, by subjecting compound (4) to the Mitsunobu reaction with compound (5).

This reaction is carried out, for example, by reacting compound (4) with compound (5) in the presence of a hydroxy group-activator (e.g., cyanomethylene tri-n-butylphosphorane, combination of diisopropyl azodicarboxylate and triphenylphosphine, a combination of diethyl azodicarboxylate and triphenylphosphine, a combination of 1,1'-(azodicarbonyl)dipiperidine and tributylphosphine etc.) in an inert solvent (e.g., toluene, tetrahydrofuran etc.).

<Reaction Scheme 3>

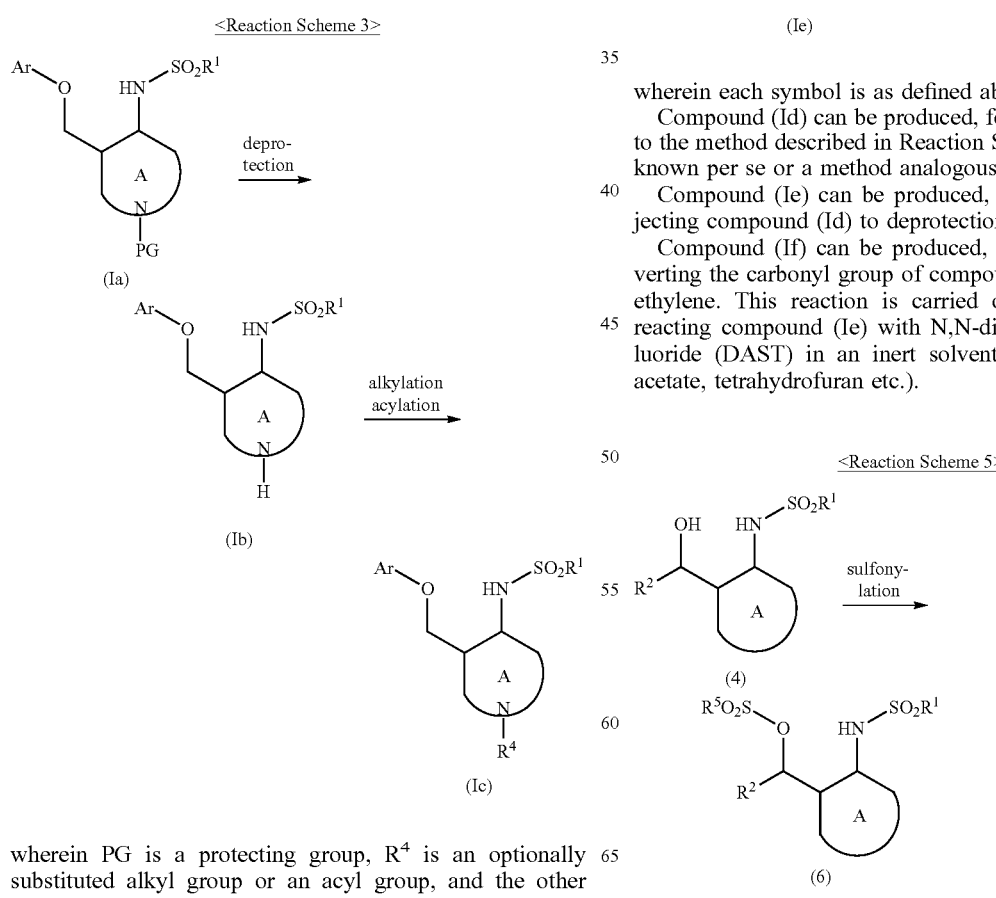

wherein PG is a protecting group, $R^4$ is an optionally substituted alkyl group or an acyl group, and the other symbols are as defined above.

Compound (Ib) can be produced, for example, by deprotecting compound (Ia) containing the nitrogen atom substituted by the protecting group PG in ring A.

Compound (Ic) can be produced, for example, by subjecting compound (Ib) to an alkylation or acylation. This reaction is carried out, for example, by reacting compound (Ib) with an alkylating agent (e.g., methyl iodide, benzyl bromide etc.) or an acylating agent (e.g., methanesulfonyl chloride, acetic anhydride etc.) in the presence of a base (e.g., triethylamine, pyridine etc.) in an inert solvent (e.g., tetrahydrofuran, toluene, diethyl ether etc.).

<Reaction Scheme 4>

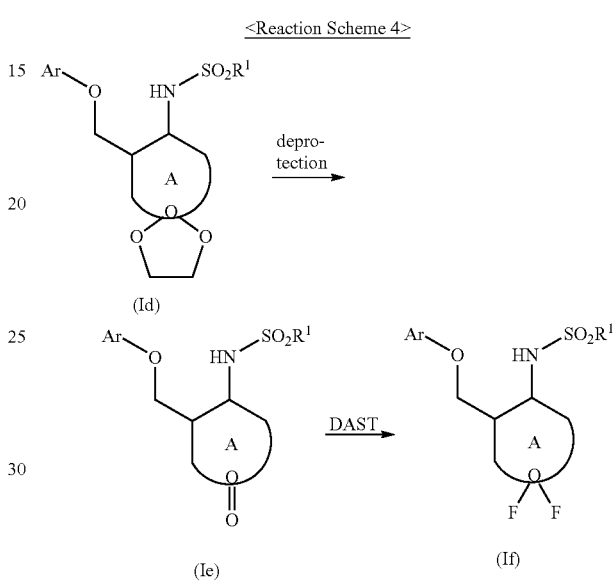

wherein each symbol is as defined above.

Compound (Id) can be produced, for example, according to the method described in Reaction Scheme 2 or a method known per se or a method analogous thereto.

Compound (Ie) can be produced, for example, by subjecting compound (Id) to deprotection.

Compound (If) can be produced, for example, by converting the carbonyl group of compound (Ie) to difluoromethylene. This reaction is carried out, for example, by reacting compound (Ie) with N,N-diethylaminosulfur trifluoride (DAST) in an inert solvent (e.g., toluene, ethyl acetate, tetrahydrofuran etc.).

<Reaction Scheme 5>

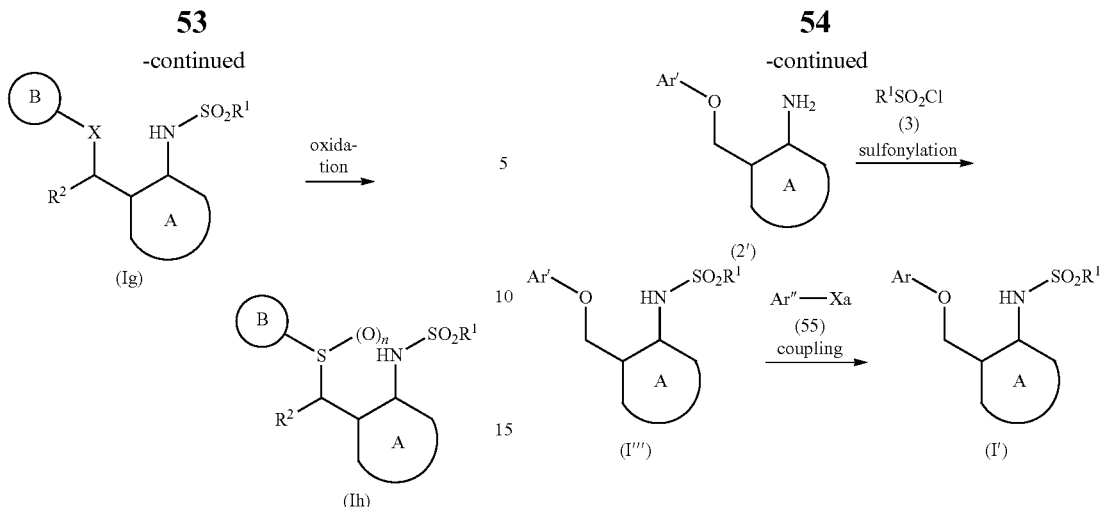

wherein $R^5$ is an optionally substituted $C_{1-6}$ alkyl group or an optionally substituted allyl group, X is an oxygen atom or a sulfur atom, and the other symbols are as defined above.

Compound (6) can be produced, for example, by sulfonylation of the hydroxyl group of compound (4).

This reaction is carried out, for example, by reacting compound (4) with a sulfonyl halide represented by the formula: $R^5SO_2X^1$ wherein $X^1$ is a halogen atom (e.g., sulfonyl chloride) in the presence of a base (e.g., triethylamine, 1,8-diazabicyclo[5.4.0]undec-7-ene etc.) in an inert solvent (e.g., N,N-dimethylformamide, acetonitrile, tetrahydrofuran, toluene, water etc.). Where necessary, a phase-transfer catalyst (e.g., tetrabutylammonium bromide, tetrabutylammonium hydrogensulfate etc.) may be used.

Compound (Ig) can be produced, for example, by subjecting compound (6) to a nucleophilic substitution reaction with compound (7). This reaction is carried out, for example, by reacting compound (6) with compound (7) in the presence of a base (e.g., potassium carbonate, sodium hydride, potassium hydroxide, potassium tert-butoxide, triethylamine, 1,8-diazabicyclo[5.4.0]undec-7-ene etc.) in an inert solvent (e.g., N,N-dimethylformamide, acetonitrile, tetrahydrofuran, toluene, dimethyl sulfoxide, water etc.). Where necessary, a phase-transfer catalyst (e.g., tetrabutylammonium bromide, tetrabutylammonium hydrogensulfate etc.) may be used.

Compound (Ih) can be produced, for example, by subjecting compound (Ig) wherein X is a sulfur atom to an oxidation reaction. This reaction is carried out, for example, by reacting compound (Ig) in the presence of an oxidant (e.g., aqueous hydrogen peroxide, sodium percarbonate, methachlorobenzoic acid etc.) in an inert solvent (e.g., ethyl acetate, acetonitrile, tetrahydrofuran, water etc.).

<Reaction Scheme 6>

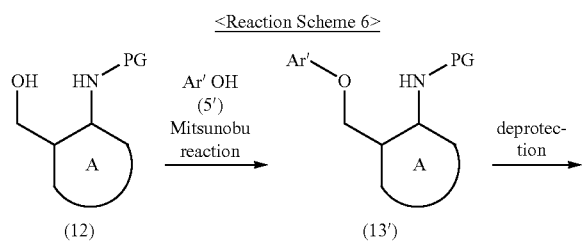

wherein Ar' is an optionally substituted 3- to 10-membered aromatic ring, Ar" is an optionally substituted 3- to 10-membered ring, Xa is a leaving group, and the other symbols are as defined above.

Examples of the "leaving group" for Xa include a halogen atom (e.g., fluorine, chlorine, bromine, iodine etc.), an optionally halogenated $C_{1-6}$ alkylsulfonyloxy (e.g., methanesulfonyloxy, ethanesulfonyloxy, trichloromethanesulfonyloxy, trifluoromethanesulfonyloxy [triflate] etc.), a boronyl group, an optionally substituted $C_{1-6}$ alkylboranyl group, an optionally substituted $C_{2-6}$ alkenylboranyl group, an optionally substituted $C_{1-6}$ alkoxyboranyl group, an optionally substituted $C_{6-14}$ arylboranyl group, an optionally substituted $C_{1-6}$ alkylstannyl group (e.g., tributylstannyl and the like), an optionally substituted $C_{2-6}$ alkenylstannyl group, an optionally substituted $C_{6-14}$ arylstannyl group, a metal-containing substituent (e.g., magnesium halide, zinc halide etc.), an optionally substituted $C_{6-14}$ arylsulfonyloxy and the like. Examples of the "optionally substituted $C_{6-14}$ arylsulfonyloxy" include $C_{6-14}$ arylsulfonyloxy optionally having 1 to 3 substituents selected from $C_{1-6}$ alkyl (e.g., methyl, ethyl, propyl, isopropyl, butyl, isobutyl, sec-butyl, tert-butyl, pentyl, hexyl etc.), $C_{1-6}$ alkoxy (e.g., methoxy, ethoxy, propoxy, isopropoxy, butoxy, isobutoxy, sec-butoxy, pentyloxy, hexyloxy etc.) and nitro, and the like, and specific examples thereof include, benzenesulfonyloxy, m-nitrobenzenesulfonyloxy, p-toluenesulfonyloxy, naphthylsulfonyloxy and the like.

Compound (12) can be produced, for example, according to the method described in Reaction Scheme 7, the methods described in Examples or Reference Examples or a method known per se or a method analogous thereto.

Compound (5') may be commercially available product, or can be produced according to a method known per se, the method shown in Reaction Schemes 14 and 15, the method described in Examples, or a method analogous thereto.

Compound (13') can be produced, for example, by subjecting compound (12) to the Mitsunobu reaction with compound (5').

This reaction is carried out, for example, by reacting compound (12) with compound (5') in the presence of a hydroxy group-activator (e.g., cyanomethylene tri-n-butylphosphorane, a combination of diisopropyl azodicarboxylate and triphenylphosphine, a combination of diethyl azodicarboxylate and triphenylphosphine, a combination of 1,1'-(azodicarbonyl)dipiperidine and tributylphosphine etc.) in an inert solvent (e.g., toluene, tetrahydrofuran etc.).

Compound (2') can be produced, for example, by subjecting compound (13') to deprotection.

Compound (I''') can be produced, for example, by subjecting compound (2') to a sulfonylation reaction.

This reaction is carried out, for example, by reacting compound (2') with compound (3) in the presence of a base (e.g., potassium carbonate, sodium hydride, sodium hydroxide, triethylamine, 1,8-diazabicyclo[5.4.0]undec-7-ene etc.) in an inert solvent (e.g., N,N-dimethylformamide, acetonitrile, tetrahydrofuran, toluene, water etc.). Where necessary, a phase-transfer catalyst (e.g., tetrabutylammonium bromide, tetrabutylammonium hydrogensulfate etc.) may be used.

Compound (I') can be produced, for example, by subjecting compound (I''') to a coupling reaction with compound (55).

This reaction may be carried out in the presence of a base, a desiccant, an additive and a metal catalyst, as necessary.

Examples of the "base" include inorganic bases such as sodium hydroxide, hydroxide barium and the like; basic salts such as sodium carbonate, potassium carbonate, cesium carbonate, sodium hydrogen carbonate, potassium fluoride, cesium fluoride, tripotassium phosphate and the like; aromatic amines such as pyridine, lutidine and the like; tertiary amines such as triethylamine, tripropylamine, tributylamine, cyclohexyldimethylamine, 4-dimethylaminopyridine, N-methylpiperidine, N-methylpyrrolidine, N-methylmorpholine and the like; alkali metals such as metal sodium and the like; alkali metal hydrides such as sodium hydride, potassium hydride and the like; metal amides such as sodium amide, lithium diisopropylamide, lithium hexamethyldisilazide and the like; metal alkoxides such as sodium methoxide, sodium ethoxide, potassium tert-butoxide and the like, and the like.

The amount of the "base" to be used is about 0.1 to 30 mol, preferably 0.8 to 10 mol, per 1 mol of compound (I''').

Examples of the "desiccant" include molecular sieves such as molecular sieves 4A, molecular sieves 3A and the like, inorganic salts such as anhydrous sodium sulfates, anhydrous magnesium sulfate and the like, and the like.

The amount of the "desiccant" to be used is about 0.1- to 500-fold weight, preferably 0.1- to 30-fold weight, relative to compound (I''').

Examples of the "additive" include cyclohexyl-1,2-diamine, N,N'-dimethylcyclohexyl-1,2-diamine, picoline acid and the like.

The amount of the "additive" to be used is about 0.01 to mol, preferably 0.01 to 10 mol, per 1 mol of compound (I''').

Examples of the "metal catalyst" include a complex composed of a metal (e.g., nickel, palladium, copper etc.) and a ligand, and the like. Examples of the palladium complex include tetrakis(triphenylphosphine)palladium(0), bis(triphenylphosphine)palladium(II)dichloride, tris(dibenzylideneacetone)dipalladium(0), trans-dichlorobis(tri-o-tolylphosphine)palladium(II), palladium(II)trifluoroacetate, palladium(II) acetate and the like. Examples of the nickel complex include nickel(II) acetylacetonate, nickel chloride 1,2-bis(diphenylphosphino)ethane complex and the like. Examples of the copper complex include copper iodide, copper bromide, copper chloride, copper acetate and the like. In addition, examples of the ligand include an acyloxy group (e.g., acetyloxy, benzoyloxy etc.), a halogen atom (e.g., fluorine, chlorine, bromine, iodine etc.), triphenylphosphine, 2,2'-bis(diphenylphosphino)-1,1'-binaphthyl, 2-(di-tert-butylphosphino)biphenyl, 2-(dicyclohexylphosphino)biphenyl, 2-(dicyclohexylphosphino)-2',6'-dimethoxy-1,1'-biphenyl, 2-(dicyclohexylphosphino)-2',-4',6'-triisopropyl-1,1'-biphenyl, 2-(dicyclohexylphosphino)-2'-(N,N-dimethylamino)biphenyl, 1,1'-bis(diphenylphosphino)ferrocene, tri-tert-butylphosphine, tricyclohexylphosphine, (9,9-dimethyl-9H-xanthene-4,5-diyl)bis(diphenylphosphine) and the like:

The amount of the "metal catalyst" to be used is generally about 0.01 to 1000 wt %, preferably about 1 to 20 wt %, relative to compound (I'''). When desired, this reaction can also be carried out under microwave irradiation by using a microwave irradiation apparatus (e.g., INITIATOR manufactured by Biotage, etc.).

This reaction is advantageously carried out without solvent or in a solvent inert to reaction. The solvent is not particularly limited as long as the reaction proceeds, and the preferable example thereof include alcohols such as methanol, ethanol, 1-propanol, 2-propanol, 1-butanol, 2-methyl-2-propanol and the like; ethers such as diethyl ether, tetrahydrofuran, dioxane, 1,2-dimethoxyethane and the like; hydrocarbons such as benzene, toluene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; water and the like, a mixed solvent thereof, and the like. The reaction temperature is about −40 to 250° C., preferably about 0 to 180° C. The reaction time is generally about 5 min to 72 hr, preferably about 5 min to 24 hr.

This reaction may be carried out under atmosphere such as nitrogen, argon and the like, as necessary.

<Reaction Scheme 7>

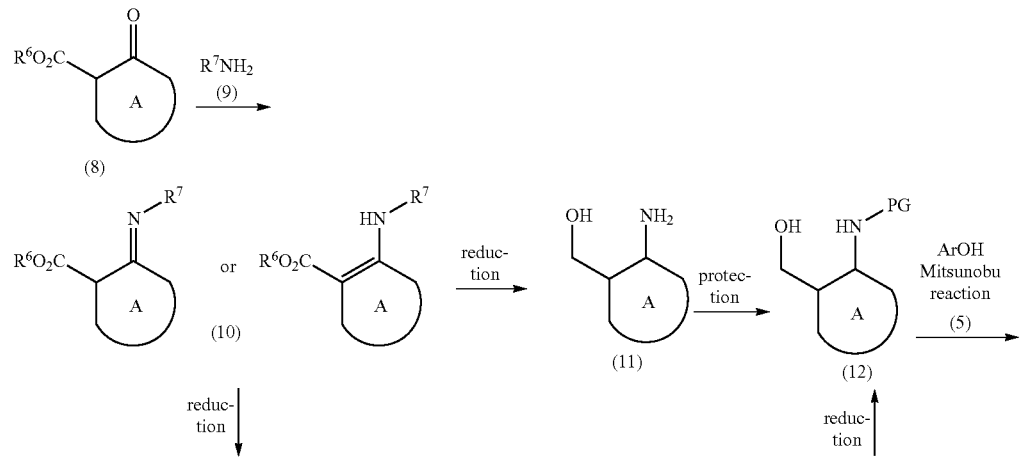

-continued

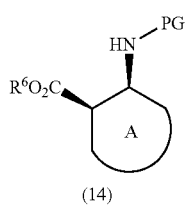

(14)

isomerization →

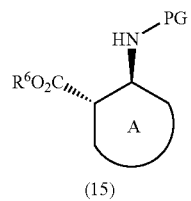

(15)

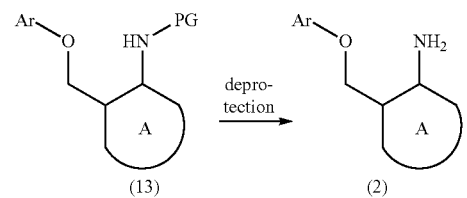

(13)

deprotection →

(2)

wherein $R^6$ is an optionally substituted $C_{1-6}$ alkyl group, $R^7$ is an optionally substituted $C_{1-6}$ alkyl group or an optionally substituted $C_{1-3}$ alkoxy group or a protecting group, and the other symbols are as defined above.

Compound (2) can be produced according to the method shown in Reaction Scheme 7 or a method analogous thereto.

Compound (8) may be commercially available product, or can be produced according to the methods described in Examples or Reference Examples or a method known per se, for example, the method described in Tetrahedron, vol. 57, pages 9045-9048 (2001), Bioorganic Medicinal Chemistry Letter, vol. 9, 1831-1836 (1999), ORGANIC FUNCTIONAL GROUP PREPARATIONS, 2nd edition, Academic Press Inc., 1989, or Comprehensive Organic Transformations: A Guide to Functional Group Preparations, 2nd edition, Wiley-VCH, 1999, Jikken Kagaku Koza (Courses in Experimental Chemistry) (the Chemical Society of Japan ed.), Jikken Kagaku Koza (the Chemical Society of Japan ed.) or the like in or a method analogous thereto.

Compound (10) can be produced, for example, by subjecting compound (8) to a dehydrating condensation reaction with compound (9). This reaction is carried out, for example, by reacting compound (8) with compound (9) in an inert solvent (e.g., ethyl acetate, toluene, pyridine, tetrahydrofuran, ethanol, methanol, water etc.).

Compound (11) can be produced, for example, by subjecting compound (10) wherein $R^7$ is an optionally substituted $C_{1-3}$ alkoxy group to a reduction reaction. This reaction is carried out, for example, by reacting compound (10) in the presence of a reducing agent (e.g., sodium bis(2-methoxyethoxy)aluminum hydride, diisobutylaluminum hydride, lithium aluminum hydride, sodium aluminum hydride etc.) in an inert solvent (e.g., toluene, tetrahydrofuran, diethyl ether etc.).

Compound (12) can be produced, for example, by subjecting compound (11) to a protection reaction.

Compound (14) can be produced, for example, by subjecting compound (10) wherein $R^7$ is a protecting group (PG) to a reduction reaction. This reaction is carried out, for example, by reacting compound (10) in the presence of a reducing agent (for example, sodium borohydride, lithium borohydride, sodium triacetoxyborohydride etc.) in an inert solvent (e.g., methanol, ethanol, tetrahydrofuran etc.). Where necessary, compound (14) can be subjected to a deprotection and protection reaction according to the method described in the method known per se, for example, Greene's PROTECTIVE GROUPS in ORGANIC SYNTHESIS, 4th Edition, Wiley-Interscience, 2006 or the like, the method described in Example or the like to convert the protecting group (PG) and the like.

Compound (15) can be produced, for example, by isomerization of cis isomer compound (14) to the corresponding trans isomer compound. This reaction is carried out, for example, by reacting compound (14) in the presence of a base (e.g., sodium methoxide, sodium ethoxide, potassium tert-butoxide, sodium hydride etc.) in an inert solvent (e.g., tetrahydrofuran, methanol, ethanol etc.).

Compound (12) can also be produced, for example, by subjecting compound (15) to a reduction reaction. This reaction is carried out, for example, by reacting compound (15) in the presence of a reducing agent (for example, sodium bis(2-methoxyethoxy)aluminum hydride, diisobutylaluminum hydride, lithium aluminum hydride, sodium aluminum hydride etc.) in an inert solvent (e.g., toluene, tetrahydrofuran, diethyl ether etc.).

Compound (13) can be produced, for example, by subjecting compound (12) to the Mitsunobu reaction with compound (5). This reaction is carried out, for example, in the same manner as in the production method of compound (I') in Reaction Scheme 2.

Compound (2) can be produced, for example, by subjecting compound (13) to deprotection.

<Reaction Scheme 8>

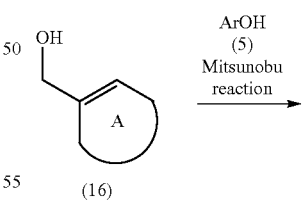

(16)

ArOH
(5)
Mitsunobu reaction →

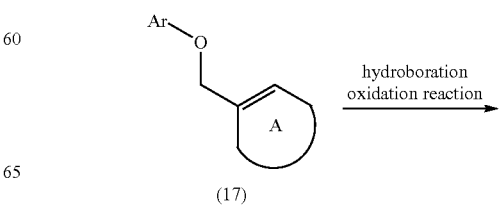

(17)

hydroboration oxidation reaction →

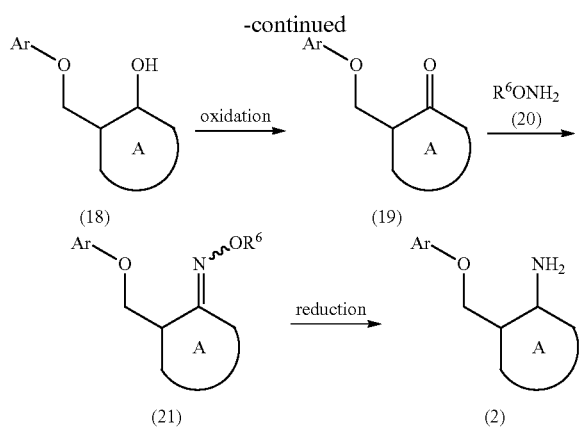

wherein each symbol is as defined above.

Compound (2) can also be produced according to the method shown in Reaction Scheme 8 or a method analogous thereto.

Compound (16) may be commercially available product, or can be produced according to the methods described in Examples or Reference Examples or a method known per se, for example, the method described in Chemical & Pharmaceutical Bulletin, vol. 37, pages 2379-2390 (1989), or a method analogous thereto.

Compound (17) can be produced, for example, by subjecting compound (16) to the Mitsunobu reaction with compound (5). This reaction is carried out, for example, in the same manner as in the production method of compound (I') in Reaction Scheme 2.

Compound (18) can be produced, for example, by subjecting compound (17) to a hydroboration-oxidation reaction. This reaction is carried out, for example, by reacting compound (17) in the presence of a borane compound (e.g., borane-tetrahydrofuran complex, 9-borabicyclo[3.3.1]nonane etc.) in an inert solvent (e.g., tetrahydrofuran, diethyl ether etc.), adding a base (e.g., aqueous sodium hydroxide solution, aqueous potassium hydroxide solution etc.), and then reacting the resulting compound with an oxidant (e.g., aqueous hydrogen peroxide etc.).

Compound (19) can be produced, for example, by subjecting compound (18) to an oxidation reaction. This reaction is carried out, for example, by reacting compound (18) in the presence of an oxidant (e.g., pyridine sulfur trioxide complex, a mixture of dimethylsulfoxide and oxalyl chloride, Dess-Martin reagent, Jones reagent, pyridinium chlorochromate, pyridinium dichromate, tetrabutylammonium perruthenate etc.) in an inert solvent (toluene, acetonitrile, tetrahydrofuran, diethyl ether, dichloromethane, ethyl acetate, dimethyl sulfoxide etc.).

Compound (21) can be produced, for example, by subjecting compound (19) to a dehydrating condensation reaction with compound (20). This reaction is carried out, for example, in the same manner as in the production method of compound (10) in Reaction Scheme 6.

In Reaction Scheme 8, compound (2) can be produced, for example, by subjecting compound (21) to a reduction reaction. This reaction is carried out, for example, in the same manner as in the production method of compound (11) in Reaction Scheme 7. This reaction is also carried out, for example, by reacting compound (21) in the presence of a metal catalyst (palladium-carbon, palladium black, palladium chloride, platinum oxide, platinum black, platinum-palladium, Raney nickel, Raney cobalt etc.) and a hydrogen source (hydrogen gas, formic acid, water etc.) in an inert solvent (toluene, tetrahydrofuran, diethyl ether, ethyl acetate, methanol, ethanol etc.).

<Reaction Scheme 9>

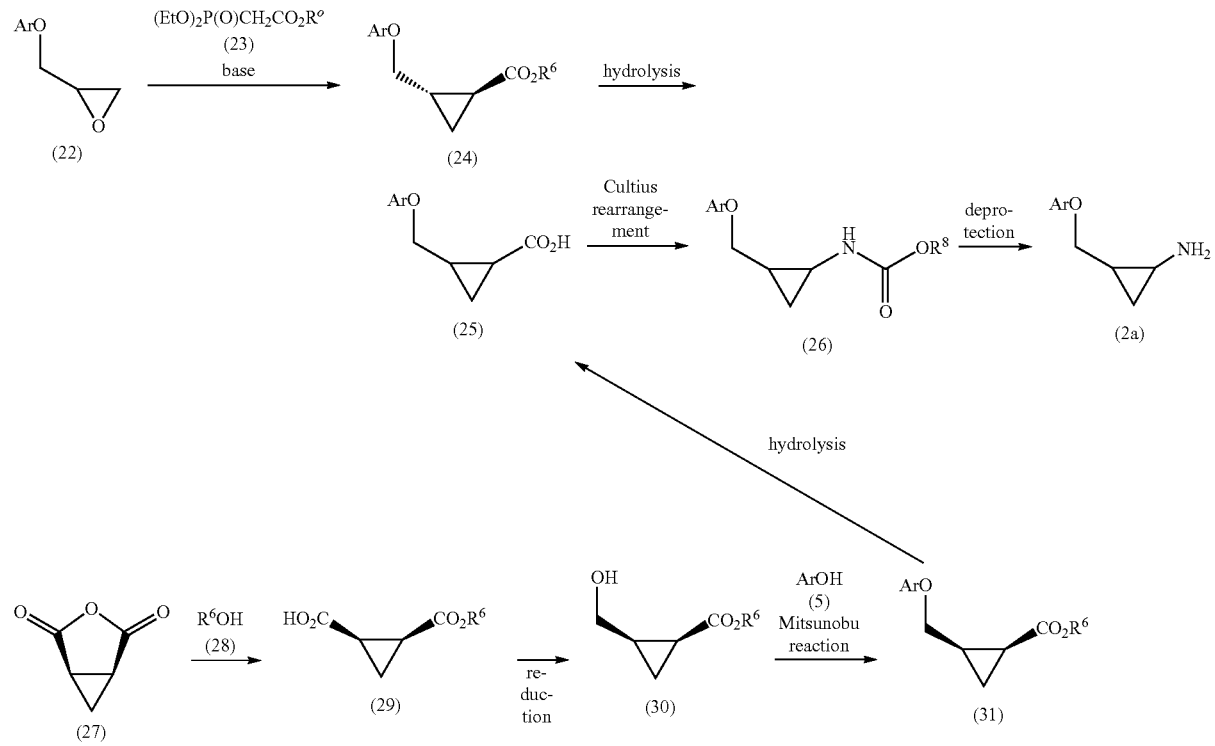

wherein R⁸ is an optionally substituted $C_{1-6}$ alkyl group, and the other symbols are as defined above.

Compound (2a) can be produced according to the method shown in Reaction Scheme 9 or a method analogous thereto. Compound (2a) is encompassed in compound (2).

Compound (22) may be commercially available product, or can be produced according to a method known per se, or a method analogous thereto.

Compound (24) can be produced, for example, by reacting compound (22) with compound (23). This reaction is carried out, for example, by reacting compound (22) with compound (23) in the presence of a base (e.g., sodium hydride, n-butyllithium etc.) in an inert solvent (e.g., tetrahydrofuran, N,N-dimethylformamide etc.).

Compound (27) may be commercially available product, or can be produced according to a method known per se, or a method analogous thereto.

Compound (29) can be produced, for example, by reacting compound (27) with compound (28). This reaction is carried out, for example, by reacting compound (27) with compound (28) as a solvent.

Compound (30) can be produced, for example, by subjecting compound (29) to a reduction reaction. This reaction is carried out, for example, by activating compound (29) with a halogenated formate (e.g., ethyl chloroformate etc.) and the like in the presence of a base (e.g., 4-methylmorpholine etc.) in an inert solvent (e.g., tetrahydrofuran, methanol, ethanol etc.), and then reacting the resulting compound with a reducing agent (e.g., sodium borohydride, lithium borohydride, sodium triacetoxyborohydride etc.)

Compound (31) can be produced, for example, by subjecting compound (30) to the Mitsunobu reaction with compound (5). This reaction is carried out, for example, in the same manner as in the production method of compound (I') in Reaction Scheme 2.

Compound (25) can be produced, for example, by subjecting compound (24) or compound (31) to hydrolysis. This reaction is carried out, for example, by reacting compound (24) or compound (31) in the presence of a base (e.g., sodium hydroxide, lithium hydroxide etc.) in an inert solvent (e.g., tetrahydrofuran, methanol, ethanol, water etc.).

Compound (26) can be produced, for example, by subjecting compound (25) to the Curtius rearrangement reaction. This reaction is carried out, for example, by reacting compound (25) with an azidophosphate ester (e.g., diphenyl azidophosphate) in the presence of a base (e.g., triethylamine, pyridine etc.) in an alcohol solvent.

Compound (2a) can be produced, for example, by subjecting compound (26) to deprotection.

-continued

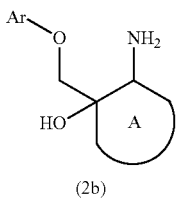

(2b)

wherein PG¹ is a primary amino-protecting group such as phthalimido group and the like, and the other symbols are as defined above.

Compound (2b) can be produced according to the method shown in Reaction Scheme 10 or a method analogous thereto. Compound (2b) is encompassed in compound (2).

Compound (32) can be produced according to the methods described in Examples or Reference Examples, a method known per se or a method analogous thereto.

Compound (33) can be produced, for example, by subjecting compound (32) to the Wittig reaction. This reaction is carried out, for example, by reacting compound (33) with halogenated alkyltriphenylphosphonium (e.g., triphenylphosphonium methyl bromide etc.) in the presence of a base (e.g., potassium tert-butoxide, sodium hydride etc.) in an inert solvent (e.g., tetrahydrofuran, N,N-dimethylformamide etc.).

Compound (34) can be produced, for example, by subjecting compound (33) to an oxidation reaction. This reaction is carried out, for example, by reacting compound (33) in the presence of an oxidant (e.g., aqueous hydrogen peroxide, sodium percarbonate, methachlorobenzoic acid etc.) in an inert solvent (e.g., ethyl acetate, acetonitrile, THF, water etc.).

Compound (35) can be produced, for example, by subjecting compound (34) to a nucleophilic substitution reaction with compound (5). This reaction is carried out, for example, by reacting compound (34) with compound (5) in the presence of a base (e.g., potassium carbonate, sodium hydride, potassium hydroxide, potassium tert-butoxide, triethylamine, 1,8-diazabicyclo[5.4.0]undec-7-ene etc.) in an inert solvent (e.g., N,N-dimethylformamide, acetonitrile, tetrahydrofuran, toluene, dimethyl sulfoxide, water etc.). Where necessary, a phase-transfer catalyst (e.g., tetrabutylammonium bromide, tetrabutylammonium hydrogensulfate etc.) may be used.

Compound (2b) can be produced, for example, by subjecting m compound (35) to deprotection.

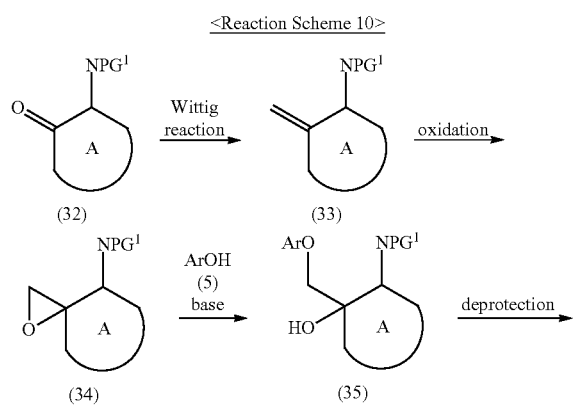

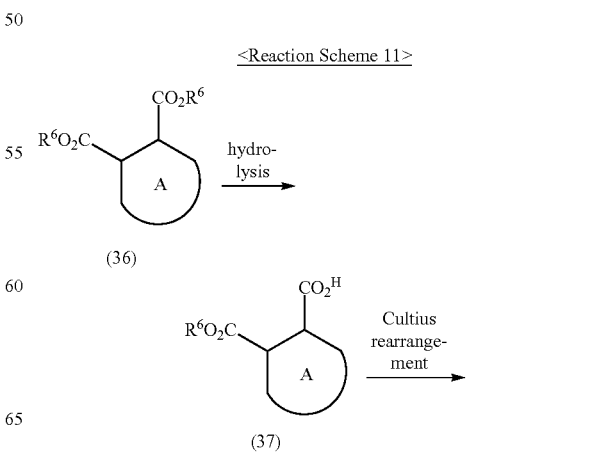

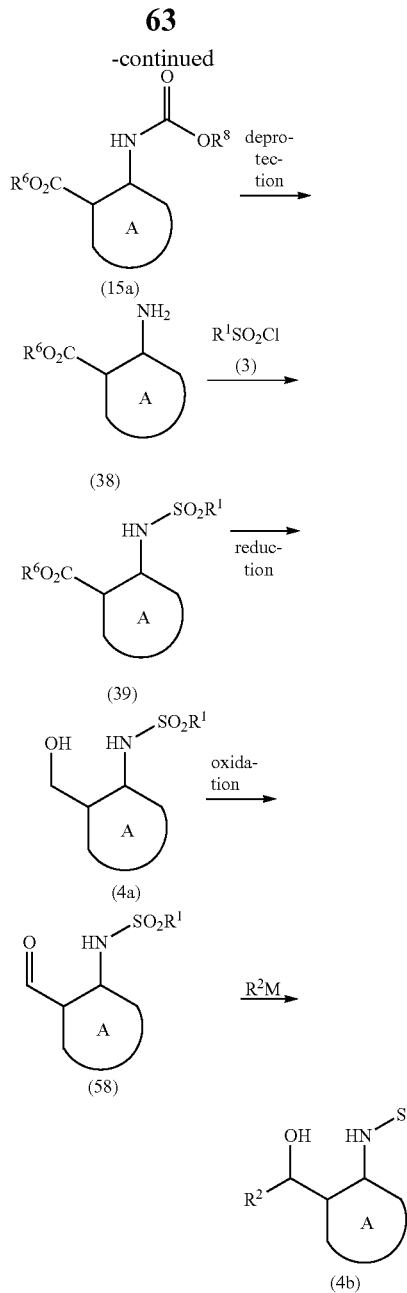

tion. This reaction is carried out, for example, in the same manner as in the production method of compound (26) in Reaction Scheme 9. Compound (15a) is encompassed in compound (15).

Compound (38) can be produced, for example, by subjecting compound (15a) to deprotection.

Compound (39) can be produced, for example, by subjecting compound (38) to a sulfonylation reaction with compound (3). This reaction is carried out, for example, in the same manner as in the production method of compound (I') in Reaction Scheme 1.

Compound (4a) can be produced, for example, by subjecting compound (39) to a reduction reaction. This reaction is carried out, for example, in the same manner as in the production method of compound (11) in Reaction Scheme 7.

Compound (58) can be produced, for example, by subjecting compound (4a) to an oxidation reaction. This reaction is carried out, for example, in the same manner as in the production method of compound (19) in Reaction Scheme 8.

Compound (4b) can be produced, for example, by subjecting compound (58) to an addition reaction with an organic metal reagent ($R^2M$). This reaction is carried out, for example, by reacting compound (58) with an organic metal reagent ($R^2M$) (e.g., organic lithium reagent, Grignard reagent, organic zinc reagent and the like) in an inert solvent (e.g., tetrahydrofuran, toluene etc.).

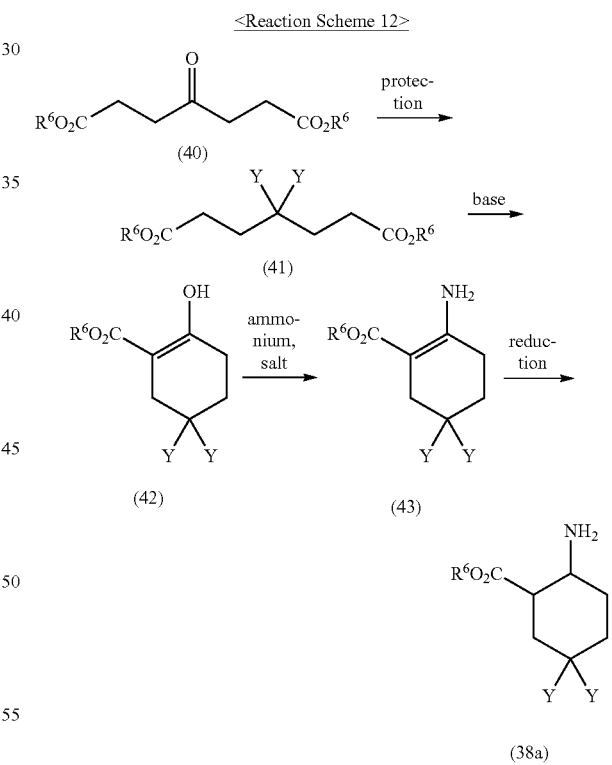

wherein M is a metal (e.g., potassium, sodium, lithium, magnesium, copper, mercury, zinc, thallium, boron, tin or the like, which is optionally complexed, and the other symbols are as defined above.

Compounds (4a) and (4b) can be produced according to the method shown in Reaction Scheme 11 or a method analogous thereto. Compounds (4a) and (4b) are encompassed in compound (4).

Compound (36) may be commercially available product, or can be produced according to the methods described in Examples or Reference Examples, a method known per se, or a method analogous thereto.

Compound (37) can be produced, for example, by subjecting compound (36) to hydrolysis. This reaction is carried out, for example, in the same manner as in the production method of compound (25) in Reaction Scheme 9.

Compound (15a) can be produced, for example, by subjecting compound (37) to the Curtius rearrangement reaction.

wherein Y is a halogen atom, or an alkoxy group optionally forming a ring, and the other symbols are as defined above.

Compound (38a) can be produced according to the method shown in Reaction Scheme 12 or a method analogous thereto. Compound (38a) is encompassed in compound (38).

Compound (40) may be commercially available product, or can be produced according to a method known per se, or a method analogous thereto.

Compound (41) may be commercially available product, or can be produced according to a method known per se, or a method analogous thereto.

Compound (41) can also be produced, for example, by the protection reaction of the carbonyl group of compound (40) using an alkylene glycol (e.g., ethylene glycol etc.).

Compound (42) can be produced, for example, by subjecting compound (41) to an intramolecular cyclization reaction. This reaction is carried out, for example, by reacting compound (41) in the presence of a base (e.g., potassium carbonate, sodium hydride, potassium hydroxide, potassium tert-butoxide, triethylamine, 1,8-diazabicyclo[5.4.0]undec-7-ene etc.) in an inert solvent (e.g., (N,N-dimethylformamide, acetonitrile, tetrahydrofuran, toluene etc.).

Compound (43) can be produced, for example, by subjecting compound (42) to a dehydrating condensation reaction with an ammonium salt (e.g., ammonium acetate etc.). This reaction is carried out, for example, in the same manner as in the production method of compound (10) in Reaction Scheme 7.

Compound (38a) can be produced, for example, by subjecting compound (43) to a reduction reaction. This reaction is carried out, for example, in the same manner as in the production method of compound (14) in Reaction Scheme 7. Where necessary, the reaction may be carried out in the presence of an acid (e.g., trifluoroacetic acid, acetic acid etc.).

-continued

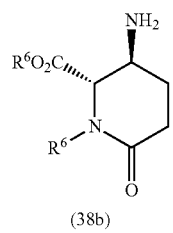

wherein each symbol is as defined above.

Compound (38b) can be produced according to the method shown in Reaction Scheme 13 or a method analogous thereto. Compound (38b) is encompassed in compound (38).

Compounds (44) and (45) may be commercially available product, or can be produced according to a method known per se, or a method analogous thereto.

Compound (46) can be produced, for example, by subjecting compound (44) to a coupling reaction (amidation reaction) with compound (45). This reaction is carried out, for example, by reacting compound (44) with compound (45) in an inert solvent (e.g., N,N-dimethylformamide, acetonitrile, dichloromethane, tetrahydrofuran etc.). Where necessary, the reaction may be carried out in the presence of a base (e.g., triethylamine, pyridine etc.).

Compound (47) can be produced, for example, by subjecting compound (46) to an intramolecular cyclization reaction. This reaction is carried out, for example, in the same manner as in the production method of compound (42) in Reaction Scheme 12.

Compound (49) can be produced, for example, by subjecting compound (47) to a dehydrating condensation reaction with compound (48). This reaction is carried out, for example, in the same manner as in the production method of compound (10) in Reaction Scheme 7.

Compound (50) can be produced, for example, by subjecting compound (49) to a reduction reaction. This reaction is carried out, for example, in the same manner as in the production method of compound (14) in Reaction Scheme 7. Where necessary, the reaction may be carried out in the presence of an acid (e.g., trifluoroacetic acid, acetic acid etc.).

Compound (51) can be produced, for example, by subjecting compound (50) to an isomerization reaction. This reaction is carried out, for example, in the same manner as in the production method of compound (15) in Reaction Scheme 7.

Compound (38b) can be produced, for example, by subjecting compound (50) to deprotection.

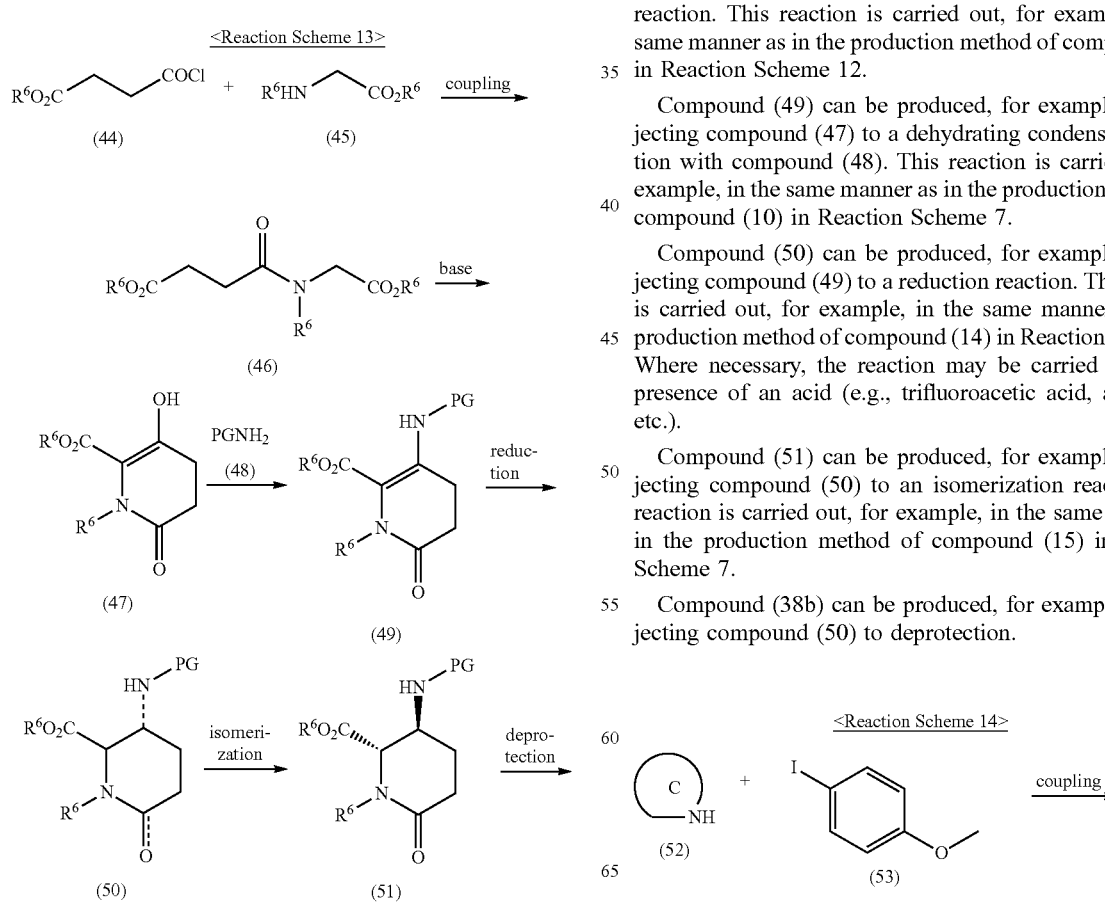

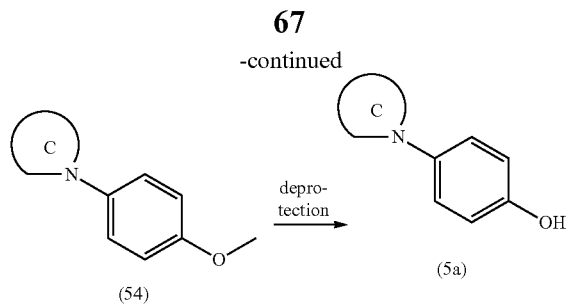

(54)  (5a)

wherein ring C is a 5- to 7-membered heterocycle.

Compound (5a) can be produced according to the method shown in Reaction Scheme 14 or a method analogous thereto. Compound (5a) is encompassed in compound (5).

Compounds (52) and (53) may be commercially available product, or can be produced according to a method known per se, or a method analogous thereto.

Compound (54) can be produced, for example, by subjecting compound (52) to a coupling reaction with compound (53). This reaction is carried out, for example, by reacting compound (52) with compound (53) in the presence of a metal catalyst (e.g., a combination of bistriphenylphosphine dichloropalladium(II) and copper(I)iodide, etc.) and a base (e.g., triethylamine, pyridine etc.) in an inert solvent (e.g., toluene, tetrahydrofuran, N,N-dimethylformamide etc.), generally, under an inert gas (e.g., argon, nitrogen etc.) atmosphere.

Compound (5a) can be produced, for example, by subjecting compound (54) to deprotection.

<Reaction Scheme 15>

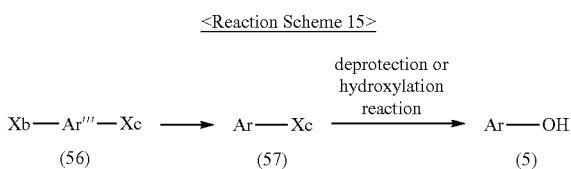

(56)  (57)  (5)

wherein Ar''' is an optionally substituted 3- to 10-membered aromatic ring, Xb is a functional group or hydrogen, Xc is a protected hydroxyl group (e.g., a benzyloxy group, a methoxy group, a t-butoxy group etc.) or a halogen atom (e.g., fluorine, chlorine, bromine, iodine etc.), and the other symbols are as defined above.

Examples of the "functional group" for Xb include a halogen atom (e.g., fluorine, chlorine, bromine, iodine etc.), a boronyl group, an optionally substituted $C_{1-6}$ alkylboranyl group, an optionally substituted $C_{2-6}$ alkenylboranyl group, an optionally substituted $C_{1-6}$ alkoxyboranyl group, an optionally substituted $C_{6-14}$ arylboranyl group, an optionally substituted $C_{1-6}$ alkylstannyl group (e.g., tributylstannyl and the like), an optionally substituted $C_{2-6}$ alkenylstannyl group, an optionally substituted $C_{6-14}$ arylstannyl group, a metal-containing substituent (e.g., magnesium halide, zinc halide etc.), hydrogen, an α-bromoacetyl group, an α-chloroacetyl group, a haloformyl group, a formyl group, a halogenated alkyl group, a carboxyl group, an optionally halogenated $C_{1-6}$ alkylsulfonyloxy (e.g., methanesulfonyloxy, ethanesulfonyloxy, trichloromethanesulfonyloxy, trifluoromethanesulfonyloxy [triflate] etc.), an optionally substituted $C_{6-14}$ arylsulfonyloxy and the like. Examples of the "optionally substituted $C_{6-14}$ arylsulfonyloxy" include $C_{6-14}$ arylsulfonyloxy optionally having 1 to 3 substituents selected from $C_{1-6}$ alkyl (e.g., methyl, ethyl, propyl, isopropyl, butyl, isobutyl, sec-butyl, tert-butyl, pentyl, hexyl etc.), $C_{1-6}$ alkoxy (e.g., methoxy, ethoxy, propoxy, isopropoxy, butoxy, isobutoxy, sec-butoxy, pentyloxy, hexyloxy etc.) and nitro, and the like, Specific examples thereof include benzenesulfonyloxy, m-nitrobenzenesulfonyloxy, p-toluenesulfonyloxy, naphthylsulfonyloxy and the like.

Compound (57) may be a commercially available product or can be produced from compound (56) according to a method described in Examples or Reference Examples, or a method known per se, which is described in ORGANIC FUNCTIONAL GROUP PREPARATIONS, 2nd edition, Academic Press Inc., 1989 or Comprehensive Organic Transformations: A Guide to Functional Group Preparations, 2nd edition, Wiley-VCH, 1999, Shin Jikken Kagaku Koza (edited by the Chemical Society of Japan), Jikken Kagaku Koza (edited by the Chemical Society of Japan) or the like (e.g., Grignard reaction, cyanation reaction, hydrolysis, dehydrating reaction, halogenation, coupling reaction, oximation reaction, reduction reaction, oxidation reaction, amidation reaction, alkylation reaction, condensation reaction, protection reaction, deprotection and the like) or a method analogous thereto.

Compound (56) may be a commercially available product or can be produced according to a method described in Examples or Reference Examples, or a method known per se, which is described in ORGANIC FUNCTIONAL GROUP PREPARATIONS, 2nd edition, Academic Press Inc., 1989 or Comprehensive Organic Transformations: A Guide to Functional Group Preparations, 2nd edition, Wiley-VCH, 1999, Shin Jikken Kagaku Koza (edited by the Chemical Society of Japan), Jikken Kagaku Koza (edited by the Chemical Society of Japan) or the like (e.g., Grignard reaction, cyanation reaction, hydrolysis, dehydrating reaction, halogenation, coupling reaction, oximation reaction, reduction reaction, oxidation reaction, amidation reaction, alkylation reaction, condensation reaction, protection reaction, deprotection and the like) or a method analogous thereto.

Compound (5) can be produced, for example, by subjecting compound (57) to deprotection or a hydroxylation reaction.

The hydroxylation reaction can be carried out in the presence of a base, a metal catalyst and a ligand.

Examples of the "base" include inorganic bases such as sodium hydroxide, potassium hydroxide, barium hydroxide and the like, and the like.

The amount of the "base" to be used is about 0.1 to 30 mol, preferably 0.8 to 10 mol, per 1 mol of compound (57).

Examples of the "metal catalyst" include complex composed of a metal such as palladium and the like and a ligand, and the like, and specific example thereof include tris (dibenzylideneacetone)dipalladium (0) and the like.

Examples of the ligand include 2-(di-tert-butylphosphino)-2',4',6'-triisopropyl-1,1'-biphenyl, triphenylphosphine, 2,2'-bis(diphenylphosphino)-1,1'-binaphthyl, 2-(di-tert-butylphosphino)biphenyl, 2-(dicyclohexylphosphino) biphenyl, (dicyclohexylphosphino)-2',6'-dimethoxy-1,1'-biphenyl, 2-(dicyclohexylphosphino)-2',4',6'-triisopropyl-1, 1'-biphenyl, 2-(dicyclohexylphosphino)-2'-(N,N-dimethylamino)biphenyl, 1,1'-bis(diphenylphosphino) ferrocene, tri-tert-butylphosphine, tricyclohexylphosphine, (9,9-dimethyl-9H-xanthene-4,5-diyl)bis(diphenylphosphine) and the like.

The amount of "metal catalyst" to be used is generally about 0.01 to 1000 wt %, preferably about 1 to 20 wt %, relative to compound (57). The amount of the "ligand" to be used is about 0.01 to 30 mol, preferably 0.01 to 1.0 mol, per 1 mol of compound (57). When desired, this reaction can also be carried out under microwave irradiation by using a microwave irradiation apparatus (e.g., INITIATOR manufactured by Biotage, etc.).

This reaction is advantageously carried out without solvent or in an inert solvent to the reaction. The solvent is not particularly limited as long as the reaction proceeds, and the preferable examples thereof include alcohols such as methanol, ethanol, 1-propanol, 2-propanol, 1-butanol, 2-methyl-2-propanol and the like; ethers such as diethyl ether, tetrahydrofuran, dioxane, 1,2-dimethoxyethane and the like; hydrocarbons such as benzene, toluene, cyclohexane, hexane and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; nitrogen-containing aromatic hydrocarbons such as pyridine, lutidine, quinoline and the like; water and the like, a mixed solvent thereof and the like is preferable. The reaction temperature is about −40 to 250° C., preferably about 0 to 180° C. The reaction time is generally about 5 min to 72 hr, preferably about 5 min to 24 hr.

This reaction may be carried out under atmosphere such as nitrogen, argon and the like, as necessary.

In the thus-obtained compounds (I), (I'), (I") and (Ia-h), a functional group in a molecule can also be converted to the object functional group by combining known chemical reactions. Examples of the chemical reaction include oxidation reaction, reduction reaction, alkylation reaction, hydrolysis, amination reaction, amidation reaction, esterification reaction, aryl coupling reaction, and deprotection and the like.

In each of the above-mentioned reactions, when the starting compounds have an amino group, a carboxyl group, a hydroxy group or a hydroxyl group as a substituent, such groups may be protected with the protecting groups generally used in peptide chemistry, etc. In such case, if necessary, such protecting groups can be removed after the reactions to obtain the objective compounds.

Examples of the amino-protecting group include formyl, and $C_{1-6}$ alkylcarbonyl (e.g., acetyl, ethylcarbonyl etc.), phenylcarbonyl, $C_{1-6}$ alkoxy-carbonyl (e.g., methoxycarbonyl, ethoxycarbonyl, tert-butoxycarbonyl etc.), phenyloxycarbonyl, $C_{7-10}$ aralkyl-carbonyl (e.g., benzylcarbonyl etc.), trityl, phthaloyl, N,N-dimethylaminomethylene and the like, each of which optionally has substituent(s). Examples of the substituent of the "amino-protecting group" include a halogen atom (e.g., fluorine, chlorine, bromine, iodine), $C_{1-6}$ alkyl-carbonyl (e.g., methylcarbonyl, ethylcarbonyl, butylcarbonyl etc.), a nitro group and the like, wherein the number of the substituents is 1-several (e.g., 3).

Examples of the carboxyl-protecting group include a $C_{1-6}$ alkyl group, a $C_{7-11}$ aralkyl group (e.g., benzyl), a phenyl group, a trityl group, a substituted silyl group (e.g., trimethylsilyl, triethylsilyl, dimethylphenylsilyl, tert-butyldimethylsilyl, tert-butyldiethylsilyl), and a $C_{2-6}$ alkenyl group (e.g., 1-allyl) and the like. These groups are optionally substituted by 1 to 3 halogen atoms, a $C_{1-6}$ alkoxy group, a nitro group etc.

Examples of the hydroxy-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 halogen atoms, a $C_{1-6}$ alkyl group, a $C_{1-6}$ alkoxy group, a nitro group etc.

Examples of the carbonyl-protecting group include cyclic acetal (e.g., 1,3-dioxane), non-cyclic acetal (e.g., di-$C_{1-6}$ alkylacetal) and the like.

Removal of the above-mentioned protecting group can be performed according to a known method, for example, the method described in Protective Groups in Organic Synthesis, John Wiley and Sons (1980) and the like. For example, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method and the like can be used.

Compounds (I), (I'), (I") and (Ia-h) can be isolated and purified by a known means, for example, solvent extraction, liquid conversion, phase transfer, concentration, crystallization, recrystallization, chromatography and the like. In addition, the starting compounds of compounds (I), (I'), (I") and (Ia-h) and salts thereof can be isolated and purified by a known means as mentioned above, and the like, or may be used, in the form of a reaction mixture without isolation, as a starting material for the next step.

In any case, where desired, compound (I) can be synthesized by using known deprotection, acylation, alkylation, hydrogenation, oxidation, reduction, carbon chain extension and substituent exchange reaction alone or in a combination of two or more thereof.

When compound (I) has isomers such as tautomer, optical isomer, stereoisomer, positional isomer, rotational isomer and the like, and any isomers and mixtures are encompassed in the compound (I). For example, when compound (I) has an optical isomer, an optical isomer separated from a racemate is also encompassed in the compound (I). These isomers can be obtained as independent products by a synthesis means or a separation means (concentration, solvent extraction, column chromatography, recrystallization and the like) known per se.

Compound (I) may be a crystal, and both a single crystal and crystal mixtures are encompassed in the compound (I). Crystals can be produced by crystallization according to crystallization methods known per se.

Compound (I) may be a pharmaceutically acceptable cocrystal or cocrystal salt. Here, the cocrystal or cocrystal salt means a crystalline substance consisting of two or more particular substances which Are solids at room temperature, each having different physical properties (e.g., structure, melting point, heat of melting, hygroscopicity, solubility, stability etc.). The cocrystal and cocrystal salt can be produced by cocrystallization method known per se.

Compound (I) may be a solvate (e.g., hydrate etc.) or a non-solvate (e.g., anhydride etc.), both of which are encompassed in the compound (I).

A compound labeled with or substituted by an isotope (e.g., $^2H$, $^3H$, $^{11}C$, $^{14}C$, $^{18}F$, $^{35}S$, $^{125}I$ and the like) is also encompassed in the compound (I) and the like. Compound (I) labeled with or substituted by an isotope can be used, for example, as a tracer used for Positron Emission Tomography (PET) (PET tracer), and is is useful in the field of medical diagnosis and the like.

A prodrug of compound (I) means a compound which is converted to the compound (I) with a reaction due to an enzyme, an gastric acid, etc. under the physiological condition in the living body, that is, a compound which is converted to the compound (I) with oxidation, reduction, hydrolysis, etc. according to an enzyme; a compound which is converted to the compound (I) by hydrolysis etc. due to gastric acid, etc. A prodrug for compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation, dimethylaminomethylcarbonylation, etc.); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I) by a method known per se.

The prodrug of compound (I) may be a compound that converts to compound (I) under physiological conditions as described in Development of Pharmaceutical Products, vol. 7, Molecule Design, 163-198, Hirokawa Shoten (1990).

Compound (I) and a prodrug thereof (hereinafter sometimes to be simply abbreviated as the compound of the present invention) show a superior AMPA receptor function enhancing action such as neural activation, enhancement of neural plasticity, enhancement of neurogenesis, enhancement of BDNF production and the like. Thus, they are also useful as a safe medicament based on these actions.

The compound of the present invention having a superior AMPA receptor function enhancing action is useful for mammals (e.g., mouse, rat, hamster, rabbit, cat, dog, bovine, sheep, monkey, human etc.) as an agent for the prophylaxis or treatment of diseases, for example, (1) psychiatric diseases [e.g., depression, major depression, bipolar depression, dysthymic disorder, emotional disorder (seasonal affective disorder and the like), recurrent depression, postpartum depression, stress disorder, depression symptom, mania, anxiety, generalized anxiety disorder, anxiety syndrome, panic disorder, phobia, social phobia, social anxiety disorder, obsessive disorder, post-traumatic stress syndrome, post-traumatic stress disorder, Tourette syndrome, autism, fragile X syndrome, Rett syndrome, adjustment disorder, bipolar disorder, neurosis, schizophrenia (e.g., positive symptom, negative symptom, cognitive impairment), neurosis, chronic fatigue syndrome, anxiety neurosis, compulsive neurosis, panic disorder, epilepsy, anxiety, anxious mental state, emotional abnormality, cyclothymia, nervous erethism, faint, addiction, low sex drive, attention deficit hyperactivity disorder (ADHD), psychotic major depression, refractory major depression, treatment-resistant depression], (2) neurodegenerative diseases [e.g., Alzheimer's disease, Alzheimer-type senile dementia, Parkinson's disease, Huntington chorea, multi-infarct dementia, frontotemporal dementia, frontotemporal dementia Parkinson's Type, progressive supranuclear palsy, Pick's syndrome, Niemann-Pick syndrome, corticobasal degeneration, Down's disease, vascular dementia, postencephalitic parkinsonism, Lewy body dementia, HIV dementia, amyotrophic lateral sclerosis (ALS), motor neurogenesis disease (MND), Creutzfeldt-Jakob disease or prion disease, cerebral palsy, progressive supranuclear palsy, multiple sclerosis], (3) age-related cognition memory disorders [e.g., age-related memory disorders, senile dementia]

(4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (5) respiratory depression caused by anesthetics, traumatic disease, or neurodegenerative disease and the like, (6) traumatic brain injury, cerebral apoplexy, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug withdrawal, migraine, stress headache, catatonic headache, diabetic neuropathy, obesity, diabetes, muscular spasm, Meniere's disease, autonomic ataxia, alopecia, glaucoma, hearing loss, hypertension, cardiac disease, tachycardia, congestive cardiac failure, hyperventilation, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, stress vomiting, stress ulcer, diarrhea, constipation, postoperative ileus, and the like.

The compound of the present invention is particularly useful as an agent for the prophylaxis or treatment of diseases such as depression, Alzheimer's disease, schizophrenia, attention deficit hyperactivity disorder (ADHD) and the like.

Since the compound of the present invention has a superior AMPA receptor function enhancing action, a superior treatment effect for the above-mentioned diseases can be expected.

The compound of the present invention is superior in in vivo kinetics (e.g., plasma drug half-life, biological availability and the like), shows low toxicity (e.g., more superior as a medicament in terms of acute toxicity, chronic toxicity, genetic toxicity, reproductive toxicity, cardiotoxicity, drug interaction, carcinogenicity, cellular disorder, phototoxicity and the like), and is superior in physicochemical properties (e.g., solubility, dissolution rate, membrane permeability, coefficient of partition, stability to heat or humidity, photostability and the like). The compound of the present invention is directly used as a medicament or a pharmaceutical composition mixed with a pharmaceutically acceptable carrier or the like to be orally or parenterally administered to mammals (e.g., humans, monkeys, cows, horses, pigs, mice, rats, hamsters, rabbits, cats, dogs, sheep and goats) in safety. Examples of the "parenteral administration route" include intravenous, intramuscular, subcutaneous, intraorgan, intranasal, intradermal, instillation, intracerebral, intrarectal, intravaginal, intraperitoneal, etc. and administration directly to the lesion.

A medicament containing the compound of the present invention can be safely administered solely or by mixing with a pharmaceutically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment; lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal administrations, and administration to the lesion).

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

While the dose of the compound of the present invention varies depending on the administration route, symptom and the like, when, for example, the compound is orally administered to a patient with schizophrenia (adult, body weight 40-80 kg, for example, 60 kg), it is, for example, 0.001-1000, preferably 0.01-100, more preferably 0.1-10, mg/kg body weight/day. This amount can be administered in 1 to 3 portions per day.

As the above-mentioned "pharmaceutically acceptable carrier", any of various organic or inorganic carriers conventionally used as materials for pharmaceutical preparations can be used. For solid preparations, excipient, lubricant, binder and disintegrant are used; and for liquid preparations, solvent, solubilizing agent, suspending agent, isotonicity agent, buffer and soothing agent and the like are used. Where necessary, preparation additive such as preservative, antioxidant, colorant, sweetening agent and the like can be used.

While the pharmaceutical composition varies according to the dosage form, administration method, carrier and the like, it can be produced according to a conventional method by adding the compound of the present invention in a proportion of generally 0.01-100% (w/w), preferably 0.1-95% (w/w), of the total amount of the preparation.

The compound of the present invention can be used in combination with other active ingredients (hereinafter to be abbreviated as concomitant drug).

Examples of the concomitant drug include the following. benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), mirtazapine, trazodone hydrochloride, nefazodone hydrochloride, bupropion hydrochloride, setiptiline maleate, agonist, (buspirone hydrochloride, tandospirone citrate, osemozotan hydrocloride etc.), 5-HT$_3$ antagonist (Cyamemazine etc.), heart non-selective β inhibitor (propranolol hydrochloride, oxprenolol hydrochloride etc.), histamine H$_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (MK-869, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), 5-HT$_{2A}$ antagonist, 5-HT$_{2A}$ inverse agonist, COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autisma, therapeutic drug for chronic fatigue syndrome, therapeutic drug for spasm, therapeutic drug for fibromyalgia syndrome, therapeutic drug for headache, therapeutic drug for insomnia (etizolam, zopiclone, triazolam, zolpidem, ramelteon, indiplon etc.), therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for Alzheimer's disease (donepezil, galanthamine, memantine etc.), therapeutic drug for Parkinson's disease, therapeutic drug for ALS (riluzole etc., neurotrophic factor etc.), therapeutic drug for lipid abnormality such as cholesterol-lowering drug (statin series (pravastatin sodium, atrovastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), apoptosis inhibitor, antiobesity drug, therapeutic drug for diabetes, therapeutic drug for hypertension, therapeutic drug for hypotension, therapeutic drug for rheumatism (DMARD), anticancer agent, therapeutic drug for parathyroid (PTH), calcium receptor antagonist, sex hormone or a derivative thereof (progesterone, estradiol, estradiol benzoate etc.), neuronal differentiation promoter, nerve regeneration promoter, non-steroidal anti-inflammatory drug (meloxicam, tenoxicam, indomethacin, ibuprofen, celecoxib, rofecoxib, aspirin, indomethacin etc.), steroid (dexamethasone, cortisone acetate etc.), anti-cytokine drug (TNF inhibitor, MAP kinase inhibitor etc.), antibody medicament, nucleic acid or nucleic acid derivative, aptamer drug and the like.

By combining the compound of, the present invention and a concomitant drug, a superior effect such as (1) the dose can be reduced as compared to single administration of the compound of the present invention or a concomitant drug, (2) the drug to be combined with the compound of the present invention can be selected according to the condition of patients (mild case, severe case and the like), (3) the period of treatment can be set longer by selecting a concomitant drug having different action and mechanism from the compound of the present invention, (4) a sustained treatment effect can be designed by selecting a concomitant drug having different action and mechanism from the compound of the present invention, (5) a synergistic effect can be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention or a pharmaceutical composition thereof and the concomitant drug or a pharmaceutical composition thereof is not restricted, and the compound of the present invention or the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the combination drug of the present invention is not particularly restricted, and it is sufficient that the compound of the present invention and the concomitant drug are combined in administration. Examples of such administration mode include the following methods: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

A medicament containing the compound of the present invention can be safely administered solely or by mixing with a pharmaceutically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal administrations, and administration to the lesion).

Examples of the pharmacologically acceptable carriers usable for the production of a combination agent in the present invention, various organic or inorganic carrier substances conventionally used as preparation materials can be mentioned. For solid preparations, for example, excipient, lubricant, binder and disintegrant can be used. For liquid preparations, for example, solvent, solubilizing agent, suspending agent, isotonicity agent, buffering agent, soothing agent and the like can be used. Where necessary, conventional preservative, antioxidant, colorant, sweetening agent, adsorbent, wetting agent and the like can be used as appropriate.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

The mixing ratio of the compound of the present invention to the concomitant drug in the combination agent of the present invention can be appropriately selected depending on an administration subject, administration route, diseases and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of additives such as a carrier and the like in the combination agent of the present invention differs depending on the form of a preparation, and usually from about 1 to about 99.99 wt %, preferably from about 10 to about 90 wt %, based on the preparation.

When the compound of the present invention and a concomitant drug are separately formulated into preparations, the contents thereof are similar to the above.

EXAMPLES

The present invention is explained in detail in the following by referring to Examples, Experimental Examples and Preparation Examples. However, the examples do not limit the present invention and the present invention can be modified within the scope of the present invention.

The "room temperature" in the following Examples is generally about 10° C. to about 35° C. The ratio for a mixed solvent is, unless otherwise specified, a volume mixing ratio and % means wt % unless otherwise specified.

In silica gel column chromatography, the indication of NH means use of aminopropylsilane-bonded silica gel. In HPLC (high performance liquid chromatography), the indication of C18 means use of octadecyl-bonded silica gel. The ratio of elution solvents is, unless otherwise specified, a volume mixing ratio.

In the following Examples, the following abbreviations are used.

SFC: supercritical fluid chromatography
HPLC: high performance liquid chromatography
DMSO: dimethyl sulfoxide
Prep-HPLC: preparative-HPLC
$Et_3N$, TEA: triethylamine
LiHMDS: lithium bis(trimethylsilyl)azanide
LDA: lithium diisopropylamide
$LiAlH_4$: lithium aluminum hydride
$NaBH(OAc)_3$: sodium triacetoxyborohydride
DCM: dichloromethane
TFA: trifluoroacetic acid
TFAA: trifluoroacetic anhydride
AcOH: acetic acid
DAST: N,N-diethylaminosulfur trifluoride
CbzCl: benzyl chloroformate
NCS: N-chlorosuccinimide
m-CPBA: 3-chloroperoxybenzoic acid
MeI: iodomethane
IPE, $iPr_2O$: diisopropyl ether
EtOAc, AcOEt, EA: ethyl acetate
THF: tetrahydrofuran
EtOH: ethanol
MeOH: methanol
$Et_2O$: diethyl ether
$Bu_3P$: tributyl phosphine
$Boc_2O$: di-tert-butyl dicarbonate
DBU: 1,8-diazabicyclo[5.4.0]undec-7-ene
KOtBu, tBuOK: potassium tert-butoxide
p-TsOH: p-toluenesulfonyl chloride
$Yb(OTf)_3$: ytterbium(III)trifluoromethanesulfonate
$Rh_2(OAc)_4$: rhodium(II)acetate dimer
$Pd_2(dba)_3$: tris(dibenzylideneacetone)dipalladium (0)
$Pd(Ph_3P)_4$: tetrakis(triphenylphosphane)palladium (0)
Dppf, DPPF: 1,1'-bis(diphenylphosphino)ferrocene
DME: 1,2-dimethoxyethane
ADDP: 1,1'-(azodicarbonyl)dipiperidine
$Et_3SiH$: triethylsilane
TBDPS-Cl: tert-butylchlorodiphenylsilane PPh₃: triphenylphosphine
DPPA: diphenylphosphoryl azide
DEAD: diethyl azodicarboxylate
TBAF: tetra-n-butylammonium fluoride
DMF: N,N-dimethylformamide
MeCN: acetonitrile
NMP: 1-methyl-2-pyrrolidone
N₂CH₂COOEt: ethyl diazoacetate
MsCl: methanesulfonyl chloride
BF₃.Et₂O: boron trifluoride etherate
nBuLi: n-butyl lithium
Ac₂O: acetic anhydride
PE: petroleum ether ¹H NMR (proton nuclear magnetic resonance spectrum) was measured by Fourier-transform type NMR. For the analysis, ACD/SpecManager (trade name) and the like were used. Very mild peaks showing protons of hydroxyl group, amino group and the like are not described. Peaks overlapping with the signals of water, deuterated solvent, and other solvent may not be described in some cases.

MS (mass spectrum) was measured by LC/MS (liquid chromatography mass spectrometer). As the ionization method, ESI (ElectroSpray Ionization) method, or APCI (Atomospheric Pressure Chemical-Ionization) method was used. The data shows Found. Generally, proton-added ion peaks ([M+H]⁺) are observed. Proton-eliminated ion peaks ([M−H]⁻, sometimes indicated as "neg" in the DESCRIPTION) are sometimes observed. When a compound having a tert-butoxycarbonyl group (-Boc) is used, a peak free of a tert-butoxycarbonyl group or tert-butyl group may be observed as a fragment ion. In addition, when a compound having a hydroxyl group (—OH) is used, a peak free of H₂O may be observed as a fragment ion. In the case of a salt, generally, a proton-added ion peak, proton-eliminated ion peak or a fragment ion peak of a free form is observed. Some compound may show a peak added with sodium (Na). When plural ion peaks of isotope are observed, they may sometimes be indicated.

Elemental analysis values (Anal.) show Calculated (Calcd) and Found (Found).

The following explains chemical structural formulas and nomenclature of the compounds of Reference Examples and Examples.

When a compound synthesized in the following Example is an enantiomer mixture, for convenience, the structural formula thereof is shown using the stereochemistry of one of them, and nomenclature of the stereochemistry employs, for example, any one of three kinds of methods of (trans- or cis-), (DL-threo- or DL-erythro-) or (3RS,4SR) and the like. As concrete examples thereof, the compounds synthesized in Example 1, Example 104 and Example 287 are used for explanation.

The compound synthesized in Example 1 is, as described in [the formula 1], an enantiomer mixture of compound 1_A which is a (3S,4S) form and compound 1_B which is a (3R,4R) form, and the chemical structure thereof is shown, for convenience, by using the stereochemistry of one of them, compound 1_A. For the stereochemistry of the enantiomer mixture (mixture of compound 1_A and 1_B), a method indicating trans- was employed.

Example 1 = Mixture of compound 1_A and compound 1_B

[formula 1]

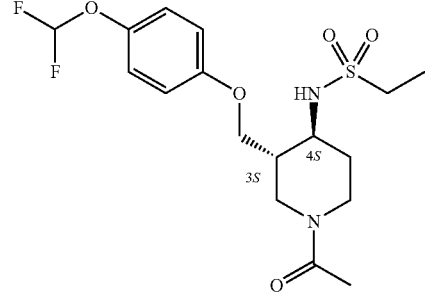

optically-active isomer of trans-N-[1-acetyl-3-{[4-(difluoromethoxy)phenoxy]methyl}piperidin-4-yl]ethanesulfonamide

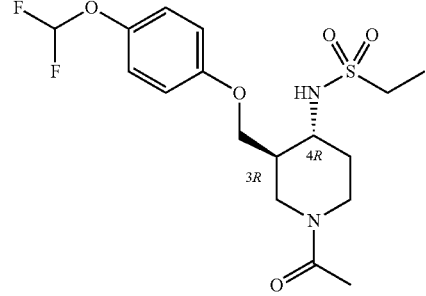

optically-active isomer of trans-N-[1-acetyl-3-{[4-(difluoromethoxy)phenoxy]methyl}piperidin-4-yl]ethanesulfonamide The compound synthesized in Example 104 is, as described in [the formula 2], an enantiomer mixture of compound 104_A and compound 104_B, and the chemical structure thereof is shown, for convenience, by using the stereochemistry of one of them, compound 104_A. For the stereochemistry of the enantiomer mixture (mixture of compound 104_A and 104_B), a method indicating DL-erythro- was employed.

Example 104 = Mixture of compound 104_A and compound 104_B

[formula 2]

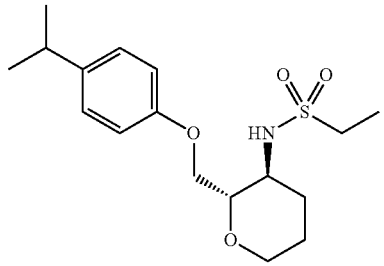

1,5-anhydro-2,3,4-trideoxy-4-[(ethylsulfonyl)amino]-6-O-[4-(propan-2-yl)phenyl]-D-erythro-hexitol

81
-continued

Compound 104_B

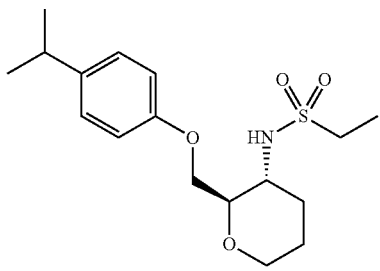

2,6-anhydro-3,4,5-trideoxy-3-[(ethylsulfonyl)amino]
-1-O-[4-(propan-2-yl)phenyl]-D-erythro-hexitol The compound synthesized in Example 287 is, as described in [the formula 3], an enantiomer mixture of compound 287_A which is a (3R,4S) form and compound 287_B which is a (3S,4R) form, and the chemical structure thereof is shown, for convenience, by using the stereochemistry of one of them, compound 287_A. For the stereochemistry of the enantiomer mixture (mixture of compound 287_A and 287_B), a method indicating (3RS,4SR) was employed. That is, the indication of in the nomenclature of the following stereochemistry means a mixture of (3R,4S) form and (3S,4R) form.

Example 287 = Mixture of compound 287_A and compound 287_B

[formula 3]

compound 287_A

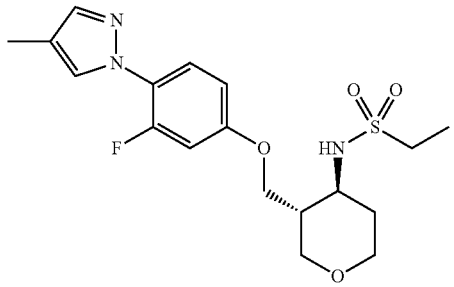

N-[(3R,4S)-3-{[3-fluoro-4-(4-methyl-1H-pyrazol-1-yl)phenoxy]methyl}
tetrahydro-2H-pyran-4-yl]ethanesulfonamide Compound 287_B

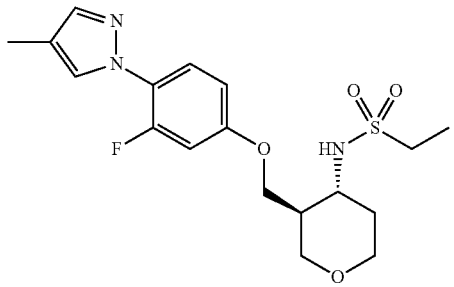

N-[(3S,4R)-3-{[3-fluoro-4-(4-methyl-1H-pyrazol-1-yl)phenoxy]methyl}
tetrahydro-2H-pyran-4-yl]ethanesulfonamide

82

Example 1 trans-N-[1-acetyl-3-{[4-(difluoromethoxy)phenoxy]
methyl}piperidin-4-yl]ethanesulfonamide A) ethyl
1-benzyl-4-(methoxyimino)piperidine-3-carboxylate A solution of ethyl 1-benzyl-4-oxopiperidine-3-carboxylate hydrochloride (25 g) and methoxyamine hydrochloride (7.7 g) in pyridine (150 ml) was stirred at 70° C. for 2 h. The mixture was diluted with EtOAc (300 ml), washed with water, and dried over MgSO$_4$. The solvent was evaporated in vacuo to give the title compound (23 g).
$^1$H NMR (300 MHz, CDCl$_3$) δ 1.22 (3H, t, J=7.1 Hz), 2.1-3.1 (5H, m), 3.46 (1H, d, J=13.4 Hz), 3.6.0 (1H, d, J=13.4 Hz), 3.83 and 3.85 (3H, each s, CH$_3$O), 3.2-4.35 (4H, m), 7.15-7.45 (5H, m).

B) tert-butyl trans-[1-benzyl-3-(hydroxymethyl)
piperidin-4-yl]carbamate

To a suspension of LAH (12 g) in Et$_2$O (100 ml) was added a solution of ethyl 1-benzyl-4-(methoxyimino)piperidine-3-carboxylate (23 g) in Et$_2$O (100 ml) at 0° C. for 1.5 h. The mixture was stirred at room temperature overnight, and quenched with water at 0° C. The insoluble materials were removed by filtration, washed with EtOAc, and the filtrate was concentrated in vacuo. A mixture of the residue, Boc$_2$O (17.3 g), EtOAc (200 ml) and sat. NaHCO$_3$ aq. (100 ml) was stirred at room temperature for 4 h. The mixture was extracted EtOAc, and the organic phase was dried over MgSO$_4$ and concentrated in vacuo. The residue was purified by column chromatography (silica gel, eluted with acetone in hexane). The obtained solid was crystallized from hexane/EtOAc to give the title compound (9.45 g).
Anal. Calcd for C$_{18}$H$_{28}$N$_2$O$_3$: C, 67.47; H, 8.81; N, 8.74. Found: C, 67.33; H, 8.95; N, 8.74.

C) tert-butyl trans-[1-benzyl-3-{[4-(difluoromethoxy)phenoxy]methyl}piperidin-4-yl]carbamate To a solution of tert-butyl trans-[1-benzyl-3-(hydroxymethyl)piperidin-4-yl]carbamate (0.50 g), 4-(difluoromethoxy)phenol (0.35 g) and ADDP (0.59 g) in toluene (10 ml) was added Bu$_3$P (0.58 ml) at room temperature. The mixture was stirred at room temperature overnight. The mixture was poured into water and extracted with EtOAc. The organic layer was separated, washed with water and brine, dried over Na$_2$SO$_4$ and concentrated in vacuo. The residue was purified by column chromatography (silica gel, eluted with EtOAc in hexane) to give the title compound (0.47 g).
$^1$H NMR (300 MHz, CDCl$_3$) δ 1.40 (9H, s), 1.46-1.54 (1H, m), 1.90-2.13 (4H, m), 2.85 (1H, d, J=12.1 Hz), 3.16 (1H, d, J=7.6 Hz), 3.36-3.52 (2H, m), 3.58 (1H, d, J=13.2 Hz), 3.77 (1H, t, J=7.9 Hz), 4.00 (1H, d, J=7.2 Hz), 4.46 (1H, d, J=7.9 Hz), 6.40 (1H, t, J=74.4 Hz), 6.82 (2H, d, J=9.1 Hz), 7.03 (2H, d, J=9.1 Hz), 7.21-7.38 (5H, m).

D) trans-N-[1-benzyl-3-{[4-(difluoromethoxy)phenoxy]methyl}piperidin-4-yl]ethanesulfonamide To a solution of tert-butyl trans-[1-benzyl-3-{[4-(difluoromethoxy)phenoxy]methyl}piperidin-4-yl]carbamate (0.47 g) in EtOAc (7 ml) was added 4 M HCl/EtOAc (2.6 ml). The mixture was stirred at room temperature for 1 h. The mixture was concentrated under vacuum and the residue was diluted with EtOAc. The solution was washed with sat. NaHCO₃ aq. and brine, dried over Na₂SO₄ and concentrated under vacuum. The residue was dissolved in THF (10 ml), and to this solution was added Et₃N (0.29 ml) and ethanesulfonyl chloride (0.15 ml). The mixture was stirred at room temperature overnight. The mixture was quenched with sat. NaHCO₂ aq. and extracted with EtOAc. The organic layer was separated, washed with brine, dried over Na₂SO₄ and concentrated in vacuo. The residue was purified by column chromatography (NH silica gel, eluted with EtOAc in hexane) to give the title compound (0.36 g).

¹H NMR (300 MHz, CDCl₃) δ 1.25 (3H, t, J=7.4 Hz), 1.60-1.74 (1H, m), 1.92-2.05 (1H, m), 2.05-2.22 (3H, m), 2.82-3.09 (4H, m), 3.27-3.44 (1H, m), 3.52 (2H, s), 3.94-4.07 (2H, m), 4.18 (1H, d, J=9.1 Hz), 6.41 (1H, t, J=74.2 Hz), 6.84 (2H, d, J=9.1 Hz), 7.05 (2H, d, J=9.1 Hz), 7.22-7.38 (5H, m).

E) trans-N-[1-acetyl-3-{[4-(difluoromethoxy)phenoxy]methyl}piperidin-4-yl]ethanesulfonamide A mixture of trans-N-[1-benzyl-3-{[4-(difluoromethoxy)phenoxy]methyl}piperidin-4-yl]ethanesulfonamide (0.31 g) and 10% Pd/C (0.018 g) in EtOAc (10 ml) was hydrogenated under balloon pressure at room temperature overnight. The catalyst was removed by filtration and the filtrate was concentrated in vacuo. The residue was dissolved in THF (5 ml), and to this was added Et₃N (0.29 ml) and Ac₂O (0.13 ml). The mixture was stirred at room temperature for 1 h.

The mixture was quenched with sat. NaHCO₂ aq. and extracted with EtOAc. The organic layer was separated, washed with brine, dried over Na₂SO₄ and concentrated in vacuo. The residue was purified by column chromatography (silica gel, eluted with EtOAc in hexane) to give the title compound (0.19 g).

¹H NMR (300 MHz, CDCl₃) δ 1.14-1.38 (3H, m), 1.44-1.63 (1H, m), 2.09-2.43 (4H, m), 2.62-3.28 (5H, m), 3.44-3.72 (1H, m), 3.79-4.31 (4H, m), 4.55-4.83 (1H, m), 6.43 (1H, t, J=74.4 Hz), 6.83-6.96 (2H, m), 7.02-7.14 (2H, m).

Example 2 trans-N-[1-acetyl-3-{[4-(2-cyanoethyl)phenoxy]methyl}piperidin-4-yl]ethanesulfonamide A) tert-butyl trans-[1-benzyl-3-{[4-(2-cyanoethyl)phenyl]methyl}piperidin-4-yl]carbamate To a solution of tert-butyl trans-[1-benzyl-3-(hydroxymethyl)piperidin-4-yl]carbamate (0.50 g) in toluene (10 ml) was added 3-(4-hydroxyphenyl)propanenitrile (0.32 g), ADDP (0.59 g) and Bu₃P (0.58 ml). The mixture was stirred at room temperature overnight. The mixture was poured into water, and extracted with EtOAc. The extract was washed with water and brine, dried over Na₂SO₄ and concentrated in vacuo. The residue was purified by column chromatography (silica gel, eluted with EtOAc in hexane) to give the title compound (0.65 g).

¹H NMR (300 MHz, CDCl₃) δ1.41 (9H, s), 1.90-2.12 (4H, m), 2.51-2.63 (2H, m), 2.79-2.94 (3H, m), 3.16 (1H, brs), 3.45 (3H, d, J=12.9 Hz), 3.54-3.63 (1H, m), 3.78 (1H, brs), 4.00 (1H, s), 4.48 (1H, d, J=8.7 Hz), 6.82 (2H, d, J=8.7 Hz), 7.11 (2H, d, J=8.3 Hz), 7.23-7.35 (5H, m).

B) trans-N-[1-benzyl-3-{[4-(2-cyanoethyl)phenoxy]methyl}piperidin-4-yl]ethanesulfonamide A mixture of tert-butyl trans-[1-benzyl-3-{[4-(2-cyanoethyl)phenyl]methyl}piperidin-4-yl]carbamate (0.65 g) and 4 M HCl/EtOAc (15 ml) was stirred at room temperature for 5 h. The mixture was concentrated under vacuum and the residue was diluted with EtOAc. The solution was washed with sat. NaHCO₃ aq. and brine, dried over Na₂SO₄ and concentrated under vacuum. The residue was dissolved in THF (10 ml), and to this solution was added Et₃N (0.43 ml) and ethanesulfonyl chloride (0.22 ml). The mixture was stirred at room temperature overnight. The mixture was quenched with sat. NaHCO₃ aq. and extracted with EtOAc. The organic layer was separated, washed with brine, dried over Na₂SO₄ and concentrated in vacuo. The residue was purified by column chromatography (NH silica gel, eluted with EtOAc in hexane) to give the title compound (0.35 g).

¹H NMR (300 MHz, CDCl₃) δ1.19-1.34 (3H, m), 1.61-1.74 (1H, m), 1.91-2.24 (4H, m), 2.51-2.63 (2H, m), 2.83-3.08 (6H, m), 3.28-3.43 (1H, m), 3.52 (2H, s), 4.00 (2H, d, J=4.5 Hz), 4.20 (1H, d, J=9.1 Hz), 6.84 (2H, d, J=8.3 Hz), 7.13 (2H, d, J=8.7 Hz), 7.21-7.38 (5H, m).

C) trans-N-[1-acetyl-3-{[4-(2-cyanoethyl)phenoxy]methyl}piperidin-4-yl]ethanesulfonamide A mixture of trans-N-[1-benzyl-3-{[4-(2-cyanoethyl)phenoxy]methyl}piperidin-4-yl]ethanesulfonamide (0.31 g) and 10% Pd/C (0.019 g) in AcOH (10 ml) was hydrogenated under balloon pressure at room temperature overnight. The catalyst was removed by filtration, and the filtrate was concentrated in vacuo. The residue was dissolved in THF (5 ml), and to this was added Et₃N (0.30 ml) and Ac₂O (0.13 ml). The mixture was stirred at room temperature for 1 h. The mixture was quenched with sat. NaHCO₃ aq. and extracted with EtOAc. The organic layer was separated, washed with brine, dried over Na₂SO₄ and concentrated in vacuo. The residue was purified by column chromatography (silica gel, eluted with EtOAc in hexane) to give the title compound (0.012 g).

¹H NMR (300 MHz, CDCl₃) δ 1.11-1.38 (3H, m), 1.44-1.97 (2H, m), 2.07-2.44 (4H, m), 2.51-3.28 (8H, m), 3.42-3.75 (1H, m), 3.75-4.28 (3H, m), 4.47-4.86 (2H, m), 6.87 (2H, dd, J=8.5, 4.4 Hz), 7.16 (2H, dd, J=8.5, 3.2 Hz).

Example 3 trans-N-[1-acetyl-3-{[4-(1H-pyrazol-1-yl)phenoxy]methyl}piperidin-4-yl]ethanesulfonamide A) tert-butyl trans-[1-benzyl-3-{[4-(1H-pyrazol-1-yl)phenoxy]methyl}piperidin-4-yl]carbamate To a solution of tert-butyl trans-[1-benzyl-3-(hydroxymethyl)piperidin-4-yl]carbamate (0.50 g) in toluene (20 ml) was added 4-(1H-pyrazol-1-yl)phenol (0.35 g), ADDP (0.59 g) and Bu₃P (0.58 ml). The mixture was stirred at room temperature overnight. The mixture was poured into water, and extracted with EtOAc. The extract was washed with water and brine, dried over Na₂SO₄ and concentrated in vacuo. The residue was purified by column chromatography (silica gel, eluted with EtOAc in hexane) to give the title compound (0.55 g).

¹H NMR (300 MHz, CDCl₃) δ1.41 (9H, s), 1.47-1.75 (1H, m), 1.91-2.15 (4H, m), 2.86 (1H, d, J=12.8 Hz), 3.19 (1H, d, J=7.2 Hz), 3.47 (2H, d, J=12.8 Hz), 3.54-3.64 (1H, m), 3.76-3.93 (1H, m), 4.05 (1H, d, J=8.7 Hz), 4.48 (1H, d, J=8.7 Hz), 6.43 (1H, t, J=2.3 Hz), 6.93 (2H, d, J=9.1 Hz), 7.23-7.35 (5H, m), 7.56 (2H, d, J=9.1 Hz), 7.69 (1H, d, J=1.5 Hz), 7.82 (1H, d, J=1.9 Hz).

B) trans-N-[1-benzyl-3-{[4-(1H-pyrazol-1-yl)phenoxy]methyl}piperidin-4-yl]ethanesulfonamide To a solution of tert-butyl trans-[1-benzyl-3-{[4-(1H-pyrazol-1-yl)phenoxy]methyl}piperidin-4-yl]carbamate (0.55 g) in EtOAc (10 ml) was added 4 M HCl/EtOAc (15 ml). The mixture was stirred at room temperature for 3 h, and concentrated under vacuum. The residue was diluted with EtOAc, and washed with sat. NaHCO$_3$ aq. and brine, dried over Na$_2$SO$_4$ and concentrated under vacuum. The residue was dissolved in THF (10 ml), and to this solution was added Et$_3$N (0.33 ml) and ethanesulfonyl chloride (0.17 ml) at room temperature. The mixture was stirred at room temperature overnight. The mixture was quenched with sat. NaHCO$_3$ aq. and extracted with EtOAc. The organic layer was separated, washed with brine, dried over Na$_2$SO$_4$ and concentrated in vacuo. The residue was purified by column chromatography (NH silica gel, eluted with EtOAc in hexane) to give the title compound (0.25 g).
$^1$H NMR (300 MHz, CDCl$_3$) δ1.18-1.31 (3H, m), 1.61-1.76 (1H, m), 1.94-2.24 (4H, m), 2.95 (3H, q, J=7.6 Hz), 3.02 (1H, d, J=3.0 Hz), 3.29-3.45 (1H, m), 3.53 (2H, s), 4.05 (2H, d, J=4.5 Hz), 4.20 (1H, d, J=9.1 Hz), 6.44 (1H, t, J=2.1 Hz), 6.95 (2H, d, J=9.1 Hz), 7.22-7.39 (5H, m), 7.58 (2H, d, J=9.1 Hz), 7.69 (1H, d, J=1.5 Hz), 7.82 (1H, d, J=2.3 Hz).

C) trans-N-[1-acetyl-3-{[4-(1H-pyrazol-1-yl)phenoxy]methyl}piperidin-4-yl]ethanesulfonamide A mixture of trans-N-[1-benzyl-3-{[4-(1H-pyrazol-1-yl)phenoxy]methyl}piperidin-4-yl]ethanesulfonamide (0.32 g) and 10% Pd/C (0.019 g) in AcOH (10 ml) was hydrogenated under balloon pressure at room temperature overnight. The catalyst was removed by filtration and the filtrate was concentrated in vacuo. The residue was dissolved in THF (5 ml) and to this was added Et$_3$N (0.30 ml) and Ac$_2$O (0.13 ml). The mixture was stirred at room temperature for 1 h. The mixture was quenched with sat. NaHCO$_3$ aq. and extracted with EtOAc. The organic layer was separated, washed with brine, dried over Na$_2$SO$_4$ and concentrated in vacuo. The residue was purified by column chromatography (silica gel, eluted with EtOAc in hexane) to give the title compound (0.14 g).
$^1$H NMR (300 MHz, CDCl$_3$) δ 1.15-1.36 (3H, m), 1.45-1.96 (2H, m), 2.05-2.39 (4H, m), 2.64-3.25 (4H, m), 3.42-3.70 (1H, m), 3.78-4.27 (3H, m), 4.53-4.83 (1H, m), 4.90-5.09 (1H, m), 6.44 (1H, s), 6.97 (2H, dd, J=9.0, 3.4 Hz), 7.59 (2H, dd, J=9.0, 2.6 Hz), 7.70 (1H, s), 7.83 (1H, s).

Example 4

1,5-anhydro-6-O-(4-cyclopropylphenyl)-2,3,4-trideoxy-4-[(ethylsulfonyl)amino]-DL-erythrohexitol A) 6-[(4-cyclopropylphenoxy)methyl]-3,4-dihydro-2H-pyran To a solution of 3,4-dihydro-2H-pyran-6-ylmethanol (1.00 g), 4-cyclopropylphenol (1.29 g) and tributylphosphine (3.54 g) in toluene (100 mL) was added 1,1'-(azodicarbonyl)dipiperidine (4.42 g) at room temperature. The reaction mixture was stirred at room temperature overnight, and the insoluble material was filtered off. The filtrate was concentrated under reduced pressure, and the residue was purified by silica gel column chromatography (hexane/ethyl acetate) to give the title compound (1.36 g).
$^1$H NMR (300 MHz, CDCl$_3$) δ 0.46-0.69 (2H, m), 0.73-0.98 (2H, m), 1.66-1.95 (3H, m), 1.95-2.13 (2H, m), 3.94-4.15 (2H, m), 4.32 (2H, s), 4.74-4.97 (1H, m), 6.71-6.89 (2H, m), 6.89-7.05 (2H, m).

B) 1,5-anhydro-6-O-(4-cyclopropylphenyl)-2,3-dideoxy-DL-erythrohexitol

To a solution of 6-[(4-cyclopropylphenoxy)methyl]-3,4-dihydro-2H-pyran (1.36 g) in tetrahydrofran (30 mL) was added borane-tetrahydrofuran complex (1 M tetrahydrofuran solution, 3.96 mL) under ice-cooling. The mixture was stirred at room temperature for 3 h, sodium hydroxide (8 M aqueous solution, 2.00 mL) and 30% hydrogen peroxide solution (4.00 mL) were sequentially added dropwise at room temperature. The mixture was stirred at room temperature for 1 h, water was added, and the mixture was extracted with ethyl acetate. The extract was washed with saturated brine, dried over anhydrous sodium sulfate, and the solvent was evaporated under reduced pressure to give the title compound (1.46 g).
$^1$H NMR (300 MHz, CDCl$_3$) δ0.46-0.73 (2H, m), 0.77-1.01 (2H, m), 1.31-1.56 (1H, m), 1.59-1.89 (3H, m), 2.10-2.40 (2H, m), 3.37-3.47 (2H, m), 3.59-3.79 (1H, m), 3.86-4.02 (1H, m), 4.11-4.23 (2H, m), 6.76-6.91 (2H, m), 6.91-7.08 (2H, m).

C) 2-[(4-cyclopropylphenoxy)methyl]dihydro-2H-pyran-3(4H)-one

To a solution of 1,5-anhydro-6-O-(4-cyclopropylphenyl)-2,3-dideoxy-DL-erythrohexitol (1.46 g) and triethylamine (2.54 mL) in dimethylsulfoxide (20 mL) was added sulfur trioxide pyridine complex (2.90 g) at 10° C. The mixture was stirred at room temperature for 2 h, ice was added to the reaction solution, and the mixture was extracted with ethyl acetate. The extract was washed with 1 M hydrochloric acid, saturated aqueous sodium hydrogencarbonate solution and saturated brine, dried over anhydrous sodium sulfate, and the solvent was evaporated under reduced pressure. The residue was purified by silica gel column chromatography (hexane/ethyl acetate) to give the title compound (0.72 g).
$^1$H NMR (300 MHz, CDCl$_3$) δ0.55-0.66 (2H, m), 0.81-0.95 (2H, m), 1.76-1.89 (1H, m), 2.00-2.15 (1H, m), 2.15-2.33 (1H, m), 2.52 (1H, ddd, J=16.3, 9.7, 6.8 Hz), 2.66 (1H, dt, J=16.2, 5.5 Hz), 3.82 (1H, ddd, J=11.7, 10.2, 3.8 Hz), 4.08-4.29 (3H, m), 4.38 (1H, dd, J=10.2, 2.6 Hz), 6.71-6.91 (2H, m), 6.91-7.10 (2H, m).

D) 2-[(4-cyclopropylphenoxy)methyl]dihydro-2H-pyran-3(4H)-one O-ethyloxime

To a solution of 2-[(4-cyclopropylphenoxy)methyl]dihydro-2H-pyran-3(4H)-one (0.70 g) and triethylamine (0.44 mL) in ethanol (5 mL) was added ethoxyamine hydrochloride (0.31 g) at room temperature. The mixture was heated under reflux for 2 h, and the solvent was evaporated under reduced pressure. Ice was added to the residue and the mixture was extracted with ethyl acetate. The extract was washed with saturated brine, dried over anhydrous sodium sulfate, and the solvent was evaporated under reduced pressure to give the title compound (0.82 g).
MS (ESI+): [M+H]$^+$290.1.

E) 3-amino-2,6-anhydro-1-O-(4-cyclopropylphenyl)-3,4,5-trideoxyhexitol

A solution of 2-[(4-cyclopropylphenoxy)methyl]dihydro-2H-pyran-3(4H)-one O-ethyloxime (0.82 g) in methanol (40 mL) was subjected to a hydrogenation catalytic reduction using H-cube Tutor™ (raney-nickel catalyst) (60° C., 10 atm, 3 h). The solvent was evaporated under reduced pressure to give the title compound (0.70 g).
MS (ESI+): [M+H]$^+$248.1.

F) 1,5-anhydro-6-O-(4-cyclopropylphenyl)-2,3,4-trideoxy-4-[(ethylsulfonyl)amino]-DL-erythrohexitol To a solution of 3-amino-2,6-anhydro-1-O-(4-cyclopropylphenyl)-3,4,5-trideoxyhexitol (0.20 g) in tetrahydrofuran (5 mL) were added triethylamine (0.56 mL) and ethanesulfonyl chloride (0.23 mL). The mixture was stirred at room temperature overnight, water was added to the reaction solution, and the mixture was extracted with ethyl acetate. The extrace was washed with saturated brine, dried over anhydrous sodium sulfate, and the solvent was evaporated under reduced pressure. The residue was purified by silica gel column chromatography (hexane/ethyl acetate) to give the title compound (0.063 g).
$^1$H NMR (300 MHz, CDCl$_3$) δ0.51-0.66 (2H, m), 0.81-0.96 (2H, m), 1.21 (3H, t, J=7.3 Hz), 1.42-1.62 (1H, m), 1.63-1.89 (3H, m), 2.28-2.45 (1H, m), 2.95 (2H, q, J=7.4 Hz), 3.32-3.58 (3H, m), 3.96-4.07 (1H, m), 4.07-4.24 (2H, m), 4.29 (1H, d, J=9.0 Hz), 6.74-6.90 (2H, m), 6.92-7.06 (2H, m).

Example 5

1,5-anhydro-6-O-(4-cyclopropylphenyl)-2,3,4-trideoxy-4-[(methylsulfonyl)amino]-DL-erythrohexitol To a solution of 3-amino-2,6-anhydro-1-O-(4-cyclopropylphenyl)-3,4,5-trideoxyhexitol (0.20 g) in tetrahydrofuran (5 mL) were added triethylamine (0.56 mL) and methanesulfonyl chloride (0.19 mL). The mixture was stirred at room temperature overnight, water was added to the reaction solution, and the mixture was extracted with ethyl acetate. The extract was washed with saturated brine, dried over anhydrous sodium sulfate, and the solvent was evaporated under reduced pressure. The residue was purified by silica gel column chromatography (hexane/ethyl acetate) to give the title compound (0.089 g).
$^1$H NMR (300 MHz, CDCl$_3$) δ0.54-0.65 (2H, m), 0.83-0.94 (2H, m), 1.40-1.58 (1H, m), 1.63-1.92 (3H, m), 2.29-2.45 (1H, m), 2.85 (2H, s), 3.31-3.44 (1H, m), 3.44-3.68 (2H, m), 3.96-4.07 (2H, m), 4.07-4.22 (2H, m), 4.45 (1H, d, J=9.0 Hz), 6.77-6.89 (2H, m), 6.92-7.04 (2H, m).

Example 6

Optically active material of trans-N-[3-{[4-(1H-pyrazol-1-yl)phenoxy]methyl}tetrahydro-2H-pyran-4-yl]ethanesulfonamide

A) ethyl 4-(benzylamino)-5,6-dihydro-2H-pyran-3-carboxylate

To a solution of tetrahydro-4H-pyran-4-one (6.67 g) in toluene (300 ml) was added LDA in hexane (60 ml, 1.1 M) quickly at 0° C. After being stirred for 1 min, to the mixture was added ethyl cyanoformate (6.0 g) in one portion and the mixture was stirred for further 1 min. The mixture was quenched with AcOH (30 ml) and water (100 ml), and extracted with AcOEt. The extract was washed with sat. NaHCO$_3$ aq. and brine, dried over Na$_2$SO$_4$ and concentrated under vacuum. The residue was dissolved in toluene (10 ml), and to this solution was added benzylamine (7.94 ml). The mixture was stirred at 100° C. for 5 h, and the solvent was evaporated under vacuum. The residue was purified by column chromatography (silica gel, eluted with EtOAc in hexane) to give the title compound (6.95 g).
$^1$H NMR (300 MHz, CDCl$_3$) δ1.26 (3H, t, J=7.2 Hz), 2.37 (2H, t, J=5.9 Hz), 3.77 (2H, t, J=5.9 Hz), 4.13 (2H, q, J=6.9 Hz), 4.33 (2H, s), 4.40 (2H, d, J=6.1 Hz), 7.21-7.41 (5H, m), 9.09 (1H, brs).

B) ethyl cis-4-(benzylamino)tetrahydro-2H-pyran-3-carboxylate

NaBH$_4$ (3.6 g) was added to AcOH (100 ml) at 10° C. and the mixture was stirred for 30 min. To a mixture was added a solution of ethyl 4-(benzylamino)-5,6-dihydro-2H-pyran-3-carboxylate (8.3 g) in AcOH (10 ml) in one portion and the mixture was stirred overnight. Evaporation of acetic acid in vacuo followed by dissolution of the residue with AcOEt. The solution was washed with sat. NaHCO$_3$ aq. and brine, dried over Na$_2$SO$_4$ and concentrated under vacuum to give the title compound (7.7 g).
$^1$H NMR (300 MHz, CDCl$_3$) δ 1.26 (3H, t, J=7.0 Hz), 1.73-1.86 (1H, m), 1.89-2.03 (1H, m), 2.83 (1H, q, J=4.0 Hz), 3.03 (1H, dt, J=8.6, 4.2 Hz), 3.49 (1H, ddd, J=11.5, 8.5, 3.4 Hz), 3.61 (1H, dd, J=11.7, 3.8 Hz), 3.78 (1H, d, J=13.2 Hz), 3.87 (1H, d, J=13.2 Hz), 3.90-4.01 (1H, m), 4.12-4.22 (3H, m), 7.21-7.37 (5H, m).

C) optically active material of ethyl trans-4-(benzylamino)tetrahydro-2H-pyran-3-carboxylate To a solution of ethyl cis-4-(benzylamino)tetrahydro-2H-pyran-3-carboxylate (7.7 g) in EtOH (150 ml) was added sodium ethoxide (6.0 g). The mixture was stirred at 60° C. under N$_2$ for 3 h, quenched with sat. NH$_4$Cl aq., and extracted with EtOAc. The organic layer was separated, washed with brine, dried over Na$_2$SO$_4$ and concentrated in vacuo. The residue was purified by column chromatography (silica gel, eluted with EtOAc in hexane). The isomeric mixture was separated by preparative HPLC(CHIRALPAK AS, eluted with hexane/2-propanol=950/50 (v/v)), and the third fraction from one with shorter retention time was collected and concentrated in vacuo to give the title compound (1.1 g). The fourth fraction from one with shorter retention time was collected and concentrated in vacuo to give enantiomer of the title compound (1.1 g).
$^1$H NMR (300 MHz, CDCl$_3$) δ 1.25 (3H, t, J=7.2 Hz), 1.36-1.54 (1H, m), 1.94-2.09 (1H, m), 2.56 (1H, td, J=10.3, 4.3 Hz), 3.03 (1H, td, J=10.4, 4.2 Hz), 3.34-3.50 (2H, m), 3.73 (1H, d, J=12.8 Hz), 3.88 (1H, d, J=12.8 Hz), 3.94-4.03 (1H, m), 4.03-4.22 (3H, m), 7.20-7.38 (5H, m).

D) optically active material of ethyl trans-4-aminotetrahydro-2H-pyran-3-carboxylate A mixture of optically active material of ethyl trans-4-(benzylamino)tetrahydro-2H-pyran-3-carboxylate (0.20 g), the third fraction in HPLC separation to process C) of Example 6, and 10% Pd/C. (0.024 g) in EtOH (10 ml) was hydrogenated under balloon pressure at room temperature overnight. The catalyst was removed by filtration and the filtrate was concentrated in vacuo to give the title compound (0.13 g).

¹H NMR (300 MHz, CDCl₃) δ 1.27 (3H, t, J=7.2 Hz), 1.39-1.54 (1H, m), 1.77-1.88 (1H, m), 2.39 (1H, td, J=10.5, 4.5 Hz), 3.12 (1H, td, J=10.7, 4.1 Hz), 3.30-3.50 (2H, m), 3.98 (1H, dd, J=11.5, 4.7 Hz), 4.09 (1H, dd, J=11.7, 4.1 Hz), 4.17 (2H, q, J=6.9 Hz).

E) optically active material of ethyl trans-4-{[(benzyloxy)carbonyl]amino}tetrahydro-2H-pyran-3-carboxylate To a solution of optically active material of ethyl trans-4-aminotetrahydro-2H-pyran-3-carboxylate (0.13 g) and Et₃N (0.16 ml) in THF (5 ml) was added CbzCl (0.13 ml). The mixture was stirred for 2 h at room temperature. The mixture was quenched with sat. NaHCO₃ aq. and extracted with EtOAc. The organic layer was separated, washed with brine, dried over Na₂SO₄ and concentrated in vacuo to give the titled compound (0.20 g).
¹H NMR (300 MHz, CDCl₃) δ 1.20 (3H, t, J=7.2 Hz), 2.07 (1H, d, J=12.1 Hz), 2.52 (1H, td, J=10.5, 4.0 Hz), 3.41-3.63 (2H, m), 3.90-4.22 (6H, m), 4.60 (1H, s), 5.09 (2H, s), 7.29-7.44 (5H, m).

F) optically active material of benzyl trans-[3-(hydroxymethyl)tetrahydro-2H-pyran-4-yl]carbamate To a solution of optically active material of ethyl trans-4-{[(benzyloxy)carbonyl]amino}tetrahydro-2H-pyran-3-carboxylate (0.20 g) in THF (5 ml) was added LAH (0.048 g) at 0° C. The mixture was stirred at room temperature for 2 h. The mixture was quenched with 1 M NaOH aq. (0.2 ml) and Na₂SO₄, and the mixture was filtered through a pad of celite. The filtrate was concentrated under vacuum and the residue was purified by column chromatography (silica gel, eluted with EtOAc in hexane) to give the title compound (0.049 g).
¹H NMR (300 MHz, CDCl₃) δ 1.39-1.66 (2H, m), 1.82-1.98 (1H, m), 3.29 (1H, dd, J=9.8, 4.5 Hz), 3.35-3.59 (3H, m), 3.66-3.88 (2H, m), 3.88-4.04 (2H, m), 4.72 (1H, d, J=8.3 Hz), 5.07-5.19 (2H, m), 7.32-7.44 (5H, m).

G) optically active material of benzyl trans-(3-((4-(1H-pyrazol-1-yl)phenoxy)methyl)tetrahydro-2H-pyran-4-yl)carbamate To a solution of optically active material of benzyl trans-[3-(hydroxymethyl)tetrahydro-2H-pyran-4-yl]carbamate (0.049 g) in toluene (3 ml) was added 4-(1H-pyrazol-1-yl)phenol (0.044 g), ADDP (0.093) and Bu₃P (0.091 ml). The mixture was stirred at room temperature overnight. The mixture was purified by column chromatography (NH silica gel, eluted with EtOAc in hexane) to give the title compound (0.026 g).
¹H NMR (300 MHz, CDCl₃) δ 1.51-1.70 (1H, m), 2.00 (2H, d, J=13.2 Hz), 3.34 (1H, t, J=11.1 Hz), 3.49 (1H, td, J=12.1, 2.3 Hz), 3.68-3.90 (2H, m), 3.94-4.11 (2H, m), 4.22 (1H, dd, J=11.3, 4.5 Hz), 4.75 (1H, d, J=9.4 Hz), 5.09 (2H, s), 6.44 (1H, t, J=2.3 Hz), 6.92 (2H, d, J=8.7 Hz), 7.33 (5H, s), 7.56 (2H, d, J=9.1 Hz), 7.70 (1H, d, J=1.5 Hz), 7.82 (1H, d, J=1.9 Hz).

H) optically active material of trans-N-(3-((4-(1H-pyrazol-1-yl)phenoxy)methyl)tetrahydro-2H-pyran-4-yl)ethanesulfonamide A mixture of optically active material of benzyl trans-(3-((4-(1H-pyrazol-1-yl)phenoxy)methyl)tetrahydro-2H-pyran-4-yl)carbamate (0.026 g) and 10% Pd/C (0.00030 g) in EtOAc (3 ml) was hydrogenated under balloon pressure at room temperature for 1 h. The catalyst was removed by filtration and the filtrate was concentrated in vacuo. The residue was dissolved in THF (2 ml), and to this solution was added Et₃N (0.025 ml) and ethanesulfonyl chloride (0.011 ml). The mixture was stirred for 8 h at room temperature. The mixture was quenched with sat. NaHCO₃ aq. and extracted with EtOAc. The organic layer was separated, washed with brine, dried over MgSO₄ and concentrated in vacuo. The residue was purified by column chromatography (silica gel, eluted with EtOAc in hexane) to give the title compound (0.0066 g).
¹H NMR (300 MHz, CDCl₃) δ 1.26 (3H, t, J=7.4 Hz), 1.62-1.80 (1H, m), 1.92-2.08 (1H, m), 2.13-2.24 (1H, m), 2.97 (2H, q, J=7.4 Hz), 3.41-3.67 (3H, m), 4.01 (1H, dd, J=11.9, 4.0 Hz), 4.07 (2H, d, J=4.5 Hz), 4.14 (1H, dd, J=11.5, 4.3 Hz), 4.32 (1H, d, J=9.4 Hz), 6.45 (1H, t, J=2.1 Hz), 6.97 (2H, d, J=9.1 Hz), 7.59 (2H, d, J=9.1 Hz), 7.70 (1H, d, J=1.5 Hz), 7.83 (1H, d, J=2.3 Hz).

Example 7

Optically active material of trans-N-{3-[(4-cyclopropylphenoxy)methyl]tetrahydro-2H-pyran-4-yl}ethanesulfonamide A) optically active material of ethyl trans-4-[(tert-butoxycarbonyl)amino]tetrahydro-2H-pyran-3-carboxylate To a solution of optically active material of ethyl trans-4-aminotetrahydro-2H-pyran-3-carboxylate (0.27 g) in THF (5 ml) was added Et₃N (0.64 ml) and Boc₂O (0.71 ml). The mixture was stirred for 2 h at room temperature. The mixture was quenched with sat. NaHCO₃ aq. and extracted with EtOAc. The organic layer was separated, washed with brine, dried over Na₂SO₄ and concentrated in vacuo. The residue was purified by column chromatography (silica gel, eluted with EtOAc in hexane) to give the title compound (0.35 g).
¹H NMR (300 MHz, CDCl₃) δ 1.26 (3H, t, J=7.0 Hz), 1.43 (9H, s), 1.46-1.57 (1H, m), 1.97-2.10 (1H, m), 2.48 (1H, td, J=10.4, 4.2 Hz), 3.41-3.64 (2H, m), 3.94 (2H, dt, J=11.5, 3.5 Hz), 4.04 (1H, dd, J=11.5, 4.3 Hz), 4.09-4.24 (2H, m), 4.57 (1H, brs).

B) optically active material of tert-butyl trans-[3-(hydroxymethyl)tetrahydro-2H-pyran-4-yl]carbamate To a solution of optically active material of ethyl trans-4-[(tert-butoxycarbonyl)amino]tetrahydro-2H-pyran-3-carboxylate (0.10 g) in THF (5 ml) was added LAH (0.033 g) at 0° C. The mixture was stirred at 0° C. for 2 h. To the reaction mixture was added water (0.13 ml), 4 M NaOH (0.13 ml) and water (0.38 ml), and the mixture was stirred for 30 min. The mixture was passed through a pad of celite and the filtrate was concentrated under vacuum. The residue was purified by column chromatography (silica gel, eluted with EtOAc in hexane) to give the title compound (0.064 g).
¹H NMR (300 MHz, CDCl₃) δ 1.46 (9H, s), 1.50-1.63 (1H, m), 1.79-1.95 (1H, m), 3.33-3.58 (3H, m), 3.58-3.66 (1H, m), 3.66-3.84 (2H, m), 3.84-4.06 (2H, m), 4.50 (1H, d, J=8.3 Hz).

C) optically active material of tert-butyl trans-{3-[(4-cyclopropylphenoxy)methyl]tetrahydro-2H-pyran-4-yl}carbamate To a solution of optically active material of tert-butyl trans-[3-(hydroxymethyl)tetrahydro-2H-pyran-4-yl]carbamate (0.064 g) in toluene (3 ml) was added 4-cyclopropylphenol (0.056 g), ADDP (0.14 g) and Bu$_3$P (0.14 ml). The mixture was stirred at room temperature overnight. The mixture was purified by column chromatography (NH silica gel, eluted with EtOAc in hexane) to give the title compound (0.077 g).

$^1$H NMR (300 MHz, CDCl$_3$) δ 0.56-0.64 (2H, m), 0.85-0.93 (2H, m), 1.42 (9H, s), 1.47-1.53 (1H, m), 1.78-1.90 (1H, m), 1.91-2.03 (2H, m), 3.27 (1H, s), 3.45 (1H, td, J=11.8, 2.1 Hz), 3.54-3.68 (1H, m), 3.75 (1H, t, J=9.1 Hz), 3.94-4.07 (2H, m), 4.16-4.27 (1H, m), 4.54 (1H, brs), 6.77 (2H, d, J=9.1 Hz), 6.99 (2H, d, J=8.3 Hz).

D) optically active material of trans-N-{3-[(4-cyclopropylphenoxy)methyl]tetrahydro-2H-pyran-4-yl}ethanesulfonamide To a solution of optically active material of tert-butyl trans-{3-[(4-cyclopropylphenoxy)methyl]tetrahydro-2H-pyran-4-yl}carbamate (0.077 g) in EtOAc (5 ml) was added 4 M HCl/EtOAc (2.2 ml). The mixture was stirred at room temperature for 1 h, and concentrated in vacuo. The residue was dissolved in THF (2 ml), and to this mixture was added Et$_3$N (0.14 ml) and ethanesulfonyl chloride (0.068 ml). The mixture was stirred at room temperature for 2 h. The mixture was quenched with sat. NaHCO$_3$ aq. and extracted with EtOAc. The organic layer was separated, washed with brine, dried over Na$_2$SO$_4$ and concentrated in vacuo. The residue was purified by column chromatography (silica gel, eluted with EtOAc in hexane) to give the title compound (0.029 g).

$^1$H NMR (300 MHz, CDCl$_3$) δ 0.52-0.69 (2H, m), 0.85-0.95 (2H, m), 1.24 (3H, t, J=7.4 Hz), 1.60-1.76 (1H, m), 1.78-1.90 (1H, m), 1.89-2.02 (1H, m), 2.13-2.25 (1H, m), 2.95 (2H, q, J=7.2 Hz), 3.39-3.65 (3H, m), 3.94-4.05 (3H, m), 4.08 (1H, dd, J=11.9, 4.3 Hz), 4.30 (1H, d, J=9.1 Hz), 6.78 (2H, d, J=8.7 Hz), 7.00 (2H, d, J=8.7 Hz).

Example 8 trans-N-[2-{[4-(1-methylethyl)phenoxy]methyl}cyclohexyl]ethanesulfonamide

A) ethyl trans-2-[(ethylsulfonyl)amino]cyclohexanecarboxylate

The title compound was obtained from ethyl trans-2-aminocyclohexanecarboxylate hydrochloride and ethanesulfonyl chloride in the same manner as in Example 4, step F.

$^1$H NMR (300 MHz, CDCl$_3$) δ1.16-1.54 (9H, m), 1.66-1.85 (2H, m), 1.89-2.07 (1H, m), 2.13-2.37 (2H, m), 2.93-3.14 (2H, m), 3.37-3.55 (1H, m), 4.15 (4H, q, J=7.2 Hz).

B) trans-N-[2-{[4-(1-methylethyl)phenoxy]methyl}cyclohexyl]ethanesulfonamide The title compound was obtained from ethyl trans-2-[(ethylsulfonyl)amino]cyclohexanecarboxylate in the same manner as in Example 7, steps B and C.

$^1$H NMR (300 MHz, CDCl$_3$) δ1.11-1.46 (13H, m), 1.55-1.85 (3H, m), 1.85-1.97 (1H, m), 2.17-2.32 (1H, m), 2.75-2.90 (1H, m), 2.90-3.02 (2H, m), 3.18-3.35 (1H, m), 3.93-4.05 (2H, m), 4.47 (1H, d, J=8.3 Hz), 6.75-6.90 (2H, m), 7.06-7.20 (2H, m).

Example 9 cis-N-[2-{[4-(1-methylethyl)phenoxy]methyl}cyclohexyl]ethanesulfonamide

The title compound was obtained from ethyl cis-2-aminocyclohexanecarboxylate in the same manner as in Example 7, steps A to D.

$^1$H NMR (300 MHz, CDCl$_3$) δ1.14-1.27 (9H, m), 1.27-1.47 (2H, m), 1.49-1.75 (5H, m), 1.90-2.03 (1H, m), 2.05-2.21 (1H, m), 2.77-2.91 (1H, m), 2.96 (2H, q, J=7.5 Hz), 3.79-3.91 (2H, m), 3.92-4.05 (1H, m), 4.75 (1H, d, J=8.7 Hz), 6.73-6.88 (2H, m, J=8.7 Hz), 7.07-7.18 (2H, m, J=8.7 Hz).

Example 10 cis-N-[2-{[4-(1-methylethyl)phenoxy]methyl}cyclopentyl]ethanesulfonamide

The title compound was obtained from ethyl cis-2-[(tert-butoxycarbonyl)amino]cyclopentanecarboxylate in the same manner as in Example 7, steps B to D.

$^1$H NMR (300 MHz, CDCl$_3$) δ1.22 (6H, d, J=6.8 Hz), 1.30 (3H, t, J=7.5 Hz), 1.51-1.68 (2H, m), 1.68-1.98 (3H, m), 1.98-2.15 (1H, m), 2.39-2.55 (1H, m), 2.77-2.93 (1H, m), 3.02 (2H, q, J=7.3 Hz), 3.87-4.03 (2H, m), 4.04-4.16 (1H, m), 4.67 (1H, d, J=9.0 Hz), 6.73-6.89 (2H, m), 7.05-7.21 (2H, m).

Example 11 trans-N-[2-{[4-(1-methylethyl)phenoxy]methyl}cyclohexyl]cyclopropanesulfonamide The title compound was obtained from ethyl trans-2-aminocyclohexanecarboxylate hydrochloride in the same manner as in Example 7, steps A to D.

$^1$H NMR (300 MHz, CDCl$_3$) δ0.62-0.77 (1H, m), 0.77-0.92 (1H, m), 0.92-1.07 (1H, m), 1.07-1.46 (11H, m), 1.52-1.85 (3H, m), 1.85-2.01 (1H, m), 2.16-2.41 (2H, m), 2.84 (1H, spt, J=6.9 Hz), 3.17-3.38 (1H, m), 3.91-4.09 (2H, m), 4.76 (1H, d, J=8.3 Hz), 6.73-6.88 (2H, m, J=8.7 Hz), 7.03-7.19 (2H, m, J=8.7 Hz).

Example 12 trans-N-[2-[(4-cyclopropylphenoxy)methyl]cyclohexyl]cyclopropanesulfonamide The title compound was obtained from ethyl trans-2-aminocyclohexanecarboxylate hydrochloride in the same manner as in Example 8, steps A and B.

$^1$H NMR (300 MHz, CDCl$_3$) δ0.49-0.64 (2H, m), 0.64-0.77 (1H, m), 0.77-0.94 (3H, m), 0.94-1.07 (1H, m), 1.07-1.45 (5H, m), 1.55-1.88 (4H, m), 1.88-1.99 (1H, m), 2.16-2.39 (2H, m), 3.16-3.38 (1H, m), 3.91-4.06 (2H, m), 4.77 (1H, d, J=8.3 Hz), 6.70-6.85 (2H, m), 6.89-7.03 (2H, m).

Example 13

N-[(1S,2S)-2-{[4-(1-methylethyl)phenoxy]methyl}cyclohexyl]ethanesulfonamide trans-N-[2-{[4-(1-methylethyl)phenoxy]methyl}cyclohexyl]ethanesulfonamide (0.24 g) was separated by SFC (column: CHIRALPAK ADH (trade name), 20 mmID×250 mL, manufactured by DAICEL CHEMICAL INDUSTRIES, LTD., mobile phase: carbon dioxide/methanol=750/250) to give the title compound (0.12 g) with a shorter retention time. The absolute configuration was determined by X-ray structural analysis.

Example 14

N-[(1R,2R)-2-{[4-(1-methylethyl)phenoxy]methyl}cyclohexyl]ethanesulfonamide trans-N-[2-{[4-(1-methylethyl)phenoxy]methyl}cyclohexyl]ethanesulfonamide (0.24 g) was separated by SFC (column: CHIRALPAK ADH (trade name), 20 mmID×250 mL, manufactured by DAICEL CHEMICAL INDUSTRIES, LTD., mobile phase: carbon dioxide/methanol=750/250) to give the title compound (0.11 g) with a longer retention time. The absolute configuration was determined by X-ray structural analysis of an enantiomer thereof.

Example 15 trans-N-[2-{[4-(1-methylethyl)phenoxy]methyl}cyclopentyl]ethanesulfonamide

The title compound was obtained from ethyl trans-2-aminocyclopentanecarboxylate hydrochloride in the same manner as in Example 8, steps A and B.

$^1$H NMR (300 MHz, CDCl$_3$) δ 1.22 (6H, d, J=7.2 Hz), 1.33 (3H, t, J=7.3 Hz), 1.40-1.55 (1H, m), 1.55-1.85 (3H, m), 1.85-2.03 (1H, m), 2.08-2.29 (2H, m), 2.85 (1H, spt, J=6.8 Hz), 3.03 (2H, q, J=7.5 Hz), 3.48-3.70 (1H, m), 3.84-4.06 (2H, m), 4.76 (1H, d, J=6.8 Hz), 6.82 (2H, d, J=8.7 Hz), 7.13 (2H, d, J=8.3 Hz).

Example 16 trans-N-[2-{[4-(1-methylethyl)phenoxy]methyl}cyclopropyl]ethanesulfonamide

A) ethyl trans-2-{[4-(1-methylethyl)phenoxy]methyl}cyclopropanecarboxylate

To a solution of sodium hydride (60%, 0.26 g) in toluene was slowly added dropwise triethyl phosphonoacetate (1.22 mL) over 5 min. The solution was stirred at room temperature for 5 min, and to the reaction solution was slowly added dropwise a solution of 2-((4-isopropylphenoxy)methyl)oxirane (0.50 g) in toluene (2.5 ml). The reaction mixture was stirred for 6 h under reflux, poured into water, and the mixture was extracted with ethyl acetate. The extract was dried over anhydrous sodium sulfate, and concentrated under reduced pressure. To a solution of the residue and triphenylphosphine (1.35 g) in tetrahydrofuran (20 mL) was added diethyl azodicarboxylate (40% toluene solution, 2.24 g) over 10 min under ice-cooling. The reaction mixture was stirred at room temperature for 2 h, and concentrated under reduced pressure. The residue was purified by silica gel column chromatography (hexane/ethyl acetate) to give the title compound (0.45 g).

$^1$H NMR (300 MHz, DMSO-d$_6$) δ 0.93-1.05 (1H, m), 1.05-1.24 (10H, m), 1.63-1.80 (2H, m), 2.74-2.90 (1H, m), 3.74-3.86 (1H, m), 3.89-4.00 (1H, m), 4.01-4.13 (2H, m), 6.78-6.89 (2H, m), 7.08-7.18 (2H, m).

B) trans-2-{[4-(1-methylethyl)phenoxy]methyl}cyclopropanecarboxylic acid

To a solution of ethyl trans-2-{[4-(1-methylethyl)phenoxy]methyl}cyclopropanecarboxylate (0.45 g) in tetrahydrofuran (8 mL) and methanol (4 mL) was added an aqueous sodium hydroxide solution (5.12 mL), and the mixture was stirred is at 50° C. for 1.5 h. The reaction mixture was poured into 1 M hydrochloric acid, and the mixture was extracted with ethyl acetate. The extract was washed with saturated brine, dried over anhydrous sodium sulfate, and concentrated under reduced pressure to give the title compound (0.40 g).

MS (ESI+): [M−H]$^+$233.0.

C) tert-butyl trans-2-{[4-(1-methylethyl)phenoxy]methyl}cyclopropyl]carbamate

A mixture of trans-2-{[4-(1-methylethyl)phenoxy]methyl}cyclopropanecarboxylic acid (1.20 g), triethylamine (1.07 mL), diphenyl azidophosphate (1.32 mL) and tert-butylalcohol (55 mL) was stirred overnight under reflux. The reaction mixture was concentrated under reduced pressure, saturated aqueous sodium hydrogencarbonate solution was added, and the mixture was extracted with ethyl acetate. The extract was washed with saturated brine, dried over anhydrous magnesium sulfate, and the solvent was evaporated under reduced pressure. The residue was purified by silica gel column chromatography (hexane/ethyl acetate) to give the title compound (0.38 g).

$^1$H NMR (300 MHz, DMSO-d$_6$) δ 0.60-0.75 (2H, m), 1.16 (6H, d, J=7.2 Hz), 1.21-1.33 (1H, m), 1.38 (9H, s), 2.41-2.58 (1H, m), 2.71-2.92 (1H, m), 3.60-3.76 (1H, m), 3.84-4.02 (1H, m), 6.76-6.87 (2H, m), 7.04 (1H, brs), 7.08-7.20 (2H, m).

D) trans-N-[2-{[4-(1-methylethyl)phenoxy]methyl}cyclopropyl]ethanesulfonamide

The title compound was obtained from tert-butyl trans-2-{[4-(1-methylethyl)phenoxy]methyl}cyclopropyl]carbamate in the same manner as in Example 1, step D.

$^1$H NMR (300 MHz, DMSO-d$_6$) δ 0.68-0.78 (1H, m), 0.78-0.90 (1H, m), 1.08-1.25 (9H, m), 1.31-1.48 (1H, m), 2.41-2.52 (1H, m), 2.74-2.90 (1H, m), 3.08 (2H, q, J=7.2 Hz), 3.71-3.81 (1H, m), 3.81-3.92 (1H, m), 6.76-6.86 (2H, m), 7.08-7.17 (2H, m), 7.40 (1H, d, J=3.8 Hz).

Example 17 trans-N-{2-[(4-cyclopropylphenoxy)methyl]cyclobutyl}ethanesulfonamide

The title compound was obtained from tert-butyl trans-[2-(hydroxymethyl)cyclobutyl]carbamate in the same manner as in Example 1, steps C and D.

$^1$H NMR (300 MHz, CDCl$_3$) δ 0.56-0.64 (2H, m), 0.85-0.94 (2H, m), 1.35 (3H, t, J=7.4 Hz), 1.53-1.68 (1H, m), 1.78-1.97 (3H, m), 2.30-2.44 (1H, m), 2.54-2.69 (1H, m), 2.93-3.12 (2H, m), 3.81 (1H, quin, J=8.1 Hz), 3.90-4.01 (2H, m), 4.52 (1H, d, J=8.3 Hz), 6.74-6.82 (2H, m), 6.96-7.03 (2H, m).

Example 18 cis-N-{2-[(4-cyclopropylphenoxy)methyl]cyclobutyl}ethanesulfonamide

A) cis-2-(ethoxycarbonyl)cyclobutanecarboxylic acid

To a solution of diethyl cis-cyclobutanecarboxylate (5.13 g) in ethanol (70 mL) was added 1 M aqueous solution of sodium hydroxide (26.9 mL) over 30 min under ice-cooling. The reaction mixture was stirred at room temperature overnight, and ethanol was concentrated under reduced pressure. The resultant aqueous solution was washed twice with diethyl ether, the aqueous layer was acidified with 6 M hydrochloric acid and extracted with ethyl acetate. The extract was washed with saturated brine, dried over anhydrous magnesium sulfate, and the solvent was evaporated under reduced pressure to give the title compound (3.18 g).
$^1$H NMR (300 MHz, CDCl$_3$) δ 1.24 (3H, t, J=7.2 Hz), 2.15-2.48 (4H, m), 3.35-3.51 (2H, m), 4.15 (2H, qd, J=7.2, 2.3 Hz).

B) ethyl cis-2-[(tert-butoxycarbonyl)amino]cyclobutanecarboxylate

The title compound was obtained from cis-2-(ethoxycarbonyl)cyclobutanecarboxylic acid in the same manner as in Example 16, step C.
$^1$H NMR (300 MHz, CDCl$_3$) δ 1.27 (3H, t, J=7.2 Hz), 1.42 (9H, s), 1.86-2.05 (2H, m), 2.13-2.43 (2H, m), 3.35 (1H, brs), 4.09-4.27 (2H, m), 4.33-4.57 (1H, m), 5.36 (1H, brs).

C) cis-N-{2-[(4-cyclopropylphenoxy)methyl]cyclobutyl}ethanesulfonamide

The title compound was obtained from ethyl cis-2-[(tert-butoxycarbonyl)amino]cyclobutanecarboxylate in the same manner as in Example 7, steps B to D.
$^1$H NMR (300 MHz, CDCl$_3$) δ 0.56-0.64 (2H, m), 0.85-0.94 (2H, m), 1.35 (3H, t, J=7.4 Hz), 1.53-1.68 (1H, m), 1.78-1.97 (3H, m), 2.30-2.44 (1H, m), 2.54-2.69 (1H, m), 2.93-3.12 (2H, m), 3.81 (1H, quin, J=8.1 Hz), 3.90-4.01 (2H, m), 4.52 (1H, d, J=8.3 Hz), 6.74-6.82 (2H, m), 6.96-7.03 (2H, m).

Example 19 cis-N-[4-{[4-(1-methylethyl)phenoxy]methyl}tetrahydrofuran-3-yl]ethanesulfonamide

A) methyl 4-(benzylamino)-2,5-dihydrofuran-3-carboxylate

To a solution of methyl 4-oxotetrahydrofuran-3-carboxylate (3.00 g) in toluene (120 mL) was added benzylamine (2.68 g), and the mixture was stirred at 100° C. for 2 h. The reaction mixture was cooled to room temperature, poured into water and extracted with ethyl acetate. The extract was dried over anhydrous sodium sulfate and concentrated under reduced pressure. The residue was purified by silica gel column chromatography (hexane/ethyl acetate) to give the title compound (2.64 g).
MS (ESI+): [M+H]$^+$ 234.4.

B) methyl cis-4-(benzylamino)tetrahydrofuran-3-carboxylate

To a solution of methyl 4-(benzylamino)-2,5-dihydrofuran-3-carboxylate (2.64 g) in acetic acid (100 mL) was slowly added sodium triacetoxyborohydride (9.60 g), and the mixture was stirred at room temperature for 16 h. The reaction mixture was concentrated, saturated aqueous sodium hydrogencarbonate solution was added and the mixture was extracted with ethyl acetate. The extract was washed with saturated aqueous sodium hydrogencarbonate solution, dried over anhydrous sodium sulfate, and concentrated under reduced pressure. The residue was purified by silica gel column chromatography (hexane/ethyl acetate) to give the title compound (1.83 g).
MS (ESI+): [M+H]$^+$ 236.3.

C) methyl cis-4-aminotetrahydrofuran-3-carboxylate

The title compound was obtained from methyl cis-4-(benzylamino)tetrahydrofuran-3-carboxylate in the same manner as in Example 6, step D.
MS (ESI+): [M+H]$^+$ 146.3.

D) cis-N-[4-{[4-(1-methylethyl)phenoxy]methyl}tetrahydrofuran-3-yl]ethanesulfonamide The title compound was obtained from methyl cis-4-aminotetrahydrofuran-3-carboxylate in the same manner as in Example 7, steps A to D.
MS (ESI+): [M−H]$^+$ 326.3.

Example 20 trans-N-[2-{[4-(1-methylethyl)phenoxy]methyl}cyclohexyl]propane-2-sulfonamide

The title compound was obtained from ethyl trans-2-aminocyclohexanecarboxylate hydrochloride in the same manner as in Example 8, steps A and B.
$^1$H NMR (300 MHz, CDCl$_3$) δ1.12-1.43 (16H, m), 1.59-1.84 (3H, m), 1.87-2.03 (1H, m), 2.18-2.33 (1H, m), 2.85 (1H, spt, J=6.9 Hz), 3.07 (1H, spt, J=6.8 Hz), 3.18-3.37 (1H, m), 3.96 (1H, dd, J=9.2, 5.5 Hz), 4.05 (1H, dd, J=9.4, 4.1 Hz), 4.27 (1H, d, J=8.3 Hz), 6.77-6.87 (2H, m), 7.06-7.17 (2H, m).

Example 21 trans-N-{2-[(4-cyclopropylphenoxy)methyl]cyclohexyl}propane-2-sulfonamide

The title compound was obtained from ethyl trans-2-aminocyclohexanecarboxylate hydrochloride in the same manner as in Example 8, steps A and B.
$^1$H NMR (300 MHz, CDCl$_3$) δ0.50-0.68 (2H, m), 0.80-0.94 (2H, m), 1.12-1.44 (10H, m), 1.59-1.89 (4H, m), 1.89-2.01 (1H, m), 2.17-2.33 (1H, m), 3.06 (1H, spt, J=6.8 Hz), 3.17-3.38 (1H, m), 3.95 (1H, dd, J=9.0, 5.3 Hz), 4.03 (1H, dd, J=9.4, 4.1 Hz), 4.28 (1H, d, J=8.7 Hz), 6.72-6.85 (2H, m), 6.92-7.10 (2H, m).

Example 22 trans-N-[4-{[4-(1-methylethyl)phenoxy]methyl}tetrahydrofuran-3-yl]ethanesulfonamide

A) methyl trans-4-(benzylamino)tetrahydrofuran-3-carboxylate

The title compound (0.19 g) was obtained during the column purification in Example 19, step B.
MS (ESI+): [M+H]⁺ 236.3.

B) methyl trans-4-aminotetrahydrofuran-3-carboxylate

The title compound was obtained from methyl trans-4-(benzylamino)tetrahydrofuran-3-carboxylate in the same manner as in Example 6, step D.
MS (ESI+): [M+H]⁺ 146.0.

C) trans-N-[4-{[4-(1-methylethyl)phenoxy]methyl}tetrahydrofuran-3-yl]ethane sulfonamide The title compound was obtained from methyl trans-4-aminotetrahydrofuran-3-carboxylate in the same manner as in Example 7, steps A to D.
MS (ESI+): [M–H]⁺ 326.5.

Example 23 trans-N-[1-benzyl-3-{[4-(1-methylethyl)phenoxy]methyl}piperidin-4-yl]ethanesulfonamide

A) ethyl 4-amino-1-benzyl-1,2,5,6-tetrahydropyridine-3-carboxylate

A mixture of ethyl 1-benzyl-4-oxopiperidine-3-carboxylate hydrochloride (6.00 g), ammonium acetate (4.66 g), N,N-dimethylacetamide (50 mL) and acetic acid (15 mL) was stirred at room temperature overnight. The reaction mixture was neutralized with 2 M aqueous sodium hydroxide solution and extracted with ethyl acetate. The extract was washed with saturated brine, dried over anhydrous magnesium sulfate, and the solvent was evaporated under reduced pressure. The residue was purified by silica gel column chromatography (NH, hexane/ethyl acetate) to give the title compound (4.78 g).
MS (ESI+): [M+H]⁺ 261.2.

B) ethyl 4-amino-1-benzylpiperidine-3-carboxylate

To a solution of ethyl 4-amino-1-benzyl-1,2,5,6-tetrahydropyridine-3-carboxylate (7.29 g) in tetrahydrofuran (70 mL) was added dropwise trifluoroacetic acid (18 mL) under ice-cooling. Sodium borohydride (2.12 g) was slowly added to the reaction mixture under ice-cooling. The reaction mixture was stirred under ice-cooling for 1 h, water was added slowly. After the H₂ evolution was ceased, the reaction mixture was neutralized with 2 M aqueous sodium hydroxide solution and extracted with ethyl acetate. The extract was washed with saturated brine, dried over anhydrous magnesium sulfate, and the solvent was evaporated under reduced pressure to give the title compound (7.15 g).
MS (ESI+): [M+H]⁺ 263.2.

C) trans-N-[1-benzyl-3-{[4-(1-methylethyl)phenoxy]methyl}piperidin-4-yl]ethanesulfonamide The title compound was obtained from ethyl 4-amino-1-benzylpiperidine-3-carboxylate in the same manner as in Example 7, steps A to D.
MS (ESI+): [M+H]⁺ 431.3.

Example 24 cis-N-[1-benzyl-3-{[4-(1-methylethyl)phenoxy]methyl}piperidin-4-yl]ethanesulfonamide

A) ethyl cis-1-benzyl-4-[(tert-butoxycarbonyl)amino]piperidin-3-carboxylate

The title compound (2.00 g) with a shorter retention time was obtained during the purification by silica gel column chromatography (hexane/ethyl acetate) in Example 23, step C.
¹H NMR (300 MHz, CDCl₃) δ 1.18 (3H, t, J=7.2 Hz), 1.43 (9H, s), 1.67-1.79 (1H, m), 1.97-2.32 (3H, m), 2.69-3.26 (3H, m), 3.34 (1H, d, J=13.6 Hz), 3.57 (1H, d, J=13.2 Hz), 3.72-3.87 (1H, m), 4.12 (2H, q, J=7.2 Hz), 5.57 (1H, d, J=7.6 Hz), 7.19-7.34 (5H, m).

B) cis-N-[1-benzyl-3-{[4-(1-methylethyl)phenoxy]methyl}piperidin-4-yl]ethanesulfonamide The title compound was obtained from ethyl cis-1-benzyl-4-[(tert-butoxycarbonyl)amino]piperidin-3-carboxylate in the same manner as in Example 7, steps B to D.
MS (ESI+): [M+H]⁺ 431.3.

Example 25 cis-N-[3-{[4-(1-methylethyl)phenoxy]methyl}piperidin-4-yl]ethanesulfonamide hydrochloride To a mixture of cis-N-[1-benzyl-3-{[4-(1-methylethyl)phenoxy]methyl}piperidin-4-yl]ethanesulfonamide (0.84 g), 10% palladium-carbon (50% water-containing, 0.08 g) and methanol (20 mL) was added 10% hydrogen chloride-methanol solution (3.56 mL). The reaction mixture was stirred at 50° C. under hydrogen atmosphere overnight. The reaction mixture was filtered and the filtrate was concentrated under reduced pressure. The obtained solid was washed with ethyl acetate and dried to give the title compound (0.68 g).
MS (ESI+): [M+H]⁺ 341.3.

Example 26 trans-2,2,2-trifluoro-N-[2-{[4-(1-methylethyl)phenoxy]methyl}cyclohexyl]ethanesulfonamide The title compound was obtained from ethyl trans-2-aminocyclohexanecarboxylate hydrochloride in the same manner as in Example 8, steps A and B.
¹H NMR (300 MHz, CDCl₃) δ1.21 (6H, d, J=7.2 Hz), 1.24-1.50 (4H, m), 1.57-1.96 (5H, m), 2.15-2.31 (1H, m), 2.85 (1H, spt, J=6.9 Hz), 3.35-3.50 (1H, m), 3.67 (2H, q, J=8.9 Hz), 3.93 (1H, dd, J=9.6, 4.3 Hz), 4.04 (1H, dd, J=9.4, 4.5 Hz), 6.76-6.89 (2H, m), 7.06-7.19 (2H, m).

Example 27 trans-N-{2-[(4-cyclopropylphenoxy)methyl]cyclohexyl}-2,2,2-trifluoroethanesulfonamide The title compound was obtained from ethyl trans-2-aminocyclohexanecarboxylate hydrochloride in the same manner as in Example 8, steps A and B.

$^1$H NMR (300 MHz, CDCl$_3$) δ0.54-0.65 (2H, m), 0.81-0.96 (2H, m), 1.14-1.48 (4H, m), 1.59-1.99 (5H, m), 2.13-2.30 (1H, m), 2.50 (1H, brs), 3.28-3.49 (1H, m), 3.68 (2H, q, J=8.9 Hz), 3.92 (1H, dd, J=9.5, 4.4 Hz), 4.02 (1H, dd, J=9.5, 4.4 Hz), 6.72-6.84 (2H, m), 6.94-7.05 (2H, m).

Example 28

N-[(1RS,2SR)-2-hydroxy-2-{[4-(1-methylethyl)phenoxy]methyl}cyclohexyl]ethanesulfonamide A) 2-(2-methylidenecyclohexyl)-1H-isoindole-1,3(2H)-dione To a solution of 2-(2-oxocyclohexyl)-1H-isoindole-1,3(2H)-dione (3.00 g) and methyltriphenylphosphonium bromide (6.61 g) in tetrahydrofuran (50 mL) was added potassium tert-butoxide (2.08 g) at room temperature. The reaction mixture was stirred at 50° C. overnight and poured into ice-water. The obtained mixture was extracted with ethyl acetate, the extract was washed with saturated brine, dried over anhydrous sodium sulfate, and the solvent was evaporated under reduced pressure. The residue was purified by silica gel column chromatography (hexane/ethyl acetate) to give the title compound (0.94 g).

$^1$H NMR (300 MHz, CDCl$_3$) δ 1.38-1.63 (2H, m), 1.75-1.91 (2H, m), 1.91-2.03 (1H, m), 2.07-2.25 (1H, m), 2.41-2.65 (2H, m), 4.39 (1H, s), 4.65-4.83 (2H, m), 7.68-7.77 (2H, m), 7.79-7.93 (2H, m).

B) 2-[(3RS,4SR)-1-oxaspiro[2.5]oct-4-yl]-1H-isoindole-1,3(2H)-dione

To a solution of 2-(2-methylidenecyclohexyl)-1H-isoindole-1,3(2H)-dione (0.92 g) in ethyl acetate (40 mL) was added m-chloroperbenzoic acid (1.88 g) under ice-cooling. The mixture was stirred at room temperature overnight, and 10% aqueous sodium sulfite solution was added under ice-cooling. The obtained mixture was extracted with ethyl acetate. The extract was washed with saturated brine, dried over anhydrous sodium sulfate, and the solvent was evaporated under reduced pressure. The residue was purified by HPLC to give the title compound (0.35 g) and the diastereomer thereof, 2-[(3RS,4RS)-1-oxaspiro[2.5]oct-4-yl]-1H-isoindole-1,3(2H)-dione (0.31 g).

$^1$H NMR (300 MHz, CDCl$_3$) δ1.31-1.56 (2H, m), 1.65-1.83 (2H, m), 1.83-1.94 (1H, m), 1.95-2.13 (2H, m), 2.35-2.42 (1H, m), 2.42-2.49 (1H, m), 3.03 (1H, m), 4.55 (1H, dd, J=13.2, 4.5 Hz), 7.65-7.76 (2H, m), 7.76-7.89 (2H, m).

C) 2-{[(1RS,2SR)-2-hydroxy-2-{[4-(1-methylethyl)phenoxy]methyl}cyclohexyl]carbamoyl}benzoic acid To a solution of 2-[(3RS,4SR)-1-oxaspiro[2.5]oct-4-yl]-1H-isoindole-1,3(2H)-dione (0.25 g) and 4-(1-methylethyl)pheneol (0.40 g) in N,N-dimethylformamide (10 mL) was added sodium hydride (60%, 0.10 g) under ice-cooling. The mixture was stirred at room temperature overnight, and the solvent was evaporated under reduced pressure. The residue was partitioned with ethyl acetate and water, and the aqueous layer was acidified with 1 M hydrochloric acid. The mixture was extracted with ethyl acetate, the extract was washed with saturated brine, dried over anhydrous sodium sulfate, and the solvent was evaporated under reduced pressure to give the title compound (0.29 g).

$^1$H NMR (300 MHz, CDCl$_3$) δ1.20 (6H, d, J=6.8 Hz), 1.27-1.60 (4H, m), 1.61-1.84 (2H, m), 1.84-1.97 (1H, m), 2.15 (1H, d, J=10.2 Hz), 2.75-2.92 (1H, m), 3.86 (1H, d, J=9.1 Hz), 4.00-4.28 (4H, m), 6.82-6.94 (2H, m), 7.09-7.17 (2H, m), 7.37-7.61 (3H, m), 7.93-8.08 (1H, m).

D) (1RS,2SR)-2-amino-1-{[4-(1-methylethyl)phenoxy]methyl}cyclohexanol

To a solution of 2-{[(1RS,2SR)-2-hydroxy-2-{[4-(1-methylethyl)phenoxy]methyl}cyclohexyl]carbamoyl}benzoic acid (0.29 g) in ethanol (15 mL) was added hydrazine monohydrate (0.34 mL) at room temperature. The mixture was heated under reflux overnight, and the solvent was evaporated under reduced pressure. To the residue was added ice, and the mixture was extracted with ethyl acetate. The extract was washed with saturated brine, dried over anhydrous sodium sulfate, and the solvent was evaporated under reduced pressure. The residue was purified by silica gel column chromatography (NH silica gel, hexane/ethyl acetate) to give the title compound (0.13 g).

$^1$H NMR (300 MHz, CDCl$_3$) δ1.22 (6H, d, J=7.2 Hz), 1.24-1.40 (1H, m), 1.40-1.63 (5H, m), 1.63-1.90 (5H, m), 2.86 (1H, spt, J=6.9 Hz), 3.06 (1H, dd, J=10.9, 4.9 Hz), 3.72 (1H, d, J=9.0 Hz), 3.83 (1H, d, J=9.0 Hz), 6.79-6.90 (2H, m), 7.07-7.19 (2H, m).

E) N-[(1RS,2SR)-2-hydroxy-2-{[4-(1-methylethyl)phenoxy]methyl}cyclohexyl]ethanesulfonamide The title compound was obtained from (1RS,2SR)-2-amino-1-{[4-(1-methylethyl)phenoxy]methyl}cyclohexanol in the same manner as in Example 4, step F.

$^1$H NMR (300 MHz, CDCl$_3$) δ1.22 (6H, d, J=6.8 Hz), 1.25-1.44 (4H, m), 1.45-1.63 (3H, m), 1.65-1.84 (2H, m), 1.85-2.08 (2H, m), 2.15 (1H, s), 2.77-2.92 (1H, m), 2.92-3.07 (2H, m), 3.34-3.48 (1H, m), 3.88 (1H, d, J=9.1 Hz), 4.05 (1H, d, J=9.1 Hz), 4.60 (1H, d, J=9.8 Hz), 6.79-6.89 (2H, m), 7.08-7.19 (2H, m, J=8.7 Hz).

Example 29 trans-N-[3-{[4-(1-methylethyl)phenoxy]methyl}piperidin-4-yl]ethanesulfonamide hydrochloride The title compound was obtained from trans-N-[1-benzyl-3-{[4-(1-methylethyl)phenoxy]methyl}piperidin-4-yl]ethanesulfonamide in the same manner as in Example 25.

MS (ESI+): [M+H]$^+$ 341.3.

Example 30 cis-N-[1-acetyl-3-{[4-(1-methylethyl)phenoxy]methyl}piperidin-4-yl]ethanesulfonamide To a solution of cis-N-[3-{[4-(1-methylethyl)phenoxy]methyl}piperidin-4-yl]ethanesulfonamide hydrochloride (0.25 g) in N,N-dimethylacetamide (2.0 mL) was added acetic anhydride (0.094 mL) and the mixture was stirred at room temperature for 1 h. The reaction mixture was neutralized with aqueous sodium hydrogencarbonate solution and stirred overnight. The formed solid was collected by filtration, washed with water and dried. The obtained solid was recrystallized from ethyl acetate-hexane to give the title compound (0.23 g).

MS (ESI+): [M+H]$^+$ 383.2.

Example 31 trans-N-[1-acetyl-3-{[4-(1-methylethyl)phenoxy] methyl}piperidin-4-yl]ethanesulfonamide The title compound was obtained from trans-N-[3-{[4-(1-methylethyl)phenoxy]methyl}piperidin-4-yl]ethanesulfonamide hydrochloride in the same manner as in Example 30.

MS (ESI+): [M+H]$^+$ 383.2.

Example 32 cis-N-[1-methyl-3-{[4-(1-methylethyl)phenoxy] methyl}piperidin-4-yl]ethanesulfonamide A mixture of cis-N-[3-{[4-(1-methylethyl)phenoxy] methyl}piperidin-4-yl]ethanesulfonamide hydrochloride (0.31 g), sodium hydrogencarbonate (0.21 g), methyl iodide (0.10 mL) and ethanol (4 mL) was stirred at room temperature overnight. To the reaction mixture was added water, and the mixture was extracted with ethyl acetate. The extract was washed with saturated brine, dried over anhydrous magnesium sulfate, and the solvent was evaporated under reduced pressure. The residue was purified by silica gel column chromatography (NH silica gel, ethyl acetate), and the obtained solid was recrystallized from ethyl acetate-hexane to give the title compound (0.10 g).

MS (ESI+): [M+H]$^+$ 355.3.

Example 33 trans-N-[1-methyl-3-{[4-(1-methylethyl)phenoxy] methyl}piperidin-4-yl]ethanesulfonamide The title compound was obtained from trans-N-[3-{[4-(1-methylethyl)phenoxy]methyl}piperidin-4-yl]ethanesulfonamide hydrochloride in the same manner as in Example 32.

MS (ESI+): [M+H]$^+$ 355.3.

Example 34 trans-N-{3-[(4-isopropylphenoxy)methyl]tetrahydro-2H-pyran-4-yl}ethanesulfonamide A) ethyl trans-4-(benzylamino)tetrahydro-2H-pyran-3-carboxylate To a solution of ethyl cis-4-(benzylamino)tetrahydro-2H-pyran-3-carboxylate (0.88 g) in ethanol (20 mL) was added sodium ethoxide (0.68 g). The reaction mixture was stirred at 60° C. for 3 h, and saturated aqueous ammonium chloride solution was added. The reaction mixture was extracted with ethyl acetate. The extract was washed with saturated brine, dried over anhydrous sodium sulfate, and the solvent was evaporated under reduced pressure. The residue was purified by silica gel column chromatography (ethyl acetate/hexane) to give the title compound (0.37 g).

$^1$H NMR (300 MHz, CDCl$_3$) δ 1.25 (3H, t, J=7.2 Hz), 1.36-1.54 (1H, m), 1.94-2.09 (1H, m), 2.56 (1H, td, J=10.3, 4.3 Hz), 3.03 (1H, td, J=10.4, 4.2 Hz), 3.34-3.50 (2H, m), 3.73 (1H, d, J=12.8 Hz), 3.88 (1H, d, J=12.8 Hz), 3.94-4.03 (1H, m), 4.03-4.22 (3H, m), 7.20-7.38 (5H, m).

B) ethyl trans-4-aminotetrahydro-2H-pyran-3-carboxylate

The title compound was obtained from ethyl trans-4-(benzylamino)tetrahydro-2H-pyran-3-carboxylate in the same manner as in Example 6, step D.

$^1$H NMR (300 MHz, CDCl$_3$) δ 1.27 (3H, t, J=7.2 Hz), 1.39-1.54 (1H, m), 1.77-1.88 (1H, m), 2.39 (1H, td, J=10.5, 4.5 Hz), 3.12 (1H, td, J=10.7, 4.1 Hz), 3.30-3.50 (2H, m), 3.98 (1H, dd, J=11.5, 4.7 Hz), 4.09 (1H, dd, J=11.7, 4.1 Hz), 4.17 (2H, q, J=6.9 Hz).

C) trans-N-{3-[(4-isopropylphenoxy)methyl]tetrahydro-2H-pyran-4-yl}ethanesulfonamide The title compound was obtained from ethyl trans-4-aminotetrahydro-2H-pyran-3-carboxylate in the same manner as in Example 7, steps A to D.

MS (ESI+): [M+H]$^+$ 342.3.

Example 35 cis-N-{3-[(4-isopropylphenoxy)methyl]tetrahydro-2H-pyran-4-yl]ethanesulfonamide

The title compound was obtained from methyl 4-oxotetrahydro-2H-pyran-3-carboxylate in the same manner as in Example 19, steps A to G.

MS (ESI+): [M+H]$^+$ 342.3.

Example 36 cis-N-[2-{[4-(1-methylethyl)phenoxy] methyl}cyclopropyl]ethanesulfonamide

A) cis-2-[(benzyloxy)carbonyl]cyclopropanecarboxylic acid

A mixture of 3-oxabicyclo[3.1.0]hexane-2,4-dione (1.08 g) and benzylalcohol (1.15 g) was stirred at 60° C. for 3 h. The mixture was purified by silica gel column chromatography (hexane/ethyl acetate) to give the title compound (1.77 g).

MS (ESI+): [M−H]$^+$ 219.1.

B) benzyl cis-2-(hydroxymethyl)cyclopropanecarboxylate

To a solution of cis-2-[(benzyloxy)carbonyl]cyclopropanecarboxylic acid (1.77 g) and 4-methylmorpholine (1.24 mL) in tetrahydrofuran (30 mL) was added ethyl chloroformate (0.923 mL) at 0° C. The reaction mixture was stirred for 30 min, and cooled to −30° C., and sodium borohydride (1.07 g) was added. Then, methanol (8.0 mL) was added dropwise over 15 min while maintaining at −10° C. or below. The reaction mixture was warmed to 0° C., and stirred at the same temperature for 1 h. Saturated aqueous ammonium chloride solution was added, and the mixture was extracted with ethyl acetate. The extract was washed with saturated brine, dried over anhydrous sodium sulfate, and concentrated under reduced pressure. The residue was purified by silica gel column chromatography (hexane/ethyl acetate) to give the title compound (1.43 g).

$^1$H NMR (300 MHz, DMSO-d$_6$) δ 0.79-0.93 (1H, m), 1.01-1.13 (1H, m), 1.44-1.62 (1H, m), 1.74-1.87 (1H, m), 3.34-3.48 (1H, m), 3.57-3.67 (1H, m), 4.52-4.62 (1H, m), 5.02-5.15 (2H, m), 7.26-7.45 (5H, m).

C) benzyl cis-2-{[4-(1-methylethyl)phenoxy] methyl}cyclopropanecarboxylate

The title compound was obtained from benzyl cis-2-(hydroxymethyl)cyclopropanecarboxylate and 4-(1-methylethyl)phenol in the same manner as in Example 1, step C.
MS (ESI+): [M–H]$^+$ 323.0.

D) cis-N-[2-{[4-(1-methylethyl)phenoxy] methyl}cyclopropyl]ethanesulfonamide

The title compound was obtained from benzyl cis-2-{[4-(1-methylethyl)phenoxy]methyl}cyclopropanecarboxylate in the same manner as in Example 16, steps B to D.

$^1$H NMR (300 MHz, DMSO-d$_6$) δ 0.56-0.69 (1H, m), 0.90-1.02 (1H, m), 1.09-1.41 (10H, m), 2.62-2.91 (2H, m), 3.08 (2H, q, J=7.3 Hz), 3.87-4.08 (2H, m), 6.78-6.89 (2H, m), 7.08-7.20 (2H, m), 7.39 (1H, d, J=2.3 Hz).

Example 37

N-[(1RS,2RS)-2-hydroxy-2-{[4-(1-methylethyl)phenoxy]methyl}cyclohexyl]ethanesulfonamide A) 2-[(3RS,4RS)-1-oxaspiro[2.5]oct-4-yl]-1H-isoindole-1,3(2H)-dione The title compound was obtained by HPLC purification in Example 28, step B.

$^1$H NMR (300 MHz, CDCl$_3$) δ1.37-1.71 (3H, m), 1.74-2.13 (4H, m), 2.55 (1H, dd, J=4.1, 1.1 Hz), 2.66-2.97 (2H, m), 4.52 (1H, dd, J=12.8, 3.8 Hz), 7.60-7.76 (2H, m), 7.76-7.89 (2H, m).

B) N-[(1RS,2RS)-2-hydroxy-2-{[4-(1-methylethyl) phenoxy]methyl}cyclohexyl]ethanesulfonamide The title compound was obtained from 2-[(3RS,4RS)-1-oxaspiro[2.5]oct-4-yl]-1H-isoindole-1,3(2H)-dione in the same manner as in Example 28, steps C to E.

$^1$H NMR (300 MHz, CDCl$_3$) δ1.23 (6H, d, J=6.8 Hz), 1.30 (3H, t, J=7.4 Hz), 1.34-1.74 (6H, m), 1.78-1.95 (1H, m), 1.99-2.17 (1H, m), 2.76-2.97 (2H, m), 2.97-3.21 (2H, m), 3.43-3.58 (1H, m), 3.91 (1H, d, J=9.8 Hz), 4.17 (1H, d, J=9.4 Hz), 5.17 (1H, d, J=9.1 Hz), 6.79-6.93 (2H, m), 7.06-7.20 (2H, m).

Example 39 trans-N-[2-{[4-(1-methylethyl)phenoxy]methyl}-4-oxocyclohexyl]ethanesulfonamide

A) ethyl 8-amino-1,4-dioxaspiro[4.5]dec-7-ene-7-carboxylate

A solution of diethyl 4-oxoheptanedioic acid (24.9 g), ethane-1,2-diol (10.7 g) and p-toluenesulfonic acid monohydrate (206 mg) in toluene (80.0 mL) was stirred under reflux overnight. The reaction mixture was neutralized with saturated aqueous sodium hydrogencarbonate solution and extracted with ethyl acetate. The extract was washed with water and saturated brine, dried over anhydrous magnesium sulfate, and the solvent was evaporated under reduced pressure. A solution of the obtained residue in tetrahydrofuran (20 mL) was added to a solution of potassium tert-butoxide (20.0 g) in tetrahydrofuran (300 mL) at room temperature over 30 min. The reaction mixture was stirred overnight, 10% aqueous citric acid solution was added, and the mixture was extracted with ethyl acetate. The extract was washed with water and saturated brine, dried over anhydrous magnesium sulfate, and the solvent was evaporated under reduced pressure. A solution of the obtained residue and ammonium acetate (33.3 g) in ethanol (140 mL) was stirred at room temperature for 2 h. The reaction mixture was neutralized with saturated aqueous sodium hydrogencarbonate solution and extracted with ethyl acetate. The extract was washed with water and saturated brine, dried over anhydrous magnesium sulfate, and the solvent was evaporated under reduced pressure. The residue was purified by silica gel column chromatography (NH silica gel, ethyl acetate/hexane) to give the title compound (11.3 g).

$^1$H NMR (300 MHz, CDCl$_3$) δ 1.26 (3H, t, J=7.2 Hz), 1.81 (2H, t, J=6.8 Hz), 2.44 (2H, t, J=6.8 Hz), 2.50 (2H, s), 3.94-4.06 (4H, m), 4.12 (2H, q, J=7.2 Hz).

B) ethyl 8-amino-1,4-dioxaspiro[4.5]decane-7-carboxylate

To a solution of ethyl 8-amino-1,4-dioxaspiro[4.5]dec-7-ene-7-carboxylate (11.3 g) in tetrahydrofuran (100 mL) was added trifluoroacetic acid (30.6 ml) over 10 min under ice-cooling, and then sodium borohydride (3.76 g) over 20 min. The reaction mixture was stirred for 30 min under ice-cooling, 8 M aqueous sodium hydroxide solution was added, and the mixture was extracted with ethyl acetate. The extract was washed with saturated aqueous sodium hydrogencarbonate solution and saturated brine, dried over anhydrous magnesium sulfate, and the solvent was evaporated under reduced pressure. The residue was purified by silica gel column chromatography (NH silica gel, ethyl acetate/hexane) to give the title compound (6.59 g).
MS (ESI+): [M+H]$^+$ 230.3.

C) ethyl 8-[(ethylsulfonyl)amino]-1,4-dioxaspiro [4.5]decane-7-carboxylate

To a solution of ethyl 8-amino-1,4-dioxaspiro[4.5]decane-7-carboxylate (5.95 g) and triethylamine (7.23 mL) in tetrahydrofuran (80 mL) was added ethanesulfonyl chloride (3.69 mL) under ice-cooling. The reaction mixture was stirred at room temperature overnight, saturated aqueous sodium carbonate solution was added. The reaction mixture was extracted with ethyl acetate. The extract was washed with water and saturated brine, dried over anhydrous magnesium sulfate, and the solvent was evaporated under reduced pressure. The residue was purified by silica gel column chromatography (ethyl acetate/hexane) to give the title compound (6.59 g).
MS (ESI+): [M+H]$^+$ 322.3.

D) N-[7-(hydroxymethyl)-1,4-dioxaspiro[4.5]dec-8-yl]ethanesulfonamide

To a suspension of lithium aluminium hydride (1.17 g) and diethyl ether (120 mL) was added dropwise a solution of ethyl 8-[(ethylsulfonyl)amino]-1,4-dioxaspiro[4.5]decane-7-carboxylate (6.59 g) in diethyl ether (10 mL) under ice-cooling over 15 min. The reaction mixture was stirred under ice-cooling for 30 min, sodium sulfate 10 hydrate (5.71 g) was added. The insoluble material was filtered off and washed with tetrahydrofuran, and the filtrate was concentrated under reduced pressure. The residue was purified by silica gel column chromatography (ethyl acetate), and the obtained oil was crystallized from hexane to give the title compound (2.36 g).

$^1$H NMR (300 MHz, CDCl$_3$) δ 1.33-1.46 (3H, m), 1.49-1.82 (4H, m), 1.84-2.17 (2H, m), 2.67 (1H, dd, J=7.7, 5.5 Hz), 2.95-3.32 (3H, m), 3.41-3.57 (1H, m), 3.62-3.83 (1H, m), 3.88-4.04 (4H, m), 4.70 (1H, d, J=9.1 Hz), 5.15 (1H, d, J=8.7 Hz).

E) trans-N-[2-{[4-(1-methylethyl)phenoxy]methyl}-4-oxocyclohexyl]ethanesulfonamide To a solution of N-[7-(hydroxymethyl)-1,4-dioxaspiro [4.5]dec-8-yl]ethanesulfonamide (1.80 g), 4-(1-methylethyl)phenol (1.32 g) and tributylphosphine (3.22 mL) in tetrahydrofuran (60 mL) was added 1,1'-(azodicarbonyl) dipiperidine (2.13 g) at room temperature. The reaction mixture was stirred at room temperature for 2 h, and concentrated under reduced pressure. To the residue was added toluene, the insoluble material was filtered off, and the filtrate was concentrated under reduced pressure. The residue was purified by silica gel column chromatography (hexane/ethyl acetate) to give oil (2.24 g). A mixture of the obtained oil (2.24 g), 2 M hydrochloric acid (6 mL) and acetone (20 mL) was stirred at room temperature overnight. To the reaction mixture was added saturated aqueous sodium hydrogencarbonate solution, and the mixture was extracted with ethyl acetate. The extract was washed with saturated brine, dried over anhydrous magnesium sulfate, and the solvent was evaporated under reduced pressure. The residue was purified by silica gel column chromatography (hexane/ethyl acetate) to give the title compound (1.09 g).

$^1$H NMR (300 MHz, CDCl$_3$) δ 1.16-1.29 (9H, m), 1.64-1.90 (1H, m), 2.09-2.25 (1H, m), 2.42-2.73 (5H, m), 2.80-3.04 (3H, m), 3.77-3.93 (2H, m), 4.17 (1H, dd, J=9.6, 3.6 Hz), 4.39 (1H, d, J=9.1 Hz), 6.78-6.87 (2H, m), 7.15 (2H, d, J=8.7 Hz).

Example 42

N-[(1RS,2RS)-2-hydroxy-2-{[4-(1-methylethyl)phenoxy]methyl}cyclopentyl]ethanesulfonamide The title compound was obtained from 2-(2-oxocyclohexyl)-1H-isoindole-1,3(2H)-dione in the same manner as in Example 28, steps A to E.

$^1$H NMR (300 MHz, CDCl$_3$) δ1.22 (6H, d, J=6.8 Hz), 1.33 (3H, t, J=7.4 Hz), 1.65-1.93 (4H, m), 1.93-2.09 (1H, m), 2.14-2.29 (1H, m), 2.86 (1H, spt, J=6.9 Hz), 2.97-3.14 (3H, m), 3.66-3.80 (1H, m), 3.98 (1H, d, J=9.1 Hz), 4.07 (1H, d, J=9.1 Hz), 4.69 (1H, d, J=9.4 Hz), 6.80-6.92 (2H, m), 7.07-7.22 (2H, m).

Example 43 trans-N-{2-[(4-oxetan-3-ylphenoxy)methyl]cyclohexyl}ethanesulfonamide

A) 4-(oxetan-3-yl)aniline

To a solution of tert-butyl [4-(oxetan-3-yl)phenyl]carbamate (10.0 g) in anhydrous DCM (160 ml) was added TFA (40 ml), and the resulting reaction mixture was stirred at 25° C. for 1 h. To the mixture was added saturated Na$_2$CO$_3$ solution slowly to adjust pH=8-9, then the aqueous layer was extracted with DCM (100 ml×2). The combined organic layers were washed with brine (100 ml), dried over anhydrous Na$_2$SO$_4$ and concentrated to give the title compound (6.00 g) as a yellow solid.

$^1$H NMR (300 MHz, CDCl$_3$) δ 3.45 (2H, brs), 4.05-4.20 (1H, m), 4.73 (2H, t, J=6.3 Hz), 5.02 (2H, dd, J=7.8, 6.0 Hz), 6.69 (2H, d, J=8.1 Hz), 7.20 (2H, d, J=8.4 Hz).

B) 3-(4-bromophenyl)oxetane

To a solution of 4-(oxetan-3-yl)aniline (6.00 g) in MeCN (120 ml) was added CuBr$_2$ (9.80 g), then the mixture was cooled to 0° C., t-BuONO (4.60 g) was added dropwise. The resulting reaction mixture was stirred at 0° C. for 4 h, followed at 25° C. for 16 h. The mixture was diluted with water (200 ml), then extracted with EtOAc (500 ml×2). The combined organic layers were washed with brine (200 ml), dried over anhydrous Na$_2$SO$_4$ and concentrated. The residue was purified by silica gel column (PE/EtOAc) twice to give the title compound (3.54 g, contains some impurity) as yellow oil.

$^1$H NMR (400 MHz, CDCl$_3$) δ 4.10-4.25 (1H, m), 4.72 (2H, t, J=6.4 Hz), 5.07 (2H, dd, J=8.4, 6.0 Hz), 7.28 (2H, d, J=8.0 Hz), 7.49 (2H, d, J=8.4 Hz).

C) 4,4,5,5-tetramethyl-2-[4-(oxetan-3-yl)phenyl]-1,3,2-dioxaborolane

A mixture of 3-(4-bromophenyl)oxetane (2.50 g), bis (pinacolato)diboron (3.60 g), Pd(dppf)Cl$_2$ (257 mg) and KOAc (3.40 g) in DMSO (25 ml) was degassed and purged with N$_2$ for three times. Then the mixture was stirred at 80° C. under N$_2$ for 16 h. The mixture was cooled to room temperature and 50 ml of water was added, then the mixture was extracted with EtOAc (50 ml×2). The combined organic layers were washed with brine (50 ml), dried over anhydrous Na$_2$SO$_4$ and concentrated. The residue was purified by silica gel column (PE/EtOAc) to give the title compound (2.00 g) as a green solid.

$^1$H NMR (400 MHz, CDCl$_3$) δ 1.35 (12H, s), 4.20-4.30 (1H, m), 4.78 (2H, t, J=6.4 Hz), 5.07 (2H, dd, J=14.4, 8.0 Hz), 7.41 (2H, d, J=8.0 Hz), 7.82 (2H, d, J=8.4 Hz).

D) 4-(oxetan-3-yl)phenol

To a solution of 4,4,5,5-tetramethyl-2-[4-(oxetan-3-yl) phenyl]-1,3,2-dioxaborolane (744 mg) in THF (25 ml) was added 1 M NaOH aq. (3.43 ml) and 30% H$_2$O$_2$ solution (0.385 ml). The mixture was stirred at room temperature for 10 min. The mixture was neutralized with 1 M HCl aq. and extracted with EtOAc. The organic layer was separated, washed with water and brine, dried over MgSO$_4$ and concentrated in vacuo. The residue was purified by column chromatography (silica gel, eluted with EtOAc in hexane) to give the title compound (23.3 mg) as a white solid.

$^1$H NMR (300 MHz, CDCl$_3$) δ 4.18 (1H, quin, J=7.6 Hz), 4.76 (2H, t, J=6.4 Hz), 5.07 (2H, dd, J=8.5, 5.9 Hz), 5.27 (1H, s), 6.80-6.87 (2H, m), 7.23-7.32 (2H, m).

E) trans-diethyl cyclohexane-1,2-dicarboxylate

To a solution of trans-cyclohexane-1,2-dicarboxylic acid (25 g) in EtOH (500 ml) was added H$_2$SO$_4$ (1.55 ml) at room temperature. After being refluxed overnight, the volatile components were concentrated off. The residue was partitioned between EtOAc and water, the organic layer was washed with sat. NaHCO$_3$ aq. and brine, dried over with Na$_2$SO$_4$, concentrated in vacuo to give trans-diethyl cyclohexane-1,2-dicarboxylate (29.9 g) as a colorless oil.

MS (API+), found: 229.3 (M+1)

F) (1RS,2RS)-2-(ethoxycarbonyl)cyclohexanecarboxylic acid

To a solution of (1RS,2RS)-diethyl cyclohexane-1,2-dicarboxylate (29.9 g) in EtOH (150 ml) was added 1 M NaOH aq. (16.37 ml) at 0° C. After being stirred at room temperature over weekend, the volatile components were concentrated off. The residue was partitioned between Et$_2$O and water and the aqueous layer was acidified with 1 M HCl aq. The mixture was extracted with EtOAc and the organic layer was washed with brine, dried over with Na$_2$SO$_4$, concentrated in vacuo to give the title compound (18.81 g) as colorless crystals.

MS (API+), found: 199.1 (M−1)

G) trans-ethyl 2-(tert-butoxycarbonylamino)cyclohexanecarboxylate

A mixture of trans-2-(ethoxycarbonyl)cyclohexanecarboxylic acid (4.00 g), Et$_3$N (3.35 ml), diphenylphosphoryl azide (4.74 ml) and t-BuOH (19.13 ml) in toluene (20 ml) was stirred at 80° C. overnight. The volatile was removed by evaporation and the residue was dissolved in THF (20 mL). To the solution were added Et$_3$N (3.35 ml) and Boc$_2$O (4.64 ml) at room temperature and the mixture was stirred overnight. The mixture was quenched with sat. NaHCO$_3$ aq. and extracted with EtOAc. The extract was washed with water and brine, dried over MgSO$_4$ and concentrated under vacuum. The residue was purified by column chromatography (silica gel, eluted with EtOAc in hexane) to give the title compound (2.266 g) as a white solid.

MS (API+), found: 172.1 (M+1-Boc)

H) trans-ethyl 2-(ethylsulfonamido)cyclohexanecarboxylate

A solution of trans-ethyl 2-(tert-butoxycarbonylamino) cyclohexanecarboxylate (2.26 g) in 4 M HCl/EtOAc (41.6 ml) was stirred at room temperature for 2 h. Removal of the solvent by evaporation afforded (1SR,2SR)-ethyl 2-aminocyclohexanecarboxylate hydrochloride (1.730 g). To a solution of (1SR,2SR)-ethyl 2-aminocyclohexanecarboxylate hydrochloride (1.730 g) in THF(dry) (40 ml) was added Et$_3$N (3.48 ml) at 0° C. After being stirred at 0° C. for 10 min, ethanesulfonyl chloride (0.945 ml) was added to the reaction mixture. The mixture was stirred at room temperature overnight. The mixture was quenched with sat. NaHCO$_3$ aq. and extracted with EtOAc. The organic layer was separated, washed with brine, dried over MgSO$_4$ and concentrated in vacuo. The residue was purified by column chromatography (silica gel, eluted with EtOAc in hexane) to give the title compound (1.520 g) as a colorless solid.

$^1$H NMR (300 MHz, CDCl$_3$) δ 1.09-1.81 (10H, m), 1.83-2.12 (3H, m), 2.17-2.35 (2H, m), 3.04 (2H, qd, J=7.3, 1.5 Hz), 3.39-3.53 (1H, m), 4.00 (1H, d, J=10.2 Hz), 4.10-4.19 (2H, m).

I) trans-N-(2-(hydroxymethyl)cyclohexyl)ethanesulfonamide

To a solution of trans-ethyl 2-(ethylsulfonamido)cyclohexanecarboxylate (1.52 g) in THF (dry) (30 ml) was added LAH (0.438 g) at 0° C. The mixture was stirred at 0° C. under a dry atmosphere (CaCl$_2$ tube) for 1 h. The mixture was quenched with 1 M NaOH aq. (1.76 ml) and stirred for further 1 h. The mixture was passed through a pad of celite and the filtrate was concentrated under vacuum. The residue was purified by column chromatography (silica gel, eluted with EtOAc in hexane) to give the title compound (0.678 g) as a colorless solid.

$^1$H NMR (300 MHz, CDCl$_3$) δ 1.16-1.56 (7H, m), 1.74 (3H, dd, J=12.8, 2.6 Hz), 1.96-2.25 (1H, m), 2.44-2.68 (1H, m), 2.95-3.36 (3H, m), 3.43-3.68 (1H, m), 3.92-4.17 (1H, m), 4.48 (1H, d, J=7.9 Hz).

J) trans-N-{2-[(4-oxetan-3-ylphenoxy)methyl] cyclohexyl}ethanesulfonamide

To a solution of trans-N-(2-(hydroxymethyl)cyclohexyl) ethanesulfonamide (100 mg), 4-(oxetan 3-yl)phenol (102 mg) and Bu$_3$P (0.223 ml) in toluene (10 ml) was added 1,1'-(azodicarbonyl)dipiperidine (228 mg) at room temperature. The mixture was stirred at room temperature overnight. The insoluble material was removed by filtration, and the filtrate was concentrated under vacuum. The residue was purified by column chromatography (silica gel, eluted with EtOAc in hexane) to give the title compound (110 mg) as a colorless oil.

$^1$H NMR (300 MHz, CDCl$_3$) δ 1.20-1.45 (7H, m), 1.61-1.85 (3H, m), 1.94 (1H, dd, J=12.7, 3.2 Hz), 2.20-2.30 (1H, m), 2.96 (2H, q, J=7.6 Hz), 3.22-3.37 (1H, m), 4.03 (2H, d, J=4.5 Hz), 4.12-4.25 (1H, m), 4.33 (1H, d, J=8.7 Hz), 4.73 (2H, t, J=6.4 Hz), 5.05 (2H, dd, J=8.5, 5.9 Hz), 6.90 (2H, d, J=8.7 Hz), 7.31 (2H, d, J=8.7 Hz).

Example 44 trans-N-{2-[(2-cyanophenoxy)methyl] cyclohexyl}ethanesulfonamide

Titled compound was synthesized by the similar method to process C) of Example 1.

$^1$H NMR (300 MHz, CDCl$_3$) δ 1.21-1.44 (7H, m), 1.68-1.88 (3H, m), 2.05-2.22 (2H, m), 2.93-3.14 (2H, m), 3.21-3.37 (1H, m), 4.08 (1H, dd, J=9.1, 6.0 Hz), 4.14 (1H, d, J=9.4 Hz), 4.25 (1H, dd, J=9.1, 3.8 Hz), 6.95-7.05 (2H, m), 7.47-7.58 (2H, m).

Example 45 trans-N-{2-[(2-fluorophenoxy)methyl] cyclohexyl}ethanesulfonamide

Titled compound was synthesized by the similar method to process C) of Example 1.

$^1$H NMR (300 MHz, CDCl$_3$) δ 1.21-1.46 (7H, m), 1.66-1.84 (3H, m), 1.93-2.04 (1H, m), 2.21-2.30 (1H, m), 3.00 (2H, q, J=7.3 Hz), 3.22-3.37 (1H, m), 4.03-4.17 (2H, m), 4.31 (1H, d, J=8.3 Hz), 6.84-7.14 (4H, m).

Example 46 cis-N-[1-methyl-4-{[4-(1-methylethyl)phenoxy] methyl}piperidin-3-yl]ethanesulfonamide A) cis-N-[1-benzyl-{[4-(1-methylethyl)phenoxy] methyl}piperidin-3-yl]ethanesulfonamide The title compound was obtained from ethyl 1-benzyl-3-oxopiperidine-4-carboxylate in the same manner as in Examples 23 and 24.

MS (ESI+): [M+H]$^+$ 431.2.

B) cis-N-[1-methyl-4-{[4-(1-methylethyl)phenoxy]methyl}piperidin-3-yl]ethanesulfonamide To a mixture of cis-N-[1-benzyl-{[4-(1-methylethyl)phenoxy]methyl}piperidin-3-yl]ethanesulfonamide (0.024 g), 10% palladium-carbon (50% water-containing, 0.020 g) and methanol (3 mL) was added 10% hydrogen chloride-methanol solution (0.10 mL). The reaction mixture was stirred at room temperature under hydrogen atmosphere overnight. The reaction mixture was filtered and the filtrate was concentrated under reduced pressure. The obtained residue was poured into a saturated aqueous sodium hydrogencarbonate solution, and the mixture was extracted with ethyl acetate. The extract was dried over anhydrous sodium sulfate, and the solvent was evaporated under reduced pressure. To a solution of the residue in tetrahydrofuran (3 mL) were added triethylamine (0.078 mL) and acetic anhydride (0.016 ml). The reaction mixture was stirred at 0° C. for 2 h, and poured into a saturated aqueous sodium hydrogencarbonate solution, and the mixture was extracted with ethyl acetate. The extract was dried over anhydrous sodium sulfate, and the solvent was evaporated under reduced pressure. The residue was purified by NH silica gel column chromatography (hexane/ethyl acetate) to give the title compound (3.6 mg).

MS (ESI+): [M+H]$^+$ 355.3.

Example 47 trans-N-[2-{[4-(trifluoromethyl)phenoxy]methyl}cyclohexyl]ethanesulfonamide

To 4-(trifluoromethyl)phenol (19 mg) were added a solution of trans-N-[2-(hydroxymethyl)cyclohexyl]ethanesulfonamide (18 mg) in toluene (0.5 mL) and a solution of tributylphosphine (39 mL) in toluene (0.25 mL), and the mixture was stirred at room temperature for 5 min. To the mixture was added a solution of 1,1'-[(E)-diazene-1,2-diyldicarbonyl]dipiperidine (40 mg) in toluene (0.25 mL), and the mixture was stirred at room temperature overnight. The reaction mixture was concentrated by air-blow, and the residue was purified by preparative HPLC (acetonitrile/10 mM aqueous ammonium bicarbonate solution) to give the title compound (8.6 mg).

MS (ESI+): [M+H]$^+$ 366.2.

Examples 48-87

The compounds of Examples 48-87 were obtained in the same manner as in Examples 1-47.

Example 88 trans-N-{2-[(4-cyanophenoxy)methyl]cyclohexyl}ethanesulfonamide

To 4-cyanophenol (14 mg) were added a solution of N-[(1S,2S)-2-(hydroxymethyl)cyclohexyl]ethanesulfonamide (18 mg) in 1,2-dimethoxyethane (0.5 mL) and a solution of cyanomethylene tributylphosphorane (39 mg) in 1,2-dimethoxyethane (0.5 mL). The mixture was stirred at 100° C. overnight. To the mixture were added ethyl acetate (3 mL) and water (1 mL), and the mixture was stirred. The organic layer was separated, concentrated, and the residue was purified by preparative HPLC (acetonitrile/10 mM aqueous ammonium bicarbonate solution) to give the title compound (21.2 mg).

MS (ESI+): [M+H]$^+$ 323.1.

Examples 89-91

The compounds of Examples 89-91 were obtained in the same manner as in Example 88.

Example 92 trans-N-[4-({2-[(ethylsulfonyl)amino]cyclohexyl}methoxy)phenyl]acetamide

To N-(4-hydroxyphenyl)acetamide (18 mg) were added a solution of N-[(1S,2S)-2-(hydroxymethyl)cyclohexyl]ethanesulfonamide (18 mg) in toluene (0.5 mL) and a solution of tributylphosphine (39 mL) in toluene (0.25 mL), and the mixture was stirred at room temperature for 5 min. To the mixture was added a solution of 1,1'-[(E)-diazene-1,2-diyldicarbonyl]dipiperidine (40 mg) in toluene (0.25 mL) and the mixture was stirred at room temperature overnight. The mixture was concentrated, and the residue was purified by preparative HPLC (0.1% solution of trifluoroacetic acid in acetonitrile/0.1% solution of trifluoroacetic acid in water) to give the title compound (4.9 mg).

MS (ESI+): [M+H]$^+$ 355.0.

Example 93

Optically active material of trans-N-[1-acetyl-3-{[4-(1-methylethyl)phenoxy]methyl}piperidin-4-yl]ethanesulfonamide A racemate of trans-N-[1-acetyl-3-{[4-(1-methylethyl)phenoxy]methyl}piperidin-4-yl]ethanesulfonamide (0.20 g) was separated by SFC (column: CHIRALPAK IC (trade name), 20 mmID×250 mL, manufactured by DAICEL CHEMICAL INDUSTRIES, LTD., mobile phase: carbon dioxide/ethanol=770/230) to give the title compound (0.081 g) with a shorter retention time.

MS (ESI+): [M+H]$^+$ 383.3.

Example 94

Optically active material of trans-N-[1-acetyl-3-{[4-(1-methylethyl)phenoxy]methyl}piperidin-4-yl]ethanesulfonamide A racemate of trans-N-[1-acetyl-3-{[4-(1-methylethyl)phenoxy]methyl}piperidin-4-yl]ethanesulfonamide (0.20 g) was separated by SFC (column: CHIRALPAK IC (trade name), 20 mmID×250 mL, manufactured by DAICEL CHEMICAL INDUSTRIES, LTD., mobile phase: carbon dioxide/ethanol=770/230) to give the title compound (0.081 g) with a longer retention time.

MS (ESI+): [M+H]$^+$ 383.3.

Example 95 trans-N-[4-{[4-(1-methylethyl)phenoxy]methyl}tetrahydro-2H-pyran-3-yl]ethanesulfonamide

A) ethyl cis-3-(benzylamino)tetrahydro-2H-pyran-4-carboxylate

The title compound was obtained from ethyl 3-oxotetrahydro-2H-pyran-4-carboxylate in the same manner as in Example 19, steps A to C.

MS (ESI+): [M+H]$^+$ 264.1.

B) ethyl trans-3-(benzylamino)tetrahydro-2H-pyran-4-carboxylate

The title compound was obtained from ethyl cis-3-(benzylamino)tetrahydro-2H-pyran-4-carboxylate in the same manner as in Example 34, step A.

MS (ESI+): [M+H]$^+$ 264.4.

C) trans-N-[4-{[4-(1-methylethyl)phenoxy]methyl}tetrahydro-2H-pyran-3-yl]ethanesulfonamide The title compound was obtained from ethyl trans-3-(benzylamino)tetrahydro-2H-pyran-4-carboxylate in the same manner as in Example 19, steps C to G.

$^1$H NMR (300 MHz, DMSO-d$_6$) δ 1.06 (3H, t, J=7.2 Hz), 1.16 (6H, d, J=6.8 Hz), 1.47-1.70 (1H, m), 1.72-1.94 (2H, m), 2.71-3.34 (6H, m), 3.75-4.12 (4H, m), 6.78-6.91 (2H, m), 7.08-7.20 (2H, m), 7.30 (1H, brs).

Example 96 trans-N-[1-ethyl-4-{[4-(1-methylethyl)phenoxy]methyl}piperidin-3-yl]ethanesulfonamide A mixture of trans-N-[1-benzyl-4-{[4-(1-methylethyl)phenoxy]methyl}piperidin-3-yl]ethanesulfonamide (0.040 g), 10% palladium-carbon (50% water-containing, 0.040 g) and ethanol (10 mL) was stirred at room temperature under hydrogen atmosphere for 5 h. The reaction mixture was filtered and the filtrate was concentrated under reduced pressure. To a solution of the obtained residue in tetrahydrofuran (10 mL) were added triethylamine (0.26 mL) and acetic anhydride (0.044 mL). The reaction mixture was stirred at room temperature for 1 h and poured into a saturated aqueous sodium hydrogencarbonate solution, and the mixture was extracted with ethyl acetate. The extract was dried over anhydrous sodium sulfate, and the solvent was evaporated under reduced pressure. The residue was purified by NH silica gel column chromatography (hexane/ethyl acetate) to give the title compound (0.14 g).

MS (ESI+): [M+H]$^+$ 369.4.

Example 97 trans-N-[1-acetyl-4-{[4-(1-methylethyl)phenoxy]methyl}piperidin-3-yl]ethanesulfonamide The title compound (0.0090 g) was obtained during the NH silica gel column chromatography (hexane/ethyl acetate) in Example 96.

MS (ESI+): [M+H]$^+$ 383.2.

Example 98 trans-N-[1-benzyl-3-{[4-(difluoromethoxy)phenoxy]methyl}piperidin-4-yl]ethanesulfonamide Titled compound was synthesized by process D) of Example 1.

Example 99 trans-N-[1-benzyl-3-{[4-(2-cyanoethyl)phenoxy]methyl}piperidin-4-yl]ethanesulfonamide Titled compound was synthesized by process B) of Example 2.

Example 100

Optically active material of trans-N-[4,4-difluoro-2-{[4-(1-methylethyl)phenoxy]methyl}cyclohexyl]ethanesulfonamide A mixture of trans-N-[2-{[4-(1-methylethyl)phenoxy]methyl}-4-oxocyclohexyl]ethanesulfonamide (1.09 g), N,N-diethylaminosulfur trifluoride (0.65 mL) and toluene (2 mL) was stirred at room temperature overnight. To the reaction mixture was added saturated aqueous sodium bicarbonate solution, and the mixture was extracted with ethyl acetate. The extract was washed with saturated brine, dried over anhydrous magnesium sulfate, and the solvent was evaporated under reduced pressure. The residue was subjected to silica gel column chromatography (hexane/ethyl acetate), and separated by HPLC (column: CHIRALPAK AD (trade name), 50 mmID×500 mL, manufactured by DAICEL CHEMICAL INDUSTRIES, LTD., mobile phase: ethanol) to give the title compound (0.22 g) with a shorter retention time.

MS (ESI+): [M−H]$^+$374.2.

Example 101

Optically active material of trans-N-[4,4-difluoro-2-{[4-(1-methylethyl)phenoxy]methyl}cyclohexyl]ethanesulfonamide The title compound (0.20 g) with a longer retention time was obtained during the separation by HPLC (column: CHIRALPAK AD (trade name), 50 mmID×500 mL, manufactured by DAICEL CHEMICAL INDUSTRIES, LTD., mobile phase: ethanol) in Example 100.

MS (ESI+): [M−H]$^+$374.2.

Example 102 trans-N-[1-benzyl-3-{[4-(1H-pyrazol-1-yl)phenoxy]methyl}piperidin-4-yl]ethanesulfonamide Titled compound was synthesized by process B) of Example 3.

Example 103

2,6-anhydro-3,4,5-trideoxy-3-[(ethylsulfonyl)amino]-1-O-[4-(1-methylethyl)phenyl]-DL-threo-hexitol The title compound was obtained from 3,4-dihydro-2H-pyran-6-ylmethanol and 4-(1-methylethyl)phenol in the same manner as in Example 4, steps A to F.

$^1$H NMR (300 MHz, CDCl$_3$) δ 1.02-1.37 (9H, m), 1.45-1.65 (1H, m), 1.67-2.01 (2H, m), 2.16 (1H, dd, J=12.7, 2.1 Hz), 2.74-3.05 (3H, m), 3.55 (1H, td, J=11.9, 2.3 Hz), 3.67-3.88 (2H, m), 3.88-4.15 (3H, m), 4.78 (1H, d, J=9.8 Hz), 6.72-6.93 (2H, m), 7.02-7.20 (2H, m).

Example 104

1,5-anhydro-2,3,4-trideoxy-4-[(ethylsulfonyl) amino]-6-O-[4-(1-methylethyl)phenyl]-DL-erythro-hexitol The title compound was obtained from 3,4-dihydro-2H-pyran-6-ylmethanol and 4-(1-methylethyl)phenol in the same manner as in Example 4, steps A to F.
$^1$H NMR (300 MHz, CDCl$_3$) δ1.09-1.30 (9H, m), 1.38-1.58 (1H, m), 1.58-1.92 (2H, m), 2.24-2.43 (1H, m), 2.74-3.04 (3H, m), 3.30-3.55 (3H, m), 3.94-4.06 (1H, m), 4.06-4.17 (1H, m), 4.17-4.28 (1H, m), 4.59 (1H, d, J=8.7 Hz), 6.76-6.92 (2H, m), 7.04-7.19 (2H, m).

Example 105 trans-N-{4-[(4-cyclopropylphenoxy)methyl]tetrahydro-2H-pyran-3-yl}ethanesulfonamide The title compound was obtained from ethyl trans-3-(benzylamino)tetrahydro-2H-pyran-4-carboxylate in the same manner as in Example 19, steps C to G.
$^1$H NMR (300 MHz, DMSO-d$_6$) δ 0.51-0.61 (2H, m), 0.81-0.92 (2H, m), 1.06 (3H, t, J=7.4 Hz), 1.45-1.68 (1H, m), 1.73-1.93 (3H, m), 2.85-3.08 (3H, m), 3.10-3.32 (2H, m), 3.74-4.09 (4H, m), 6.76-6.86 (2H, m), 6.94-7.04 (2H, m), 7.30 (1H, d, J=8.7 Hz).

Example 107 trans-N-{2-[(4-isopropylphenoxy)methyl]piperidin-3-yl}ethanesulfonamide hydrochloride To a solution of tert-butyl trans-3-(ethylsulfonamido)-2-((4-isopropylphenoxy)methyl)piperidine-1-carboxylate (0.022 g) in ethyl acetate (5 mL) was added 4 M solution (2.2 mL) of hydrochloric acid in ethyl acetate. The reaction mixture was stirred at room temperature for 1 h, and the solvent was evaporated under reduced pressure to give the title compound (0.019 g).
MS (ESI+): [M+H]$^+$ 341.2.

Example 108 trans-N-{1-acetyl-2-[(4-isopropylphenoxy)methyl] piperidin-3-yl}ethanesulfonamide The title compound was obtained from trans-N-(2-((4-isopropylphenoxy)methyl)piperidin-3-yl)ethanesulfonamide hydrochloride in the same manner as in Example 30.
MS (ESI+): [M+H]$^+$ 383.2.

Example 109

Optically active material of trans-N-[4-{[4-(1-methylethyl phenoxy]methyl}tetrahydro-2H-pyran-3-yl]ethanesulfonamide trans-N-[4-{[4-(1-methylethyl)phenoxy] methyl}tetrahydro-2H-pyran-3-yl]ethanesulfonamide (0.065 g) obtained in Example 95 was separated by SFC (column: CHIRALPAK ADH (trade name), 20 mmID×250 mL, manufactured by DAICEL CHEMICAL INDUSTRIES, LTD., mobile phase: carbon dioxide/methanol=750/250) to give the title compound (0.028 g) with a shorter retention time.

Example 110

Optically active material of trans-N-[4-{[4-(1-methylethyl)phenoxy]methyl}tetrahydro-2H-pyran-3-yl]ethanesulfonamide trans-N-[4-{[4-(1-methylethyl)phenoxy] methyl}tetrahydro-2H-pyran-3-yl]ethanesulfonamide (0.065 g) obtained in Example 95 was separated by SFC (column: CHIRALPAK ADH (trade name), 20 mmID×250 mL, manufactured by DAICEL CHEMICAL INDUSTRIES, LTD., mobile phase: carbon dioxide/methanol=750/250) to give the title compound (0.028 g) with a longer retention time.

Example 111

2,6-anhydro-1-O-(4-cyclopropylphenyl)-3,4,5-trideoxy-3-[(ethylsulfonyl)amino]-DL-threo-hexitol The title compound was obtained from 3-amino-2,6-anhydro-1-O-(4-cyclopropylphenyl)-3,4,5-trideoxyhexitol and ethanesulfonyl chloride in the same manner as in Example 4, step F.
$^1$H NMR (300 MHz, CDCl$_3$) δ 0.51-0.67 (2H, m), 0.83-0.97 (2H, m), 1.22 (3H, t, J=7.3 Hz), 1.48-1.62 (1H, m), 1.70-2.03 (3H, m), 2.08-2.24 (1H, m), 2.95 (2H, q, J=7.2 Hz), 3.55 (1H, td, J=12.0, 2.4 Hz), 3.69-3.85 (2H, m), 3.88-4.10 (3H, m), 4.73 (1H, d, J=9.8 Hz), 6.73-6.85 (2H, m), 6.92-7.05 (2H, m).

Example 112

2,6-anhydro-1-O-(4-cyclopropylphenyl)-3,4,5-trideoxy-3-[(methylsulfonyl)amino]-DL-threo-hexitol The title compound was obtained from 3-amino-2,6-anhydro-1-O-(4-cyclopropylphenyl)-3,4,5-trideoxyhexitol and methanesulfonyl chloride in the same manner as in Example 4, step F.
$^1$H NMR (300 MHz, CDCl$_3$) δ 0.48-0.69 (2H, m), 0.77-0.99 (2H, m), 1.42-1.62 (1H, m), 1.67-1.97 (3H, m), 2.04-2.27 (1H, m), 2.85 (3H, s), 3.45-3.63 (1H, m), 3.71-3.87 (2H, m), 3.87-4.12 (3H, m), 4.88 (1H, d, J=9.4 Hz), 6.67-6.89 (2H, m), 6.91-7.07 (2H, m).

Example 113 trans-N-[1-benzyl-4-{[4-(1-methylethyl)phenoxy] methyl}piperidin-3-yl]ethanesulfonamide The title compound was obtained from ethyl 1-benzyl-3-oxopiperidine-4-carboxylate hydrochloride in the same manner as in Example 1, steps A to D.
MS (ESI+): [M+H]$^+$ 431.3.

Example 114 trans-N-[4-{[4-(1-methylethyl)phenoxy] methyl}piperidin-3-yl]ethanesulfonamide

The title compound was obtained from trans-N-[1-benzyl-4-{[4-(1-methylethyl)phenoxy]methyl}piperidin-3-yl]ethanesulfonamide in the same manner as in Example 6, step D.
MS (ESI+): [M+H]$^+$ 341.1.

Example 115

Optically active material of trans-N-{3-[(4-cyclopropylphenoxy)methyl]tetrahydro-2H-pyran-4-yl}ethanesulfonamide Titled compound was synthesized from ethyl trans-4-(benzylamino)tetrahydro-2H-pyran-3-carboxylate, the fourth fraction in HPLC separation to process C) of Example 6, by process B) of Example 3.

Example 116 trans-N-ethyl-3-[(ethylsulfonyl)amino]-4-{[4-(1-methylethyl)phenoxy]methyl}piperidine-1-carboxamide To a solution of trans-N-[4-{[4-(1-methylethyl)phenoxy]methyl}piperidin-3-yl]ethanesulfonamide (0.010 g) in tetrahydrofuran (10 mL) were added triethylamine (0.0042 mL) and ethyl isocyanate (0.0024 mL) at 0° C. The reaction mixture was stirred at room temperature overnight and poured into saturated aqueous sodium hydrogencarbonate solution, and the mixture was extracted with ethyl acetate. The extract was dried over anhydrous sodium sulfate, and the solvent was evaporated under reduced pressure. The residue was purified by basic silica gel column chromatography (methanol/ethyl acetate) to give the title compound (0.0020 g).
MS (ESI+): [M+H]$^+$ 412.3.

Example 117 trans-N-[4-{[4-(1-methylethyl)phenoxy]methyl}-1-(methylsulfonyl)piperidin-3-yl]ethanesulfonamide To a solution of trans-N-[4-{[4-(1-methylethyl)phenoxy]methyl}piperidin-3-yl]ethanesulfonamide (0.010 g) in tetrahydrofuran (10 mL) were added triethylamine (0.021 mL) and methanesulfonyl chloride (0.0068 mL) at 0° C. The reaction mixture was stirred at room temperature overnight and poured into saturated aqueous sodium hydrogencarbonate solution, and the mixture was extracted with ethyl acetate. The extract was dried over anhydrous sodium sulfate, and the solvent was evaporated under reduced pressure. The residue was purified by basic silica gel column chromatography (methanol/ethyl acetate) to give the title compound (0.0020 g).
MS (ESI+): [M+H]$^+$ 419.3.

Example 118

Optically active material of trans-N-[1-acetyl-3-{[4-(1H-pyrazol-1-yl)phenoxy]methyl}piperidin-4-yl]ethanesulfonamide trans-N-[1-acetyl-3-{[4-(1H-pyrazol-1-yl)phenoxy]methyl}piperidin-4-yl]ethanesulfonamide (0.087 g) was separated by HPLC (column: CHIRALCEL OJ (50 mmID× 500 mL, DAICEL corporation, mobile phase: NeOH 100%) to give the title compound with shorter retention time (0.046 g).

Example 119

Optically active material of trans-N-[1-acetyl-3-{[4-(1H-pyrazol-1-yl)phenoxy]methyl}piperidin-4-yl]ethanesulfonamide trans-N-[1-acetyl-3-{[4-(1H-pyrazol-1-yl)phenoxy]methyl}piperidin-4-yl]ethanesulfonamide (0.087 g) was separated by HPLC (column: CHIRALCEL OJ (50 mmID× 500 mL, DAICEL corporation, mobile phase: MeOH 100%) to give the title compound with longer retention time (0.049 g).

Example 120

Optically active material of trans-N-[3-{[4-(1H-pyrazol-1-yl)phenoxy]methyl}tetrahydro-2H-pyran-4-yl]ethanesulfonamide Titled compound was synthesized from ethyl trans-4-(benzylamino)tetrahydro-2H-pyran-3-carboxylate, the fourth fraction in HPLC separation to process C) of Example 6, by process D) of Example 6 and processes A) to D) of Example 7.
$^1$H NMR (300 MHz, CDCl$_3$) δ 1.26 (3H, t, J=7.4 Hz), 1.62-1.80 (1H, m), 1.92-2.08 (1H, m), 2.13-2.24 (1H, m), 2.97 (2H, q, J=7.4 Hz), 3.41-3.67 (3H, m), 4.01 (1H, dd, J=11.9, 4.0 Hz), 4.07 (2H, d, J=4.5 Hz), 4.14 (1H, dd, J=11.5, 4.3 Hz), 4.32 (1H, d, J=9.4 Hz), 6.45 (1H, t, J=2.1 Hz), 6.97 (2H, d, J=9.1 Hz), 7.59 (2H, d, J=9.1 Hz), 7.70 (1H, d, J=1.5 Hz), 7.83 (1H, d, J=2.3 Hz).

Example 121 trans-N-[2-({[4-(1-methylethyl)phenyl]sulfanyl}methyl)cyclohexyl]ethanesulfonamide A) trans-{2-[(ethylsulfonyl)amino]cyclohexyl}methyl 4-methylbenzenesulfonate To a solution of trans-N-[2-(hydroxymethyl)cyclohexyl]ethanesulfonamide (0.20 g) and Et$_3$N (0.25 ml) in toluene (5 ml) was added TsCl (0.21 g). The mixture was stirred at 60° C. overnight. The mixture was quenched with sat. NaHCO$_3$ aq. at room temperature and extracted with EtOAc. The organic layer was separated, washed with brine, dried over MgSO$_4$ and concentrated in vacuo. The residue was purified by column chromatography (silica gel, eluted with EtOAc in hexane) to give the title compound (0.26 g).
$^1$H NMR (300 MHz, CDCl$_3$) δ 1.11-1.30 (5H, m), 1.34 (3H, t, J=7.4 Hz), 1.73 (2H, brs), 1.81-1.91 (1H, m), 2.10-2.21 (1H, m), 2.45 (3H, s), 2.94-3.16 (3H, m), 3.96 (1H, d, J=9.8 Hz), 4.07 (1H, dd, J=10.2, 6.0 Hz), 4.16 (1H, dd, J=9.8, 3.8 Hz), 7.35 (2H, d, J=7.9 Hz), 7.80 (2H, d, J=8.3 Hz).

B) trans-N-[2-({[4-(1-methylethyl) phenyl]sulfanyl}methyl)cyclohexyl]ethanesulfonamide To a solution of trans-{2-[(ethylsulfonyl)amino]cyclohexyl}methyl 4-methylbenzenesulfonate (0.050 g) and 4-(1-methylethyl)benzenethiol (0.025 ml) in DMSO (2 ml) was added KOtBu (0.022 g), and the mixture was stirred at room temperature for 1 h. The mixture was diluted with EtOAc and washed with water and brine. The organic layer was dried over Na$_2$SO$_4$ and concentrated in vacuo. The residue was purified by column chromatography (silica gel, eluted with EtOAc in hexane) to give the title compound (0.047 g).
$^1$H NMR (300 MHz, CDCl$_3$) δ 1.09-1.50 (13H, m), 1.72 (2H, brs), 2.14 (2H, d, J=10.6 Hz), 2.75 (1H, dd, J=12.9, 8.3 Hz), 2.87 (1H, dt, J=13.9, 6.9 Hz), 2.95-3.21 (3H, m), 3.39 (1H, dd, J=12.9, 3.8 Hz), 3.96 (1H, d, J=9.1 Hz), 7.10-7.36 (4H, m).

Example 122

Optically active material of trans-N-[1-acetyl-3-{[4-(difluoromethoxy)phenoxy]methyl}piperidin-4-yl]ethanesulfonamide trans-N-[1-acetyl-3-{[4-(difluoromethoxy)phenoxy]methyl}piperidin-4-yl]ethanesulfonamide (0.14 g) was separated by HPLC (column: CHIRALPAK IC, 50 mmID× 500 mL, DAICEL corporation, mobile phase: Hexane/EtOH=400/600 (v/v)) to give the title compound with smaller retention time (0.045 g).

Example 123

Optically active material of trans-N-[1-acetyl-3-{[4-(difluoromethoxy)phenoxy]methyl}piperidin-4-yl]ethanesulfonamide trans-N-[1-acetyl-3-{[4-(difluoromethoxy)phenoxy]methyl}piperidin-4-yl]ethanesulfonamide (0.014 g) was separated by HPLC (column: CHIRALPAK IC, 50 mmID× 500 mL, DAICEL corporation, mobile phase: Hexane/EtOH=400/600 (v/v)) to give the title compound with longer retention time (0.044 g).

Example 124

Optically active material of trans-N-[3-{[4-(difluoromethoxy)phenoxy]methyl}tetrahydro-2H-pyran-4-yl]ethanesulfonamide Titled compound was synthesized by the similar method to processes C) and D) of Example 7.

$^1$H NMR (300 MHz, CDCl$_3$) δ 1.27 (3H, t, J=7.4 Hz), 1.60-1.77 (1H, m), 1.90-2.04 (1H, m), 2.10-2.21 (1H, m), 2.97 (2H, q, J=7.4 Hz), 3.37-3.66 (3H, m), 3.93-4.07 (3H, m), 4.11 (1H, dd, J=11.7, 4.2 Hz), 4.22 (1H, d, J=9.4 Hz), 6.42 (1H, t, J=74.4 Hz), 6.87 (2H, d, J=9.1 Hz), 7.06 (2H, d, J=9.1 Hz).

Reference Example 1

N-[(1SR,2SR)-2-({[4-(1-methylethyl)phenyl]sulfinyl}methyl)cyclohexyl]ethanesulfonamide To a solution of trans-N-[2-({[4-(1-methylethyl)phenyl]sulfanyl}methyl)cyclohexyl]ethanesulfonamide (0.074 g) in ethyl acetate (3 mL) was added m-chloroperbenzoic acid (0.056 g) under ice-cooling. The reaction mixture was stirred under ice-cooling for 10 min., and saturated aqueous sodium hydrogencarbonate solution and sodium thiosulfate were added. The reaction mixture was extracted with ethyl acetate, and the extract was washed with saturated aqueous sodium hydrogencarbonate solution and saturated brine, dried over anhydrous sodium sulfate, and the solvent was evaporated under reduced pressure. The residue was purified by silica gel column chromatography (ethyl acetate/hexane) to give the title compound (0.074 g).

$^1$H NMR (300 MHz, CDCl$_3$) δ 1.19-1.45 (14H, m), 1.47-1.83 (2H, m), 2.06-2.34 (2H, m), 2.41-2.65 (1H, m), 2.89-3.17 (4H, m), 3.21-3.39 (1H, m), 5.13 (1H, t, J=8.5 Hz), 7.32-7.43 (2H, m), 7.48-7.66 (2H, m).

Reference Example 2

N-[(1SR,2SR)-2-({[4-(1-methylethyl)phenyl]sulfonyl}methyl)cyclohexyl]ethanesulfonamide To a solution of trans-N-[2-({[4-(1-methylethyl)phenyl]sulfinyl}methyl)cyclohexyl]ethanesulfonamide (0.039 g) in ethyl acetate (2 mL) was added m-chloroperbenzoic acid (0.022 g) under ice-cooling. The reaction mixture was stirred at room temperature for 30 min., and saturated aqueous sodium hydrogencarbonate solution and sodium thiosulfate were added. The reaction mixture was extracted with ethyl acetate, and the extract was washed with saturated aqueous sodium hydrogencarbonate solution and saturated brine, dried over anhydrous sodium sulfate, and the solvent was evaporated under reduced pressure. The residue was purified by silica gel column chromatography (ethyl acetate/hexane) to give the title compound (0.037 g).

$^1$H NMR (300 MHz, CDCl$_3$) δ 1.21-1.47 (13H, m), 1.66-1.90 (2H, m), 1.98-2.18 (2H, m), 2.18-2.36 (1H, m), 2.83-3.19 (5H, m), 3.59 (1H, dd, J=14.0, 3.0 Hz), 4.62 (1H, d, J=8.7 Hz), 7.41 (2H, d, J=8.3 Hz), 7.86 (2H, d, J=8.3 Hz).

Example 127 trans-N-[1-methyl-2-{[4-(1-methylethyl)phenoxy]methyl}-6-oxopiperidin-3-yl]ethanesulfonamide A) ethyl 3-(benzylamino)-1-methyl-6-oxo-1,4,5,6-tetrahydropyridine-2-carboxylate To a solution of sarcosine ethyl ester hydrochloride (25.0 g) in N,N-dimethylacetamide (80 mL) was added ethyl 4-chloro-4-oxobutanoate (24.4 mL) under ice-cooling over 30 min. The reaction mixture was stirred at room temperature for 30 min., water was added, and the mixture was extracted with ethyl acetate. The extract was washed with saturated brine, dried over anhydrous magnesium sulfate, and the solvent was evaporated under reduced pressure. The residue was purified by silica gel column chromatography (hexane/ethyl acetate) to give oil (29.4 g). A solution of the obtained oil (29.4 g) in toluene (100 mL) was added to a mixture of potassium tert-butoxide (30.1 g) and toluene (260 mL) over 30 min. The reaction mixture was stirred at room temperature for 1 h, 10% aqueous citric acid solution was added, and the mixture was extracted with ethyl acetate. The extract was washed with saturated brine, dried over anhydrous magnesium sulfate, and the solvent was evaporated under reduced pressure to give oil (13.6 g). A mixture of the obtained oil (13.6 g), benzylamine (8.77 g) and toluene (100 mL) was stirred under reflux for 2 h while azeotropic dehydration was occurred. To the reaction mixture was added saturated aqueous sodium bicarbonate solution, and the mixture was extracted with ethyl acetate. The extract was washed with saturated brine, dried over anhydrous magnesium sulfate, and the solvent was evaporated under reduced pressure. The residue was purified by silica gel column chromatography (hexane/ethyl acetate) to give the title compound (9.85 g).

MS (ESI+): [M+H]$^+$ 289.1.

B) ethyl trans-3-(benzylamino)-1-methyl-6-oxopiperidine-2-carboxylate

To a solution of ethyl 3-(benzylamino)-1-methyl-6-oxo-1,4,5,6-tetrahydropyridine-2-carboxylate (9.85 g) in tetrahydrofuran (150 mL) was added dropwise trifluoroacetic acid (21.1 mL) under ice-cooling. To the reaction mixture was slowly added sodium borohydride (2.58 g). The reaction mixture was stirred for 1 h under ice-cooling, and water was slowly added. After forming was ceased, the reaction mixture was neutralized with 2 M aqueous sodium hydroxide solution, and the mixture was extracted with ethyl acetate. The extract was washed with saturated brine, dried over anhydrous magnesium sulfate, and the solvent was evaporated under reduced pressure to give oil (7.43 g). A mixture of the obtained oil (6.93 g), sodium ethoxide (3.25 g) and ethanol (40 mL) was stirred at 40° C. for 1 h. To the reaction mixture was added 10% aqueous citric acid solution, and the mixture was extracted with ethyl acetate. The extract was washed with saturated brine, dried over anhydrous magnesium sulfate, and the solvent was evaporated under reduced pressure. The residue was purified by silica gel column chromatography (hexane/ethyl acetate) to give the title compound (5.41 g).

MS (ESI+): [M+H]$^+$ 291.2.

C) ethyl trans-3-[(ethylsulfonylamino)]-1-methyl-6-oxopiperidine-2-carboxylate

A mixture of ethyl trans-3-(benzylamino)-1-methyl-6-oxopiperidine-2-carboxylate (5.79 g), 10% palladium-carbon (50% water-containing, 0.50 g) and ethanol (50 mL) was stirred at room temperature overnight under hydrogen atmosphere. The reaction mixture was filtered, and the filtrate was concentrated under reduced pressure to give oil (4.26 g). To a mixture of is the obtained oil (4.26 g), triethylamine (5.56 mL) and tetrahydrofuran (50 mL) was added ethanesulfonyl chloride (2.83 mL) under ice-cooling. The reaction mixture was stirred for 1 h under ice-cooling, and filtered. The filtrate was concentrated under reduced pressure, and the residue was purified by silica gel column chromatography (NH, hexane/ethyl acetate) to give the title compound (5.21 g).

MS (ESI+): [M+H]$^+$ 293.1.

D) trans-N-[1-methyl-2-{[4-(1-methylethyl)phenoxy]methyl}-6-oxopiperidin-3-yl]ethanesulfonamide The title compound was obtained from ethyl trans-3-[(ethylsulfonylamino)]-1-methyl-6-oxopiperidine-2-carboxylate in the same manner as in Example 8, step B.

MS (ESI+): [M+H]$^+$ 369.1.

Example 128 trans-N-{1-acetyl-3-[(4-cyclopropylphenoxy)methyl]piperidin-4-yl}ethanesulfonamide Titled compound was synthesized by the similar method to processes C) to E) of Example 1.

$^1$H NMR (300 MHz, CDCl$_3$) δ 0.55-0.66 (2H, m), 0.84-0.96 (2H, m), 1.13-1.34 (3H, m), 1.41-1.58 (1H, m), 1.68-1.94 (2H, m), 2.11 (3H, s), 2.13-2.42 (1H, m), 2.64-2.80 (1H, m), 2.85-3.04 (2H, m), 3.07-3.25 (1H, m), 3.44-3.71 (1H, m), 3.75-4.07 (2H, m), 4.06-4.19 (1H, m), 4.41 (1H, dd, J=13.0, 9.3 Hz), 4.51-4.79 (1H, m), 6.75-6.85 (2H, m), 6.95-7.06 (2H, m).

Example 129 trans-N-[4-oxo-2-{[4-(1H-pyrazol-1-yl)phenoxy]methyl}cyclohexyl]ethanesulfonamide A) ethyl 8-amino-1,4-dioxaspiro[4.5]dec-7-ene-7-carboxylate A solution of diethyl 4-oxoheptanedioate (24.9 g), ethane-1,2-diol (10.74 g) and 4-methylbenzenesulfonic acid hydrate (0.206 g) in toluene (80 ml) was refluxed overnight using a Dean-Stark apparatus. The mixture was neutralized with sat. NaHCO$_3$ aq. and extracted with EtOAc. The organic layer was separated, washed with water and brine, dried over MgSO$_4$ and concentrated in vacuo to give a colorless oil (29.3 g). To a solution of KOtBu (20.0 g) in THF (300 ml) was added a solution of above oil (29.3 g) in THF (20 ml) for 30 min. The mixture was stirred at room temperature overnight. The resulting suspension was acidified with 10% citric acid aq. and extracted with EtOAc. The organic layer was separated, washed with water and brine, dried over MgSO$_4$ and concentrated in vacuo to give yellow oil (21.9 g). A mixture of the oil (21.9 g) and ammonium acetate (33.3 g) in EtOH (140 ml) was stirred at room temperature for 2 h. The mixture was neutralized with sat. NaHCO$_3$ aq. and extracted with EtOAc. The organic layer was separated, washed with water and brine, dried over MgSO$_4$ and concentrated in vacuo. The residue was purified by column chromatography (NH silica gel, eluted with EtOAc in hexane) to give the title compound (11.3 g) as a yellow oil.

MS (API+), found: 228.4 (M+1)

B) ethyl 8-amino-1,4-dioxaspiro[4.5]decane-7-carboxylate

To a cold (0° C.) solution of ethyl 8-amino-1,4-dioxaspiro[4.5]dec-7-ene-7-carboxylate (11.3 g) in THF (100 ml) was added TFA (30.6 ml) for 10 min. To the mixture was added NaBH$_4$ (3.76 g) at 0° C. for 20 min. After being stirred at 0° C. for 30 min, the mixture was quenched with 8 M NaOH aq. at 0° C. and extracted with EtOAc. The organic layer was separated, washed with sat. NaHCO$_3$ aq. and brine, dried over MgSO$_4$ and concentrated in vacuo. The residue was passed though a NH silica gel pad and eluted with EtOAc to give the title compound (5.95 g) as a yellow oil.

MS (API+), found: 230.3 (M+1)

C) ethyl 8-(ethylsulfonamido)-1,4-dioxaspiro[4.5]decane-7-carboxylate

To a solution of ethyl 8-amino-1,4-dioxaspiro[4.5]decane-7-carboxylate (5.95 g) and Et$_3$N (7.23 ml) in THF (80 ml) was added ethanesulfonyl chloride (3.69 ml) at 0° C. The mixture was neutralized with sat. NaHCO$_3$ aq. and extracted with EtOAc. The organic layer was separated, washed with water and brine, dried over MgSO$_4$ and concentrated in vacuo. The residue was purified by column chromatography (silica gel, eluted with EtOAc in hexane) to give the title compound (6.59 g) as a pale yellow oil.

MS (API+), found: 322.3 (M+1)

D) N-(7-(hydroxymethyl)-1,4-dioxaspiro[4.5]decan-8-yl)ethanesulfonamide

To a suspension of LAH (1.17 g) in Et$_2$O (120 ml) was added a solution of ethyl 8-(ethylsulfonamido)-1,4-dioxaspiro[4.5]decane-7-carboxylate (6.59 g) in Et$_2$O (10 ml) at 0°

C. for 15 min. The mixture was stirred at 0° C. for 30 min, and was quenched with sodium sulfate decahydrate (5.71 g) at 0° C. The insoluble material was removed by filtration, washed with THF and the filtrate was concentrated in vacuo. The residue was passed though a silica gel pad and eluted with EtOAc. The obtained oil was crystallized from hexane to give the title compound (2.36 g) as a colorless solid.

$^1$H NMR (300 MHz, CDCl$_3$) δ 1.33-1.46 (3H, m), 1.49-1.82 (4H, m), 1.84-2.17 (2H, m), 2.67 (1H, dd, J=7.7, 5.5 Hz), 2.95-3.32 (3H, m), 3.41-3.57 (1H, m), 3.62-3.83 (1H, m), 3.88-4.04 (4H, m), 4.70 (1H, d, J=9.1 Hz), 5.15 (1H, d, J=8.7 Hz).

E) trans-N-[7-{[4-(1H-pyrazol-1-yl)phenoxy]methyl}-1,4-dioxaspiro[4.5]decan-8-yl]ethanesulfonamide To a solution of N-[7-(hydroxymethyl)-1,4-dioxaspiro[4.5]decan-8-yl]ethanesulfonamide (0.81 g), 4-(1H-pyrazol-1-yl)phenol (0.60 g) and ADDP (1.10 g) in toluene (30 ml) was added Bu$_3$P (1.07 ml) at room temperature. The mixture was stirred at room temperature overnight. The mixture was purified by column chromatography (silica gel, eluted with EtOAc in hexane) to give the title compound (0.43 g).

$^1$H NMR (300 MHz, CDCl$_3$) δ 1.23 (3H, t, J=7.4 Hz), 1.33-2.32 (6H, m), 2.88-2.98 (2H, m), 3.33-3.51 (1H, m), 3.91-4.02 (6H, m), 4.14 (1H, dd, J=9.1, 4.5 Hz), 4.20 (1H, d, J=9.1 Hz), 6.44 (1H, t, J=1.9 Hz), 6.97 (2H, d, J=9.1 Hz), 7.59 (2H, d, J=9.1 Hz), 7.69 (1H, d, J=1.5 Hz), 7.83 (1H, d, J=2.3 Hz).

F) trans-N-[4-oxo-2-{[4-(1H-pyrazol-1-yl)phenoxy]methyl}cyclohexyl]ethanesulfonamide To a solution of trans-N-[7-{[4-(1H-pyrazol-1-yl)phenoxy]methyl}-1,4-dioxaspiro[4.5]decan-8-yl]ethanesulfonamide (0.43 g) in acetone (5 ml) was added 1 M HCl aq. (5.1 ml). The mixture was stirred at room temperature for 1 h. The solvent was removed by evaporation and the residue was diluted with EtOAc, washed with sat. NaHCO$_3$ aq. and brine, and the organic phase was concentrated under vacuum. The residue was purified by column chromatography (silica gel, eluted with EtOAc in hexane) to give the title compound (0.24 g).

$^1$H NMR (300 MHz, CDCl$_3$) δ 1.25 (3H, t, J=7.2 Hz), 1.72-1.90 (1H, m), 2.12-2.29 (1H, m), 2.46-2.75 (5H, m), 2.98 (2H, q, J=7.3 Hz), 3.81-4.00 (2H, m), 4.23 (2H, dt, J=9.1, 4.5 Hz), 6.45 (1H, t, J=2.1 Hz), 6.98 (2H, d, J=9.1 Hz), 7.61 (2H, d, J=9.1 Hz), 7.70 (1H, d, J=1.9 Hz), 7.84 (1H, d, J=2.3 Hz).

Example 130 trans-N-[4,4-difluoro-2-{[4-(1H-pyrazol-1-yl)phenoxy]methyl}cyclohexyl]ethanesulfonamide To a solution of trans-N-[4-oxo-2-{[4-(1H-pyrazol-1-yl)phenoxy]methyl}cyclohexyl]ethanesulfonamide (0.22 g) in EtOAc (5 ml) was added DAST (0.15 ml). The mixture was stirred at room temperature for 3 h. The mixture was quenched with sat. NaHCO$_3$ aq. and extracted with EtOAc. The organic layer was separated, washed with brine, dried over Na$_2$SO$_4$ and concentrated in vacuo. The residue was purified by column chromatography (silica gel, eluted with EtOAc in hexane) and preparative HPLC (C18, eluted with H$_2$O in acetonitrile containing 0.1% TFA). The desired fraction was neutralized with sat. NaHCO$_3$ aq. and extracted with EtOAc. The organic layer was separated, dried over Na$_2$SO$_4$ and concentrated in vacuo to give the titled compound (0.056 g).

$^1$H NMR (300 MHz, CDCl$_3$) δ 1.21 (3H, t, J=7.3 Hz), 1.64-2.41 (7H, m), 2.93 (2H, q, J=7.2 Hz), 3.49 (1H, brs), 3.97 (1H, dd, J=9.2, 2.4 Hz), 4.06-4.15 (1H, m), 4.17-4.26 (1H, m), 6.45 (1H, t, J=2.1 Hz), 6.98 (2H, d, J=9.0 Hz), 7.61 (2H, d, J=9.0 Hz), 7.70 (1H, d, J=1.9 Hz), 7.83 (1H, d, J=2.3 Hz).

Example 131 trans-N-{3-[(4-acetyl-3-fluorophenoxy)methyl]tetrahydro-2H-pyran-4-yl}ethanesulfonamide Titled compound was synthesized by similar method of processes G) and H) of Example 6.

$^1$H NMR (300 MHz, CDCl$_3$) δ 1.30 (3H, t, J=7.4 Hz), 1.62-1.80 (1H, m), 1.93-2.08 (1H, m), 2.08-2.19 (1H, m), 2.59 (3H, d, J=4.9 Hz), 2.99 (2H, qd, J=7.4, 1.3 Hz), 3.36-3.63 (3H, m), 3.96-4.18 (4H, m), 4.23 (1H, d, J=9.4 Hz), 6.63 (1H, dd, J=12.8, 2.3 Hz), 6.75 (1H, dd, J=8.7, 2.3 Hz), 7.88 (1H, t, J=8.7 Hz).

Example 132 trans-N-[3-{[4-(3,5-dimethyl-1H-pyrazol-1-yl)phenoxy]methyl}tetrahydro-2H-pyran-4-yl]ethanesulfonamide A) 1-(4-methoxyphenyl)-3,5-dimethyl-1H-pyrazole A mixture of quinolin-8-ol (0.62 g), 1-iodo-4-methoxybenzene (10 g), copper(I)iodide (0.81 g), K$_2$CO$_3$ (6.50 g) and 3,5-dimethyl-1H-pyrazole (4.31 g) in DMSO (25 ml) was stirred at 120° C. under N$_2$ for 2 days. The mixture was poured into water and extracted with EtOAc. The organic layer was separated, washed with brine and, dried over MgSO$_4$ and concentrated in vacuo. The residue was purified by column chromatography (NH silica gel, eluted with EtOAc in hexane) to give the title compound (5.03 g).

$^1$H NMR (300 MHz, CDCl$_3$) δ 2.24 (3H, s), 2.29 (3H, s), 3.84 (3H, s), 5.96 (1H, s), 6.90-7.00 (2H, m), 7.28-7.37 (2H, m).

B) 4-(3,5-dimethyl-1H-pyrazol-1-yl)phenol

A mixture of 1-(4-methoxyphenyl)-3,5-dimethyl-1H-pyrazole (4.7 g) and 48% hydrogen bromide (25 ml) in AcOH (50 ml) was stirred at 100° C. for 36 h. It was concentrated in vacuo, added NaHCO$_3$, and extracted with EtOAc. The extract was washed with brine, dried over MgSO$_4$, filtered, and concentrated in vacuo.

The residue was purified by column chromatography (silica gel, eluted with EtOAc in hexane). The residue was washed with IPE to give the title compound (2.45 g).

$^1$H NMR (300 MHz, CDCl$_3$) δ 2.19 (3H, s), 2.30 (3H, s), 5.96 (1H, s), 6.55-6.71 (2H, m), 7.00-7.14 (2H, m), 9.63 (1H, brs).

C) trans-N-[3-{[4-(3,5-dimethyl-1H-pyrazol-1-yl)phenoxy]methyl}tetrahydro-2H-pyran-4-yl]ethanesulfonamide Titled compound was synthesized by similar method to processes C) and D) of Example 7.

$^1$H NMR (300 MHz, CDCl$_3$) δ 1.27 (3H, t, J=7.4 Hz), 1.61-1.80 (1H, m), 1.99 (1H, td, J=10.6, 4.5 Hz), 2.12-2.22 (1H, m), 2.24 (3H, s), 2.28 (3H, s), 2.97 (2H, q, J=7.2 Hz), 3.38-3.68 (3H, m), 3.95-4.04 (1H, m), 4.06 (2H, d, J=4.5 Hz), 4.13 (1H, dd, J=11.7, 3.8 Hz), 4.25 (1H, d, J=9.1 Hz), 5.97 (1H, s), 6.95 (2H, d, J=9.1 Hz), 7.33 (2H, d, J=9.1 Hz).

Example 133 trans-N-[3-({4-[3,5-bis(trifluoromethyl)-1H-pyrazol-1-yl]phenoxy}methyl)tetrahydro-2H-pyran-4-yl]ethanesulfonamide

A) 1-(4-methoxyphenyl)-3,5-bis(trifluoromethyl)-1H-pyrazole

A mixture of pTsOH.H$_2$O (0.23 g), 1,1,1,5,5,5-hexafluoropentane-2,4-dione (5.00 g) and (4-methoxyphenyl)hydrazine hydrochloride (5.46 g) in toluene (100 ml) was stirred at 100° C. for 3 h. It was added silica gel and concentrated in vacuo. The residue was purified by column chromatography (silica gel, eluted with EtOAc in hexane) to give the title compound (6.28 g).

$^1$H NMR (300 MHz, CDCl$_3$) δ 3.87 (3H, s), 6.94-7.03 (2H, m), 7.04 (1H, s), 7.35-7.44 (2H, m).

B) 4-(3,5-bis(trifluoromethyl)-1H-pyrazol-1-yl)phenol

Titled compound was synthesized by similar method to process B) of Example 132.

$^1$H NMR (300 MHz, CDCl$_3$) δ 5.36 (1H, s), 6.88-6.97 (2H, m), 7.04 (1H, s), 7.30-7.43 (2H, m).

C) trans-N-[3-({4-[3,5-bis(trifluoromethyl)-1H-pyrazol-1-yl]phenoxy}methyl)tetrahydro-2H-pyran-4-yl]ethanesulfonamide Titled compound was synthesized by similar method to processes C) and D) of Example 7.

$^1$H NMR (300 MHz, CDCl$_3$) δ 1.28 (3H, t, J=7.4 Hz), 1.63-1.80 (1H, m), 1.93-2.10 (1H, m), 2.11-2.22 (1H, m), 2.97 (2H, q, J=7.2 Hz), 3.41-3.66 (3H, m), 3.96-4.27 (5H, m), 7.00 (2H, d, J=9.1 Hz), 7.04 (1H, s), 7.41 (2H, d, J=8.7 Hz).

Example 134 trans-N-[3-{[4-(4-methyl-1H-pyrazol-1-yl)phenoxy]methyl}tetrahydro-2H-pyran-4-yl]ethanesulfonamide

A) 1-(4-methoxyphenyl)-4-methyl-1H-pyrazole

A mixture of quinolin-8-ol (0.35 g), 1-iodo-4-methoxybenzene (5.7 g), copper(I)iodide (0.464 g), K$_2$CO$_3$ (4.04 g) and 4-methyl-1H-pyrazole (2 g) in DMSO (50 ml) was stirred at 150° C. under N$_2$ overnight. The mixture was poured into sat. NH$_4$Cl aq. and extracted with EtOAc. The organic layer was separated, washed with brine, dried over MgSO$_4$ and concentrated in vacuo. The residue was purified by column chromatography (NH silica gel, eluted with EtOAc in hexane) to give the title compound (4.21 g).

$^1$H NMR (300 MHz, CDCl$_3$) δ 2.15 (3H, s), 3.83 (3H, s), 6.90-7.00 (2H, m), 7.49 (1H, s), 7.51-7.58 (2H, m), 7.60 (1H, s).

B) 4-(4-methyl-1H-pyrazol-1-yl)phenol

A mixture of 1-(4-methoxyphenyl)-4-methyl-1H-pyrazole (4.2 g) and 48% hydrogen bromide (30 ml) in AcOH (100 ml) was stirred at 130° C. overnight. It was concentrated in vacuo, added sat. NaHCO$_3$ aq., and extracted with EtOAc. The extract was washed with brine, dried over MgSO$_4$, filtered, and concentrated in vacuo. The residue was purified by column chromatography (silica gel, eluted with EtOAc in hexane) to give the title compound (3.87 g).

$^1$H NMR (300 MHz, DMSO-d$_6$) δ2.08 (3H, s), 6.73-6.92 (2H, m), 7.45 (1H, s), 7.49-7.58 (2H, m), 8.05 (1H, s), 9.53 (1H, s).

C) ethyl trans-4-[(tert-butoxycarbonyl)amino]tetrahydro-2H-pyran-3-carboxylate A solution of ethyl trans-4-(benzylamino)tetrahydro-2H-pyran-3-carboxylate (848 mg) in EtOH (20 ml) was added 10% Pd/C (171 mg, 50% wet). The mixture was stirred under hydrogen atmosphere at room temperature for 3 h. The catalyst was removed by filtration and the filtrate was concentrated in vacuo. The residue was dissolved in THF (10 ml), and to this solution was added Et$_3$N (0.90 ml) and Boc$_2$O (1.12 ml). The mixture was stirred at room temperature overnight. The mixture was quenched with sat. NaHCO$_3$ aq. and extracted with EtOAc. The organic phase was washed with brine, dried over Na$_2$SO$_4$ and concentrated in vacuo. The residue was purified by column chromatography (silica gel, eluted with EtOAc in hexane) to give the title compound (788 mg).

$^1$H NMR (300 MHz, CDCl$_3$) δ1.26 (3H, t, J=7.0 Hz), 1.43 (9H, s), 1.46-1.57 (1H, m), 1.97-2.10 (1H, m), 2.48 (1H, td, J=10.4, 4.2 Hz), 3.41-3.64 (2H, m), 3.94 (2H, dt, J=11.5, 3.5 Hz), 4.04 (1H, dd, J=11.5, 4.3 Hz), 4.09-4.24 (2H, m), 4.57 (1H, brs).

D) tert-butyl trans-[3-(hydroxymethyl)tetrahydro-2H-pyran-4-yl]carbamate

To a solution of ethyl trans-4-[(tert-butoxycarbonyl)amino]tetrahydro-2H-pyran-3-carboxylate (1.13 g) in THF (30 ml) was added LAH (392 mg) at 0° C. The mixture was stirred at room temperature for 1 h. To the mixture was added 1 M NaOH aq. (1.6 ml) at 0° C. and the mixture was stirred for another 20 min. The mixture was passed through a pad of celite, and the filtrate was concentrated under vacuum. The residue was purified by column chromatography (silica gel, eluted with EtOAc in hexane) to give the title compound (819 mg).

$^1$H NMR (300 MHz, CDCl$_3$) δ 1.46 (9H, s), 1.50-1.63 (1H, m), 1.79-1.95 (1H, m), 3.33-3.58 (3H, m), 3.58-3.66 (1H, m), 3.66-3.84 (2H, m), 3.84-4.06 (2H, m), 4.50 (1H, d, J=8.3 Hz).

E) tert-butyl trans-[3-{[4-(4-methyl-1H-pyrazol-1-yl)phenoxy]methyl}tetrahydro-2H-pyran-4-yl]carbamate To a solution of tert-butyl trans-[3-(hydroxymethyl)tetrahydro-2H-pyran-4-yl]carbamate (80 mg), 4-(4-methyl-1H- pyrazol-1-yl)phenol (90 mg) and ADDP (175 mg) in toluene (8 ml) was added Bu$_3$P (0.171 ml) at room temperature. The mixture was stirred at room temperature overnight. The mixture purified by column chromatography (silica gel, eluted with EtOAc in hexane) to give the title compound (117 mg).

$^1$H NMR (300 MHz, CDCl$_3$) δ 1.42 (9H, s), 1.48-1.64 (1H, m), 1.93-2.06 (2H, m), 2.15 (3H, s), 3.25-3.37 (1H, m), 3.47 (1H, td, J=11.8, 2.1 Hz), 3.58-3.74 (1H, m), 3.75-3.89 (1H, m), 3.95-4.04 (1H, m), 4.07 (1H, dd, J=9.5, 3.8 Hz), 4.18-4.28 (1H, m), 4.46-4.59 (1H, m), 6.92 (2H, d, J=9.1 Hz), 7.49 (1H, s), 7.53 (2H, d, J=9.1 Hz), 7.60 (1H, s).

F) trans-N-[3-{[4-(4-methyl-1H-pyrazol-1-yl)phenoxy]methyl}tetrahydro-2H-pyran-4-yl]ethanesulfonamide A mixture of tert-butyl trans-[3-{[4-(4-methyl-1H-pyrazol-1-yl)phenoxy]methyl}tetrahydro-2H-pyran-4-yl]carbamate (117 mg) and 4 M HCl/EtOAc (7.55 ml) was stirred at room temperature for 5 h. The solvent was removed by evaporation and the residue was dissolved in THF (5 ml). To this was added Et$_3$N (0.126 ml) and ethanesulfonyl chloride (0.043 ml) at room temperature, and the mixture was stirred overnight. The mixture was quenched with sat. NaHCO$_2$ aq. and extracted with EtOAc. The organic layer was separated, washed with brine, dried over Na$_2$SO$_4$ and concentrated in vacuo. The residue was purified by column chromatography (silica gel, eluted with EtOAc in hexane) to give the title compound (64 mg).

$^1$H NMR (300 MHz, CDCl$_3$) δ 1.26 (3H, t, J=7.4 Hz), 1.69 (1H, qd, J=12.1, 4.5 Hz), 1.98 (1H, td, J=10.6, 4.5 Hz), 2.12-2.24 (4H, m), 2.97 (2H, q, J=7.4 Hz), 3.40-3.70 (3H, m), 4.00 (1H, dd, J=12.7, 3.6 Hz), 4.05 (2H, d, J=4.5 Hz), 4.13 (1H, dd, J=11.9, 4.3 Hz), 4.34 (1H, d, J=9.1 Hz), 6.94 (2H, d, J=9.1 Hz), 7.50 (1H, s), 7.55 (2H, d, J=9.1 Hz), 7.61 (1H, s).

Example 135 trans-N-{3-[(4-acetylphenoxy)methyl]tetrahydro-2H-pyran-4-yl}ethanesulfonamide

Titled compound was synthesized by similar method to processes C) and D) of Example 7.

$^1$H NMR (300 MHz, CDCl$_3$) δ 1.26 (3H, t, J=7.4 Hz), 1.63-1.82 (1H, m), 2.00 (1H, qd, J=10.0, 4.9 Hz), 2.08-2.21 (1H, m), 2.56 (3H, s), 2.96 (2H, q, J=7.2 Hz), 3.38-3.65 (3H, m), 3.94-4.05 (1H, m), 4.05-4.21 (3H, m), 4.39 (1H, brs), 6.93 (2H, d, J=8.7 Hz), 7.93 (2H, d, J=9.1 Hz).

Example 136 trans-N-{3-[(4-acetyl-2-fluorophenoxy)methyl]tetrahydro-2H-pyran-4-yl}ethanesulfonamide Titled compound was synthesized by similar method to processes C) and D) of Example 7.

$^1$H NMR (300 MHz, CDCl$_3$) δ 1.30 (3H, t, J=7.4 Hz), 1.62-1.82 (1H, m), 1.98-2.20 (2H, m), 2.55 (3H, s), 2.94-3.10 (2H, m), 3.39-3.65 (3H, m), 3.95-4.08 (1H, m), 4.10-4.29 (3H, m), 4.53 (1H, d, J=9.1 Hz), 7.00 (1H, t, J=8.3 Hz), 7.63-7.76 (2H, m).

Example 137 trans-N-{3-[(4-pyridin-2-ylphenoxy)methyl]tetrahydro-2H-pyran-4-yl}ethanesulfonamide The title compound was obtained from tert-butyl trans-[3-(hydroxymethyl)tetrahydro-2H-pyran-4-yl]carbamate and 4-pyridin-2-ylphenol in the same manner as in Example 7, steps C and D.

$^1$H NMR (300 MHz, CDCl$_3$) δ 1.24 (3H, t, J=7.4 Hz), 1.60-1.81 (1H, m), 1.85-2.09 (1H, m), 2.09-2.30 (1H, m), 2.96 (2H, q, J=7.2 Hz), 3.41-3.70 (3H, m), 3.91-4.25 (4H, m), 4.31 (1H, d, J=9.1 Hz), 6.92-7.06 (2H, m), 7.14-7.24 (1H, m), 7.63-7.82 (2H, m), 7.88-8.02 (2H, m), 8.57-8.72 (1H, m).

Example 138 trans-N-{3-[(4-pyridin-3-ylphenoxy)methyl]tetrahydro-2H-pyran-4-yl}ethanesulfonamide A) 4-(pyridin-3-yl)phenol A mixture of Na$_2$CO$_3$ (2.364 g), Pd(PPh$_3$)$_4$ (0.387 g), 3-bromopyridine (1.762 g) and 4-hydroxyphenylboronic acid (2 g) in DME (50 ml) and water (10 ml) was stirred at 80° C. under N$_2$ overnight. It was added silica gel and concentrated in vacuo. The residue was purified by column chromatography (silica gel, eluted with EtOAc in hexane) to give the title compound (1.852 g) as a white solid.

MS (API+), found: 172.1 (M+1)

B) trans-N-{3-[(4-pyridin-3-ylphenoxy)methyl]tetrahydro-2H-pyran-4-yl}ethanesulfonamide Titled compound was synthesized by similar method to processes C) and D) of Example 7.

$^1$H NMR (300 MHz, CDCl$_3$) δ 1.28 (3H, t, J=7.4 Hz), 1.63-1.82 (1H, m), 1.96-2.11 (1H, m), 2.11-2.23 (1H, m), 2.92-3.06 (2H, m), 3.38-3.68 (3H, m), 3.96-4.06 (1H, m), 4.06-4.22 (3H, m), 4.74 (1H, d, J=9.1 Hz), 7.00 (2H, d, J=8.7 Hz), 7.35 (1H, dd, J=7.6, 4.9 Hz), 7.51 (2H, d, J=9.1 Hz), 7.83 (1H, d, J=7.9 Hz), 8.56 (1H, brs), 8.81 (1H, brs).

Example 139 trans-N-[3-{[4-(4-methyl-1H-imidazol-1-yl)phenoxy]methyl}tetrahydro-2H-pyran-4-yl]ethanesulfonamide A) 1-(4-methoxyphenyl)-4-methyl-1H-imidazole Titled compound was synthesized by similar method to process A) of Example 132.

$^1$H NMR (300 MHz, CDCl$_3$) δ 2.29 (3H, s), 3.84 (3H, s), 6.84-7.04 (3H, m), 7.23-7.31 (2H, m), 7.65 (1H, s).

B) 4-(4-methyl-1H-imidazol-1-yl)phenol

A mixture of title compound and 4-(5-methyl-1H-imidazol-1-yl)-5-methyl-1H-imidazole was obtained by similar method to process B) of Example 132. This mixture was crystallized from MeOH/IPE, and recrystallized from MeOH/IPE to give the title compound (0.88 g).

$^1$H NMR (300 MHz, DMSO-d$_6$) δ 2.08 (1H, s), 2.14 (3H, s), 6.79-6.89 (1H, m), 7.25 (1H, s), 7.29-7.43 (1H, m), 7.90 (1H, d, J=1.5 Hz), 9.66 (1H, s).

C) trans-N-[3-{[4-(4-methyl-1H-imidazol-1-yl)phenoxy]methyl}tetrahydro-2H-pyran-4-yl]ethanesulfonamide Titled compound was synthesized by similar method to processes C) and D) of Example 7.

$^1$H NMR (300 MHz, CDCl$_3$) δ 1.30 (3H, t, J=7.4 Hz), 1.63-1.80 (1H, m), 1.91-2.09 (1H, m), 2.09-2.21 (1H, m), 2.29 (3H, s), 2.99 (2H, q, J=7.3 Hz), 3.38-3.66 (3H, m), 3.95-4.19 (4H, m), 4.34 (1H, d, J=9.1 Hz), 6.92 (1H, s), 6.96 (2H, d, J=8.7 Hz), 7.22-7.31 (2H, m), 7.65 (1H, s).

Example 140 trans-N-[3-{[4-(4-chloro-1H-pyrazol-1-yl)phenoxy]methyl}tetrahydro-2H-pyran-4-yl]ethanesulfonamide A) 1-(4-methoxyphenyl)-1H-pyrazole A mixture of K$_2$CO$_3$ (18.1 g), quinolin-8-ol (1.58 g), copper(I)iodide (2.08 g), 1H-pyrazole (7.42 g) and 1-iodo-4-methoxybenzene (25.5 g) in DMSO was stirred at 140° C. under N$_2$ overnight. The mixture was poured into sat. NH$_4$Cl aq. and extracted with EtOAc. The organic layer was separated, washed with brine, dried over MgSO$_4$ and concentrated in vacuo. The residue was purified by column chromatography (NH silica gel, eluted with EtOAc in hexane) to give the title compound (13.7 g) as pale orange oil.

MS (API+), found: 175.0 (M+1)

B) 4-chloro-1-(4-methoxyphenyl)-1H-pyrazole

A mixture of 1-(4-methoxyphenyl)-1H-pyrazole (13.7 g) and NCS (11.6 g) in THF (300 ml) was stirred at 70° C. for 5 h. The mixture was quenched with sat. NaHCO$_3$ aq. and extracted with EtOAc. The organic layer was separated, washed with brine, dried over Na$_2$SO$_4$ and concentrated in vacuo. The residue was washed with hexane to give the title compound (15.0 g) as white solid.

MS (API+), found: 209.0 (M+1)

$^1$H NMR (300 MHz, CDCl$_3$) δ 3.84 (3H, s), 6.88-7.09 (2H, m), 7.47-7.58 (2H, m), 7.61 (1H, s), 7.81 (1H, s).

C) 4-(4-chloro-1H-pyrazol-1-yl)phenol

A mixture of 4-chloro-1-(4-methoxyphenyl)-1H-pyrazole (24.5 g) and 48% HBr (100 ml) in AcOH (100 ml) was stirred at 130° C. overnight. The mixture was concentrated under vacuum, neutralized with sat. NaHCO$_3$ aq. and extracted with EtOAc. The organic layer was separated, washed with water and brine, dried over Na$_2$SO$_4$ and filtered. The filtrate was treated with activated charcoal powder. The insoluble material was removed is by filtration, and the filtrate was concentrated in vacuo to give the title compound (20.90 g) as off-white solid.

MS (API+), found: 194.8 (M+1)

$^1$H NMR (300 MHz, CDCl$_3$) δ 6.20-6.56 (1H, m), 6.78-6.90 (2H, m), 7.36-7.49 (2H, m), 7.63 (1H, s), 7.78 (1H, s).

D) trans-N-[3-{[4-(4-chloro-1H-pyrazol-1-yl)phenoxy]methyl}tetrahydro-2H-pyran-4-yl]ethanesulfonamide Titled compound was synthesized by similar method of processes G) and H) of Example 6.

$^1$H NMR (300 MHz, CDCl$_3$) δ 1.28 (3H, t, J=7.4 Hz), 1.62-1.79 (1H, m), 1.91-2.07 (1H, m), 2.12-2.22 (1H, m), 2.98 (2H, q, J=7.2 Hz), 3.40-3.53 (2H, m), 3.53-3.66 (1H, m), 3.96-4.24 (5H, m), 6.97 (2H, d, J=9.1 Hz), 7.53 (2H, d, J=9.1 Hz), 7.60 (1H, s), 7.81 (1H, s).

Example 141 trans-N-[4,4-difluoro-2-{[4-(4-methyl-1H-pyrazol-1-yl)phenoxy]methyl}cyclohexyl]ethanesulfonamide A) 5,5-difluoro-2-hydroxycyclohex-1-ene-1-carboxylate To a solution of diethyl 4,4-difluoroheptanedioate (6.01 g) in THF (80 ml) was added NaH (1.91 g) at 0° C. The mixture was stirred at 80° C. for 5 h. The mixture was quenched with sat. NH$_4$Cl aq. and 1 M HCl aq. and extracted with EtOAc. The organic layer was separated, washed with brine, dried over Na$_2$SO$_4$ and concentrated in vacuo. The residue was purified by column chromatography (silica gel, eluted with EtOAc in hexane) to give the title compound (4.05 g).

$^1$H NMR (300 MHz, CDCl$_3$) δ 1.31 (3H, t, J=7.0 Hz), 2.12 (2H, tt, J=13.3, 6.8 Hz), 2.55 (2H, t, J=7.0 Hz), 2.75 (2H, t, J=14.3 Hz), 4.24 (2H, q, J=7.2 Hz), 12.26 (1H, s).

B) ethyl 2-(benzylamino)-5,5-difluorocyclohex-1-ene-1-carboxylate

A mixture of ethyl 5,5-difluoro-2-hydroxycyclohex-1-ene-1-carboxylate (4.05 g) and benzylamine (3.22 ml) in toluene (100 ml) was stirred at 100° C. overnight. The solvent was removed by evaporation, and the residue was purified by column chromatography (silica gel, eluted with EtOAc in hexane) to give the title compound (5.36 g).

$^1$H NMR (300 MHz, CDCl$_3$) δ 1.27 (3H, t, J=7.2 Hz), 2.03 (2H, tt, J=13.3, 6.7 Hz), 2.47-2.60 (2H, m), 2.72-2.89 (2H, m), 4.14 (2H, q, J=7.2 Hz), 4.41 (2H, d, J=6.4 Hz), 7.11-7.42 (5H, m), 9.38 (1H, brs).

C) ethyl cis-2-(benzylamino)-5,5-difluorocyclohexanecarboxylate

NaBH$_4$ (2.06 g) was added to AcOH (80 ml) at 10° C., and the mixture was stirred for 30 min. To the mixture was added a solution of ethyl 2-(benzylamino)-5,5-difluorocyclohex-1-ene-1-carboxylate (5.36 g) in AcOH (10 ml) was added in one portion, and the reaction was stirred for 3 h. Evaporation of acetic acid in vacuo followed by dissolution of the residue with EtOAc. The solution was washed with sat. NaHCO$_3$ aq. and brine, dried over Na$_2$SO$_4$ and concentrated under vacuum. The residue was purified by column chromatography (silica gel, eluted with EtOAc in hexane) to give the title compound (3.84 g).

$^1$H NMR (300 MHz, CDCl$_3$) δ 1.25 (3H, t, J=7.2 Hz), 1.36-1.53 (1H, m), 1.64-2.39 (5H, m), 2.55-2.70 (1H, m), 2.89 (1H, td, J=10.5, 2.6 Hz), 3.72 (1H, d, J=13.2 Hz), 3.88 (1H, d, J=13.2 Hz), 4.10-4.23 (2H, m), 7.17-7.38 (5H, m).

D) ethyl cis-2-[(tert-butoxycarbonyl)amino]-5,5-difluorocyclohexanecarboxylate

A mixture of ethyl cis-2-(benzylamino)-5,5-difluorocyclohexanecarboxylate (3.79 g) and 10% Pd/C (678 mg, 50% wet) in EtOH (70 ml) was hydrogenated under balloon pressure at room temperature for 3 h. The catalyst was removed by filtration and the filtrate was concentrated in vacuo. The residue was dissolved in THF (50 ml), and to this solution was added Et$_3$N (2.66 ml) and Boc$_2$O (3.55 ml). The mixture was stirred at room temperature overnight, and quenched with sat. NaHCO$_3$ aq. and extracted with EtOAc. The organic layer was separated, washed with brine, dried over Na$_2$SO$_4$ and concentrated in vacuo. The residue was purified by column chromatography (silica gel, eluted with EtOAc in hexane) to give the title compound (3.63 g).

$^1$H NMR (300 MHz, CDCl$_3$) δ 1.27 (3H, t, J=7.2 Hz), 1.43 (9H, s), 1.73-2.23 (5H, m), 2.24-2.48 (1H, m), 2.90 (1H, dt, J=8.2, 4.4 Hz), 3.98-4.10 (1H, m), 4.17 (2H, dtt, J=10.8, 7.3, 3.7 Hz), 5.21 (1H, brs).

E) ethyl trans-2-[(tert-butoxycarbonyl)amino]-5,5-difluorocyclohexanecarboxylate To a solution of ethyl cis-2-[(tert-butoxycarbonyl)amino]-5,5-difluorocyclohexanecarboxylate (3.63 g) in EtOH (80 ml) was added sodium ethoxide (1.21 g) at 0° C. The mixture was stirred at 80° C. for 4 h. The mixture was quenched with sat. NH$_4$Cl aq. at room temperature and extracted with EtOAc. The organic layer was separated, washed with brine, dried over Na$_2$SO$_4$ and concentrated in vacuo. The residue was purified by column chromatography (silica gel, eluted with EtOAc in hexane) to give the title compound (2.23 g).

$^1$H NMR (300 MHz, CDCl$_3$) δ 1.27 (3H, t, J=7.0 Hz), 1.42 (9H, s), 1.47-1.66 (1H, m), 1.74-2.00 (1H, m), 2.01-2.20 (3H, m), 2.20-2.36 (1H, m), 2.59 (1H, td, J=11.6, 3.2 Hz), 3.76 (1H, d, J=10.2 Hz), 4.16 (2H, q, J=7.2 Hz), 4.51 (1H, brs).

F) tert-butyl trans-[4,4-difluoro-2-(hydroxymethyl)cyclohexyl]carbamate

To a solution of ethyl trans-2-[(tert-butoxycarbonyl)amino]-5,5-difluorocyclohexanecarboxylate (3.37 g) in THF (80 ml) was added LAH (999 mg) at 0° C. The mixture was stirred at 0° C. for 30 min. To this mixture was added 1 M NaOH aq. (4 ml) and the resulting mixture was passed through a pad of celite. The filtrate was concentrated under vacuum. The residue was purified by column chromatography (silica gel, eluted with EtOAc in hexane) to give the title compound (2.69 g).

$^1$H NMR (300 MHz, CDCl$_3$) δ 1.46 (9H, s), 1.51-2.24 (6H, m), 3.25-3.41 (1H, m), 3.49-3.64 (2H, m), 3.70-3.84 (1H, m), 4.44 (1H, d, J=6.4 Hz).

G) tert-butyl trans-[4,4-difluoro-2-{[4-(4-methyl-1H-pyrazol-1-yl)phenoxy]methyl}cyclohexyl]carbamate A mixture of tert-butyl trans-[4,4-difluoro-2-(hydroxymethyl)cyclohexyl]carbamate (150 mg), 4-(4-methyl-1H-pyrazol-1-yl)phenol (128 mg), ADDP (214 mg) and tributylphosphine (0.21 ml) in toluene (8 ml) was stirred at room temperature overnight. The mixture was purified by column chromatography (silica gel, eluted with EtOAc in hexane) to give the title compound (210 mg).

$^1$H NMR (300 MHz, CDCl$_3$) δ1.39 (9H, s), 1.58-2.13 (6H, m), 2.15 (3H, s), 3.54-3.69 (2H, m), 3.85-3.94 (1H, m), 3.98-4.07 (1H, m), 4.44-4.52 (1H, m), 6.93 (2H, d, J=8.7 Hz), 7.49 (1H, s), 7.53 (2H, d, J=9.1 Hz), 7.60 (1H, s).

H) trans-N-[4,4-difluoro-2-{[4-(4-methyl-1H-pyrazol-1-yl)phenoxy]methyl}cyclohexyl]ethanesulfonamide A mixture of tert-butyl trans-[4,4-difluoro-2-{[4-(4-methyl-1H-pyrazol-1-yl)phenoxy]methyl}cyclohexyl]carbamate (210 mg) and 4 M HCl/EtOAc (7.5 ml) was stirred at room temperature overnight. The resulting white precipitate was collected by filtration. To the suspension of the residue in THF (5 ml) was added Et$_3$N (0.21 ml) and ethanesulfonyl chloride (0.071 ml). The mixture was stirred at room temperature for 4 h, and quenched with sat. NaHCO$_3$ aq. and extracted with EtOAc. The organic layer was separated, washed with brine, dried over Na$_2$SO$_4$ and concentrated in vacuo. The residue was purified by column chromatography (silica gel, eluted with EtOAc in hexane) to give the title compound (21.1 mg).

$^1$H NMR (300 MHz, CDCl$_3$) δ 1.20 (3H, t, J=7.3 Hz), 1.57-2.10 (5H, m), 2.15 (3H, s), 2.22-2.40 (2H, m), 2.91 (2H, q, J=7.2 Hz), 3.38-3.59 (1H, m), 3.94 (1H, d, J=7.5 Hz), 4.16 (1H, d, J=7.5 Hz), 4.45 (1H, d, J=9.4 Hz), 6.94 (2H, d, J=9.0 Hz), 7.42-7.70 (4H, m).

Example 142 trans-N-[4,4-difluoro-2-{[4-(3-methyl-1H-pyrazol-1-yl)phenoxy]methyl}cyclohexyl]ethanesulfonamide A) 1-(4-methoxyphenyl)-3-methyl-1H-pyrazole and 1-(4-methoxyphenyl)-5-methyl-1H-pyrazole Titled compounds were synthesized by similar method to process A) of Example 132. A mixture was purified by column chromatography (silica gel, eluted with EtOAc in hexane) to give 1-(4-methoxyphenyl)-3-methyl-1H-pyrazole (2.47 g) as a white solid, and 1-(4-methoxyphenyl)-5-methyl-1H-pyrazole (1.21 g) as a pale yellow oil.

1-(4-methoxyphenyl)-3-methyl-1H-pyrazole:
MS (API+), found: 189.2 (M+1)
1-(4-methoxyphenyl)-5-methyl-1H-pyrazole:
MS (API+), found: 189.2 (M+1)

B) 4-(3-methyl-1H-pyrazol-1-yl)phenol

Titled compound was synthesized by similar method to process B) of Example 132.
MS (API+), found: 175.1 (M+1)

C) trans-N-[4,4-difluoro-2-{[4-(3-methyl-1H-pyrazol-1-yl)phenoxy]methyl}cyclohexyl]ethanesulfonamide Titled compound was synthesized by similar method of processes G) and H) of Example 6.

$^1$H NMR (300 MHz, CDCl$_3$) δ 1.19 (3H, t, J=7.3 Hz), 1.57-2.32 (7H, m), 2.37 (3H, s), 2.91 (2H, q, J=7.2 Hz), 3.40-3.58 (1H, m), 3.93 (1H, dd, J=9.2, 2.4 Hz), 4.16 (1H, dd, J=9.2, 1.7 Hz), 4.39 (1H, d, J=9.4 Hz), 6.22 (1H, d, J=2.3 Hz), 6.88-7.01 (2H, m), 7.50-7.61 (2H, m), 7.71 (1H, d, J=2.3 Hz).

Example 143 trans-N-[4,4-difluoro-2-{[4-(5-methyl-1H-pyrazol-1-yl)phenoxy]methyl}cyclohexyl]ethanesulfonamide A) 4-(5-methyl-1H-pyrazol-1-yl)phenol Titled compound was synthesized by similar method to process B) of Example 132.
MS (API+), found: 175.1 (M+1)

B) trans-N-[4,4-difluoro-2-{[4-(5-methyl-1H-pyrazol-1-yl)phenoxy]methyl}cyclohexyl]ethanesulfonamide Titled compound was synthesized by similar method of processes G) and H) of Example 6.

$^1$H NMR (300 MHz, CDCl$_3$) δ 1.21 (3H, t, J=7.3 Hz), 1.60-2.39 (10H, m), 2.92 (2H, q, J=7.5 Hz), 3.45 (1H, qd, J=10.2, 3.6 Hz), 3.94 (1H, dd, J=9.2, 2.4 Hz), 4.09 (1H, dd, J=9.4, 3.0 Hz), 4.98 (1H, d, J=9.4 Hz), 6.17 (1H, d, J=0.8 Hz), 6.90-7.01 (2H, m), 7.31-7.40 (2H, m), 7.54 (1H, d, J=1.5 Hz).

Reference Example 3 tert-butyl ((3S,4S)-3-(hydroxymethyl)tetrahydro-2H-pyran-4-yl)carbamate

A) ethyl 4-oxotetrahydro-2H-pyran-3-carboxylate

1 M of LiHMDS in THF (1 L) was added to a solution of tetrahydro-4H-pyran-4-one (90 g) in toluene (1.2 L) below −70° C. The resulting mixture was stirred at −70° C. for 30 min. Ethyl chloroformate (110 g) was added and the reaction mixture was stirred at rt for 10 min. The reaction mixture was quenched with AcOH (140 g) and H$_2$O (200 mL), the organic layer was separated and washed with brine (800 mL), dried over Na$_2$SO$_4$ and concentrated to dryness. The residue was purified by silica gel column (PE/EtOAc) to give 53 g of the title compound as a colorless oil, which was used in the next step directly.

B) ethyl 4-(((1S)-1-phenylethyl)amino)-5,6-dihydro-2H-pyran-3-carboxylate

A mixture of ethyl 4-oxotetrahydro-2H-pyran-3-carboxylate (250 g), ethyl 4-oxotetrahydro-2H-pyran-3-carboxylate (182 g) and TsOH (28.5 g) in toluene (1.5 L) was refluxed overnight. The reaction was extracted with EtOAc (2 L), washed with saturated NaHCO$_3$ (1 L×3) and brine (1 L), dried over Na$_2$SO$_4$ and concentrated to dryness. The residue was purified by silica gel column (PE/EtOAc) to give 255 g of the title compound as a yellow oil, which was used in the next step directly.

C) ethyl (3S,4S)-4-(((1S)-1-phenylethyl)amino)tetrahydro-2H-pyran-3-carboxylate hydrobromide To a stirred solution of ethyl 4-(((1S)-1-phenylethyl)amino)-5,6-dihydro-2H-pyran-3-carboxylate (218 g) in toluene (1.5 L) was added MgSO$_4$ (380 g), stirred for 20 min at rt. Then AcOH (250 mL) and NaBH(OAc)$_3$ (250 g) was added at 0° C. After being stirred at room temperature for 5 h, the reaction was quenched with water and adjusted pH to 8 with conc aq NH$_3$.H$_2$O. The mixture was extracted with EtOAc (2 L). The organic layer was separated, washed with brine, dried over Na$_2$SO$_4$ and concentrated in vacuo. The residue was purified by column chromatography (PE/EtOAc) to give crude of ethyl (3S,4S)-4-(((1S)-1-phenylethyl)amino)tetrahydro-2H-pyran-3-carboxylate (176 g) as an oil.

$^1$H NMR (400 MHz, CDCl$_3$) δ 1.25-1.38 (6H, m), 1.55-1.68 (1H, m), 1.82-1.95 (1H, m), 2.04 (1H, brs), 2.80-2.85 (2H, m), 3.30-3.90 (1H, m), 3.43 (1H, dd, J=11.6, 2.8 Hz), 3.84-3.92 (2H, m), 4.14-4.24 (3H, m), 7.21-7.25 (1H, m), 7.29-7.35 (4H, m).

It was dissolved in DCM (300 mL) cooled to 0° C. 35% (w/w), HBr solution in AcOH (154 g) was added. Then toluene (1.5 L) was added. The mixture was stand at rt for 8 h, filtered, washed with toluene, dried under vacuum. The solid was dissolved in DCM (as few as possible), then toluene (4-5 times (V/V) of DCM) was added. The mixture was stand for 3 h at rt, filtered and dried. This procedure was repeated 3-5 times to give 116 g of the title compound was afforded by recrystallized from (DCM/toluene=⅕) as a white solid (>95% ee).

D) ethyl (3S,4S)-4-aminotetrahydro-2H-pyran-3-carboxylate hydrobromide

A mixture of ethyl (3S,4S)-4-(((1S)-1-phenylethyl)amino)tetrahydro-2H-pyran-3-carboxylate hydrobromide (73 g) and 10% Pd/C (15 g, 50% wet.) in EtOH (800 mL) was hydrogenated under 55 psi at 45° C. for 12 h. The reaction mixture was filtered and the filtrate was concentrated under reduced pressure to dryness to give 44.5 g of the title compound as a solid.

$^1$H NMR (300 MHz, DMSO-d$_6$) δ 1.20 (3H, t, J=7.2 Hz), 1.71-1.75 (1H, m), 1.92-1.97 (1H, m), 3.30 (1H, d, J=3.2 Hz), 3.33-3.49 (1H, m), 3.50-3.59 (2H, m), 3.81-3.86 (1H, m), 4.08-4.16 (3H, m), 8.00 (3H, brs).

E) ethyl (3S,4S)-4-((tert-butoxycarbonyl)amino)tetrahydro-2H-pyran-3-carboxylate A mixture of ethyl (3S,4S)-4-aminotetrahydro-2H-pyran-3-carboxylate hydrobromide (44.5 g), Boc$_2$O (57 g) and Et$_3$N (70.7 g) in MeOH/DCM=1/1 (1 L) was stirred at rt overnight. The reaction was concentrated to dryness and the residue was dissolved in EtOAc. The organic layer was washed with brine, dried over Na$_2$SO$_4$ and concentrated in vacuo. The residue was purified by column chromatography (PE/EtOAc) to give 45 g of the title compound as a colorless oil.

$^1$H NMR (400 MHz, CDCl$_3$) δ 1.29 (3H, td, J=7.2, 0.8 Hz), 1.42 (9H, s), 1.65-1.71 (1H, m), 1.96-2.13 (1H, m), 2.73 (1H, d, J=3.2 Hz), 3.43-3.49 (1H, td, J=11.6, 2.8 Hz), 3.54-3.58 (1H, dd, J=11.6, 3.2 Hz), 3.87-4.04 (2H, m), 4.15-4.21 (2H, q, J=7.2 Hz), 4.27-4.30 (1H, dd, J=11.6, 1.6 Hz), 5.59 (1H, d, J=9.4 Hz).

F) ethyl (3R,4S)-4-((tert-butoxycarbonyl)amino)tetrahydro-2H-pyran-3-carboxylate Na (7.3 g) was added to EtOH (280 mL) and stirred at 0° C. until Na was completely consumed. Then a solution of ethyl (3S,4S)-4-((tert-butoxycarbonyl)amino)tetrahydro-2H-pyran-3-carboxylate (58 g) in EtOH (150 mL) was added to the above solution and the reaction mixture was stirred at rt overnight. The reaction mixture was partitioned between 0.5 M HCl (1.5 L) and EtOAc (1 L), the organic phase was separated and washed with brine (1 L), dried over Na$_2$SO$_4$ and concentrated to dryness. The residue was purified by silica gel column (PE/EtOAc) to give 35 g of the title compound as a white solid.

$^1$H NMR (400 MHz, CDCl$_3$) δ 1.27 (3H, t, J=7.2 Hz), 1.43 (9H, s), 1.46-1.53 (1H, m), 1.96-2.13 (1H, m), 2.46-2.53 (1H, m), 3.48 (1H, td, J=11.6, 2.4 Hz), 3.58 (1H, t,

J=11.2 Hz), 3.93-3.97 (2H, m), 4.03-4.07 (1H, dd, J=11.6, 4.0 Hz), 4.12-4.18 (2H, m), 4.61 (1H, brs).

G) tert-butyl ((3S,4S)-3-(hydroxymethyl)tetrahydro-2H-pyran-4-yl)carbamate

LiBH$_4$ (2.5 g) was added to a solution of ethyl (3R,4S)-4-((tert-butoxycarbonyl)amino)tetrahydro-2H-pyran-3-carboxylate (21.0 g) in anhydrous THF (200 mL) and the reaction mixture was stirred at rt overnight. The reaction mixture was quenched with conc aqueous NH$_4$Cl, then extracted with EtOAc (500 mL×3). The organic layer was washed with brine, dried over Na$_2$SO$_4$ and concentrated in vacuo. The residue was purified by column chromatography (PE/EtOAc) to give 12.6 g of the title compound as a white solid.

$^1$H NMR (400 MHz, CDCl$_3$) δ 1.30-1.40 (1H, m), 1.46 (9H, s), 1.50-1.63 (1H, m), 1.79-1.95 (1H, m), 3.33-3.58 (3H, m), 3.66-3.84 (2H, dd, J=12.8, 3.6 Hz), 3.89-3.93 (1H, dd, J=11.6, 4 Hz), 3.96-4.01 (1H, m), 4.62 (1H, d, J=7.6 Hz).

Reference Example 4 tert-butyl ((3S,4S)-3-(hydroxymethyl)tetrahydro-2H-pyran-4-yl)carbamate

A) ethyl 4-oxotetrahydro-2H-pyran-3-carboxylate

LiHMDS (1.10 L, 1 M in THF) was added to a solution of tetrahydro-4H-pyran-4-one (100 g) in toluene (1.5 L) quickly below 10° C. during 10 min. The resulting mixture was stirred at 10° C. for 10 min. Ethyl chloroformate (119 g) was added to the above solution and the resulting mixture was stirred at 10° C. for 10 min. The reaction mixture was quenched with AcOH (140 mL) and followed with H$_2$O (200 mL) below 10° C. and then filtered through a pad of Celite, the organic layer was separated and washed with brine (800 mL), dried over Na$_2$SO$_4$ and concentrated under reduced pressure to dryness. The reaction was conducted at 100 g scale twice in parallel. The residue was purified by silica gel column (PE/EtOAc) to give 86.0 g of the title compound as a colorless oil.

$^1$H NMR (400 MHz, CDCl$_3$) δ 1.23-1.35 (3H, m), 2.28-2.42 (2H, m), 3.80-3.92 (2H, m), 4.20-4.30 (4H, m), 11.85 (1H, brs).

B) ethyl 4-(((1S)-1-phenylethyl)amino)-5,6-dihydro-2H-pyran-3-carboxylate

A mixture of ethyl 4-hydroxy-5,6-dihydro-2H-pyran-3-carboxylate (86.0 g), (S)-1-phenylethylamine (60.5 g) and p-TsOH (8.60 g) in toluene (1 L) was refluxed for 12 h using a Dean-Stark apparatus. The reaction mixture was concentrated to dryness. The residue was purified by silica gel column (PE/EtOAc) to give 55.0 g of the title compound as a yellow oil.

$^1$H NMR (400 MHz, CDCl$_3$) δ 1.28 (3H, t, J=7.2 Hz), 1.50 (3H, d, J=6.8 Hz), 2.03 (1H, dt, J=11.2, 5.6 Hz), 2.38 (1H, dt, J=11.2, 5.6 Hz), 3.58-3.75 (2H, m), 4.10-4.20 (2H, m), 4.30 (2H, s), 4.68-4.65 (1H, m), 7.20-7.28 (3H, m), 7.30-7.36 (2H, m), 9.11 (1H, d, J=7.2 Hz).

C) ethyl (3S,4S)-4-(((1S)-1-phenylethyl)amino)tetrahydro-2H-pyran-3-carboxylate

A mixture of ethyl 4-(((1S)-1-phenylethyl)amino)-5,6-dihydro-2H-pyran-3-carboxylate (48.0 g), AcOH (15 mL) and PtO$_2$ (4.00 g) in THF/MeOH (96 mL/1.4 L) was hydrogenated under 4 MPa at 40° C. for 48 h. The reaction mixture was filtered through a pad of Celite and the filtrate was concentrated to dryness. The residue was diluted with EtOAc (800 mL) and the organic layer was washed with 1 M NaOH (200 mL), brine (300 mL), dried over Na$_2$SO$_4$ and concentrated to dryness to give 35.0 g of crude compound (ratio of isomers: 92/3/5) as a colorless oil. 90.0 g of accumulated crude was purified by prep-SFC (Column: Chiralcel AD, 10 μm, 250×50 mm; Mobile phase: A: Supercritical CO$_2$, B: EtOH, A:B=75:25 at 250 ml/min), the obtained solution was concentrated to dryness to give 65.0 g of the title compound as a colorless oil.

$^1$H NMR (400 MHz, CDCl$_3$) δ 1.25-1.38 (6H, m), 1.55-1.68 (1H, m), 1.82-1.95 (1H, m), 2.01 (1H, brs), 2.78-2.90 (2H, m), 3.30-3.40 (1H, m), 3.43 (1H, dd, J=11.6, 2.4 Hz), 3.82-3.96 (2H, m), 4.12-4.28 (3H, m), 7.18-7.28 (1H, m), 7.29-7.40 (4H, m).

D) ethyl (3R,4S)-4-(((1S)-1-phenylethyl)amino)tetrahydro-2H-pyran-3-carboxylate

A mixture of ethyl (3S,4S)-4-(((1S)-1-phenylethyl)amino)tetrahydro-2H-pyran-3-carboxylate (25.0 g) and KOtBu (25.3 g) in EtOH (500 mL) was heated to reflux for 16 h. Then concentrated H$_2$SO$_4$ (26.5 g) was added and the reaction mixture was heated to reflux for 16 h. The mixture was cooled to 10° C. and poured into ice water (500 mL), basified with 1 M NaOH to pH=9 and extracted with EtOAc (200 mL×3). The combined extract was washed with brine (300 mL), dried over Na$_2$SO$_4$ and concentrated to dryness. The residue was purified by silica gel column (PE/EtOAc) to give 12.0 g of crude as a colorless oil. The obtained oil was further purified by prep-HPLC (Prep-HPLC was performed at conditions: Silica gel column: Fuji C18 (300×25), YMC 250×20; Wavelength: 220 nm; Mobile phase: A CH$_3$CN (0.1% TFA as additive); B water (0.1% TFA as additive)), and most of CH$_3$CN was removed by evaporation under reduced pressure. The remaining solvent was basified with 1 M NaOH to pH=9, extracted with EtOAc (100 mL×3), the combined extract was washed with brine (150 mL), dried over Na$_2$SO$_4$ and concentrated under reduced pressure to afford 4.00 g of the title compound as a colorless oil.

$^1$H NMR (400 MHz, CD$_3$CN) δ 1.18-1.30 (7H, m), 1.69-1.78 (1H, m), 2.18 (1H, brs), 2.35 (1H, td, J=10.0, 4.0 Hz), 2.88 (1H, td, J=10.0, 4.4 Hz), 3.28 (1H, td, J=11.6, 2.8 Hz), 3.35 (1H, t, J=11.2 Hz), 3.76-3.88 (2H, m), 2.88 (1H, dd, J=11.2, 4.0 Hz), 4.08-4.20 (2H, m), 7.15-7.25 (1H, m), 7.26-7.36 (4H, m).

E) ethyl (3R,4S)-4-aminotetrahydro-2H-pyran-3-carboxylate

A mixture of ethyl (3R,4S)-4-(((1S)-1-phenylethyl)amino)tetrahydro-2H-pyran-3-carboxylate (4.00 g) and 10% Pd/C (0.400 g, 50% wet) in EtOH (50 mL) was hydrogenated under 50 psi at 45° C. for 2 hours. The reaction mixture was filtered through a pad of Celite and the filtrate was concentrated to dryness to give 2.40 g of the title compound as a colorless oil.

$^1$H NMR (400 MHz, CDCl$_3$) δ 1.20-1.30 (3H, m), 1.36-1.50 (3H, m), 1.75-1.85 (1H, m), 2.31-2.42 (1H, m), 3.03-3.15 (1H, m), 3.27-3.35 (1H, m), 3.28-3.45 (1H, m), 3.90-3.99 (1H, m), 4.05 (1H, dd, J=11.2, 4.4 Hz), 4.14 (2H, qd, J=7.2, 2.0 Hz).

F) ethyl (3R,4S)-4-((tert-butoxycarbonyl)amino)
tetrahydro-2H-pyran-3-carboxylate A mixture of ethyl (3R,4S)-4-aminotetrahydro-2H-pyran-3-carboxylate (2.40 g), Boc$_2$O (4.54 g) and Et$_3$N (2.81 g) in THF (100 mL) was stirred at 5° C. for 12 h. The reaction mixture was concentrated to dryness and the residue was purified by silica gel column (PE/EtOAc) to give 3.20 g of the title compound as a white solid.

$^1$H NMR (400 MHz, CDCl$_3$) δ 1.25 (3H, t, J=7.2 Hz), 1.42 (9H, s), 1.48-1.51 (1H, m), 1.95-2.10 (1H, m), 2.47 (1H, td, J=10.5, 4.5 Hz), 3.40-3.62 (2H, m), 3.80-3.96 (2H, m), 4.03 (1H, dd, J=11.4, 4.2 Hz), 4.14 (2H, qd, J=6.9, 1.5 Hz), 4.59 (1H, brs).

G) tert-butyl ((3S,4S)-3-(hydroxymethyl)tetrahydro-2H-pyran-4-yl)carbamate

LAH (1.16 g) was added portionwise to a solution of ethyl (3R,4S)-4-((tert-butoxycarbonyl)amino)tetrahydro-2H-pyran-3-carboxylate (3.20 g) in anhydrous THF (50 mL) and the reaction mixture was stirred at 5° C. for 20 minutes. The reaction mixture was quenched with 8 M aq. NaOH (3 mL). Then Na$_2$SO$_4$ (10 g) was added and the resulting mixture was filtered through a pad of Celite and the filtrate was concentrated to dryness. The residue was purified by silica gel column (PE/EtOAc) to give 2.40 g of the title compound as a white solid.

Reference Example 5 tert-butyl ((3S,4S)-3-(hydroxymethyl)tetrahydro-2H-pyran-4-yl)carbamate

A) ethyl (3S,4S)-4-aminotetrahydro-2H-pyran-3-carboxylate

A mixture of ethyl (3S,4S)-4-(((1S)-1-phenylethyl)amino)tetrahydro-2H-pyran-3-carboxylate (35.0 g), 10% Pd/C (3.50 g, 50% wet) in EtOH (350 mL) was hydrogenated under 55 psi at 40° C. for 8 h. The reaction mixture was filtered through a pad of Celite and the filtrate was concentrated to dryness to give 21.0 g of the title compound as a colorless oil.

$^1$H NMR (400 MHz, CDCl$_3$) δ 1.23 (3H, t, J=7.2 Hz), 1.64 (2H, brs), 1.70-1.86 (2H, m), 2.68-2.73 (1H, m), 3.28-3.34 (1H, m), 3.48-3.56 (1H, m), 3.68 (1H, dd, J=11.6, 4.0 Hz), 3.80-3.89 (1H, m), 4.05 (1H, dd, J=11.6, 6.8 Hz), 4.13 (2H, q, J=7.2 Hz).

B) ethyl (3S,4S)-4-((tert-butoxycarbonyl)amino)
tetrahydro-2H-pyran-3-carboxylate A mixture of ethyl (3S,4S)-4-aminotetrahydro-2H-pyran-3-carboxylate (21.0 g), Boc$_2$O (33.3 g) and TEA (25.7 g) in THF (500 mL) was stirred at 15° C. for 1 h. The reaction mixture was concentrated to dryness and the residue was purified by silica gel column (PE/EtOAc) to give 25.0 g of the title compound as a colorless oil.

$^1$H NMR (400 MHz, CDCl$_3$) δ 1.28 (3H, t, J=7.2 Hz), 1.43 (9H, s), 1.65-1.74 (1H, m), 1.98-2.12 (1H, m), 2.70-2.79 (1H, m), 3.47 (1H, td, J=11.6, 2.8 Hz), 3.57 (1H, dd, J=12.0, 2.8 Hz), 3.89-4.02 (2H, m), 4.19 (2H, q, J=7.2 Hz), 4.25-4.36 (1H, m), 5.58 (1H, d, J=8.8 Hz).

C) ethyl (3R,4S)-4-((tert-butoxycarbonyl)amino)
tetrahydro-2H-pyran-3-carboxylate Na (3.16 g) was added to EtOH (100 mL) and stirred at 0° C. until Na was completely consumed. Then a solution of ethyl (3S,4S)-4-((tert-butoxycarbonyl)amino)tetrahydro-2H-pyran-3-carboxylate (25.0 g) in EtOH (150 mL) was added to the above solution and the reaction mixture was stirred at 0-5° C. for 1 h. The reaction mixture was partitioned between 0.5 M HCl (800 mL) and EtOAc (200 mL), and the organic phase was separated and washed with brine (300 mL), dried over Na$_2$SO$_4$ and concentrated to dryness. The residue was purified by silica gel column (PE/EtOAc) to give 17.0 g of the title compound as a white solid.

$^1$H NMR (400 MHz, CDCl$_3$) δ 1.25 (3H, t, J=6.8 Hz), 1.42 (9H, s), 1.48-1.60 (1H, m), 1.98-2.08 (1H, m), 2.47 (1H, td, J=10.4, 4.0 Hz), 3.47 (1H, td, J=11.6, 2.4 Hz), 3.55 (1H, t, J=11.2 Hz), 3.85-3.98 (2H, m), 4.02 (1H, dd, J=11.6, 4.4 Hz), 4.10-4.20 (2H, m), 4.60 (1H, brs).

D) tert-butyl ((3S,4S)-3-(hydroxymethyl)tetrahydro-2H-pyran-4-yl)carbamate

LAH (7.91 g) was added portionwise to a solution of ethyl (3R,4S)-4-((tert-butoxycarbonyl)amino)tetrahydro-2H-pyran-3-carboxylate (19.0 g) in anhydrous THF (200 mL) and the reaction mixture was stirred at 0° C. for 10 min. The reaction mixture was quenched with 8 M aq. NaOH (6 mL). Then Na$_2$SO$_4$ (30 g) and THF (800 mL) was added and the resulting mixture stirred for 30 min. The resulting mixture was filtered through a pad of Celite and the filtrate was concentrated to dryness. The residue was purified by silica gel column (PE/EtOAc) to give 8.50 g of the title compound as a white solid.

$^1$H NMR (300 MHz, CDCl$_3$) δ1.32-1.41 (1H, m), 1.45 (9H, s), 1.50-1.61 (1H, m), 1.86 (1H, dt, J=12.6, 2.1 Hz), 3.31-3.48 (2H, m), 3.49-3.58 (1H, m), 3.60-3.68 (1H, m), 3.69-3.80 (2H, m), 3.90 (1H, dd, J=11.4, 4.2 Hz), 3.97 (1H, dd, J=11.4, 4.5 Hz), 4.55 (1H, d, J=8.1 Hz).

Reference Example 6 tert-butyl ((3SR,4SR)-3-(hydroxymethyl)tetrahydro-2H-pyran-4-yl)carbamate

A) ethyl 4-oxotetrahydro-2H-pyran-3-carboxylate

To a mixture of dihydro-2H-pyran-4(3H)-one (15 g) in toluene (150 ml) was added LDA (82 ml) at 0° C. The mixture was stirred at 0° C. under N$_2$ for 10 min. Ethyl carbonocyanidate (16.33 g) was added to a solution at 0° C. The mixture was stirred at 0° C. under N$_2$ for 10 min. AcOH was added to the mixture. The mixture was poured into water and extracted with EtOAc. The organic layer was separated, washed with brine, dried over MgSO$_4$ and concentrated in vacuo. The residue was purified by column chromatography (silica gel, eluted with EtOAc in hexane) to give the title compound (6.00 g) as a dark yellow oil.

$^1$H NMR (300 MHz, CDCl$_3$) δ1.29 (3H, t, J=7.2 Hz), 2.31-2.44 (2H, m) 3.85 (2H, t, J=5.7 Hz), 4.16-4.44 (4H, m), 11.85 (1H, s).

B) ethyl 4-(benzylamino)-5,6-dihydro-2H-pyran-3-carboxylate

A mixture of phenylmethanamine (8.59 g) and ethyl 4-oxotetrahydro-2H-pyran-3-carboxylate (11.5 g) in toluene (300 ml) was stirred at 150° C. (Dean-Stark) for 2 h. It was concentrated in vacuo. The residue was purified by column chromatography (silica gel, eluted with EtOAc in hexane) to give the title compound (16.23 g) as a yellow oil.

LC/MS [M+1]: 262.2

C) ethyl 4-(benzylamino)-5,6-dihydro-2H-pyran-3-carboxylate

To a solution of dihydro-2H-pyran-4(3H)-one (4.08 ml) in toluene (200 ml) was added LDA in THF/hexane (40.0 ml) quickly at 0° C. After being stirred for 1 min, to the mixture was added ethyl carbonocyanidate (3.96 ml) in one portion and the mixture was stirred for further 1 min. The mixture was quenched with AcOH (20 ml) and extracted with AcOEt. The extract was washed with sat. NaHCO$_3$ aq. and brine, dried over Na$_2$SO$_4$ and concentrated under vacuum. The residue was dissolved in toluene (200 ml) and to this was added benzylamine (5.29 ml). The mixture was stirred at 100° C. overnight. The solvent was removed by evaporation, and the residue was purified by column chromatography (silica gel, eluted with EtOAc in hexane) to give the title compound (5.18 g) as a pale yellow oil.

LC/MS [M+1]: 262.3

D) ethyl (3SR,4SR)-4-(benzylamino)tetrahydro-2H-pyran-3-carboxylate

A solution of NaBH(OAc)$_3$ was prepared by adding NaBH$_4$ (8.08 g) to AcOH (250 ml) at 10° C. After the H$_2$ evolution ceased (30 min), a solution of ethyl 4-(benzylamino)-5,6-dihydro-2H-pyran-3-carboxylate (18.6 g) in AcOH (50 ml) was added in one portion, and the reaction was stirred at room temperature for 2 h. After removal of the solvent, the mixture was quenched with 8 N NaOH aq. (>pH 10) and extracted with EtOAc. The organic layer was separated, washed with brine, dried over Na$_2$SO$_4$ and concentrated in vacuo to give the title compound (18.50 g) which was used in the next step without purifications.

LC/MS [M+1]: 264.2

E) ethyl (3SR,4SR)-4-((tert-butoxycarbonyl)amino)tetrahydro-2H-pyran-3-carboxylate A mixture of ethyl (3SR,4SR)-4-(benzylamino)tetrahydro-2H-pyran-3-carboxylate (10.23 g) and 10% Pd/C (2.067 g) in EtOH (200 ml) was hydrogenated under balloon pressure at room temperature for 5 h. The catalyst was removed by filtration and the filtrate was concentrated in vacuo. The residue was dissolved in THF(dry) (100 ml), and to this was added Et$_3$N (10.83 ml) and Boc$_2$O (13.53 ml) at room temperature. The mixture was stirred overnight. The mixture was quenched with sat. NaHCO$_3$ aq. and extracted with EtOAc. The organic layer was separated, washed with brine, dried over Na$_2$SO$_4$ and concentrated in vacuo. The residue was purified by column chromatography (silica gel, eluted with EtOAc in hexane) to give the title compound (9.70 g) as a colorless oil.

LC/MS [M-Boc+1]: 174.1

F) ethyl (3SR,4SR)-4-((tert-butoxycarbonyl)amino)tetrahydro-2H-pyran-3-carboxylate A mixture of ethyl 4-(benzylamino)-5,6-dihydro-2H-pyran-3-carboxylate (1 g), Boc$_2$O (1.333 ml), and 10% Pd/C (100 mg) in AcOEt (40 ml) was stirred at room temperature under H$_2$ for 20 h. The mixture was filtered by celite. The filtrate was concentrated in vacuo. The residue was purified by column chromatography (silica gel, eluted with EtOAc in hexane) to give the title compound (0.330 g) as colorless oil.

LC/MS [M-Boc+1]: 174.2

G) ethyl (3RS,4SR)-4-((tert-butoxycarbonyl)amino)tetrahydro-2H-pyran-3-carboxylate To a solution of ethyl (3SR,4SR)-4-(tert-butoxycarbonylamino)tetrahydro-2H-pyran-3-carboxylate (9.7 g) in EtOH (200 ml) was added sodium ethanolate (2.90 g) at room temperature. The mixture was stirred at 80° C. for 2 h. The mixture was quenched with sat. NH$_4$Cl aq. at room temperature and extracted with EtOAc. The organic layer was separated, washed with brine, dried over Na$_2$SO$_4$ and concentrated in vacuo. The residue was purified by column chromatography (silica gel, eluted with EtOAc in hexane) to give the title compound (6.01 g) as a off-white solid.

$^1$H NMR (300 MHz, CDCl$_3$) δ 1.26 (3H, t, J=7.2 Hz), 1.45-1.57 (1H, m), 1.93-2.10 (1H, m), 2.48 (1H, td, J=10.3, 4.4 Hz), 3.4.0-3.64 (2H, m), 3.83-3.99 (2H, m), 4.04 (1H, dd, J=11.4, 4.2 Hz), 4.08-4.23 (2H, m), 4.55 (1H, brs).

H) ethyl (3RS,4SR)-4-(benzylamino)tetrahydro-2H-pyran-3-carboxylate

To a solution of (3RS,4RS)-ethyl 4-(benzylamino)tetrahydro-2H-pyran-3-carboxylate (875 mg) in EtOH (dry) (20 ml) was added portionwise sodium ethanolate (678 mg) at room temperature. The mixture was stirred at 60° C. under Ar for 3 h. The mixture was quenched with water at room temperature and extracted with EtOAc. The organic layer was separated, washed with water, dried over MgSO$_4$, and concentrated in vacuo. The residue was purified by column chromatography (silica gel, eluted with EtOAc in hexane) to give the title compound (370 mg) as a colorless oil.

LC/MS [M+1]: 264.1

I) ethyl (3RS,4SR)-4-aminotetrahydro-2H-pyran-3-carboxylate

To a solution of (3RS,4SR)-ethyl 4-(benzylamino)tetrahydro-2H-pyran-3-carboxylate (446 mg) in EtOH (40 ml) was hydrogenated under hydrogen atmosphere (10 bar) at 40° C. for 4.5 h. The mixture was concentrated in vacuo to give the title compound (290 mg) as a colorless oil.

J) ethyl (3RS,4SR)-4-((tert-butoxycarbonyl)amino)tetrahydro-2H-pyran-3-carboxylate A mixture of (3RS,4SR)-ethyl 4-(benzylamino)tetrahydro-2H-pyran-3-carboxylate (848 mg) and 10% Pd/C (171 mg) in EtOH (20 ml) was hydrogenated under balloon pressure at room temperature for 3 h. The catalyst was removed by filtration and the filtrate was concentrated in vacuo. The residue was dissolved in THF(dry) (10 ml), and to this was added Et$_3$N (0.898 ml) and Boc$_2$O (1.122 ml) at room temperature. The mixture was stirred overnight. The mixture was quenched with sat. NaHCO$_3$ aq. and extracted with EtOAc. The organic layer was separated, washed with brine, dried over Na$_2$SO$_4$ and concentrated in vacuo. The residue was purified by column chromatography (silica gel, eluted with EtOAc in hexane) to give the title compound (788 mg) as a white solid.

LC/MS [M-Boc+1]: 174.1

K) ethyl (3RS,4SR)-4-((tert-butoxycarbonyl)amino)tetrahydro-2H-pyran-3-carboxylate To a solution of (3RS,4SR)-ethyl 4-aminotetrahydro-2H-pyran-3-carboxylate (287 mg) and Et$_3$N (0.693 ml) in THF (dry) (10 ml) was added Boc$_2$O (0.462 ml) at room temperature. The mixture was stirred at room temperature for 10 h. The mixture was quenched with water and, after removal of THF by evaporation, extracted with EtOAc. The organic layer was separated, washed with brine, dried over MgSO$_4$, and concentrated in vacuo. The residue was purified by column chromatography (silica gel, eluted with EtOAc in hexane) to give the title compound (335 mg) as a off-white solid.

$^1$H NMR (300 MHz, CDCl$_3$) δ 1.26 (3H, t, J=7.0 Hz), 1.43 (9H, s), 1.46-1.54 (1H, m), 1.97-2.09 (1H, m), 2.41-2.55 (1H, m), 3.41-3.65 (2H, m), 3.85-4.00 (2H, m), 4.00-4.09 (1H, m), 4.09-4.21 (2H, m), 4.50-4.64 (1H, m).

L) tert-butyl ((3SR,4SR)-3-(hydroxymethyl)tetrahydro-2H-pyran-4-yl)carbamate

To a mixture of ethyl (3RS,4SR)-4-(tert-butoxycarbonylamino)tetrahydro-2H-pyran-3-carboxylate (6.0 g) in THF(dry) (100 ml) was added 2M LAH in THF (21.95 ml) at 0° C. The mixture was stirred at 0° C. under N$_2$ for 1 h. It was added MgSO$_4$, water and EtOAc at the same temperature and stirred for 10 min. It was filtered. The filtrate was concentrated in vacuo to give the title compound (4.50 g) as a white solid.

$^1$H NMR (300 MHz, CDCl$_3$) δ 1.33-1.64 (11H, m), 1.80-1.94 (1H, m), 3.30-3.66 (4H, m), 3.66-3.83 (2H, m), 3.86-4.10 (2H, m), 4.51 (1H, d, J=7.2 Hz).

Reference Example 7 tert-butyl ((1S,2S)-4,4-difluoro-2-(hydroxymethyl) cyclohexyl)carbamate

A) diethyl 4,4-difluoroheptanedioate

To a mixture of diethyl 4-oxopimelate (250 g) and EtOH (12.5 mL) in a polytetrafluoroethylene flask was added DAST (440 g) carefully at 5° C. The reaction mixture was stirred at 5-10° C. for 10 days and then warmed to 40° C. for 2 days. The reaction mixture was quenched by carefully pouring into ice water (4 L), and to the above solution was added CaCl$_2$ (125 g) with stirring and finally Na$_2$CO$_3$ was added until no bubbling. The resulting mixture was extracted with EtOAc (800 mL×3). The combined extract was washed with brine (800 mL), dried over Na$_2$SO$_4$ and concentrated to dryness. The residue was purified by silica gel column (PE/EtOAc) to give 96.0 g of the title compound as a colorless oil.

1H-NMR (CDCl$_3$, 300 MHz) δ: 1.25 (6H, t, J=7.2 Hz), 2.10-2.30 (4H, m), 2.45-2.58 (4H, m), 4.13 (4H, q, J=7.2 Hz).

B) ethyl 5,5-difluoro-2-hydroxycyclohex-1-ene-1-carboxylate

A mixture of diethyl 4,4-difluoroheptanedioate (50 g) and potassium 2-methylpropan-2-olate (24.47 g) in toluene (500 ml) was stirred at 80° C. for 3 h. The mixture was poured into 1 N HCl aq. (500 mL) and extracted with EtOAc (300 mL×2). The organic layer was separated, washed with brine, dried over MgSO$_4$ and concentrated in vacuo. The residue was purified by short pad column chromatography (silica gel, eluted with EtOAc in hexane) to give the title compound (40.0 g) as a yellow oil.

$^1$H NMR (300 MHz, CDCl$_3$) δ 1.31 (3H, t, J=7.2 Hz), 2.12 (2H, tt, J=13.4, 7.0 Hz), 2.55 (2H, t, J=7.0 Hz), 2.75 (2H, t, J=14.5 Hz), 4.24 (2H, q, J=7.0 Hz), 12.25 (1H, s).

C) ethyl 5,5-difluoro-2-(((1S)-1-phenylethyl)amino) cyclohex-1-ene-1-carboxylate A mixture of ethyl 5,5-difluoro-2-hydroxycyclohex-1-enecarboxylate (39.9 g), (S)-1-phenylethanamine (25.8 g) and TsOH.H$_2$O (1.84 g) in toluene (500 ml) was stirred at 140° C. overnight. It was concentrated in vacuo. The residue was purified by short NH silica gel pad column (eluent: Hex/EtOAc) to give a yellow oil. The residue was then filtered through silica gel pad (100 g, eluent: Hex/EtOAc=80/20, 750 mL) to give the title compound (62.3 g) as a yellow oil.

$^1$H NMR (300 MHz, CDCl$_3$) δ 1.30 (3H, t, J=7.1 Hz), 1.50 (3H, d, J=6.7 Hz), 1.72-2.03 (2H, m), 2.13-2.32 (1H, m), 2.45-2.62 (1H, m), 2.68-2.88 (2H, m), 4.12-4.22 (2H, m), 4.60 (1H, quin, J=6.9 Hz), 7.11-7.43 (5H, m), 9.42 (1H, d, J=7.1 Hz).

D) ethyl (1R,2S)-5,5-difluoro-2-(((1S)-1-phenylethyl)amino)cyclohexanecarboxylate hydrobromide NaBH$_4$ (15.78 g) was added to a solution of isobutyric acid (258 ml) at 0° C. The mixture was stirred at 0° C. for 1 h. Ethyl 5,5-difluoro-2-(((1S)-1-phenylethyl)amino)cyclohex-1-ene-1-carboxylate (43 g) was added to the solution at 0° C. The mixture was stirred at 0° C. overnight, warmed to room temperature, and stirred at room temperature for 24 h. It was purified together with next batch. NaBH$_4$ (15.41 g) was added to isobutyric acid (239 g) at 0° C. The mixture was stirred at 0° C. for 1 h. Ethyl 5,5-difluoro-2-(((1S)-1-phenylethyl)amino)cyclohex-1-ene-1-carboxylate (42 g) was added to the solution at 0° C. The mixture was stirred at 0° C. overnight. It was warmed to room temperature and stirred for 24 h. It was combined with the first batch. The mixture was poured into sat. NaHCO$_3$ aq. at 0° C. and extracted with EtOAc. The organic layer was separated, washed with water and brine, dried over MgSO$_4$ and concentrated in vacuo (remove most of isobutyric acid). The residue was purified by short pad column chromatography (NH silica gel, with hexane) to give ethyl 5,5-difluoro-2-(((S)-1-phenylethyl)amino)cyclohexanecarboxylate as a pale yellow oil. It was transformed into salt with next batch.

NaBH$_4$ (22.75 g) was added to isobutyric acid (353 g) at 0° C. The mixture was stirred at 0° C. for 1 h. Ethyl 5,5-difluoro-2-(((1S)-1-phenylethyl)amino)cyclohex-1-ene-1-carboxylate (62 g) was added to the solution at 0° C. The mixture was stirred at 0° C. for 3 days. The mixture was poured into sat. NaHCO$_3$ aq. at 0° C. and extracted with EtOAc. The organic layer was separated, washed with water and brine, dried over MgSO$_4$ and concentrated in vacuo. The residue was purified by column chromatography (NH silica gel, eluted with hexane) to give ethyl 5,5-difluoro-2-(((S)-1-phenylethyl)amino)cyclohexanecarboxylate as a yellow oil. It was mixed with the first batch.

The oil (139 g) and EtOAc (650 mL) was added 25% hydrogen bromide (150 g, AcOH solution) at 0° C. to give a white solid. It was added IPE (100 mL) and stirred at the same temperature for 30 min. The solid was collected by filtration and washed with IPE to give the title compound (89.70 g) as a white solid.

$^1$H NMR (300 MHz, DMSO-d$_6$) δ 1.24 (3H, t, J=7.0 Hz), 1.47 (1H, d, J=10.2 Hz), 1.55-2.09 (6H, m), 2.14-2.38 (1H, m), 2.45 (1H, brs), 3.26-3.60 (2H, m), 4.04-4.31 (2H, m), 4.40-4.57 (1H, m), 7.33-7.74 (5H, m), 8.76 (1H, brs), 9.06 (1H, brs).

E) ethyl (1R,2S)-5,5-difluoro-2-(((1S)-1-phenyl-ethyl)amino)cyclohexanecarboxylate 100 mg of the ethyl (1R,2S)-5,5-difluoro-2-(((1S)-1-phenylethyl)amino)cyclohexanecarboxylate hydrobromide was partitioned between EtOAc (20 mL) and 0.5 M NaOH (20 mL), and the organic layer was separated and washed with brine (10 mL), dried over $Na_2SO_4$ and concentrated under reduced pressure to dryness to give 50 mg of the title compound as a colorless oil.

$^1$H NMR (400 MHz, $CD_3OD$) δ 1.30 (3H, t, J=7.2 Hz), 1.58-1.90 (5H, m), 1.95-2.35 (3H, m), 2.58-2.70 (1H, m), 3.31-3.41 (2H, m), 4.15-4.25 (1H, m), 4.26-4.36 (1H, m), 4.45-4.58 (1H, m), 7.42-7.51 (3H, m), 7.53-7.60 (2H, m).

F) ethyl (1R,2S)-2-amino-5,5-difluorocyclohexanecarboxylate

A mixture of ethyl (1R,2S)-5,5-difluoro-2-(((1S)-1-phenylethyl)amino)cyclohexanecarboxylate (35.0 g), 10% Pd/C (3.50 g, 50% wet) in EtOH (350 mL) was hydrogenated under 55 psi at 40° C. for 8 h. The reaction mixture was filtered through a pad of Celite, and the filtrate was concentrated to dryness to give 23.0 g of the title compound as a colorless oil.

$^1$H NMR ($CDCl_3$, 400 MHz) δ 1.25 (3H, t, J=7.2 Hz), 1.32 (2H, brs), 1.70-1.81 (2H, m), 1.82-1.93 (1H, m), 1.97-2.20 (2H, m), 2.21-2.41 (1H, m), 2.68-2.96 (1H, m), 3.51-3.60 (1H, m), 4.15 (2H, q, J=7.2 Hz).

G) ethyl (1R,2S)-2-((tert-butoxycarbonyl)amino)-5,5-difluorocyclohexanecarboxylate A mixture of ethyl (1R,2S)-2-amino-5,5-difluorocyclohexanecarboxylate (23.0 g), $Boc_2O$ (29.0 g) and TEA (16.8 g) in THF (300 mL) was stirred at 15° C. for 1 h. The reaction mixture was concentrated to dryness and the residue was washed with PE (50 mL×3), and then dried over high vacuum to give 33.0 g of the title compound as a white solid.

$^1$H NMR ($CDCl_3$, 400 MHz) δ 1.26 (3H, t, J=7.2 Hz), 1.42 (9H, s), 1.73-1.85 (1H, m), 1.86-2.02 (2H, m), 2.05-2.20 (2H, m), 2.28-2.43 (1H, m), 2.86-2.95 (1H, m), 3.98-4.09 (1H, m), 4.10-4.22 (2H, m), 5.16-5.30 (1H, m).

H) ethyl (1S,2S)-2-((tert-butoxycarbonyl)amino)-5,5-difluorocyclohexanecarboxylate To EtOH (200 mL) was added Na (3.70 g) with stirring and the reaction mixture was stirred at 0° C. until Na was completely consumed. Then a solution of ethyl (1R,2S)-2-((tert-butoxycarbonyl)amino)-5,5-difluorocyclohexanecarboxylate (33.0 g) in EtOH (100 mL) was added to the above solution and the reaction mixture was stirred at 0-5° C. for 2 h. The reaction mixture was partitioned between 0.5 M HCl (2 L) and EtOAc (500 mL). The organic phase was separated, washed with brine (300 mL), dried over $Na_2SO_4$ and concentrated to dryness. The residue was purified three times by silica gel column (PE/EtOAc) to give 20.0 g of the title compound as a white solid.

$^1$H NMR ($CDCl_3$, 400 MHz) δ 1.26 (3H, t, J=7.2 Hz), 1.41 (9H, s), 1.50-1.61 (1H, m), 1.75-1.95 (1H, m), 2.05-2.31 (4H, m), 2.58 (1H, td, J=11.2, 3.6 Hz), 3.68-3.82 (1H, m), 4.15 (2H, q, J=7.2 Hz), 4.49-4.60 (1H, m).

I) tert-butyl ((1S,2S)-4,4-difluoro-2-(hydroxymethyl)cyclohexyl)carbamate

To a solution of ethyl (1S,2S)-2-((tert-butoxycarbonyl)amino)-5,5-difluorocyclohexanecarboxylate (5.00 g) in anhydrous THF (100 mL) was added LAH (1.85 g) portionwise and the reaction mixture was stirred at 0° C. for 20 min. The reaction mixture was quenched with 8 M aq. NaOH (5 mL). Then $Na_2SO_4$ (30 g) and THF (300 mL) was added and the resulting mixture was stirred for 30 min. Then the resulting mixture was filtered through a pad of Celite and the filtrate was concentrated to dryness to give 3.60 g of crude of the title compound as an off-white solid. This batch was combined with next batch for purification. To a solution of ethyl (1S,2S)-2-((tert-butoxycarbonyl)amino)-5,5-difluorocyclohexanecarboxylate (15.0 g) in anhydrous THF (300 mL) was added LAH (5.56 g) portionwise and the reaction mixture was stirred at 0° C. for 20 min. The reaction mixture was quenched with 8 M aq. NaOH (15 mL). Then $Na_2SO_4$ (100 g) and THF (1.5 L) was added and the resulting mixture stirred for 30 min. Then the resulting mixture was filtered through a pad of Celite and the filtrate was concentrated to dryness. The residue from two batches was purified by silica gel column (PE/EtOAc) to give 14.0 g of the title compound as a white solid.

$^1$H NMR ($CDCl_3$, 400 MHz) δ 1.45 (9H, s), 1.48-1.52 (1H, m), 1.53-1.62 (1H, m), 1.72-1.90 (1H, m), 1.92-2.20 (4H, m), 3.32 (1H, t, J=10.4 Hz), 3.49-3.60 (1H, m), 3.61-3.69 (1H, m), 3.71-3.80 (1H, m), 4.53 (1H, d, J=7.6 Hz).

Reference Example 8 tert-butyl ((1SR,2SR)-4,4-difluoro-2-(hydroxymethyl)cyclohexyl)carbamate

A) ethyl 2-(benzylamino)-5,5-difluorocyclohex-1-ene-1-carboxylate

A mixture of ethyl 5,5-difluoro-2-hydroxycyclohex-1-enecarboxylate (4.05 g) and benzylamine (3.22 ml) in toluene (100 ml) was stirred at 100° C. overnight. The solvent was removed by evaporation, and the residue was purified by column chromatography (silica gel, eluted with EtOAc in hexane) to give the title compound (5.36 g) as a pale yellow oil.

LC/MS [M+1]: 296.2

B) ethyl (1RS,2SR)-2-((tert-butoxycarbonyl)amino)-5,5-difluorocyclohexanecarboxylate A solution of $NaBH(OAc)_3$ was prepared by adding $NaBH_4$ (2.06 g) to AcOH (80 ml) at 10° C. After the $H_2$ evolution ceased (30 min), a solution of ethyl 2-(benzylamino)-5,5-difluorocyclohex-1-enecarboxylate (5.36 g) in AcOH (10 ml) was added in one portion, and the reaction was stirred for 3 h. Evaporation of acetic acid in vacuo followed by dissolution of the residue with EtOAc. The solution was washed with sat. $NaHCO_3$ aq. and brine, dried over $Na_2SO_4$ and concentrated under vacuum. The residue was purified by column chromatography (silica gel, eluted with EtOAc in hexane) to give ethyl (1RS,2SR)-2-(benzylamino)-5,5-difluorocyclohexanecarboxylate (3.84 g) as a colorless oil and ethyl (1SR,2SR)-2-(benzylamino)-5,5-difluorocyclohexanecarboxylate (475 mg). Ethyl (1SR,2SR)-2-(benzylamino)-5,5-difluorocyclohexanecarboxylate

LC/MS [M+1]: 298.3

A mixture of ethyl (1RS,2SR)-2-(benzylamino)-5,5-difluorocyclohexanecarboxylate (3.79 g) and 10% Pd/C (0.678 g) in EtOH (70 ml) was hydrogenated under balloon pressure at room temperature for 3 h. The catalyst was removed by filtration and the filtrate was concentrated in vacuo. To a solution of the residue in THF(dry) (50 ml) was added Et₃N (2.66 ml) and Boc₂O (3.55 ml) at room temperature. The mixture was stirred overnight. The mixture was quenched with sat. NaHCO₃ aq. and extracted with EtOAc. The organic layer was separated, washed with brine, dried over Na₂SO₄ and concentrated in vacuo. The residue was purified by column chromatography (silica gel, eluted with EtOAc in hexane) to give the title compound (3.63 g) as a white solid.

LC/MS [M-Boc+1]: 208.3

C) ethyl (1SR,2SR)-2-((tert-butoxycarbonyl)amino)-5,5-difluorocyclohexanecarboxylate To a solution of ethyl (1RS,2SR)-2-(tert-butoxycarbonylamino)-5,5-difluorocyclohexanecarboxylate (3.63 g) in EtOH (80 ml) was added sodium ethanolate (1.21 g) at room temperature. The mixture was stirred at 80° C. for 4 h. The mixture was quenched with sat. NH₄Cl aq. at room temperature and extracted with EtOAc. The organic layer was separated, washed with brine, dried over Na₂SO₄ and concentrated in vacuo. The residue was purified by column chromatography (silica gel, eluted with EtOAc in hexane) to give the title compound (2.23 g) as a white solid. LC/MS [M-Boc+1]: 208.1

D) ethyl (1SR,2SR)-2-((tert-butoxycarbonyl)amino)-5,5-difluorocyclohexanecarboxylate A mixture of ethyl (1SR,2SR)-2-(benzylamino)-5,5-difluorocyclohexanecarboxylate (475 mg) and 10% Pd/C (8.50 mg) in EtOH (10.0 ml) was hydrogenated under balloon pressure at room temperature overnight. The catalyst was removed by filtration and the filtrate was concentrated in vacuo. To a solution of the residue in THF(dry) (10 ml) was added Et₃N (0.334 ml) and Boc₂O (0.445 ml) at room temperature. The mixture was stirred for 3 h. The mixture was quenched with sat. NaHCO₃ aq. and extracted with EtOAc. The organic layer was separated, washed with brine, dried over Na₂SO₄ and concentrated in vacuo.

The residue was purified by column chromatography (silica gel, eluted with EtOAc in hexane) to give the title compound (423 mg) as a white solid.

LC/MS [M-Boc+1]: 208.3

E) tert-butyl ((1SR,2SR)-4,4-difluoro-2-(hydroxymethyl)cyclohexyl)carbamate

To a solution of ethyl (1SR,2SR)-2-(tert-butoxycarbonylamino)-5,5-difluorocyclohexanecarboxylate (145 mg) in THF(dry) (10 ml) was added LAH (43.0 mg) at 0° C. The mixture was stirred at 0° C. for 1 h. To the mixture was added 1 N NaOH aq. (0.18 ml) and stirred at room temperature. The resulting mixture was passed through a pad of celite, and the filtrate was concentrated under vacuum. The residue was purified by column chromatography (silica gel, eluted with EtOAc in hexane) to give the title compound (120 mg) as a white solid.

¹H NMR (300 MHz, CDCl₃) δ 1.46 (9H, s), 1.51-2.24 (6H, m), 3.25-3.41 (1H, m), 3.49-3.64 (2H, m), 3.70-3.84 (1H, m), 4.44 (1H, d, J=6.4 Hz).

Reference Example 9 tert-butyl ((3R,4S)-4-(hydroxymethyl)tetrahydro-2H-pyran-3-yl)carbamate

Prep-HPLC was performed at conditions: Column: Fuji C18 (300×25), YMC 250×20; Wavelength: 220 nm; Mobile phase: A CH₃CN (0.1% NH₃.H₂O); B water (0.1% NH₃.H₂O).

A) ethyl 4-hydroxybutanoate

A mixture of gamma-butyrolactone (100 g×3) and conc. H₂SO₄ (1.50 mL×3) in EtOH (600 mL×3) was stirred at 20° C. for 5 days. The mixture from three batches was combined and CaCO₃ (66.0 g) was added to the mixture. The mixture was stirred at 20° C. for 2 h. The mixture was filtered through a pad of K₂CO₃ three times and the filtrate was concentrated to dryness under reduced pressure. The crude product was purified by distillation under reduced pressure (80° C./4 mmHg) to afford 200 g of crude of the title compound with 84% ¹H NMR purity as a colorless oil.

¹H NMR (400 MHz, CDCl₃) δ 1.20 (3H, t, J=7.2 Hz), 1.75-1.88 (2H, m), 2.36 (2H, t, J=7.2 Hz), 2.70 (1H, brs), 3.60 (2H, t, J=6.4 Hz), 4.07 (2H, q, J=7.2 Hz).

B) 4-hydroxybutanoic acid potassium salt

To the mixture of gamma-butyrolactone (1200 g) in methanol (3 L) was added KOH (781 g) in methanol (6 L) dropwise at room temperature. The mixture was stirred at room temperature for 4 h. The mixture was concentrate to give the title compound as a white solid, which was washed with EtOAc, and used in the next step directly.

C) ethyl 4-hydroxybutanoate

To the mixture of 4-hydroxybutanoic acid potassium salt (1981 g) in DMF (10 L) was added bromoethane (2260 g) dropwise at room temperature, then the mixture was stirred at room temperature overnight. The mixture was poured into water (30 L) and extracted with EtOAc (8 L×4). The organic layer was washed with water (5 L×4), brine (5 L×4), dried over Na₂SO₄, and concentrated to give the title compound (1665 g) as a yellow oil.

¹H NMR (400 MHz, CDCl₃) δ 4.104-4.158 (2H, m), 3.658-3.689 (2H, m), 2.406-2.442 (2H, m), 2.080 (1H, brs), 1.842-1.909 (2H, m), 1.235-1.270 (3H, m).

D) ethyl 4-(2-ethoxy-2-oxoethoxy)butanoate

To a mixture of ethyl 4-hydroxybutanoate (100 g) and Rh₂(OAc)₄ (3.34 g) in DCM (1000 mL) was added dropwise a solution of ethyl diazoacetate (130 g) in DCM (200 mL) at 20° C. for 1 h, and the mixture was stirred at 20° C. for 16 h. The mixture was filtered through a pad of celite and the filtrate was concentrated to dryness under reduced pressure. The crude product was purified by distillation under reduced pressure (120° C./3 mmHg) to afford 150 g of the title compound as a pale yellow oil.

¹H NMR (300 MHz, DMSO-d₆) δ 1.05-1.25 (6H, m), 1.60-1.80 (2H, m), 2.31 (2H, t, J=7.2 Hz), 3.42 (2H, t, J=6.3 Hz), 3.90-4.20 (6H, m).

E) ethyl 4-(2-ethoxy-2-oxoethoxy)butanoate

To the mixture of ethyl 4-hydroxybutanoate (1665 g), ethyl diazoacetate (1438 g) in DCM (6 L) was added BF$_3$.Et$_2$O (550 ml) dropwise at room temperature. The mixture was refluxed for 15 h. The mixture was poured into ice water (5 L) and extracted with DCM (5 L×3). The organic layer was washed with brine (5 L×3), dried over Na$_2$SO$_4$, and concentrated to give the crude, which was purified by column chromatography (silica gel, eluted with PE/EtOAc) to afford the title compound (1264 g) as an oil.

$^1$H NMR (400 MHz, CDCl$_3$) δ 1.220-1.249 (6H, m), 1.805-1.973 (2H, m), 2.311-2.387 (2H, m), 3.358-3.539 (2H, m), 3.986 (2H, s), 4.024-4.086 (2H, m), 4.117-4.190 (2H, m).

F) ethyl 5-hydroxy-3,6-dihydro-2H-pyran-4-carboxylate

To a solution of ethyl 4-(2-ethoxy-2-oxoethoxy)butanoate (150 g) in toluene (1.5 L) was added dropwise a solution of t-BuOK in THF (757 mL, 1 M in THF) at 20° C., and the mixture was stirred at 20° C. for 16 h. The mixture was poured into 1 M HCl aq. solution (1 L) at 0° C. The aqueous phase was extracted with EtOAc (1 L×3), and the combined organic phase was dried over Na$_2$SO$_4$ and concentrated to dryness under reduced pressure. The crude product was purified by silica gel column (PE/EtOAc) to afford 65.0 g of the title compound as a pale yellow oil.

$^1$H NMR (300 MHz, DMSO-d$_6$) δ 1.20 (3H, t, J=7.2 Hz), 2.10-2.30 (2H, m), 3.66 (2H, t, J=5.4 Hz), 4.00-4.08 (2H, m), 4.15 (2H, q, J=7.2 Hz), 11.68 (1H, brs).

G) ethyl 5-(((1S)-1-phenylethyl)amino)-3,6-dihydro-2H-pyran-4-carboxylate

A mixture of ethyl 5-hydroxy-3,6-dihydro-2H-pyran-4-carboxylate (60.0 g), (S)-(−)-1-phenylethylamine (43.0 g) and Yb(OTf)$_3$ (10.8 g) in anhydrous toluene (600 mL) was heated to reflux equipping with a Dean-Stark apparatus under nitrogen atmosphere for 16 h. The mixture was filtered through a pad of celite, and the filtrate was concentrated to dryness under reduced pressure. The crude product as purified by silica gel column (PE/EtOAc, 0.1% TEA as additive) to give 91.0 g of the title compound as a colorless oil, which gradually solidified at about 20° C.

$^1$H NMR (400 MHz, DMSO-d$_6$) δ 1.21 (3H, t, J=7.2 Hz), 1.39 (3H, d, J=7.6 Hz), 2.15-2.30 (2H, m), 3.45-3.65 (2H, m), 3.84 (1H, d, J=16.4 Hz), 4.00-4.15 (2H, m), 4.42 (1H, d, J=16.4 Hz), 4.55-4.65 (1H, m), 7.20-7.42 (5H, m), 8.96 (1H, d, J=8.1 Hz).

H) ethyl (3R,4R)-3-(((1S)-1-phenylethyl)amino)tetrahydro-2H-pyran-4-carboxylate A mixture of ethyl 5-(((1S)-1-phenylethyl)amino)-3,6-dihydro-2H-pyran-4-carboxylate (38.0 g), PtO$_2$ (8.00 g), THF (80 mL), EtOH (1.2 L) and AcOH (12.0 g) was stirred at 60° C. under 4 MPa H$_2$ atmosphere for 2 days. The mixture was filtered through a pad of celite and the filtrate was concentrated to dryness under reduced pressure. The residue was partitioned between DCM (500 mL) and sat. aq. NaHCO$_3$ (500 mL), and the aqueous phase was extracted with DCM (500 mL×3). The combined organic phase was dried over Na$_2$SO$_4$ and concentrated to dryness under reduced pressure. The crude product was purified by silica gel column (PE/EtOAc, 0.1% TEA as additive) to give 25.0 g of crude, which was further purified by prep-HPLC (0.1% NH$_3$.H$_2$O as additive). Most of solvent was removed under reduced pressure, and the residue was partitioned between EtOAc (100 ml) and water (100 mL). The aqueous phase was extracted with EtOAc (100 mL×3), and the combined organic phase was dried over Na$_2$SO$_4$ and concentrated to dryness under reduced pressure to give 20.0 g of the title compound as a colorless oil.

$^1$H NMR (400 MHz, CDCl$_3$) δ 1.20-1.38 (3H, m), 1.31 (3H, t, J=7.2 Hz), 1.60-1.70 (1H, m), 1.85 (1H, brs), 1.95-2.08 (1H, m), 2.65-2.75 (1H, m), 3.00-3.10 (1H, m), 3.30-3.42 (2H, m), 3.57-3.68 (1H, m), 3.75-3.92 (2H, m), 4.15-4.28 (2H, m), 7.15-7.35 (5H, m).

I) ethyl (3R,4S)-3-(((1S)-1-phenylethyl)amino)tetrahydro-2H-pyran-4-carboxylate 1st Batch To a solution of ethyl (3R,4R)-3-(((1S)-1-phenylethyl)amino)tetrahydro-2H-pyran-4-carboxylate (11.0 g) in absolute EtOH (100 mL) was added t-BuOK (8.89 g), and the mixture was stirred at 60° C. under nitrogen atmosphere for 16 h. The mixture was concentrated to dryness under reduced pressure. The residue was partitioned between EtOAc (100 mL) and saturated aqueous NH$_4$Cl (100 mL), and the aqueous phase was extracted with EtOAc (100 mL×3). The combined organic phase was dried over. Na$_2$SO$_4$ and concentrated to dryness under reduced pressure. The crude product was purified by silica gel column (PE/EtOAc, 0.1% TEA as additive) to give 3.20 g of crude of the title compound (contained 5% of starting material based on $^1$H NMR), 3.00 g of mixture (the ratio of product/starting material was 1:1 on HPLC) and 3.00 g of starting material as a yellow pale oil.

2nd batch

To a solution of ethyl (3R,4R)-3-(((1S)-1-phenylethyl)amino)tetrahydro-2H-pyran-4-carboxylate (10.0 g) in absolute EtOH (100 mL) was added t-BuOK (8.09 g), and the mixture was stirred at 60° C. under nitrogen atmosphere for 16 h. The mixture was concentrated to dryness under reduced pressure. The residue was partitioned between EtOAc (100 mL) and saturated aqueous NH$_4$Cl (100 mL), and the aqueous phase was extracted with EtOAc (100 mL×3). The combined organic phase was dried over Na$_2$SO$_4$ and concentrated to dryness under reduced pressure. The crude product was combined with 1st batch, and the combined crude product was purified by prep-HPLC (0.1% NH$_3$.H$_2$O as additive). Most of solvent was removed by distillation under reduced pressure, and the residue was partitioned between EtOAc (100 mL) and water (100 mL). The aqueous phase was extracted with EtOAc (100 mL×3), and the aqueous phase was extracted with EtOAc (100 mL×3). The combined organic phase was dried over Na$_2$SO$_4$ and concentrated to dryness under reduced pressure to give 9.00 g of the title compound as a yellow pale oil and 2.00 g of starting material was recovered.

$^1$H NMR (400 MHz, CDCl$_3$) δ 1.25-1.35 (6H, m), 1.75-1.82 (2H, m), 2.28-2.42 (1H, m), 2.85-2.95 (2H, m), 3.25-3.35 (1H, m), 3.63-3.72 (1H, m), 3.75-3.90 (2H, m), 4.21 (2H, q, J=6.8 Hz), 7.18-7.35 (5H, m).

J) ethyl (3R,4S)-3-aminotetrahydro-2H-pyran-4-carboxylate

A mixture of ethyl (3R,4S)-3-(((1S)-1-phenylethyl)amino)tetrahydro-2H-pyran-4-carboxylate (10.0 g) and Pd(OH)$_2$/C (1.00 g, 20%, dry) in EtOH (200 mL) was stirred under a hydrogen balloon pressure at 30° C. for 16 h. The mixture was filtered through a pad of celite. The filtrate was concentrated to dryness under reduced pressure to give 5.80 g of the title compound as a colorless oil.

$^1$H NMR (400 MHz, DMSO-d$_6$) δ 1.19 (3H, t, J=7.2 Hz), 1.42 (2H, brs), 1.49-1.63 (1H, m), 1.67-1.81 (1H, m), 2.14-2.29 (1H, m), 2.65-2.77 (1H, m), 2.87 (1H, t, J=10.8 Hz), 3.21 (1H, td, J=12.0, 2.4 Hz), 3.65-3.85 (2H, m), 4.08 (2H, q, J=7.2 Hz).

K) ethyl (3R,4S)-3-((tert-butoxycarbonyl)amino) tetrahydro-2H-pyran-4-carboxylate To a mixture of ethyl (3R,4S)-3-aminotetrahydro-2H-pyran-4-carboxylate (5.20 g) and Et$_3$N (9.10 g) in THF (100 ml) was added Boc$_2$O (7.85 g) at 20° C., and the mixture was stirred at 30° C. for 16 h. The mixture was concentrated to dryness under reduced pressure. The resulting solid was washed with PE (50 mL) to give 8.00 g of the title compound as a white solid.

$^1$H NMR (300 MHz, DMSO-d$_6$) δ 1.13 (3H, t, J=6.9 Hz), 1.35 (9H, s), 1.48-1.68 (1H, m), 1.70-1.85 (1H, m), 2.40-2.56 (1H, m), 2.92 (1H, t, J=10.5 Hz), 3.10-3.25 (1H, m), 3.45-3.60 (1H, m), 3.61-3.70 (1H, m), 3.71-3.82 (1H, m), 3.90-4.13 (2H, m), 6.84 (1H, d, J=9.0 Hz).

L) tert-butyl ((3R,4S)-4-(hydroxymethyl)tetrahydro-2H-pyran-3-yl)carbamate

To a solution of ethyl (3R,4S)-3-((tert-butoxycarbonyl) amino)tetrahydro-2H-pyran-4-carboxylate (8.30 g) in anhydrous THF (100 mL) was added NaBH$_4$ (4.64 g) and CaCl$_2$ (6.75 g) in one portion at 20° C., and the mixture was stirred at 30° C. for 16 h. To the mixture was added dropwise 1 M aq. HCl (50 ml) at 0° C., and the aqueous phase was extracted with EtOAc (50 mL×3). The combined organic phase was dried over Na$_2$SO$_4$ and concentrated to dryness under reduced pressure. The crude product was washed with PE/EtOAc (50 mL, 10/1) to give 6.60 g of the title compound as a white solid.

$^1$H NMR (400 MHz, CDCl$_3$) δ 1.32-1.45 (1H, m), 1.46 (9H, s), 1.55-1.65 (1H, m), 1.77-1.90 (1H, m), 3.06 (1H, t, J=10.4 Hz), 3.36 (1H, td, J=12.0, 2.0 Hz), 3.42-3.52 (1H, m), 3.55-3.68 (1H, m), 3.70-3.80 (1H, m), 3.95-4.15 (2H, m), 4.45 (1H, d, J=8.8 Hz).

Reference Example 10

1,5-anhydro-4-((tert-butoxycarbonyl)amino)-2,3,4-trideoxy-D-erythro-hexitol

A) 1,3-di-O-acetyl-2,6-anhydro-4,5-dideoxy-D-threo-hex-4-enitol

To the solution of 1,3,4-tri-O-acetyl-2,6-anhydro-5-deoxy-D-arabino-hex-5-enitol (195 g) and Et$_3$SiH (87.8 g) in CH$_2$Cl$_2$ (2 L) was added BF$_3$.Et$_2$O (104 g) dropwisely at 0° C. under N$_2$. After the addition, the reaction was stirred at room temperature for 2 h. Aq. NaHCO$_3$ (2 M, 500 mL) was added to quench the reaction. The mixture was extracted with CH$_2$Cl$_2$ (400 mL×3). The organic layer was separated, washed with brine (300 mL), dried over Na$_2$SO$_4$ and concentrated to give the title compound (153 g) as a light yellow oil.

$^1$H NMR (400 MHz, CDCl$_3$) δ 2.032 (3H, s), 2.074 (3H, s), 3.798-3.835 (1H, m), 4.093-4.192 (3H, m), 4.245-4.299 (1H, m), 5.027-5.045 (1H, m), 5.920-5.959 (1H, m), 6.020-6.057 (1H, m).

B) 1,5-anhydro-2,3-dideoxy-D-threo-hex-2-enitol

Na (8.2 g) was dissolved in MeOH (1.2 L) and then cooled to 0° C. 1,3-di-O-acetyl-2,6-anhydro-4,5-dideoxy-D-threo-hex-4-enitol (153 g) dissolved in MeOH (300 mL) was added into the above solution dropwisely at 0° C. The reaction was stirred at room temperature overnight. NH$_4$Cl (30 g) was added to quench the reaction and then filtered. The filtration was concentrated. The residue was diluted with CH$_2$Cl$_2$ (200 mL) and filtered. The filtration was concentrated to give the title compound (93 g) as a yellow oil.

C) 1,5-anhydro-2,3-dideoxy-D-threo-hex-2-enitol

The mixture of 1,5-anhydro-2,3-dideoxy-D-threo-hex-2-enitol (93 g) and Pd/C (9 g) in MeOH (1.5 L) was stirred at room temperature under a H$_2$ balloon for 3 h. The mixture was then filtered. The filtration was concentrated to give the title compound (94.6 g) as a light yellow oil.

$^1$H NMR (400 MHz, CDCl$_3$) δ 1.374-1.429 (1H, m), 1.605-1.694 (1H, m), 1.897-2.076 (2H, m), 2.992 (2H, brs), 3.367-3.394 (1H, m), 3.459-3.540 (1H, m), 3.739-3.827 (2H, m), 3.864-3.872 (1H, m), 4.012-4.056 (1H, m).

D) 1,5-anhydro-6-O-(tert-butyl(diphenyl)silyl)-2,3-dideoxy-D-threo-hexitol

To the solution of 1,5-anhydro-2,3-dideoxy-D-threo-hex-2-enitol (94.6 g) and imidozale (136 g) in DMF (1.5 L) was added TBDPS-Cl (197 g) dropwisely at 0° C. under N$_2$. The reaction was stirred at room temperature overnight. Water (800 mL) was added to quench the reaction. The mixture was extracted with EtOAc (400 mL×3). The organic layer was combined, washed with brine (300 mL), dried over Na$_2$SO$_4$ and concentrated to give the crude product, which was purified by column chromatography on silica gel (PE/EtOAc) to give the title compound (204 g) as a colorless oil.

$^1$H NMR (400 MHz, CDCl$_3$) δ 1.062 (9H, s), 1.364-1.398 (1H, m), 1.599-1.639 (1H, m), 1.960-2.028 (2H, m), 2.627-2.650 (1H, m), 3.383-3.485 (2H, m), 3.783-3.822 (2H, m), 3.973-4.008 (2H, m), 7.361-7.451 (6H, m), 7.665-7.723 (4H, m).

E) 1,5-anhydro-4-azido-6-O-(tert-butyl(diphenyl) silyl)-2,3,4-trideoxy-D-erythro-hexitol To the solution of 1,5-anhydro-6-O-(tert-butyl(diphenyl) silyl)-2,3-dideoxy-D-threo-hexitol (137 g) and PPh$_3$ (291 g) in THF (2.7 L) was added a mixture of DPPA (289 g) and DEAD (285 g) in THF (300 mL) dropwisely at 0° C. under N$_2$. The reaction was stirred at room temperature overnight. The solution was concentrated, and the residue was purified by column chromatography on silica gel (PE/EtOAc) to give the title compound (120 g) as a yellow-orange oil.

F) 4-amino-1,5-anhydro-6-O-(tert-butyl(diphenyl) silyl)-2,3,4-trideoxy-D-erythro-hexitol The mixture of 1,5-anhydro-4-azido-6-O-(tert-butyl(diphenyl)silyl)-2,3,4-trideoxy-D-erythro-hexitol (80 g) and Pd/C (8 g) in NeOH (1.2 L) was stirred at room temperature under 15 psi H$_2$ for 5 h. The mixture was filtered, and the filtration was concentrated. This reaction was performed again to give the title compound (130 g, 2 batches) as a grey oil.

G) 1,5-anhydro-4-((tert-butoxycarbonyl)amino)-6-O-(tert-butyl(diphenyl)silyl)-2,3,4-trideoxy-D-erythro-hexitol To the solution of 4-amino-1,5-anhydro-6-O-(tert-butyl (diphenyl)silyl)-2,3,4-trideoxy-D-erythro-hexitol (130 g)

and Et₃N (71 g) in CH₂Cl₂ (1.5 L) was added Boc₂O (92 g). The reaction was stirred at room temperature overnight. The reaction was concentrated, and the residue was purified by column chromatography on silica gel (PE/EtOAc) to give the title compound (140 g) as a white solid.

¹H NMR (400 MHz, CDCl₃) δ 1.060 (9H, s), 1.201-1.290 (1H, m), 1.367 (9H, s), 1.527-1.710 (2H, m), 2.160-2.250 (1H, m), 3.080-3.160 (1H, m), 3.302-3.410 (2H, m), 3.751-3.780 (2H, m), 3.900-3.990 (1H, m), 4.550-4.610 (1H, m), 7.354-7.416 (6H, m), 7.662-7.694 (4H, m).

H) 1,5-anhydro-4-((tert-butoxycarbonyl)amino)-2,3,4-trideoxy-D-erythro-hexitol

To the solution of 1,5-anhydro-4-((tert-butoxycarbonyl)amino)-6-O-(tert-butyl(diphenyl)silyl)-2,3,4-trideoxy-D-erythro-hexitol (140 g) in THF (2 L) was added a solution of TBAF (155.8 g) in THF (500 mL) dropwisely at 0° C. under N₂. The resulting reaction was stirred at room temperature for 2 h. The reaction was poured into aq. NH₄Cl (3 M, 500 mL). The mixture was extracted with EtOAc (400 mL×3). The organic layer was separated, washed with brine (300 mL), dried over Na₂SO₄, and concentrated to give the crude product, which was purified by chromatography (PE/EtOAc=1:010:1) to give the title compound (57.7 g) as a white solid.

¹H NMR (400 MHz, CDCl₃) δ 1.317-1.353 (1H, m), 1.437 (9H, s), 1.641-1.791 (2H, m), 2.076-2.107 (1H, m), 2.911-2.932 (1H, m), 3.311-3.376 (1H, m), 3.498-3.599 (2H, m), 3.659-3.678 (1H, m), 3.985-4.018 (1H, m), 4.424-4.442 (1H, m).

Reference Example 11

1,5-anhydro-4-((tert-butoxycarbonyl)amino)-2,3,4-trideoxy-D-erythro-hexitol

Prep-HPLC was performed at conditions: Column: Fuji C18 (300×25), YMC 250×20; Wavelength: 220 nm; Mobile phase: A CH₃CN (0.1% NH₃.H₂O or neutral condition); B water (0.1% NH₃.H₂O or neutral condition).

A) 4,6-di-O-acetyl-1,5-anhydro-2,3-dideoxy-D-erythro-hex-2-enitol

To a solution of tri-O-acetyl-D-glucal (92.5 g) and triethylsilane (65.2 mL) in DCM (900 mL) was added dropwise BF₃.Et₂O (43.3 mL) at 0° C. The mixture was stirred at 20° C. for 2.5 h, and the reaction mixture was quenched with 10% aq. NaHCO₃ (200 mL), diluted with DCM (500 mL), and the separated organic layer was washed with water (300 mL×3) and brine (300 mL), and then dried over Na₂SO₄. The solution was concentrated under reduced pressure to afford 72.8 g of the title compound as a colorless oil.

¹H NMR (300 MHz, CDCl₃) δ 2.06 (3H, s), 2.08 (3H, s), 3.62-3.78 (1H, m), 4.10-4.28 (4H, m), 5.18-5.29 (1H, m), 5.69-5.80 (1H, m), 5.86-5.98 (1H, m).

B) 1,5-anhydro-2,3-dideoxy-D-erythro-hex-2-enitol

Sodium (3.90 g) was dissolved in absolute methanol (520 mL) and a solution of 4,6-di-O-acetyl-1,5-anhydro-2,3-dideoxy-D-erythro-hex-2-enitol (72.8 g) in absolute methanol (200 mL) was added dropwise at 0° C. The resulting mixture was stirred at 25° C. for 16 h. The mixture was quenched by NH₄Cl solid (9.01 g), and the suspension was filtered, and the filtrate was concentrated under reduced pressure. The residue was diluted with DCM (200 mL), and the mixture was filtered. The solution was concentrated under reduced pressure to afford 44.2 g of the title compound as a colorless oil.

¹H NMR (300 MHz, CDCl₃) δ 1.65-1.92 (2H, m), 3.70-3.92 (1H, m), 4.08-4.28 (3H, m), 5.70-5.88 (2H, m).

C) 1,5-anhydro-2,3-dideoxy-D-erythro-hexitol

A mixture of 1,5-anhydro-2,3-dideoxy-D-erythro-hex-2-enitol (44.2 g) and Pd/C (4.40 g, 10%) in methanol (440 mL) was hydrogenated under H₂ atmosphere (15 psi) at 25° C. for 16 h. The reaction mixture was filtered, and the filtrate was concentrated under reduced pressure to afford 44.9 g of the title compound as a colorless oil.

¹H NMR (400 MHz, CDCl₃) δ 1.36-1.50 (1H, m), 1.59-1.77 (2H, m), 2.03-2.18 (1H, m), 3.08-3.17 (1H, m), 3.31-3.42 (1H, m), 3.51-3.59 (1H, m), 3.62-3.70 (2H, m), 3.75-3.88 (2H, m), 3.90-3.96 (1H, m).

D) 1,5-anhydro-6-O-(tert-butyl(diphenyl)silyl)-2,3-dideoxy-D-erythro-hexitol

To a stirred solution of 1,5-anhydro-2,3-dideoxy-D-erythro-hexitol (44.9 g) and imidazole (65.2 g) in DMF (500 ml) was added tert-butylchlorodiphenylsilane (88.5 mL) at 0° C. After stirring for 4 h, the reaction mixture was diluted with EtOAc (1000 ml). The organic layer was washed with water (200 mL×5) and brine (200 mL), and dried over Na₂SO₄. The solution was concentrated under reduced pressure, and the residue was purified by column chromatography (PE/EtOAc) to afford 70.9 g of the title compound as a colorless oil.

¹H NMR (400 MHz, CDCl₂) δ 1.09 (9H, s), 1.41-1.52 (1H, m), 1.62-1.77 (2H, m), 2.10-2.22 (1H, m), 3.10-3.39 (2H, m), 3.50 (1H, brs), 3.62-3.72 (1H, m), 3.75-3.82 (1H, m), 3.84-3.96 (2H, m), 7.33-7.53 (6H, m), 7.60-7.78 (4H, m).

E) (2R)-2-(((tert-butyl(diphenyl)silyl)oxy)methyl)dihydro-2H-pyran-3(4H)-one

To a solution of 1,5-anhydro-6-O-(tert-butyl(diphenyl)silyl)-2,3-dideoxy-D-erythro-hexitol (70.5 g) in anhydrous DCM (700 mL) was added pyridinium chlorochromate (122 g) and powdered 4 Å molecular sieve (70.0 g), and the mixture was stirred at 25° C. for 4 h. The mixture was filtered, and the filtrate was concentrated. The residue was purified by column chromatography (PE/EtOAc) to afford 56.5 g of the title compound as a white solid.

¹H NMR (400 MHz, CDCl₂) δ 1.02 (9H, s), 1.91-2.31 (2H, m), 2.41-2.72 (2H, m), 3.66-3.79 (1H, m), 3.89-4.02 (3H, m), 4.11-4.26 (1H, m), 7.29-7.48 (6H, m), 7.58-7.77 (4H, m).

F) (2S)-2-(((tert-butyl(diphenyl)silyl)oxy)methyl)-N-ethoxydihydro-2H-pyran-3(4H)-imine A mixture of NaOAc (13.7 g), O-ethylhydroxylamine hydrochloride (16.2 g) and (2R)-2-(((tert-butyl(diphenyl)silyl)oxy)methyl)dihydro-2H-pyran-3(4H)-one (56.0 g) in absolute ethanol (500 mL) was stirred at 80° C. for 4 h. After cooling to room temperature, the mixture was filtered, and the filtrate was concentrated under reduced pressure. The residue was dissolved in EtOAc (500 mL), and the organic phase was washed with water (300 mL) and brine (300 mL), dried over Na₂SO₄ and concentrated under reduced pressure to afford 62.0 g of the title compound as a colorless oil. It was used for the next reaction without further purification.
¹H NMR (400 MHz, CDCl₃) δ 1.01-1.10 (9H, m), 1.13-1.28 (3H, m), 1.70-2.05 (2H, m), 3.58-3.77 (1H, m), 3.85-3.95 (1H, m), 3.97-4.20 (4.6H, m), 4.88-4.96 (0.4H, m), 7.35-7.48 (6H, m), 7.66-7.77 (4H, m).

G) 1,5-anhydro-4-((tert-butoxycarbonyl)amino)-6-O-(tert-butyl(diphenyl)silyl)-2,3,4-trideoxy-D-erythro-hexitol A mixture of (2S)-2-(((tert-butyl(diphenyl)silyl)oxy)methyl)-N-ethoxydihydro-2H-pyran-3(4H)-imine (62.0 g) and Raney-Ni (6.20 g) in EtOH (620 ml) was hydrogenated under H₂ atmosphere (3 MPa) at 60° C. for 7 days. Then Boc₂O (32.7 g) was added to the mixture. The resulting mixture was hydrogenated under H₂ atmosphere (3 MPa) at 60° C. for 72 h. After cooling to room temperature, the mixture was filtered, and the filtrate was concentrated under reduced pressure to afford a mixture of colorless oil (70.3 g).
The mixture (70.3 g) was dissolved in THF (500 mL) and Boc₂O (32.7 g) was added. The resulting mixture was stirred at 25° C. for 16 h. The mixture was diluted with EtOAc (1000 mL), and the solution was washed with water (300 mL×3). The organic phase was dried over Na₂SO₄ and concentrated under reduced pressure. The residue was purified by prep-HPLC (neutral condition) and the solution was concentrated to dryness under reduced pressure to afford 20.3 g of the title compound (100% ee).
¹H NMR (400 MHz, CDCl₃) δ 1.06 (9H, s), 1.18-1.35 (1H, m), 1.37 (9H, s), 1.55-1.75 (2H, m, overlapped with H₂O), 2.20 (1H, d, J=11.2 Hz), 3.05-3.16 (1H, m), 3.22-3.47 (2H, m), 3.70-3.82 (2H, m), 3.93 (1H, dt, J=11.2, 2.0 Hz), 4.58 (1H, brs), 7.31-7.48 (6H, m), 7.62-7.75 (4H, m).

H) 1,5-anhydro-4-((tert-butoxycarbonyl)amino)-2,3,4-trideoxy-D-erythro-hexitol

To a solution of 1,5-anhydro-4-((tert-butoxycarbonyl)amino)-6-O-(tert-butyl(diphenyl)silyl)-2,3,4-trideoxy-D-erythro-hexitol (20.0 g) in THF (200 ml) was added TBAF (1 M in THF, 85.0 mL) dropwise at 0° C., and the resulting mixture was stirred at 25° C. for 2 h. The mixture was poured into saturated aqueous solution of NH₄Cl (200 mL), and extracted with EtOAc (200 mL×3). The combined organic layer was washed with brine (200 mL), dried over Na₂SO₄ and concentrated under reduced pressure. The residue was purified by column chromatography (PE/EtOAc) to afford the 8.62 g of the title compound as an off-white solid.
¹H NMR (400 MHz, CDCl₃) δ 1.20-1.40 (1H, m), 1.44 (9H, s), 1.62-1.70 (1H, m), 1.72-1.88 (1H, m), 2.05-2.18 (1H, m), 2.92 (1H, d, J=9.6 Hz), 3.35 (1H, td, J=11.8, 2.6 Hz), 3.45-3.73 (4H, m), 3.95-4.06 (1H, m), 4.41 (1H, brd, J=8.0 Hz).

Reference Example 12 tert-butyl ((2SR,3SR)-2-(hydroxymethyl)tetrahydro-2H-pyran-3-yl)carbamate

A) 3,4-dihydro-2H-pyran-6-ylmethanol

To a solution of 3,4-Dihydro-2H-pyran (10.85 ml) in THF(dry) (40 ml) was added n-BuLi (1.6 M in hexane) (111 ml) at 0° C. After being stirred at 50° C. for 2 h, paraformaldehyde (3.21 g) was added to the reaction mixture in portionwise at 0° C. After being stirred at 50° C. overnight, the mixture was quenched with water at 0° C. and extracted with EtOAc. The organic layer was separated, washed with brine, dried over Na₂SO₄ and concentrated in vacuo. The residue was purified by column chromatography (silica gel, eluted with EtOAc in hexane) to give the title compound (4.95 g) as a pale yellow oil.
LC/MS [M+1]: 115.01

B) tert-butyl(3,4-dihydro-2H-pyran-6-ylmethoxy)diphenylsilane

A mixture of 1H-imidazole (8.59 g), tert-butylchlorodiphenylsilane (19.07 g) and (3,4-dihydro-2H-pyran-6-yl)methanol (7.2 g) in DMF (dry) (100 ml) was stirred at room temperature for 2 days. It was added NH silica gel and concentrated in vacuo. The residue was purified by column chromatography (silica gel, eluted with EtOAc in hexane) to give the title compound (16.12 g) as a colorless syrup.
¹H NMR (300 MHz, CDCl₃) δ 1.06 (9H, s), 1.73-1.87 (2H, m), 1.97-2.07 (2H, m), 3.90-3.99 (2H, m), 4.01 (2H, d, J=1.1 Hz), 4.81 (1H, t, J=3.6 Hz), 7.31-7.51 (6H, m), 7.59-7.78 (4H, m).

C) (2RS,3SR)-2-(((tert-butyldiphenylsilyl)oxy)methyl)tetrahydro-2H-pyran-3-ol

To a mixture of tert-butyl((3,4-dihydro-2H-pyran-6-yl)methoxy)diphenylsilane (16.1 g) in THF(dry) (304 ml) was added BH₃.THF (49.5 ml) at 0° C. The mixture was stirred at 0° C. under N₂ for 2 h. It was added sodium hydroxide (8 M, 28.5 ml) and hydrogen peroxide (38.8 g) successively at the same temperature and the mixture was stirred at room temperature for 2 h. It was added sat. Na₂SO₃ and extracted with EtOAc. The organic layer was separated, washed with brine, dried over MgSO₄ and concentrated in vacuo. The residue was purified by column chromatography (silica gel, eluted with EtOAc in hexane) to give the title compound (13.34 g) as a colorless syrup.
¹H NMR (300 MHz, CDCl₃) δ 0.99-1.10 (9H, m), 1.34-1.53 (1H, m), 1.58-1.75 (2H, m), 2.07-2.22 (1H, m), 3.11-3.38 (2H, m), 3.45 (1H, d, J=1.9 Hz), 3.58-3.99 (4H, m), 7.33-7.50 (6H, m), 7.62-7.75 (4H, m).

D) 2-(((tert-butyl(diphenyl)silyl)oxy)methyl)dihydro-2H-pyran-3(4H)-one

A mixture of Et₃N (15.01 ml), SO₃.pyridine (17.14 g) and (2RS,3SR)-2-(((tert-butyldiphenylsilyl)oxy)methyl)tetrahydro-2H-pyran-3-ol (13.3 g) in DMSO (100 ml) was stirred at room temperature overnight. The mixture was poured into brine and extracted with EtOAc. The organic layer was separated, washed with brine, dried over MgSO₄ and concentrated in vacuo. The residue was purified by column chromatography (silica gel, eluted with EtOAc in hexane) to give the title compound (10.06 g) as a yellow oil.
¹H NMR (300 MHz, CDCl₃) δ 1.03 (9H, s), 1.91-2.11 (1H, m), 2.12-2.31 (1H, m), 2.40-2.76 (2H, m), 3.75 (1H, ddd, J=11.7, 8.7, 4.2 Hz), 3.90-4.02 (3H, m), 4.04-4.27 (1H, m), 7.31-7.49 (6H, m), 7.61-7.79 (4H, m).

E) 2-(((tert-butyl(diphenyl)silyl)oxy)methyl)-N-ethoxydihydro-2H-pyran-3(4H)-imine A mixture of 2-(((tert-butyldiphenylsilyl)oxy)methyl)dihydro-2H-pyran-3(4H)-one (10 g), O-ethylhydroxylamine hydrochloride (2.91 g) and triethylamine (3.02 g) in EtOH (200 ml) was stirred at 80° C. for 2 h. The mixture was poured into brine and extracted with EtOAc. The organic layer was separated, washed with brine, dried over MgSO$_4$ and concentrated in vacuo to give the titled compound (11.6 g) as a pale yellow gel.

LC/MS [M+1]: 412.2

F) 2-(((tert-butyldiphenylsilyl)oxy)methyl)tetrahydro-2H-pyran-3-amine

A mixture of 2-(((tert-butyldiphenylsilyl)oxy)methyl)dihydro-2H-pyran-3(4H)-one O-ethyl oxime (11.6 g), 2-(((tert-butyldiphenylsilyl)oxy)methyl)dihydro-2H-pyran-3(4H)-one O-ethyl oxime (11.6 g) in EtOH (500 ml) was hydrogenated (Raney Ni, 10 bar) at 60° C. for 5 days. The mixture was concentrated in vacuo to give the title compound (10.43 g) as a pale yellow oil.

LC/MS [M+1]: 370.2

G) tert-butyl ((2SR,3SR)-2-(((tert-butyldiphenylsilyl)oxy)methyl)tetrahydro-2H-pyran-3-yl)carbamate A mixture of Boc$_2$O (7.54 ml) and 2-(((tert-butyldiphenylsilyl)oxy)methyl)tetrahydro-2H-pyran-3-amine (10 g) in THF(dry) (250 ml) was stirred at room temperature for 2 days. It was concentrated in vacuo. The residue was purified by column chromatography (silica gel, eluted with EtOAc in hexane) to give the title compound (4.36 g) as a colorless oil.

$^1$H NMR (300 MHz, CDCl$_3$) δ 1.06 (9H, s), 1.18-1.46 (10H, m), 1.50-1.74 (2H, m), 2.12-2.28 (1H, m), 3.05-3.17 (1H, m), 3.22-3.47 (2H, m), 3.68-3.85 (2H, m), 3.93 (1H, dt, J=11.2, 2.1 Hz), 4.56 (1H, brs), 7.31-7.50 (6H, m), 7.61-7.74 (4H, m).

LC/MS [M-Boc+1]: 370.1

H) tert-butyl ((2SR,3SR)-2-(hydroxymethyl)tetrahydro-2H-pyran-3-yl)carbamate

A mixture of tert-butyl ((2SR,3SR)-2-(((tert-butyldiphenylsilyl)oxy)methyl)tetrahydro-2H-pyran-3-yl)carbamate (4.3 g) and TBAF (11.0 ml) in THF(dry) (100 ml) was stirred at room temperature for 2 h. The mixture was poured into sat. NH$_4$Cl aq. and extracted with EtOAc. The organic layer was separated, washed with brine, dried over MgSO$_4$ and concentrated in vacuo. The residue was purified by column chromatography (silica gel, eluted with EtOAc in hexane) to give the title compound (1.93 g) as a white solid.

$^1$H NMR (300 MHz, CDCl$_3$) δ 1.19-1.54 (10H, m), 1.60-1.90 (2H, m), 2.05-2.17 (1H, m), 2.93 (1H, d, J=9.8 Hz), 3.35 (1H, td, J=11.7, 2.6 Hz), 3.43-3.76 (4H, m), 3.89-4.07 (1H, m), 4.43 (1H, d, J=7.9 Hz).

Reference Example 13 tert-butyl ((2S,3S)-2-(hydroxymethyl)tetrahydro-2H-pyran-3-yl)carbamate

A) ((2R,3S,6S)-3-acetoxy-6-methoxy-3,6-dihydro-2H-pyran-2-yl)methyl acetate

The mixture of (2R,3S,4R)-2-(acetoxymethyl)-3,4-dihydro-2H-pyran-3,4-diyl diacetate (2.0 g), ferric sulfate n-hydrate (0.307 g), MeOH (0.892 ml) and CH$_3$CN (15 ml) was heated at 80° C. for 10 min under microwave irradiation. The mixture was passed through a pad of celite, and the filtrate was concentrated under vacuum. The residue was purified by column chromatography (NH silica gel, eluted with EtOAc in hexane) to give the title compound (1.640 g) as a colorless oil.

$^1$H NMR (300 MHz, DMSO-d$_6$) δ 2.03 (3H, s), 2.05 (3H, s), 3.33 (3H, s), 3.86-3.96 (1H, m), 4.10-4.16 (2H, m), 4.93 (1H, s), 5.11-5.23 (1H, m), 5.79-5.97 (2H, m).

B) ((2S,3S,6S)-3-azido-6-methoxy-3,6-dihydro-2H-pyran-2-yl)methyl acetate

To a solution of ((2R,3S,6S)-3-acetoxy-6-methoxy-3,6-dihydro-2H-pyran-2-yl)methyl acetate (500 mg), allylpalladium chloride dimer (37.5 mg), 1,4-bis(diphenylphosphino)butane (175 mg) in THF(dry) (10 ml) was added azidotrimethylsilane (0.404 ml) at room temperature. The mixture was stirred at 50° C. under N$_2$ for 2 h. The mixture was quenched with water at room temperature and extracted with EtOAc. The organic layer was separated, washed with brine, dried over Na$_2$SO$_4$ and concentrated in vacuo. The residue was purified by column chromatography (silica gel, eluted with EtOAc in hexane) to give the title compound (222 mg) as a colorless oil.

$^1$H NMR (300 MHz, CDCl$_3$) δ 2.12 (3H, s), 3.44 (3H, s), 3.90 (2H, s), 4.22-4.42 (2H, m), 4.91 (1H, d, J=2.3 Hz), 5.83-6.08 (2H, m).

C) ((2S,3S)-3-azido-3,6-dihydro-2H-pyran-2-yl)methyl acetate

To a solution of ((2S,3S,6S)-3-azido-6-methoxy-3,6-dihydro-2H-pyran-2-yl)methyl acetate (222 mg) and Et$_3$SiH (0.468 ml) in CH$_3$CN (5 ml) was added BF$_3$.OEt$_2$ (0.371 ml) at room temperature. The mixture was stirred for 1 h. The mixture was quenched with sat. NaHCO$_2$ aq. and extracted with EtOAc. The organic layer was separated, washed with brine, dried over Na$_2$SO$_4$ and concentrated in vacuo. The residue was purified by column chromatography (silica gel, eluted with EtOAc in hexane) to give the title compound (160 mg) as a colorless oil.

$^1$H NMR (300 MHz, CDCl$_2$) δ 2.12 (3H, s), 3.60 (1H, ddd, J=8.5, 5.8, 2.6 Hz), 3.82 (1H, dt, J=8.2, 2.3 Hz), 4.14-4.29 (3H, m), 4.31-4.42 (1H, m), 5.82-5.93 (1H, m), 6.06 (1H, dq, J=10.4, 2.3 Hz).

D) ((2S,3S)-3-((tert-butoxycarbonyl)amino)tetrahydro-2H-pyran-2-yl)methyl acetate A mixture of ((2S,3S)-3-azido-3,6-dihydro-2H-pyran-2-yl)methyl acetate (160 mg) and 10% Pd/C (173 mg) in EtOAc (10 ml) was hydrogenated under balloon pressure at room temperature for 3 h. To a mixture was added Et$_3$N (0.136 ml) and Boc$_2$O (0.283 ml), and the mixture was stirred overnight. The mixture was passed through a pad of celite, and the filtrate was concentrated under vacuum. The residue was purified by column chromatography (silica gel, eluted with EtOAc in hexane) to give the title compound (152 mg) as a off-white solid.

$^1$H NMR (300 MHz, CDCl$_3$) δ 1.24-1.38 (1H, m), 1.43 (9H, s), 1.61-1.85 (2H, m), 2.10 (3H, s), 3.21-3.29 (1H, m), 3.35 (1H, td, J=11.6, 3.2 Hz), 3.47 (1H, brs), 3.92-4.04 (1H, m), 4.05-4.23 (2H, m), 4.23-4.33 (1H, m), 4.37 (1H, d, J=9.0 Hz).

E) tert-butyl ((2S,3S)-2-(hydroxymethyl)tetrahydro-2H-pyran-3-yl)carbamate

To a solution of ((2S,3S)-3-((tert-butoxycarbonyl)amino)tetrahydro-2H-pyran-2-yl)methyl acetate (152 mg) in MeOH (5 ml) was added K$_2$CO$_3$ (92 mg) at room temperature. The mixture was stirred for 30 min. The mixture was quenched with sat. NH$_4$Cl aq. and extracted with EtOAc. The organic layer was separated, washed with brine, dried over Na$_2$SO$_4$ and concentrated in vacuo. The residue was purified by column chromatography (silica gel, eluted with EtOAc in hexane) to give tert-butyl ((2S,3S)-2-(hydroxymethyl)tetrahydro-2H-pyran-3-yl)carbamate (94 mg) as a colorless oil.

$^1$H NMR (300 MHz, CDCl$_3$) δ 1.24-1.40 (1H, m), 1.44 (9H, s), 1.56-1.89 (2H, m), 2.02-2.17 (1H, m), 2.93 (1H, d, J=10.0 Hz), 3.35 (1H, td, J=11.8, 2.7 Hz), 3.46-3.77 (4H, m), 3.95-4.08 (1H, m), 4.42 (1H, d, J=8.1 Hz).

Reference Example 14 tert-butyl ((3S,4S)-3-(hydroxymethyl)tetrahydro-2H-thiopyran-4-yl)carbamate

Prep-HPLC was performed at conditions: Column: Fuji C18 (300×25), YMC 250×20; Wavelength: 220 nm; Mobile phase: A CH$_3$CN (0.1% NH$_3$.H$_2$O or neutral condition); B water (0.1% NH$_3$.H$_2$O or neutral condition).

A) methyl 4-oxotetrahydro-2H-thiopyran-3-carboxylate

To a stirred suspension of NaH (25.2 g, 60% in mineral oil) in anhydrous THF (300 mL) was added absolute methanol (21.3 g) via a dropping funnel over 30 min at 0° C. The ice-bath was removed and stirring continued at 25° C. for 1 h. The mixture was cooled in an ice-bath and dimethyl 3,3'-thiodipropionate (100 g) was added via a dropping funnel over 1 h. The ice-bath was removed and the mixture was stirred at 25° C. for 16 h. The mixture was quenched by saturated aqueous solution of NH$_4$Cl (500 mL), and the mixture was extracted with DCM (300 mL×3). The combined organic phase was dried over Na$_2$SO$_4$ and concentrated under reduced pressure. The crude product was purified by silica gel column (PE/EtOAc) to afford 55.5 g of the title compound as a pale yellow oil.

(Note: It was a keto-enol mixture and the ratio of keto-enol was about 6/4 based on $^1$H NMR)

$^1$H NMR (300 MHz, CDCl$_3$) δ 2.52-2.62 (1H, m), 2.68-2.86 (2H, m), 2.90-2.99 (1H, m), 3.03 (0.6H, dd, J=13.8, 3.6 Hz, keto), 3.22-3.33 (1.4H, m), 3.64-3.68 (0.6H, m, keto), 3.73-3.80 (3H, m), 12.48 (0.4H, brs, enol).

B) methyl 4-(((1S)-1-(4-methoxyphenyl)ethyl)amino)-5,6-dihydro-2H-thiopyran-3-carboxylate A mixture of (S)-(−)-1-(4-methoxyphenyl)-ethylamine (25.0 g), methyl 4-oxotetrahydro-2H-thiopyran-3-carboxylate (28.8 g), MgSO$_4$ (28.8 g) and Yb(OTf)$_3$ (512 mg) in toluene (300 mL) was stirred at reflux for 16 h. After cooling to room temperature, the mixture was filtered though a pad of silica gel (100 g). The filtrate was concentrated under reduced pressure to afford 42.1 g of the title compound as a yellow solid.

$^1$H NMR (400 MHz, CDCl$_3$) δ 1.49 (3H, d, J=6.8 Hz), 2.30-2.41 (1H, m), 2.45-2.68 (3H, m), 3.35-3.49 (2H, m), 3.72 (3H, s), 3.79 (3H, s), 4.52-4.65 (1H, m), 6.86 (2H, d, J=8.4 Hz), 7.15 (2H, d, J=8.4 Hz), 9.60 (1H, brd, J=6.8 Hz).

C) methyl (3R,4S)-4-(((1S)-1-(4-methoxyphenyl)ethyl)amino)tetrahydro-2H-thiopyran-3-carboxylate To mixture of methyl 4-(((1S)-1-(4-methoxyphenyl)ethyl)amino)-5,6-dihydro-2H-thiopyran-3-carboxylate (42.0 g) and molecular sieves (84.0 g, 4 Å, powder) in acetic acid (140 mL) and DCM (420 mL) was added NaBH(OAc)$_3$ (145 g) portionwise at 0° C. The mixture was stirred at 0° C. for 1 h and 25° C. for 16 h. The mixture was filtered, and the filtrate was concentrated under reduced pressure. The residue was diluted with DCM (400 mL), and the mixture was neutralized by concentrated NH$_3$.H$_2$O until pH=6-7. The mixture was extracted with DCM (200 mL×3). The combined organic layer was washed with brine (300 mL), and dried over Na$_2$SO$_4$, concentrated under reduced pressure. The crude product was purified by prep-HPLC (0.1% NH$_3$.H$_2$O as additive) to afford 37.8 g of mixture. The mixture was further separated by chiral SFC (Column: Chiralcel AD, 5 μm, 250×30 mm; Mobile phase: A: Supercritical CO$_2$, B: EtOH, A:B=95:5) to afford 20.2 g of the title compound.

$^1$H NMR (400 MHz, CDCl$_3$) δ 1.24 (3H, d, J=6.4 Hz), 1.73-1.86 (1H, m), 1.92-2.02 (1H, m), 2.31-2.40 (1H, m), 2.55 (1H, d, J=11.6 Hz), 2.65-2.73 (1H, m), 2.85-2.91 (1H, m), 3.01-3.11 (2H, m), 3.74 (3H, s), 3.75-3.86 (4H, m), 6.85 (2H, d, J=8.4 Hz), 7.23 (2H, d, J=8.4 Hz).

D) methyl (3R,4S)-4-((tert-butoxycarbonyl)amino)tetrahydro-2H-thiopyran-3-carboxylate Parallel Reaction:

To a solution of methyl (3R,4S)-4-(((1S)-1-(4-methoxyphenyl)ethyl)amino)tetrahydro-2H-thiopyran-3-carboxylate (3.00 g×4) in formic acid (60 mL×4) was added Et$_3$SiH (12.4 mL×4), and the mixture was stirred at reflux for 72 h. After cooling to room temperature, the four batches were combined and the mixture was concentrated under reduced pressure to give the formic acid salt as a yellow oil. The mixture was dissolved in CH$_3$CN (60 mL), and HCl (1 M in water, 200 mL) was added. Most of CH$_3$CN was removed by evaporation under reduced pressure, and the remaining solvent was removed by lyophilization to afford 8.18 g of the titled compound HCl salt as an off-white solid. To a solution of the solid (4.09 g×2, crude) in DCM (100 mL×2) was added Boc$_2$O (6.34 g×2) and TEA (16.2 mL×2). The resulting mixture was stirred at 22° C. for 16 h. The mixture was diluted with EtOAc (50 mL), and the organic phase was washed with water (20 mL) and brine (20 mL), dried over Na$_2$SO$_4$ and concentrated under reduced pressure. The residue was purified by column chromatography (PE/EtOAc) to afford 7.23 g of the title compound as an off-white solid.

$^1$H NMR (400 MHz, CDCl$_3$) δ 1.43 (9H, s), 1.92-2.03 (1H, m), 2.04-2.18 (1H, m), 2.48-2.76 (2H, m), 2.80-2.88 (1H, m), 3.02-3.13 (2H, m), 3.65-3.82 (5H, m), 5.57 (1H, brd, J=8.8 Hz).

E) methyl (3S,4S)-4-((tert-butoxycarbonyl)amino)tetrahydro-2H-thiopyran-3-carboxylate Parallel Reaction:

Sodium (500 mg×2) was dissolved in absolute methanol (20 mL×2), and a solution of methyl (3R,4S)-4-((tert-butoxycarbonyl)amino)tetrahydro-2H-thiopyran-3-carboxylate (3.00 g×2) in absolute methanol (10 mL) was added dropwise at 0° C. The resulting mixture was stirred at 20° C. for 4 h. The reaction was quenched by saturated aqueous solution of NH$_4$Cl (30 mL×2), and the mixture was extracted by EtOAc (30 mL×3). The combined organic phase was washed with brine (20 mL), dried over Na$_2$SO$_4$ and concentrated under reduced pressure. The residue was purified by column chromatography (PE/EtOAc) to afford 3.40 g of the title compound as a white solid.

¹H NMR (400 MHz, CDCl₃) δ 1.42 (9H, s), 1.58-1.68 (1H, m, overlap with water signal), 2.25-2.38 (1H, m), 2.55-2.66 (2H, m), 2.69-2.78 (2H, m), 2.91 (1H, dd, J=13.8, 10.6 Hz), 3.61-3.80 (4H, m), 4.54 (1H, brs).

F) tert-butyl ((3S,4S)-3-(hydroxymethyl)tetrahydro-2H-thiopyran-4-yl)carbamate

1st Batch:

To a solution of methyl (3S,4S)-4-((tert-butoxycarbonyl)amino)tetrahydro-2H-thiopyran-3-carboxylate (1.00 g) in anhydrous THF (15 mL) was added LAH (415 mg) at 0° C. The mixture was stirred at 20° C. for 4 h. The mixture was quenched by NaOH (1 N in water, 1 mL) and stirred at 20° C. for 10 min. Na₂SO₄ (2 g) was added and the mixture was filtered, the filtrate was concentrated under reduced pressure. The residue was combined with the next batch for further purification.

2nd Batch:

To a solution of methyl (3S,4S)-4-((tert-butoxycarbonyl)amino)tetrahydro-2H-thiopyran-3-carboxylate (2.40 g) in anhydrous THF (50 mL) was added LAH (995 mg) at 0° C. The mixture was stirred at 20° C. for 2 h. The mixture was quenched by NaOH (1 M in water, 3 mL) and stirred at 20° C. for 10 min. Na₂SO₄ (2 g) was added and the mixture was filtered, the filtrate was concentrated under reduced pressure. The residue was combined with the last batch and purified by column chromatography (PE/EtOAc) to afford 2.01 g of the title compound as a white solid.

¹H NMR (400 MHz, CDCl₃) δ 1.38-1.50 (10H, m), 1.55-1.68 (1H, m, overlap with water), 2.21-2.30 (1H, m), 2.52-2.65 (2H, m), 2.74 (1H, td, J=13.0, 2.4 Hz), 2.94 (1H, dd, J=13.6, 11.6 Hz), 3.35-3.55 (2H, m), 3.60 (1H, dd, J=10.4, 4.4 Hz), 3.76-3.88 (1H, m), 4.51 (1H, brd, J=8.8 Hz).

Reference Example 15 tert-butyl ((3R,4S)-3-((4-(4-chloro-1H-pyrazol-1-yl)phenoxy)methyl)tetrahydro-2H-pyran-4-yl)carbamate A) 4-chloro-1-(4-methoxyphenyl)-1H-pyrazole A mixture of K₂CO₃ (7.79 g), 4-chloro-1H-pyrazole (5.3 g), 1-iodo-4-methoxybenzene (11.0 g), copper(I)iodide (0.895 g) and quinolin-8-ol (0.682 g) in DMSO (50 ml) was stirred at 140° C. under N₂ overnight. The mixture was poured into sat. NH₄Cl aq. and extracted with EtOAc. The organic layer was separated, washed with brine, dried over MgSO₄ and concentrated in vacuo. The residue was purified by column chromatography (NH silica gel, eluted with EtOAc in hexane) to give the title compound (9.40 g) as a off-white solid.

¹H NMR (300 MHz, CDCl₃) δ3.84 (3H, s), 6.88-7.09 (2H, m), 7.47-7.58 (2H, m), 7.61 (1H, s), 7.81 (1H, s).

B) tert-butyl ((3R,4S)-3-((4-(4-chloro-1H-pyrazol-1-yl)phenoxy)methyl)tetrahydro-2H-pyran-4-yl)carbamate A mixture of tert-butyl ((3S,4S)-3-(hydroxymethyl)tetrahydro-2H-pyran-4-yl)carbamate (2.0 g), 4-(4-chloro-1H-pyrazol-1-yl)phenol (2.02 g), ADDP (2.84 g) and Bu₃P (2.77 ml) in toluene (120 ml) was stirred at room temperature overnight. The mixture was purified by column chromatography (NH silica gel, eluted with EtOAc in hexane) to give the title compound (3.19 g) as a white solid.

¹H NMR (300 MHz, CDCl₃) δ 1.42 (9H, s), 1.48-1.66 (1H, m), 1.92-2.06 (2H, m), 3.32 (1H, t, J=11.0 Hz), 3.48 (1H, td, J=11.8, 2.3 Hz), 3.58-3.74 (1H, m), 3.77-3.90 (1H, m), 4.00 (1H, dd, J=11.9, 3.2 Hz), 4.08 (1H, dd, J=9.5, 3.9 Hz), 4.22 (1H, dd, J=11.4, 4.1 Hz), 4.51 (1H, d, J=8.1 Hz), 6.89-6.99 (2H, m), 7.46-7.56 (2H, m), 7.60 (1H, s), 7.80 (1H, d, J=0.8 Hz).

Example 144

N-[(3R,4S)-4-{[4-(5-fluoropyridin-2-yl)phenoxy]methyl}tetrahydro-2H-pyran-3-yl]methanesulfonamide The solution of tert-butyl ((3R,4S)-4-(hydroxymethyl)tetrahydro-2H-pyran-3-yl)carbamate (0.028 g) in THF(dry) (2 ml) was added a suspension of 4-(5-fluoropyridin-2-yl)phenol (0.023 g), bis(2-methoxyethyl)azodicarboxylate (0.031 g) and triphenylphosphine, polystyrene-supported (71 mg, 2.2 mmol/g) in THF(dry) (2 ml). The mixture was stirred at room temperature for 5 h. Bis(2-methoxyethyl)azodicarboxylate (0.031 g) and Triphenylphosphine, polystyrene-supported (0.034 g, 2.2 mmol/g) was added to the reaction mixture. The mixture was stirred at room temperature overnight. The reaction mixture was poured into EtOAc (3 mL) and 2% NaHCO₃ aq. (1 mL), and stirred for 5 min. The organic layer was filtered on Top-Phase Separation Filter Tube, and the filtrate was evaporated by blowing away with the air at 60° C. The residue was purified by preparative HPLC (Actus Triart C18, eluted with MeCN/10 mM NH₄HCO₃ aq. 10:90→100:0). Pure fractions were combined and concentrated by blowing away with the air at 60° C. Current produced intermediate was dissolved in 3.2M HCl/MeOH (1 ml) and the solution was stirred at 50° C. for 10 minutes. The solvent was removed by blowing away with the air at 60° C. The solution of MsCl (0.027 g) in THF(dry) (1 ml) was added dropwise to a solution of the residue and triethylamine (0.036 g) in THF(dry) (1 ml) with stirring. The mixture was stirred at room temperature for 5 h and then concentrated by blowing away with the air at 60° C. The residue was purified by preparative HPLC (Actus Triart C18, eluted with MeCN/10 mM NH₄HCO₃ aq. 5:95→100:0). Pure fractions were combined and concentrated by blowing away with the air at 60° C. to afford the title compound (4.8 mg).

Example 145

N-[(3R,4S)-4-{[4-(5-cyanopyridin-2-yl)phenoxy]methyl}tetrahydro-2H-pyran-3-yl]methanesulfonamide Titled compound was synthesized by similar method to Example 144.

Example 146

N-[(3R,4S)-4-{[4-(4-methyl-1H-pyrazol-1-yl)phenoxy]methyl}tetrahydro-2H-pyran-3-yl]methanesulfonamide Titled compound was synthesized by similar method to Example 144.

Example 147

N-[(3R,4S)-4-{[2-fluoro-4-(4-methyl-1H-pyrazol-1-yl)phenoxy]methyl}tetrahydro-2H-pyran-3-yl]methanesulfonamide Titled compound was synthesized by similar method to Example 144.

Example 148

N-[(3R,4S)-4-({4-[4-(trifluoromethyl)-1H-pyrazol-1-yl]phenoxy}methyl)tetrahydro-2H-pyran-3-yl]methanesulfonamide Titled compound was synthesized by similar method to Example 144.

Example 149

N-[(3R,4S)-4-{[4-(2-methyl-1,3-oxazol-4-yl)phenoxy]methyl}tetrahydro-2H-pyran-3-yl]methanesulfonamide Titled compound was synthesized by similar method to Example 144.

Example 150

N-[(3R,4S)-4-{[4-(5-methyl-1,3-thiazol-2-yl)phenoxy]methyl}tetrahydro-2H-pyran-3-yl]methanesulfonamide Titled compound was synthesized by similar method to Example 144.

Example 151

N-[(3R,4S)-4-{[4-(2-methyl-1,3-thiazol-4-yl)phenoxy]methyl}tetrahydro-2H-pyran-3-yl]methanesulfonamide Titled compound was synthesized by similar method to Example 144.

Example 152

N-[(3R,4S)-4-{[4-(5-fluoropyridin-2-yl)phenoxy]methyl}tetrahydro-2H-pyran-3-yl]ethanesulfonamide Titled compound was synthesized by similar method to Example 144.

Example 153

N-[(3R,4S)-4-{[4-(5-cyanopyridin-2-yl)phenoxy]methyl}tetrahydro-2H-pyran-3-yl]ethanesulfonamide Titled compound was synthesized by similar method to Example 144.

Example 154

N-[(3R,4S)-4-{[4-(4-methyl-1H-pyrazol-1-yl)phenoxy]methyl}tetrahydro-2H-pyran-3-yl]ethanesulfonamide Titled compound was synthesized by similar method to Example 144.

Example 155

N-[(3R,4S)-4-{[4-(4-chloro-1H-pyrazol-1-yl)phenoxy]methyl}tetrahydro-2H-pyran-3-yl]ethanesulfonamide Titled compound was synthesized by similar method to Example 144.

Example 156

N-[(3R,4S)-4-{[2-fluoro-4-(4-methyl-1H-pyrazol-1-yl)phenoxy]methyl}tetrahydro-2H-pyran-3-yl]ethanesulfonamide Titled compound was synthesized by similar method to Example 144.

Example 157

N-[(3R,4S)-4-{[4-(4-chloro-1H-pyrazol-1-yl)-2-fluorophenoxy]methyl}tetrahydro-2H-pyran-3-yl]ethanesulfonamide Titled compound was synthesized by similar method to Example 144.

Example 158

N-[(3R,4S)-4-({4-[4-(trifluoromethyl)-1H-pyrazol-1-yl]phenoxy}methyl)tetrahydro-2H-pyran-3-yl]ethanesulfonamide Titled compound was synthesized by similar method to Example 144.

Example 159

N-[(3R,4S)-4-{[4-(2-methyl-1,3-oxazol-4-yl)phenoxy]methyl}tetrahydro-2H-pyran-3-yl]ethanesulfonamide Titled compound was synthesized by similar method to Example 144.

Example 160

N-[(3R,4S)-4-{[4-(5-methyl-1,3-thiazol-2-yl)phenoxy]methyl}tetrahydro-2H-pyran-3-yl]ethanesulfonamide Titled compound was synthesized by similar method to Example 144.

Example 161

N-[(3R,4S)-4-{[4-(2-methyl-1,3-thiazol-4-yl)phenoxy]methyl}tetrahydro-2H-pyran-3-yl]ethanesulfonamide Titled compound was synthesized by similar method to Example 144.

Example 162

1,5-anhydro-2,3,4-trideoxy-6-O-[4-(5-fluoropyridin-2-yl)phenyl]-4-[(methylsulfonyl)amino]-DL-erythro-hexitol To a solution of tert-butyl ((2SR,3SR)-2-(hydroxymethyl)tetrahydro-2H-pyran-3-yl)carbamate (0.083 g) and 4-(5-fluoropyridin-2-yl)phenol (0.023 g) in DME (1 ml) was added cyanomethylenetributylphosphorane (0.104 g) at room temperature. The mixture was stirred at 100° C. overnight. The reaction mixture was evaporated by blowing away with the air at 60° C. The residue was purified by preparative HPLC (Actus Triart C18, eluted with MeCN/10 mM NH$_4$HCO$_3$ aq. 5:95→100:0). Pure fractions were combined and concentrated by blowing away with the air at 60° C. To the residue was added 2 M HCl/2-propanol (1 ml) and is portioned among three tubes. The mixture was stirred at 50° C. for 1 h and then evaporated by blowing away with the air at 60° C. The solution of MsCl (0.027 g) was added dropwise to a solution of the residue and DBU (0.072 ml) in pyridine (1 ml) at ambient temperature. After stirring for 3 h MsCl (0.027 g) was added to a the reaction mixture. The mixture was stirred at room temperature overnight and then evaporated by blowing away with the air at 60° C. The residue was purified by preparative HPLC (Actus Triart C18, eluted with MeCN/10 mM NH$_4$HCO$_3$ aq. 5:95→100:0). Pure fractions were combined and concentrated by blowing away with the air at 60° C. to afford the title compound (13.6 mg).

Example 163

1,5-anhydro-6-O—[4-(5-chloropyridin-2-yl)phenyl]-2,3,4-trideoxy-4-[(methylsulfonyl)amino]-DL-erythro-hexitol Titled compound was synthesized by similar method to Example 162.

Example 164

1,5-anhydro-6-O-[4-(5-cyanopyridin-2-yl)phenyl]-2,3,4-trideoxy-4-[(methylsulfonyl)amino]-DL-erythro-hexitol Titled compound was synthesized by similar method to Example 162.

Example 165

1,5-anhydro-2,3,4-trideoxy-6-O-[4-(4-methyl-1H-pyrazol-1-yl)phenyl]-4-[(methylsulfonyl)amino]-DL-erythro-hexitol Titled compound was synthesized by similar method to Example 162.

Example 166

1,5-anhydro-6-O-[4-(4-chloro-1H-pyrazol-1-yl)phenyl]-2,3,4-trideoxy-4-[(methylsulfonyl)amino]-DL-erythro-hexitol Titled compound was synthesized by similar method to Example 162.

Example 167

1,5-anhydro-2,3,4-trideoxy-6-O-[2-fluoro-4-(4-methyl-1H-pyrazol-1-yl)phenyl]-4-[(methylsulfonyl)amino]-DL-erythro-hexitol Titled compound was synthesized by similar method to Example 162.

Example 168

1,5-anhydro-6-O-[4-(4-chloro-1H-pyrazol-1-yl)-2-fluorophenyl]-2,3,4-trideoxy-4-[(methylsulfonyl)amino]-DL-erythro-hexitol Titled compound was synthesized by similar method to Example 162.

Example 169

1,5-anhydro-2,3,4-trideoxy-4-[(methylsulfonyl)amino]-6-O-{4-[4-(trifluoromethyl)-1H-pyrazol-1-yl]phenyl}-DL-erythro-hexitol Titled compound was synthesized by similar method to Example 162.

Example 170

1,5-anhydro-2,3,4-trideoxy-6-O-[4-(5-methylisoxazol-3-yl)phenyl]-4-[(methylsulfonyl)amino]-DL-erythro-hexitol Titled compound was synthesized by similar method to Example 162.

Example 171

1,5-anhydro-2,3,4-trideoxy-4-[(methylsulfonyl)amino]-6-O-[4-(5-methyl-1,3-thiazol-2-yl)phenyl]-DL-erythro-hexitol Titled compound was synthesized by similar method to Example 162.

Example 172

1,5-anhydro-2,3,4-trideoxy-4-[(methylsulfonyl)amino]-6-O-[4-(2-methyl-1,3-thiazol-4-yl)phenyl]-DL-erythro-hexitol Titled compound was synthesized by similar method to Example 162.

Example 173

1,5-anhydro-2,3,4-trideoxy-4-[(ethylsulfonyl)amino]-6-O-[4-(5-fluoropyridin-2-yl)phenyl]-DL-erythro-hexitol Titled compound was synthesized by similar method to Example 162.

Example 174

1,5-anhydro-6-O-[4-(5-chloropyridin-2-yl)phenyl]-2,3,4-trideoxy-4-[(ethylsulfonyl)amino]-DL-erythro-hexitol Titled compound was synthesized by similar method to Example 162.

Example 175

1,5-anhydro-6-O-[4-(5-cyanopyridin-2-yl)phenyl]-2,3,4-trideoxy-4-[(ethylsulfonyl)amino]-DL-erythro-hexitol Titled compound was synthesized by similar method to Example 162.

Example 176

1,5-anhydro-2,3,4-trideoxy-4-[(ethylsulfonyl)amino]-6-O-[4-(4-methyl-1H-pyrazol-1-yl)phenyl]-DL-erythro-hexitol Titled compound was synthesized by similar method to Example 162.

Example 177

1,5-anhydro-6-O-[4-(4-chloro-1H-pyrazol-1-yl)phenyl]-2,3,4-trideoxy-4-[(ethylsulfonyl)amino]-DL-erythro-hexitol Titled compound was synthesized by similar method to Example 162.

Example 178

1,5-anhydro-2,3,4-trideoxy-4-[(ethylsulfonyl)amino]-6-O-[2-fluoro-4-(4-methyl-1H-pyrazol-1-yl)phenyl]-DL-erythro-hexitol Titled compound was synthesized by similar method to Example 162.

Example 179

1,5-anhydro-6-O-[4-(4-chloro-1H-pyrazol-1-yl)-2-fluorophenyl]-2,3,4-trideoxy-4-[(ethylsulfonyl)amino]-DL-erythro-hexitol Titled compound was synthesized by similar method to Example 162.

Example 180

1,5-anhydro-2,3,4-trideoxy-4-[(ethylsulfonyl)amino]-6-O-[4-(5-methylisoxazol-3-yl)phenyl]-DL-erythro-hexitol Titled compound was synthesized by similar method to Example 162.

Example 181

1,5-anhydro-2,3,4-trideoxy-4-[(ethylsulfonyl)amino]-6-O-[4-(5-methyl-1,3-thiazol-2-yl)phenyl]-DL-erythro-hexitol To a solution of tert-butyl ((2SR,3SR)-2-(hydroxymethyl)tetrahydro-2H-pyran-3-yl)carbamate (0.083 g) and 4-(5-methyl-1,3-thiazol-2-yl)phenol (0.083 g) in DME (1 ml) was added cyanomethylenetributylphosphorane (0.104 g) at room temperature. The mixture was stirred at 100° C. overnight. The reaction mixture was evaporated by blowing away with the air at 60° C. The residue was purified by preparative HPLC (Actus Triart C18, eluted with MeCN/10 mM $NH_4HCO_3$ aq. 5:95→100:0). Pure fractions were combined and concentrated by blowing away with the air at 60° C. To the residue was added 2 M HCl/2-propanol (1 ml) and portioned among three tubes. The mixture was stirred at 50° C. for 1 h and then evaporated by blowing away with the air at 60° C. The solution of ethanesulfonyl chloride (0.031 g) was added dropwise to a solution of the residue and DBU (0.072 ml) in pyridine (1 ml) at ambient temperature. After stirring for 3 h ethanesulfonyl chloride (0.031 g) was added to the reaction mixture. The mixture was stirred at room temperature overnight and then evaporated by blowing away with the air at 60° C. The residue was purified by preparative HPLC (Actus Triart C18, eluted with MeCN/10 mM $NH_4HCO_3$ aq. 5:95→100:0). Pure fractions were combined and concentrated by blowing away with the air at 60° C. to afford the title compound (11.9 mg).

MS (API+), found: 397.2 (M+1)

Example 182

1,5-anhydro-2,3,4-trideoxy-4-[(ethylsulfonyl)amino]-6-O-[4-(2-methyl-1,3-thiazol-4-yl)phenyl]-DL-erythro-hexitol Titled compound was synthesized by similar method to Example 181.

Example 183

1,5-anhydro-4-[(cyclopropylsulfonyl)amino]-2,3,4-trideoxy-6-O-[4-(5-fluoropyridin-2-yl)phenyl]-DL-erythro-hexitol Titled compound was synthesized by similar method to Example 181.

Example 184

1,5-anhydro-6-O-[4-(5-chloropyridin-2-yl)phenyl]-4-[(cyclopropylsulfonyl)amino]-2,3,4-trideoxy-DL-erythro-hexitol Titled compound was synthesized by similar method to Example 181.

Example 185

1,5-anhydro-6-O-[4-(5-cyanopyridin-2-yl)phenyl]-4-[(cyclopropylsulfonyl)amino]-2,3,4-trideoxy-DL-erythro-hexitol Titled compound was synthesized by similar method to Example 181.

Example 186

1,5-anhydro-4-[(cyclopropylsulfonyl)amino]-2,3,4-trideoxy-6-O-[4-(4-methyl-1H-pyrazol-1-yl)phenyl]-DL-erythro-hexitol Titled compound was synthesized by similar method to Example 181.

Example 187

1,5-anhydro-6-O-[4-(4-chloro-1H-pyrazol-1-yl)phenyl]-4-[(cyclopropylsulfonyl)amino]-2,3,4-trideoxy-DL-erythro-hexitol Titled compound was synthesized by similar method to Example 181.

Example 188

1,5-anhydro-4-[(cyclopropylsulfonyl)amino]-2,3,4-trideoxy-6-O-[2-fluoro-4-(4-methyl-1H-pyrazol-1-yl)phenyl]-DL-erythro-hexitol Titled compound was synthesized by similar method to Example 181.

Example 189

1,5-anhydro-6-O-[4-(4-chloro-1H-pyrazol-1-yl)-2-fluorophenyl]-4-[(cyclopropylsulfonyl)amino]-2,3,4-trideoxy-DL-erythro-hexitol Titled compound was synthesized by similar method to Example 181.

Example 190

1,5-anhydro-4-[(cyclopropylsulfonyl)amino]-2,3,4-trideoxy-6-O-[4-(5-methylisoxazol-3-yl)phenyl]-DL-erythro-hexitol Titled compound was synthesized by similar method to Example 181.

Example 191

1,5-anhydro-4-[(cyclopropylsulfonyl)amino]-2,3,4-trideoxy-6-O-[4-(2-methyl-1,3-oxazol-4-yl)phenyl]-DL-erythro-hexitol Titled compound was synthesized by similar method to Example 181.

Example 192

1,5-anhydro-4-[(cyclopropylsulfonyl)amino]-2,3,4-trideoxy-6-O-[4-(5-methyl-1,3-thiazol-2-yl)phenyl]-DL-erythro-hexitol Titled compound was synthesized by similar method to Example 181.

Example 193

1,5-anhydro-4-[(cyclopropylsulfonyl)amino]-2,3,4-trideoxy-6-O-[4-(2-methyl-1,3-thiazol-4-yl)phenyl]-DL-erythro-hexitol Titled compound was synthesized by similar method to Example 181.

Example 194

N-[(1S,2S)-4,4-difluoro-2-{[4-(5-methyl-1,3-thiazol-2-yl)phenoxy]methyl}cyclohexyl]methanesulfonamide To a solution of tert-butyl ((1S,2S)-4,4-difluoro-2-(hydroxymethyl)cyclohexyl)carbamate (0.096 g) and 4-(5-methylthiazol-2-yl)phenol (0.083 g) in DME (1 ml) was added cyanomethylenetributylphosphorane (0.104 g) at room temperature. The mixture was stirred at 100° C. 3 h. The reaction mixture was poured into IPE (3 mL) and H$_2$O (1 mL), and stirred for 5 min. The organic layer was evaporated by blowing away with the air at 60° C. The residue was purified by preparative HPLC (Actus Triart C18, eluted with MeCN/10 mM NH$_4$HCO$_3$ aq. 10:90→100:0). Pure fractions were combined and concentrated by blowing away with the air at 60° C. To the residue was added 0.36 M HCl/MeOH (1 ml). The mixture was heated at 50° C. for 1 h and then evaporated by blowing away with the air at 60° C. The residue was purified by preparative HPLC (Actus Triart C18, eluted with MeCN/10 mM NH$_4$HCO$_3$ aq. 5:95→100:0). Pure fractions were combined and concentrated by blowing away with the air at 60° C. to afford product. MsCl (0.055 g) was added dropwise to a solution of residue and DBU (0.073 g) in THF(dry) (1 ml) at room temperature. The mixture was stirred at room temperature for 3 h and then evaporated by blowing away with the air at 60° C. The residue was purified by preparative HPLC (Actus Triart C18, eluted with MeCN/10 mM NH$_4$HCO$_3$ aq. 5:95→100:0). Pure fractions were combined and concentrated by blowing away with the air at 60° C. to afford the title compound (17.3 mg).

Example 195

N-[(1S,2S)-2-{[(2'-cyano-4'-fluorobiphenyl-4-yl)oxy]methyl}-4,4-difluorocyclohexyl]methanesulfonamide A) 4-fluoro-4'-hydroxy-[1,1'-biphenyl]-2-carbonitrile A mixture of (4-hydroxyphenyl)boronic acid (2.069 g), 2-bromo-5-fluorobenzonitrile (2.5 g), Na$_2$CO$_3$ (3.97 g) and Pd(Ph$_3$P)$_4$ (0.433 g) in DME (50 ml) and water (10 ml) was stirred at 80° C. under N$_2$ overnight. It was added silica gel and concentrated in vacuo. The residue was purified by column chromatography (silica gel, eluted with EtOAc in hexane) to give the title compound (1.951 g) as a pale yellow solid.

MS (API+), found: 212.0 (M−1)

B) N-[(1S,2S)-2-{[(2'-cyano-4'-fluorobiphenyl-4-yl)oxy]methyl}-4,4-difluorocyclohexyl]methanesulfonamide Titled compound was synthesized by similar method to Example 194.

Example 196

N-[(1S,2S)-4,4-difluoro-2-{[4-(piperidin-1-ylcarbonyl)phenoxy]methyl}cyclohexyl]methanesulfonamide A) (4-(benzyloxy)phenyl)(piperidin-1-yl)methanone A mixture of 4-(benzyloxy)benzoic acid (3.5 g), piperidine (2.61 g), HOBt (Anhydrous) (2.486 g) and WSC(HCl) (3.53 g) in DMF (dry) (50 ml) was stirred at room temperature overnight. The mixture was poured into sat. NaHCO$_3$ aq. and extracted with EtOAc. The organic layer was separated, washed with 1 M NaOH aq., 1 M HCl, and brine, dried over MgSO$_4$ and concentrated in vacuo to give the title compound (4.83 g) as a white solid.

MS (API+), found: 296.1 (M+1)

B) (4-hydroxyphenyl)(piperidin-1-yl)methanone

A mixture of (4-(benzyloxy)phenyl)(piperidin-1-yl)methanone (4.8 g) and 10% Pd/C (500 mg) in EtOH (100 ml) was hydrogenated under balloon pressure at room temperature for 3 h. The catalyst was removed by filtration and the filtrate was concentrated in vacuo to give the title compound (2320 mg) as white solid.

MS (API+), found: 206.1 (M+1)

C) N-[(1S,2S)-4,4-difluoro-2-{[4-(piperidin-1-ylcarbonyl)phenoxy]methyl}cyclohexyl]methanesulfonamide Titled compound was synthesized by similar method to Example 194.

Example 197

4-({(1S,2S)-5,5-difluoro-2-[(methylsulfonyl)amino]cyclohexyl}methoxy)-N,N-diethylbenzamide Titled compound was synthesized by similar method to Example 196.

Example 198

N-[(1S,2S)-4,4-difluoro-2-{[4-(5-methyl-1,3-thiazol-2-yl)phenoxy]methyl}cyclohexyl]ethanesulfonamide Titled compound was synthesized by similar method to Example 194.

Example 199

N-[(1S,2S)-2-{[(2'-cyano-4'-fluorobiphenyl-4-yl)oxy]methyl}-4,4-difluorocyclohexyl]ethanesulfonamide Titled compound was synthesized by similar method to Example 194.

Example 200

N-[(1S,2S)-4,4-difluoro-2-{[4-(piperidin-1-ylcarbonyl)phenoxy]methyl}cyclohexyl]ethanesulfonamide Titled compound was synthesized by similar method to Example 194.

Example 201

N,N-diethyl-4-({(1S,2S)-2-[(ethylsulfonyl)amino]-5,5-difluorocyclohexyl}methoxy)benzamide Titled compound was synthesized by similar method to Example 194.

Example 202

N-[(1S,2S)-4,4-difluoro-2-{[4-(5-methyl-1,3-thiazol-2-yl)phenoxy]methyl}cyclohexyl]cyclopropanesulfonamide Titled compound was synthesized by similar method to Example 194.

Example 203

N-[(1S,2S)-2-{[(2'-cyano-4'-fluorobiphenyl-4-yl)oxy]methyl}-4,4-difluorocyclohexyl]cyclopropanesulfonamide Titled compound was synthesized by similar method to Example 194.

Example 204

N-[(1S,2S)-4,4-difluoro-2-{[4-(piperidin-1-ylcarbonyl)phenoxy]methyl}cyclohexyl]cyclopropanesulfonamide Titled compound was synthesized by similar method to Example 194.

Example 205

N-[(3R,4S)-4-{[4-(5-chloropyridin-2-yl)phenoxy]methyl}tetrahydro-2H-pyran-3-yl]methanesulfonamide The solution of tert-butyl ((3R,4S)-4-(hydroxymethyl)tetrahydro-2H-pyran-3-yl)carbamate (0.028 g) in THF (2 ml) was added a suspension of 4-(5-chloropyridin-2-yl)phenol (0.025 g), (E)-bis(2-methoxyethyl)diazene-1,2-dicarboxylate (0.031 g) and triphenylphosphine, polystyrene-supported (0.071 g, 2.2 mmol/g) in THF (2 ml). The mixture was stirred at room temperature for 5 h. (E)-bis(2-methoxyethyl)diazene-1,2-dicarboxylate (0.031 g) and triphenylphosphine, polystyrene-supported (0.034 g, 2.2 mmol/g)

were added to the reaction mixture. The mixture was stirred at room temperature overnight. The reaction mixture was poured into EtOAc (3 ml) and 2% NaHCO$_3$ aq. (1 ml), and stirred for 5 min. The organic layer was filtered on Top-Phase Separation Filter Tube, and the filtrate was evaporated by blowing away with the air at 60° C. The residue was purified by preparative HPLC (Actus Triart C18, eluted with MeCN/10 mM NH$_4$HCO$_3$ aq. 10:90→100:0). Pure fractions were combined and concentrated by blowing away with the air at 60° C. Current produced intermediate was dissolved in 3.2 M HCl/MeOH (1 ml) and the solution was stirred at 50° C. for 10 min. The solvent was removed by blowing away with the air at 60° C. The solution of MsCl (0.027 g) in THF (1 ml) was added dropwise to a solution of the residue and triethylamine (0.036 g) in THF (1 ml) with stirring. The mixture was stirred at room temperature for 5 h and then concentrated by blowing away with the air at 60° C. The residue was purified by preparative HPLC (Actus Triart C18, eluted with MeCN/10 mM NH$_4$HCO$_3$ aq. 5:95→100:0). Pure fractions were combined and concentrated by blowing away with the air at 60° C. to afford the title compound (3.8 mg).

MS (API+), found: 397.2 (M+1)

Example 206N-[(3R,4S)-4-{[4-(4-chloro-1H-pyrazol-1-yl)phenoxy]methyl}tetrahydro-2H-pyran-3-yl]methanesulfonamide The solution of tert-butyl ((3R,4S)-4-(hydroxymethyl)tetrahydro-2H-pyran-3-yl)carbamate (0.028 g) in THF (2 ml) was added a suspension of 4-(4-chloro-1H-pyrazol-1-yl)phenol (0.023 g), (E)-bis(2-methoxyethyl)diazene-1,2-dicarboxylate (0.031 g) and triphenylphosphine, polystyrene-supported (0.071 g, 2.2 mmol/g) in THF (2 ml). The mixture was stirred at room temperature for 5 h. (E)-bis(2-methoxyethyl)diazene-1,2-dicarboxylate (0.031 g) and triphenylphosphine, polystyrene-supported (0.034 g, 2.2 mmol/g) were added to the reaction mixture. The mixture was stirred at room temperature overnight. The reaction mixture was poured into EtOAc (3 ml) and 2% NaHCO$_3$ aq. (1 ml), and stirred for 5 min. The organic layer was filtered on Top-Phase Separation Filter Tube, and the filtrate was evaporated by blowing away with the air at 60° C. The residue was purified by preparative HPLC (Actus Triart C18, eluted with MeCN/10 mM NH$_4$HCO$_3$ aq. 10:90→100:0). Pure fractions were combined and concentrated by blowing away with the air at 60° C. Current produced intermediate was dissolved in 3.2 M HCl/MeOH (1 ml) and the solution was stirred at 50° C. for 10 min. The solvent was removed by blowing away with the air at 60° C. The solution of MsCl (0.027 g) in THF (1 ml) was added dropwise to a solution of the residue and triethylamine (0.036 g) in THF (1 ml) with stirring. The mixture was stirred at room temperature for 5 h and then concentrated by blowing away with the air at 60° C. The residue was purified by preparative HPLC (Actus Triart. C18, eluted with MeCN/10 mM NH$_4$HCO$_3$ aq. 5:95→100:0). Pure fractions were combined and concentrated by blowing away with the air at 60° C. to afford the title compound (6.5 mg).

MS (API+), found: 386.2 (M+1)

Example 207N-[(3R,4S)-4-{[4-(4-chloro-1H-pyrazol-1-yl)-2-fluorophenoxy]methyl}tetrahydro-2H-pyran-3-yl]methanesulfonamide The solution of tert-butyl ((3R,4S)-4-(hydroxymethyl)tetrahydro-2H-pyran-3-yl)carbamate (0.028 g) in THF (2 ml) was added a suspension of 4-(4-chloro-1H-pyrazol-1-yl)-2-fluorophenol (0.026 g), (E)-bis(2-methoxyethyl)diazene-1,2-dicarboxylate (0.031 g) and triphenylphosphine, polystyrene-supported (0.071 g, 2.2 mmol/g) in THF (2 ml). The mixture was stirred at room temperature for 5 h. The progress of the reaction was followed by LC-MS analysis. The reaction was not completed. (E)-bis(2-methoxyethyl)diazene-1,2-dicarboxylate (0.031 g) and triphenylphosphine, polystyrene-supported (0.034 g, 2.2 mmol/g) were added to the reaction mixture. The mixture was stirred at room temperature overnight. The reaction mixture was poured into EtOAc (3 ml) and 2% NaHCO$_3$ aq. (1 ml), and stirred for 5 min. The organic layer was filtered on Top-Phase Separation Filter Tube, and the filtrate was evaporated by blowing away with the air at 60° C. The residue was purified by preparative HPLC (Actus Triart C18, eluted with MeCN/10 mM NH$_4$HCO$_3$ aq. 10:90→100:0). Pure fractions were combined and concentrated by blowing away with the air at 60° C. Current produced intermediate was dissolved in 3.2 M HCl/MeOH (1 ml) and the solution was stirred at 50° C. for 10 min. The solvent was removed by blowing away with the air at 60° C. The solution of MsCl (0.027 g) in THF (1 ml) was added dropwise to a solution of the residue and triethylamine (0.036 g) in THF (1 ml) with stirring. The mixture was stirred at room temperature for 5 h and then concentrated by blowing away with the air at 60° C. The residue was purified by preparative HPLC (Actus Triart C18, eluted with MeCN/10 mM NH$_4$HCO$_3$ aq. 5:95→100:0). Pure fractions were combined and concentrated by blowing away with the air at 60° C. to afford the title compound (7.5 mg).

MS (API+), found: 404.2 (M+1)

Example 208N-[(3R,4S)-4-{[4-(5-methylisoxazol-3-yl)phenoxy]methyl}tetrahydro-2H-pyran-3-yl]methanesulfonamide Titled compound was synthesized by similar method to Example 207.

Example 209N-[(3R,4S)-4-{[4-(5-chloropyridin-2-yl)phenoxy]methyl}tetrahydro-2H-pyran-3-yl]ethanesulfonamide The solution of tert-butyl ((3R,4S)-4-(hydroxymethyl)tetrahydro-2H-pyran-3-yl)carbamate (0.028 g) in THF (2 ml) was added a suspension of 4-(5-chloropyridin-2-yl)phenol (0.025 g), (E)-bis(2-methoxyethyl)diazene-1,2-dicarboxylate (0.031 g) and triphenylphosphine, polystyrene-supported (0.071 g, 2.2 mmol/g) in THF (2 ml). The mixture was stirred at room temperature for 5 h. (E)-bis(2-methoxyethyl)diazene-1,2-dicarboxylate (0.031 g) and triphenylphosphine, polystyrene-supported (0.034 g, 2.2 mmol/g) were added to the reaction mixture. The mixture was stirred at room temperature overnight. The reaction mixture was poured into EtOAc (3 ml) and 2% NaHCO$_3$ aq. (1 ml), and stirred for 5 min. The organic layer was filtered on Top-Phase Separation Filter Tube, and the filtrate was evaporated by blowing away with the air at 60° C. The residue was purified by preparative HPLC (Actus Triart C18, eluted with MeCN/10 mM NH$_4$HCO$_3$ aq. 10:90→100:0). Pure fractions were combined and concentrated by blowing away with the air at 60° C. Current produced intermediate was dissolved in 3.2 M HCl/MeOH (1 ml) and the solution was stirred at 50° C. for 10 min. The solvent was removed by blowing away with the air at 60° C. The solution of ethanesulfonyl chloride (0.031 g) in THF (1 ml) was added dropwise to a solution of the residue and triethylamine (0.036 g) in THF (1 ml) with stirring. The mixture was stirred at room temperature for 5 h and then concentrated by blowing away with the air at 60° C. The residue was purified by preparative HPLC (Actus Triart C18, eluted with MeCN/10 mM NH$_4$HCO$_3$ aq. 5:95→100:0). Pure fractions were combined and concentrated by blowing away with the air at 60° C. to afford the title compound (3.8 mg).
MS (API+), found: 411.2 (M+1)

Example 210

N-[(3R,4S)-4-{[4-(5-methylisoxazol-3-yl)phenoxy]methyl}tetrahydro-2H-pyran-3-yl]ethanesulfonamide Titled compound was synthesized by similar method to Example 209.

Example 211

1,5-anhydro-2,3,4-trideoxy-6-O-[4-(2-methyl-1,3-oxazol-4-yl)phenyl]-4-[(methylsulfonyl)amino]-DL-erythro-hexitol Titled compound was synthesized by similar method to Example 209.

Example 212

1,5-anhydro-2,3,4-trideoxy-4-[(ethylsulfonyl)amino]-6-O-[4-(2-methyl-1,3-oxazol-4-yl)phenyl]-DL-erythro-hexitol Titled compound was synthesized by similar method to Example 209.

Example 213

N-[(1S,2S)-2-{[4-(4-cyano-1H-pyrazol-1-yl)phenoxy]methyl}-4,4-difluorocyclohexyl]methanesulfonamide A) 4-bromo-1-(4-methoxyphenyl)-1H-pyrazole A mixture of 1-bromopyrrolidine-2,5-dione (19.0 g) and 1-(4-methoxyphenyl)-1H-pyrazole (17.7 g) in THF (300 ml) was stirred at room temperature overnight. It was added SiO$_2$ and concentrated in vacuo. The residue was purified by column chromatography (silica gel, eluted with EtOAc in hexane) to give the title compound (24.2 g) as a white solid.
MS (API+), found: 253.0 (M+1)

B) 1-(4-methoxyphenyl)-1H-pyrazole-4-carbonitrile

A mixture of Pd$_2$(dba)$_3$ (0.478 g), DPPF (0.578 g), dicyanozinc (1.23 g) and 4-bromo-1-(4-methoxyphenyl)-1H-pyrazole (2.64 g) in DMF (40 ml) was stirred at 120° C. under N$_2$ for 4 days. After cooling to room temperature, the mixture was added water and extracted with EtOAc. The organic layer was separated, washed with brine, dried over MgSO$_4$ and concentrated in vacuo. The residue was purified by column chromatography (silica gel, eluted with EtOAc in hexane) to give the title compound (1.57 g) as a pale yellow solid.
MS (API+), found: 200.1 (M+1)

C) 1-(4-hydroxyphenyl)-1H-pyrazole-4-carbonitrile

A mixture of 1-(4-methoxyphenyl)-1H-pyrazole-4-carbonitrile (510 mg), aluminum trichloride (2.05 g) and dodecane-1-thiol (3.68 ml) in toluene (20 ml) was stirred at 0° C. for 1 h. The mixture was quenched with 1 M HCl aq. and extracted with EtOAc. The organic layer was separated, washed with water and brine, dried over Na$_2$SO$_4$ and concentrated in vacuo. The residue was purified by column chromatography (NH silica gel, eluted with EtOAc in hexane) to give the title compound (372 mg) as a white solid.
MS (API+), found: 186.0 (M+1)

D) N-[(1S,2S)-2-{[4-(4-cyano-1H-pyrazol-1-yl)phenoxy]methyl}-4,4-difluorocyclohexyl]methanesulfonamide Titled compound was synthesized by similar method to Example 209.

Example 214

N-[(1S,2S)-2-{[4-(4-cyano-1H-pyrazol-1-yl)-2-fluorophenoxy]methyl}-4,4-difluorocyclohexyl]methanesulfonamide A) 1-(3-fluoro-4-methoxyphenyl)-1H-pyrazole-4-carbonitrile A mixture of 4-bromo-1-(3-fluoro-4-methoxyphenyl)-1H-pyrazole (4.99 g), DPPF (1.020 g, 1.84 mmol), dicyanozinc (2.161 g), and Pd$_2$(dba)$_3$ (0.843 g) in DMF (180 ml) was stirred at 120° C. under N$_2$ for 45 h. After cooling to rt, the mixture was added SiO$_2$, concentrated in vacuo, and purified by column chromatography (silica gel, eluted with EtOAc in hexane) then crystallization from EtOAc-IPE to give the title compound (2.61 g) as a white solid.
MS (API+), found: 218.1 (M+1)

B) 1-(3-fluoro-4-hydroxyphenyl)-1H-pyrazole-4-carbonitrile

To a mixture of 1-(3-fluoro-4-methoxyphenyl)-1H-pyrazole-4-carbonitrile (2.00 g) and dodecane-1-thiol (8.82 ml) in toluene (80 ml) was added aluminum trichloride (14.7 g) at 0° C. The mixture was stirred at 0° C. to rt overnight. The mixture was added 1 M HCl aq. at 0° C., and stirred at 0° C. for 15 min. The precipitate was collected and crystallized from EtOAc-IPE to give the title compound (1.47 g) as a pale yellow solid.
MS (API+), found: 204.1 (M+1)

C) N-[(1S,2S)-2-{[4-(4-cyano-1H-pyrazol-1-yl)-2-fluorophenoxy]methyl}-4,4-difluorocyclohexyl]methanesulfonamide Titled compound was synthesized by similar method to Example 209.

Example 215

N-[(1S,2S)-2-{[4-(5-cyano-3-fluoropyridin-2-yl)phenoxy]methyl}-4,4-difluorocyclohexyl]methanesulfonamide A) 5-bromo-3-fluoro-2-(4-methoxyphenyl)pyridine A mixture of 2,5-dibromo-3-fluoropyridine (6.7 g), (4-methoxyphenyl)boronic acid (4.79 g), Pd(Ph$_3$P)$_4$ (0.911 g) and Na$_2$CO$_3$ (5.57 g) in DME and water was stirred at 80° C. under N$_2$ overnight. It was added NH silica gel and concentrated in vacuo. The residue was purified by column chromatography (silica gel, eluted with EtOAc in hexane) to give the title compound (4.55 g) as a white solid.

MS (API+), found: 282.0 (M+1)

B) 5-fluoro-6-(4-methoxyphenyl)nicotinonitrile

A mixture of 5-bromo-3-fluoro-2-(4-methoxyphenyl)pyridine (4.5 g), DPPF (0.531 g), dicyanozinc (1.87 g) and Pd$_2$(dba)$_3$ (0.438 g) in DMF (75 ml) was stirred at 100° C. under N$_2$ for 3 h. The mixture was poured into brine and extracted with EtOAc. The organic layer was separated, washed with brine, dried over MgSO$_4$ and concentrated in vacuo. The residue was purified by column chromatography (silica gel, eluted with EtOAc in hexane) to give the title compound (3.29 g) as a white solid.

MS (API+), found: 229.1 (M+1)

C) S-dodecyl 5-fluoro-6-(4-hydroxyphenyl)pyridine-3-carbothioate

A mixture of 5-fluoro-6-(4-methoxyphenyl)nicotinonitrile (3.28 g), AlCl$_3$ (9.58 g) and 1-dodecanethiol (14.5 g) in toluene (150 ml) was stirred at room temperature for 3 h. The mixture was neutralized with 0.1 M HCl at room temperature and extracted with EtOAc/EtOH. The organic layer was separated, washed with water and brine, dried over MgSO$_4$ and concentrated in vacuo. The residue was washed with IPE to give the title compound (4.24 g) as a yellow solid.

$^1$H NMR (300 MHz, DMSO-d$_6$) δ 0.75-0.91 (3H, m), 1.13-1.48 (18H, m), 1.63 (2H, quin, J=7.2 Hz), 3.11 (2H, t, J=7.2 Hz), 6.86-6.99 (2H, m), 7.92 (2H, dd, J=8.7, 1.1 Hz), 8.12 (1H, dd, J=11.7, 1.9 Hz), 8.95 (1H, t, J=1.7 Hz), 10.11 (1H, s).

D) 5-fluoro-6-(4-hydroxyphenyl)nicotinamide

A mixture of S-dodecyl 5-fluoro-6-(4-hydroxyphenyl)pyridine-3-carbothioate (2 g) and 8 M ammonia (10 ml, MeOH solution) in EtOH (50 ml) was stirred at 70° C. overnight. A mixture of S-dodecyl 5-fluoro-6-(4-hydroxyphenyl)pyridine-3-carbothioate (1.8 g) and 8 M ammonia (8 ml, MeOH solution) in EtOH (50 ml) was stirred at 70° C. overnight. Each mixture was combined. The mixture was poured into 1 M HCl aq. and extracted with EtOAc. The organic layer was separated, washed with brine, dried over MgSO$_4$ and concentrated in vacuo. The residue was purified by column chromatography (silica gel, eluted with EtOAc in hexane) to give the title compound (1.75 g) as a white solid.

MS (API+), found: 233.0 (M+1)

E) 5-fluoro-6-(4-hydroxyphenyl)nicotinonitrile

To a mixture of 5-fluoro-6-(4-hydroxyphenyl)nicotinamide (185 mg) in pyridine (10 ml) was added TFAA (0.563 ml) at 0° C. The mixture was stirred at room temperature for 2 h. The mixture was poured into 1 M HCl aq. and extracted with EtOAc. The organic layer was separated, washed with 1 M HCl, sat. NaHCO$_3$ aq. and brine, dried over MgSO$_4$ and concentrated in vacuo. The residue was purified by column chromatography (silica gel, eluted with EtOAc in hexane) to give the title compound (136 mg) as a white solid.

MS (API+), found: 213.0 (M−1)

F) N-[(1S,2S)-2-{[4-(5-cyano-3-fluoropyridin-2-yl)phenoxy]methyl}-4,4-difluorocyclohexyl]methanesulfonamide To a solution of tert-butyl ((1S,2S)-4,4-difluoro-2-(hydroxymethyl)cyclohexyl)carbamate (0.096 g) and 5-fluoro-6-(4-hydroxyphenyl)nicotinonitrile (0.093 g) in DME (1 ml) was added cyanomethylenetributylphosphorane (0.104 g) at room temperature. The mixture was stirred at 100° C. for 3 h. The reaction mixture was poured into IPE (3 ml) and H$_2$O (1 ml), and stirred for 5 min. The organic layer was evaporated by blowing away with the air at 60° C. The residue was purified by preparative HPLC (Actus Triart C18, eluted with MeCN/10 mM NH$_4$HCO$_3$ aq. 10:90→100:0). Pure fractions were combined and concentrated by blowing away with the air at 60° C. To the residue was added 0.36 M HCl/MeOH (1 ml). The mixture was heated at 50° C. for 1 h and then evaporated by blowing away with the air at 60° C. The residue was purified by preparative HPLC (Actus Triart C18, eluted with MeCN/10 mM NH$_4$HCO$_3$ aq. 5:95→100:0). Pure fractions were combined and concentrated by blowing away with the air at 60° C. to afford product. MsCl (0.055 g) was added dropwise to a solution of residue and DBU (0.073 g) in THF (1 ml) at room temperature. The mixture was stirred at room temperature for 3 h and then evaporated by blowing away with the air at 60° C. The residue was purified by preparative HPLC (Actus Triart C18, eluted with MeCN/10 mM NH$_4$HCO$_3$ aq. 5:95→100:0). Pure fractions were combined and concentrated by blowing away with the air at 60° C. to afford the title compound (9.5 mg).

MS (API+), found: 440.2 (M+1)

Example 216

N-[(1S,2S)-4,4-difluoro-2-{[4-(5-methylisoxazol-3-yl)phenoxy]methyl}cyclohexyl]methanesulfonamide A) 4-(5-methylisoxazol-3-yl)phenol To a mixture of 4-methoxybenzaldehyde oxime (5 g) in DMF (49.4 ml) was added NCS (6.63 g) at 0° C. The mixture was stirred at room temperature for 1 h. Et$_3$N (6.92 ml) and prop-1-en-2-yl acetate (8.28 g) was added successively to the mixture at 0° C. The mixture was stirred at room temperature overnight. The mixture was poured into brine and extracted with EtOAc. The organic layer was separated, washed with brine, dried over MgSO$_4$ and concentrated in vacuo. The residue was purified by column chromatography (silica gel, eluted with EtOAc in hexane). The residue was crystallized from EtOAc-hexane to give 3,4-bis(4-methoxyphenyl)-1,2,5-oxadiazole (0.186 g) as a white solid. The mother liqur was concentrated in vacuo to give 3-(4-methoxyphenyl)-5-methylisoxazole (1.09 g) as a white solid. A mixture of 1-dodecanethiol (5.78 g), AlCl$_3$ (3.81 g) and 3-(4-methoxyphenyl)-5-methylisoxazole (1.08 g) in toluene (50 ml) was stirred at 0° C. for 1 h. The mixture was quenched with 1 M HCl aq. at 0° C. and extracted with EtOAc. The organic layer was separated, washed with brine, dried over MgSO$_4$ and concentrated in vacuo. The residue was purified by column chromatography (silica gel, eluted with EtOAc in hexane) to give the title compound (0.648 g) as a white solid.

MS (API+), found: 176.1 (M+1)

B) N-[(1S,2S)-4,4-difluoro-2-{[4-(5-methylisoxazol-3-yl)phenoxy]methyl}cyclohexyl]methanesulfonamide Titled compound was synthesized by similar method to Example 215.

Example 217

N-[(1S,2S)-4,4-difluoro-2-{[3-fluoro-4-(5-methylisoxazol-3-yl)phenoxy]methyl}cyclohexyl]methanesulfonamide Titled compound was synthesized by similar method to Example 215.

Example 218

N-[(1S,2S)-4,4-difluoro-2-{[2-fluoro-4-(5-methylisoxazol-3-yl)phenoxy]methyl}cyclohexyl]methanesulfonamide

A) 3-fluoro-4-methoxybenzaldehyde oxime

A mixture of 3-fluoro-4-methoxybenzaldehyde (8 g), sodium acetate (6.39 g) and hydroxylamine hydrochloride (4.33 g) in EtOH (200 ml) was stirred at 80° C. overnight. The mixture was poured into brine and extracted with EtOAc. The organic layer was separated, washed with brine, dried over MgSO$_4$ and concentrated in vacuo to give the title compound (8.68 g) as a pale yellow solid.

MS (API+), found: 180.1 (M+1)

B) 3-(3-fluoro-4-methoxyphenyl)-5-methylisoxazole

To a mixture of 3-fluoro-4-methoxybenzaldehyde oxime (14 g) in DMF (200 ml) was added a mixture of NCS (13.3 g) at 0° C. The mixture was stirred at room temperature for 2 h. prop-1-en-2-yl acetate (24 g) and Et$_3$N were added to the solution dropwise at 0° C. The mixture was stirred at room temperature for 2 days. The mixture was poured into brine and extracted with EtOAc. The organic layer was separated, washed with brine, dried over MgSO$_4$ and concentrated in vacuo. The residue was purified by column chromatography (silica gel, eluted with EtOAc in hexane) to give impure 3-(3-fluoro-4-methoxyphenyl)-5-methylisoxazole as orange oil. The residue was triturated from IPE-hexane to give by-product. The mother liquor was concentrated to give the title compound (5.26 g).

MS (API+), found: 208.1 (M+1)

C) 2-fluoro-4-(5-methylisoxazol-3-yl)phenol

A mixture of 3-(3-fluoro-4-methoxyphenyl)-5-methylisoxazole (5.2 g), dodecane-1-thiol (15.2 g) and AlCl$_3$ (10.0 g) in toluene (100 ml) was stirred at room temperature for 2 h. The mixture was quenched with 1 M HCl at 0° C. and extracted with EtOAc. The organic layer was separated, washed with water and brine, dried over MgSO$_4$ and concentrated in vacuo. The residue was purified by column chromatography (silica gel, eluted with EtOAc in hexane) to a pale yellow oil. It was triturated from hexane-IPE to give the title compound (1.63 g) as a white solid.

MS (API+), found: 194.1 (M+1)

D) N-[(1S,2S)-4,4-difluoro-2-{[2-fluoro-4-(5-methylisoxazol-3-yl)phenoxy]methyl}cyclohexyl]methanesulfonamide Titled compound was synthesized by similar method to Example 215.

Example 219

N-[(1S,2S)-2-{[4-(4-cyano-1H-pyrazol-1-yl)phenoxy]methyl}-4,4-difluorocyclohexyl]ethanesulfonamide Titled compound was synthesized by similar method to Example 215.

Example 220

N-[(1S,2S)-2-{[4-(4-cyano-1H-pyrazol-1-yl)-2-fluorophenoxy]methyl}-4,4-difluorocyclohexyl]ethanesulfonamide Titled compound was synthesized by similar method to Example 215.

Example 221

N-[(1S,2S)-2-{[4-(5-cyanopyridin-2-yl)phenoxy]methyl}-4,4-difluorocyclohexyl]ethanesulfonamide Titled compound was synthesized by similar method to Example 215.

Example 222

N-[(1S,2S)-2-{[4-(5-cyano-3-fluoropyridin-2-yl)phenoxy]methyl}-4,4-difluorocyclohexyl]ethanesulfonamide To a solution of tert-butyl ((1S,2S)-4,4-difluoro-2-(hydroxymethyl)cyclohexyl)carbamate (0.096 g) and 5-fluoro-6-(4-hydroxyphenyl)nicotinonitrile (0.093 g) in DME (1 ml) was added cyanomethylenetributylphosphorane (0.104 g) at room temperature. The mixture was stirred at 100° C. for 3 h. The reaction mixture was poured into IPE (3 ml) and H$_2$O (1 ml), and stirred for 5 min. The organic layer was evaporated by blowing away with the air at 60° C. The residue was purified by preparative HPLC (Actus Triart C18, eluted with MeCN/10 mM NH$_4$HCO$_3$ aq. 10:90→100:0). Pure fractions were combined and concentrated by blowing away with the air at 60° C. To the residue was added 0.36 M HCl/MeOH (1 ml). The mixture was heated at 50° C. for 1 h and then evaporated by blowing away with the air at 60° C. The residue was purified by preparative HPLC (Actus Triart C18, eluted with MeCN/10 mM NH$_4$HCO$_3$ aq. 5:95→100:0). Pure fractions were combined and concentrated by blowing away with the air at 60° C. to afford product. MsCl (0.055 g) was added dropwise to a solution of residue and DBU (0.073 g) in THF (1 ml) at room temperature. The mixture was stirred at room temperature for 3 h and then evaporated by blowing away with the air at 60° C. The residue was purified by preparative HPLC (Actus Triart C18, eluted with MeCN/10 mM NH$_4$HCO$_3$ aq. 5:95→100:

0). Pure fractions were combined and concentrated by blowing away with the air at 60° C. to afford the title compound (8.7 mg).

MS (API+), found: 454.2 (M+1)

Example 223

N-[(1S,2S)-4,4-difluoro-2-{[4-(5-methylisoxazol-3-yl)phenoxy]methyl}cyclohexyl]ethanesulfonamide Titled compound was synthesized by similar method to Example 222.

Example 224

N-[(1S,2S)-4,4-difluoro-2-{[3-fluoro-4-(5-methylisoxazol-3-yl)phenoxy]methyl}cyclohexyl]ethanesulfonamide Titled compound was synthesized by similar method to Example 222.

Example 225

N-[(1S,2S)-4,4-difluoro-2-{[2-fluoro-4-(5-methylisoxazol-3-yl)phenoxy]methyl}cyclohexyl]ethanesulfonamide Titled compound was synthesized by similar method to Example 222.

Example 226

N-[(1S,2S)-2-{[4-(4-cyano-1H-pyrazol-1-yl)phenoxy]methyl}-4,4-difluorocyclohexyl]cyclopropanesulfonamide Titled compound was synthesized by similar method to Example 222.

Example 227

N-[(1S,2S)-2-{[4-(4-cyano-1H-pyrazol-1-yl)-2-fluorophenoxy]methyl}-4,4-difluorocyclohexyl]cyclopropanesulfonamide Titled compound was synthesized by similar method to Example 222.

Example 228

N-[(1S,2S)-2-{[4-(5-cyanopyridin-2-yl)phenoxy]methyl}-4,4-difluorocyclohexyl]cyclopropanesulfonamide Titled compound was synthesized by similar method to Example 222.

Example 229

N-[(1S,2S)-2-{[4-(5-cyano-3-fluoropyridin-2-yl)phenoxy]methyl}-4,4-difluorocyclohexyl]cyclopropanesulfonamide Titled compound was synthesized by similar method to Example 222.

Example 230

N-[(1S,2S)-4,4-difluoro-2-{[4-(5-methylisoxazol-3-yl)phenoxy]methyl}cyclohexyl]cyclopropanesulfonamide Titled compound was synthesized by similar method to Example 222.

Example 231

N-[(1S,2S)-4,4-difluoro-2-{[3-fluoro-4-(5-methylisoxazol-3-yl)phenoxy]methyl}cyclohexyl]cyclopropanesulfonamide Titled compound was synthesized by similar method to Example 222.

Example 232

N-[(1S,2S)-4,4-difluoro-2-{[2-fluoro-4-(5-methylisoxazol-3-yl)phenoxy]methyl}cyclohexyl]cyclopropanesulfonamide Titled compound was synthesized by similar method to Example 222

Example 233

N-[(3R,4S)-4-{[4-(5-chloropyridin-2-yl)phenoxy]methyl}tetrahydro-2H-pyran-3-yl]methanesulfonamide A) (3R,4S)-4-((4-(5-chloropyridin-2-yl)phenoxy)methyl)tetrahydro-2H-pyran-3-amine hydrochloride To a mixture of tert-butyl ((3R,4S)-4-(hydroxymethyl)tetrahydro-2H-pyran-3-yl)carbamate (177 mg), 4-(5-chloropyridin-2-yl)phenol (189 mg), Bu$_3$P (0.378 ml) in toluene (15 ml) was added ADDP (387 mg). The mixture was stirred at room temperature overnight. EtOAc was added to the mixture and the resulted insoluble materials were removed by filtration. The mixture was concentrated in vacuo and the residue was purified by column chromatography (silica gel, eluted with EtOAc in hexane) and concentrated. The residue was diluted to EtOAc (10 ml) and 4 N HCl/EtOAc (3 ml) was added to the mixture. The mixture was stirred at room temperature overnight. 4 N HCl/AcOEt (3 ml) was added to the mixture and this was stirred at room temperature over weekend. The insoluble material was washed with a mixture of EtOAc and IPE, collected and dried in vacuo to give the title compound (182 mg) as a pale yellow powder.

MS (API+), found: 319.1.

B) N-[(3R,4S)-4-{[4-(5-chloropyridin-2-yl)phenoxy]methyl}tetrahydro-2H-pyran-3-yl]methanesulfonamide Methanesulfonyl chloride (0.159 ml) was added to a mixture of (3R,4S)-4-((4-(5-chloropyridin-2-yl)phenoxy)methyl)tetrahydro-2H-pyran-3-amine hydrochloride (182 mg) and triethylamine (0.714 ml) in THF (6 ml). The mixture was stirred at room temperature overnight. The mixture was quenched with sat. NaHCO$_3$ aq. and extracted with EtOAc. The residue was crystallized from THF-EtOAc/hexane at 0° C. to give the title compound (133 mg) as off-white crystals.

¹H NMR (300 MHz, DMSO-d₆) δ 1.54-1.70 (1H, m), 1.78-1.96 (2H, m), 2.86 (3H, s), 2.99-3.11 (1H, m), 3.18-3.28 (2H, m), 3.80-3.95 (2H, m), 4.03-4.21 (2H, m), 7.02-7.10 (2H, m), 7.35 (1H, d, J=8.3 Hz), 7.91-7.95 (2H, m), 7.99-8.08 (2H, m), 8.59-8.69 (1H, m).

MS (API+), found: 397.1 (M+1)

Example 234

N-[(3R,4S)-4-{[4-(4-chloro-1H-pyrazol-1-yl)phenoxy]methyl}tetrahydro-2H-pyran-3-yl]methanesulfonamide A) tert-butyl ((3R,4S)-4-((4-(4-chloro-1H-pyrazol-1-yl)phenoxy)methyl)tetrahydro-2H-pyran-3-yl)carbamate A mixture of tert-butyl ((3R,4S)-4-(hydroxymethyl)tetrahydro-2H-pyran-3-yl)carbamate (300 mg), 4-(4-chloro-1H-pyrazol-1-yl)phenol (328 mg), AMP (491 mg) and Bu₃P (0.480 ml) in toluene (20 ml) was stirred at room temperature overnight. The mixture was purified by column chromatography (silica gel, eluted with EtOAc in hexane) to give the title compound (232 mg) as a white solid.

MS (API+), found: 408.2 (M+1)

B) N-[(3R,4S)-4-{[4-(4-chloro-1H-pyrazol-1-yl)phenoxy]methyl}tetrahydro-2H-pyran-3-yl]methanesulfonamide A mixture of tert-butyl ((3R,4S)-4-((4-(4-chloro-1H-pyrazol-1-yl)phenoxy)methyl)tetrahydro-2H-pyran-3-yl)carbamate (232 mg) and 4 M HCl/EtOAc (8 ml) was stirred at room temperature overnight. To the mixture was added IPE and the resulting precipitate was collected by filtration, washed with IPE and hexane. A mixture of the residue, Et₃N (0.103 ml) and MsCl (0.038 ml) in THF (2 ml) was stirred at room temperature for 20 min. The mixture was quenched with sat. NaHCO₃ aq. and extracted with EtOAc. The organic layer was separated, washed with brine, dried over Na₂SO₄ and concentrated in vacuo. The residue was purified by column chromatography (silica gel, eluted with 30%-80% EtOAc in hexane) to give the title compound (68.0 mg) as a white solid.

¹H NMR (300 MHz, CDCl₃) δ 1.69-1.99 (3H, m), 2.88 (3H, s), 3.11-3.22 (1H, m), 3.36-3.58 (2H, m), 3.95-4.04 (1H, m), 4.04-4.14 (2H, m), 4.19 (1H, dd, J=11.1, 4.7 Hz), 4.64 (1H, d, J=8.3 Hz), 6.93-7.03 (2H, m), 7.49-7.57 (2H, m), 7.61 (1H, s), 7.81 (1H, s).

Example 235

N-[(3R,4S)-4-{[4-(4-chloro-1H-pyrazol-1-yl)-2-fluorophenoxy]methyl}tetrahydro-2H-pyran-3-yl]methanesulfonamide A) 1-(3-fluoro-4-methoxyphenyl)-1H-pyrazole A mixture of 4-bromo-2-fluoro-1-methoxybenzene (25 g), 1H-pyrazole (12.5 g), salicylaldoxime (3.34 g), cesium carbonate (79 g), and copper(I)oxide (0.872 g) in CH₃CN (200 ml) was degased then stirred at 83° C. under N₂ for 64 h. After cooling to room temperature, the mixture was filtered by celite. The filtrate was added SiO₂, concentrated in vacuo, and purified by column chromatography (silica gel, eluted with EtOAc in hexane) to give the title compound (14.3 g) as a white solid.

MS (API+), found: 193.1 (M+1)

B) 4-chloro-1-(3-fluoro-4-methoxyphenyl)-1H-pyrazole

A mixture of NCS (8.68 g) and 1-(3-fluoro-4-methoxyphenyl)-1H-pyrazole (5 g) in THF (200 ml) was stirred at 60° C. overnight. After cooling to room temperature, the mixture was added SiO₂, concentrated in vacuo, then purified by column chromatography (silica gel, eluted with EtOAc in hexane) to give the title compound (5.15 g) as a white solid.

MS (API+), found: 227.1 (M+1)

C) 4-(4-chloro-1H-pyrazol-1-yl)-2-fluorophenol

A mixture of hydrogen bromide (25.7 ml, 48%) and 4-chloro-1-(3-fluoro-4-methoxyphenyl)-1H-pyrazole (5.15 g) in AcOH (100 ml) was stirred 130° C. overnight. It was concentrated in vacuo, added sat. NaHCO₃ aq. and extracted with EtOAc. The extract was washed with brine, dried over MgSO₄, filtered, and concentrated in vacuo. The residue was purified by column chromatography (silica gel, eluted with EtOAc in hexane) to give the title compound (4.70 g) as a off-white solid.

MS (API+), found: 213.0 (M+1)

D) tert-butyl ((3R,4S)-4-((4-(4-chloro-1H-pyrazol-1-yl)-2-fluorophenoxy)methyl)tetrahydro-2H-pyran-3-yl)carbamate A mixture of tert-butyl ((3R,4S)-4-(hydroxymethyl)tetrahydro-2H-pyran-3-yl)carbamate (300 mg), 4-(4-chloro-1H-pyrazol-1-yl)-2-fluorophenol (359 mg), ADDP (491 mg) and Bu₃P (0.480 ml) in toluene (15 ml) was stirred at room temperature for 3 days. The mixture was purified by column chromatography (NH silica gel, eluted with EtOAc in hexane) to give the title compound (231 mg) as a white solid.

MS (API+), found: 326.2 (M+1-Boc)

E) N-[(3R,4S)-4-{[4-(4-chloro-1H-pyrazol-1-yl)-2-fluorophenoxy]methyl}tetrahydro-2H-pyran-3-yl]methanesulfonamide A mixture of tert-butyl ((3R,4S)-4-((4-(4-chloro-1H-pyrazol-1-yl)-2-fluorophenoxy)methyl)tetrahydro-2H-pyran-3-yl)carbamate (231 mg) and 4 M HCl/EtOAc (10 ml) was stirred at room temperature overnight. To the mixture was added IPE and the resulting precipitate was collected by filtration, washed with IPE and hexane to give (3R,4S)-4-((4-(4-chloro-1H-pyrazol-1-yl)-2-fluorophenoxy)methyl)tetrahydro-2H-pyran-3-amine hydrochloride (188 mg) as an off-white solid. A mixture of (3R,4S)-4-((4-(4-chloro-1H-pyrazol-1-yl)-2-fluorophenoxy)methyl)tetrahydro-2H-pyran-3-amine hydrochloride (94 mg), Et₃N (0.109 ml) and MsCl (0.040 ml) in THF(dry) (2 ml) was stirred at room temperature for 10 min. The mixture was quenched with sat. NaHCO₃ aq. and extracted with EtOAc. The organic layer was separated, washed with brine, dried over Na₂SO₄ and concentrated in vacuo. The residue was purified by column chromatography (silica gel, eluted with EtOAc in hexane) to give the title compound (85 mg) as a white solid.

¹H NMR (300 MHz, CDCl₃) δ 1.68-1.85 (1H, m), 1.85-2.03 (2H, m), 2.94 (3H, s), 3.17 (1H, dd, J=11.0, 10.2 Hz), 3.36-3.58 (2H, m), 3.94-4.06 (1H, m), 4.09-4.25 (3H, m), 4.70 (1H, d, J=8.3 Hz), 7.05 (1H, t, J=8.7 Hz), 7.27-7.35 (1H, m), 7.45 (1H, dd, J=11.7, 2.6 Hz), 7.61 (1H, s), 7.81 (1H, d, J=0.8 Hz).

Example 236

N-[(3R,4S)-4-{[4-(5-chloropyridin-2-yl)phenoxy]methyl}tetrahydro-2H-pyran-3-yl]ethanesulfonamide A mixture of (3R,4S)-4-((4-(5-chloropyridin-2-yl)phenoxy)methyl)tetrahydro-2H-pyran-3-amine hydrochloride (68 mg), TEA (0.21 ml) and ethanesulfonyl chloride (0.054 ml) in THF (5.0 ml) was stirred at room temperature for 12 h. The mixture was added MeOH and silica gel, concentrated in vacuo, and purified by column chromatography (silica gel, eluted with EtOAc in hexane) followed by crystallization from EtOAc-IPE to give the title compound (47 mg) as a white solid.
$^1$H NMR (300 MHz, DMSO-$d_6$) δ 1.08 (3H, t, J=7.3 Hz), 1.61 (1H, dd, J=12.8, 5.1 Hz), 1.78-1.94 (2H, m), 2.89-3.00 (2H, m), 3.01-3.11 (1H, m), 3.19-3.29 (2H, m), 3.80-3.98 (2H, m), 4.00-4.20 (2H, m), 7.01-7.12 (2H, m), 7.32 (1H, d, J=8.1 Hz), 7.95 (2H, d, J=1.9 Hz), 7.99-8.09 (2H, m), 8.64 (1H, t, J=1.6 Hz).

Example 237

N-[(1S,2S)-2-{[4-(5-cyano-3-fluoropyridin-2-yl)phenoxy]methyl}-4,4-difluorocyclohexyl]methanesulfonamide A) tert-butyl ((1S,2S)-2-((4-(5-cyano-3-fluoropyridin-2-yl)phenoxy)methyl)-4,4-difluorocyclohexyl)carbamate A mixture of tert-butyl ((1S,2S)-4,4-difluoro-2-(hydroxymethyl)cyclohexyl)carbamate (200 mg), 5-fluoro-6-(4-hydroxyphenyl)nicotinonitrile (210 mg), ADDP (285 mg) and Bu$_3$P (0.279 ml) in toluene (12 ml) was stirred at room temperature overnight. The mixture was purified by column chromatography (NH silica gel, eluted with EtOAc in hexane) to give the title compound (289 mg) as a white solid.
MS (API+), found: 362.2 (M+1-Boc)

B) N-[(1S,2S)-2-{[4-(5-cyano-3-fluoropyridin-2-yl)phenoxy]methyl}-4,4-difluorocyclohexyl]methanesulfonamide A mixture of tert-butyl ((1S,2S)-2-((4-(5-cyano-3-fluoropyridin-2-yl)phenoxy)methyl)-4,4-difluorocyclohexyl)carbamate (289 mg) and 4 M HCl/EtOAc (10 ml) was stirred at room temperature overnight. The resulting precipitate was collected by filtration and washed with IPE. A mixture of the residue, Et$_3$N (0.262 ml) and MsCl (0.097 ml) in THF (7 ml) was stirred at room temperature for 2 h. The mixture was quenched with sat. NaHCO$_3$ aq. and extracted with EtOAc. The organic layer was separated, washed with brine, dried over Na$_2$SO$_4$ and concentrated in vacuo. The residue was purified by column chromatography (silica gel, eluted with EtOAc in hexane) to give the title compound (190 mg) as a white solid.
$^1$H NMR (300 MHz, CDCl$_3$) δ 1.61-2.41 (7H, m), 2.84 (3H, s), 3.46-3.64 (1H, m), 4.02 (1H, dd, J=9.3, 2.5 Hz), 4.21-4.34 (2H, m), 6.98-7.09 (2H, m), 7.71 (1H, dd, J=10.7, 1.8 Hz), 8.01-8.11 (2H, m), 8.73 (1H, t, J=1.5 Hz).

Example 238

N-[(1S,2S)-2-{[4-(5-cyano-3-fluoropyridin-2-yl)phenoxy]methyl}-4,4-difluorocyclohexyl]ethanesulfonamide A) 6-(4-(((1S,2S)-2-amino-5,5-difluorocyclohexyl)methoxy)phenyl)-5-fluoronicotinonitrile hydrochloride A mixture of tert-butyl ((1S,2S)-4,4-difluoro-2-(hydroxymethyl)cyclohexyl)carbamate (360 mg), 5-fluoro-6-(4-hydroxyphenyl)nicotinonitrile (349 mg), Bu$_3$P (0.670 ml) and ADDP (685 mg) in toluene (40 ml) was stirred at room temperature overnight. EtOAc was added to the mixture and the resulted insoluble materials were removed by filtration. The mixture was concentrated in vacuo and the residue was purified by column chromatography (silica gel, eluted with EtOAc in hexane) and concentrated. The residue was diluted to EtOAc (20 ml) and 4 M HCl/EtOAc (5 ml) was added to a mixture at room temperature. The mixture was stirred at room temperature overnight. The insoluble material was washed with EtOAc, collected and dried in vacuo to give the title compound (385 mg) as an yellow powder.
MS (API+), found: 362.1.

B) N-[(1S,2S)-2-{[4-(5-cyano-3-fluoropyridin-2-yl)phenoxy]methyl}-4,4-difluorocyclohexyl]ethanesulfonamide Ethanesulfonyl chloride (0.184 ml) was added to a mixture of 6-(4-(((1S,2S)-2-amino-5,5-difluorocyclohexyl)methoxy)phenyl)-5-fluoronicotinonitrile is hydrochloride (385 mg) and triethylamine (1.35 ml) in THF (10 ml). The mixture was stirred at room temperature overnight. The mixture was quenched with sat. NaHCO$_3$ aq. and extracted with EtOAc. The organic layer was separated, washed with brine and concentrated in vacuo. The residue was diluted with EtOAc and purified by column chromatography (silica gel, eluted with EtOAc in hexane) and concentrated. The residue was crystallized from EtOAc/hexane at 0° C. to give the title compound (203 mg) as off-white crystals.
$^1$H NMR (300 MHz, DMSO-$d_6$) δ 1.11 (3H, t, J=7.3 Hz), 1.50-1.75 (1H, m), 1.96-2.12 (5H, m), 2.19-2.32 (2H, m), 2.89-3.02 (2H, m), 4.03-4.24 (2H, m), 7.08-7.17 (2H, m), 7.23-7.31 (1H, m), 7.95-8.05 (2H, m), 8.47 (1H, dd, J=11.6, 1.6 Hz), 8.95 (1H, t, J=1.5 Hz).
MS (API+), found: 454.1 (M+1)

Example 239

N-[(3RS,4SR)-3-{[4-(5-chloropyridin-2-yl)phenoxy]methyl}tetrahydro-2H-pyran-4-yl]methanesulfonamide A) 4-(5-chloropyridin-2-yl)phenol A mixture of (4-hydroxyphenyl)boronic acid (2.69 g), 2-bromo-5-chloropyridine (2.5 g), Na$_2$CO$_3$ (4.13 g) and Pd(Ph$_3$P)$_4$ (0.450 g) in DME (70 ml) and water (15 ml) was stirred at 80° C. under N$_2$ overnight. It was added silica gel and concentrated in vacuo. The residue was purified by column chromatography (silica gel, eluted with EtOAc in hexane) to give the title compound (2.09 g) as a yellow solid.
LC/MS [M+1]: 206.1

B) tert-butyl ((3RS,4SR)-3-((4-(5-chloropyridin-2-yl)phenoxy)methyl)tetrahydro-2H-pyran-4-yl)carbamate A mixture of Bu₃P (0.320 ml), ADDP (327 mg), 4-(5-chloropyridin-2-yl)phenol (200 mg) and tert-butyl (3SR,4SR)-3-(hydroxymethyl)tetrahydro-2H-pyran-4-ylcarbamate (150 mg) in toluene (20 ml) and THF(dry) (5 ml) was stirred at room temperature for 3 days. The mixture was poured into 1 N NaOH aq. and extracted with EtOAc. The organic layer was separated, washed with 1 N NaOH aq. and brine, dried over MgSO₄ and concentrated in vacuo. The residue was purified by column chromatography (silica gel, eluted with EtOAc in hexane) to give the title compound (251 mg) as a white solid.
LC/MS [M+1]: 419.1

C) N-[(3RS,4SR)-3-{[4-(5-chloropyridin-2-yl)phenoxy]methyl}tetrahydro-2H-pyran-4-yl]methanesulfonamide A mixture of 4M hydrogen chloride in EtOAc (5 mL) and tert-butyl (3RS,4SR)-3-((4-(5-chloropyridin-2-yl)phenoxy)methyl)tetrahydro-2H-pyran-4-ylcarbamate (155 mg) was stirred at room temperature for 30 min. It was concentrated in vacuo. The residue was added THF (25 mL), Et₃N (562 mg) and MsCl (212 mg) at room temperature, and stirred at the same temperature overnight. It was added silica gel and concentrated in vacuo. The residue was purified by column chromatography (silica gel, eluted with EtOAc in hexane) to give N-((3RS,4SR)-3-((4-(5-chloropyridin-2-yl)phenoxy)methyl)tetrahydro-2H-pyran-4-yl)methanesulfonamide (72.1 mg) as a white solid. The solid was crystallized from IPE-EtOAc-hexane to give the title compound as a white solid.
¹H NMR (300 MHz, DMSO-d₆) δ 1.43-1.73 (1H, m), 1.81-2.06 (2H, m), 2.90 (3H, s), 3.24-3.50 (3H, m), 3.85 (1H, d, J=9.1 Hz), 3.93-4.09 (2H, m), 4.12-4.30 (1H, m), 6.94-7.09 (2H, m), 7.30 (1H, d, J=8.3 Hz), 7.91-7.96 (2H, m), 7.99-8.07 (2H, m), 8.64 (1H, t, J=1.7 Hz).

Example 240

N-[(3RS,4SR)-3-{[4-(5-fluoropyridin-2-yl)phenoxy]methyl}tetrahydro-2H-pyran-4-yl]ethanesulfonamide A) 4-(5-fluoropyridin-2-yl)phenol A mixture of Pd(Ph₃P)₄ (0.524 g), 2-bromo-5-fluoropyridine (2.66 g), Na₂CO₃ (3.20 g) and 4-hydroxyphenylboronic acid (2.5 g) in DME (60 ml) and water (12 ml) was stirred at 80° C. under N₂ for 2 days. It was added silica gel and concentrated in vacuo. The residue was purified by column chromatography (silica gel, eluted with EtOAc in hexane) to give the title compound (1.52 g) as a pale yellow solid.
LC/MS [M+1]: 190.1

B) tert-butyl ((3RS,4SR)-3-((4-(5-fluoropyridin-2-yl)phenoxy)methyl)tetrahydro-2H-pyran-4-yl)carbamate A mixture of Bu₃P (0.853 ml), ADDP (873 mg), 4-(5-fluoropyridin-2-yl)phenol (425 mg) and tert-butyl (3SR,4SR)-3-(hydroxymethyl)tetrahydro-2H-pyran-4-ylcarbamate (400 mg) in THF(dry) (25 ml) was stirred at room temperature overnight. The mixture was poured into 1 N NaOH aq. and extracted with EtOAc. The organic layer was separated, washed with 1 N NaOH aq. and brine, dried over MgSO₄ and concentrated in vacuo. The residue was purified by column chromatography (silica gel, eluted with EtOAc in hexane) to give the title compound (631 mg) as a white solid.
LC/MS [M+1]: 403.2

C) N-[(3RS,4SR)-3-{[4-(5-fluoropyridin-2-yl)phenoxy]methyl}tetrahydro-2H-pyran-4-yl]ethanesulfonamide A mixture of 2 M HCl/EtOH (5 ml) and tert-butyl (3RS,4SR)-3-((4-(5-fluoropyridin-2-yl)phenoxy)methyl)tetrahydro-2H-pyran-4-ylcarbamate (213 mg) was stirred at room temperature for 1 h. It was concentrated in vacuo. The residue was added THF(dry) (25 ml), triethylamine (803 mg) and ethanesulfonyl chloride (340 mg) at room temperature. The mixture was stirred at room temperature overnight. It was added silica gel and concentrated in vacuo. The residue was purified by column chromatography (silica gel, eluted with EtOAc in hexane) to give the title compound (182 mg) as a pale yellow solid. The solid was crystallized from EtOAc-hexane-IPE to give the title compound as a pale yellow solid.
¹H NMR (300 MHz, DMSO-d₆) δ 1.13 (3H, t, J=7.2 Hz), 1.47-1.72 (1H, m), 1.82-2.07 (2H, m), 2.97 (2H, q, J=7.4 Hz), 3.21-3.46 (3H, m), 3.72-3.91 (1H, m), 3.93-4.09 (2H, m), 4.14-4.28 (1H, m), 6.94-7.09 (2H, m), 7.29 (1H, d, J=8.7 Hz), 7.67-7.85 (1H, m), 7.89-8.10 (3H, m), 8.59 (1H, d, J=3.0 Hz).

Example 241

N-[(3RS,4SR)-3-{[4-(5-fluoropyridin-2-yl)phenoxy]methyl}tetrahydro-2H-pyran-4-yl]cyclopropanesulfonamide A mixture of tert-butyl ((3RS,4SR)-3-((4-(5-fluoropyridin-2-yl)phenoxy)methyl)tetrahydro-2H-pyran-4-yl)carbamate (183 mg) and 2 M HCl/EtOH (5 ml) was stirred at room temperature for 1 h. The mixture was poured into sat. NaHCO₃ aq. and extracted with EtOAc. The organic layer was separated, washed with sat. NaHCO₃ aq. and brine, dried over MgSO₄ and concentrated in vacuo. The residue was added THF(dry) (25 ml), DBU (0.686 ml) and cyclopropanesulfonyl chloride (192 mg) at room temperature. The mixture was stirred at room temperature overnight. It was added silica gel and concentrated in vacuo. The residue was purified by column chromatography (silica gel, eluted with EtOAc in hexane) to give the title compound (61.8 mg) as a white solid. The solid was crystallized from EtOAc-hexane to give the title compound as a solid.
¹H NMR (300 MHz, DMSO-d₆) δ 0.78-0.96 (4H, m), 1.52-1.71 (1H, m), 1.86-2.05 (2H, m), 2.52-2.64 (1H, m), 3.26-3.48 (3H, m), 3.76-3.91 (1H, m), 3.93-4.11 (2H, m), 4.22 (1H, dd, J=9.7, 3.2 Hz), 6.95-7.09 (2H, m), 7.34 (1H, d, J=8.7 Hz), 7.70-7.86 (1H, m), 7.91-8.03 (3H, m), 8.59 (1H, d, J=3.0 Hz).

Example 242

N-[(3RS,4SR)-3-{[4-(5-methyl-1,3-thiazol-2-yl)phenoxy]methyl}tetrahydro-2H-pyran-4-yl]cyclopropanesulfonamide A) 4-(5-methyl-1,3-thiazol-2-yl)phenol A mixture of (4-hydroxyphenyl)boronic acid (3.87 g), 2-bromo-5-methylthiazole (2 g), Pd(Ph₃P)₄ (0.389 g) and Na₂CO₃ (3.57 g) in DME (50 ml) and water (10 ml) was stirred at 80° C. under N₂ overnight. It was added silica gel and concentrated in vacuo. The residue was purified by column chromatography (silica gel, eluted with EtOAc in hexane) to give the title compound (1.12 g) as a white solid.
LC/MS [M+1]: 192.0

B) tert-butyl ((3RS,4SR)-3-((4-(5-methyl-1,3-thiazol-2-yl)phenoxy)methyl)tetrahydro-2H-pyran-4-yl)carbamate A mixture of Bu₃P (0.320 ml), ADDP (327 mg), 4-(5-methylthiazol-2-yl)phenol (161 mg) and tert-butyl (3SR,4SR)-3-(hydroxymethyl)tetrahydro-2H-pyran-4-ylcarbamate (150 mg) in toluene (25 ml) and THF(dry) (5 ml) was stirred at room temperature overnight. The mixture was poured into 1 N NaOH aq. and extracted with EtOAc. The organic layer was separated, washed with 1N NaOH aq. and brine, dried over MgSO₄ and concentrated in vacuo. The residue was purified by column chromatography (silica gel, eluted with EtOAc in hexane) to give the title compound (260 mg) as a white amorphous solid.
LC/MS [M+1]: 405.2

C) N-[(3RS,4SR)-3-{[4-(5-methyl-1,3-thiazol-2-yl)phenoxy]methyl}tetrahydro-2H-pyran-4-yl]cyclopropanesulfonamide A mixture of tert-butyl (3RS,4SR)-3-((4-(5-methylthiazol-2-yl)phenoxy)methyl)tetrahydro-2H-pyran-4-ylcarbamate (135 mg) and 2 M HCl/EtOH (5 ml) was stirred at room temperature for 1 h. It was concentrated in vacuo. The residue was added THF(dry) (25 ml), triethylamine (507 mg) and cyclopropanesulfonyl chloride (235 mg) at room temperature. The mixture was stirred at room temperature overnight. Then it was added DBU (0.151 ml) at room temperature and stirred at room temperature for 3 h. It was added NH silica gel and concentrated in vacuo. The residue was purified by column chromatography (NH silica gel, eluted with EtOAc in hexane) to give yellow oil. The residue was purified by preparative HPLC (L-Column 2 ODS, eluted with H₂O in acetonitrile containing 0.1% TFA). The desired fraction was neutralized with sat. NaHCO₃ aq. and extracted with EtOAc. The organic layer was separated, dried over MgSO₄ and concentrated in vacuo. The residue was purified by column chromatography (silica gel, eluted with EtOAc in hexane) to give the title compound (12.2 mg) as a white solid.
¹H NMR (300 MHz, CDCl₃) δ 0.72-0.98 (2H, m), 1.03-1.25 (2H, m), 1.60-1.81 (1H, m), 1.89-2.08 (1H, m), 2.13-2.26 (1H, m), 2.27-2.42 (1H, m), 2.71 (3H, s), 3.36-3.68 (3H, m), 3.92-4.19 (4H, m), 4.30 (1H, brs), 6.85-6.95 (2H, m), 7.38-7.48 (2H, m), 7.68 (1H, s).

Example 243

N-[(3RS,4SR)-3-{[3-fluoro-4-(5-fluoropyridin-2-yl)phenoxy]methyl}tetrahydro-2H-pyran-4-yl]cyclopropanesulfonamide A) 5-fluoro-2-(2-fluoro-4-methoxyphenyl)pyridine A mixture of Na₂CO₃ (3.12 g), Pd(Ph₃P)₄ (0.340 g), 2-bromo-5-fluoropyridine (1.73 g) and (2-fluoro-4-methoxyphenyl)boronic acid (2.5 g) in DME (50 ml) and water (10 ml) was stirred at 80° C. under N₂ overnight. It was added silica gel and concentrated in vacuo. The residue was purified by column chromatography (silica gel, eluted with EtOAc in hexane) to give the title compound (2.34 g) as a white solid.
LC/MS [M+1]: 222.1

B) 3-fluoro-4-(5-fluoropyridin-2-yl)phenol

A mixture of 1-dodecanethiol (10.5 g), AlCl₃ (6.93 g) and 5-fluoro-2-(2-fluoro-4-methoxyphenyl)pyridine (2.3 g) in toluene (50 ml) was stirred at 0° C. for 3 h. The mixture was quenched with 1 N HCl aq. at 0° C. and extracted with EtOAc. The organic layer was separated, washed with sat. NaHCO₃ aq. and brine, dried over MgSO₄ and concentrated in vacuo. The residue was triturated from hexane to give the title compound (1.79 g) as a white solid.
LC/MS [M+1]: 208.0

C) tert-butyl ((3RS,4SR)-3-((3-fluoro-4-(5-fluoropyridin-2-yl)phenoxy)methyl)tetrahydro-2H-pyran-4-yl)carbamate A mixture of Bu₃P (0.853 ml), ADDP (873 mg), 3-fluoro-4-(5-fluoropyridin-2-yl)phenol (466 mg) and tert-butyl ((3SR,4SR)-3-(hydroxymethyl)tetrahydro-2H-pyran-4-yl)carbamate (400 mg) in THF(dry) (25 ml) was stirred at room temperature overnight. The mixture was poured into 1 N NaOH aq. and extracted with EtOAc. The organic layer was separated, washed with 1 N NaOH aq. and brine, dried over MgSO₄ and concentrated in vacuo. The residue was purified by column chromatography (silica gel, eluted with EtOAc in hexane) to give the title compound (606 mg) as a white solid.
LC/MS [M+1]: 421.2

D) N-[(3RS,4SR)-3-{[3-fluoro-4-(5-fluoropyridin-2-yl)phenoxy]methyl}tetrahydro-2H-pyran-4-yl]cyclopropanesulfonamide A mixture of 2 M HCl/EtOH (5 ml) and tert-butyl ((3RS,4SR)-3-((3-fluoro-4-(5-fluoropyridin-2-yl)phenoxy)methyl)tetrahydro-2H-pyran-4-yl)carbamate (200 mg) was stirred at room temperature for 1 h. It was concentrated in vacuo. The residue was added THF(dry) (25 ml), triethylamine (722 mg), DBU (0.717 ml) and cyclopropanesulfonyl chloride (334 mg) at room temperature. The mixture was stirred at room temperature overnight. It was added sat. NaHCO₃ aq. and silica gel and concentrated in vacuo. The residue was purified by column chromatography (silica gel, eluted with EtOAc in hexane) to give the title compound (51.0 mg) as a pale yellow solid. The solid was crystallized from EtOAc-hexane to give the title compound as a pale yellow solid.
¹H NMR (300 MHz, DMSO-d₆) δ 0.81-0.97 (4H, m), 1.62 (1H, qd, J=11.9, 4.5 Hz), 1.81-2.06 (2H, m), 2.54-2.67 (1H, m), 3.25-3.47 (3H, m), 3.80-3.91 (1H, m), 3.96-4.09 (2H, m), 4.22 (1H, dd, J=10.0, 3.2 Hz), 6.85-7.00 (2H, m), 7.33 (1H, d, J=8.7 Hz), 7.72-7.95 (3H, m), 8.67 (1H, d, J=1.9 Hz).

Example 244

N-[(3RS,4SR)-3-{[4-(5-chloropyridin-2-yl)-3-fluorophenoxy]methyl}tetrahydro-2H-pyran-4-yl]methanesulfonamide A) 5-chloro-2-(2-fluoro-4-methoxyphenyl)pyridine A mixture of Pd(Ph₃P)₄ (0.450 g), 2-bromo-5-chloropyridine (2.5 g), Na₂CO₃ (4.13 g) and (2-fluoro-4-methoxyphenyl)boronic acid (2.5 g) in DME (50 ml) and water (10 ml) was stirred at 80° C. under $N_2$ overnight. The mixture was added NH silica gel and concentrated in vacuo. The residue was purified by column chromatography (silica gel, eluted with EtOAc in hexane) to give 5-chloro-2-(2-fluoro-4-methoxyphenyl)pyridine (3.02 g) as a white solid.

LC/MS [M+1]: 238.0

B) 4-(5-chloropyridin-2-yl)-3-fluorophenol

A mixture of 1-dodecanethiol (12.9 g) and 5-chloro-2-(2-fluoro-4-methoxyphenyl)pyridine (3.02 g) in toluene (50 ml) was stirred at room temperature for 2 h. The mixture was quenched with 1 M HCl aq. at 0° C. and extracted with EtOAc. The organic layer was separated, washed with sat. $NaHCO_3$ aq. and brine, dried over $MgSO_4$ and concentrated in vacuo. The residue was purified by column chromatography (silica gel, eluted with EtOAc in hexane) to give the title compound (2.67 g) as a white solid.

LC/MS [M+1]: 224.2

C) tert-butyl ((3RS,4SR)-3-((4-(5-chloropyridin-2-yl)-3-fluorophenoxy)methyl)tetrahydro-2H-pyran-4-yl)carbamate A mixture of $Bu_3P$ (0.853 ml), ADDP (873 mg), 4-(5-chloropyridin-2-yl)-3-fluorophenol (503 mg) and tert-butyl ((3SR,4SR)-3-(hydroxymethyl)tetrahydro-2H-pyran-4-yl)carbamate (400 mg) in THF(dry) (20 ml) was stirred at room temperature overnight. The mixture was poured into 1 N NaOH aq. and extracted with EtOAc. The organic layer was separated, washed with 1 N NaOH aq. and brine, dried over $MgSO_4$ and concentrated in vacuo. The residue was purified by column chromatography (silica gel, eluted with EtOAc in hexane) to give the title compound (697 mg) as a white solid.

LC/MS [M+1]: 437.2

D) N-[(3RS,4SR)-3-{[4-(5-chloropyridin-2-yl)-3-fluorophenoxy]methyl}tetrahydro-2H-pyran-4-yl]methanesulfonamide A mixture of tert-butyl ((3RS,4SR)-3-((4-(5-chloropyridin-2-yl)-3-fluorophenoxy)methyl)tetrahydro-2H-pyran-4-yl)carbamate (204 mg) and 2M hydrogen chloride in EtOH (5 ml) was stirred at room temperature for 1 h. It was concentrated in vacuo. The residue was added THF(dry) (25 ml), triethylamine (709 mg) and methanesulfonyl chloride (267 mg) at room temperature. The mixture was stirred at room temperature overnight. It was added sat. $NaHCO_3$ aq. and silica gel and concentrated in vacuo. The residue was purified by column chromatography (silica gel, eluted with EtOAc in hexane) to give the title compound (152 mg) as a white solid. The solid was crystallized from EtOAc-hexane-IPE to give a desired product as a white solid.

$^1$H NMR (300 MHz, DMSO-$d_6$) δ 1.59 (1H, qd, J=11.9, 4.5 Hz), 1.81-2.03 (2H, m), 2.91 (3H, s), 3.23-3.47 (3H, m), 3.78-3.93 (1H, m), 3.96-4.10 (2H, m), 4.13-4.23 (1H, m), 6.88-7.01 (2H, m), 7.32 (1H, d, J=8.3 Hz), 7.77 (1H, dd, J=8.7, 1.5 Hz), 7.85-7.95 (1H, m), 8.00 (1H, dd, J=8.7, 2.7 Hz), 8.72 (1H, d, J=2.3 Hz).

Example 245

N-[(3RS,4SR)-3-{[4-(5-chloropyridin-2-yl)-2-fluorophenoxy]methyl}tetrahydro-2H-pyran-4-yl]methanesulfonamide A) 5-chloro-2-(3-fluoro-4-methoxyphenyl)pyridine A mixture of $Na_2CO_3$ (4.13 g), $Pd(Ph_3P)_4$ (0.450 g), 2-bromo-5-chloropyridine (2.5 g) and (3-fluoro-4-methoxyphenyl)boronic acid (2.5 g) in DME (50 ml) and water (10 ml) was stirred at 80° C. under $N_2$ overnight. It was added NH-silica gel and concentrated in vacuo. The residue was purified by column chromatography (silica gel, eluted with EtOAc in hexane) to give the title compound (2.77 g) as a white solid.

LC/MS [M+1]: 238.0

B) 4-(5-chloropyridin-2-yl)-2-fluorophenol

A mixture of 1-dodecanethiol (11.7 g), $AlCl_3$ (7.71 g) and 5-chloro-2-(3-fluoro-4-methoxyphenyl)pyridine (2.75 g) in toluene (50 ml) was stirred at room temperature for 2 h. The mixture was quenched with 1 M HCl aq. at 0° C. and extracted with EtOAc. The organic layer was separated, washed with sat. $NaHCO_3$ aq. and brine, dried over $MgSO_4$ and concentrated in vacuo. The residue was purified by column chromatography (silica gel, eluted with EtOAc in hexane) to give the title compound (2.48 g) as a white solid.

LC/MS [M+1]: 224.0

C) tert-butyl ((3RS,4SR)-3-((4-(5-chloropyridin-2-yl)-2-fluorophenoxy)methyl)tetrahydro-2H-pyran-4-yl)carbamate A mixture of $Bu_3P$ (0.853 ml), ADDP (873 mg), 4-(5-chloropyridin-2-yl)-2-fluorophenol (503 mg) and tert-butyl ((3SR,4SR)-3-(hydroxymethyl)tetrahydro-2H-pyran-4-yl)carbamate (400 mg) in THF(dry) (20 ml) was stirred at room temperature overnight. The mixture was poured into 1 N NaOH aq. and extracted with EtOAc. The organic layer was separated, washed with 1 N NaOH aq. and brine, dried over $MgSO_4$ and concentrated in vacuo. The residue was purified by column chromatography (silica gel, eluted with EtOAc in hexane) to give the title compound (770 mg) as a white solid.

LC/MS [M+23]: 459.2

D) N-[(3RS,4SR)-3-{[4-(5-chloropyridin-2-yl)-2-fluorophenoxy]methyl}tetrahydro-2H-pyran-4-yl]methanesulfonamide A mixture of tert-butyl ((3RS,4SR)-3-((4-(5-chloropyridin-2-yl)-2-fluorophenoxy)methyl)tetrahydro-2H-pyran-4-yl)carbamate (253 mg) and 2 M HCl/EtOH (5 ml) was stirred at room temperature for 1 h. It was concentrated in vacuo. The residue was added THF(dry) (25 ml), triethylamine (879 mg) and methanesulfonyl chloride (332 mg) at room temperature. The mixture was stirred at room temperature overnight. It was added sat. $NaHCO_3$ aq. and silica gel and concentrated in vacuo. The residue was purified by column chromatography (silica gel, eluted with EtOAc in hexane) to give the title compound (183 mg) as a white solid. The solid was crystallized from EtOAc-hexane-IPE to give the title compound as a white solid.

$^1$H NMR (300 MHz, DMSO-$d_6$) δ 1.50-1.69 (1H, m), 1.86-2.04 (2H, m), 2.87-2.97 (3H, m), 3.26-3.46 (3H, m), 3.86 (1H, d, J=10.2 Hz), 3.96-4.16 (2H, m), 4.19-4.36 (1H, m), 7.19-7.38 (2H, m), 7.85-8.07 (4H, m), 8.59-8.73 (1H, m).

Example 246

N-[(3R,4S)-3-{[4-(5-cyanopyridin-2-yl)phenoxy]methyl}tetrahydro-2H-pyran-4-yl]cyclopropanesulfonamide A) 6-(4-hydroxyphenyl)nicotinonitrile A mixture of $Pd(Ph_3P)_4$ (0.838 g), $Na_2CO_3$ (11.53 g), 6-bromonicotinonitrile (6.63 g) and (4-hydroxyphenyl)boronic acid (7.5 g) in DME (150 ml) and water (25 ml) was stirred at 80° C. under $N_2$ for 2 days. It was added silica gel and concentrated in vacuo. The residue was purified by column chromatography (silica gel, eluted with EtOAc in hexane) to give the title compound (6.69 g) as a pale yellow solid.

LC/MS [M+1]: 197.0

B) tert-butyl ((3R,4S)-3-((4-(5-cyanopyridin-2-yl)phenoxy)methyl)tetrahydro-2H-pyran-4-yl)carbamate A mixture of $Bu_3P$ (0.853 ml), ADDP (873 mg), 6-(4-hydroxyphenyl)nicotinonitrile (407 mg) and tert-butyl ((3S,4S)-3-(hydroxymethyl)tetrahydro-2H-pyran-4-yl)carbamate (400 mg) in THF(dry) (20 ml) was stirred at room temperature overnight. The mixture was poured into 1 N NaOH aq. and extracted with EtOAc.

The organic layer was separated, washed with 1 N NaOH aq. and brine, dried over $MgSO_4$ and concentrated in vacuo. The residue was purified by column chromatography (silica gel, eluted with EtOAc in hexane) to give the title compound (612 mg) as a white solid.

$^1$H NMR (300 MHz, $CDCl_3$) δ 1.43 (9H, s), 1.48-1.68 (1H, m), 1.89-2.13 (2H, m), 3.32 (1H, t, J=10.9 Hz), 3.48 (1H, td, J=11.7, 1.5 Hz), 3.67 (1H, qd, J=10.2, 4.0 Hz), 3.81-3.94 (1H, m), 4.01 (1H, dd, J=11.5, 2.8 Hz), 4.14 (1H, dd, J=9.6, 3.6 Hz), 4.23 (1H, dd, J=11.5, 3.2 Hz), 4.53 (1H, d, J=8.7 Hz), 6.92-7.06 (2H, m), 7.77 (1H, d, J=8.7 Hz), 7.95 (1H, dd, J=8.3, 1.9 Hz), 7.98-8.07 (2H, m), 8.89 (1H, d, J=1.5 Hz).

C) N-[(3R,4S)-3-{[4-(5-cyanopyridin-2-yl)phenoxy]methyl}tetrahydro-2H-pyran-4-yl]cyclopropanesulfonamide A mixture of tert-butyl ((3R,4S)-3-((4-(5-cyanopyridin-2-yl)phenoxy)methyl)tetrahydro-2H-pyran-4-yl)carbamate (210 mg) and 2 M HCl/EtOH (5 ml) was stirred at room temperature for 1 h. It was concentrated in vacuo. The residue was added THF(dry) (25 ml), triethylamine (778 mg), DBU (0.773 ml) and cyclopropanesulfonyl chloride (361 mg) at room temperature. The mixture was stirred at room temperature overnight. It was added sat. $NaHCO_3$ aq. and silica gel and concentrated in vacuo. The residue was purified by column chromatography (silica gel, eluted with EtOAc in hexane) to give the title compound (118 mg) as a pale yellow solid. The solid was crystallized from EtOAc-hexane-IPE to give the title compound as a pale yellow solid.

$^1$H NMR (300 MHz, DMSO-$d_6$) δ 0.75-0.96 (4H, m), 1.51-1.70 (1H, m), 1.81-2.06 (2H, m), 2.52-2.63 (1H, m), 3.34-3.46 (3H, m), 3.78-3.93 (1H, m), 3.97-4.10 (2H, m), 4.24 (1H, dd, J=9.8, 3.0 Hz), 7.02-7.12 (2H, m), 7.33 (1H, d, J=8.7 Hz), 8.08-8.19 (3H, m), 8.31 (1H, dd, J=8.5, 2.1 Hz), 8.96-9.14 (1H, m).

Example 247

N-[(3R,4S)-3-{[3-fluoro-4-(5-methylisoxazol-3-yl)phenoxy]methyl}tetrahydro-2H-pyran-4-yl]methanesulfonamide A)
1-(2-fluoro-4-methoxyphenyl)-N-hydroxymethanimine A mixture of sodium acetate (13.6 g), hydroxylamine hydrochloride (8.43 g) and 2-fluoro-4-methoxybenzaldehyde (17 g) in EtOH (200 ml) was stirred at 80° C. for 2 days. The mixture was poured into brine and extracted with EtOAc. The organic layer was separated, washed with brine, dried over $MgSO_4$ and concentrated in vacuo to give the title compound (18.7 g) as a yellow solid.

LC/MS [M+1]: 170.1

B) 3-(2-fluoro-4-methoxyphenyl)-5-methyl-1,2-oxazole

NCS (17.5 g) was added to a solution of 2-fluoro-4-methoxybenzaldehyde oxime (18.5 g) in DMF (300 ml) at 0° C. The mixture was stirred at 0° C. for 2 h and at room temperature for 1 h. It was added prop-1-en-2-yl acetate (16.4 g) and triethylamine (76 ml) successively at 0° C. and stirred at room temperature overnight. The mixture was poured into brine and extracted with EtOAc. The organic layer was separated, washed with brine, dried over $MgSO_4$ and concentrated in vacuo. The residue was purified by column chromatography (silica gel, eluted with EtOAc in hexane) to give the title compound (6.44 g) as a yellow oil.

LC/MS [M+1]: 208.1

C) 3-fluoro-4-(5-methyl-1,2-oxazol-3-yl)phenol

A mixture of 1-dodecanethiol (31.3 g), 3-(2-fluoro-4-methoxyphenyl)-5-methylisoxazole (6.4 g) and $AlCl_3$ (20.6 g) in toluene (300 ml) was stirred at room temperature for 3 h. The mixture was quenched with 1 N HCl aq. at 0° C. and extracted with EtOAc. The organic layer was separated, washed with brine, dried over $MgSO_4$ and concentrated in vacuo. The residue was purified by column chromatography (silica gel, eluted with EtOAc in hexane). The residue was washed with IPE-hexane to give the title compound (2.57 g) as a pale yellow solid.

LC/MS [M+1]: 194.0

D) tert-butyl ((3R,4S)-3-((3-fluoro-4-(5-methyl-1,2-oxazol-3-yl)phenoxy)methyl)tetrahydro-2H-pyran-4-yl)carbamate A mixture of tert-butyl ((3S,4S)-3-(hydroxymethyl)tetrahydro-2H-pyran-4-yl)carbamate (400 mg), 3-fluoro-4-(5-methylisoxazol-3-yl)phenol (370 mg), tributylphosphine (700 mg) and ADDP (873 mg) in THF(dry) (25 ml) was stirred at room temperature overnight. The mixture was poured into 1 N NaOH aq. and extracted with EtOAc. The organic layer was separated, washed with 1 N NaOH aq. and brine, dried over $MgSO_4$ and concentrated in vacuo. The residue was purified by column chromatography (silica gel, eluted with EtOAc in hexane) to give the title compound (662 mg) as a white solid.

$^1$H NMR (300 MHz, $CDCl_3$) δ 1.42 (9H, s), 1.48-1.68 (1H, m), 1.88-2.03 (2H, m), 2.47 (3H, d, J=0.8 Hz), 3.23-3.38 (1H, m), 3.47 (1H, td, J=11.9, 2.3 Hz), 3.57-3.73 (1H, m), 3.75-3.91 (1H, m), 3.94-4.30 (3H, m), 4.43-4.61 (1H, m), 6.37 (1H, dd, J=3.8, 0.8 Hz), 6.67 (1H, dd, J=12.6, 2.4 Hz), 6.75 (1H, dd, J=8.5, 2.4 Hz), 7.86 (1H, t, J=8.5 Hz).

E) N-[(3R,4S)-3-{[3-fluoro-4-(5-methylisoxazol-3-yl)phenoxy]methyl}tetrahydro-2H-pyran-4-yl]methanesulfonamide A mixture of tert-butyl ((3R,4S)-3-((3-fluoro-4-(5-methylisoxazol-3-yl)phenoxy)methyl)tetrahydro-2H-pyran-4-yl)carbamate (180 mg) and 2 M HCl/EtOH (5 ml) was stirred at room temperature for 1 h. It was concentrated in vacuo.

The residue was added THF(dry) (25 ml), triethylamine (672 ml) and methanesulfonyl chloride (254 mg) at room temperature. The mixture was stirred at room temperature overnight. It was added sat. NaHCO$_3$ aq. and silica gel and concentrated in vacuo. The residue was purified by column chromatography (silica gel, eluted with EtOAc in hexane) to give the title compound (134 mg) as a white solid. The solid was crystallized from EtOAc-hexane-IPE to give the title compound as an off-white solid.

$^1$H NMR (300 MHz, CDCl$_3$) δ 1.71 (1H, qd, J=12.1, 4.5 Hz), 1.89-2.09 (1H, m), 2.10-2.26 (1H, m), 2.47 (3H, s), 2.90 (3H, s), 3.35-3.74 (3H, m), 3.95-4.23 (4H, m), 4.44 (1H, d, J=9.0 Hz), 6.37 (1H, d, J=3.8 Hz), 6.70 (1H, dd, J=12.6, 2.4 Hz), 6.77 (1H, dd, J=8.7, 2.6 Hz), 7.88 (1H, t, J=8.7 Hz).

Example 248

N-[(3R,4S)-3-{[3-fluoro-4-(5-methylisoxazol-3-yl)phenoxy]methyl}tetrahydro-2H-pyran-4-yl]ethanesulfonamide A mixture of tert-butyl ((3R,4S)-3-((3-fluoro-4-(5-methylisoxazol-3-yl)phenoxy)methyl)tetrahydro-2H-pyran-4-yl)carbamate (210 mg) and 2 M HCl/EtOH (5 ml) was stirred at room temperature for 1 h. It was concentrated in vacuo. The residue was added THF(dry) (25 ml), triethylamine (784 mg) and ethanesulfonyl chloride (332 mg) at room temperature. The mixture was stirred at room temperature overnight. It was added sat. NaHCO$_3$ aq. and silica gel and concentrated in vacuo. The residue was purified by column chromatography (silica gel, eluted with EtOAc in hexane) to give the title compound (138 mg) as a pale yellow solid. The solid was crystallized from EtOAc-hexane-IPE to give the title compound as a pale yellow solid.

$^1$H NMR (300 MHz, CDCl$_3$) δ 1.29 (3H, t, J=7.3 Hz), 1.61-1.80 (1H, m), 1.85-2.07 (1H, m), 2.08-2.23 (1H, m), 2.47 (3H, s), 2.98 (2H, q, J=7.4 Hz), 3.37-3.68 (3H, m), 3.92-4.18 (4H, m), 4.26 (1H, d, J=9.4 Hz), 6.38 (1H, d, J=3.4 Hz), 6.70 (1H, dd, J=12.4, 2.6 Hz), 6.77 (1H, dd, J=8.7, 2.6 Hz), 7.88 (1H, t, J=8.7 Hz).

Example 249

N-[(3R,4S)-3-{[3-fluoro-4-(5-methylisoxazol-3-yl)phenoxy]methyl}tetrahydro-2H-pyran-4-yl]cyclopropanesulfonamide A mixture of tert-butyl ((3R,4S)-3-((3-fluoro-4-(5-methylisoxazol-3-yl)phenoxy)methyl)tetrahydro-2H-pyran-4-yl)carbamate (220 mg) and 2 M HCl/EtOH (5 ml) was stirred at room temperature for 1 h. It was concentrated in vacuo. The residue was added THF(dry) (25 ml), triethylamine (822 mg), DBU (0.816 ml) and cyclopropanesulfonyl chloride (380 mg) at room temperature. The mixture was stirred at room temperature overnight. It was added sat. NaHCO$_3$ aq. and silica gel and concentrated in vacuo. The residue was purified by column chromatography (silica gel, eluted with EtOAc in hexane) to give the title compound (117 mg) as a pale yellow solid. The solid was crystallized from EtOAc-hexane-IPE to give the title compound as a pale yellow solid.

$^1$H NMR (300 MHz, CDCl$_3$) δ 0.76-0.95 (2H, m), 1.03-1.23 (2H, m), 1.62-1.81 (1H, m), 1.91-2.07 (1H, m), 2.13-2.25 (1H, m), 2.36 (1H, tt, J=8.0, 4.9 Hz), 2.47 (3H, d, J=0.8 Hz), 3.36-3.65 (3H, m), 3.93-4.21 (4H, m), 4.35 (1H, d, J=9.0 Hz), 6.37 (1H, dd, J=3.8, 0.8 Hz), 6.69 (1H, dd, J=12.4, 2.3 Hz), 6.77 (1H, dd, J=8.7, 2.3 Hz), 7.87 (1H, t, J=8.5 Hz).

Example 250

N-[(3R,4S)-3-{[2,3-difluoro-4-(5-fluoropyridin-2-yl)phenoxy]methyl}tetrahydro-2H-pyran-4-yl]ethanesulfonamide A)
2-(2,3-difluoro-4-methoxyphenyl)-5-fluoropyridine A mixture of Na$_2$CO$_3$ (3.85 g), Pd(Ph$_3$P)$_4$ (0.419 g), 2-bromo-5-fluoropyridine (2.128 g) and (2,3-difluoro-4-methoxyphenyl)boronic acid (2.5 g) in DME (50 ml) and water (10 ml) was stirred at 80° C. under N$_2$ overnight. It was added silica gel and concentrated in vacuo. The residue was purified by column chromatography (silica gel, eluted with EtOAc in hexane) to give the title compound (2.83 g) as a white solid.

LC/MS [M+1]: 240.1

B) 2,3-difluoro-4-(5-fluoropyridin-2-yl)phenol

A mixture of AlCl$_3$ (4.68 g), 1-dodecanethiol (7.11 g) and 2-(2,3-difluoro-4-methoxyphenyl)-5-fluoropyridine (2.8 g) in toluene (30 ml) was stirred at room temperature for 3 h. The mixture was quenched with 1 N HCl aq. at 0° C. and extracted with EtOAc. The organic layer was separated, washed with sat. NaHCO$_3$ aq. and brine, dried over MgSO$_4$ and concentrated in vacuo. The residue was triturated from hexane to give the title compound (2.83 g) as a white solid.

LC/MS [M+1]: 226.0

C) tert-butyl ((3R,4S)-3-((2,3-difluoro-4-(5-fluoropyridin-2-yl)phenoxy)methyl)tetrahydro-2H-pyran-4-yl)carbamate A mixture of Bu$_3$P (0.853 ml), ADDP (873 mg), 2,3-difluoro-4-(5-fluoropyridin-2-yl)phenol (467 mg) and tert-butyl ((3S,4S)-3-(hydroxymethyl)tetrahydro-2H-pyran-4-yl)carbamate (400 mg) in THF(dry) (25 ml) was stirred at room temperature overnight. The mixture was poured into 1 N NaOH aq. and extracted with EtOAc. The organic layer was separated, washed with 1 N NaOH aq. and brine, dried over MgSO$_4$ and concentrated in vacuo. The residue was purified by column chromatography (silica gel, eluted with EtOAc in hexane) to give the title compound (139 mg) as a white solid.

$^1$H NMR (300 MHz, CDCl$_3$) δ 1.37-1.73 (10H, m), 1.89-2.15 (2H, m), 3.26-3.40 (1H, m), 3.40-3.55 (1H, m), 3.57-3.74 (1H, m), 3.88-4.07 (2H, m), 4.14-4.33 (2H, m), 4.47-4.59 (1H, m), 6.78-6.88 (1H, m), 7.47 (1H, td, J=8.5, 3.0 Hz), 7.66 (1H, td, J=8.7, 2.3 Hz), 7.75 (1H, ddd, J=8.7, 4.4, 1.7 Hz), 8.54 (1H, d, J=3.0 Hz).

D) N-[(3R,4S)-3-{[2,3-difluoro-4-(5-fluoropyridin-2-yl)phenoxy]methyl}tetrahydro-2H-pyran-4-yl]ethanesulfonamide A mixture of tert-butyl ((3R,4S)-3-((2,3-difluoro-4-(5-fluoropyridin-2-yl)phenoxy)methyl)tetrahydro-2H-pyran-4-yl)carbamate (68 mg) and 2 M HCl/EtOH (5 ml) was stirred at room temperature for 1 h. It was concentrated in vacuo. The residue was added THF(dry) (15 ml), triethylamine (235 mg) and ethanesulfonyl chloride (100 mg) at room temperature. The mixture was stirred at room temperature overnight. It was added sat. NaHCO₃ aq. and silica gel and concentrated in vacuo. The residue was purified by column chromatography (silica gel, eluted with EtOAc in hexane) to give the title compound (21.5 mg) as a pale yellow gum.

¹H NMR (300 MHz, CDCl₃) δ 1.33 (3H, t, J=7.3 Hz), 1.62-1.79 (1H, m), 1.97-2.09 (1H, m), 2.12-2.22 (1H, m), 2.97-3.08 (2H, m), 3.41-3.68 (3H, m), 4.01 (1H, d, J=8.7 Hz), 4.10-4.24 (4H, m), 6.81-6.91 (1H, m), 7.47 (1H, td, J=8.3, 3.0 Hz), 7.63-7.79 (2H, m), 8.55 (1H, d, J=3.0 Hz).

Example 251

N-[(3R,4S)-4-{[4-(3,5-difluoropyridin-2-yl)phenoxy]methyl}tetrahydro-2H-pyran-3-yl]ethanesulfonamide A) 4-(3,5-difluoropyridin-2-yl)phenol A mixture of Na₂CO₃ (5.69 g), Pd(Ph₃P)₄ (0.465 g), 2-bromo-3,5-difluoropyridine (2.60 g) and (4-hydroxyphenyl)boronic acid (3.7 g) in DME (75 ml) and water (15 ml) was stirred at 80° C. under N₂ for 2 days. It was added silica gel and concentrated in vacuo. The residue was purified by column chromatography (silica gel, eluted with EtOAc in hexane) to give the title compound (2.10 g) as a pale yellow solid.

LC/MS [M+1]: 208.1

B) tert-butyl ((3R,4S)-4-((4-(3,5-difluoropyridin-2-yl)phenoxy)methyl)tetrahydro-2H-pyran-3-yl)carbamate A mixture of Bu₃P (0.853 ml), ADDP (873 mg), 4-(3,5-difluoropyridin-2-yl)phenol (466 mg) and tert-butyl ((3R,4S)-4-(hydroxymethyl)tetrahydro-2H-pyran-3-yl)carbamate (400 mg) in THF(dry) (25 ml) was stirred at room temperature overnight. The mixture was poured into 1 N NaOH aq. and extracted with EtOAc. The organic layer was separated, washed with 1 N NaOH aq. and brine, dried over MgSO₄ and concentrated in vacuo. The residue was purified by column chromatography (silica gel, eluted with EtOAc in hexane) to give the title compound (443 mg) as a white solid.

¹H NMR (300 MHz, CDCl₃) δ 1.42 (9H, s), 1.56-1.76 (1H, m), 1.84-2.06 (2H, m), 3.01-3.16 (1H, m), 3.32-3.49 (1H, m), 3.52-3.72 (1H, m), 3.85-4.22 (4H, m), 4.42-4.62 (1H, m), 6.93-7.04 (2H, m 7.21-7.34 (1H, m), 7.82-7.94 (2H, m), 8.40 (1H, d, J=2.3 Hz).

C) N-[(3R,4S)-4-{[4-(3,5-difluoropyridin-2-yl)phenoxy]methyl}tetrahydro-2H-pyran-3-yl]ethanesulfonamide A mixture of tert-butyl ((3R,4S)-4-((4-(3,5-difluoropyridin-2-yl)phenoxy)methyl)tetrahydro-2H-pyran-3-yl)carbamate (145 mg) and 2 M HCl/EtOH (5 ml) was stirred at room temperature for 1 h. It was concentrated in vacuo. The residue was added THF(dry) (25 ml), triethylamine (523 mg) and ethanesulfonyl chloride (222 mg) at room temperature. The mixture was stirred at room temperature overnight. It was added sat. NaHCO₃ aq. and silica gel and concentrated in vacuo. The residue was purified by column chromatography (silica gel, eluted with EtOAc in hexane) to give the title compound (89 mg) as a pale yellow solid. The solid was crystallized from EtOAc-hexane to give the title compound as a pale yellow solid.

¹H NMR (300 MHz, CDCl₃) δ 1.26 (3H, t, J=7.4 Hz), 1.73-2.02 (3H, m), 2.97 (2H, q, J=7.2 Hz), 3.12-3.23 (1H, m), 3.35-3.58 (2H, m), 3.95-4.05 (1H, m), 4.12 (2H, d, J=4.5 Hz), 4.22 (1H, d, J=6.1 Hz), 4.34-4.45 (1H, m), 6.93-7.06 (2H, m), 7.21-7.32 (1H, m), 7.84-7.96 (2H, m), 8.41 (1H, s).

Example 252

N-[(3R,4S)-3-{[4-(5-fluoropyrimidin-2-yl)phenoxy]methyl}tetrahydro-2H-pyran-4-yl]ethanesulfonamide A) 4-(5-fluoropyrimidin-2-yl)phenol A mixture of Pd(Ph₃P)₄ (0.916 g), Na₂CO₃ (8.40 g), 2-chloro-5-fluoropyrimidine (3.5 g) and (4-hydroxyphenyl)boronic acid (5.46 g) in DME (70 ml) and water (15 ml) was stirred at 80° C. under N₂ overnight. It was added silica gel and concentrated in vacuo. The residue was purified by column chromatography (silica gel, eluted with EtOAc in hexane) to give the title compound (3.17 g) as a white solid.

LC/MS [M+1]: 191.1

B) tert-butyl ((3R,4S)-3-((4-(5-fluoropyrimidin-2-yl)phenoxy)methyl)tetrahydro-2H-pyran-4-yl)carbamate A mixture of tert-butyl ((3S,4S)-3-(hydroxymethyl)tetrahydro-2H-pyran-4-yl)carbamate (250 mg), 4-(5-fluoropyrimidin-2-yl)phenol (267 mg), tributylphosphine (437 mg) and ADDP (545 mg) in THF(dry) (25 ml) was stirred at room temperature overnight. The mixture was poured into 1 N NaOH aq. and extracted with EtOAc. The organic layer was separated, washed with 1 N NaOH aq. and brine, dried over MgSO₄ and concentrated in vacuo. The residue was purified by column chromatography (silica gel, eluted with EtOAc in hexane) to give the title compound (374 mg) as a white solid.

¹H NMR (300 MHz, CDCl₃) δ 1.43 (9H, s), 1.47-1.68 (1H, m), 1.92-2.12 (2H, m), 3.23-3.39 (1H, m), 3.48 (1H, td, J=11.7, 2.3 Hz), 3.58-3.76 (1H, m), 3.80-3.93 (1H, m), 3.94-4.06 (1H, m), 4.13 (1H, dd, J=9.8, 3.8 Hz), 4.18-4.32 (1H, m), 4.52 (1H, d, J=7.9 Hz), 6.92-7.03 (2H, m), 8.26-8.37 (2H, m), 8.60 (2H, s).

C) N-[(3R,4S)-3-{[4-(5-fluoropyrimidin-2-yl)phenoxy]methyl}tetrahydro-2H-pyran-4-yl]ethanesulfonamide A mixture of tert-butyl ((3R,4S)-3-((4-(5-fluoropyrimidin-2-yl)phenoxy)methyl)tetrahydro-2H-pyran-4-yl)carbamate (190 mg) and 4 M HCl/EtOAc (5 ml) was stirred at room temperature for 1 h. It was concentrated in vacuo. The residue was added THF(dry) (25 ml), triethylamine (715 mg) and ethanesulfonyl chloride (303 mg) at room temperature. The mixture was stirred at room temperature for 1 h. It was added sat. NaHCO₃ and silica gel and concentrated in vacuo. The residue was purified by column chromatography (silica gel, eluted with EtOAc in hexane) to give the title compound (101 mg) as a pale yellow solid. The solid was crystallized from EtOAc-hexane to give the title compound as a pale yellow solid.

¹H NMR (300 MHz, DMSO-d₆) δ 1.13 (3H, t, J=7.3 Hz), 1.51-1.69 (1H, m), 1.85-2.02 (2H, m), 2.97 (2H, q, J=7.3 Hz), 3.32-3.43 (3H, m), 3.79-3.90 (1H, m), 3.95-4.09 (2H, m), 4.20 (1H, dd, J=9.8, 3.0 Hz), 7.01-7.12 (2H, m), 7.30 (1H, d, J=8.7 Hz), 8.23-8.33 (2H, m), 8.92 (2H, s).

Example 253

N-[(3R,4S)-3-{[4-(5-chloropyrimidin-2-yl)phenoxy]methyl}tetrahydro-2H-pyran-4-yl]ethanesulfonamide A) 4-(5-chloropyrimidin-2-yl)phenol A mixture of Pd(Ph$_3$P)$_4$ (1.07 g), Na$_2$CO$_3$ (9.82 g), 2,5-dichloropyrimidine (4.6 g) and (4-hydroxyphenyl)boronic acid (5.11 g) in DME (70 ml) and water (15 ml) was stirred at 80° C. under N$_2$ overnight. It was added silica gel and concentrated in vacuo. The residue was purified by column chromatography (silica gel, eluted with EtOAc in hexane) to give the title compound (2.76 g) as a white solid.
MS (API−), found: 205.0.

B) tert-butyl ((3R,4S)-3-((4-(5-chloropyrimidin-2-yl)phenoxy)methyl)tetrahydro-2H-pyran-4-yl)carbamate A mixture of tert-butyl ((3S,4S)-3-(hydroxymethyl)tetrahydro-2H-pyran-4-yl)carbamate (250 mg), 4-(5-chloropyrimidin-2-yl)phenol (335 mg), tributylphosphine (437 mg) and ADDP (545 mg) in THF (25 ml) was stirred at room temperature overnight. The mixture was poured into 1 N NaOH aq. and extracted with EtOAc. The organic layer was separated, is washed with 1 N NaOH aq. and brine, dried over MgSO$_4$ and concentrated in vacuo. The residue was purified by column, chromatography (silica gel, eluted with EtOAc in hexane) to give the title compound (367 mg) as a white solid.
$^1$H NMR (300 MHz, CDCl$_3$) δ 1.42 (9H, s), 1.48-1.67 (1H, m), 1.92-2.09 (2H, m), 3.20-3.40 (1H, m), 3.48 (1H, td, J=11.7, 2.3 Hz), 3.58-3.74 (1H, m), 3.79-3.94 (1H, m), 3.95-4.06 (1H, m), 4.14 (1H, dd, J=9.6, 3.6 Hz), 4.18-4.32 (1H, m), 4.52 (1H, d, J=7.2 Hz), 6.92-7.01 (2H, m), 8.28-8.41 (2H, m), 8.68 (2H, s).

C) N-[(3R,4S)-3-{[4-(5-chloropyrimidin-2-yl)phenoxy]methyl}tetrahydro-2H-pyran-4-yl]ethanesulfonamide A mixture of tert-butyl ((3R,4S)-3-((4-(5-chloropyrimidin-2-yl)phenoxy)methyl)tetrahydro-2H-pyran-4-yl)carbamate (200 mg) and 4N hydrogen chloride in EtOAc (5 ml) was stirred at room temperature for 1 h. It was concentrated in vacuo. The residue was added THF (25 ml), triethylamine (723 mg) and ethanesulfonyl chloride (306 mg) at room temperature. The mixture was stirred at room temperature for 1 h. It was added sat. NaHCO$_3$ aq. and silica gel and concentrated in vacuo. The residue was purified by column chromatography (silica gel, eluted with EtOAc in hexane) to give the title compound (146 mg) as a pale yellow solid. The solid was crystallized from EtOAc-hexane-IPE to give the title compound as a pale yellow solid.
$^1$H NMR (300 MHz, DMSO-d$_6$) δ 1.13 (3H, t, J=7.2 Hz), 1.48-1.72 (1H, m), 1.85-2.03 (2H, m), 2.98 (2H, q, J=7.3 Hz), 3.32-3.44 (3H, m), 3.78-3.90 (1H, m), 3.96-4.09 (2H, m), 4.14-4.24 (1H, m), 7.01-7.12 (2H, m), 7.30 (1H, d, J=8.7 Hz), 8.27-8.35 (2H, m), 8.94 (2H, s).

Example 254

N-[(3R,4S)-3-{[4-(5-chloropyridin-2-yl)phenoxy]methyl}tetrahydro-2H-pyran-4-yl]methanesulfonamide A) tert-butyl ((3R,4S)-3-((4-(5-chloropyridin-2-yl)phenoxy)methyl)tetrahydro-2H-pyran-4-yl)carbamate A mixture of tert-butyl ((3S,4S)-3-(hydroxymethyl)tetrahydro-2H-pyran-4-yl)carbamate (100 mg), 4-(5-chloropyridin-2-yl)phenol (116 mg), ADDP (164 mg) and Bu$_3$P (0.160 ml) in toluene (8 ml) was stirred at room temperature over weekend. The mixture was purified by column chromatography (NH silica gel, eluted with EtOAc in hexane) to give the title compound (156 mg) as a white solid.
MS (API+), found: 419.2.

B) N-[(3R,4S)-3-{[4-(5-chloropyridin-2-yl)phenoxy]methyl}tetrahydro-2H-pyran-4-yl]methanesulfonamide A mixture of tert-butyl ((3R,4S)-3-((4-(5-chloropyridin-2-yl)phenoxy)methyl)tetrahydro-2H-pyran-4-yl)carbamate (750 mg) and 4 M HCl/EtOAc (5 ml) was stirred at room temperature for 1 h. It was concentrated in vacuo. The residue was added THF (25 ml), triethylamine (2.72 g) and methanesulfonyl chloride (1.03 g) at room temperature. The mixture was stirred at room temperature for 2 days. It was added sat. NaHCO$_3$ aq. and silica gel and concentrated in vacuo. The residue was purified by column chromatography (silica gel, eluted with EtOAc in hexane) to give the title compound (568 mg) as a white solid. The solid was crystallized from EtOAc-hexane-IPE to give the title compound as a white solid.
$^1$H NMR (300 MHz, DMSO-d$_6$) δ 1.46-1.71 (1H, m), 1.81-2.05 (2H, m), 2.90 (3H, s), 3.32-3.47 (3H, m), 3.77-3.91 (1H, m), 3.94-4.10 (2H, m), 4.18 (1H, dd, J=9.8, 3.0 Hz), 6.95-7.10 (2H, m), 7.31 (1H, d, J=8.7 Hz), 7.94 (2H, d, J=1.1 Hz), 8.03 (2H, d, J=9.0 Hz), 8.64 (1H, t, J=1.5 Hz).

Example 255

N-[(3R,4S)-3-{[4-(5-chloropyridin-2-yl)-3-fluorophenoxy]methyl}tetrahydro-2H-pyran-4-yl]methanesulfonamide or N-[(3S,4R)-3-{[4-(5-chloropyridin-2-yl)-3-fluorophenoxy]methyl}tetrahydro-2H-pyran-4-yl]methanesulfonamide Racemic mixture of N-((3RS,4SR)-3-((4-(5-chloropyridin-2-yl)-3-fluorophenoxy)methyl)tetrahydro-2H-pyran-4-yl)methanesulfonamide (89.5 mg) was separated by HPLC (column: CHIRALPAK AD (LF001), 50 mmID×500 mL, DAICEL corporation, mobile phase: EtOH) to give the title compound with a shorter retention time (38.9 mg) as a white solid.
MS (API+), found: 414.9.

Example 256

N-[(3R,4S)-3-{[4-(5-chloro-3-fluoropyridin-2-yl)phenoxy]methyl}tetrahydro-2H-pyran-4-yl]cyclopropanesulfonamide A) 4-(5-chloro-3-fluoropyridin-2-yl)phenol A mixture of Pd(Ph$_3$P)$_4$ (0.418 g), 2,5-dichloro-3-fluoropyridine (2 g), Na$_2$CO$_3$ (3.83 g) and (4-hydroxyphenyl)

boronic acid (3.32 g) in DME (50 ml) and water (10 ml) was stirred at 80° C. under N₂ overnight. It was added silica gel and concentrated in vacuo. The residue was purified by column chromatography (silica gel, eluted with EtOAc in hexane) to give the title compound (1.94 g) as a white solid.
MS (API+), found: 224.0.

B) tert-butyl ((3R,4S)-3-((4-(5-chloro-3-fluoropyridin-2-yl)phenoxy)methyl)tetrahydro-2H-pyran-4-yl)carbamate A mixture of Bu₃P (0.427 ml), ADDP (436 mg), 4-(5-chloro-3-fluoropyridin-2-yl)phenol (232 mg) and tert-butyl ((3S,4S)-3-(hydroxymethyl)tetrahydro-2H-pyran-4-yl)carbamate (200 mg) in THF (20 ml) was stirred at room temperature overnight. The mixture was poured into 1 M NaOH aq. and extracted with EtOAc. The organic layer was separated, washed with 1 M NaOH aq. and brine, dried over MgSO₄ and concentrated in vacuo. The residue was purified by column chromatography (silica gel, eluted with EtOAc in hexane) to give the title compound (298 mg) as a white solid.
MS (API+), found: 437.2.

C) N-[(3R,4S)-3-{[4-(5-chloro-3-fluoropyridin-2-yl)phenoxy]methyl}tetrahydro-2H-pyran-4-yl]cyclopropanesulfonamide A mixture of tert-butyl ((3R,4S)-3-((4-(5-chloro-3-fluoropyridin-2-yl)phenoxy)methyl)tetrahydro-2H-pyran-4-yl)carbamate (291 mg) and 2 M HCl/EtOH (5 ml) was stirred at room temperature for 1 h. It was concentrated in vacuo. The residue was added THF (20 ml), triethylamine (1.01 g), DBU (1.00 ml) and cyclopropanesulfonyl chloride (468 mg) at room temperature. The mixture was stirred at room temperature overnight. It was added sat. NaHCO₃ aq. and silica gel and concentrated in vacuo. The residue was purified by column chromatography (silica gel, eluted with EtOAc in hexane) to give the title compound (211 mg) as a white solid. The solid was crystallized from EtOAc-hexane-IPE to give the title compound as a white solid.
¹H NMR (300 MHz, DMSO-d₆) δ 0.76-1.00 (4H, m), 1.47-1.77 (1H, m), 1.81-2.06 (2H, m), 2.53-2.64 (1H, m), 3.29-3.47 (3H, m), 3.80-3.92 (1H, m), 3.93-4.11 (2H, m), 4.23 (1H, dd, J=10.0, 3.2 Hz), 7.02-7.12 (2H, m), 7.33 (1H, d, J=8.7 Hz), 7.80-7.93 (2H, m), 8.15 (1H, dd, J=11.3, 1.9 Hz), 8.53-8.63 (1H, m).

Example 257

N-[(3R,4S)-3-{[4-(5-chloro-1,3-thiazol-2-yl)phenoxy]methyl}tetrahydro-2H-pyran-4-yl]ethanesulfonamide A) 2-(4-methoxyphenyl)-1,3-thiazole A mixture of (4-methoxyphenyl)boronic acid (25 g), 2-bromothiazole (18.0 g), Na₂CO₃ (23.3 g) and Pd(Ph₃P)₄ (2.53 g) in DME (250 ml) and water (50 ml) was stirred at 80° C. under N₂ overnight. It was added silica gel and concentrated in vacuo. The residue was purified by column chromatography (NH silica gel, eluted with EtOAc in hexane) and column chromatography (silica gel, eluted with EtOAc in hexane) to give the title compound (9.86 g) as a colorless oil.
MS (API+), found: 192.0.

B) 5-chloro-2-(4-methoxyphenyl)-1,3-thiazole

To a mixture of 2-(4-methoxyphenyl)-1,3-thiazole (1.15 g) in THF (25 ml) was added n-BuLi (5.64 ml, 1.6M in hexane) at 0° C. The mixture was stirred at 0° C. under N₂ for 1.5 h. NCS (0.883 g) was added to the mixture at 0° C. The mixture was stirred at room temperature under N₂ for 2 h. The mixture was poured into sat. NH₄Cl aq. and extracted with EtOAc. The organic layer was separated, washed with brine, dried over MgSO₄ and concentrated in vacuo. The residue was purified by column chromatography (silica gel, eluted with EtOAc in hexane) to give 5-chloro-2-(4-methoxyphenyl)-1,3-thiazole (0.626 g) as a pale yellow solid.
MS (API+), found: 226.1.

C) 4-(5-chloro-1,3-thiazol-2-yl)phenol

A mixture of 5-chloro-2-(4-methoxyphenyl)-1,3-thiazole (1.2 g), 1-dodecanethiol (3.23 g) and AlCl₃ (2.13 g) in toluene (35 ml) was stirred at 0° C. for 1 h and at room temperature for 1 h. The mixture was poured into 1 N HCl aq. and extracted with EtOAc. The organic layer was separated, washed with brine, dried over MgSO₄ and concentrated in vacuo. The residue was triturated from hexane to give the title compound (1.00 g) as a yellow solid.
MS (API−), found: 209.9.

D) tert-butyl ((3R,4S)-3-((4-(5-chloro-1,3-thiazol-2-yl)phenoxy)methyl)tetrahydro-2H-pyran-4-yl)carbamate A mixture of tert-butyl ((3S,4S)-3-(hydroxymethyl)tetrahydro-2H-pyran-4-yl)carbamate (400 mg), 4-(5-chloro-1,3-thiazol-2-yl)phenol (439 mg), Bu₃P (0.853 ml) and ADDP (873 mg) in THF (25 ml) was stirred at room temperature overnight. The mixture was poured into 1 N NaOH aq. and extracted with EtOAc. The organic layer was separated, washed with 1 M NaOH aq. and brine, dried over MgSO₄ and concentrated in vacuo. The residue was purified by column chromatography (silica gel, eluted with EtOAc in hexane) to give the title compound (621 mg) as a white solid.
¹H NMR (300 MHz, CDCl₃) δ 1.42 (9H, s), 1.48-1.68 (1H, m), 1.88-2.08 (2H, m), 3.31 (1H, t, J=11.1 Hz), 3.48 (1H, td, J=11.8, 2.1 Hz), 3.57-3.75 (1H, m), 3.77-3.92 (1H, m), 3.94-4.05 (1H, m), 4.05-4.15 (1H, m), 4.16-4.31 (1H, m), 4.52 (1H, d, J=8.3 Hz), 6.85-6.98 (2H, m), 7.57 (1H, s), 7.72-7.84 (2H, m).

E) N-[(3R,4S)-3-{[4-(5-chloro-1,3-thiazol-2-yl)phenoxy]methyl}tetrahydro-2H-pyran-4-yl]ethanesulfonamide A mixture of tert-butyl ((3R,4S)-3-((4-(5-chloro-1,3-thiazol-2-yl)phenoxy)methyl)tetrahydro-2H-pyran-4-yl)carbamate (230 mg) and 2 M HCl/EtOH (5 ml) was stirred at room temperature for 1 h. It was concentrated in vacuo. The residue was added THF (25 ml), triethylamine (822 mg) and ethanesulfonyl chloride (348 mg) at room temperature. The mixture was stirred at room temperature overnight. It was added sat. NaHCO₃ aq. and silica gel and concentrated in vacuo. The residue was purified by column chromatography (silica gel, eluted with EtOAc in hexane) to give the title compound (146 mg) as a pale yellow gum. The solid was triturated from EtOAc-hexane to give the title compound as a pale yellow solid.
¹H NMR (300 MHz, DMSO-d₆) δ 1.13 (3H, t, J=7.3 Hz), 1.50-1.68 (1H, m), 1.83-2.00 (2H, m), 2.97 (2H, q, J=7.2 Hz), 3.25-3.43 (3H, m), 3.77-3.90 (1H, m), 3.96-4.07 (2H, m), 4.13-4.21 (1H, m), 6.98-7.10 (2H, m), 7.29 (1H, d, J=8.7 Hz), 7.78-7.86 (2H, m), 7.87 (1H, s).

Example 258

1,5-anhydro-2,3,4-trideoxy-4-[(ethylsulfonyl)amino]-6-O-[4-(5-methyl-1,3-thiazol-2-yl)phenyl]-D-erythro-hexitol A) tert-butyl ((2S,3S)-2-((4-(5-methylthiazol-2-yl)phenoxy)methyl)tetrahydro-2H-pyran-3-yl)carbamate A mixture of tert-butyl ((2S,3S)-2-(hydroxymethyl)tetrahydro-2H-pyran-3-yl)carbamate (150 mg), 4-(5-methylthiazol-2-yl)phenol (149 mg), Bu$_3$P (0.320 ml) and ADDP (327 mg) in THF (10 ml) was stirred at room temperature for 3 days. The mixture was concentrated in vacuo. The residue was purified by column chromatography (silica gel, eluted with EtOAc in hexane) to give the title compound (48.5 mg) as a white solid.
MS (API+), found: 405.2.

B) 1,5-anhydro-2,3,4-trideoxy-4-((ethylsulfonyl)amino)-6-O-(4-(5-methyl-1,3-thiazol-2-yl)phenyl)-D-erythro-hexitol A mixture of tert-butyl ((2S,3S)-2-((4-(5-methylthiazol-2-yl)phenoxy)methyl)tetrahydro-2H-pyran-3-yl)carbamate (45 mg) and 2 M HCl/EtOH (3 ml) was stirred at room temperature for 1 h. It was concentrated in vacuo. The residue was added THF (15 ml), triethylamine (169 mg) and ethanesulfonyl chloride (71.5 mg) at room temperature. The mixture was stirred at room temperature for 1 h. It was added sat. NaHCO$_3$ aq. and silica gel and concentrated in vacuo. The residue was purified by column chromatography (silica gel, eluted with EtOAc in hexane). The residue was purified by preparative HPLC (L-Column 2 ODS, eluted with H$_2$O in acetonitrile containing 0.1% TFA). The desired fraction was neutralized with sat. NaHCO$_3$ aq. and extracted with EtOAc. The organic layer was separated, dried over MgSO$_4$ and concentrated in vacuo to give the title compound (3.20 mg) as a pale yellow solid.
$^1$H NMR (300 MHz, CDCl$_3$) δ 1.24 (3H, t, J=7.4 Hz), 1.39-1.53 (1H, m), 1.67-1.93 (2H, m), 2.33-2.45 (1H, m), 2.49 (3H, d, J=1.1 Hz), 2.97 (2H, q, J=7.6 Hz), 3.37-3.59 (3H, m), 3.98-4.08 (1H, m), 4.11 (1H, d, J=9.5 Hz), 4.17-4.25 (1H, m), 4.27-4.35 (1H, m), 6.92-7.04 (2H, m), 7.41-7.46 (1H, m), 7.76-7.85 (2H, m).

Example 259

N-[(1S,2S)-2-{[4-(5-cyanopyrimidin-2-yl)phenoxy]methyl}-4,4-difluorocyclohexyl]methanesulfonamide A) 2-(4-hydroxyphenyl)pyrimidine-5-carbonitrile A mixture of 4-(5-chloropyrimidin-2-yl)phenol (1.5 g), dicyanozinc (0.852 g), DPPF (0.402 g) and Pd$_2$(dba)$_3$ (0.332 g) in DMF (10 ml) was stirred at 120° C. under N$_2$ overnight. The mixture was poured into brine and extracted with EtOAc. The organic layer was separated, washed with brine, dried over MgSO$_4$ and concentrated in vacuo. The residue was purified by column chromatography (silica gel, eluted with EtOAc in hexane) to give the title compound (0.431 g) as a off-white solid.
MS (API+), found: 197.99.

B) tert-butyl ((1S,2S)-2-((4-(5-cyanopyrimidin-2-yl)phenoxy)methyl)-4,4-difluorocyclohexyl)carbamate A mixture of Bu$_3$P (0.930 ml), ADDP (951 mg), tert-butyl ((1S,2S)-4,4-difluoro-2-(hydroxymethyl)cyclohexyl)carbamate (500 mg) and 2-(4-hydroxyphenyl)pyrimidine-5-carbonitrile (409 mg) in toluene (25 ml) was stirred at room temperature overnight. The mixture was concentrated in vacuo. The residue was purified by column chromatography (silica gel, eluted with EtOAc in hexane) to give the title compound (690 mg) as a white solid.
$^1$H NMR (300 MHz, CDCl$_3$) δ 1.39 (9H, s), 1.49-1.69 (2H, m), 1.69-2.27 (4H, m), 2.44 (1H, brs), 3.52-3.71 (1H, m), 3.91-4.04 (1H, m), 4.05-4.18 (1H, m), 4.35-4.54 (1H, m), 6.92-7.07 (2H, m), 8.38-8.53 (2H, m), 8.96 (2H, s).

C) N-[(1S,2S)-2-{[4-(5-cyanopyrimidin-2-yl)phenoxy]methyl}-4,4-difluorocyclohexyl]methanesulfonamide A mixture of tert-butyl ((1S,2S)-2-((4-(5-cyanopyrimidin-2-yl)phenoxy)methyl)-4,4-difluorocyclohexyl)carbamate (225 mg) and 2 M HCl/EtOH (5 ml) was stirred at room temperature for 1 h. It was concentrated in vacuo. The residue was added THF (20 ml), triethylamine (768 mg) and methanesulfonyl chloride (290 mg) at room temperature. The mixture was stirred at room temperature for 1 h. It was added sat. NaHCO$_3$ aq. and silica gel and concentrated in vacuo. The residue was purified by column chromatography (silica gel, eluted with EtOAc in hexane) to give the title compound (174 mg) as a white solid. The solid was crystallized from EtOAc-hexane to give the title compound as a white solid.
$^1$H NMR (300 MHz, CDCl$_3$) δ 1.59-2.45 (7H, m), 2.84 (3H, s), 3.43-3.67 (1H, m), 3.93-4.09 (1H, m), 4.21-4.36 (2H, m), 6.98-7.07 (2H, m), 8.43-8.51 (2H, m), 8.97 (2H, s).

Example 260

N-[(1SR,2SR)-2-{[4-(5-cyanopyridin-2-yl)phenoxy]methyl}-4,4-difluorocyclohexyl]methanesulfonamide A) tert-butyl ((1SR,2SR)-2-((4-(5-cyanopyridin-2-yl)phenoxy)methyl)-4,4-difluorocyclohexyl)carbamate A mixture of Bu$_3$P (0.744 ml), ADDP (761 mg), 6-(4-hydroxyphenyl)nicotinonitrile (385 mg) and tert-butyl (1SR,2SR)-4,4-difluoro-2-(hydroxymethyl)cyclohexylcarbamate (400 mg) in THF (30 ml) was stirred at room temperature overnight. The mixture was poured into 1 N NaOH aq. and extracted with EtOAc. The organic layer was separated, washed with 1 N NaOH aq. and brine, dried over MgSO$_4$ and concentrated in vacuo. The residue was purified by column chromatography (silica gel, eluted with EtOAc in hexane) to give the title compound (555 mg) as a pale yellow solid.
$^1$H NMR (300 MHz, CDCl$_3$) δ 1.40 (9H, s), 1.50-1.69 (3H, m), 1.70-2.01 (1H, m), 2.02-2.26 (2H, m), 2.37-2.49 (1H, m), 3.50-3.72 (1H, m), 3.96 (1H, d, J=8.0 Hz), 4.02-4.15 (1H, m), 4.40-4.52 (1H, m), 6.94-7.04 (2H, m), 7.78 (1H, d, J=8.3 Hz), 7.95 (1H, dd, J=8.5, 2.1 Hz), 8.01 (2H, d, J=8.7 Hz), 8.89 (1H, d, J=1.9 Hz).

B) N-[(1SR,2SR)-2-{[4-(5-cyanopyridin-2-yl)phenoxy]methyl}-4,4-difluorocyclohexyl]methanesulfonamide A mixture of tert-butyl (1SR,2SR)-2-((4-(5-cyanopyridin-2-yl)phenoxy)methyl)-4,4-difluorocyclohexylcarbamate (205 mg) and 2 M HCl/EtOH (5 ml) was stirred at room temperature for 1 h. It was concentrated in vacuo. The residue was added THF (25 ml), triethylamine (703 mg) and methanesulfonyl chloride (265 mg) at room temperature and stirred at the same temperature for 4 h. It was added silica gel and concentrated in vacuo. The residue was purified by column chromatography (silica gel, eluted with EtOAc in hexane) to give the title compound (132 mg) as a pale yellow solid. The solid was crystallized from IPE-EtOAc-hexane to give the title compound as a white solid.

$^1$H NMR (300 MHz, CDCl$_3$) δ 1.60-2.40 (7H, m), 2.84 (3H, s), 3.45-3.62 (1H, m), 4.01 (1H, dd, J=9.4, 2.3 Hz), 4.21-4.30 (1H, m), 4.36 (1H, d, J=9.4 Hz), 6.97-7.08 (2H, m), 7.77 (1H, dd, J=8.3, 0.8 Hz), 7.96 (1H, dd, J=8.3, 2.3 Hz), 7.99-8.08 (2H, m), 8.89 (1H, dd, J=2.3, 0.8 Hz).

Example 261

N-[(3RS,4SR)-3-{[4-(5-chloro-1,3-thiazol-2-yl)phenoxy]methyl}tetrahydro-2H-pyran-4-yl]ethanesulfonamide A) tert-butyl ((3RS,4SR)-3-((4-(5-chloro-1,3-thiazol-2-yl)phenoxy)methyl)tetrahydro-2H-pyran-4-yl)carbamate A mixture of ADDP (596 mg), Bu$_3$P (0.583 ml), 4-(5-chloro-1,3-thiazol-2-yl)phenol (250 mg) and tert-butyl ((3SR,4SR)-3-(hydroxymethyl)tetrahydro-2H-pyran-4-yl)carbamate (273 mg) in THF (20 ml) was stirred at room temperature overnight. The mixture was poured into 1 N NaOH aq. and extracted with EtOAc. The organic layer was separated, washed with 1 N NaOH aq. and brine, dried over MgSO$_4$ and concentrated in vacuo. The residue was purified by column chromatography (silica gel, eluted with EtOAc in hexane) to give tert-butyl ((3RS,4SR)-3-((4-(5-chloro-1,3-thiazol-2-yl)phenoxy)methyl)tetrahydro-2H-pyran-4-yl)carbamate (308 mg) as a white solid.

$^1$H NMR (300 MHz, CDCl$_3$) δ 1.42 (9H, s), 1.49-1.67 (1H, m), 1.90-2.06 (2H, m), 3.16-3.39 (1H, m), 3.47 (1H, td, J=11.7, 2.3 Hz), 3.57-3.72 (1H, m), 3.78-3.92 (1H, m), 4.00 (1H, dd, J=11.7, 3.0 Hz), 4.05-4.15 (1H, m), 4.22 (1H, dd, J=11.5, 4.0 Hz), 4.51 (1H, d, J=8.3 Hz), 6.86-6.96 (2H, m), 7.57 (1H, s), 7.71-7.81 (2H, m).

B) N-[(3RS,4SR)-3-{[4-(5-chloro-1,3-thiazol-2-yl)phenoxy]methyl}tetrahydro-2H-pyran-4-yl]ethanesulfonamide A mixture of 2 M HCl/EtOH (5 ml) and tert-butyl ((3RS,4SR)-3-((4-(5-chloro-1,3-thiazol-2-yl)phenoxy)methyl)tetrahydro-2H-pyran-4-yl)carbamate (100 mg) was stirred at room temperature for 1 h. It was concentrated in vacuo. The residue was added THF (25 ml), triethylamine (357 mg) and ethanesulfonyl chloride (151 mg) at room temperature. The mixture was stirred at room temperature overnight. It was added silica gel and concentrated in vacuo. The residue was purified by column chromatography (silica gel, eluted with EtOAc in hexane) to give the title compound (53.4 mg) as a white solid. The solid was crystallized from EtOAc-hexane-IPE to give a desired product as a white solid.

$^1$H NMR (300 MHz, DMSO-d$_6$) δ 1.13 (3H, t, J=7.3 Hz), 1.49-1.71 (1H, m), 1.83-2.04 (2H, m), 2.97 (2H, q, J=7.4 Hz), 3.29-3.47 (3H, m), 3.85 (1H, d, J=10.9 Hz), 3.95-4.09 (2H, m), 4.18 (1H, d, J=10.2 Hz), 7.05 (2H, d, J=8.7 Hz), 7.29 (1H, d, J=8.7 Hz), 7.83 (2H, d, J=8.7 Hz), 7.86-7.92 (1H, m).

Example 262

N-[(3RS,4SR)-3-{[4-(5-chloro-3-fluoropyridin-2-yl)phenoxy]methyl}tetrahydro-2H-pyran-4-yl]cyclopropanesulfonamide A) tert-butyl ((3RS,4SR)-3-((4-(5-chloro-3-fluoropyridin-2-yl)phenoxy)methyl)tetrahydro-2H-pyran-4-yl)carbamate A mixture of Bu$_3$P (0.853 ml), ADDP (873 mg), 4-(5-chloro-3-fluoropyridin-2-yl)phenol (503 mg) and tert-butyl ((3SR,4SR)-3-(hydroxymethyl)tetrahydro-2H-pyran-4-yl)carbamate (400 mg) in THF (25 ml) was stirred at room temperature overnight. The mixture was poured into 1 N NaOH aq. and extracted with EtOAc. The organic layer was separated, washed with 1 N NaOH aq. and brine, dried over MgSO$_4$ and concentrated in vacuo. The residue was purified by column chromatography (silica gel, eluted with EtOAc in hexane) to give the title compound (622 mg) as a white solid.

$^1$H NMR (300 MHz, CDCl$_3$) δ 1.43 (9H, s), 1.48-1.67 (1H, m), 1.90-2.16 (2H, m), 3.31 (1H, t, J=11.1 Hz), 3.48 (1H, td, J=11.8, 2.1 Hz), 3.56-3.75 (1H, m), 3.79-3.92 (1H, m), 3.93-4.05 (1H, m), 4.13 (1H, dd, J=9.4, 3.8 Hz), 4.18-4.32 (1H, m), 4.52 (1H, d, J=6.8 Hz), 6.91-7.02 (2H, m), 7.50 (1H, dd, J=10.7, 2.1 Hz), 7.86-7.99 (2H, m), 8.40-8.48 (1H, m).

B) N-[(3RS,4SR)-3-{[4-(5-chloro-3-fluoropyridin-2-yl)phenoxy]methyl}tetrahydro-2H-pyran-4-yl]cyclopropanesulfonamide A mixture of tert-butyl ((3RS,4SR)-3-((4-(5-chloro-3-fluoropyridin-2-yl)phenoxy)methyl)tetrahydro-2H-pyran-4-yl)carbamate (220 mg) and 2 M HCl/EtOH (5 ml) was stirred at room temperature for 1 h. It was concentrated in vacuo. The residue was added THF (25 ml), DBU (0.759 ml), triethylamine (764 mg) and cyclopropanesulfonyl chloride (354 mg) at room temperature. The mixture was stirred at room temperature overnight. It was added sat. NaHCO$_3$ aq. and silica gel and concentrated in vacuo. The residue was purified by column chromatography (silica gel, eluted with EtOAc in hexane) to give the title compound (62.3 mg) as a white solid. The solid was crystallized from EtOAc-hexane-IPE to give a desired product as a white solid.

$^1$H NMR (300 MHz, CDCl$_3$) δ 0.71-0.97 (2H, m), 1.00-1.25 (2H, m), 1.62-1.81 (1H, m), 1.92-2.10 (1H, m), 2.15-2.27 (1H, m), 2.35 (1H, tt, J=8.0, 4.9 Hz), 3.40-3.71 (3H, m), 3.93-4.06 (1H, m), 4.08-4.23 (3H, m), 4.31 (1H, d, J=9.1 Hz), 6.94-7.04 (2H, m), 7.50 (1H, dd, J=10.6, 2.3 Hz), 7.87-7.99 (2H, m), 8.41-8.49 (1H, m).

Example 263

N-[(3RS,4SR)-3-{[4-(2-methyl-1,3-thiazol-4-yl)phenoxy]methyl}tetrahydro-2H-pyran-4-yl]methanesulfonamide A) 4-(2-methyl-1,3-thiazol-4-yl)phenol A mixture of Pd(Ph$_3$P)$_4$ (0.195 g), Na$_2$CO$_3$.10H$_2$O (3.21 g), 4-bromo-2-methylthiazole (1 g) and 4-hydroxyphenylboronic acid (0.930 g) in DME (25 ml) and water (5 ml) was stirred at 80° C. under N₂ overnight. It was added silica gel and concentrated in vacuo. The residue was purified by column chromatography (silica gel, eluted with EtOAc in hexane) to give the title compound (0.530 g) as a pale yellow solid.

MS (API+), found: 192.0.

B) tert-butyl (3RS,4SR)-3-((4-(2-methyl-1,3-thiazol-4-yl)phenoxy)methyl)tetrahydro-2H-pyran-4-ylcarbamate A mixture of Bu₃P (0.430 ml), ADDP (440 mg), 4-(2-methyl-1,3-thiazol-4-yl)phenol (250 mg) and tert-butyl (3SR,4SR)-3-(hydroxymethyl)tetrahydro-2H-pyran-4-ylcarbamate (202 mg) in toluene (25 ml) was stirred at room temperature overnight. The mixture was poured into 1 M NaOH aq. and extracted with EtOAc. The organic layer was separated, washed with 1 M NaOH aq. and brine, dried over MgSO₄ and concentrated in vacuo. The residue was purified by column chromatography (silica gel, eluted with EtOAc in hexane) to give the title compound (260 mg) as a white solid.

MS (API+), found: 405.2.

C) N-[(3RS,4SR)-3-{[4-(2-methyl-1,3-thiazol-4-yl)phenoxy]methyl}tetrahydro-2H-pyran-4-yl]methanesulfonamide A mixture of 2 M HCl/EtOH (5 ml) and (3RS,4SR)-3-((4-(2-methyl-1,3-thiazol-4-yl)phenoxy)methyl)tetrahydro-2H-pyran-4-amine (86.8 mg) was stirred at room temperature for 1 h. It was concentrated in vacuo. The residue was added THF (25 ml), Et₃N (0.596 ml) and methanesulfonyl chloride (163 mg) and stirred at the same temperature overnight. It was added silica gel and concentrated in vacuo. The residue was purified by column chromatography (silica gel, eluted with EtOAc in hexane) to give the title compound (96 mg) as a white solid. The solid was crystallized from EtOAc-hexane-IPE to give a desired product as a white solid.

¹H NMR (300 MHz, DMSO-d₆) δ 1.45-1.68 (1H, m), 1.80-2.03 (2H, m), 2.69 (3H, s), 2.89 (3H, s), 3.23-3.46 (3H, m), 3.85 (1H, d, J=10.2 Hz), 3.91-4.08 (2H, m), 4.09-4.21 (1H, m), 6.90-7.04 (2H, m), 7.30 (1H, d, J=8.7 Hz), 7.74 (1H, s), 7.79-7.93 (2H, m).

Example 264

N-[(3R,4S)-4-{[2-fluoro-4-(5-fluoropyridin-2-yl)phenoxy]methyl}tetrahydro-2H-pyran-3-yl]cyclopropanesulfonamide A) 5-fluoro-2-(3-fluoro-4-methoxyphenyl)pyridine A mixture of Na₂CO₃ (3.12 g), Pd(Ph₃P)₄ (0.340 g), 2-bromo-5-fluoropyridine (1.73 g) and (3-fluoro-4-methoxyphenyl)boronic acid (2.5 g) in DME (50 ml) and water (10 ml) was stirred at 80° C. under N₂ overnight. It was added silica gel and concentrated in vacuo. The residue was purified by column chromatography (silica gel, eluted with EtOAc in hexane) to give the title compound (2.28 g) as a white solid.

MS (API+), found: 222.1.

B) 2-fluoro-4-(5-fluoropyridin-2-yl)phenol

A mixture of dodecane-1-thiol (6.04 g), AlCl₃ (3.98 g) and 5-fluoro-2-(3-fluoro-4-methoxyphenyl)pyridine (2.2 g) in toluene (50 ml) was stirred at 0° C. for 2 h. The mixture was quenched with 1 N HCl aq. at 0° C. and extracted with EtOAc. The organic layer was separated, washed with sat. NaHCO₃ aq. and brine, dried over MgSO₄ and concentrated in vacuo. The residue was triturated from hexane to give a white solid. It was purified by column chromatography (silica gel, eluted with EtOAc in hexane) to give the title compound (1.50 g) as a white solid.

MS (API+), found: 208.0.

C) tert-butyl ((3R,4S)-4-((2-fluoro-4-(5-fluoropyridin-2-yl)phenoxy)methyl)tetrahydro-2H-pyran-3-yl)carbamate A mixture of Bu₃P (0.853 ml), ADDP (873 mg), 2-fluoro-4-(5-fluoropyridin-2-yl)phenol (430 mg) and tert-butyl ((3R,4S)-4-(hydroxymethyl)tetrahydro-2H-pyran-3-yl)carbamate (400 mg) in THF (20 ml) was stirred at room temperature overnight. The mixture was poured into 1 N NaOH aq. and extracted with EtOAc. The organic layer was separated, washed with 1 N NaOH aq. and brine, dried over MgSO₄ and concentrated in vacuo. The residue was purified by column chromatography (silica gel, eluted with EtOAc in hexane) to give the title compound (556 mg) as a white solid.

¹H NMR (300 MHz, CDCl₃) δ 1.42 (9H, s), 1.59-1.68 (1H, m), 1.89-2.12 (2H, m), 3.09 (1H, t, J=10.4 Hz), 3.42 (1H, t, J=11.1 Hz), 3.54-3.70 (1H, m), 3.90-4.12 (3H, m), 4.20 (1H, dd, J=9.4, 4.1 Hz), 4.56 (1H, d, J=7.2 Hz), 7.02 (1H, t, J=8.5 Hz), 7.44 (1H, td, J=8.5, 3.0 Hz), 7.59-7.68 (2H, m), 7.73 (1H, dd, J=12.6, 2.1 Hz), 8.50 (1H, d, J=2.6 Hz).

D) N-[(3R,4S)-4-{[2-fluoro-4-(5-fluoropyridin-2-yl)phenoxy]methyl}tetrahydro-2H-pyran-3-yl]cyclopropanesulfonamide A mixture of tert-butyl ((3R,4S)-4-((2-fluoro-4-(5-fluoropyridin-2-yl)phenoxy)methyl)tetrahydro-2H-pyran-3-yl)carbamate (190 mg) and 4 M HCl/EtOAc (5 ml) was stirred at room temperature for 1 h. It was concentrated in vacuo. The residue was added THF(dry) (25 ml), triethylamine (686 mg), DBU (0.681 ml) and cyclopropanesulfonyl chloride (318 mg) at room temperature. The mixture was stirred at room temperature overnight. It was added sat. NaHCO₃ aq. and silica gel and concentrated in vacuo. The residue was purified by column chromatography (silica gel, eluted with EtOAc in hexane) to give the title compound (102 mg) as a white solid. The solid was crystallized from EtOAc-hexane-IPE to give a desired product as a white solid.

¹H NMR (300 MHz, DMSO-d₆) δ 0.74-0.96 (4H, m), 1.55-1.74 (1H, m), 1.80-2.01 (2H, m), 2.53-2.63 (1H, m), 3.02-3.13 (1H, m), 3.19-3.36 (2H, m), 3.87 (1H, dd, J=11.5, 3.6 Hz), 3.94 (1H, dd, J=10.6, 4.5 Hz), 4.11-4.21 (1H, m), 4.23-4.34 (1H, m), 7.20-7.30 (1H, m), 7.36 (1H, d, J=8.3 Hz), 7.75-7.95 (3H, m), 8.03 (1H, dd, J=8.9, 4.3 Hz), 8.61 (1H, d, J=2.6 Hz).

Example 265

N-[(3R,4S)-3-({4-[4-(trifluoromethyl)-1H-pyrazol-1-yl]phenoxy}methyl)tetrahydro-2H-pyran-4-yl]methanesulfonamide A) 4-iodo-1-(4-methoxyphenyl)-1H-pyrazole To a mixture of sodium acetate (2.431 g) and 1-(4-methoxyphenyl)-1H-pyrazole (2.58 g) in water (50 ml) was added a mixture of iodine (18.8 g) and potassium iodide (4.92 g) in water (75 ml) at 100° C. The mixture was stirred at 100° C. for 2 days. It was added sat. $Na_2SO_3$ aq. and extracted with EtOAc. The organic layer was separated, washed with brine, dried over $MgSO_4$ and concentrated in vacuo to give the title compound (4.62 g) as a white solid.

LC/MS [M+1]: 301.0

B) 1-(4-methoxyphenyl)-4-(trifluoromethyl)-1H-pyrazole

A mixture of 4-iodo-1-(4-methoxyphenyl)-1H-pyrazole (1.64 g), methyl 2,2-difluoro-2-(fluorosulfonyl)acetate (5.25 g), copper(I)iodide (1.25 g) and HMPA (4.75 ml) in DMF (30 ml) was stirred at 150° C. overnight. The mixture was poured into water at room temperature and filtered through a pad of celite. The filtrate was extracted with EtOAc. The organic layer was separated, washed with water and brine, dried over $Na_2SO_4$ and concentrated in vacuo. The residue was purified by column chromatography (silica gel, eluted with EtOAc in hexane) to give the title compound (1.09 g) as an off-white solid.

$^1$H NMR (300 MHz, $CDCl_3$) δ 3.86 (3H, s), 6.94-7.06 (2H, m), 7.53-7.63 (2H, m), 7.87 (1H, s), 8.08 (1H, d, J=0.8 Hz).

C) 4-(4-(trifluoromethyl)-1H-pyrazol-1-yl)phenol

A mixture of 1-(4-methoxyphenyl)-4-(trifluoromethyl)-1H-pyrazole (1.09 g), aluminum trichloride (3.00 g) and dodecane-1-thiol (5.39 ml) in toluene (25 ml) was stirred at 0° C. for 1 h. The mixture was quenched with 1 M HCl aq. at 0° C. and extracted with EtOAc. The organic layer was separated, washed with brine, dried over $Na_2SO_4$ and concentrated in vacuo. The residue was purified by column chromatography (silica gel, eluted with EtOAc in hexane) to give the title compound (1.01 g) as a white solid.

$^1$H NMR (300 MHz, $CDCl_3$) δ 5.11 (1H, s), 6.87-6.98 (2H, m), 7.48-7.58 (2H, m), 7.87 (1H, s), 8.07 (1H, s).

D) tert-butyl ((3S,4S)-3-(hydroxymethyl)tetrahydro-2H-pyran-4-yl)carbamate

A mixture of $Bu_3P$ (0.320 ml), ADDP (327 mg), 4-(4-(trifluoromethyl)-1H-pyrazol-1-yl)phenol (163 mg) and tert-butyl ((3S,4S)-3-(hydroxymethyl)tetrahydro-2H-pyran-4-yl)carbamate (150 mg) in toluene (10 ml) was stirred at room temperature overnight. The mixture was concentrated in vacuo. The residue was purified by column chromatography (silica gel, eluted with EtOAc in hexane) to give the title compound (250 mg) as a yellow solid.

$^1$H NMR (300 MHz, $CDCl_3$) δ 1.44 (9H, s), 1.47-1.68 (1H, m), 1.86-2.11 (2H, m), 3.32 (1H, t, J=11.2 Hz), 3.48 (1H, td, J=11.9, 2.3 Hz), 3.59-3.76 (1H, m), 3.78-3.91 (1H, m), 3.96-4.05 (1H, m), 4.05-4.14 (1H, m), 4.16-4.31 (1H, m), 4.50 (1H, d, J=10.4 Hz), 6.92-7.01 (2H, m), 7.50-7.61 (2H, m), 7.87 (1H, s), 8.07 (1H, s).

E) N-[(3R,4S)-3-({4-[4-(trifluoromethyl)-1H-pyrazol-1-yl]phenoxy}methyl)tetrahydro-2H-pyran-4-yl]methanesulfonamide A mixture of tert-butyl ((3R,4S)-3-((4-(4-(trifluoromethyl)-1H-pyrazol-1-yl)phenoxy)methyl)tetrahydro-2H-pyran-4-yl)carbamate (250 mg) and 4 M HCl/EtOAc (5 ml) was stirred at room temperature for 1 h. It was concentrated in vacuo. The residue was added THF (15 ml), triethylamine (860 mg) and methanesulfonyl chloride (324 mg) at room temperature. The mixture was stirred at room temperature overnight. It was added sat. $NaHCO_3$ aq. and silica gel and concentrated in vacuo. The residue was purified by column chromatography (silica gel, eluted with EtOAc in hexane) to give the title compound (149 mg) as a white solid. The solid was crystallized from EtOAc-hexane to give a desired product as a white solid.

$^1$H NMR (300 MHz, $CDCl_3$) δ 1.61-1.83 (1H, m), 1.90-2.07 (1H, m), 2.11-2.24 (1H, m), 2.90 (3H, s), 3.39-3.55 (2H, m), 3.56-3.75 (1H, m), 3.97-4.19 (4H, m), 4.33 (1H, d, J=9.1 Hz), 6.94-7.07 (2H, m), 7.53-7.64 (2H, m), 7.87 (1H, s), 8.08 (1H, s).

Example 266

N-[(3S,4R)-3-{[4-(5-chloropyridin-2-yl)-2-fluorophenoxy]methyl}tetrahydro-2H-pyran-4-yl]methanesulfonamide or N-[(3R,4S)-3-{[4-(5-chloropyridin-2-yl)-2-fluorophenoxy]methyl}tetrahydro-2H-pyran-4-yl]methanesulfonamide N-[(3RS,4SR)-3-{[4-(5-chloropyridin-2-yl)-2-fluorophenoxy]methyl}tetrahydro-2H-pyran-4-yl]methanesulfonamide (90 mg) was separated by HPLC (column: CHIRALPAK OD (0), 50 mmID×500 mL, DAICEL corporation, mobile phase: MeOH) to give the title compound with a longer retention time (38.1 mg) as a white solid.

MS (API+), found: 414.9.

Example 267

N-[(1S,2S)-4,4-difluoro-2-{[4-(1-methyl-2-oxo-1,2-dihydropyridin-3-yl)phenoxy]methyl}cyclohexyl] ethanesulfonamide

A) 3-bromo-1-methylpyridin-2(1H)-one

A mixture of iodomethane (1.22 g), 3-bromopyridin-2-ol (500 mg) and potassium carbonate (1.19 g) in DMF (2 ml) was stirred at 80° C. for 1 h. The mixture was poured into water and extracted with EtOAc. The organic layer was separated, washed with brine, dried over $MgSO_4$ and concentrated in vacuo. The residue was purified by column chromatography (silica gel, eluted with EtOAc in hexane) to give the title compound (352 mg) as a colorless oil.

MS (API+), found: 187.9.

B) 3-(4-(benzyloxy)phenyl)-1-methylpyridin-2(1H)-one

A mixture of (4-(benzyloxy)phenyl)boronic acid (619 mg), 3-bromo-1-methylpyridin-2(1H)-one (340 mg), $Pd(Ph_3P)_4$ (62.7 mg) and sodium carbonate (383 mg) in DME (15 ml) and water (5 ml) was stirred at 80° C. under $N_2$ overnight. It was added NH silica gel and concentrated in vacuo. The residue was purified by column chromatography (silica gel, eluted with EtOAc in hexane) to give the title compound (425 mg) as a white solid.

MS (API+), found: 292.1.

C) 3-(4-hydroxyphenyl)-1-methylpyridin-2(1H)-one

A mixture of 3-(4-(benzyloxy)phenyl)-1-methylpyridin-2 (1H)-one (930 mg) and 10% Pd/C (90 mg) in MeOH (25 ml) and THF (25 ml) was hydrogenated under balloon pressure at room temperature overnight. The catalyst was removed by filtration and the filtrate was concentrated in vacuo to give the title compound (559 mg) as white solid.

MS (API+), found: 202.0.

D) tert-butyl ((1S,2S)-4,4-difluoro-2-((4-(1-methyl-2-oxo-1,2-dihydropyridin-3-yl)phenoxy)methyl)cyclohexyl)carbamate A mixture of 3-(4-hydroxyphenyl)-1-methylpyridin-2(1H)-one (230 mg), tert-butyl ((1S,2S)-4,4-difluoro-2-(hydroxymethyl)cyclohexyl)carbamate (276 mg), Bu₃P (0.513 ml) and ADDP (524 mg) in toluene (15 ml) was stirred at room temperature overnight. The mixture was concentrated in vacuo. The residue was purified by column chromatography (silica gel, eluted with EtOAc in hexane) then column chromatography (NH silica gel, eluted with EtOAc in hexane) then to give the title compound (316 mg) as a white amorphous solid.

$^1$H NMR (300 MHz, CDCl$_3$) δ 1.32-1.49 (9H, m), 1.48-1.98 (4H, m), 2.00-2.25 (3H, m), 3.47-3.69 (4H, m), 3.78-3.96 (1H, m), 3.98-4.13 (1H, m), 4.56 (1H, d, J=7.9 Hz), 6.23 (1H, t, J=6.8 Hz), 6.85-6.99 (2H, m), 7.19-7.32 (1H, m), 7.44 (1H, dd, J=7.0, 2.0 Hz), 7.60-7.72 (2H, m).

E) N-[(1S,2S)-4,4-difluoro-2-{[4-(1-methyl-2-oxo-1,2-dihydropyridin-3-yl)phenoxy]methyl}cyclohexyl]ethanesulfonamide A mixture of tert-butyl ((1S,2S)-4,4-difluoro-2-((4-(1-methyl-2-oxo-1,2-dihydropyridin-3-yl)phenoxy)methyl)cyclohexyl)carbamate (155 mg) and 2 M HCl/EtOH (5 ml) was stirred at room temperature for 1 h. It was concentrated in vacuo. The residue was added THF (25 ml), triethylamine (525 mg) and ethanesulfonyl chloride (222 mg) at room temperature. The mixture was stirred at room temperature for 1 h. It was added sat. NaHCO$_3$ aq. and silica gel and concentrated in vacuo. The residue was purified by column chromatography (silica gel, eluted with EtOAc in hexane) to give the title compound (62.1 mg) as a colorless gum. The solid was crystallized from EtOAc-hexane-IPE to give a desired product as a off-white solid.

$^1$H NMR (300 MHz, DMSO-d$_6$) δ 1.11 (3H, t, J=7.3 Hz), 1.45-1.72. (1H, m), 1.77-2.13 (5H, m), 2.26 (1H, d, J=5.3 Hz), 2.96 (2H, q, J=7.2 Hz), 3.16-3.40 (1H, m), 3.49 (3H, s), 3.94-4.07 (1H, m), 4.08-4.20 (1H, m), 6.29 (1H, t, J=7.0 Hz), 6.87-7.01 (2H, m), 7.26 (1H, d, J=9.0 Hz), 7.56 (1H, dd, J=7.0, 2.1 Hz), 7.62-7.74 (3H, m).

Example 268

N-[(1S,2S)-2-{[4-(5-cyanopyridin-2-yl)phenoxy]methyl}-4,4-difluorocyclohexyl]methanesulfonamide A) tert-butyl ((1S,2S)-2-((4-(5-cyanopyridin-2-yl)phenoxy)methyl)-4,4-difluorocyclohexyl)carbamate A mixture of tert-butyl ((1S,2S)-4,4-difluoro-2-(hydroxymethyl)cyclohexyl)carbamate (200 mg), 6-(4-hydroxyphenyl)nicotinonitrile (177 mg), ADDP (380 mg) and Bu₃P (0.372 ml) in THF (10 ml) was stirred at room temperature overnight. The mixture was poured into 1 M NaOH aq. and extracted with EtOAc. The organic layer was separated, washed with 1 M NaOH aq. and brine, dried over MgSO$_4$ and concentrated in vacuo. The residue was purified by column chromatography (silica gel, eluted with EtOAc in hexane) to give the title compound (328 mg) as a white solid.

$^1$H NMR (300 MHz, DMSO-d$_6$) δ 1.20-1.63 (10H, m), 1.76-2.16 (5H, m) 2.17-2.38 (1H, m), 3.38-3.62 (1H, m), 3.86-4.12 (2H, m), 6.85-6.97 (1H, m), 7.00-7.16 (2H, m), 8.08-8.19 (3H, m), 8.31 (1H, dd, J=8.5, 2.1 Hz), 9.02 (1H, d, J=1.5 Hz).

B) N-[(1S,2S)-2-{[4-(5-cyanopyridin-2-yl)phenoxy]methyl}-4,4-difluorocyclohexyl]methanesulfonamide A mixture of tert-butyl ((1S,2S)-2-((4-(5-cyanopyridin-2-yl)phenoxy)methyl)-4,4-difluorocyclohexyl)carbamate (700 mg) and 2 M HCl/EtOH (10 ml) was stirred at room temperature for 1 h. It was concentrated in vacuo. The residue was added THF (20 ml), triethylamine (2.40 g) and methanesulfonyl chloride (904 mg) at room temperature. The mixture was stirred at room temperature for 1 h. It was added sat. NaHCO$_3$ aq. and silica gel and concentrated in vacuo. The residue was purified by column chromatography (silica gel, eluted with EtOAc in hexane) to give the title compound (630 mg) as a white solid. The solid was crystallized from EtOAc-hexane to give a desired product as a white solid.

$^1$H NMR (300 MHz, DMSO-d$_6$) δ 1.47-1.72 (1H, m), 1.82-2.16 (5H, m), 2.27 (1H, brs), 2.88 (3H, brs), 3.33-3.45 (1H, m), 3.96-4.30 (2H, m), 7.00-7.17 (2H, m), 7.22-7.38 (1H, m), 8.05-8.23 (3H, m), 8.24-8.39 (1H, m), 9.03 (1H, brs).

Example 269

N-[(3R,4S)-3-{[4-(4-chloro-1H-pyrazol-1-yl)phenoxy]methyl}tetrahydro-2H-pyran-4-yl]methanesulfonamide A) tert-butyl ((3R,4S)-3-((4-(4-chloro-1H-pyrazol-1-yl)phenoxy)methyl)tetrahydro-2H-pyran-4-yl)carbamate To a solution of tert-butyl ((3S,4S)-3-(hydroxymethyl)tetrahydro-2H-pyran-4-yl)carbamate (16.1 g), Et$_3$N (14.6 ml) in THF (120 ml) was added MsCl (6.47 ml) at 0° C. The mixture was stirred at room temperature overnight. The mixture was quenched with sat. NaHCO$_3$ aq. and extracted with EtOAc. The organic layer was separated, washed with brine, dried over Na$_2$SO$_4$ and concentrated in vacuo. A mixture of the residue, 4-(4-chloro-1H-pyrazol-1-yl)phenol (14.2 g) and Cs$_2$CO$_3$ (27.2 g) in DMF (180 ml) was stirred at 80° C. for 6 h. The mixture was added water and the resulting precipitate was collected by filtration and dried under vacuum to give the title compound (24.9 g) as off-white solid.

$^1$H NMR (300 MHz, CDCl$_3$) δ 1.42 (9H, s), 1.46-1.66 (1H, m), 1.91-2.08 (2H, m), 3.31 (1H, t, J=11.0 Hz), 3.48 (1H, td, J=11.8, 2.3 Hz), 3.58-3.74 (1H, m), 3.77-3.90 (1H, m), 4.00 (1H, dd, J=11.7, 3.4 Hz), 4.08 (1H, dd, J=9.6, 3.8 Hz), 4.22 (1H, dd, J=11.6, 3.9 Hz), 4.53 (1H, d, J=8.3 Hz), 6.89-7.00 (2H, m), 7.43-7.57 (2H, m), 7.60 (1H, d, J=0.4 Hz), 7.80 (1H, d, J=0.6 Hz).

B) N-[(3R,4S)-3-{[4-(4-chloro-1H-pyrazol-1-yl)phenoxy]methyl}tetrahydro-2H-pyran-4-yl]methanesulfonamide A mixture of tert-butyl ((3R,4S)-3-((4-(4-chloro-1H-pyrazol-1-yl)phenoxy)methyl)tetrahydro-2H-pyran-4-yl)carbamate (26.5 g) and 4 M HCl/EtOAc (300 ml) was stirred at room temperature for 2 h. The resulting precipitate was collected by filtration, and washed with IPE. To a suspension of the HCl salt and Et$_3$N (27.2 ml) in THF (200 ml) was added MsCl (7.54 ml) at room temperature. The mixture was stirred for 30 min. The mixture was quenched with sat. NaHCO$_3$ aq. and extracted with EtOAc. The organic layer was separated, washed with brine, dried over Na$_2$SO$_4$ and concentrated in vacuo to give the title compound (22.5 g) as off-white solid.

C) N-[(3R,4S)-3-{[4-(4-chloro-1H-pyrazol-1-yl) phenoxy]methyl}tetrahydro-2H-pyran-4-yl]methanesulfonamide To N-[(3R,4S)-3-{[4-(4-chloro-1H-pyrazol-1-yl)phenoxy]methyl}tetrahydro-2H-pyran-4-yl]methanesulfonamide (53.9 g) was added EtOH (1000 ml)/EtOAc (700 ml)/THF (160 ml) at 100° C., and the insoluble material was removed by filtration. The filtrate was concentrated under vacuum, and the residue was crystallized from EtOH (1500 ml) (110° C. to room temperature for 2 h) twice to give the title compound (41.1 g) as a white powder.

D) N-[(3R,4S)-3-{[4-(4-chloro-1H-pyrazol-1-yl) phenoxy]methyl}tetrahydro-2H-pyran-4-yl]methanesulfonamide N-((3R,4S)-3-((4-(4-chloro-1H-pyrazol-1-yl)phenoxy) methyl)tetrahydro-2H-pyran-4-yl)methanesulfonamide (1.22 g) was purified by column chromatography (silica gel, eluted with EtOAc in hexane) to give a white solid. The solid was crystallized from EtOH to give the title compound (1.02 g) as a white solid.

$^1$H NMR (300 MHz, CDCl$_2$) δ 1.61-1.81 (1H, m), 1.91-2.07 (1H, m), 2.10-2.24 (1H, m), 2.89 (3H, s), 3.41-3.56 (2H, m), 3.56-3.71 (1H, m), 3.96-4.19 (4H, m), 4.43 (1H, d, J=9.0 Hz), 6.93-7.02 (2H, m), 7.49-7.58 (2H, m), 7.61 (1H, s), 7.81 (1H, s).

MS (API+), found: 386.1 (M+1)

Anal. Calcd for C$_{16}$H$_{20}$N$_3$O$_4$SCl: C, 49.80; H, 5.22; N, 10.89. Found: C, 49.84; H, 5.27; N, 10.82.

Example 270

N-[(3RS,4SR)-3-{[4-(4-chloro-1H-pyrazol-1-yl) phenoxy]methyl}tetrahydro-2H-pyran-4-yl]methanesulfonamide A) tert-butyl ((3RS,4SR)-3-((4-(4-chloro-1H-pyrazol-1-yl)phenoxy)methyl)tetrahydro-2H-pyran-4-yl) carbamate A mixture of tert-butyl ((3SR,4SR)-3-(hydroxymethyl) tetrahydro-2H-pyran-4-yl)carbamate (500 mg), 4-(4-chloro-1H-pyrazol-1-yl)phenol (631 mg), ADDP (709 mg) and Bu$_3$P (0.693 ml) in toluene (30 ml) was stirred at room temperature overnight. The mixture was purified by column chromatography (silica gel, eluted with EtOAc in hexane) to give the title compound (819 mg) as a white solid.

$^1$H NMR (300 MHz, CDCl$_3$) δ 1.42 (9H, s), 1.47-1.66 (1H, m), 1.91-2.07 (2H, m), 3.32 (1H, t, J=11.0 Hz), 3.48 (1H, td, J=11.9, 2.3 Hz), 3.57-3.74 (1H, m), 3.76-3.90 (1H, m), 4.00 (1H, dd, J=11.7, 3.4 Hz), 4.08 (1H, dd, J=9.8, 3.8 Hz), 4.22 (1H, dd, J=11.7, 4.2 Hz), 4.51 (1H, d, J=8.3 Hz), 6.88-7.00 (2H, m), 7.45-7.56 (2H, m), 7.60 (1H, s), 7.80 (1H, s).

B) N-[(3RS,4SR)-3-{[4-(4-chloro-1H-pyrazol-1-yl) phenoxy]methyl}tetrahydro-2H-pyran-4-yl]methanesulfonamide A mixture of tert-butyl ((3RS,4SR)-3-((4-(4-chloro-1H-pyrazol-1-yl)phenoxy)methyl)tetrahydro-2H-pyran-4-yl) carbamate (400 mg) and 4 M HCl/EtOAc (10 ml) was stirred at room temperature overnight. The resulting precipitate was collected by filtration. A mixture of the residue, Et$_3$N (0.410 ml), MsCl (0.152 ml) and THF (5 ml) was stirred at room temperature for 3 h. The mixture was quenched with sat. NaHCO$_3$ aq. and extracted with EtOAc. The organic layer was separated, washed with brine, dried over Na$_2$SO$_4$ and concentrated in vacuo. The residue was purified by column chromatography (silica gel, eluted with EtOAc in hexane) to give the title compound (337 mg) as a white solid.

$^1$H NMR (300 MHz, CDCl$_3$) δ 1.62-1.79 (1H, m), 1.91-2.06 (1H, m), 2.11-2.24 (1H, m), 2.90 (3H, s), 3.41-3.56 (2H, m), 3.56-3.71 (1H, m), 3.96-4.09 (3H, m), 4.13 (1H, dd, J=11.9, 4.0 Hz), 4.34 (1H, d, J=9.1 Hz), 6.93-7.01 (2H, m), 7.49-7.57 (2H, m), 7.60 (1H, s), 7.81 (1H, s).

Example 271

N-[(3RS,4SR)-3-{[4-(4-chloro-1H-pyrazol-1-yl) phenoxy]methyl}tetrahydro-2H-pyran-4-yl]cyclopropanesulfonamide A mixture of tert-butyl (3RS,4SR)-3-((4-(4-chloro-1H-pyrazol-1-yl)phenoxy)methyl)tetrahydro-2H-pyran-4-ylcarbamate (300 mg) and 4 M HCl/EtOAc (12 ml) was stirred at room temperature overnight. The resulting precipitate was collected by filtration to give (3RS,4SR)-3-((4-(4-chloro-1H-pyrazol-1-yl)phenoxy)methyl)tetrahydro-2H-pyran-4-amine hydrochloride (241 mg) as a white solid. A mixture of (3RS,4SR)-3-((4-(4-chloro-1H-pyrazol-1-yl)phenoxy) methyl)tetrahydro-2H-pyran-4-amine hydrochloride (60 mg), Et$_3$N (0.121 ml) and cyclopropanesulfonyl chloride (0.036 ml) in THF (2 ml) was stirred at room temperature for 1 h. To the mixture was added DBU (0.053 ml) and the mixture was stirred at room temperature overnight. The mixture was quenched with sat. NaHCO$_3$ aq. and extracted with EtOAc. The organic layer was separated, washed with brine, dried over MgSO$_4$ and concentrated in vacuo. The residue was purified by column chromatography (silica gel, eluted with EtOAc in hexane), and the residue was crystallized from EtOAc-IPE-hexane to give the title compound (50 mg) as a white solid.

$^1$H NMR (300 MHz, CDCl$_3$) δ 0.78-0.95 (2H, m), 1.07-1.22 (2H, m), 1.62-1.80 (1H, m), 1.93-2.07 (1H, m), 2.15-2.27 (1H, m), 2.35 (1H, tt, J=8.0, 4.6 Hz), 3.40-3.67 (3H, m), 3.95-4.21 (4H, m), 4.28 (1H, d, J=9.1 Hz), 6.92-7.02 (2H, m), 7.48-7.57 (2H, m), 7.60 (1H, s), 7.80 (1H, d, J=0.8 Hz).

Example 272

N-[(3RS,4SR)-3-{[4-(4-methyl-1H-pyrazol-1-yl) phenoxy]methyl}tetrahydro-2H-pyran-4-yl]cyclopropanesulfonamide A) tert-butyl (3RS,4SR)-3-((4-(4-methyl-1H-pyrazol-1-yl)phenoxy)methyl)tetrahydro-2H-pyran-4-ylcarbamate A mixture of tert-butyl (3SR,4SR)-3-(hydroxymethyl) tetrahydro-2H-pyran-4-ylcarbamate (400 mg), 4-(4-methyl-1H-pyrazol-1-yl)phenol (452 mg), ADDP (567 mg) and Bu₃P (0.555 ml) in toluene (20 ml) was stirred at room temperature overnight. The mixture was purified by column chromatography (silica gel, eluted with EtOAc in hexane) to give the title compound (616 mg) as a white solid.

MS (API+), found: 388.3 (M+1)

B) N-[(3RS,4SR)-3-{[4-(4-methyl-1H-pyrazol-1-yl) phenoxy]methyl}tetrahydro-2H-pyran-4-yl]cyclopropanesulfonamide A mixture of tert-butyl (3RS,4SR)-3-((4-(4-methyl-1H-pyrazol-1-yl)phenoxy)methyl)tetrahydro-2H-pyran-4-ylcarbamate (100 mg) and 4 M HCl/EtOAc (4 ml) was stirred at room temperature overnight, and the solvent was removed under reduced pressure. A mixture of the residue, DBU (0.117 ml), cyclopropanesulfonyl chloride (0.053 ml) and CH₃CN (2 ml) was stirred at room temperature overnight. The mixture was quenched with sat. NaHCO₃ aq. and extracted with EtOAc. The organic layer was separated, washed with brine, dried over Na₂SO₄ and concentrated in vacuo. The residue was purified by column chromatography (silica gel, eluted with EtOAc in hexane) to give the title compound (57 mg) as a white powder.

$^1$H NMR (300 MHz, CDCl₃) δ 0.74-0.93 (2H, m), 1.03-1.21 (2H, m), 1.64-1.79 (1H, m), 1.90-2.08 (1H, m), 2.15 (3H, s), 2.16-2.26 (1H, m), 2.29-2.41 (1H, m), 3.46 (2H, q, J=11.1 Hz), 3.53-3.67 (1H, m), 3.94-4.11 (3H, m), 4.14 (1H, dd, J=11.9, 4.3 Hz), 4.56 (1H, d, J=8.7 Hz), 6.89-6.99 (2H, m), 7.49 (1H, s), 7.50-7.57 (2H, m), 7.60 (1H, s).

Example 273

N-{(3RS,4SR)-3-[(4-acetylphenoxy)methyl]tetrahydro-2H-pyran-4-yl}methanesulfonamide A) tert-butyl ((3RS,4SR)-3-((4-acetylphenoxy) methyl)tetrahydro-2H-pyran-4-yl)carbamate A mixture of tert-butyl ((3SR,4SR)-3-(hydroxymethyl) tetrahydro-2H-pyran-4-yl)carbamate (400 mg), 1-(4-hydroxyphenyl)ethanone (353 mg), ADDP (567 mg) and Bu₃P (0.555 ml) in toluene (25 ml) was stirred at room temperature overnight. The mixture was purified by column chromatography (silica gel, eluted with EtOAc in hexane) to give the title compound (562 mg) as a white solid.

MS (API+), found: 250.1 (M+1-Boc)

B) N-{(3RS,4SR)-3-[(4-acetylphenoxy)methyl]tetrahydro-2H-pyran-4-yl}methanesulfonamide A mixture of tert-butyl ((3RS,4SR)-3-((4-acetylphenoxy) methyl)tetrahydro-2H-pyran-4-yl)carbamate (100 mg) and 4 M HCl/EtOAc (5 ml) was stirred at room temperature for 1 h. The resulting white precipitate was collected by filtration, and washed with hexane. A mixture of the solid, Et₃N (0.120 ml) and MsCl (0.044 ml) in THF (3 ml) was stirred at room temperature for 5 h. The mixture was quenched with sat. NaHCO₃ aq. and extracted with EtOAc. The organic layer was separated, washed with brine, dried over Na₂SO₄ and concentrated in vacuo. The residue was crystallized from THF-hexane to give the title compound (79 mg) as a white solid.

$^1$H NMR (300 MHz, DMSO-d₆) δ 1.49-1.66 (1H, m), 1.83-2.00 (2H, m), 2.89 (3H, s), 3.27-3.45 (6H, m), 3.84 (1H, d, J=11.7 Hz), 3.96-4.10 (2H, m), 4.15-4.24 (1H, m), 6.99-7.07 (2H, m), 7.30 (1H, d, J=8.7 Hz), 7.88-7.98 (2H, m).

Example 274 N-{(3RS,4SR)-3-[(4-acetylphenoxy) methyl]tetrahydro-2H-pyran-4-yl}-2,2,2-trifluoroethanesulfonamide A mixture of tert-butyl ((3RS,4SR)-3-((4-acetylphenoxy) methyl)tetrahydro-2H-pyran-4-yl)carbamate (461 mg) and 4 M HCl/EtOAc (20 ml) was stirred at room temperature for 1 h. The resulting precipitate was collected by filtration to give 1-(4-(((3RS,4SR)-4-aminotetrahydro-2H-pyran-3-yl) methoxy)phenyl)ethanone hydrochloride (376 mg) as white solid.

A mixture of 1-(4-(((3RS,4SR)-4-aminotetrahydro-2H-pyran-3-yl)methoxy)phenyl)ethanone hydrochloride (100 mg), Et₃N (0.146 ml) and 2,2,2-trifluoroethanesulfonyl chloride (0.077 ml) was stirred at room temperature overnight. The mixture was quenched with sat. NaHCO₃ aq. and extracted with EtOAc. The organic layer was separated, washed with brine, dried over Na₂SO₄ and concentrated in vacuo. The residue was purified by column chromatography (silica gel, eluted with EtOAc in hexane) to give the title compound (41 mg) as a white gum.

$^1$H NMR (300 MHz, CDCl₃) δ 1.76 (1H, qd, J=12.0, 4.7 Hz), 1.95-2.18 (2H, m), 2.55 (3H, s), 3.47 (2H, q, J=11.3 Hz), 3.58-3.82 (3H, m), 4.00 (1H, d, J=10.9 Hz), 4.05-4.20 (3H, m), 5.41-5.70 (1H, m), 6.91 (2H, d, J=8.7 Hz), 7.92 (2H, d, J=8.3 Hz).

Example 275

N-[(3S,4R)-3-{[4-(5-chloropyridin-2-yl)phenoxy] methyl}tetrahydro-2H-pyran-4-yl]ethanesulfonamide or N-[(3R,4S)-3-{[4-(5-chloropyridin-2-yl) phenoxy]methyl}tetrahydro-2H-pyran-4-yl] ethanesulfonamide A) tert-butyl (3RS,4SR)-3-((4-(5-chloropyridin-2-yl)phenoxy)methyl)tetrahydro-2H-pyran-4-ylcarbamate A mixture of Bu₃P (0.320 ml), ADDP (327 mg), 4-(5-chloropyridin-2-yl)phenol (200 mg) and tert-butyl (3SR, 4SR)-3-(hydroxymethyl)tetrahydro-2H-pyran-4-ylcarbamate (150 mg) in toluene (20 ml) and THF (5 ml) was stirred at room temperature for 3 days. The mixture was poured into 1 M NaOH aq. and extracted with EtOAc. The organic layer was separated, washed with 1 M NaOH aq. and brine, dried over MgSO₄ and concentrated in vacuo. The residue was purified by column chromatography (silica gel, eluted with EtOAc in hexane) to give the title compound (251 mg) as a white solid.

MS (API+), found: 419.1 (M+1)

B) N-((3RS,4SR)-3-((4-(5-chloropyridin-2-yl)phenoxy)methyl)tetrahydro-2H-pyran-4-yl)ethanesulfonamide A mixture of tert-butyl (3RS,4SR)-3-((4-(5-chloropyridin-2-yl)phenoxy)methyl)tetrahydro-2H-pyran-4-ylcarbamate (251 mg) and 2 M HCl/EtOH (5 ml) was stirred at room temperature for 30 min. It was concentrated in vacuo. The residue was added THF (20 ml), triethylamine (909 mg) and ethanesulfonyl chloride (385 mg) at room temperature. The mixture was stirred at the same temperature for 3 h. It was added silica gel and concentrated in vacuo. The residue was purified by column chromatography (silica gel, eluted with EtOAc in hexane) to give the title compound (155 mg) as a white solid. The solid was crystallized from EtOAc-hexane-IPE to give a desired product as a white solid.

$^1$H NMR (300 MHz, DMSO-$d_6$) δ 1.13 (3H, t, J=7.2 Hz), 1.47-1.69 (1H, m), 1.77-2.00 (2H, m), 2.98 (2H, q, J=7.2 Hz), 3.23-3.46 (3H, m), 3.77-3.90 (1H, m), 3.93-4.09 (2H, m), 4.18 (1H, dd, J=9.8, 3.0 Hz), 6.95-7.11 (2H, m), 7.30 (1H, d, J=8.7 Hz), 7.85-7.99 (2H, m), 7.99-8.12 (2H, m), 8.64 (1H, t, J=1.5 Hz). C)

N-[(3S,4R)-3-{[4-(5-chloropyridin-2-yl)phenoxy] methyl}tetrahydro-2H-pyran-4-yl]ethanesulfonamide or N-[(3R,4S)-3-{[4-(5-chloropyridin-2-yl) phenoxy]methyl}tetrahydro-2H-pyran-4-yl] ethanesulfonamide N-[(3RS,4SR)-3-{[4-(5-chloropyridin-2-yl)phenoxy] methyl}tetrahydro-2H-pyran-4-yl]ethanesulfonamide was separated by a preparative HPLC(CHIRALPAK IC, 50 mmIDx500 mL, 2-propanol/diethylamine=1000/1) to give N-[(3S,4R)-3-{[4-(5-chloropyridin-2-yl)phenoxy] methyl}tetrahydro-2H-pyran-4-yl]ethanesulfonamide or N-[(3R,4S)-3-{[4-(5-chloropyridin-2-yl)phenoxy] methyl}tetrahydro-2H-pyran-4-yl]ethanesulfonamide with a longer retention time (14 mg) as a white powder.

MS (API+), found: 411.1.

Example 276

N-[(1S,2S)-4,4-difluoro-2-{[4-(4-methyl-1H-pyrazol-1-yl)phenoxy]methyl}cyclohexyl]methanesulfonamide A) tert-butyl ((1S,2S)-4,4-difluoro-2-((4-(4-methyl-1H-pyrazol-1-yl)phenoxy)methyl)cyclohexyl)carbamate A mixture of tert-butyl ((1S,2S)-4,4-difluoro-2-(hydroxymethyl)cyclohexyl)carbamate (209 mg), 4-(4-methyl-1H-pyrazol-1-yl)phenol (178 mg), ADDP (298 mg) and Bu$_3$P (0.292 ml) in toluene (12 ml) was stirred at room temperature overnight. The mixture was purified by column chromatography (silica gel, eluted with EtOAc in hexane) to give the title compound (309 mg) as a white solid.

MS (API+), found: 422.2.

B) N-[(1S,2S)-4,4-difluoro-2-{[4-(4-methyl-1H-pyrazol-1-yl)phenoxy]methyl}cyclohexyl]methanesulfonamide A mixture of tert-butyl ((1S,2S)-4,4-difluoro-2-((4-(4-methyl-1H-pyrazol-1-yl)phenoxy)methyl)cyclohexyl)carbamate (309 mg) and 4 M HCl/EtOAc (12 ml) was stirred at room temperature for 3 days. The solvent was removed by evaporation to give (1S,2S)-4,4-difluoro-2-((4-(4-methyl-1H-pyrazol-1-yl)phenoxy)methyl)cyclohexanamine hydrochloride (327 mg) as a white amorphous powder. A mixture of (1S,2S)-4,4-difluoro-2-((4-(4-methyl-1H-pyrazol-1-yl) phenoxy)methyl)cyclohexanamine hydrochloride (111 mg), DBU (0.140 ml) and MsCl (0.048 ml) in CH$_3$CN (2 ml) was stirred at room temperature overnight. The mixture was quenched with sat. NaHCO$_3$ aq. and extracted with EtOAc. The organic layer was separated, washed with brine, dried over Na$_2$SO$_4$ and concentrated in vacuo. The residue was purified by column chromatography (silica gel, eluted with EtOAc in hexane) to give the title compound (39 mg) as a white solid.

$^1$H NMR (300 MHz, CDCl$_3$) δ 1.64-2.05 (6H, m), 2.15 (3H, s), 2.82 (3H, s), 3.49-3.57 (1H, m), 3.93 (2H, d, J=12.1 Hz), 4.21 (1H, s), 4.41 (1H, d, J=7.6 Hz), 6.95 (2H, d, J=8.7 Hz), 7.50 (1H, s), 7.55 (2H, d, J=8.7 Hz), 7.61 (1H, s).

Example 277

N-[(3R,4S)-3-{[4-(4-chloro-1H-pyrazol-1-yl)phenoxy]methyl}tetrahydro-2H-pyran-4-yl]cyclopropanesulfonamide A mixture of tert-butyl ((3R,4S)-3-((4-(4-chloro-1H-pyrazol-1-yl)phenoxy)methyl)tetrahydro-2H-pyran-4-yl)carbamate (312 mg) and 4 M HCl/EtOAc (15 ml) was stirred at room temperature overnight. The resulting white precipitate was collected by filtration, and washed with IPE to give (3R,4S)-3-((4-(4-chloro-1H-pyrazol-1-yl)phenoxy)methyl) tetrahydro-2H-pyran-4-amine hydrochloride (258 mg) as a white solid. A mixture of (3R,4S)-3-((4-(4-chloro-1H-pyrazol-1-yl)phenoxy)methyl)tetrahydro-2H-pyran-4-amine hydrochloride (86 mg), Et$_3$N (0.104 ml), cyclopropanesulfonyl chloride (0.051 ml) and DMAP (15 mg) in THF (3 ml) was stirred at room temperature for 3 days. The mixture was quenched with sat. NaHCO$_3$ aq. and extracted with EtOAc. The organic layer was separated, washed with brine, dried over Na$_2$SO$_4$ and concentrated in vacuo. The residue was purified by column chromatography (silica gel, eluted with EtOAc in hexane) to give the title compound (98 mg) as a white solid.

$^1$H NMR (300 MHz, CDCl$_3$) δ 0.76-0.96 (2H, m), 1.05-1.23 (2H, m), 1.63-1.80 (1H, m), 1.90-2.08 (1H, m), 2.13-2.25 (1H, m), 2.35 (1H, tt, J=8.0, 4.9 Hz), 3.36-3.66 (3H, m), 3.95-4.22 (4H, m), 4.50 (1H, d, J=9.1 Hz), 6.91-7.03 (2H, m), 7.46-7.56 (2H, m), 7.60 (1H, s), 7.80 (1H, s).

Example 278

N-[(3R,4S)-3-{[(2'-fluorobiphenyl-4-yl)oxy] methyl}tetrahydro-2H-pyran-4-yl]methanesulfonamide A) tert-butyl ((3R,4S)-3-(((2'-fluoro-[1,1'-biphenyl]-4-yl)oxy)methyl)tetrahydro-2H-pyran-4-yl) carbamate A mixture of tert-butyl ((3S,4S)-3-(hydroxymethyl)tetrahydro-2H-pyran-4-yl)carbamate (100 mg), 2'-fluoro-[1,1'-biphenyl]-4-ol (106 mg), ADDP (164 mg) and Bu$_3$P (0.160 ml) in toluene (8 ml) was stirred at room temperature overnight. The mixture was purified by column chromatography (silica gel, eluted with EtOAc in hexane) to give the title compound (141 mg) as a white solid.

MS (API+), found: 302.2.

B) N-[(3R,4S)-3-{[(2'-fluorobiphenyl-4-yl)oxy] methyl}tetrahydro-2H-pyran-4-yl]methanesulfonamide A mixture of tert-butyl ((3R,4S)-3-(((2'-fluoro-[1,1'-biphenyl]-4-yl)oxy)methyl)tetrahydro-2H-pyran-4-yl)carbamate (141 mg) and 4 M HCl/EtOAc (10 ml) was stirred at room temperature overnight. To the mixture was added hexane and the resulting precipitate was collected by filtration. A mixture of the residue, Et$_3$N (0.147 ml) and MsCl (0.054 ml) in THF (5 ml) was stirred at room temperature for 2 h. The mixture was quenched with sat. NaHCO$_3$ aq. and extracted with EtOAc. The organic layer was separated, washed with brine, dried over Na$_2$SO$_4$ and concentrated in vacuo. The residue was purified by column chromatography (silica gel, eluted with EtOAc in hexane) to give the title compound (88 mg) as a white solid.

¹H NMR (300 MHz, CDCl₃) δ 1.62-1.81 (1H, m), 1.91-2.08 (1H, m), 2.14-2.25 (1H, m), 2.90 (3H, s), 3.42-3.57 (2H, m), 3.57-3.73 (1H, m), 3.95-4.18 (4H, m), 4.49 (1H, d, J=8.7 Hz), 6.92-7.03 (2H, m), 7.07-7.23 (2H, m), 7.23-7.33 (1H, m), 7.39 (1H, td, J=7.7, 1.9 Hz), 7.44-7.54 (2H, m).

Example 279

N'-[(3RS,4SR)-3-{[4-(4-chloro-1H-pyrazol-1-yl)phenoxy]methyl}tetrahydro-2H-pyran-4-yl]-N,N-dimethylsulfamide A mixture of tert-butyl ((3RS,4SR)-3-((4-(4-chloro-1H-pyrazol-1-yl)phenoxy)methyl)tetrahydro-2H-pyran-4-yl) carbamate (413 mg) and 4 M HCl/EtOAc (15 ml) was stirred at room temperature overnight. The resulting white precipitate was collected by filtration, and washed with IPE to give (3RS,4SR)-3-((4-(4-chloro-1H-pyrazol-1-yl)phenoxy)methyl)tetrahydro-2H-pyran-4-amine hydrochloride (330 mg) as a white solid. To a solution of (3RS,4SR)-3-((4-(4-chloro-1H-pyrazol-1-yl)phenoxy)methyl)tetrahydro-2H-pyran-4-amine hydrochloride (165 mg) and DBU (0.217 ml) in CH₃CN (3 ml) was added dimethylsulfamoyl chloride (0.102 ml) at room temperature. The mixture was stirred at room temperature overnight. The mixture was quenched with sat. NaHCO₃ aq. and extracted with EtOAc. The organic layer was separated, washed with brine, dried over Na₂SO₄ and concentrated in vacuo. The residue was purified by column chromatography (silica gel, eluted with EtOAc in hexane) to give the title compound (69 mg) as a white solid.

¹H NMR (300 MHz, CDCl₃) δ 1.58-1.73 (1H, m), 1.91-2.07 (1H, m), 2.17-2.29 (1H, m), 2.73 (6H, s), 3.37-3.55 (3H, m), 3.95-4.07 (2H, m), 4.08-4.18 (2H, m), 4.22 (1H, d, J=9.1 Hz), 6.91-7.01 (2H, m), 7.48-7.57 (2H, m), 7.60 (1H, s), 7.81 (1H, s).

Example 280

1,1,1-trifluoro-N-[(3RS,4SR)-3-{[4-(4-methyl-1H-pyrazol-1-yl)phenoxy]methyl}tetrahydro-2H-pyran-4-yl]methanesulfonamide A) tert-butyl (3RS,4SR)-3-((4-(4-methyl-1H-pyrazol-1-yl)phenoxy)methyl)tetrahydro-2H-pyran-4-ylcarbamate A mixture of tert-butyl (3SR,4SR)-3-(hydroxymethyl)tetrahydro-2H-pyran-4-ylcarbamate (400 mg), 4-(4-methyl-1H-pyrazol-1-yl)phenol (452 mg), ADDP (567 mg) and Bu₃P (0.555 ml) in toluene (20 ml) was stirred at room temperature overnight. The mixture was purified by column chromatography (silica gel, eluted with EtOAc in hexane) to give the title compound (616 mg) as a white solid, which was used in the next step directly.

B) 1,1,1-trifluoro-N-[(3RS,4SR)-3-{[4-(4-methyl-1H-pyrazol-1-yl)phenoxy]methyl}tetrahydro-2H-pyran-4-yl]methanesulfonamide A mixture of tert-butyl (3RS,4SR)-3-((4-(4-methyl-1H-pyrazol-1-yl)phenoxy)methyl)tetrahydro-2H-pyran-4-ylcarbamate (100 mg) and 4 M HCl/EtOAc (4 ml) was stirred at room temperature overnight, and the solvent was removed under reduced pressure. A mixture of the residue, DBU (0.117 ml), trifluoromethanesulfonyl chloride (0.054 ml) and CH₃CN (2 ml) was stirred at room temperature for 3 h. The mixture was quenched with sat. NaHCO₃ aq. and extracted with EtOAc. The organic layer was separated, washed with brine, dried over Na₂SO₄ and concentrated in vacuo. The residue was purified by column chromatography (silica gel, eluted with EtOAc in hexane) to give the title compound (38 mg) as a white powder.

¹H NMR (300 MHz, CDCl₃) δ 1.66-1.97 (2H, m), 2.02-2.13 (1H, m), 2.16 (3H, s), 3.19 (1H, t, J=11.3 Hz), 3.35-3.63 (3H, m), 3.82 (1H, dd, J=9.3, 4.0 Hz), 3.98 (1H, dd, J=11.7, 4.2 Hz), 4.14 (1H, dd, J=11.9, 4.3 Hz), 6.76-6.85 (2H, m), 7.45-7.52 (3H, m), 7.56 (1H, s).

Example 281

N-[(3RS,4SR)-3-{[4-(1,5-dimethyl-1H-pyrazol-3-yl)phenoxy]methyl}tetrahydro-2H-pyran-4-yl]methanesulfonamide A) 5-(4-(benzyloxy)phenyl)-1,3-dimethyl-1H-pyrazole and 3-(4-(benzyloxy)phenyl)-1,5-dimethyl-1H-pyrazole A mixture of 1-(4-(benzyloxy)phenyl)butane-1,3-dione (875 mg) and methylhydrazine (0.190 ml) in EtOH (20 ml) was refluxed for 3 h. The solvent was removed by evaporation and the residue was dissolved in EtOAc. The solution was washed with 1 M HCl aq. and brine, dried over Na₂SO₄ and concentrated under vacuum. The residue was purified by column chromatography (silica gel, eluted with EtOAc in hexane) to give a mixture of the title compounds (912 mg) as a white solid.

MS (API+), found: 279.2.

B) 4-(1,3-dimethyl-1H-pyrazol-5-yl)phenol and 4-(1,5-dimethyl-1H-pyrazol-3-yl)phenol A mixture of 5-(4-(benzyloxy)phenyl)-1,3-dimethyl-1H-pyrazole and 3-(4-(benzyloxy)phenyl)-1,5-dimethyl-1H-pyrazole (912 mg) and 10% Pd/C (174 mg) in EtOH (30 ml) and EtOAc (15 ml) was hydrogenated under balloon pressure at room temperature overnight. The catalyst was removed by filtration and the filtrate was concentrated in vacuo. The crude materials were purified using a preparative HPLC to give 4-(1,3-dimethyl-1H-pyrazol-5-yl)phenol (174 mg) with a shorter retention time, and 4-(1,5-dimethyl-1H-pyrazol-3-yl)phenol (332 mg) with a longer retention time.

4-(1,3-dimethyl-1H-pyrazol-5-yl)phenol:
MS (API+), found: 189.1.
4-(1,5-dimethyl-1H-pyrazol-3-yl)phenol
MS (API+), found: 189.1.

C) tert-butyl ((3RS,4SR)-3-((4-(1,5-dimethyl-1H-pyrazol-3-yl)phenoxy)methyl)tetrahydro-2H-pyran-4-yl)carbamate A mixture of tert-butyl ((3SR,4SR)-3-(hydroxymethyl)tetrahydro-2H-pyran-4-yl)carbamate (200 mg), 4-(1,5-dimethyl-1H-pyrazol-3-yl)phenol (171 mg), ADDP (327 mg) and Bu₃P (0.320 ml) in toluene (8 ml) was stirred at room temperature overnight. The mixture was purified by column chromatography (silica gel, eluted with EtOAc in hexane) to give the title compound (301 mg) as a white solid.

MS (API+), found: 402.2 (M+1)

D) N-[(3RS,4SR)-3-{[4-(1,5-dimethyl-1H-pyrazol-3-yl)phenoxy]methyl}tetrahydro-2H-pyran-4-yl]methanesulfonamide A mixture of tert-butyl ((3RS,4SR)-3-((4-(1,5-dimethyl-1H-pyrazol-3-yl)phenoxy)methyl)tetrahydro-2H-pyran-4-yl)carbamate (301 mg) and 4 M HCl/EtOAc (10 ml) was stirred at room temperature for 4 h. The resulting precipitate was collected by filtration, and washed with IPE to give (3RS,4SR)-3-((4-(1,5-dimethyl-1H-pyrazol-3-yl)phenoxy)methyl)tetrahydro-2H-pyran-4-amine hydrochloride (279 mg) as a white solid. A mixture of (3RS,4SR)-3-((4-(1,5-dimethyl-1H-pyrazol-3-yl)phenoxy)methyl)tetrahydro-2H-pyran-4-amine hydrochloride (80 mg), Et$_3$N (0.099 ml) and MsCl (0.037 ml) in CH$_3$CN (2 ml) was stirred at room temperature overnight. The mixture was quenched with sat. NaHCO$_3$ aq. and extracted with EtOAc. The organic layer was separated, washed with brine, dried over Na$_2$SO$_4$ and concentrated in vacuo. The residue was purified by column chromatography (silica gel, eluted with EtOAc in hexane) to give the title compound (67 mg) as a white solid.

$^1$H NMR (300 MHz, CDCl$_3$) δ 1.61-1.77 (1H, m), 1.88-2.03 (1H, m), 2.13-2.24 (1H, m), 2.29 (3H, s), 2.84 (3H, s), 3.41-3.55 (2H, m), 3.56-3.72 (1H, m), 3.80 (3H, s), 3.98 (2H, dd, J=9.8, 3.4 Hz), 4.04-4.15 (2H, m), 4.49 (1H, d, J=8.7 Hz), 6.24 (1H, s), 6.89 (2H, d, J=8.7 Hz), 7.62-7.72 (2H, m).

Example 282

1,5-anhydro-4-[(cyclopropylsulfonyl)amino]-2,3,4-trideoxy-6-β-[4-(5-fluoropyridin-2-yl)phenyl]-D-erythro-hexitol A) 4-(5-fluoropyridin-2-yl)phenol A mixture of Pd(Ph$_3$P)$_4$ (0.524 g), 2-bromo-5-fluoropyridine (2.66 g), Na$_2$CO$_3$ (3.20 g) and 4-hydroxyphenylboronic acid (2.5 g) in DME (60 ml) and water (12 ml) was stirred at 80° C. under N$_2$ for 2 days. It was added silica gel and concentrated in vacuo. The residue was purified by column chromatography (silica gel, eluted with EtOAc in hexane) to give the title compound (1.520 g) as a pale yellow solid.

MS (API+), found: 190.1.

B) tert-butyl ((2S,3S)-2-((4-(5-fluoropyridin-2-yl)phenoxy)methyl)tetrahydro-2H-pyran-3-yl)carbamate A mixture of tert-butyl ((2S,3S)-2-(hydroxymethyl)tetrahydro-2H-pyran-3-yl)carbamate (300 mg), 4-(5-fluoropyridin-2-yl)phenol (294 mg), ADDP (491 mg) and Bu$_3$P (0.480 ml) in toluene (15 ml) was stirred at room temperature overnight. The mixture was purified by column chromatography (silica gel, eluted with EtOAc in hexane) to give the title compound (328 mg) as a white solid.

MS (API+), found: 403.1.

C) 1,5-anhydro-4-[(cyclopropylsulfonyl)amino]-2,3,4-trideoxy-6O-[4-(5-fluoropyridin-2-yl)phenyl]-D-erythro-hexitol A mixture of tert-butyl ((2S,3S)-2-((4-(5-fluoropyridin-2-yl)phenoxy)methyl)tetrahydro-2H-pyran-3-yl)carbamate (328 mg) and 4 M HCl/EtOAc (15 ml) was stirred at room temperature overnight. The resulting precipitate was collected by filtration, and washed with IPE to give (2S,3S)-2-((4-(5-fluoropyridin-2-yl)phenoxy)methyl)tetrahydro-2H-pyran-3-amine hydrochloride (330 mg) as an off-white solid. A mixture of (2S,3S)-2-((4-(5-fluoropyridin-2-yl)phenoxy)methyl)tetrahydro-2H-pyran-3-amine hydrochloride (110 mg), Et$_3$N (0.136 ml), cyclopropanesulfonyl chloride (0.066 ml) and DMAP (20 mg) in THF (4 ml) was stirred at room temperature overnight. The mixture was quenched with sat. NaHCO$_3$ aq. and extracted with EtOAc. The organic layer was separated, washed with brine, dried over Na$_2$SO$_4$ and concentrated in vacuo. The residue was purified by column chromatography (silica gel, eluted with EtOAc in hexane). The residue was crystallized from EtOAc-IPE to give the title compound (80 mg) as a white solid.

$^1$H NMR (300 MHz, CDCl$_3$) δ 0.75-0.96 (2H, m), 1.04-1.23 (2H, m), 1.44-1.61 (1H, m), 1.66-1.94 (2H, m), 2.29-2.51 (2H, m), 3.37-3.61 (3H, m), 3.98-4.10 (1H, m), 4.17-4.28 (2H, m), 4.30-4.40 (1H, m), 6.97-7.07 (2H, m), 7.43 (1H, td, J=8.4, 2.8 Hz), 7.64 (1H, dd, J=8.7, 4.2 Hz), 7.81-7.92 (2H, m), 8.49 (1H, d, J=3.0 Hz).

Example 283

N-[(3R,4S)-4-{[4-(5-fluoropyrimidin-2-yl)phenoxy]methyl}tetrahydro-2H-pyran-3-yl]methanesulfonamide A) (3R,4S)-4-((4-(5-fluoropyrimidin-2-yl)phenoxy)methyl)tetrahydro-2H-pyran-3-amine hydrochloride A mixture of tert-butyl ((3R,4S)-4-(hydroxymethyl)tetrahydro-2H-pyran-3-yl)carbamate (150 mg), 4-(5-fluoropyrimidin-2-yl)phenol (148 mg), Bu$_3$P (0.320 ml) and ADDP (327 mg) in toluene (15 ml) was stirred at room temperature overnight. EtOAc was added to the mixture and the resulted insoluble materials were removed by filtration. The mixture was concentrated in vacuo and the residue was purified by column chromatography (silica gel, eluted with EtOAc in hexane) and concentrated. The residue was diluted to EtOAc (10 ml) and 4 N HCl/EtOAc (3 ml) was added to a mixture at room temperature. The mixture was stirred at room temperature overnight. The insoluble material was washed with IPE, collected and dried in vacuo to give the title compound (151 mg) as a pale yellow powder.

MS (API+), found: 304.2.

B) N-[(3R,4S)-4-{[4-(5-fluoropyrimidin-2-yl)phenoxy]methyl}tetrahydro-2H-pyran-3-yl]methanesulfonamide Methanesulfonyl chloride (0.137 ml) was added to a mixture of (3R,4S)-4-((4-(5-fluoropyrimidin-2-yl)phenoxy)methyl)tetrahydro-2H-pyran-3-amine hydrochloride (150 mg) and triethylamine (0.616 ml) in THF (5 ml) at room temperature. The mixture was stirred at room temperature overnight. The mixture was quenched with sat. NaHCO$_3$ aq. at room temperature and extracted with EtOAc. The organic layer was separated, washed with brine and concentrated in vacuo. The residue was crystallized from EtOAc/IPE at 0° C. to give the title compound (94 mg) as off-white crystals.

$^1$H NMR (300 MHz, DMSO-d$_6$) δ 1.51-1.73 (1H, m), 1.75-1.98 (2H, m), 2.86 (3H, s), 2.99-3.10 (1H, m), 3.20-3.29 (2H, m), 3.81-3.96 (2H, m), 4.05-4.23 (2H, m), 7.04-7.13 (2H, m), 7.35 (1H, brs), 8.24-8.32 (2H, m), 8.84-8.96 (2H, m).

Example 284

N-[(3R,4S)-4-{[4-(5-chloropyrimidin-2-yl)phenoxy]methyl}tetrahydro-2H-pyran-3-yl]methanesulfonamide A) (3R,4S)-4-((4-(5-fluoropyrimidin-2-yl)phenoxy)methyl)tetrahydro-2H-pyran-3-amine hydrochloride A mixture of tert-butyl ((3R,4S)-4-(hydroxymethyl)tetrahydro-2H-pyran-3-yl)carbamate (150 mg), 4-(5-chloropyrimidin-2-yl)phenol (161 mg), Bu₃P (0.320 ml) and ADDP (327 mg) in toluene (15 ml) was stirred at room temperature overnight. EtOAc was added to the mixture and the resulted insoluble materials were removed by filtration. The mixture was concentrated in vacuo and the residue was purified by column chromatography (silica gel, eluted with EtOAc in hexane) and concentrated. The residue was diluted to EtOAc (10 ml) and 4 N HCl/EtOAc (3 ml) was added to a mixture at room temperature. The mixture was stirred at room temperature overnight. The insoluble material was washed with IPE, collected and dried in vacuo to give the title compound (134 mg) as a pale yellow powder.

MS (API+), found: 320.2.

B) N-[(3R,4S)-4-{[4-(5-chloropyrimidin-2-yl)phenoxy]methyl}tetrahydro-2H-pyran-3-yl]methanesulfonamide Methanesulfonyl chloride (0.116 ml) was added to a mixture of (3R,4S)-4-((4-(5-chloropyrimidin-2-yl)phenoxy)methyl)tetrahydro-2H-pyran-3-amine hydrochloride (134 mg) and triethylamine (0.525 ml) in THF (5 ml) at room temperature. The mixture was stirred at room temperature overnight. The mixture was quenched with sat. NaHCO₃ aq. at room temperature and extracted with EtOAc. The residue was crystallized from EtOAc/IPE-hexane at 0° C. to give the title compound (80 mg) as a off-white crystals.

¹H NMR (300 MHz, DMSO-d₆) δ 1.52-1.71 (1H, m), 1.77-1.96 (2H, m), 2.86 (3H, s), 2.99-3.10 (1H, m), 3.16-3.29 (2H, m), 3.79-3.97 (2H, m), 4.06-4.25 (2H, m), 7.07-7.14 (2H, m), 7.35 (1H, d, J=8.3 Hz), 8.27-8.34 (2H, m), 8.94 (2H, s).

Example 285

N-[(3RS,4SR)-3-{[4-(4-chloro-1H-pyrazol-1-yl)-2-fluorophenoxy]methyl}tetrahydro-2H-pyran-4-yl]ethanesulfonamide

A) tert-butyl (3RS,4SR)-3-((4-(4-chloro-1H-pyrazol-1-yl)-2-fluorophenoxy)methyl)tetrahydro-2H-pyran-4-ylcarbamate To a solution of tert-butyl ((3RS,4RS)-3-(hydroxymethyl)tetrahydro-2H-pyran-4-ylcarbamate (0.36 g) in toluene (200 ml) was added 4-(4-chloro-1H-pyrazol-1-yl)-2-fluorophenol (0.49 g), 1,1'-(azodicarbonyl)dipiperidine (0.78 g) and Bu₃P (0.76 ml) at room temperature. The mixture was stirred overnight. The mixture was purified by column chromatography (NH silica gel, eluted with EtOAc in hexane) to give the title compound (0.16 g) as a white solid.

MS (API+), found: 370.1 (M+1-tBu).

B) (3RS,4SR)-3-((4-(4-chloro-1H-pyrazol-1-yl)-2-fluorophenoxy)methyl)tetrahydro-2H-pyran-4-amine hydrochloride A mixture of tert-butyl (3RS,4SR)-3-((4-(4-chloro-1H-pyrazol-1-yl)-2-fluorophenoxy)methyl)tetrahydro-2H-pyran-4-ylcarbamate (0.16 g) and 2 M HCl/EtOH (4.0 ml) in EtOAc (4.0 ml) was stirred at room temperature for 4 h. The solvent was removed in vacuo to give the title compound (132 mg) as a white solid.

MS (API+), found: 326.1.

C) N-[(3RS,4SR)-3-{[4-(4-chloro-1H-pyrazol-1-yl)-2-fluorophenoxy]methyl}tetrahydro-2H-pyran-4-yl]ethanesulfonamide A mixture of TEA (0.41 ml), ethanesulfonyl chloride (0.10 ml) and (3RS,4SR)-3-((4-(4-chloro-1H-pyrazol-1-yl)-2-fluorophenoxy)methyl)tetrahydro-2H-pyran-4-amine hydrochloride (0.13 g) in THF (5.0 ml) was stirred at room temperature overnight. It was added silica gel and concentrated in vacuo. The residue was purified by column chromatography (silica gel, eluted with EtOAc in hexane), followed by preparative HPLC (MeCN-water with TFA) to give the title compound (35 mg) as a pale yellow solid.

¹H NMR (300 MHz, DMSO-d₆) δ 1.14 (3H, t, J=7.2 Hz), 1.53-1.67 (1H, m), 1.87-1.99 (2H, m), 2.99 (2H, q, J=7.3 Hz), 3.33-3.42 (3H, m), 3.80-3.90 (1H, m), 3.98-4.13 (2H, m), 4.18-4.26 (1H, m), 7.22-7.35 (2H, m), 7.60 (1H, dt, J=9.1, 2.1 Hz), 7.74 (1H, dd, J=12.3, 2.8 Hz), 7.85 (1H, s), 8.73 (1H, s).

Example 286

N-D[(3RS,4SR)-3-{[2-fluoro-4-(4-methyl-1H-pyrazol-1-yl)phenoxy]methyl}tetrahydro-2H-pyran-4-yl]ethanesulfonamide

A) 4-bromo-1-(3-fluoro-4-methoxyphenyl)-1H-pyrazole

A mixture of 1-bromopyrrolidine-2,5-dione (6.1 g) and 1-(3-fluoro-4-methoxyphenyl)-1H-pyrazole (6.0 g) in THF (200 ml) was stirred at room temperature overnight. The mixture was added silica gel, concentrated in vacuo, then purified by column chromatography (silica gel, eluted with EtOAc in hexane) to give the title compound (8.3 g) as a white solid.

MS (API+), found: 271.0.

B) 1-(3-fluoro-4-methoxyphenyl)-4-methyl-1H-pyrazole

A mixture of 4-bromo-1-(3-fluoro-4-methoxyphenyl)-1H-pyrazole (4.3 g), methylboronic acid (1.0 g), cesium carbonate (10 g), and Pd(PPh₃)₄ (1.8 g) in DME (200 ml) was stirred at 90° C. overnight. The mixture was added silica gel, concentrated in vacuo, then purified by column chromatography (silica gel, eluted with EtOAc in hexane) to give the title compound (0.24 g) as a white solid.

MS (API+), found: 207.1.

C) 2-fluoro-4-(4-methyl-1H-pyrazol-1-yl)phenol

A mixture of 48% hydrogen bromide (1.3 ml) and 1-(3-fluoro-4-methoxyphenyl)-4-methyl-1H-pyrazole (0.24 g) in AcOH (5.0 ml) was stirred at 130° C. overnight. It was concentrated in vacuo, added sat. NaHCO₃ aq., and extracted with EtOAc. The extract was washed with brine, dried over MgSO₄, filtered, and concentrated in vacuo. The residue was purified by column chromatography (silica gel, eluted with EtOAc in hexane) to give the title compound (0.20 g) as a off-white solid.
MS (API+), found: 193.1.

D) tert-butyl ((3RS,4SR)-3-((2-fluoro-4-(4-methyl-1H-pyrazol-1-yl)phenoxy)methyl)tetrahydro-2H-pyran-4-yl)carbamate To a solution of tert-butyl ((3SR,4SR)-3-(hydroxymethyl)tetrahydro-2H-pyran-4-yl)carbamate (0.20 g) in THF (15 ml) was added 2-fluoro-4-(4-methyl-1H-pyrazol-1-yl)phenol (0.20 g), ADDP (438 mg) and Bu$_3$P (0.43 ml) at room temperature. The mixture was stirred at room temperature overnight. The mixture was added silica gel, and concentrated. It was purified by column chromatography (silica gel, eluted with EtOAc in hexane) to give the title compound (139 mg) as a white solid.
MS (API+), found: 350.1 (M+1-tBu).

E) (3RS,4SR)-3-((2-fluoro-4-(4-methyl-1H-pyrazol-1-yl)phenoxy)methyl)tetrahydro-2H-pyran-4-amine hydrochloride To a solution of tert-butyl ((3RS,4SR)-3-((2-fluoro-4-(4-methyl-1H-pyrazol-1-yl)phenoxy)methyl)tetrahydro-2H-pyran-4-yl)carbamate (0.16 g) in EtOAc (4.0 ml) was added 2 M HCl/EtOH (4.0 ml) at room temperature. The mixture was stirred overnight. The solvent was removed to give the title compound (0.13 g) as a white solid.
MS (API+), found: 306.1.

F) N-[(3RS,4SR)-3-{[2-fluoro-4-(4-methyl-1H-pyrazol-1-yl)phenoxy]methyl}tetrahydro-2H-pyran-4-yl]ethanesulfonamide A mixture of TEA (0.43 ml), ethanesulfonyl chloride (0.11 ml) and (3RS,4SR)-3-((2-fluoro-4-(4-methyl-1H-pyrazol-1-yl)phenoxy)methyl)tetrahydro-2H-pyran-4-amine hydrochloride (0.13 g) in THF (5.0 ml) was stirred at room temperature overnight. It was added silica gel and concentrated in vacuo. The residue was purified by column chromatography (silica gel, eluted with EtOAc in hexane), then preparative HPLC (MeCN-water) to give the title compound (85 mg) as a pale yellow amorphous solid.
$^1$H NMR (300 MHz, DMSO-d$_6$) δ 1.14 (3H, t, J=7.2 Hz), 1.49-1.72 (1H, m), 1.84-2.01 (2H, m), 2.08 (3H, s), 2.92 (2H, q, J=7.2 Hz), 3.34-3.49 (3H, m), 3.75-3.93 (1H, m), 3.96-4.13 (2H, m), 4.21 (1H, dd, J=9.8, 3.4 Hz), 7.13-7.35 (2H, m), 7.48-7.60 (2H, m), 7.67 (1H, dd, J=12.8, 2.6 Hz), 8.21 (1H, s).

Example 287

N-[(3RS,4SR)-3-{[3-fluoro-4-(4-methyl-1H-pyrazol-1-yl)phenoxy]methyl}tetrahydro-2H-pyran-4-yl]ethanesulfonamide

A) 3-fluoro-4-(4-methyl-1H-pyrazol-1-yl)phenol

A mixture of 4-bromo-3-fluorophenol (4.7 g), 4-methyl-1H-pyrazole (2.0 g), picolinic acid (0.60 g), cesium carbonate (12 g), and copper(I)iodide (0.23 g) in DMF (100 ml) was degassed then stirred at 130° C. under N$_2$ for 16 h. After cooling to room temperature, the mixture was added 6 M HCl aq. (9.0 ml) and water, then extracted with EtOAc. The organic layer was washed with water, dried (MgSO$_4$), and concentrated in vacuo. The residue was purified by column chromatography (silica gel, eluted with EtOAc in hexane) to give the title compound (0.73 g) as pale yellow solid.
MS (API+), found: 193.1.

B) tert-butyl ((3RS,4SR)-3-((3-fluoro-4-(4-methyl-1H-pyrazol-1-yl)phenoxy)methyl)tetrahydro-2H-pyran-4-yl)carbamate A mixture of tert-butyl ((3SR,4SR)-3-(hydroxymethyl)tetrahydro-2H-pyran-4-yl)carbamate (0.15 g), 3-fluoro-4-(4-methyl-1H-pyrazol-1-yl)phenol (0.14 g), ADDP (0.32 g), and tributylphosphine (0.32 ml) in THF(dry)(20 ml) was stirred at room temperature for 18 h. The mixture was added silica gel, concentrated in vacuo, and purified by column chromatography (silica gel, eluted with EtOAc in hexane) to give the title compound (0.24 g) as colorless oil.
MS (API+), found: 406.2.

C) (3RS,4SR)-3-((3-fluoro-4-(4-methyl-1H-pyrazol-1-yl)phenoxy)methyl)tetrahydro-2H-pyran-4-amine hydrochloride A mixture of tert-butyl ((3RS,4SR)-3-((3-fluoro-4-(4-methyl-1H-pyrazol-1-yl)phenoxy)methyl)tetrahydro-2H-pyran-4-yl)carbamate (0.24 g) and 2 M HCl/EtOH (10 ml) in EtOH (5.0 ml) was stirred at room temperature for 3 h. The solvent was removed in vacuo to give the title compound (0.21 g) as a pale yellow solid.
MS (API+), found: 306.1.

D) N-[(3RS,4SR)-3-{[3-fluoro-4-(4-methyl-1H-pyrazol-1-yl)phenoxy]methyl}tetrahydro-2H-pyran-4-yl]ethanesulfonamide A mixture of (3RS,4SR)-3-((3-fluoro-4-(4-methyl-1H-pyrazol-1-yl)phenoxy)methyl)tetrahydro-2H-pyran-4-amine hydrochloride (0.21 g), TEA (0.67 ml) and ethanesulfonyl chloride (0.17 ml) in THF (10 ml) was stirred at room temperature for 16 h. The mixture was added MeOH and silica gel, concentrated in vacuo, and purified by column chromatography (silica gel, eluted with EtOAc in hexane) to give the title compound (64 mg) as pale yellow amorphous powder.
$^1$H NMR (300 MHz, DMSO-d$_6$) δ 1.14 (3H, t, J=7.2 Hz), 1.55-1.64 (1H, m), 1.85-1.98 (2H, m), 2.09 (3H, s), 2.99 (2H, q, J=7.3 Hz), 3.25-3.41 (3H, m), 3.80-3.89 (1H, m), 3.96-4.07 (2H, m), 4.11-4.18 (1H, m), 6.85-6.92 (1H, m), 7.04 (1H, dd, J=13.3, 2.7 Hz), 7.30 (1H, d, J=8.7 Hz), 7.54 (1H, s), 7.61 (1H, t, J=9.1 Hz), 7.85 (1H, d, J=3.0 Hz).

Example 288

N-[(3R,4S)-3-{[4-(4-chloro-1H-pyrazol-1-yl)-3-fluorophenoxy]methyl}tetrahydro-2H-pyran-4-yl]methanesulfonamide

A) 3-fluoro-4-(1H-pyrazol-1-yl)phenol

A mixture of 4-bromo-3-fluorophenol (133 g), 1H-pyrazole (95 g), salicylaldoxime (19 g), cesium carbonate (340 g), and copper(I)iodide (13 g) in DMF (1.0 l) was degassed then stirred at 130° C. under. N$_2$ for 64 h. After cooling to room temperature, the mixture was added 6 M HCl aq. (400 ml) and water, then extracted with EtOAc. The organic layer was washed with water, dried (MgSO$_4$), and concentrated in vacuo. The residue was purified by column chromatography (NH silica gel, eluted with EtOAc then silica gel, eluted with EtOAc in hexane) to give the title compound (25 g) as pale yellow solid.
MS (API+), found: 179.1.

B) 4-(4-chloro-1H-pyrazol-1-yl)-3-fluorophenol

A mixture of 3-fluoro-4-(1H-pyrazol-1-yl)phenol (4.0 g) and 1-chloropyrrolidine-2,5-dione (3.0 g) in THF (220 ml) was stirred at 60° C. for 20 h. After cooling to room temperature, the mixture was added silica gel, concentrated in vacuo, and purified by column chromatography (silica gel, eluted with EtOAc in hexane) to give the title compound (1.9 g) as a white solid.
MS (API+), found: 213.0.

C) tert-butyl ((3R,4S)-3-((4-(4-chloro-1H-pyrazol-1-yl)-3-fluorophenoxy)methyl)tetrahydro-2H-pyran-4-yl)carbamate A mixture of tert-butyl ((3S,4S)-3-(hydroxymethyl)tetrahydro-2H-pyran-4-yl)carbamate (0.10 g), 4-(4-chloro-1H-pyrazol-1-yl)-3-fluorophenol (0.10 g), ADDP (0.22 g), and tributylphosphine (0.21 ml) in THF (7.0 ml) was stirred at room temperature for 18 h. The mixture was added MeOH and NH silica gel, concentrated in vacuo, and purified by column chromatography (NH silica gel, eluted with EtOAc in hexane) to give the title compound (0.12 g) as a white solid.
MS (API+), found: 370.1.

D) (3R,4S)-3-((4-(4-chloro-1H-pyrazol-1-yl)-3-fluorophenoxy)methyl)tetrahydro-2H-pyran-4-amine hydrochloride A mixture of tert-butyl ((3R,4S)-3-((4-(4-chloro-1H-pyrazol-1-yl)-3-fluorophenoxy)methyl)tetrahydro-2H-pyran-4-yl)carbamate (0.12 mg) and 2 M HCl/EtOH (4.0 ml) in EtOH (2.0 ml) was stirred at room temperature for 3 h. The solvent was removed in vacuo to give the title compound (98 mg) as a pale yellow solid.
MS (API+), found: 326.1.

E) N-[(3R,4S)-3-{[4-(4-chloro-1H-pyrazol-1-yl)-3-fluorophenoxy]methyl}tetrahydro-2H-pyran-4-yl]methanesulfonamide A mixture of (3R,4S)-3-((4-(4-chloro-1H-pyrazol-1-yl)-3-fluorophenoxy)methyl)tetrahydro-2H-pyran-4-amine hydrochloride (98 mg), TEA (0.30 ml) and methanesulfonyl chloride (0.063 ml) in THF (10 ml) was stirred at room temperature for 16 h. The mixture was added MeOH and silica gel, concentrated in vacuo, and purified by column chromatography (silica gel, eluted with EtOAc in hexane) followed by recrystallization from EtOAc-IPE to give the title compound (57 mg) as a white solid.
$^1$H NMR (300 MHz, DMSO-$d_6$) δ 1.50-1.66 (1H, m), 1.85-2.03 (2H, m), 2.91 (3H, s), 3.35-3.43 (3H, m), 3.80-3.91 (1H, m), 3.96-4.09 (2H, m), 4.13-4.21 (1H, m), 6.92 (1H, dt, J=9.1, 1.7 Hz), 7.09 (1H, dd, J=12.9, 2.7 Hz), 7.31 (1H, d, J=8.3 Hz), 7.61 (1H, t, J=8.9 Hz), 7.86 (1H, s), 8.37 (1H, d, J=2.3 Hz).

Example 289

N-[(3R,4S)-3-{[4-(4-chloro-1H-pyrazol-1-yl)-2,5-difluorophenoxy]methyl}tetrahydro-2H-pyran-4-yl]ethanesulfonamide A) 1-(4-bromo-2,5-difluorophenyl)-1H-pyrazole A mixture of sodium hydride (0.90 g), 1H-pyrazole (1.5 g), and 1-bromo-2,4,5-trifluorobenzene (4.8 g) in DMF (100 ml) was stirred at room temperature for 16 h. After cooling to room temperature, the mixture was diluted with EtOAc, washed with water, dried (MgSO$_4$) and concentrated in vacuo. The residue was purified by column chromatography (silica gel, eluted with EtOAc in hexane) to give the title compound (3.5 g) as a white solid.
MS (API+), found: 259.0.

B) 2,5-difluoro-4-(1H-pyrazol-1-yl)phenol

A mixture of 1-(4-bromo-2,5-difluorophenyl)-1H-pyrazole (3.5 g), Pd$_2$(dba)$_3$ (0.37 g), di-tert-butyl(2',4',6'-triisopropyl-[1,1'-biphenyl]-2-yl)phosphine (0.97 mg), and potassium hydroxide (2.3 g) in NMP (40 ml) and water (40 ml) was degassed then stirred at 90° C. overweekend under N$_2$. After cooling to room temperature, the mixture was added silica gel, concentrated in vacuo, and purified by column chromatography (silica gel, eluted with EtOAc in hexane) to give the title compound (2.0 g) as a white solid.
MS (API+), found: 197.0.

C) 4-(4-chloro-1H-pyrazol-1-yl)-2,5-difluorophenol

A mixture of 2,5-difluoro-4-(1H-pyrazol-1-yl)phenol (0.37 g) and 1-chloropyrrolidine-2,5-dione (0.25 g) in THF (19 ml) was stirred at 60° C. for 20 h. After cooling to room temperature, the mixture was added silica gel, concentrated in vacuo, and purified by column chromatography (silica gel, eluted with EtOAc in hexane) to give the title compound (0.12 g) as a white solid.
MS (API+), found: 230.9.

D) tert-butyl ((3R,4S)-3-((4-(4-chloro-1H-pyrazol-1-yl)-2,5-difluorophenoxy)methyl)tetrahydro-2H-pyran-4-yl)carbamate A mixture of tert-butyl ((3S,4S)-3-(hydroxymethyl)tetrahydro-2H-pyran-4-yl)carbamate (0.12 g), 4-(4-chloro-1H-pyrazol-1-yl)-2,5-difluorophenol (0.12 g), ADDP (0.25 g), and tributylphosphine (0.25 ml) in THF (10 ml) was stirred at room temperature for 70 h. The mixture was added MeOH and NH silica gel, concentrated in vacuo, and purified by column chromatography (NH silica gel, eluted with EtOAc in hexane) to give the title compound (0.14 g) as a white solid.
MS (API+), found: 388.1.

E) (3R,4S)-3-((4-(4-chloro-1H-pyrazol-1-yl)-2,5-difluorophenoxy)methyl)tetrahydro-2H-pyran-4-amine hydrochloride A mixture of tert-butyl ((3R,4S)-3-((4-(4-chloro-1H-pyrazol-1-yl)-2,5-difluorophenoxy)methyl)tetrahydro-2H-pyran-4-yl)carbamate (0.14 g) and 2 N HCl/EtOH (5.0 ml) in MeOH (2.0 ml) was stirred at room temperature for 3 h. The solvent was removed in vacuo to give the title compound (0.11 g) as a pale yellow solid.
MS (API+), found: 344.1.

F) N-[(3R,4S)-3-{[4-(4-chloro-1H-pyrazol-1-yl)-2,5-difluorophenoxy]methyl}tetrahydro-2H-pyran-4-yl]ethanesulfonamide A mixture of (3R,4S)-3-((4-(4-chloro-1H-pyrazol-1-yl)-2,5-difluorophenoxy)methyl)tetrahydro-2H-pyran-4-amine hydrochloride (55 mg), TEA (0.16 ml) and methanesulfonyl chloride (0.041 ml) in THF (5.0 ml) was stirred at room temperature for 12 h. The mixture was added TEA (0.16 ml) and methanesulfonyl chloride (0.041 ml) and stirred at room temperature for 20 h. The mixture was added MeOH and silica gel, concentrated in vacuo, and purified by column chromatography (silica gel, eluted with EtOAc in hexane) followed by recrystallization from EtOAc-IPE to give the title compound (4.8 mg) as a white solid.

$^1$H NMR (300 MHz, DMSO-d$_6$) δ 1.16 (3H, t, J=7.4 Hz), 1.55-1.67 (1H, m), 1.88-2.00 (2H, m), 3.00 (2H, q, J=7.2 Hz), 3.33-3.42 (3H, m), 3.79-3.89 (1H, m), 3.95-4.04 (1H, m), 4.12-4.26 (2H, m), 7.30 (1H, d, J=8.7 Hz), 7.39 (1H, dd, J=12.7, 7.7 Hz), 7.67 (1H, dd, J=11.5, 7.4 Hz), 7.90 (1H, s), 8.42 (1H, d, J=2.3 Hz).

Example 290

N-[(3R,4S)-3-{[4-(4-chloro-1H-pyrazol-1-yl)-3,5-difluorophenoxy]methyl}tetrahydro-2H-pyran-4-yl]methanesulfonamide A) 3,5-difluoro-4-(1H-pyrazol-1-yl)phenol A mixture of 4-bromo-3,5-difluorophenol (4.3 g), 1H-pyrazole (2.8 g), salicylaldoxime (0.57 g), cesium carbonate (10 g), and copper(I)iodide (0.40 g) in DMF (50 ml) was degassed then stirred at 130° C. under N$_2$ for 64 h. After cooling to room temperature, the mixture was added 6 M HCl aq. (400 ml) and water, then extracted with EtOAc. The organic layer was washed with water, dried (MgSO$_4$), and concentrated in vacuo. The residue was purified by column chromatography (silica gel, eluted with EtOAc in hexane) to give the title compound (0.33 g) as pale yellow solid.

MS (API+), found: 197.0.

B) 4-(4-chloro-1H-pyrazol-1-yl)-3,5-difluorophenol

A mixture of 3,5-difluoro-4-(1H-pyrazol-1-yl)phenol (0.20 g) and 1-chloropyrrolidine-2,5-dione (0.13 g) in THF (10 ml) was stirred at 60° C. for 20 h. After cooling to room temperature, the mixture was added silica gel, concentrated in vacuo, and purified by column chromatography (silica gel, eluted with EtOAc in hexane) to give the title compound (76 mg) as a white solid.

MS (API+), found: 231.0.

C) tert-butyl ((3R,4S)-3-((4-(4-chloro-1H-pyrazol-1-yl)-3,5-difluorophenoxy)methyl)tetrahydro-2H-pyran-4-yl)carbamate A mixture of tert-butyl ((3S,4S)-3-(hydroxymethyl)tetrahydro-2H-pyran-4-yl)carbamate (76 mg), 4-(4-chloro-1H-pyrazol-1-yl)-3,5-difluorophenol (76 mg), ADDP (0.17 g), and tributylphosphine (0.16 ml) in THF(dry)(5 ml) was stirred at room temperature for 70 h. The mixture was added MeOH and NH silica gel, concentrated in vacuo, and purified by column chromatography (NH silica gel, eluted with EtOAc in hexane) to give the title compound (38 mg) as a white solid.

MS (API+), found: 444.2.

D) (3R,4S)-3-((4-(4-chloro-1H-pyrazol-1-yl)-3,5-difluorophenoxy)methyl)tetrahydro-2H-pyran-4-amine hydrochloride A mixture of tert-butyl ((3R,4S)-3-((4-(4-chloro-1H-pyrazol-1-yl)-3,5-difluorophenoxy)methyl)tetrahydro-2H-pyran-4-yl)carbamate (38 mg) and 2 M HCl/EtOH (5.0 ml) in MeOH (2.0 ml) was stirred at room temperature for 3 h. The solvent was removed in vacuo to give the title compound (32 mg) as a pale yellow solid.

MS (API+), found: 344.1.

E) N-[(3R,4S)-3-{[4-(4-chloro-1H-pyrazol-1-yl)-3,5-difluorophenoxy]methyl}tetrahydro-2H-pyran-4-yl]methane sulfonamide A mixture of (3R,4S)-3-((4-(4-chloro-1H-pyrazol-1-yl)-3,5-difluorophenoxy)methyl)tetrahydro-2H-pyran-4-amine hydrochloride (16 mg), TEA (0.047 ml) and methanesulfonyl chloride (0.010 ml) in THF (10 ml) was stirred at room temperature for 16 h. The mixture was added MeOH and silica gel, concentrated in vacuo, and purified by column chromatography (silica gel, eluted with EtOAc in hexane) followed by recrystallization from EtOAc-IPE to give the title compound (3.2 mg) as a white solid.

$^1$H NMR (300 MHz, DMSO-d$_6$) δ 1.54-1.66 (1H, m), 1.85-2.01 (2H, m), 2.93 (3H, s), 3.34-3.43 (3H, m), 3.80-3.89 (1H, m), 3.94-4.03 (1H, m), 4.05-4.21 (2H, m), 6.97-7.07 (2H, m), 7.32 (1H, d, J=8.3 Hz), 7.90 (1H, s), 8.36 (1H, s).

Example 291

N-[(3R,4S)-3-{[4-(4-chloro-1H-pyrazol-1-yl)-2-fluorophenoxy]methyl}tetrahydro-2H-pyran-4-yl]methanesulfonamide A) tert-butyl ((3R,4S)-3-((4-(4-chloro-1H-pyrazol-1-yl)-2-fluorophenoxy)methyl)tetrahydro-2H-pyran-4-yl)carbamate A mixture of tert-butyl ((3S,4S)-3-(hydroxymethyl)tetrahydro-2H-pyran-4-yl)carbamate (0.32 g), 4-(4-chloro-1H-pyrazol-1-yl)-2-fluorophenol (0.39 g), ADDP (0.71 g), and tributylphosphine (0.69 ml) in THF (15 ml) was stirred at room temperature for 18 h. The mixture was added MeOH and NH silica gel, concentrated in vacuo, and purified by column chromatography (NH silica gel, eluted with EtOAc in hexane) to give the title compound (0.39 g) as a white solid.

MS (API+), found: 370.1.

B) (3R,4S)-3-((4-(4-chloro-1H-pyrazol-1-yl)-2-fluorophenoxy)methyl)tetrahydro-2H-pyran-4-amine hydrochloride A mixture of tert-butyl ((3R,4S)-3-((4-(4-chloro-1H-pyrazol-1-yl)-2-fluorophenoxy)methyl)tetrahydro-2H-pyran-4-yl)carbamate (0.39 g) and 4 M HCl/EtOAc (15 ml) in EtOH (12 ml) was stirred at room temperature for 3 h. The solvent was removed in vacuo to give the title compound (0.33 g) as a pale yellow solid.

MS (API+), found: 326.1.

C) N-[(3R,4S)-3-{[4-(4-chloro-1H-pyrazol-1-yl)-2-fluorophenoxy]methyl}tetrahydro-2H-pyran-4-yl]methanesulfonamide A mixture of (3R,4S)-3-((4-(4-chloro-1H-pyrazol-1-yl)-2-fluorophenoxy)methyl)tetrahydro-2H-pyran-4-amine hydrochloride (0.33 g), TEA (1.0 ml) and methanesulfonyl chloride (0.21 ml) in THF (10 ml) was stirred at room temperature for 16 h. The mixture was added MeOH and silica gel, concentrated in vacuo, and purified by column chromatography (silica gel, eluted with EtOAc in hexane) followed by recrystallization from EtOAc-IPE to give the title compound (0.28 g) as a white solid.

$^1$H NMR (300 MHz, DMSO-d$_6$) δ 1.52-1.66 (1H, m), 1.86-2.00 (2H, m), δ 2.91 (3H, s), 3.32-3.43 (3H, m), 3.80-3.90 (1H, m), 3.98-4.13 (2H, m), 4.18-4.26 (1H, m), 7.23-7.33 (2H, m), 7.57-7.63 (1H, m), 7.70-7.77 (1H, m), 7.85 (1H, s), 8.73 (1H, s).

Example 292

N-[(3RS,4SR)-3-{[4-(1,3-thiazol-2-yl)phenoxy]methyl}tetrahydro-2H-pyran-4-yl]ethanesulfonamide Titled compound was synthesized by the similar method to Example 239.

Example 293

N-[(3RS,4SR)-3-{[4-(6-chloropyridin-3-yl)phenoxy]methyl}tetrahydro-2H-pyran-4-yl]ethanesulfonamide Titled compound was synthesized by the similar method to Example 239.

Example 294

N-[(3RS,4SR)-3-{[4-(5-methylpyridin-2-yl)phenoxy]methyl}tetrahydro-2H-pyran-4-yl]ethanesulfonamide Titled compound was synthesized by the similar method to Example 239.

Example 295

N-[(3RS,4SR)-3-{[4-(2-methyl-1,3-thiazol-5-yl)phenoxy]methyl}tetrahydro-2H-pyran-4-yl]ethanesulfonamide Titled compound was synthesized by the similar method to Example 239.

Example 296

N-[(3RS,4SR)-3-{[4-(5-chloropyridin-2-yl)-3-fluorophenoxy]methyl}tetrahydro-2H-pyran-4-yl]ethanesulfonamide Titled compound was synthesized by the similar method to Example 243.

Example 297

N-[(3R,4S)-3-{[4-(5-cyanopyridin-2-yl)phenoxy]methyl}tetrahydro-2H-pyran-4-yl]ethanesulfonamide Titled compound was synthesized by the similar method to Example 246.

Example 298

N-[(3R,4S)-3-{[2,3-difluoro-4-(5-fluoropyridin-2-yl)phenoxy]methyl}tetrahydro-2H-pyran-4-yl]methanesulfonamide Titled compound was synthesized by the similar method to Example 250.

Example 299

N-[(3R,4S)-4-{[4-(5-chloro-3-fluoropyridin-2-yl)phenoxy]methyl}tetrahydro-2H-pyran-3-yl]ethanesulfonamide Titled compound was synthesized by the similar method to Example 251.

Example 300

N-[(3R,4S)-3-{[4-(tetrahydro-2H-pyran-4-yl)phenoxy]methyl}tetrahydro-2H-pyran-4-yl]methanesulfonamide A) 4-(4-methoxyphenyl)-3,6-dihydro-2H-pyran (4-methoxyphenyl)magnesium bromide (100 ml) was added to a solution of dihydro-2H-pyran-4(3H)-one (4.55 g) in THF(dry) at 0° C. The mixture was stirred at room temperature under N$_2$ for 2 days. The mixture was neutralized with 1 M HCl aq. at 0° C. and stirred at room temperature for 3 h. It was extracted with EtOAc. The organic layer was separated, washed with water and brine, dried over MgSO$_4$ and concentrated in vacuo. The residue was purified by column chromatography (silica gel, eluted with EtOAc in hexane) to give the title compound (7.32 g) as a white Solid.
LC/MS [M+1]: 191.1

B) 4-(4-methoxyphenyl)tetrahydro-2H-pyran

A mixture of 10% Pd/C (420 mg) and 4-(4-methoxyphenyl)-3,6-dihydro-2H-pyran (4.2 g) in MeOH (150 ml) was stirred at room temperature under H$_2$ for 3 h. It was filtered through celite pad. The filtrate was concentrated in vacuo to give the title compound (4.34 g) as a colorless oil.
$^1$H NMR (300 MHz, CDCl$_3$) δ 1.67-1.90 (4H, m), 2.62-2.80 (1H, m), 3.40-3.58 (2H, m), 3.79 (3H, s), 3.96-4.11 (2H, m), 6.81-6.91 (2H, m), 7.08-7.21 (2H, m).

C) N-[(3R,4S)-3-{[4-(tetrahydro-2H-pyran-4-yl)phenoxy]methyl}tetrahydro-2H-pyran-4-yl]methanesulfonamide Titled compound was synthesized by the similar method to processes B) to D) of Example 250.

Example 301

N-[(3R,4S)-3-{[4-(5-chloropyridin-2-yl)-2-fluorophenoxy]methyl}tetrahydro-2H-pyran-4-yl]methanesulfonamide or N-[(3S,4R)-3-{[4-(5-chloropyridin-2-yl)-2-fluorophenoxy]methyl}tetrahydro-2H-pyran-4-yl]methanesulfonamide N-[(3RS,4SR)-3-{[4-(5-chloropyridin-2-yl)-2-fluorophenoxy]methyl}tetrahydro-2H-pyran-4-yl]methanesulfonamide (90 mg) was separated by HPLC (column: CHIRAL- PAK OD (0), 50 mmID×500 mL, DAICEL corporation, mobile phase: MeOH) to give the titled compound with shorter retention time (38.1 mg) as a white solid.

Example 302

N-[(3RS,4SR)-3-{[4-(4-ethyl-1H-pyrazol-1-yl)phenoxy]methyl}tetrahydro-2H-pyran-4-yl]ethanesulfonamide A) 4-bromo-1-(4-methoxyphenyl)-1H-pyrazole A mixture of 1-bromopyrrolidine-2,5-dione (19.0 g) and 1-(4-methoxyphenyl)-1H-pyrazole (17.7 g) in THF (300 ml) was stirred at room temperature overnight. It was added silica gel and concentrated in vacuo. The residue was purified by column chromatography (silica gel, eluted with EtOAc in hexane) to give the title compound (24.2 g) as a white solid.

LC/MS [M+1]: 253.0

B) 1-(4-methoxyphenyl)-4-vinyl-1H-pyrazole

A mixture of Pd(Ph$_3$P)$_4$ (0.685 g), sodium carbonate decahydrate (6.78 g), 4,4,5,5-tetramethyl-2-vinyl-1,3,2-dioxaborolane (5 g) and 4-bromo-1-(4-methoxyphenyl)-1H-pyrazole (3 g) in DME (80 ml) and water (16 ml) was stirred at 80° C. under N$_2$ overnight. It was added silica gel and concentrated in vacuo. The residue was purified by column chromatography (NH silica gel, eluted with EtOAc in hexane) to give a white solid (3.08 g), which was used to the next reaction without further purification.

LC/MS [M+1]: 201.1

C) 4-ethyl-1-(4-methoxyphenyl)-1H-pyrazole

A mixture of 1-(4-methoxyphenyl)-4-vinyl-1H-pyrazole compound with 4-bromo-1-(4-methoxyphenyl)-1H-pyrazole (1:1) (3.0 g) and 10% Pd/C (300 mg, 50% wet) in THF (150 ml) and EtOH (50 ml) was stirred at room temperature under H$_2$ for 2 days. It was filtered. The filtrate was concentrated in vacuo. The residue was purified by column chromatography (silica gel, eluted with EtOAc in hexane) to give 4-ethyl-1-(4-methoxyphenyl)-1H-pyrazole (446 mg) as a colorless oil.

LC/MS [M+1]: 203.1

D) N-[(3RS,4SR)-3-{[4-(4-ethyl-1H-pyrazol-1-yl)phenoxy]methyl}tetrahydro-2H-pyran-4-yl]ethanesulfonamide Titled compound was synthesized by the similar method to Example 243.

Example 303

N-[(3RS,4SR)-3-((4-(3,5-difluoropyridin-2-yl)phenoxy)methyl)tetrahydro-2H-pyran-4-yl]methanesulfonamide Titled compound was synthesized by the similar method to Example 239.

Example 304

N-[(3RS,4SR)-3-{[4-(3,5-difluoropyridin-2-yl)phenoxy]methyl}tetrahydro-2H-pyran-4-yl]ethanesulfonamide Titled compound was synthesized by the similar method to Example 239.

Example 305

N-[(3RS,4SR)-3-{[2-fluoro-4-(5-fluoropyridin-2-yl)phenoxy]methyl}tetrahydro-2H-pyran-4-yl]methanesulfonamide Titled compound was synthesized by the similar method to Example 243.

Example 306

N-[(3RS,4SR)-3-{[2-fluoro-4-(5-fluoropyridin-2-yl)phenoxy]methyl}tetrahydro-2H-pyran-4-yl]ethanesulfonamide Titled compound was synthesized by the similar method to Example 243.

Example 307

N-[(3RS,4SR)-3-{[2-fluoro-4-(5-fluoropyridin-2-yl)phenoxy]methyl}tetrahydro-2H-pyran-4-yl]cyclopropanesulfonamide Titled compound was synthesized by the similar method to Example 243.

Example 308

N-[(3RS,4SR)-3-{[4-(5-chloro-1,3-thiazol-2-yl)phenoxy]methyl}tetrahydro-2H-pyran-4-yl]methanesulfonamide Titled compound was synthesized by the similar method to processes A) and B) of Example 257 and processes B), C) and D) of Example 243.

Example 309

N-[(3RS,4SR)-3-{[3-fluoro-4-(5-fluoropyridin-2-yl)phenoxy]methyl}tetrahydro-2H-pyran-4-yl]methanesulfonamide Titled compound was synthesized by the similar method to Example 243.

Example 310

N-[(3RS,4SR)-3-{[3-fluoro-4-(5-fluoropyridin-2-yl)phenoxy]methyl}tetrahydro-2H-pyran-4-yl]ethanesulfonamide Titled compound was synthesized by the similar method to Example 243.

Example 311

N-[(3RS,4SR)-3-{[4-(5-chloro-3-fluoropyridin-2-yl)phenoxy]methyl}tetrahydro-2H-pyran-4-yl]methanesulfonamide Titled compound was synthesized by the similar method to Example 239.

Example 312

N-[(3R,4S)-3-{[4-(5-chloro-1,3-thiazol-2-yl)phenoxy]methyl}tetrahydro-2H-pyran-4-yl]cyclopropanesulfonamide Titled compound was synthesized by the similar method to 257.

Example 313

N-[(3R,4S)-3-{[3-fluoro-4-(5-fluoropyridin-2-yl)phenoxy]methyl}tetrahydro-2H-pyran-4-yl]ethanesulfonamide or N-[(3S,4R)-3-{[3-fluoro-4-(5-fluoropyridin-2-yl)phenoxy]methyl}tetrahydro-2H-pyran-4-yl]ethanesulfonamide N-[(3RS,4SR)-3-{[3-fluoro-4-(5-fluoropyridin-2-yl)phenoxy]methyl}tetrahydro-2H-pyran-4-yl]ethanesulfonamide (70.8 mg) was separated by HPLC (column: CHIRALPAK AD (LF001), 50 mmID×500 mL, DAICEL corporation, mobile phase: EtOH) to give titled compound with shorter retention time (29.6 mg) as a white solid.

Example 314

N-[(3R,4S)-3-{[4-(5-chloro-3-fluoropyridin-2-yl)phenoxy]methyl}tetrahydro-2H-pyran-4-yl]ethanesulfonamide or N-[(3S,4R)-3-{[4-(5-chloro-3-fluoropyridin-2-yl)phenoxy]methyl}tetrahydro-2H-pyran-4-yl]ethanesulfonamide N-[(3RS,4SR)-3-{[4-(5-chloro-3-fluoropyridin-2-yl)phenoxy]methyl}tetrahydro-2H-pyran-4-yl]ethanesulfonamide (66 mg) was separated by HPLC (column: CHIRALPAK AD (LF001), 50 mmID×500 mL, DAICEL corporation, mobile phase: EtOH) to give titled compound with shorter retention time (33.2 mg) as a white solid.

Example 315

N-{(3RS,4SR)-3-[(4-pyridin-3-ylphenoxy)methyl]tetrahydro-2H-pyran-4-yl}propane-1-sulfonamide Titled compound was synthesized by the similar method to Example 239.

Example 316

N-[(3RS,4SR)-3-{[4-(1,3-thiazol-5-yl)phenoxy]methyl}tetrahydro-2H-pyran-4-yl]propane-1-sulfonamide Titled compound was synthesized by the similar method to Example 239.

Example 317

N-[(3RS,4SR)-3-{[4-(1,3-thiazol-4-yl)phenoxy]methyl}tetrahydro-2H-pyran-4-yl]ethanesulfonamide Titled compound was synthesized by the similar method to Example 239.

Example 318

N-{(3RS,4SR)-3-[(4-pyridin-2-ylphenoxy)methyl]tetrahydro-2H-pyran-4-yl}propane-1-sulfonamide Titled compound was synthesized by the similar method to Example 239.

Example 319

N-[(3RS,4SR)-3-({4-[6-(trifluoromethyl)pyridin-3-yl]phenoxy}methyl)tetrahydro-2H-pyran-4-yl]ethanesulfonamide Titled compound was synthesized by the similar method to Example 239.

Example 320

N-[(3RS,4SR)-3-({4-[4-(trifluoromethyl)pyridin-2-yl]phenoxy}methyl)tetrahydro-2H-pyran-4-yl]ethanesulfonamide Titled compound was synthesized by the similar method to Example 239.

Example 321

N-[(3RS,4SR)-3-{[4-(6-methylpyridin-3-yl)phenoxy]methyl}tetrahydro-2H-pyran-4-yl]ethanesulfonamide Titled compound was synthesized by the similar method to Example 239.

Example 322

N-[(3RS,4SR)-3-{[4-(2-methylpyridin-3-yl)phenoxy]methyl}tetrahydro-2H-pyran-4-yl]ethanesulfonamide A) 4-(2-methylpyridin-3-yl)phenol A mixture of $Na_2CO_3$ (1.23 g), $Pd(Ph_3P)_4$ (0.202 g), 3-bromo-2-methylpyridine (1 g) and 4-hydroxyphenylboronic acid (0.962 g) in DME (15 ml) and water (5 ml) was stirred at 80° C. under $N_2$ overnight. It was added silica gel and concentrated in vacuo. The residue was purified by column chromatography (silica gel, eluted with EtOAc in hexane) to give the title compound (0.409 g) as a white solid. LC/MS [M+1]: 186.1

B) tert-butyl ((3RS,4SR)-3-((4-(2-methylpyridin-3-yl)phenoxy)methyl)tetrahydro-2H-pyran-4-yl)carbamate A mixture of $Bu_3P$ (0.444 ml), ADDP (454 mg), 4-(2-methylpyridin-3-yl)phenol (250 mg) and tert-butyl (3SR, 4SR)-3-(hydroxymethyl)tetrahydro-2H-pyran-4-ylcarbamate (208 mg) in toluene (25 ml) was stirred at room temperature overnight. The mixture was poured into 1 M NaOH aq. and extracted with EtOAc. The organic layer was separated, washed with 0.1M NaOH aq. and brine, dried over MgSO$_4$ and concentrated in vacuo. The residue was purified by column chromatography (silica gel, eluted with EtOAc in hexane) to give the title compound (320 mg) as a colorless amorphous solid.

LC/MS [M+1]: 399.2

C) N-[(3RS,4SR)-3-{[4-(2-methylpyridin-3-yl)phenoxy]methyl}tetrahydro-2H-pyran-4-yl]ethanesulfonamide A mixture of 2 M HCl/EtOH (10 ml) and tert-butyl (3RS,4SR)-3-((4-(2-methylpyridin-3-yl)phenoxy)methyl)tetrahydro-2H-pyran-4-ylcarbamate (320 mg) was stirred at room temperature for 10 min. It was concentrated in vacuo. The residue was added CH$_3$CN (20 ml), triethylamine (813 mg) and ethanesulfonyl chloride (516 mg) at room temperature and stirred at room temperature for 3 h. It was added NH silica gel and concentrated in vacuo. The residue was purified by column chromatography (NH silica gel, eluted with EtOAc in hexane) to give titled compound (100 mg) as a off-white solid. It was crystallized from IPE-hexane-EtOAc to give a pale yellow solid.

$^1$H NMR (300 MHz, CDCl$_3$) δ 1.29 (3H, t, J=7.3 Hz), 1.60-1.82 (1H, m), 1.89-2.10 (1H, m), 2.11-2.25 (1H, m), 2.50 (3H, s), 2.90-3.08 (2H, m), 3.34-3.71 (3H, m), 3.88-4.21 (4H, m), 4.26 (1H, d, J=9.0 Hz), 6.91-7.05 (2H, m), 7.17 (1H, dd, J=7.7, 4.7 Hz), 7.20-7.30 (2H, m), 7.49 (1H, dd, J=7.5, 1.9 Hz), 8.48 (1H, dd, J=4.7, 1.7 Hz).

Example 323

N-[(3RS,4SR)-3-{[4-(2-methyl-1,3-thiazol-4-yl)phenoxy]methyl}tetrahydro-2H-pyran-4-yl]ethanesulfonamide Titled compound was synthesized by the similar method to Example 239.

Example 324

N-[(3RS,4SR)-3-({4-[4-(1-methylethyl)-1H-pyrazol-1-yl]phenoxy}methyl)tetrahydro-2H-pyran-4-yl]ethanesulfonamide Titled compound was synthesized by the similar method to Example 302

Example 325

N-[(3RS,4SR)-3-({4-[4-(trifluoromethyl)-1H-pyrazol-1-yl]phenoxy}methyl)tetrahydro-2H-pyran-4-yl]ethanesulfonamide Titled compound was synthesized by the similar method to processes A) and B) of Example 265 and processes B), C) and D) of Example 243.

Example 326

N-[(3RS,4SR)-3-{[4-(5-chloropyridin-2-yl)phenoxy]methyl}tetrahydro-2H-pyran-4-yl]ethanesulfonamide Titled compound was synthesized by the similar method to Example 239.

Example 327

N-[(3RS,4SR)-3-{[4-(4-methylpyridin-2-yl)phenoxy]methyl}tetrahydro-2H-pyran-4-yl]ethanesulfonamide Titled compound was synthesized by the similar method to Example 239.

Example 328

N-[(1SR,2SR)-2-{[4-(4-cyano-1H-pyrazol-1-yl)phenoxy]methyl}-4,4-difluorocyclohexyl]ethanesulfonamide A) 1-(4-methoxyphenyl)-1H-pyrazole-4-carbonitrile A mixture of Pd$_2$(dba)$_3$ (0.478 g), DPPF (0.578 g), dicyanozinc (1.225 g) and 4-bromo-1-(4-methoxyphenyl)-1H-pyrazole (2.64 g) in DMF (40 ml) was stirred at 120° C. under N$_2$ for 4 days. After cooling to room temperature, the mixture was added water and extracted with EtOAc. The organic layer was separated, washed with brine, dried over MgSO$_4$ and concentrated in vacuo. The residue was purified by column chromatography (silica gel, eluted with EtOAc in hexane) to give the title compound (1.57 g) as a pale yellow solid.

LC/MS [M+1]: 200.1

B) 1-(4-hydroxyphenyl)-1H-pyrazole-4-carbonitrile

A mixture of 1-(4-methoxyphenyl)-1H-pyrazole-4-carbonitrile (510 mg), aluminum trichloride (2.05 g) and dodecane-1-thiol (3.68 ml) in toluene (20 ml) was stirred at 0° C. for 1 h. The mixture was quenched with 1 N HCl aq. and extracted with EtOAc. The organic layer was separated, washed with water and brine, dried over Na$_2$SO$_4$ and concentrated in vacuo. The residue was purified by column chromatography (NH silica gel, eluted with EtOAc in hexane) to give the title compound (372 mg) as a white solid.

LC/MS [M+1]: 186.0

C) N-[(1SR,2SR)-2-{[4-(4-cyano-1H-pyrazol-1-yl)phenoxy]methyl}-4,4-difluorocyclohexyl]ethanesulfonamide Titled compound was synthesized by the similar method to processes B) and C) of Example 260.

Example 329

N-[(3RS,4SR)-3-{[4-(4-cyano-1H-pyrazol-1-yl)phenoxy]methyl}tetrahydro-2H-pyran-4-yl]ethanesulfonamide Titled compound was synthesized by the similar method to process A) of Example 328 and processes B), C) and D) of Example 243.

Example 330

N-[(3RS,4SR)-3-{[4-(5-methyl-1,3-thiazol-2-yl)phenoxy]methyl}tetrahydro-2H-pyran-4-yl]ethanesulfonamide Titled compound was synthesized by the similar method to Example 239.

Example 331

N-[(3RS,4SR)-3-{[4-(4-methyl-1,3-thiazol-2-yl)phenoxy]methyl}tetrahydro-2H-pyran-4-yl]ethanesulfonamide Titled compound was synthesized by the similar method to Example 239.

Example 332

N-[(3RS,4SR)-3-{[4-(1-methyl-1H-pyrazol-4-yl)phenoxy]methyl}tetrahydro-2H-pyran-4-yl]ethanesulfonamide Titled compound was synthesized by the similar method to Example 239.

Example 333

N-[(3RS,4SR)-3-{[4-(5-methyl-1,3-thiazol-2-yl)phenoxy]methyl}tetrahydro-2H-pyran-4-yl]methanesulfonamide Titled compound was synthesized by the similar method to Example 239.

Example 334

N-[(1SR,2SR)-2-{[4-(5-cyanopyridin-2-yl)phenoxy]methyl}-4,4-difluorocyclohexyl]ethanesulfonamide Titled compound was synthesized by the similar method to Example 260.

Example 335

N-[(3RS,4SR)-3-{[4-(5-fluoropyridin-2-yl)phenoxy]methyl}tetrahydro-2H-pyran-4-yl]methanesulfonamide Titled compound was synthesized by the similar method to Example 239.

Example 336

N-[(3RS,4SR)-3-{[4-(2-methyl-1,3-oxazol-4-yl)phenoxy]methyl}tetrahydro-2H-pyran-4-yl]ethanesulfonamide A) 4-(4-methoxyphenyl)-2-methyl-1,3-oxazole A mixture of acetamide (3.09 g) and 2-bromo-1-(4-methoxyphenyl)ethanone (8 g) was stirred at 130° C. for 30 min. Then it was added acetamide (3.09 g) at the same temperature and stirred for d h at the same temperature. The residue was purified by column chromatography (silica gel, eluted with EtOAc is in hexane) to give the title compound (3.73 g) as a yellow solid.

LC/MS [M+1]: 190.1

B) N-[(3RS,4SR)-3-{[4-(2-methyl-1,3-oxazol-4-yl)phenoxy]methyl}tetrahydro-2H-pyran-4-yl]ethanesulfonamide Titled compound was synthesized by the similar method to processes B), C) and D) of Example 243.

Example 337

N-[(3RS,4SR)-3-{[4-(2-methyl-1,3-oxazol-4-yl)phenoxy]methyl}tetrahydro-2H-pyran-4-yl]propane-1-sulfonamide Titled compound was synthesized by the similar method to Example 336.

Example 338

2,2,2-trifluoro-N-[(3RS,4SR)-3-{[4-(2-methyl-1,3-oxazol-4-yl)phenoxy]methyl}tetrahydro-2H-pyran-4-yl]ethanesulfonamide Titled compound was synthesized by the similar method to Example 336.

Example 339

N-[(3RS,4SR)-3-{[4-(5-methyl-1,3-oxazol-2-yl)phenoxy]methyl}tetrahydro-2H-pyran-4-yl]ethanesulfonamide A) N-(2-hydroxypropyl)-4-methoxybenzamide To a mixture of 4-methoxybenzoyl chloride (16 g) in THF (150 ml) was added a mixture of triethylamine (28.5 g) and 1-aminopropan-2-ol (8.45 g) in THF (150 ml) at 0° C. The mixture was stirred at room temperature overnight. It was filtered through NH silica gel pad. The filtrate was concentrated in vacuo to give the title compound (20.0 g) as a white solid.

LC/MS [M+1]: 210.2

B) 4-methoxy-N-(2-oxopropyl)benzamide

A mixture of Et$_3$N (55.0 ml), SO$_3$.py (20.9 g) and N-(2-hydroxypropyl)-4-methoxybenzamide (5.5 g) in DMSO (100 ml) was stirred at room temperature for 2 days. The mixture was poured into brine and extracted with EtOAc. The organic layer was separated, washed with brine, dried over MgSO$_4$ and concentrated in vacuo. The residue was purified by column chromatography (silica gel, eluted with EtOAc in hexane) to give the title compound (3.83 g) as a white solid.

LC/MS [M+1]: 208.1

C) 2-(4-methoxyphenyl)-5-methyl-1,3-oxazole

A mixture of Burgess reagent (1.50 g) and 4-methoxy-N-(2-oxopropyl)benzamide (650 mg) in THF (20 ml) was stirred at 80° C. under N$_2$ for 1 h. The mixture was poured into brine and extracted with EtOAc. The organic layer was separated, washed with brine, dried over MgSO$_4$ and concentrated in vacuo. The residue was purified by column chromatography (silica gel, eluted with EtOAc in hexane) to give the title compound (530 mg) as a colorless oil.

LC/MS [M+1]: 190.1

D) N-[(3RS,4SR)-3-{[4-(5-methyl-1,3-oxazol-2-yl)phenoxy]methyl}tetrahydro-2H-pyran-4-yl]ethanesulfonamide Titled compound was synthesized by the similar method to processes B), C) and D) of Example 243.

Example 340

N-[(3RS,4SR)-3-{[4-(5-methyl-1,3-oxazol-2-yl)phenoxy]methyl}tetrahydro-2H-pyran-4-yl]propane-1-sulfonamide Titled compound was synthesized by the similar method to Example 339.

Example 341

N-[(3R,4S)-3-{[4-(4-ethyl-1H-pyrazol-1-yl)phenoxy]methyl}tetrahydro-2H-pyran-4-yl]ethanesulfonamide or N-[(3S,4R)-3-{[4-(4-ethyl-1H-pyrazol-1-yl)phenoxy]methyl}tetrahydro-2H-pyran-4-yl]ethanesulfonamide Titled compound was synthesized by the similar method to steps A), B) and C) of Example 302 and steps B), C) and D) of Example 255.

Example 342

N-[(3RS,4SR)-3-{[4-(4-ethyl-1H-pyrazol-1-yl)phenoxy]methyl}tetrahydro-2H-pyran-4-yl]methanesulfonamide Titled compound was synthesized by the similar method to Example 302.

Example 343

N-[(3RS,4SR)-3-{[4-(5-methylisoxazol-3-yl)phenoxy]methyl}tetrahydro-2H-pyran-4-yl]methanesulfonamide Titled compound was synthesized by the similar method to processes A), B) and C) of Example 247 and processes B) and C) of Example 239.

Example 344

N-[(3RS,4SR)-3-{[4-(5-methylisoxazol-3-yl)phenoxy]methyl}tetrahydro-2H-pyran-4-yl]ethanesulfonamide Titled compound was synthesized by the similar method to Example 343.

Example 345

N-[(3RS,4SR)-3-{[4-(5-methylisoxazol-3-yl)phenoxy]methyl}tetrahydro-2H-pyran-4-yl]cyclopropanesulfonamide Titled compound was synthesized by the similar method to Example 343.

Example 346

N-[(3RS,4SR)-3-{[4-(4-ethyl-1H-pyrazol-1-yl)phenoxy]methyl}tetrahydro-2H-pyran-4-yl]cyclopropanesulfonamide Titled compound was synthesized by the similar method to Example 302.

Example 347

N-[(3RS,4SR)-3-{[4-(1,3-dimethyl-1H-pyrazol-5-yl)phenoxy]methyl}tetrahydro-2H-pyran-4-yl]ethanesulfonamide Titled compound was synthesized by the similar method to Example 239.

Example 348

N-[(3RS,4SR)-3-({4-[6-(trifluoromethyl)pyridin-3-yl]phenoxy}methyl)tetrahydro-2H-pyran-4-yl]methanesulfonamide Titled compound was synthesized by the similar method to Example 239.

Example 349

N-[(3RS,4SR)-3-({4-[6-(trifluoromethyl)pyridin-3-yl]phenoxy}methyl)tetrahydro-2H-pyran-4-yl]cyclopropanesulfonamide Titled compound was synthesized by the similar method to Example 239.

Example 350

N-[(3RS,4SR)-3-({4-[5-(trifluoromethyl)pyridin-2-yl]phenoxy}methyl)tetrahydro-2H-pyran-4-yl]methanesulfonamide Titled compound was synthesized by the similar method to Example 239.

Example 351

N-[(3RS,4SR)-3-({4-[5-(trifluoromethyl)pyridin-2-yl]phenoxy}methyl)tetrahydro-2H-pyran-4-yl]ethanesulfonamide rac A) 4-(5-(trifluoromethyl)pyridin-2-yl)phenol A mixture of (4-hydroxyphenyl)boronic acid (4.88 g), Pd(Ph$_3$P)$_4$ (0.614 g), 2-bromo-5-(trifluoromethyl)pyridine (4 g) and (4-hydroxyphenyl)boronic acid (4.88 g) in DME (75 ml) and water (15 ml) was stirred at 80° C. under N$_2$ overnight. It was added silica gel and concentrated in vacuo.

The residue was purified by column chromatography (silica gel, eluted with EtOAc in hexane) to give the title compound (3.21 g) as a yellow solid.
LC/MS [M+1]: 240.0

B) tert-butyl ((3RS,4SR)-3-((4-(5-(trifluoromethyl) pyridin-2-yl)phenoxy)methyl)tetrahydro-2H-pyran-4-yl)carbamate A mixture of Bu$_3$P (0.427 ml), ADDP (436 mg), 4-(5-(trifluoromethyl)pyridin-2-yl)phenol (496 mg) and tert-butyl ((3SR,4SR)-3-(hydroxymethyl)tetrahydro-2H-pyran-4-yl)carbamate (400 mg) in THF (25 ml) was stirred at room temperature overnight. The mixture was poured into 1 M NaOH aq. and extracted with EtOAc. The organic layer was separated, washed with 1 M NaOH aq. and brine, dried over MgSO$_4$ and concentrated in vacuo. The residue was purified by column chromatography (silica gel, eluted with EtOAc in hexane) to give the title compound (197 mg) as a white solid.
LC/MS [M+1]: 453.2

C) N-[(3RS,4SR)-3-((4-(5-(trifluoromethyl)pyridin-2-yl)phenoxy)methyl)tetrahydro-2H-pyran-4-yl]ethanesulfonamide A mixture of tert-butyl ((3RS,4SR)-3-((4-(5-(trifluoromethyl)pyridin-2-yl)phenoxy)methyl)tetrahydro-2H-pyran-4-yl)carbamate (98 mg) and 2 M HCl/EtOH (5 ml) was stirred at room temperature for 1 h. It was concentrated in vacuo. The residue was added THF (25 ml), triethylamine (329 mg) and ethanesulfonyl chloride (139 mg) at room temperature. The mixture was stirred at room temperature overnight. It was added silica gel and concentrated in vacuo. The residue was purified by column chromatography (silica gel, eluted with EtOAc in hexane) to give the title compound (50.2 mg) as a pale yellow solid. The solid was crystallized from EtOAc-hexane-IPE to give a desired product as a pale yellow solid.
$^1$H NMR (300 MHz, DMSO-d$_6$) δ 1.13 (3H, t, J=7.2 Hz), 1.50-1.70 (1H, m), 1.85-2.01 (2H, m), 2.98 (2H, q, J=7.3 Hz), 3.32-3.46 (3H, m), 3.79-3.90 (1H, m), 3.97-4.11 (2H, m), 4.20 (1H, dd, J=9.8, 3.0 Hz), 7.03-7.13 (2H, m), 7.30 (1H, d, J=8.7 Hz), 8.09-8.18 (3H, m), 8.19-8.25 (1H, m), 8.92-9.03 (1H, m).

Example 352

N-[(3RS,4SR)-3-({4-[2-(trifluoromethyl)-1,3-oxazol-4-yl]phenoxy}methyl)tetrahydro-2H-pyran-4-yl]methanesulfonamide Titled compound was synthesized by the similar method to Example 336.
$^1$H NMR (300 MHz, CDCl$_3$) δ 1.61-1.83 (1H, m), 1.89-2.08 (1H, m), 2.11-2.26 (1H, m), 2.88 (3H, s), 3.34-3.56 (2H, m), 3.57-3.76 (1H, m), 3.93-4.27 (4H, m), 4.35 (1H, d, J=8.7 Hz), 6.89-7.02 (2H, m), 7.63-7.75 (2H, m), 7.95 (1H, s).

Example 353

N-[(3RS,4SR)-3-({4-[2-(trifluoromethyl)-1,3-oxazol-4-yl]phenoxy}methyl)tetrahydro-2H-pyran-4-yl]ethanesulfonamide Titled compound was synthesized by the similar method to Example 336.

$^1$H NMR (300 MHz, CDCl$_3$) δ 1.26 (3H, t, J=7.4 Hz), 1.70 (1H, qd, J=12.1, 4.7 Hz), 1.88-2.07 (1H, m), 2.11-2.28 (1H, m), 2.97 (2H, q, J=7.2 Hz), 3.36-3.70 (3H, m), 3.94-4.05 (1H, m), 4.06-4.24 (4H, m), 6.92-7.00 (2H, m), 7.65-7.74 (2H, m), 7.94 (1H, s).

Example 354

N-[(3RS,4SR)-3-({4-[4-(trifluoromethyl)-1H-pyrazol-1-yl]phenoxy}methyl)tetrahydro-2H-pyran-4-yl]methanesulfonamide Titled compound was synthesized by the similar method to Example 325.

Example 355

N-[(3RS,4SR)-3-({4-[4-(trifluoromethyl)-1H-pyrazol-1-yl]phenoxy}methyl)tetrahydro-2H-pyran-4-yl]cyclopropanesulfonamide Titled compound was synthesized by the similar method to Example 325.

Example 356

N-[(3RS,4SR)-3-{[4-(5-fluoro-3-methylpyridin-2-yl)phenoxy]methyl}tetrahydro-2H-pyran-4-yl]methanesulfonamide Titled compound was synthesized by the similar method to Example 239.

Example 357

N-[(3RS,4SR)-3-{[4-(5-fluoro-3-methylpyridin-2-yl)phenoxy]methyl}tetrahydro-2H-pyran-4-yl]ethanesulfonamide Titled compound was synthesized by the similar method to Example 239.

Example 358

N-[(3RS,4SR)-3-{[4-(5-fluoro-3-methylpyridin-2-yl)phenoxy]methyl}tetrahydro-2H-pyran-4-yl]cyclopropanesulfonamide Titled compound was synthesized by the similar method to Example 239.

Example 359

N-[(3RS,4SR)-3-({4-[2-(trifluoromethyl)-1,3-thiazol-4-yl]phenoxy}methyl)tetrahydro-2H-pyran-4-yl]methanesulfonamide A) 4-(4-methoxyphenyl)-2-(trifluoromethyl)-1,3-thiazole A mixture of 2-bromo-1-(4-methoxyphenyl)ethanone (1.60 mg) and 2,2,2-trifluoroethanethioamide (900 mg) in EtOH (20 ml) was stirred at 100° C. overnight. Then it was added 2-bromo-1-(4-methoxyphenyl)ethanone (3194 mg) and stirred at 100° C. for 2 days. It was added silica gel and concentrated in vacuo. The residue was purified by column chromatography (silica gel, eluted with EtOAc in hexane) to give the title compound (390 mg) as a yellow oil.
LC/MS [M+1]: 260.1

B) N-[(3RS,4SR)-3-({4-[2-(trifluoromethyl)-1,3-thiazol-4-yl]phenoxy}methyl)tetrahydro-2H-pyran-4-yl]methanesulfonamide Titled compound was synthesized by the similar method to processes B), C) and D) of Example 243.

Example 360

N-[(3RS,4SR)-3-({4-[2-(trifluoromethyl)-1,3-thiazol-4-yl]phenoxy}methyl)tetrahydro-2H-pyran-4-yl]ethanesulfonamide Titled compound was synthesized by the similar method to Example 359.

Example 361

N-[(3RS,4SR)-3-({4-[2-(trifluoromethyl)-1,3-thiazol-4-yl]phenoxy}methyl)tetrahydro-2H-pyran-4-yl]cyclopropanesulfonamide Titled compound was synthesized by the similar method to Example 359.

Example 362

N-[(3RS,4SR)-3-{[4-(3,5-difluoropyridin-2-yl)phenoxy]methyl}tetrahydro-2H-pyran-4-yl]cyclopropanesulfonamide Titled compound was synthesized by the similar method to Example 239.

Example 363

N-[(3RS,4SR)-3-{[4-(5-chloro-1,3-thiazol-2-yl)phenoxy]methyl}tetrahydro-2H-pyran-4-yl]cyclopropanesulfonamide Titled compound was synthesized by the similar method to Example 308.

Example 364

N-[(3RS,4SR)-3-{[4-(5-chloropyridin-2-yl)-3-fluorophenoxy]methyl}tetrahydro-2H-pyran-4-yl]cyclopropanesulfonamide Titled compound was synthesized by the similar method to Example 243.

Example 365

N-[(3RS,4SR)-3-{[4-(5-chloropyridin-2-yl)-2-fluorophenoxy]methyl}tetrahydro-2H-pyran-4-yl]ethanesulfonamide Titled compound was synthesized by the similar method to Example 243.

Example 366

N-[(3RS,4SR)-3-{[4-(5-chloropyridin-2-yl)-2-fluorophenoxy]methyl}tetrahydro-2H-pyran-4-yl]cyclopropanesulfonamide Titled compound was synthesized by the similar method to Example 243.

Example 367

N-[(3RS,4SR)-3-{[(2'-cyano-4'-fluorobiphenyl-4-yl)oxy]methyl}tetrahydro-2H-pyran-4-yl]methanesulfonamide Titled compound was synthesized by the similar method to Example 239.

Example 368

N-[(3RS,4SR)-3-{[(2'-cyano-4'-fluorobiphenyl-4-yl)oxy]methyl}tetrahydro-2H-pyran-4-yl]ethanesulfonamide Titled compound was synthesized by the similar method to Example 239.

Example 369

N-[(3RS,4SR)-3-{[(2'-cyano-4'-fluorobiphenyl-4-yl)oxy]methyl}tetrahydro-2H-pyran-4-yl]cyclopropanesulfonamide Titled compound was synthesized by the similar method to Example 239.
$^1$H NMR (300 MHz, DMSO-$d_6$) δ 0.79-0.96 (4H, m), 1.51-1.72 (1H, m), 1.85-2.06 (2H, m), 2.53-2.63 (1H, m), 3.33-3.47 (3H, m), 3.79-3.92 (1H, m), 3.94-4.11 (2H, m), 4.23 (1H, dd, J=9.6, 2.1 Hz), 7.00-7.12 (2H, m), 7.33 (1H, d, J=8.3 Hz), 7.43-7.55 (2H, m), 7.56-7.72 (2H, m), 7.86-7.98 (1H, m).

Example 370

N-[(3RS,4SR)-3-{[4-(5-chloro-3-fluoropyridin-2-yl)phenoxy]methyl}tetrahydro-2H-pyran-4-yl]ethanesulfonamide Titled compound was synthesized by the similar method to Example 239.

Example 371

N-[(3R,4S)-3-{[4-(5-cyanopyridin-2-yl)phenoxy]methyl}tetrahydro-2H-pyran-4-yl]methanesulfonamide Titled compound was synthesized by the similar method to Example 246.

Example 372

N-[(3R,4S)-4-{[2-fluoro-4-(5-fluoropyridin-2-yl)
phenoxy]methyl}tetrahydro-2H-pyran-3-yl]methane-
sulfonamide Titled compound was synthesized by the similar method to steps B) and C) of Example 251.

Example 373

N-[(3R,4S)-4-{[2-fluoro-4-(5-fluoropyridin-2-yl)
phenoxy]methyl}tetrahydro-2H-pyran-3-yl]ethane-
sulfonamide Titled compound was synthesized by the similar method to Example 372.

Example 374

N-[(3R,4S)-4-{[4-(3,5-difluoropyridin-2-yl)phe-
noxy]methyl}tetrahydro-2H-pyran-3-yl]methanesul-
fonamide Titled compound was synthesized by the similar method to Example 251.

Example 375

N-[(3R,4S)-4-{[4-(5-chloro-3-fluoropyridin-2-yl)
phenoxy]methyl}tetrahydro-2H-pyran-3-yl]methane-
sulfonamide Titled compound was synthesized by the similar method to Example 251.

Example 376

N-[(3R,4S)-3-{[4-(5-fluoropyrimidin-2-yl)phenoxy]
methyl}tetrahydro-2H-pyran-4-yl]methanesulfona-
mide Titled compound was synthesized by the similar method to Example 246.

Example 377

N-[(3R,4S)-3-{[4-(5-chloropyrimidin-2-yl)phenoxy]
methyl}tetrahydro-2H-pyran-4-yl]methanesulfona-
mide Titled compound was synthesized by the similar method to Example 246.

Example 378

N-[(3R,4S)-3-{[4-(3,5-difluoropyridin-2-yl)phe-
noxy]methyl}tetrahydro-2H-pyran-4-yl]methanesul-
fonamide or N-[(3S,4R)-3-{[4-(3,5-difluoropyridin-
2-yl)phenoxy]methyl}tetrahydro-2H-pyran-4-yl]
methanesulfonamide N-[(3RS,4SR)-3-{[4-(3,5-difluoropyridin-2-yl)phenoxy]
methyl}tetrahydro-2H-pyran-4-yl]methanesulfonamide
(89.4 mg) was separated by HPLC (column: CHIRALPAK
AD (LF001), 50 mmID×500 mL, DAICEL corporation, mobile phase: EtOH) to give the titled compound with shorter retention time (41.8 mg) as a white solid.

Example 379

N-[(3S,4R)-3-{[4-(3,5-difluoropyridin-2-yl)phe-
noxy]methyl}tetrahydro-2H-pyran-4-yl]methanesul-
fonamide or N-[(3R,4S)-3-{[4-(3,5-difluoropyridin-
2-yl)phenoxy]methyl}tetrahydro-2H-pyran-4-yl]
methanesulfonamide N-[(3RS,4SR)-3-{[4-(3,5-difluoropyridin-2-yl)phenoxy]
methyl}tetrahydro-2H-pyran-4-yl]methanesulfonamide
(89.4 mg) was separated by HPLC (column: CHIRALPAK
AD (LF001), 50 mmID×500 mL, DAICEL corporation, mobile phase: EtOH) to give the titled compound with longer retention time (46.7 mg) as a white solid.

Example 380

N-[(3S,4R)-3-{[4-(5-chloropyridin-2-yl)-3-fluoro-
phenoxy]methyl}tetrahydro-2H-pyran-4-yl]methane-
sulfonamide or N-[(3R,4S)-3-{[4-(5-chloropyridin-
2-yl)-3-fluorophenoxy]methyl}tetrahydro-2H-pyran-
4-yl]methanesulfonamide N-[(3RS,4SR)-3-{[4-(5-chloropyridin-2-yl)-3-fluorophe-
noxy]methyl}tetrahydro-2H-pyran-4-yl]methanesulfona-
mide (89.5 mg) was separated by HPLC (column: CHIRAL-
PAK AD (LF001), 50 mmID×500 mL, DAICEL
corporation, mobile phase: EtOH) to give the titled com-
pound with longer retention time (45.8 mg) as a white solid.

Example 381

N-[(3R,4S)-3-{[4-(5-chloro-3-fluoropyridin-2-yl)
phenoxy]methyl}tetrahydro-2H-pyran-4-yl]methane-
sulfonamide or N-[(3S,4R)-3-{[4-(5-chloro-3-fluo-
ropyridin-2-yl)phenoxy]methyl}tetrahydro-2H-
pyran-4-yl]methanesulfonamide N-[(3RS,4SR)-3-{[4-(5-chloro-3-fluoropyridin-2-yl)phe-
noxy]methyl}tetrahydro-2H-pyran-4-yl]methanesulfona-
mide (89.1 mg) was separated by HPLC (column: CHIRAL-
PAK AD (LF001), 50 mmID×500 mL, DAICEL
corporation, mobile phase: EtOH) to give the titled com-
pound with shorter retention time (40.9 mg) as a white solid.

Example 382

N-[(3S,4R)-3-{[4-(5-chloro-3-fluoropyridin-2-yl)
phenoxy]methyl}tetrahydro-2H-pyran-4-yl]methane-
sulfonamide or N-[(3R,4S)-3-{[4-(5-chloro-3-fluo-
ropyridin-2-yl)phenoxy]methyl}tetrahydro-2H-
pyran-4-yl]methanesulfonamide N-[(3RS,4SR)-3-{[4-(5-chloro-3-fluoropyridin-2-yl)phe-
noxy]methyl}tetrahydro-2H-pyran-4-yl]methanesulfona-
mide (89.1 mg) was separated by HPLC (column: CHIRAL-
PAK AD (LF001), 50 mmID×500 mL, DAICEL
corporation, mobile phase: EtOH) to give the titled com-
pound with longer retention time (45.6 mg) as a white solid.

Example 383

N-[(3R,4S)-4-{[4-(5-chloro-3-fluoropyridin-2-yl) phenoxy]methyl}tetrahydro-2H-pyran-3-yl]cyclopropanesulfonamide A) 4-(5-chloro-3-fluoropyridin-2-yl)phenol A mixture of Pd(Ph$_3$P)$_4$ (0.418 g), 2,5-dichloro-3-fluoropyridine (2 g), Na$_2$CO$_3$ (3.83 g) and (4-hydroxyphenyl) boronic acid (3.32 g) in DME (50 ml) and water (10 ml) was stirred at 80° C. under N$_2$ overnight. It was added silica gel and concentrated in vacuo. The residue was purified by column chromatography (silica gel, eluted with EtOAc in hexane) to give 4-(5-chloro-3-fluoropyridin-2-yl)phenol (1.944 g) as a white solid.
LC/MS [M+1]: 224.0

B) tert-butyl ((3R,4S)-4-((4-(5-chloro-3-fluoropyridin-2-yl)phenoxy)methyl)tetrahydro-2H-pyran-3-yl) carbamate A mixture of Bu$_3$P (0.853 ml), ADDP (873 mg), 4-(5-chloro-3-fluoropyridin-2-yl)phenol (464 mg) and tert-butyl ((3R,4S)-4-(hydroxymethyl)tetrahydro-2H-pyran-3-yl)carbamate (400 mg) in THF (25 ml) was stirred at room temperature overnight. The mixture was poured into 1M NaOH aq. and extracted with EtOAc. The organic layer was separated, washed with 1M NaOH aq. and brine, dried over MgSO$_4$ and concentrated in vacuo. The residue was purified by column chromatography (silica gel, eluted with EtOAc in hexane) to give tert-butyl ((3R,4S)-4-((4-(5-chloro-3-fluoropyridin-2-yl)phenoxy)methyl)tetrahydro-2H-pyran-3-yl) carbamate (454 mg) as a white solid.
$^1$H NMR (300 MHz, CDCl$_3$) δ 1.42 (9H, s), 1.52-1.76 (1H, m), 1.84-2.09 (2H, m), 3.01-3.17 (1H, m), 3.33-3.49 (1H, m), 3.62 (1H, ddt, J=14.2, 9.7, 4.9 Hz), 3.84-4.23 (4H, m), 4.52 (1H, d, J=7.5 Hz), 6.92-7.05 (2H, m), 7.50 (1H, dd, J=10.5, 1.9 Hz), 7.87-7.99 (2H, m), 8.45 (1H, dd, J=1.9, 1.1 Hz).

C) N-[(3R,4S)-4-((4-(5-chloro-3-fluoropyridin-2-yl) phenoxy)methyl)tetrahydro-2H-pyran-3-yl]cyclopropanesulfonamide A mixture of tert-butyl ((3R,4S)-4-((4-(5-chloro-3-fluoropyridin-2-yl)phenoxy)methyl)tetrahydro-2H-pyran-3-yl) carbamate (140 mg) and hydrogen chloride (5 ml) was stirred at room temperature for 1 h. It was concentrated in vacuo. The residue was added THF (20 ml), triethylamine (486 mg), DBU (0.483 ml) and cyclopropanesulfonyl chloride (225 mg) at room temperature. The mixture was stirred at room temperature overnight. It was added sat. NaHCO$_3$ and silica gel and concentrated in vacuo. The residue was purified by column chromatography (silica gel, eluted with EtOAc in hexane) to give N-((3R,4S)-4-((4-(5-chloro-3-fluoropyridin-2-yl)phenoxy)methyl)tetrahydro-2H-pyran-3-yl)cyclopropanesulfonamide (19.30 mg) as a white solid. The solid was crystallized from EtOAc-hexane-IPE to give a desired product as a white solid.
$^1$H NMR (300 MHz, DMSO-d$_6$) δ 0.69-0.98 (4H, m), 1.48-1.71 (1H, m), 1.75-2.05 (2H, m), 2.52-2.64 (1H, m), 2.96-3.13 (1H, m), 3.15-3.27 (2H, m), 3.76-4.00 (2H, m), 4.02-4.13 (1H, m), 4.15-4.27 (1H, m), 7.03-7.15 (2H, m), 7.37 (1H, d, J=8.3 Hz), 7.82-7.94 (2H, m), 8.08-8.20 (1H, m), 8.54-8.62 (1H, m).

Example 384

N-[(3R,4S)-4-{[2-fluoro-4-(5-methylisoxazol-3-yl) phenoxy]methyl}tetrahydro-2H-pyran-3-yl]ethanesulfonamide Titled compound was synthesized by the similar method to processes A), B) and C) of Example 247 and Example 372.

Example 385

1,1,1-trifluoro-N-[(3R,4S)-3-{[3-fluoro-4-(5-methylisoxazol-3-yl)phenoxy]methyl}tetrahydro-2H-pyran-4-yl]methanesulfonamide Titled compound was synthesized by the similar method to Example 247.

Example 386

N-[(3R,4S)-3-{[4-(5-chloro-1,3-thiazol-2-yl)phenoxy]methyl}tetrahydro-2H-pyran-4-yl]methanesulfonamide Titled compound was synthesized by the similar method to Example 257.

Example 387

N-[(3R,4S)-3-{[2-fluoro-4-(5-methylisoxazol-3-yl) phenoxy]methyl}tetrahydro-2H-pyran-4-yl]methanesulfonamide Titled compound was synthesized by the similar method to Example 247.

Example 388

N-[(3R,4S)-3-{[2-fluoro-4-(5-methylisoxazol-3-yl) phenoxy]methyl}tetrahydro-2H-pyran-4-yl]ethanesulfonamide Titled compound was synthesized by the similar method to Example 247.

Example 389

N-[(3R,4S)-4-{[2-fluoro-4-(5-methylisoxazol-3-yl) phenoxy]methyl}tetrahydro-2H-pyran-3-yl]methanesulfonamide Titled compound was synthesized by the similar method to Example 384.

Example 390

N-[(3R,4S)-3-{[2-fluoro-4-(5-methylisoxazol-3-yl) phenoxy]methyl}tetrahydro-2H-pyran-4-yl]cyclopropanesulfonamide Titled compound was synthesized by the similar method to Example 247.

Example 391

N-[(3R,4S)-4-{[2-fluoro-4-(5-methylisoxazol-3-yl)
phenoxy]methyl}tetrahydro-2H-pyran-3-yl]cyclo-
propanesulfonamide Titled compound was synthesized by the similar method to Example 384.

Example 392

1,5-anhydro-6-O-[4-(5-chloro-3-fluoropyridin-2-yl)
phenyl]-2,3,4-trideoxy-4-[(methylsulfonyl)amino]-
D-erythro-hexitol A) 1,5-anhydro-4-((tert-butoxycarbonyl)amino)-6-
O-(4-(5-chloro-3-fluoropyridin-2-yl)phenyl)-2,3,4-
trideoxy-D-erythro-hexitol A mixture of tert-butyl ((2S,3S)-2-(hydroxymethyl)tetrahydro-2H-pyran-3-yl)carbamate (1.04 g), 4-(5-chloro-3-fluoropyridin-2-yl)phenol (1.307 g), ADDP (1.702 g) and Bu$_3$P (1.664 ml) in toluene (70 ml) was stirred at room temperature overnight. The mixture was purified by column chromatography (silica gel, eluted with EtOAc in hexane) to give titled compound (1.390 g) as a white solid.
LC/MS [M+1]: 437.2

B) 1,5-anhydro-6-O-[4-(5-chloro-3-fluoropyridin-2-
yl)phenyl]-2,3,4-trideoxy-4-[(methylsulfonyl)
amino]-D-erythro-hexitol A mixture of tert-butyl ((2S,3S)-2-((4-(5-chloro-3-fluoropyridin-2-yl)phenoxy)methyl)tetrahydro-2H-pyran-3-yl) carbamate (105 mg) and 2M hydrogen chloride in EtOH (5 ml) was stirred at room temperature for 1 h. It was concentrated in vacuo. The residue was added THF(dry) (25 ml), triethylamine (365 mg) and methanesulfonyl chloride (138 mg) at room temperature. The mixture was stirred at room temperature for 1 h. It was added sat. NaHCO$_3$ and slice gel and concentrated in vacuo. The residue was purified by column chromatography (silica gel, eluted with EtOAc in hexane) to give titled compound (63.7 mg) as a white solid. The solid was crystallized from EtOAc-hexane to give a desired product as a white solid.

Example 393

1,5-anhydro-6-O-[4-(5-chloro-3-fluoropyridin-2-yl)
phenyl]-2,3,4-trideoxy-4-[(ethylsulfonyl)amino]-D-
erythro-hexitol Titled compound was synthesized by the similar method to Example 392.

Example 394

1,5-anhydro-6-O-[4-(5-chloropyrimidin-2-yl)phenyl]-2,3,4-trideoxy-4-[(methylsulfonyl)amino]-D-
erythro-hexitol Titled compound was synthesized by the similar method to process A) of Example 239 and Example 392

Example 395

1,5-anhydro-6-O-[4-(5-chloropyrimidin-2-yl)phenyl]-2,3,4-trideoxy-4-[(ethylsulfonyl)amino]-D-
erythro-hexitol Titled compound was synthesized by the similar method to Example 394.

Example 396

1,5-anhydro-6-O-[4-(5-chloropyridin-2-yl)phenyl]-2,
3,4-trideoxy-4-[(methylsulfonyl)amino]-D-erythro-
hexitol Titled compound was synthesized by the similar method to Example 394.

Example 397

1,5-anhydro-6-O-[4-(5-chloropyridin-2-yl)phenyl]-2,
3,4-trideoxy-4-[(ethylsulfonyl)amino]-D-erythro-
hexitol Titled compound was synthesized by the similar method to Example 394.

Example 398

1,5-anhydro-2,3,4-trideoxy-6-O-[4-(5-fluoropyrimidin-2-yl)phenyl]-4-[(methylsulfonyl)amino]-D-
erythro-hexitol Titled compound was synthesized by the similar method to Example 394.

Example 399

1,5-anhydro-2,3,4-trideoxy-4-[(ethylsulfonyl)
amino]-6-O-[4-(5-fluoropyrimidin-2-yl)phenyl]-D-
erythro-hexitol Titled compound was synthesized by the similar method to Example 394.

Example 400

1,5-anhydro-4-[(cyclopropylsulfonyl)amino]-2,3,4-
trideoxy-6-O-[4-(5-fluoropyrimidin-2-yl)phenyl]-D-
erythro-hexitol Titled compound was synthesized by the similar method to Example 394.

Example 401

N-[(3S,4R)-3-{[3-fluoro-4-(5-fluoropyridin-2-yl)
phenoxy]methyl}tetrahydro-2H-pyran-4-yl]ethane-
sulfonamide or N-[(3R,4S)-3-{[3-fluoro-4-(5-fluoro-
pyridin-2-yl)phenoxy]methyl}tetrahydro-2H-pyran-
4-yl]ethanesulfonamide N-[(3RS,4SR)-3-{[3-fluoro-4-(5-fluoropyridin-2-yl)phenoxy]methyl}tetrahydro-2H-pyran-4-yl]ethanesulfonamide (70.8 mg) was separated by HPLC (column: CHIRALPAK AD (LF001), 50 mmID×500 mL, DAICEL corporation, mobile phase: EtOH) to give the titled compound with longer retention time (31.1 mg) as a white solid.

Example 402

N-[(3R,4S)-3-{[4-(5-chloropyridin-2-yl)-2-fluoro-phenoxy]methyl}tetrahydro-2H-pyran-4-yl]ethane-sulfonamide or N-[(3S,4R)-3-{[4-(5-chloropyridin-2-yl)-2-fluorophenoxy]methyl}tetrahydro-2H-pyran-4-yl]ethanesulfonamide N-[(3RS,4SR)-3-{[4-(5-chloropyridin-2-yl)-2-fluorophenoxy]methyl}tetrahydro-2H-pyran-4-yl]ethanesulfonamide (82.8 mg) was separated by HPLC (column: CHIRALPAK OD, 50 mmID×500 mL, DAICEL corporation, mobile phase: MeOH) to give the titled compound with shorter retention time (42.9 mg) as a white solid.

Example 403

N-[(3S,4R)-3-{[4-(5-chloropyridin-2-yl)-2-fluoro-phenoxy]methyl}tetrahydro-2H-pyran-4-yl]ethane-sulfonamide or N-[(3R,4S)-3-{[4-(5-chloropyridin-2-yl)-2-fluorophenoxy]methyl}tetrahydro-2H-pyran-4-yl]ethanesulfonamide N-[(3RS,4SR)-3-{[4-(5-chloropyridin-2-yl)-2-fluorophenoxy]methyl}tetrahydro-2H-pyran-4-yl]ethanesulfonamide (82.8 mg) was separated by HPLC (column: CHIRALPAK OD, 50 mmID×500 mL, DAICEL corporation, mobile phase: MeOH) to give the titled compound with longer retention time (36.2 mg) as a white solid.

Example 404

N-[(3R,4S)-3-{[4-(5-chloropyridin-2-yl)-3-fluoro-phenoxy]methyl}tetrahydro-2H-pyran-4-yl]cyclo-propanesulfonamide or N-[(3S,4R)-3-{[4-(5-chloro-pyridin-2-yl)-3-fluorophenoxy]methyl}tetrahydro-2H-pyran-4-yl]cyclopropanesulfonamide N-[(3RS,4SR)-3-{[4-(5-chloropyridin-2-yl)-3-fluorophenoxy]methyl}tetrahydro-2H-pyran-4-yl]cyclopropanesulfonamide (82.9 mg) was separated by HPLC (column: CHIRALPAK AD (LF001), 50 mmID×500 mL, DAICEL corporation, mobile phase: EtOH) to give the titled compound with shorter retention time (36.3 mg) as a white solid.

Example 405

N-[(3S,4R)-3-{[4-(5-chloro-3-fluoropyridin-2-yl) phenoxy]methyl}tetrahydro-2H-pyran-4-yl]ethane-sulfonamide or N-[(3R,4S)-3-{[4-(5-chloro-3-fluo-ropyridin-2-yl)phenoxy]methyl}tetrahydro-2H-pyran-4-yl]ethanesulfonamide N-[(3RS,4SR)-3-{[4-(5-chloropyridin-2-yl)-2-fluorophenoxy]methyl}tetrahydro-2H-pyran-4-yl]ethanesulfonamide (66 mg) was separated by HPLC (column: CHIRALPAK AD (LF001), 50 mmID×500 mL, DAICEL corporation, mobile phase: EtOH) to give the titled compound with longer retention time (32.9 mg) as a white solid.

Example 406

N-[(3R,4S)-3-{[4-(5-chloropyridin-2-yl)-2-fluoro-phenoxy]methyl}tetrahydro-2H-pyran-4-yl]cyclo-propanesulfonamide or N-[(3S,4S)-3-{[4-(5-chloro-pyridin-2-yl)-2-fluorophenoxy]methyl}tetrahydro-2H-pyran-4-yl]cyclopropanesulfonamide N-[(3RS,4SR)-3-{[4-(5-chloropyridin-2-yl)-2-fluorophe-noxy]methyl}tetrahydro-2H-pyran-4-yl]cyclopropanesulfo-namide (83.9 mg) was separated by HPLC (column: CHIRALPAK AD (LF001), 50 mmID×500 mL, DAICEL corporation, mobile phase: EtOH) to give the titled compound with shorter retention time (45.3 mg) as a white solid.

Example 407

N-[(1S,2S)-2-{[4-(5-cyanopyrimidin-2-yl)phenoxy] methyl}-4,4-difluorocyclohexyl]ethanesulfonamide Titled compound was synthesized by the similar method to Example 268.

Example 408

N-[(3R,4S)-3-{[4-(5-cyanothiophen-2-yl)phenoxy] methyl}tetrahydro-2H-pyran-4-yl]methanesulfona-mide Titled compound was synthesized by the similar method to Example 246.

Example 409

N-[(3R,4S)-3-{[4-(5-cyanothiophen-2-yl)phenoxy] methyl}tetrahydro-2H-pyran-4-yl]ethanesulfona-mide Titled compound was synthesized by the similar method to Example 246.

Example 410

N-[(3R,4S)-3-{[4-(5-cyanothiophen-2-yl)phenoxy] methyl}tetrahydro-2H-pyran-4-yl]cyclopropanesul-fonamide Titled compound was synthesized by the similar method to Example 246.

Example 411

N-[(3R,4S)-4-{[4-(5-cyanothiophen-2-yl)phenoxy] methyl}tetrahydro-2H-pyran-3-yl]methanesulfona-mide Titled compound was synthesized by the similar method to Example 251.

Example 412

N-[(3R,4S)-4-{[4-(5-cyanothiophen-2-yl)phenoxy] methyl}tetrahydro-2H-pyran-3-yl]ethanesulfona-mide Titled compound was synthesized by the similar method to Example 251.

Example 413

N-[(3R,4S)-3-{[4-(tetrahydro-2H-pyran-4-yl)phenoxy]methyl}tetrahydro-2H-pyran-4-yl]ethanesulfonamide Titled compound was synthesized by the similar method to Example 300.

Example 414

N-[(3R,4S)-3-{[4-(tetrahydro-2H-pyran-4-yl)phenoxy]methyl}tetrahydro-2H-pyran-4-yl]cyclopropanesulfonamide Titled compound was synthesized by the similar method to Example 300.

Example 415

N-[(3R,4S)-3-({4-[(4-chloro-1H-pyrazol-1-yl)methyl]phenoxy}methyl)tetrahydro-2H-pyran-4-yl]methanesulfonamide A) 4-(1H-pyrazol-1-ylmethyl)phenol A mixture of 4-(chloromethyl)phenyl acetate (1193 mg), 1H-pyrazole (400 mg) and $K_2CO_3$ (1624 mg) in DMF (25 ml) was stirred at 120° C. for 3 h. 1 M NaOH aq. (20 ml) was added to the solution at room temperature. The mixture was stirred at 60° C. for 1 h. The mixture was neutralized with 1 M HCl aq. and extracted with EtOAc. The organic layer was separated, washed with water and brine, dried over $MgSO_4$ and concentrated in vacuo. The residue was purified by column chromatography (silica gel, eluted with EtOAc in hexane) to give 4-((1H-pyrazol-1-yl)methyl)phenol (663 mg) as a white solid.

$^1$H NMR (300 MHz, DMSO-$d_6$) δ 5.17 (2H, s), 6.22 (1H, t, J=2.0 Hz), 6.62-6.77 (2H, m), 6.99-7.12 (2H, m), 7.41 (1H, dd, J=1.7, 0.6 Hz), 7.72 (1H, dd, J=2.1, 0.6 Hz), 9.38 (1H, s).

B) tert-butyl ((3R,4S)-3-((4-(1H-pyrazol-1-ylmethyl)phenoxy)methyl)tetrahydro-2H-pyran-4-yl)carbamate Titled compound was synthesized by the similar method to processes B) and C) of Example 246.

LC/MS [M+1]: 366.1

C) N-[(3R,4S)-3-({4-[(4-chloro-1H-pyrazol-1-yl)methyl]phenoxy}methyl)tetrahydro-2H-pyran-4-yl]methanesulfonamide A mixture of N-((3R,4S)-3-((4-((1H-pyrazol-1-yl)methyl)phenoxy)methyl)tetrahydro-2H-pyran-4-yl)methanesulfonamide (93 mg) and NCS (44.2 mg) in THF(dry) (3 ml) was stirred at 70° C. overnight. It was concentrated in vacuo. The residue was purified by column chromatography (silica gel, eluted with EtOAc in hexane) to give N-((3R,4S)-3-((4-((4-chloro-1H-pyrazol-1-yl)methyl)phenoxy)methyl)tetrahydro-2H-pyran-4-yl)methanesulfonamide (98 mg) as a colorless gum. It was triturated from Hex-EtOAc to give a desired product as a white solid.

Example 416

N-[(1S,2S)-4,4-difluoro-2-{[4-(1-methyl-2-oxo-1,2-dihydropyridin-3-yl)phenoxy]methyl}cyclohexyl]methanesulfonamide Titled compound was synthesized by the similar method to Example 267.

Example 417

N-[(1S,2S)-4,4-difluoro-2-{[4-(1-methyl-2-oxo-1,2-dihydropyridin-4-yl)phenoxy]methyl}cyclohexyl]methanesulfonamide Titled compound was synthesized by the similar method to Example 267.

Example 418

N-[(1S,2S)-4,4-difluoro-2-{[4-(1-methyl-2-oxo-1,2-dihydropyridin-4-yl)phenoxy]methyl}cyclohexyl]ethanesulfonamide Titled compound was synthesized by the similar method to Example 267.

Example 419

N-[(3R,4S)-4-{[4-(tetrahydro-2H-pyran-4-yl)phenoxy]methyl}tetrahydro-2H-pyran-3-yl]methanesulfonamide Titled compound was synthesized by the similar method to processes A) and B) of Example 300, process B) of Example 243 and Example 372.

Example 420

N-[(3R,4S)-4-{[4-(tetrahydro-2H-pyran-4-yl)phenoxy]methyl}tetrahydro-2H-pyran-3-yl]ethanesulfonamide Titled compound was synthesized by the similar method to Example 419.

Example 421

N-[(1S,2S)-4,4-difluoro-2-{[4-(tetrahydro-2H-pyran-4-yl)phenoxy]methyl}cyclohexyl]methanesulfonamide Titled compound was synthesized by the similar method to processes A) and B) of Example 300, process B) of Example 243, and Example 268.

Example 422

N-[(1S,2S)-4,4-difluoro-2-{[4-(tetrahydro-2H-pyran-4-yl)phenoxy]methyl}cyclohexyl]ethanesulfonamide Titled compound was synthesized by the similar method to Example 421.

Example 423

N-[(1S,2S)-2-({4-[1-(2,2-difluoroethyl)-2-oxopiperidin-3-yl]phenoxy}methyl)-4,4-difluorocyclohexyl]methanesulfonamide A) 3-(4-(benzyloxy)phenyl)-1-(2,2-difluoroethyl)pyridin-2(1H)-one Titled compound was synthesized by the similar method to processes A) and B) of Example 267.
LC/MS [M+1]: 342.1

B) 1-(2,2-difluoroethyl)-3-(4-hydroxyphenyl)piperidin-2-one

A mixture of 3-(4-(benzyloxy)phenyl)-1-(2,2-difluoroethyl)pyridin-2(1H)-one (1.4 g) and 10% Pd/C (55% wet, 4.36 g) in MeOH (30 ml) was hydrogenated under balloon pressure at room temperature for 2 days. The catalyst was removed by filtration and the filtrate was concentrated in vacuo. The residue was purified by column chromatography (silica gel, eluted with EtOAc in hexane) to give 1-(2,2-difluoroethyl)-3-(4-hydroxyphenyl)pyridin-2(1H)-one as a white solid.
LC/MS [M+1]: 256.1

C) N-[(1S,2S)-2-({4-[1-(2,2-difluoroethyl)-2-oxopiperidin-3-yl]phenoxy}methyl)-4,4-difluorocyclohexyl]methanesulfonamide Titled compound was synthesized by the similar method to Example 268.

Example 424

N-[(1S,2S)-2-({4-[1-(2,2-difluoroethyl)-2-oxopiperidin-3-yl]phenoxy}methyl)-4,4-difluorocyclohexyl]ethanesulfonamide Titled compound was synthesized by the similar method to Example 423.

Example 425

N-[(3R,4S)-3-{[2,3-difluoro-4-(1H-pyrazol-1-yl)phenoxy]methyl}tetrahydro-2H-pyran-4-yl]methanesulfonamide hydrochloride A) 1-(benzyloxy)-2,3-difluoro-4-iodobenzene A mixture of 2,3-difluoro-4-iodophenol (867 mg), $K_2CO_3$ (562 mg) and benzylbromide (0.422 ml) in DMF (dry) (10 ml) was stirred at room temperature overnight. The mixture was quenched with water, and the resulting precipitate was collected by filtration to give the title compound (1.13 g) as off-white solid.
$^1$H NMR (300 MHz, CDCl$_3$) δ 5.14 (2H, s), 6.61 (1H, ddd, J=9.0, 7.3, 1.9 Hz), 7.29-7.46 (6H, m).

B) 1-(4-(benzyloxy)-2,3-difluorophenyl)-1H-pyrazole

A mixture of 1H-pyrazole (0.376 g), 1-(benzyloxy)-2,3-difluoro-4-iodobenzene (1.74 g), copper(I)oxide (72 mg), picolinaldehyde oxime (0.246 g) and $Cs_2CO_3$ (4.09 g) in propionitrile (30 ml) was stirred at 100° C. overnight. The mixture was quenched with sat. NH$_4$Cl aq. at room temperature and extracted with EtOAc. The organic layer was separated, washed with water and brine, dried over $Na_2SO_4$ and concentrated in vacuo. The residue was purified by column chromatography (silica gel, eluted with 0%-30% EtOAc in hexane) to give the title compound (0.414 g) as a white solid.
MS (API+), found: 287.2 (M+1)

C) 2,3-difluoro-4-(1H-pyrazol-1-yl)phenol

Titled compound was synthesized by the similar method to process C) of Example 267.
MS (API+), found: 197.2 (M+1)

D) tert-butyl ((3R,4S)-3-((2,3-difluoro-4-(1H-pyrazol-1-yl)phenoxy)methyl)tetrahydro-2H-pyran-4-yl)carbamate Titled compound was synthesized by the similar method to process C) of Example 7.
MS (API+), found: 410.2 (M+1)

E) N-[(3R,4S)-3-{[2,3-difluoro-4-(1H-pyrazol-1-yl)phenoxy]methyl}tetrahydro-2H-pyran-4-yl]methanesulfonamide hydrochloride A mixture of tert-butyl ((3R,4S)-3-((2,3-difluoro-4-(1H-pyrazol-1-yl)phenoxy)methyl)tetrahydro-2H-pyran-4-yl)carbamate (113 mg) and 4 M HCl/EtOAc (5 ml) was stirred at room is temperature overnight. The resulting precipitate was collected by filtration. A mixture of the residue, triethylamine (84 mg) and methanesulfonyl chloride (63.2 mg) in THF(dry) (3 ml) was stirred at room temperature overnight. The mixture was quenched with sat. NaHCO$_3$ aq. and extracted with EtOAc. The organic layer was separated, washed with brine, dried over $Na_2SO_4$ and concentrated in vacuo. The residue was purified by column chromatography (silica gel, eluted with 20%-80% EtOAc in hexane). To the residue was added 4 M HCl/EtOAc (1 ml) and crystallized from EtOAc-IPE-hexane to give the title compound (73.0 mg) as white solid.

Example 426

N-[(3R,4S)-3-{[2-fluoro-4-(5-fluoropyridin-2-yl)phenoxy]methyl}tetrahydro-2H-pyran-4-yl]ethanesulfonamide or N-[(3S,4R)-3-{[2-fluoro-4-(5-fluoropyridin-2-yl)phenoxy]methyl}tetrahydro-2H-pyran-4-yl]ethanesulfonamide A) 5-fluoro-2-(3-fluoro-4-methoxyphenyl)pyridine Titled compound was synthesized by the similar method to process A) of Example 195.
MS (API+), found: 222.1 (M+1)

B) 2-fluoro-4-(5-fluoropyridin-2-yl)phenol

Titled compound was synthesized by the similar method to process C) of Example 213.
MS (API+), found: 208.0 (M+1)

C) N-((3RS,4SR)-3-((2-fluoro-4-(5-fluoropyridin-2-yl)phenoxy)methyl)tetrahydro-2H-pyran-4-yl)ethanesulfonamide Titled compound was synthesized by similar method of processes C) and D) of Example 7.
MS (API+), found: 413.1 (M+1)

D) N-[(3R,4S)-3-{[2-fluoro-4-(5-fluoropyridin-2-yl)phenoxy]methyl}tetrahydro-2H-pyran-4-yl]ethanesulfonamide or N-[(3S,4R)-3-{[2-fluoro-4-(5-fluoropyridin-2-yl)phenoxy]methyl}tetrahydro-2H-pyran-4-yl]ethanesulfonamide N-((3R,4S)-3-((2-fluoro-4-(5-fluoropyridin-2-yl)phenoxy)methyl)tetrahydro-2H-pyran-4-yl)ethanesulfonamide or N-((3S,4R)-3-((2-fluoro-4-(5-fluoropyridin-2-yl)phenoxy)methyl)tetrahydro-2H-pyran-4-yl)ethanesulfonamide (85 mg) was separated by HPLC (column: CHIRALCEL OD (50 mmID×500 mmL, DAICEL corporation, mobile phase: MeOH 100%) to give the title compound (35 mg) with shorter retention time as white powder.

Example 427

N-[(3R,4S)-3-{[4-(3,5-difluoropyridin-2-yl)phenoxy]methyl}tetrahydro-2H-pyran-4-yl]ethanesulfonamide or N-[(3S,4R)-3-{[4-(3,5-difluoropyridin-2-yl)phenoxy]methyl}tetrahydro-2H-pyran-4-yl]ethanesulfonamide A) 4-(3,5-difluoropyridin-2-yl)phenol Titled compound was synthesized by the similar method to process A) of Example 195.
MS (API+), found: 208.1 (M+1)

B) N-((3RS,4SR)-3-((4-(3,5-difluoropyridin-2-yl)phenoxy)methyl)tetrahydro-2H-pyran-4-yl)ethanesulfonamide Titled compound was synthesized by similar method of processes C) and D) of Example 7.
MS (API+), found: 413.2 (M+1)

C) N-[(3R,4S)-3-{[4-(3,5-difluoropyridin-2-yl)phenoxy]methyl}tetrahydro-2H-pyran-4-yl]ethanesulfonamide or N-[(3S,4R)-3-{[4-(3,5-difluoropyridin-2-yl)phenoxy]methyl}tetrahydro-2H-pyran-4-yl]ethanesulfonamide N-((3RS,4SR)-3-((4-(3,5-difluoropyridin-2-yl)phenoxy)methyl)tetrahydro-2H-pyran-4-yl)ethanesulfonamide (83 mg) was separated by HPLC (column: CHIRALCEL AD (50 mmID×500 mL, DAICEL corporation, mobile phase: EtOH 100%), to give the title compound (41 mg) with shorter retention time as white powder.

Example 428

N-[(3R,4S)-3-{[3-fluoro-4-(5-fluoropyridin-2-yl)phenoxy]methyl}tetrahydro-2H-pyran-4-yl]methanesulfonamide or N-[(3S,4R)-3-{[3-fluoro-4-(5-fluoropyridin-2-yl)phenoxy]methyl}tetrahydro-2H-pyran-4-yl]methanesulfonamide A) 5-fluoro-2-(2-fluoro-4-methoxyphenyl)pyridine Titled compound was synthesized by the similar method to process A) of Example 195.
MS (API+), found: 222.1 (M+1)

B) 3-fluoro-4-(5-fluoropyridin-2-yl)phenol

Titled compound was synthesized by the similar method to process C) of Example 213.
MS (API+), found: 208.0 (M+1)

C) N-((3RS,4SR)-3-((3-fluoro-4-(5-fluoropyridin-2-yl)phenoxy)methyl)tetrahydro-2H-pyran-4-yl)methanesulfonamide Titled compound was synthesized by similar method of processes C) and D) of Example 7.
MS (API+), found: 399.1 (M+1)

D) N-[(3R,4S)-3-{[3-fluoro-4-(5-fluoropyridin-2-yl)phenoxy]methyl}tetrahydro-2H-pyran-4-yl]methanesulfonamide or N-[(3S,4R)-3-{[3-fluoro-4-(5-fluoropyridin-2-yl)phenoxy]methyl}tetrahydro-2H-pyran-4-yl]methanesulfonamide N-((3RS,4SR)-3-((3-fluoro-4-(5-fluoropyridin-2-yl)phenoxy)methyl)tetrahydro-2H-pyran-4-yl)methanesulfonamide (83 mg) was separated by HPLC (column: CHIRALCEL AD (50 mmID×500 mL, DAICEL corporation, mobile phase: EtOH 100%), to give the title compound (45 mg) with shorter retention time as white powder.

Example 429

N-[(3RS,4SR)-3-{[4-(trifluoroacetyl)phenoxy]methyl}tetrahydro-2H-pyran-4-yl]ethanesulfonamide A) 2,2,2-trifluoro-1-(4-hydroxyphenyl)ethanone A mixture of 2,2,2-trifluoro-1-(4-methoxyphenyl)ethanone (1.0 g) and lithium chloride (0.623 g) in DMF(dry) (20 ml) was stirred at 160° C. for 4 h. The mixture was poured into water at room temperature and added 1 M HCl aq., and extracted with EtOAc. The organic layer was separated, washed with brine, dried over $Na_2SO_4$ and concentrated in vacuo. The residue was purified by column chromatography (silica gel, eluted with 0%-30% EtOAc in hexane) to give the title compound (0.257 g) as a white solid.
MS (API+), found: 189.1 (M−1)

B) N-[(3RS,4SR)-3-{[4-(trifluoroacetyl)phenoxy]methyl}tetrahydro-2H-pyran-4-yl]ethanesulfonamide Titled compound was synthesized by similar method of processes C) and D) of Example 7.

Example 430

N-[(3RS,4SR)-3-{[4-(3-methyl-1H-pyrazol-1-yl)phenoxy]methyl}tetrahydro-2H-pyran-4-yl]ethanesulfonamide Titled compound was synthesized by similar method of processes C) and D) of Example 7.

Example 431

N-[(3RS,4SR)-3-{[4-(5-methyl-1H-pyrazol-1-yl)phenoxy]methyl}tetrahydro-2H-pyran-4-yl]ethanesulfonamide Titled compound was synthesized by similar method of processes C) and D) of Example 7.

Example 432

N-[(3RS,4SR)-3-({4-[3-(trifluoromethyl)-1H-pyrazol-1-yl]phenoxy}methyl)tetrahydro-2H-pyran-4-yl]ethanesulfonamide A) 1-(4-methoxyphenyl)-3-(trifluoromethyl)-1H-pyrazole Titled compound was synthesized by similar method of process A) of Example 132.
$^1$H NMR (300 MHz, CDCl$_3$) δ 3.85 (3H, s), 6.69 (1H, d, J=2.3 Hz), 6.99 (2H, d, J=8.7 Hz), 7.60 (2H, d, J=9.1 Hz), 7.77-7.90 (1H, m).

B) 4-(3-(trifluoromethyl)-1H-pyrazol-1-yl)phenol

Titled compound was synthesized by similar method of process B) of Example 132.
MS (API+), found: 227.0 (M−1)

C) N-[(3RS,4SR)-3-({4-[3-(trifluoromethyl)-1H-pyrazol-1-yl]phenoxy}methyl)tetrahydro-2H-pyran-4-yl]ethanesulfonamide Titled compound was synthesized by similar method of processes C) and D) of Example 7.

Example 433

N-[(3S,4R)-3-{[4-(4-chloro-1H-pyrazol-1-yl)phenoxy]methyl}tetrahydro-2H-pyran-4-yl]ethanesulfonamide or N-[(3R,4S)-3-{[4-(4-chloro-1H-pyrazol-1-yl)phenoxy]methyl}tetrahydro-2H-pyran-4-yl]ethanesulfonamide A) N-((3RS,4SR)-3-((4-(4-chloro-1H-pyrazol-1-yl)phenoxy)methyl)tetrahydro-2H-pyran-4-yl)ethanesulfonamide Titled compound was synthesized by similar method of processes C) and D) of Example 7.
MS (API+), found: 400.1 (m+1)

B) N-[(3S,4R)-3-{[4-(4-chloro-1H-pyrazol-1-yl)phenoxy]methyl}tetrahydro-2H-pyran-4-yl]ethanesulfonamide or N-[(3R,4S)-3-{[4-(4-chloro-1H-pyrazol-1-yl)phenoxy]methyl}tetrahydro-2H-pyran-4-yl]ethanesulfonamide N-((3RS,4SR)-3-((4-(4-chloro-1H-pyrazol-1-yl)phenoxy)methyl)tetrahydro-2H-pyran-4-yl)ethanesulfonamide (99 mg) was separated by HPLC (column: CHIRALCEL AD (50 mmID×500 mL, DAICEL corporation, mobile phase: EtOH 100%), to give the title compound (48 mg) with longer retention time as white powder.

Example 434

N-[(1SR,2SR)-2-{[4-(4-chloro-1H-pyrazol-1-yl)phenoxy]methyl}-4,4-difluorocyclohexyl]ethanesulfonamide Titled compound was synthesized by similar method of processes C) and D) of Example 7.

Example 435

N-[(1S,2S)-4,4-difluoro-2-{[4-(1H-pyrazol-1-yl)phenoxy]methyl}cyclohexyl]ethanesulfonamide or N-[(1R,2R)-4,4-difluoro-2-{[4-(1H-pyrazol-1-yl)phenoxy]methyl}cyclohexyl]ethanesulfonamide N-((1SR,2SR)-2-((4-(1H-pyrazol-1-yl)phenoxy)methyl)-4,4-difluorocyclohexyl)ethanesulfonamide (316 mg) was separated by HPLC (column: CHIRALPAK AD (50 mmID×500 mL, DAICEL corporation, mobile phase: EtOH 100%), to give the title compound (137 mg) with shorter retention time as a white solid.

Example 436

N-{(1SR,2SR)-4,4-difluoro-2-[(4-pyridin-2-ylphenoxy)methyl]cyclohexyl}ethanesulfonamide A) 4-(pyridin-2-yl)phenol Titled compound was synthesized by similar method of process A) of Example 132 and process C) of Example 267.
MS (API+), found: 172.0 (M+1)

B) N-{(1SR,2SR)-4,4-difluoro-2-[(4-pyridin-2-ylphenoxy)methyl]cyclohexyl}ethanesulfonamide Titled compound was synthesized by similar method of processes C) and D) of Example 7.

Example 437

N-{(1SR,2SR)-4,4-difluoro-2-[(4-pyridin-2-ylphenoxy)methyl]cyclohexyl}methanesulfonamide Titled compound was synthesized by similar method of processes C) and D) of Example 7.

Example 438

N-[(3RS,4SR)-3-{[4-(4-chloro-1H-pyrazol-1-yl)phenoxy]methyl}tetrahydro-2H-pyran-4-yl]-2,2,2-trifluoroethanesulfonamide Titled compound was synthesized by similar method of processes C) and D) of Example 7.

Example 439

N-[(3RS,4SR)-3-{[4-(4-chloro-1H-pyrazol-1-yl)phenoxy]methyl}tetrahydro-2H-pyran-4-yl]-2-methoxyethanesulfonamide Titled compound was synthesized by similar method of processes C) and D) of Example 7.

Example 440

N-[(3R,4S)-3-{[4-(4-methyl-1H-pyrazol-1-yl)phenoxy]methyl}tetrahydro-2H-pyran-4-yl]ethanesulfonamide or N-[(3S,4R)-3-{[4-(4-methyl-1H-pyrazol-1-yl)phenoxy]methyl}tetrahydro-2H-pyran-4-yl]ethanesulfonamide N-((3RS,4SR)-3-((4-(4-methyl-1H-pyrazol-1-yl)phenoxy)methyl)tetrahydro-2H-pyran-4-yl)ethanesulfonamide (288 mg) was separated by HPLC (column: CHIRALPAK AD (50 mmID×500 mL, DAICEL corporation, mobile phase: MeOH/2-propanol=500/500 (v/v)) to give the title compound (131 mg) with shorter retention time as a white solid.

Example 441

N-[(3RS,4SR)-3-{[4-(1,3-oxazol-5-yl)phenoxy]methyl}tetrahydro-2H-pyran-4-yl]ethanesulfonamide A) 5-(4-(benzyloxy)phenyl)oxazole To a mixture of 4-(benzyloxy)benzaldehyde (2.0 g) and sodium methoxide (1.527 g) in MeOH (10 ml) was added TOSMIC (2.208 g) at room temperature. The mixture was stirred at 70° C. overnight. To the mixture was added water and the resulting precipitate was collected by filtration. The residue was purified by column chromatography (silica gel, eluted with 0%-50% EtOAc in hexane) to give the title compound (1.910 g) as a pale yellow solid.
MS (API+), found: 252.1 (M+1)

B) 4-(oxazol-5-yl)phenol

Titled compound was synthesized by the similar method to process C) of Example 267.
MS (API+), found: 162.1 (M+1)

C) N-[(3RS,4SR)-3-{[4-(1,3-oxazol-5-yl)phenoxy]methyl}tetrahydro-2H-pyran-4-yl]ethanesulfonamide Titled compound was synthesized by similar method of processes C) and D) of Example 7.

Example 442

1-chloro-N-[(3RS,4SR)-3-{[4-(4-chloro-1H-pyrazol-1-yl)phenoxy]methyl}tetrahydro-2H-pyran-4-yl]methanesulfonamide Titled compound was synthesized by similar method of processes C) and D) of Example 7.

Example 443

N-[(1SR,2SR)-4,4-difluoro-2-{[4-(4-methyl-1H-pyrazol-1-yl)phenoxy]methyl}cyclohexyl]cyclopropanesulfonamide Titled compound was synthesized by similar method of processes C) and D) of Example 7.

Example 444

N'-[(1SR,2SR)-4,4-difluoro-2-{[4-(4-methyl-1H-pyrazol-1-yl)phenoxy]methyl}cyclohexyl]-N,N-dimethylsulfamide Titled compound was synthesized by similar method of processes C) and D) of Example 7.

Example 445

N-[(3SR,4SR)-1-acetyl-3-{[4-(4-chloro-1H-pyrazol-1-yl)phenoxy]methyl}piperidin-4-yl]ethanesulfonamide Titled compound was synthesized by a similar method to processes E) to H) of Example 1.

Example 446

N-{(3RS,4SR)-3-[(4-acetylphenoxy)methyl]tetrahydro-2H-pyran-4-yl}-1,1,1-trifluoromethanesulfonamide Titled compound was synthesized by similar method of processes C) and D) of Example 7.

Example 447

N-[(3R,4S)-3-{[4-(1-cyano-1-methylethyl)-2-fluorophenoxy]methyl}tetrahydro-2H-pyran-4-yl]cyclopropanesulfonamide A) 2-(3-fluoro-4-methoxyphenyl)acetonitrile The aqueous solution of KCN (4.48 g) in water (10.00 ml) was added dropwise to a solution of 4-(chloromethyl)-2-fluoro-1-methoxybenzene (8.00 g) in DMSO (100 ml) at room temperature. The mixture was stirred at room temperature overnight. The mixture was quenched with sat. NaHCO$_3$ aq. at room temperature and extracted with EtOAc. The organic layer was separated, washed with brine, dried over MgSO$_4$ and concentrated in vacuo to give the title compound (7.50 g) as a pale yellow solid.
$^1$H NMR (300 MHz, CDCl$_3$) δ 3.69 (2H, s), 3.90 (3H, s), 6.91-6.99 (1H, m), 7.01-7.09 (2H, m).

B) 2-(3-fluoro-4-methoxyphenyl)-2-methylpropanenitrile

The solution of KOtBu (11.21 g) in THF(dry) (50 ml) was added dropwise to a solution of 2-(3-fluoro-4-methoxyphenyl)acetonitrile (7.50 g) and MeI (7.10 ml) in THF(dry) (100 ml) at 0° C. The mixture was stirred at room temperature under a dry atmosphere (CaCl$_2$ tube) for 4 h. The mixture was diluted with water at room temperature and extracted with EtOAc. The organic layer was separated, washed with brine, dried over MgSO$_4$ and concentrated in vacuo. The residue was purified by column chromatography (silica gel, eluted with 5%-30% EtOAc in hexane) to give the title compound (6.31 g) as a pale yellow solid, which was used in the next step directly.

C) 2-(3-fluoro-4-hydroxyphenyl)-2-methylpropanenitrile

A mixture of 2-(3-fluoro-4-methoxyphenyl)-2-methylpropanenitrile (6.30 g) and aluminum trichloride (13.04 g) in toluene (40 ml) was stirred at 70° C. under a dry atmosphere (CaCl$_2$ tube) overnight. The mixture was poured into iced water at 0° C., acidified by 1 M HCl aq. and extracted with EtOAc. The organic layer was separated, washed with brine, dried over MgSO$_4$ and concentrated in vacuo. The residue was purified by column chromatography (silica gel, eluted with 5%-40% EtOAc in hexane) to give the title compound (5.62 g, %) as a pale yellow oil.
MS (API+), found: 178.0 (M−1)

D) N-((3RS,4SR)-3-((4-(2-cyanopropan-2-yl)-2-fluorophenoxy)methyl)tetrahydro-2H-pyran-4-yl)cyclopropanesulfonamide Titled compound was synthesized by similar method of processes C) and D) of Example 7.

Example 448

N-[(3S,4R)-3-{[4-(4-chloro-1H-pyrazol-1-yl)phenoxy]methyl}tetrahydro-2H-pyran-4-yl]methanesulfonamide N-((3RS,4SR)-3-((4-(4-chloro-1H-pyrazol-1-yl)phenoxy)methyl)tetrahydro-2H-pyran-4-yl)methanesulfonamide (330 mg) was separated by HPLC (column: CHIRALPAK AD (50 mmID×500 mL, DAICEL corporation, mobile phase: MeOH/EtOH/DEA=50/50/0.1 (v/v/v)) to give the title compound (155 mg) with shorter retention time as a white solid.

Example 449

N-[(3RS,4SR)-3-{[4-(1,3-dimethyl-1H-pyrazol-5-yl)phenoxy]methyl}tetrahydro-2H-pyran-4-yl]methanesulfonamide Titled compound was synthesized by similar method of processes C) and D) of Example 7.

Example 450

N-[(3RS,4SR)-3-{[4-(1,5-dimethyl-1H-pyrazol-3-yl)phenoxy]methyl}tetrahydro-2H-pyran-4-yl]ethanesulfonamide Titled compound was synthesized by similar method of processes C) and D) of Example 7.

Example 451

N'-[(3RS,4SR)-3-{[4-(1,5-dimethyl-1H-pyrazol-3-yl)phenoxy]methyl}tetrahydro-2H-pyran-4-yl]-N,N-dimethylsulfamide Titled compound was synthesized by similar method of processes C) and D) of Example 7.

Example 452

N'-[(3RS,4SR)-3-{[4-(1,3-dimethyl-1H-pyrazol-5-yl)phenoxy]methyl}tetrahydro-2H-pyran-4-yl]-N,N-dimethylsulfamide Titled compound was synthesized by similar method of processes C) and D) of Example 7.

Example 453

N-[(3R,4S)-3-{[4-(4-methoxy-1H-pyrazol-1-yl)phenoxy]methyl}tetrahydro-2H-pyran-4-yl]ethanesulfonamide

A) 1-(4-(benzyloxy)phenyl)-1H-pyrazole

Titled compound was synthesized by the similar method to process A) of Example 425.
MS (API+), found: 251.0 (M+1)

B) 1-(4-(benzyloxy)phenyl)-1H-pyrazole-4-carbaldehyde

To N,N-dimethylformamide (16 ml) was added phosphoryl trichloride (8 ml) dropwise at 0° C. Then 1-(4-(benzyloxy)phenyl)-1H-pyrazole (2.73 g) was added to this cold mixture. The reaction mixture was allowed to warm to room temperature and then heated at reflux for 2 h. The mixture was poured into sat. NaHCO$_3$ aq. at room temperature and extracted with EtOAc. The organic layer was separated, washed with sat. NaHCO$_3$ aq. and brine, dried over Na$_2$SO$_4$ and concentrated in vacuo. A mixture of the residue, K$_2$CO$_3$ (4.52 g) and benzyl bromide (1.295 ml) in DMF(dry) (30 ml) was stirred at room temperature for 2 h. The mixture was poured into water and extracted with EtOAc. The organic layer was separated, washed with water and brine, dried over Na$_2$SO$_4$ and concentrated in vacuo. The residue was purified by column chromatography (silica gel, eluted with 0%-50% EtOAc in hexane) to give the title compound (2.460 g) as a yellow solid.
MS (API+), found: 279.1 (M+1)

C) 1-(4-(benzyloxy)phenyl)-4-methoxy-1H-pyrazole

To a solution of 1-(4-(benzyloxy)phenyl)-1H-pyrazole-4-carbaldehyde (2.46 g) in EtOAc (40 ml) was added m-CPBA (5.45 g) at room temperature. The mixture was stirred at 70° C. for 2 h. The mixture was quenched with sat. NaHCO$_3$ aq. and extracted with EtOAc. The organic layer was separated, washed with brine, dried over Na$_2$SO$_4$ and concentrated in vacuo. A mixture of the residue and K$_2$CO$_3$ (2.443 g) in MeOH (40.0 ml) was stirred at room temperature for 20 min. The solvent was removed by evaporation and the residue was dissolved in EtOAc. The mixture was washed with 1 M HCl aq. and brine, dried over MgSO$_4$ and concentrated under vacuum. A mixture of the residue, K$_2$CO$_3$ (2.443 g) and MeI (1.105 ml) in DMF(dry) (40.0 ml) was stirred at room temperature overnight. The mixture was quenched with water and extracted with EtOAc. The organic layer was separated, washed with water and brine, dried over Na$_2$SO$_4$ and concentrated in vacuo. The residue was purified by column chromatography (silica gel, eluted with 0%-50% EtOAc in hexane) to give the title compound (0.413 g) as a white solid.
$^1$H NMR (300 MHz, CDCl$_3$) δ 3.87 (3H, s), 5.11 (2H, s), 7.01-7.10 (2H, m), 7.28-7.48 (5H, m), 7.55-7.64 (2H, m), 8.07 (1H, s), 8.30 (1H, d, J=0.6 Hz).

D) 4-(4-methoxy-1H-pyrazol-1-yl)phenol

Titled compound was synthesized by the similar method to process C) of Example 267.
MS (API+), found: 191.2 (M+1)

E) N-[(3R,4S)-3-{[4-(4-methoxy-1H-pyrazol-1-yl)phenoxy]methyl}tetrahydro-2H-pyran-4-yl]ethanesulfonamide Titled compound was synthesized by similar method of processes C) and D) of Example 7.

Example 454

N-[(3R,4S)-3-{[4-(4-chloro-1H-pyrazol-1-yl)-2-fluorophenoxy]methyl}tetrahydro-2H-pyran-4-yl]ethanesulfonamide Titled compound was synthesized by similar method of processes C) and D) of Example 7.

Example 455

N'-[(1S,2S)-4,4-difluoro-2-{[4-(4-methyl-1H-pyrazol-1-yl)phenoxy]methyl}cyclohexyl]-N,N-dimethylsulfamide Titled compound was synthesized by similar method of processes C) and D) of Example 7.

Example 456

N-[(3RS,4SR)-3-{[4-(4-chloro-1H-pyrazol-1-yl)phenoxy]methyl}tetrahydro-2H-pyran-4-yl]-1,1,1-trifluoromethanesulfonamide Titled compound was synthesized by similar method of processes C) and D) of Example 7.

Example 457 ethyl 4-({(1S,2S)-2-[(ethylsulfonyl)amino]-5,5-difluorocyclohexyl}methoxy)benzoate Titled compound was synthesized by similar method of processes C) and D) of Example 71.

Example 458

N-[(1S,2S)-4,4-difluoro-2-{[4-(4-methyl-1H-pyrazol-1-yl)phenoxy]methyl}cyclohexyl]ethanesulfonamide Titled compound was synthesized by similar method of processes C) and D) of Example 7.

Example 459

N'-[(3R,4S)-3-{[2-fluoro-4-(4-methyl-1H-pyrazol-1-yl)phenoxy]methyl}tetrahydro-2H-pyran-4-yl]-N,N-dimethylsulfamide A) 2-fluoro-4-(4-methyl-1H-pyrazol-1-yl)phenol Titled compound was synthesized by similar method of process A) of Example 287.
MS (API+), found: 193.0 (M+1)

B) N'-[(3R,4S)-3-{[2-fluoro-4-(4-methyl-1H-pyrazol-1-yl)phenoxy]methyl}tetrahydro-2H-pyran-4-yl]-N,N-dimethylsulfamide Titled compound was synthesized by similar method of processes C) and D) of Example 7.

Example 460

N-((3R,4S)-4-((4-(4-chloro-1H-pyrazol-1-yl)phenoxy)methyl)tetrahydro-2H-pyran-3-yl)cyclopropanesulfonamide Titled compound was synthesized by similar method of processes C) and D) of Example 7.

Example 461

N-[(3R,4S)-4-{[4-(4-chloro-1H-pyrazol-1-yl)phenoxy]methyl}tetrahydro-2H-pyran-3-yl]cyclopropanesulfonamide Titled compound was synthesized by similar method of processes C) and D) of Example 7.

Example 462

N-[(3R,4S)-3-{[4-(4-chloro-1H-pyrazol-1-yl)-2,3-difluorophenoxy]methyl}tetrahydro-2H-pyran-4-yl]methanesulfonamide A) tert-butyl ((3R,4S)-3-((4-(4-chloro-1H-pyrazol-1-yl)-2,3-difluorophenoxy)methyl)tetrahydro-2H-pyran-4-yl)carbamate A mixture of tert-butyl ((3R,4S)-3-((2,3-difluoro-4-(1H-pyrazol-1-yl)phenoxy)methyl)tetrahydro-2H-pyran-4-yl)carbamate (100 mg) and NCS (82 mg) in THF(dry) (2 ml) was stirred at 70° C. overnight. The mixture was quenched with sat. NaHCO₃ aq. and extracted with EtOAc. The organic layer was separated, washed with brine, dried over Na₂SO₄ and concentrated in vacuo. The residue was purified by column chromatography (silica gel, eluted with 0%-40% EtOAc in hexane) to give the title compound (76 mg) as a white solid.
MS (API+), found: 344.2 (M+1-Boc)

B) N-[(3R,4S)-3-{[4-(4-chloro-1H-pyrazol-1-yl)-2,3-difluorophenoxy]methyl}tetrahydro-2H-pyran-4-yl]methanesulfonamide Titled compound was synthesized by similar method of processes C) and D) of Example 7.

Example 463

N-[(3R,4S)-3-({4-[4-(difluoromethoxy)-1H-pyrazol-1-yl]phenoxy}methyl)tetrahydro-2H-pyran-4-yl]methanesulfonamide A) 1-(4-(benzyloxy)phenyl)-1H-pyrazol-4-ol A mixture of 1-(4-(benzyloxy)phenyl)-1H-pyrazole-4-carbaldehyde (244 mg) and m-CPBA (540 mg) in EtOAc (5 ml) was stirred at 70° C. for 2 h. The mixture was quenched with sat. NaHCO₃ aq. and extracted with EtOAc. The organic layer was separated, washed with brine, dried over Na₂SO₄ and concentrated in vacuo. To a solution of the residue in MeOH (5 ml) was added K₂CO₃ (242 mg) at room temperature. The mixture was stirred for 10 min. The mixture was quenched with sat. NH₄Cl aq. and extracted with EtOAc. The organic layer was separated, washed with brine, dried over Na₂SO₄ and concentrated in vacuo. The residue was purified by column chromatography (silica gel, eluted with 0%-40% EtOAc in hexane) to give the title compound (144 mg) as a off-white solid.

MS (API+), found: 267.1 (M+1)

B) 1-(4-(benzyloxy)phenyl)-4-(difluoromethoxy)-1H-pyrazole

A mixture of 1-(4-(benzyloxy)phenyl)-1H-pyrazol-4-ol (168 mg) and 8 M NaOH aq. (0.789 ml) in THF(dry) (5 ml) was stirred at room temperature for 2 h under chlorodifluoromethane atmosphere. The mixture was neutralized with 1 N HCl aq. at 0° C. and extracted with EtOAc. The organic layer was separated, washed with water and brine, dried over Na₂SO₄ and concentrated in vacuo. The residue was purified by column chromatography (silica gel, eluted with 0%-30% EtOAc in hexane) to give the title compound (156 mg) as a off-white solid.

MS (API+), found: 317.2 (M+1)

C) 4-(4-(difluoromethoxy)-1H-pyrazol-1-yl)phenol

Titled compound was synthesized by similar method of process C) of Example 267.

MS (API+), found: 227.0 (M+1)

D) N-[(3R,4S)-3-({4-[4-(difluoromethoxy)-1H-pyrazol-1-yl]phenoxy}methyl)tetrahydro-2H-pyran-4-yl] methanesulfonamide Titled compound was synthesized by similar method of processes C) and D) of Example 7.

Example 464

N-[(3R,4S)-3-({4-[4-(difluoromethoxy)-1H-pyrazol-1-yl]phenoxy}methyl)tetrahydro-2H-pyran-4-yl] cyclopropanesulfonamide Titled compound was synthesized by similar method of processes C) and D) of Example 7.

Example 465

1,5-anhydro-2,3,4-trideoxy-4-[(ethylsulfonyl) amino]-6-O-[4-(5-fluoropyridin-2-yl)phenyl]-D-erythro-hexitol Titled compound was synthesized by the similar method to process C) of Example 282.

Example 466

N-[(3R,4S)-3-{[4-(4-chloro-3-methyl-1H-pyrazol-1-yl)phenoxy]methyl}tetrahydro-2H-pyran-4-yl]methanesulfonamide A) tert-butyl ((3R,4S)-3-((4-(3-methyl-1H-pyrazol-1-yl)phenoxy)methyl)tetrahydro-2H-pyran-4-yl) carbamate Titled compound was synthesized by similar method of process C) of Example 7.

MS (API+), found: 388.3 (M+1)

B) tert-butyl ((3R,4S)-3-((4-(4-chloro-3-methyl-1H-pyrazol-1-yl)phenoxy)methyl)tetrahydro-2H-pyran-4-yl)carbamate A mixture of tert-butyl ((3R,4S)-3-((4-(3-methyl-1H-pyrazol-1-yl)phenoxy)methyl)tetrahydro-2H-pyran-4-yl) carbamate (279 mg) and NCS (144 mg) in THF(dry) (7 ml) was stirred at 70° C. overnight. The mixture was quenched with sat. NaHCO₃ aq. and extracted with EtOAc. The organic layer was separated, washed with brine, dried over Na₂SO₄ and concentrated in vacuo. The residue was purified by column chromatography (silica gel, eluted with 0%-50% EtOAc in hexane) to give the title compound (156 mg) as a off-white solid.

MS (API+), found: 422.2 (M+1)

C) N-[(3R,4S)-3-{[4-(4-chloro-3-methyl-1H-pyrazol-1-yl)phenoxy]methyl}tetrahydro-2H-pyran-4-yl] methanesulfonamide Titled compound was synthesized by similar method of process D) of Example 7.

¹H NMR (300 MHz, CDCl₃) δ 1.62-1.78 (1H, m), 1.91-2.05 (1H, m), 2.12-2.24 (1H, m), 2.32 (3H, s), 2.88 (3H, s), 3.41-3.55 (2H, m), 3.56-3.70 (1H, m), 3.96-4.18 (4H, m), 4.36 (1H, d, J=8.7 Hz), 6.91-6.98 (2H, m), 7.46-7.55 (2H, m), 7.73 (1H, s).

Example 467

N-[(3R,4S)-3-({[6-(4-chloro-1H-pyrazol-1-yl)pyridin-3-yl]oxy}methyl)tetrahydro-2H-pyran-4-yl]cyclopropanesulfonamide A) 5-(benzyloxy)-2-fluoropyridine Titled compound was synthesized by similar method of process A) of Example 425.

MS (API+), found: 204.2 (M+1)

B) 5-(benzyloxy)-2-(1H-pyrazol-1-yl)pyridine

A mixture of 1H-pyrazole (3.18 g), 5-(benzyloxy)-2-fluoropyridine (7.3 g) and K₂CO₃ (7.45 g) in DMSO (70 ml) was stirred at room temperature for 10 min. The mixture was stirred at 150° C. over weekend. The mixture was poured into water at room temperature and resulting precipitate was collected by filtration. The residue was washed with water and hexane to give the title compound (6.49 g) as off-white solid.

MS (API+), found: 252.1 (M+1)

C) 5-(benzyloxy)-2-(4-chloro-1H-pyrazol-1-yl)pyridine

A mixture of 5-(benzyloxy)-2-(1H-pyrazol-1-yl)pyridine (750 mg) and NCS (996 mg) in THF(dry) (10 ml) was stirred at 60° C. for 1 h. The mixture was quenched with sat. NaHCO₃ aq. and extracted with EtOAc. The organic layer was separated, washed with brine, dried over Na₂SO₄ and concentrated in vacuo. The residue was purified by column chromatography (silica gel, eluted with 0%-20% EtOAc in hexane) to give the title compound (850 mg) as a white solid.

MS (API+), found: 286.1 (M+1)

D) 6-(4-chloro-1H-pyrazol-1-yl)pyridin-3-ol

Titled compound was synthesized by similar method of process C) of Example 267.
MS (API+), found: 196.0 (M+1)

E) N-[(3R,4S)-3-({[6-(4-chloro-1H-pyrazol-1-yl)pyridin-3-yl]oxy}methyl)tetrahydro-2H-pyran-4-yl]cyclopropanesulfonamide Titled compound was synthesized by similar method of processes C) and D) of Example 7.

Example 468

N-[(1S,2S)-2-({[6-(4-chloro-1H-pyrazol-1-yl)pyridin-3-yl]oxy}methyl)-4,4-difluorocyclohexyl]methanesulfonamide Titled compound was synthesized by similar method of processes C) and D) of Example 7.

Example 469

1,5-anhydro-2,3,4-trideoxy-6-O-[4-(5-fluoropyridin-2-yl)phenyl]-4-[(methylsulfonyl)amino]-D-erythro-hexitol Titled compound was synthesized by similar method of processes C) and D) of Example 7.

Example 470

N'-[(3R,4S)-3-{[4-(4-chloro-1H-pyrazol-1-yl)phenoxy]methyl}tetrahydro-2H-pyran-4-yl]-N,N-dimethylsulfamide Titled compound was synthesized by similar method of processes C) and D) of Example 7.

Example 471

N-[(3R,4S)-3-{[2-fluoro-4-(5-fluoropyridin-2-yl)phenoxy]methyl}tetrahydro-2H-pyran-4-yl]ethanesulfonamide or N-[(3S,4R)-3-{[2-fluoro-4-(5-fluoropyridin-2-yl)phenoxy]methyl}tetrahydro-2H-pyran-4-yl]ethanesulfonamide

A) 5-fluoro-2-(3-fluoro-4-methoxyphenyl)pyridine

Titled compound was synthesized by similar method of process A) of Example 195.
MS (API+), found: 222.1 (M+1)

B) 2-fluoro-4-(5-fluoropyridin-2-yl)phenol

Titled compound was synthesized by similar method of process C) of Example 213.
MS (API+), found: 208.0 (M+1)

C) N-((3RS,4SR)-3-((2-fluoro-4-(5-fluoropyridin-2-yl)phenoxy)methyl)tetrahydro-2H-pyran-4-yl)ethanesulfonamide Titled compound was synthesized by similar method of processes C) and D) of Example 7.
MS (API+), found: 413.1 (M+1)

D) N-[(3R,4S)-3-{[2-fluoro-4-(5-fluoropyridin-2-yl)phenoxy]methyl}tetrahydro-2H-pyran-4-yl]ethanesulfonamide or N-[(3S,4R)-3-{[2-fluoro-4-(5-fluoropyridin-2-yl)phenoxy]methyl}tetrahydro-2H-pyran-4-yl]ethanesulfonamide N-((3RS,4SR)-3-((2-fluoro-4-(5-fluoropyridin-2-yl)phenoxy)methyl)tetrahydro-2H-pyran-4-yl)ethanesulfonamide (85 mg) was separated by HPLC (column: CHIRALCEL OD (50 mmID×500 mL, DAICEL corporation, mobile phase: MeOH 100%) to give the title compound (37 mg) with longer retention time as white powder.

Example 472

N-[(3R,4S)-3-{[4-(3,5-difluoropyridin-2-yl)phenoxy]methyl}tetrahydro-2H-pyran-4-yl]ethanesulfonamide or N-[(3S,4R)-3-{[4-(3,5-difluoropyridin-2-yl)phenoxy]methyl}tetrahydro-2H-pyran-4-yl]ethanesulfonamide N-((3RS,4SR)-3-((4-(3,5-difluoropyridin-2-yl)phenoxy)methyl)tetrahydro-2H-pyran-4-yl)ethanesulfonamide (83 mg) was separated by HPLC (column: CHIRALPAK AD (50 mmID×500 mL, DAICEL corporation, mobile phase: EtOH 100%) to give the title compound (44 mg) with longer retention time as white powder.

Example 473

N-[(3R,4S)-3-{[2-fluoro-4-(5-fluoropyridin-2-yl)phenoxy]methyl}tetrahydro-2H-pyran-4-yl]cyclopropanesulfonamide or N-[(3S,4R)-3-{[2-fluoro-4-(5-fluoropyridin-2-yl)phenoxy]methyl}tetrahydro-2H-pyran-4-yl]cyclopropanesulfonamide Titled compound was synthesized by similar method of processes C) and D) of Example 7.
MS (API+), found: 425.1 (M+1)

B) N-[(3R,4S)-3-{[2-fluoro-4-(5-fluoropyridin-2-yl)phenoxy]methyl}tetrahydro-2H-pyran-4-yl]cyclopropanesulfonamide or N-[(3S,4R)-3-{[2-fluoro-4-(5-fluoropyridin-2-yl)phenoxy]methyl}tetrahydro-2H-pyran-4-yl]cyclopropanesulfonamide N-((3RS,4SR)-3-((2-fluoro-4-(5-fluoropyridin-2-yl)phenoxy)methyl)tetrahydro-2H-pyran-4-yl)cyclopropanesulfonamide (83 mg) was separated by HPLC (column: CHIRALPAK AD (50 mmID×500 mL, DAICEL corporation, mobile phase: EtOH 100%) to give the title compound (33 mg) with shorter retention time as white powder.

Example 474

N-[(3R,4S)-3-{[2-fluoro-4-(5-fluoropyridin-2-yl)phenoxy]methyl}tetrahydro-2H-pyran-4-yl]cyclopropanesulfonamide or N-[(3S,4R)-3-{[2-fluoro-4-(5-fluoropyridin-2-yl)phenoxy]methyl}tetrahydro-2H-pyran-4-yl]cyclopropanesulfonamide N-((3RS,4SR)-3-((2-fluoro-4-(5-fluoropyridin-2-yl)phenoxy)methyl)tetrahydro-2H-pyran-4-yl)cyclopropanesulfonamide (83 mg) was separated by HPLC (column: CHIRALPAK AD (50 mmID×500 mL, DAICEL corporation, mobile phase: EtOH 100%) to give the title compound (40 mg) with shorter retention time as white powder.

Example 475

N-[(3R,4S)-3-{[2-fluoro-4-(5-fluoropyridin-2-yl) phenoxy]methyl}tetrahydro-2H-pyran-4-yl]methanesulfonamide or N-[(3S,4R)-3-{[2-fluoro-4-(5-fluoropyridin-2-yl)phenoxy]methyl}tetrahydro-2H-pyran-4-yl]methanesulfonamide A) N-((3RS,4SR)-3-((2-fluoro-4-(5-fluoropyridin-2-yl)phenoxy)methyl)tetrahydro-2H-pyran-4-yl)methanesulfonamide Titled compound was synthesized by similar method of processes C) and D) of Example 7.
MS (API+), found: 399.1 (M+1)

B) N-[(3R,4S)-3-{[2-fluoro-4-(5-fluoropyridin-2-yl) phenoxy]methyl}tetrahydro-2H-pyran-4-yl]methanesulfonamide or N-[(3S,4R)-3-{[2-fluoro-4-(5-fluoropyridin-2-yl)phenoxy]methyl}tetrahydro-2H-pyran-4-yl]methanesulfonamide N-((3RS,4SR)-3-((2-fluoro-4-(5-fluoropyridin-2-yl)phenoxy)methyl)tetrahydro-2H-pyran-4-yl)methanesulfonamide (83 mg) was separated by HPLC (column: CHIRALCEL OD, 50 mmID×500 mL, DAICEL corporation, mobile phase: MeOH 100%) to give the title compound (44 mg) with shorter retention time as white powder.

Example 476

N-[(3R,4S)-3-{[2-fluoro-4-(5-fluoropyridin-2-yl) phenoxy]methyl}tetrahydro-2H-pyran-4-yl]methanesulfonamide or N-[(3S,4R)-3-{[2-fluoro-4-(5-fluoropyridin-2-yl)phenoxy]methyl}tetrahydro-2H-pyran-4-yl]methanesulfonamide N-((3RS,4SR)-3-((2-fluoro-4-(5-fluoropyridin-2-yl)phenoxy)methyl)tetrahydro-2H-pyran-4-yl)methanesulfonamide (83 mg) was separated by HPLC (column: CHIRALCEL OD, 50 mmID×500 mmL, DAICEL corporation, mobile phase: MeOH 100%) to give the title compound (42 mg) with longer retention time as white powder.

Example 477

N-[(3R,4S)-3-{[3-fluoro-4-(5-fluoropyridin-2-yl) phenoxy]methyl}tetrahydro-2H-pyran-4-yl]methanesulfonamide or N-[(3S,4R)-3-{[3-fluoro-4-(5-fluoropyridin-2-yl)phenoxy]methyl}tetrahydro-2H-pyran-4-yl]methanesulfonamide N-((3RS,4SR)-3-((2-fluoro-4-(5-fluoropyridin-2-yl)phenoxy)methyl)tetrahydro-2H-pyran-4-yl)methanesulfonamide (83 mg) was separated by HPLC (column: CHIRALPAK AD, 50 mmID×500 mmL, DAICEL corporation, mobile phase: EtOH 100%) to give the title compound (43 mg) with longer retention time as white powder.

Example 478

1,1,1-trifluoro-N-[(3R,4S)-3-{[4-(4-methyl-1H-pyrazol-1-yl)phenoxy]methyl}tetrahydro-2H-pyran-4-yl]methanesulfonamide Titled compound was synthesized by similar method of processes C) and D) of Example 7.

Example 479

N-[(3R,4S)-3-{[4-(4-methoxy-1H-pyrazol-1-yl)phenoxy]methyl}tetrahydro-2H-pyran-4-yl]methanesulfonamide Titled compound was synthesized by similar method of processes C) and D) of Example 7.

Example 480

N-[(3R,4S)-3-{[4-(4-methoxy-1H-pyrazol-1-yl)phenoxy]methyl}tetrahydro-2H-pyran-4-yl]cyclopropanesulfonamide Titled compound was synthesized by similar method of processes C) and D) of Example 7.

Example 481

N-[(1S,2S)-4,4-difluoro-2-{[4-(2-oxopyrrolidin-1-yl) phenoxy]methyl}cyclohexyl]methanesulfonamide The title compound was obtained in the same manner as in Example 233, steps A and B.

Example 482

N-[(1S,2S)-4,4-difluoro-2-{[4-(2-oxopyrrolidin-1-yl) phenoxy]methyl}cyclohexyl]ethanesulfonamide A) tert-butyl ((1S,2S)-4,4-difluoro-2-((4-(2-oxopyrrolidin-1-yl)phenoxy)methyl)cyclohexyl)carbamate To the mixture of tert-butyl ((1S,2S)-4,4-difluoro-2-(hydroxymethyl)cyclohexyl)carbamate (505 mg), 1-(4-hydroxyphenyl)pyrrolidin-2-one (489 mg), ADDP (961 mg) in THF (30 ml), Bu$_3$P (0.939 ml) was added. Then the mixture was stirred at room temperature overnight and concentrated in vacuo. The residue was purified by column chromatography (silica gel, eluted with EtOAc in hexane) to give tert-butyl ((1S,2S)-4,4-difluoro-2-((4-(2-oxopyrrolidin-1-yl)phenoxy)methyl)cyclohexyl)carbamate (487 mg) as a pale yellow gum.
$^1$H NMR (300 MHz, CDCl$_3$) δ 1.40 (9H, s), 1.65-1.97 (4H, m), 2.08-2.22 (4H, m), 2.34-2.50 (1H, m), 2.59 (2H, t, J=8.0 Hz), 3.49-3.66 (1H, m), 3.77-3.91 (3H, m), 3.95-4.04 (1H, m), 4.44-4.55 (1H, m), 6.82-6.93 (2H, m), 7.42-7.56 (2H, m).

B) N-[(1S,2S)-4,4-difluoro-2-{[4-(2-oxopyrrolidin-1-yl)phenoxy]methyl}cyclohexyl]ethanesulfonamide 4N HCl in EtOAc (10 ml) was added to a mixture of tert-butyl (1SR,2SR)-4,4-difluoro-2-((4-(pyridin-2-yl)phenoxy)methyl)cyclohexylcarbamate (487 mg) in EtOAc (2 ml) at room temperature. The mixture was stirred at room temperature for 1 h. Hexane was added to the mixture and the mixture was concentrated in vacuo. The residue was washed with EtOAc-hexane, collected and dried in vacuo to give 1-(4-(((1S,2S)-2-amino-5,5-difluorocyclohexyl) methoxy)phenyl)pyrrolidin-2-one hydrochloride (332 mg) as a pale pink powder. Ethanesulfonyl chloride (0.053 ml) was added to a mixture of 1-(4-(((1S,2S)-2-amino-5,5-difluorocyclohexyl)methoxy)phenyl)pyrrolidin-2-one hydrochloride (100 mg) and triethylamine (0.386 ml) in THF (3 ml) at room temperature. The mixture was stirred at room temperature overnight. The mixture was quenched with sat. NaHCO$_3$ aq. at room temperature and extracted with EtOAc. The organic layer was separated, washed with brine and concentrated in vacuo. The residue was diluted with EtOAc and purified by column chromatography (silica gel, eluted with EtOAc in hexane) and concentrated. The residue was crystallized from EtOAc/hexane at 0° C. to give N-((1S,2S)-4,4-difluoro-2-((4-(2-oxopyrrolidin-1-yl)phenoxy) methyl)cyclohexyl)ethanesulfonamide (21 mg) as off-white crystals.

$^1$H NMR (300 MHz, DMSO-d$_6$) δ 1.09 (3H, t, J=7.4 Hz), 1.51-1.71 (1H, m), 1.82-2.24 (9H, m), 2.42-2.46 (2H, m), 2.94 (2H, q, J=7.4 Hz), 3.78 (2H, t, J=7.0 Hz), 3.90-4.13 (2H, m), 6.93 (2H, d, J=9.1 Hz), 7.24 (1H, d, J=9.1 Hz), 7.55 (2H, d, J=9.1 Hz).

Example 483

N-[(1S,2S)-4,4-difluoro-2-{[4-(2-oxopyrrolidin-1-yl) phenoxy]methyl}cyclohexyl]cyclopropanesulfonamide The title compound was obtained in the same manner as in Example 233, steps A and B.

Example 484

N-[(1S,2S)-2-{[4-(5-cyanopyridin-2-yl)-2-fluorophenoxy]methyl}-4,4-difluorocyclohexyl]methanesulfonamide A) 6-(3-fluoro-4-methoxyphenyl)nicotinonitrile Titled compound was synthesized by similar method of process A) of Example 195.
MS (API+), found: 229.1.

B) 6-(3-fluoro-4-hydroxyphenyl)nicotinonitrile

Aluminum trichloride (4.22 g) was added to a mixture of 6-(3-fluoro-4-methoxyphenyl)nicotinonitrile (2.4065 g) in toluene (50 ml). The mixture was stirred at 70° C. under N$_2$ overnight. EtOAc and silica-gel were added to the mixture and the mixture was stirred at room temperature for 5 h. The insoluble material was removed by filtration. The mixture was poured into water and extracted with EtOAc. The organic layer was separated, washed with brine, dried over Na$_2$SO$_4$ and concentrated in vacuo to give a dark red residue. This was subjected to the next reaction without further purification.
MS (API+), found: 215.1.

C) N-[(1S,2S)-2-{[4-(5-cyanopyridin-2-yl)-2-fluorophenoxy]methyl}-4,4-difluorocyclohexyl]methanesulfonamide The title compound was obtained in the same manner as in Example 233, steps A and B.

Example 485

N-[(1S,2S)-2-{[4-(5-cyanopyridin-2-yl)-2-fluorophenoxy]methyl}-4,4-difluorocyclohexyl]methanesulfonamide A) 5-fluoro-6-(3-fluoro-4-methoxyphenyl)nicotinonitrile A mixture of Pd(PPh$_3$)$_4$ (0.309 g), Na$_2$CO$_3$ (4.25 g), 2,5-dibromo-3-fluoropyridine (3.41 g) and (3-fluoro-4-methoxyphenyl)boronic acid (2.5 g) in DME (80 ml) and water (15 ml) was stirred at 80° C. under N$_2$ for 2 days. The mixture was poured into water and extracted with EtOAc. The organic layer was separated, washed with brine, dried over Na$_2$SO$_4$ and concentrated in vacuo. The residue was diluted with EtOAc and this was filtered through silica-gel pad and concentrated to give a pale yellow solid. This solid was diluted to DMF (40 ml) and dicyanozinc (1.174 g) and Pd$_2$(dba)$_3$ (0.275 g) were added to the mixture. The whole was stirred at 100° C. under N$_2$ overnight. NH-silica gel was added to the mixture and the mixture was stirred at room temperature for 5 h. The insoluble material was removed by filtration, and the filtrate was eluted through NH-silica gel column with EtOAc and concentrated in vacuo. The residue was purified by column chromatography (silica gel, eluted with 5%-40% EtOAc in hexane) to give a mixture including the desired product. This was diluted with THF and silica-gel was added to the mixture and concentrated. The mixture supported on silica-gel was purified by column chromatography (silica gel, eluted with 10%-30% EtOAc in hexane) to give 5-fluoro-6-(3-fluoro-4-methoxyphenyl)nicotinonitrile (1.130 g) as an yellow solid.
MS (API+), found: 247.2

B) 5-fluoro-6-(3-fluoro-4-hydroxyphenyl)nicotinonitrile

Aluminum trichloride (487 mg) was added to a mixture of 5-fluoro-6-(3-fluoro-4-methoxyphenyl)nicotinonitrile (300 mg) in toluene (5 ml). The mixture was stirred at 70° C. under N$_2$ overnight. The mixture was quenched with 1 N HCl aq. at room temperature and extracted with EtOAc. The organic layer was separated, washed with sat. NaHCO$_3$ aq. and brine, dried over Na$_2$SO$_4$ and concentrated in vacuo. The residue was purified by column chromatography (silica gel, eluted with 5%-35% EtOAc in hexane) to give 5-fluoro-6-(3-fluoro-4-hydroxyphenyl)nicotinonitrile (182 mg) as a pale yellow solid.
MS (API−), found: 231.2.

C) N-[(1S,2S)-2-{[4-(5-cyanopyridin-2-yl)-2-fluorophenoxy]methyl}-4,4-difluorocyclohexyl]methanesulfonamide The title compound was obtained in the same manner as in Example 233, steps A and B.

Example 486

N-[(1S,2S)-2-{[4-(5-cyano-3-fluoropyridin-2-yl)-2-fluorophenoxy]methyl}-4,4-difluorocyclohexyl]ethanesulfonamide The title compound was obtained in the same manner as in Example 485.

Example 487

N-[(1S,2S)-4,4-difluoro-2-{[4-(1-methyl-6-oxo-1,4,5,6-tetrahydropyridazin-3-yl)phenoxy]methyl}cyclohexyl]methanesulfonamide A) 6-(4-methoxyphenyl)-2-methyl-4,5-dihydropyridazin-3(2H)-one Methylhydrazine (1.644 ml) was added to a mixture of 4-(4-methoxyphenyl)-4-oxobutanoic acid (5 g) in EtOH (120 ml) at room temperature. The mixture was stirred at 70° C. overnight and concentrated. IPE was added to the mixture and the residue was collected by filtration and dried in vacuo to give 6-(4-methoxyphenyl)-2-methyl-4,5-dihydropyridazin-3(2H)-one (4.58 g) as a colorless crystal.
MS (API+), found: 219.1.

B) 6-(4-hydroxyphenyl)-2-methyl-4,5-dihydropyridazin-3(2H)-one

1-Dodecanethiol (1.646 ml) was added to a mixture of aluminum trichloride (916 mg) and 6-(4-methoxyphenyl)-2-methyl-4,5-dihydropyridazin-3(2H)-one (300 mg) in toluene (5 ml) at 0° C. The mixture was stirred at 0° C. to room temperature over weekend. The mixture was quenched with 1 N HCl aq. at room temperature and extracted with EtOAc. The organic layer was separated, washed with sat. NaHCO$_3$ aq. and brine, dried over Na$_2$SO$_4$ and concentrated in vacuo. The residue was washed with hexane, collected by filtration and dried in vacuo to give 6-(4-hydroxyphenyl)-2-methyl-4,5-dihydropyridazin-3(2H)-one (258 mg) as a white solid.
MS (API+), found: 205.1.

C) N-[(1S,2S)-4,4-difluoro-2-{[4-(1-methyl-6-oxo-1,4,5,6-tetrahydropyridazin-3-yl)phenoxy]methyl}cyclohexyl]methanesulfonamide The title compound was obtained in the same manner as in Example 233, steps A and B.

Example 488

N-[(1S,2S)-2-{[4-(3,3-difluoro-2-oxopyrrolidin-1-yl)phenoxy]methyl}-4,4-difluorocyclohexyl]methanesulfonamide A) 1-(4-methoxyphenyl)pyrrolidin-2-one Copper(I)iodide (2.238 g) was added to the mixture of picolinic acid (1.447 g), K$_3$PO$_4$ (24.94 g), 1-iodo-4-methoxybenzene (17.87 g) and pyrrolidin-2-one (5 g) in DMSO (50 ml). The mixture was stirred at 130° C. under N$_2$ overnight. After cooling to room temperature, EtOAc (150 ml) and water (200 ml) were added to the mixture and the insoluble solid was removed by filtration. The mixture was extracted with EtOAc. The organic layer was separated, washed with brine, dried over Na$_2$SO$_4$ and the insoluble solid was removed by filtration through NH-silica pad (eluted with EtOAc). The mixture was concentrated in vacuo and the residue was washed with hexane and dried in vacuo to give 1-(4-methoxyphenyl)pyrrolidin-2-one (8.33 g) as light brown crystals.
MS (API+), found: 192.1.

B) 3,3-difluoro-1-(4-methoxyphenyl)pyrrolidin-2-one

A THF solution of LiHMDS (3.77 ml, 1 M) was added to a suspension of 1-(4-methoxyphenyl)pyrrolidin-2-one (300 mg) in THF (6 ml) at −78° C. The mixture was stirred at −78° C. under N$_2$ for 20 min. Then N-fluoro-N-(phenylsulfonyl)benzenesulfonamide (1088 mg) was added to the mixture at −78° C. Then the mixture was stirred at 0° C. to room temperature under N$_2$ for 2 days. The mixture was quenched with water at room temperature and extracted with EtOAc. The organic layer was separated, washed with brine, dried over Na$_2$SO$_4$ and concentrated in vacuo. The is residue was purified by column chromatography (NH silica gel, eluted with 1%-50% EtOAc in hexane, following silica gel, eluted with 5%-40% EtOAc in hexane) and concentrated in vacuo to give 3,3-difluoro-1-(4-methoxyphenyl)pyrrolidin-2-one (139 mg) as a white solid.
MS (API+), found: 228.1.

C) N-[(1S,2S)-2-{[4-(3,3-difluoro-2-oxopyrrolidin-1-yl)phenoxy]methyl}-4,4-difluorocyclohexyl]methanesulfonamide The title compound was obtained in the same manner as in Example 487, steps B and C.

Example 489

N-[(3RS,4SR)-3-{[4-(4-chloro-1H-pyrazol-1-yl)-3-fluorophenoxy]methyl}tetrahydro-2H-pyran-4-yl]ethanesulfonamide Titled compound was synthesized by the similar method to Example 233.

Example 490

N-[(3RS,4SR)-3-{[2-fluoro-4-(1H-pyrazol-1-yl)phenoxy]methyl}tetrahydro-2H-pyran-4-yl]ethanesulfonamide Titled compound was synthesized by the similar method to Example 233.

Example 491

N-[(1SR,2SR)-4,4-difluoro-2-{[2-fluoro-4-(1H-pyrazol-1-yl)phenoxy]methyl}cyclohexyl]ethanesulfonamide Titled compound was synthesized by the similar method to Example 233.

Example 492

N-[(3RS,4SR)-3-{[3-chloro-4-(1H-pyrazol-1-yl)phenoxy]methyl}tetrahydro-2H-pyran-4-yl]ethanesulfonamide A) 2-chloro-4-(1H-pyrazol-1-yl)phenol Titled compound was synthesized by the similar method to Example 289.

B) N-[(3RS,4SR)-3-{[3-chloro-4-(1H-pyrazol-1-yl)phenoxy]methyl}tetrahydro-2H-pyran-4-yl]ethanesulfonamide Titled compound was synthesized by the similar method to Example 233.

Example 493

N-[(3RS,4SR)-3-{[3-fluoro-4-(1H-pyrazol-1-yl)phenoxy]methyl}tetrahydro-2H-pyran-4-yl]ethanesulfonamide Titled compound was synthesized by the similar method to Example 233.

Example 494

N-[(3RS,4SR)-3-{[3-methyl-4-(1H-pyrazol-1-yl)phenoxy]methyl}tetrahydro-2H-pyran-4-yl]ethanesulfonamide A) 3-methyl-4-(1H-pyrazol-1-yl)phenol Titled compound was synthesized by the similar method to Example 132.

B) N-[(3RS,4SR)-3-{[3-methyl-4-(1H-pyrazol-1-yl)phenoxy]methyl}tetrahydro-2H-pyran-4-yl]ethanesulfonamide Titled compound was synthesized by the similar method to Example 233.

Example 495

N-[(3RS,4SR)-3-{[3-chloro-4-(4-chloro-1H-pyrazol-1-yl)phenoxy]methyl}tetrahydro-2H-pyran-4-yl]ethanesulfonamide A) 3-chloro-4-(4-chloro-1H-pyrazol-1-yl)phenol Titled compound was synthesized by the similar method to Example 289 and Example 140.

B) N-[(3RS,4SR)-3-{[3-chloro-4-(4-chloro-1H-pyrazol-1-yl)phenoxy]methyl}tetrahydro-2H-pyran-4-yl]ethanesulfonamide Titled compound was synthesized by the similar method to Example 233.

Example 496

N-[(3R,4S)-3-{[2-fluoro-4-(4-methyl-1H-pyrazol-1-yl)phenoxy]methyl}tetrahydro-2H-pyran-4-yl]methanesulfonamide Titled compound was synthesized by the similar method to Example 233.

Example 497

N-[(3RS,4SR)-3-{[3-chloro-4-(4-methyl-1H-pyrazol-1-yl)phenoxy]methyl}tetrahydro-2H-pyran-4-yl]ethanesulfonamide A) 3-chloro-4-(4-methyl-1H-pyrazol-1-yl)phenol Titled compound was synthesized by the similar method to Example 289.

B) N-[(3RS,4SR)-3-{[3-chloro-4-(4-methyl-1H-pyrazol-1-yl)phenoxy]methyl}tetrahydro-2H-pyran-4-yl]ethanesulfonamide Titled compound was synthesized by the similar method to Example 233.

Example 498

N-[(3R,4S)-4-{[4-(4-chloro-1H-pyrazol-1-yl)-3-fluorophenoxy]methyl}tetrahydro-2H-pyran-3-yl]methanesulfonamide Titled compound was synthesized by the similar method to Example 233.

Example 499

N-[(3R,4S)-4-{[4-(4-chloro-1H-pyrazol-1-yl)-3-fluorophenoxy]methyl}tetrahydro-2H-pyran-3-yl]ethanesulfonamide Titled compound was synthesized by the similar method to Example 233.

Example 500

N-[(3R,4S)-3-{[4-(4-chloro-1H-pyrazol-1-yl)-2,5-difluorophenoxy]methyl}tetrahydro-2H-pyran-4-yl]methanesulfonamide Titled compound was synthesized by the similar method to Example 233.

Example 501

1,5-anhydro-6-O-[4-(5-cyanopyridin-2-yl)phenyl]-2,3,4-trideoxy-4-[(methylsulfonyl)amino]-D-erythrohexitol Titled compound was synthesized by the similar method to Example 233.

Example 502

1,5-anhydro-6-O-[4-(5-cyanopyridin-2-yl)phenyl]-2,3,4-trideoxy-4-[(ethylsulfonyl)amino]-D-erythro-hexitol Titled compound was synthesized by the similar method to Example 233.

Example 503

N-[(3R,4S)-3-{[4-(4-chloro-1H-pyrazol-1-yl)-3-fluorophenoxy]methyl}tetrahydro-2H-pyran-4-yl]ethanesulfonamide Titled compound was synthesized by the similar method to Example 233.

Example 504

N-((3R,4S)-3-(((5-(2-cyanophenyl)pyridin-2-yl)oxy)methyl)tetrahydro-2H-pyran-4-yl)methanesulfonamide

A) N-((3R,4S)-3-(((5-bromopyridin-2-yl)oxy)methyl)tetrahydro-2H-pyran-4-yl)methanesulfonamide Titled compound was synthesized by the similar method to Example 233.

B) N-((3R,4S)-3-(((5-(2-cyanophenyl)pyridin-2-yl)oxy)methyl)tetrahydro-2H-pyran-4-yl)methanesulfonamide The mixture of N-((3R,4S)-3-(((5-bromopyridin-2-yl)oxy)methyl)tetrahydro-2H-pyran-4-yl)methanesulfonamide (0.11 g), (2-cyanophenyl)boronic acid (0.063 g), dicyclohexyl(2',4',6'-triisopropyl-[1,1'-biphenyl]-2-yl)phosphine (0.014 g), Pd(OAc)$_2$ (0.004 g), and potassium fluoride (0.084 g) in MeOH (1.0 ml) and toluene (1.0 ml) was heated at 120° C. for 1 h under microwave irradiation. After cooling to room temperature, the mixture was added silica gel, concentrated in vacuo, and purified by column chromatography (silica gel, eluted with 0%-50% EtOAc in hexane) to give the title compound (0.083 g) as colorless amorphous solid.

Example 508

N-[(1S,2SR,3SR,5R)-2-{[4-(5-cyanopyridin-2-yl)phenoxy]methyl}-8-oxabicyclo[3.2.1]oct-3-yl]methanesulfonamide

A) ethyl 3-(((S)-1-phenylethyl)amino)-8-oxabicyclo[3.2.1]oct-2-ene-2-carboxylate To a solution of ethyl 3-oxo-8-oxabicyclo[3.2.1]octane-2-carboxylate (3.65 g) and (S)-1-phenylethanamine (2.46 g) in toluene (40 ml) was added acetic acid (2.21 g) at room temperature. The mixture was stirred at 100° C. under Ar overnight. After evaporation, the residue was purified by column chromatography (NH silica gel, eluted with EtOAc in hexane) to give the title compound (4.35 g) as a pale yellow oil.

$^1$H NMR (300 MHz, CDCl$_3$) δ 1.26-1.33 (3H, m), 1.48 (3H, t, J=6.8 Hz), 1.57-2.08 (5H, m), 2.26-2.92 (1H, m), 4.06-4.28 (2H, m), 4.35-4.62 (2H, m), 5.01 (1H, d, J=1.1 Hz), 7.13-7.41 (5H, m), 8.93-9.15 (1H, m).

B) (1SR,5RS)-ethyl 3-(((S)-1-phenylethyl)amino)-8-oxabicyclo[3.2.1]oct-2-ene-2-carboxylate A diastereomeric mixture of ethyl 3-(((S)-1-phenylethyl)amino)-8-oxabicyclo[3.2.1]oct-2-ene-2-carboxylate (4.35 g) was separated by preparative HPLC (column: CHIRALCEL OD(NL001), 50 mmID×500 mL, DAICEL corporation, mobile phase: hexane/2-ethanol=800/200 (v/v)) to give (1SR,5RS)-ethyl 3-(((S)-1-phenylethyl)amino)-8-oxabicyclo[3.2.1]oct-2-ene-2-carboxylate (2.12 g, >99% de) with a shorter retention time as a pale yellow oil, and (1RS,5SR)-ethyl 3-(((S)-1-phenylethyl)amino)-8-oxabicyclo[3.2.1]oct-2-ene-2-carboxylate (2.09 g, >99% de) with a longer retention time as a white solid.

(1SR,5RS)-ethyl 3-(((S)-1-phenylethyl)amino)-8-oxabicyclo[3.2.1]oct-2-ene-2-carboxylate:

$^1$H NMR (300 MHz, CDCl$_3$) δ 1.21-1.36 (5H, m), 1.47 (3H, d, J=6.8 Hz), 1.78 (1H, d, J=17.0 Hz), 1.84-1.99 (3H, m), 2.76-2.89 (1H, m), 4.11-4.25 (2H, m), 4.39-4.47 (1H, m), 4.55 (1H, quin, J=7.1 Hz), 4.97-5.05 (1H, m), 7.19-7.26 (3H, m), 7.29-7.37 (2H, m), 8.99 (1H, d, J=7.2 Hz).

(1RS,5SR)-ethyl 3-(((S)-1-phenylethyl)amino)-8-oxabicyclo[3.2.1]oct-2-ene-2-carboxylate:

$^1$H NMR (300 MHz, CDCl$_3$) δ 1.29 (3H, t, J=7.0 Hz), 1.49 (3H, d, J=6.8 Hz), 1.55-1.69 (1H, m), 1.89-2.13 (4H, m), 2.42 (1H, dd, J=17.0, 5.3 Hz), 4.12-4.26 (2H, m), 4.43 (1H, t, J=6.0 Hz), 4.52 (1H, quin, J=7.0 Hz), 4.94-5.07 (1H, m), 7.12-7.40 (5H, m), 9.07 (1H, d, J=7.2 Hz).

C) (1S,2SR,3SR,5R)-ethyl 3-(((S)-1-phenylethyl)amino)-8-oxabicyclo[3.2.1]octane-2-carboxylate To a solution of (1SR,5RS)-ethyl 3-(((S)-1-phenylethyl)amino)-8-oxabicyclo[3.2.1]oct-2-ene-2-carboxylate, which was obtained in section B) of Example 508, in AcOH (30 ml) was added portionwise NaBH(AcO)$_3$ (5.63 g). The mixture was stirred at room temperature overnight. After evaporation, the residue was diluted with EtOAc and sat. NaHCO$_3$ aq. was added. The phases were separated, and the aqueous phase was extracted with EtOAc. The organic layers were separated, washed with water and brine, dried over MgSO$_4$, and concentrated in vacuo to give the title compound (1.62 g) as a colorless oil.

$^1$H NMR (300 MHz, CDCl$_3$) δ 1.27 (3H, d, J=6.4 Hz), 1.32 (3H, t, J=7.2 Hz), 1.51 (3H, t, J=13.8 Hz), 1.75-2.09 (4H, m), 2.38-2.50 (1H, m), 3.05 (1H, dd, J=5.9, 3.6 Hz), 3.38 (1H, t, J=5.7 Hz), 3.67 (1H, q, J=6.4 Hz), 4.14-4.29 (3H, m), 4.51 (1H, dd, J=7.2, 3.4 Hz), 7.19-7.35 (5H, m).

D) (1S,2SR,3SR,5R)-ethyl 3-amino-8-oxabicyclo[3.2.1]octane-2-carboxylate

A mixture of (1S,2SR,3SR,5R)-ethyl 3-(((S)-1-phenylethyl)amino)-8-oxabicyclo[3.2.1]octane-2-carboxylate (1.61 g) and 10% Pd(OH)$_2$ (0.16 g) in EtOH (50 ml) was hydrogenated under balloon pressure at room temperature overnight. The catalyst was removed by filtration and the filtrate was concentrated in vacuo to give the title compound (1.03 g) as pale yellow oil.

$^1$H NMR (300 MHz, CDCl$_3$) δ 1.29 (3H, t, J=7.2 Hz), 1.91 (1H, d, J=14.7 Hz), 2.02 (2H, t, J=8.1 Hz), 2.13-2.27 (2H, m), 2.39-2.50 (1H, m), 3.04 (1H, dd, J=5.3, 4.2 Hz), 3.82 (1H, t, J=5.7 Hz), 4.23 (2H, qd, J=7.2, 1.5 Hz), 4.40 (1H, t, J=5.1 Hz), 4.57-4.67 (1H, m), 4.86 (2H, brs).

E) (1S,2SR,3SR,5R)-ethyl 3-((tert-butoxycarbonyl)amino)-8-oxabicyclo[3.2.1]octane-2-carboxylate To a solution of (1S,2SR,3SR,5R)-ethyl 3-amino-8-oxabicyclo[3.2.1]octane-2-carboxylate (800 mg) and Et₃N (1.12 ml) in THF (20 ml) was added Boc₂O (1.12 ml) at 0° C. The mixture was stirred at room temperature under Ar overnight. The mixture was quenched with water and extracted with EtOAc. The organic layer was separated, washed with citric acid aq. and brine, dried over MgSO₄ and concentrated in vacuo. The residue was purified by column chromatography (silica gel, eluted with EtOAc in hexane) to give the title compound (1.10 g) as a colorless oil.

¹H NMR (300 MHz, CDCl₃) δ 1.25 (3H, t, J=7.0 Hz), 1.42 (9H, s), 1.79 (1H, d, J=14.7 Hz), 1.91-2.21 (4H, m), 2.22-2.33 (1H, m), 3.13 (1H, dd, J=6.2, 3.6 Hz), 4.13 (2H, dtt, J=10.6, 7.1, 3.6 Hz), 4.23-4.34 (1H, m), 4.37-4.44 (1H, m), 4.47 (1H, dd, J=6.6, 3.6 Hz), 5.10 (1H, d, J=6.4 Hz).

F) (1S,2SR,3SR,5R)-ethyl 3-((tert-butoxycarbonyl)amino)-8-oxabicyclo[3.2.1]octane-2-carboxylate To a solution of (1S,2SR,3SR,5R)-ethyl 3-((tert-butoxycarbonyl)amino)-8-oxabicyclo[3.2.1]octane-2-carboxylate (1 g) in EtOH (50 ml) was added portionwise sodium ethoxide (0.341 g) at room temperature. The mixture was stirred at 80° C. for 2 h. The solvent was removed by evaporation and the residue was acidified with 10% citric acid aq. and diluted with EtOAc. To the mixture was added brine, extracted with EtOAc and washed with brine, dried over Na₂SO₄ and concentrated under vacuum. The residue was purified by column chromatography (silica gel, eluted with EtOAc in hexane) to give the title compound (0.635 g) as a off-white solid.

¹H NMR (300 MHz, CDCl₃) δ 1.28 (3H, t, J=7.2 Hz), 1.44 (9H, s), 1.78-1.91 (1H, m), 1.98-2.18 (3H, m), 2.44 (1H, dt, J=14.6, 5.9 Hz), 2.66 (1H, brs), 4.19 (3H, q, J=7.2 Hz), 4.41 (1H, t, J=5.1 Hz), 4.69-4.88 (2H, m).

G) tert-butyl ((1S,2SR,3SR,5R)-2-(hydroxymethyl)-8-oxabicyclo[3.2.1]octan-3-yl)carbamate To a solution of (1S,2SR,3SR,5R)-ethyl 3-((tert-butoxycarbonyl)amino)-8-oxabicyclo[3.2.1]octane-2-carboxylate (700 mg) in THF (35 ml) was added LAH (213 mg) at 0° C. The mixture was stirred at 0° C. under Ar for 1 h. To the reaction mixture was added EtOH-EtOAc 1:1 (1.4 ml) and 1 M NaOH (2.8 ml) at −20° C. and the mixture was stirred at room temperature for 30 min. The mixture was passed through a pad of celite and the filtrate was concentrated under vacuum. The residue was purified by column chromatography (silica gel, eluted with EtOAc in hexane) to give the title compound (515 mg) as a white solid.

¹H NMR (300 MHz, CDCl₃) δ 1.43-1.49 (9H, m), 1.60-1.70 (2H, m), 1.74-1.86 (1H, m), 1.91-2.14 (3H, m), 2.28-2.44 (1H, m), 2.68 (1H, brs), 3.66-3.85 (3H, m), 4.40 (2H, d, J=5.7 Hz), 4.72 (1H, brs).

H) tert-butyl ((1S,2SR,3SR,5R)-2-((4-(5-cyanopyridin-2-yl)phenoxy)methyl)-8-oxabicyclo[3.2.1]octan-3-yl)carbamate A mixture of tert-butyl ((1S,2SR,3SR,5R)-2-(hydroxymethyl)-8-oxabicyclo[3.2.1]octan-3-yl)carbamate (150 mg), 6-(4-hydroxyphenyl)nicotinonitrile (160 mg), ADDP (221 mg) and Bu₃P (0.216 ml) was stirred at room temperature under Ar overnight. The insoluble material was removed by filtration, and the filtrate was concentrated in vacuo. The residue was purified by column chromatography (silica gel, eluted with EtOAc in hexane) to give the title compound (220 mg) as a pale yellow solid.

¹H NMR (300 MHz, CDCl₃) δ 1.46 (9H, s), 1.49-1.57 (1H, m), 1.82-1.93 (1H, m), 1.96-2.36 (5H, m), 3.66-3.73 (1H, m), 4.07-4.23 (2H, m), 4.41 (1H, t, J=5.5 Hz), 4.52 (1H, d, J=7.2 Hz), 4.81 (1H, brs), 7.01-7.09 (2H, m), 7.75-7.81 (1H, m), 7.95 (1H, dd, J=8.5, 2.1 Hz), 7.98-8.05 (2H, m), 8.89 (1H, d, J=1.5 Hz).

I) N-[(1S,2SR,3SR,5R)-2-{[4-(5-cyanopyridin-2-yl)phenoxy]methyl}-8-oxabicyclo[3.2.1]oct-3-yl]methanesulfonamide TFA (1 ml) was added to a solution of tert-butyl ((1S,2SR,3SR,5R)-2-((4-(5-cyanopyridin-2-yl)phenoxy)methyl)-8-oxabicyclo[3.2.1]octan-3-yl)carbamate (200 mg) in THF (2.5 ml). The mixture was stirred at room temperature for 1 h. The solvent was removed by evaporation and the residue was neutralized with sat. NaHCO₃ aq. at 0° C. and extracted with EtOAc. The organic layer was separated, washed with water and brine, dried over MgSO₄ and concentrated in vacuo. The residue was added THF (2.5 ml), triethylamine (0.191 ml) and methanesulfonyl chloride (0.053 ml). The mixture was stirred at room temperature overnight. The mixture was quenched with water and extracted with EtOAc. The organic layer was separated, washed with water and brine, dried over MgSO₄ and concentrated in vacuo. The residue was purified by column chromatography (silica gel, eluted with EtOAc in hexane) to give the title compound (129 mg) as a white solid.

Example 509

N-[(3S,4S)-3-{[4-(4-methyl-1H-pyrazol-1-yl)phenoxy]methyl}tetrahydro-2H-thiopyran-4-yl]methanesulfonamide To tert-butyl ((3S,4S)-3-(hydroxymethyl)tetrahydro-2H-thiopyran-4-yl)carbamate (49 mg) were added a solution of 4-(4-methyl-1H-pyrazol-1-yl)phenol (70 mg) in toluene, 1,1-(azodicarbonyl)dipiperidine (61 mg) and tributylphosphine (49 mg), and the mixture was stirred at room temperature overnight. To the reaction solution were added water (1 mL) and ethyl acetate (3 mL), and the mixture was stirred. The organic layer was passed through a phase separation filter, and the solvent in the separated solution was evaporated by air-blow apparatus. The residue was purified by HPLC (column: YMC Triart C18, mobile phase: acetonitrile/10 mM aqueous ammonium acetate solution), and the solvent was evaporated by air-blow apparatus. To the residue were added methanol (0.5 mL) and 4 N hydrogen chloride/cyclopentyl methyl ether solution (0.3 mL), and the mixture was stirred for 3 h. The solvent was evaporated by air-blow apparatus. The residue was purified by HPLC (column: YMC Triart C18, mobile phase: acetonitrile/10 mM aqueous ammonium acetate solution), and the solvent was evaporated by air-blow apparatus. The residue was dissolved in tetrahydrofuran (0.5 mL), methanesulfonyl chloride (0.3 mL) was added, and the mixture was stirred for 3 h. The solvent was evaporated by air-blow apparatus. The residue was purified by HPLC (column: YMC Triart C18, mobile phase: acetonitrile/10 mM aqueous ammonium acetate solution), and the solvent was evaporated by air-blow apparatus to give the title compound (9.2 mg).

Example 510

N-[(3S,4S)-3-{[4-(4-chloro-1H-pyrazol-1-yl)phenoxy]methyl}tetrahydro-2H-thiopyran-4-yl]methanesulfonamide Titled compound was synthesized by the similar method to Example 509.

Example 511

N-[(3S,4S)-3-{[4-(4-cyano-1H-pyrazol-1-yl)phenoxy]methyl}tetrahydro-2H-thiopyran-4-yl]methanesulfonamide Titled compound was synthesized by the similar method to Example 509.

Example 512

N-[(3S,4S)-3-{[4-(4-cyano-1H-pyrazol-1-yl)-2-fluorophenoxy]methyl}tetrahydro-2H-thiopyran-4-yl]methanesulfonamide Titled compound was synthesized by the similar method to Example 509.

Example 513

N-[(3S,4S)-3-{[4-(5-chloropyridin-2-yl)-2-fluorophenoxy]methyl}tetrahydro-2H-thiopyran-4-yl]methanesulfonamide Titled compound was synthesized by the similar method to Example 509.

Example 514

N-[(3S,4S)-3-{[4-(3,5-difluoropyridin-2-yl)phenoxy]methyl}tetrahydro-2H-thiopyran-4-yl]methanesulfonamide Titled compound was synthesized by the similar method to Example 509.

Example 515

N-[(3S,4S)-3-{[4-(5-chloro-3-fluoropyridin-2-yl)phenoxy]methyl}tetrahydro-2H-thiopyran-4-yl]methanesulfonamide Titled compound was synthesized by the similar method to Example 509.

Example 516

N-[(3S,4S)-3-{[4-(5-cyanopyridin-2-yl)phenoxy]methyl}tetrahydro-2H-thiopyran-4-yl]methanesulfonamide Titled compound was synthesized by the similar method to Example 509.

Example 517

N-[(3S,4S)-3-{[4-(5-methyl-1,3-thiazol-2-yl)phenoxy]methyl}tetrahydro-2H-thiopyran-4-yl]methanesulfonamide Titled compound was synthesized by the similar method to Example 509.

Example 518

N-[(3S,4S)-3-{[4-(1-methyl-2-oxo-1,2-dihydropyridin-3-yl)phenoxy]methyl}tetrahydro-2H-thiopyran-4-yl]methanesulfonamide Titled compound was synthesized by the similar method to Example 509.

Example 519

N-[(3S,4S)-3-{[4-(tetrahydro-2H-pyran-4-yl)phenoxy]methyl}tetrahydro-2H-thiopyran-4-yl]methanesulfonamide Titled compound was synthesized by the similar method to Example 509.

Example 520

N-[(3S,4S)-3-{[4-(4-methyl-1H-pyrazol-1-yl)phenoxy]methyl}tetrahydro-2H-thiopyran-4-yl]ethanesulfonamide Titled compound was synthesized by the similar method to Example 509.

Example 521

N-[(3S,4S)-3-{[4-(4-chloro-1H-pyrazol-1-yl)phenoxy]methyl}tetrahydro-2H-thiopyran-4-yl]ethanesulfonamide Titled compound was synthesized by the similar method to Example 509.

Example 522

N-[(3S,4S)-3-{[4-(4-cyano-1H-pyrazol-1-yl)phenoxy]methyl}tetrahydro-2H-thiopyran-4-yl]ethanesulfonamide Titled compound was synthesized by the similar method to Example 509.

Example 523

N-[(3S,4S)-3-{[4-(4-cyano-1H-pyrazol-1-yl)-2-fluorophenoxy]methyl}tetrahydro-2H-thiopyran-4-yl]ethanesulfonamide Titled compound was synthesized by the similar method to Example 509.

Example 524

N-[(3S,4S)-3-{[4-(3,5-difluoropyridin-2-yl)phenoxy]methyl}tetrahydro-2H-thiopyran-4-yl]ethanesulfonamide Titled compound was synthesized by the similar method to Example 509.

Example 525

N-[(3S,4S)-3-{[4-(5-chloro-3-fluoropyridin-2-yl)phenoxy]methyl}tetrahydro-2H-thiopyran-4-yl]ethanesulfonamide Titled compound was synthesized by the similar-method to Example 509.

Example 526

N-[(3S,4S)-3-{[4-(5-cyanopyridin-2-yl)phenoxy]methyl}tetrahydro-2H-thiopyran-4-yl]ethanesulfonamide Titled compound was synthesized by the similar method to Example 509.

Example 527

N-[(3S,4S)-3-{[4-(5-methyl-1,3-thiazol-2-yl)phenoxy]methyl}tetrahydro-2H-thiopyran-4-yl]ethanesulfonamide Titled compound was synthesized by the similar method to Example 509.

Example 528

N-[(3S,4S)-3-{[4-(1-methyl-2-oxo-1,2-dihydropyridin-3-yl)phenoxy]methyl}tetrahydro-2H-thiopyran-4-yl]ethanesulfonamide Titled compound was synthesized by the similar method to Example 509.

Example 529

N-[(3S,4S)-3-{[4-(tetrahydro-2H-pyran-4-yl)phenoxy]methyl}tetrahydro-2H-thiopyran-4-yl]ethanesulfonamide Titled compound was synthesized by the similar method to Example 509.

The Example compounds and Reference Example compounds produced according to the above-mentioned method, or a method analogous thereto are shown in the following Tables. In the Tables, MS shows Found, and "ND" shows that the peak is not detected.

TABLE 1-1

| Ex. No. | IUPAC Name | Structure | Salt | MS |
|---|---|---|---|---|
| 1 | trans-N-[1-acetyl-3-{[4-(difluoromethoxy)phenoxy]methyl}piperidin-4-yl]ethanesulfonamide | 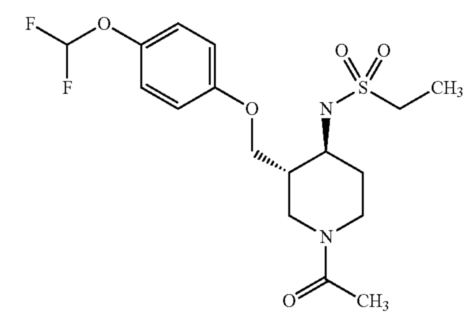 [SMILES: CCS(=O)(=O)N[C@H]1CCN(C(C)=O)C[C@@H]1COc1ccc(OC(F)F)cc1] | | 407.0 |
| 2 | trans-N-[1-acetyl-3-{[4-(2-cyanoethyl)phenoxy]methyl}piperidin-4-yl]ethanesulfonamide | 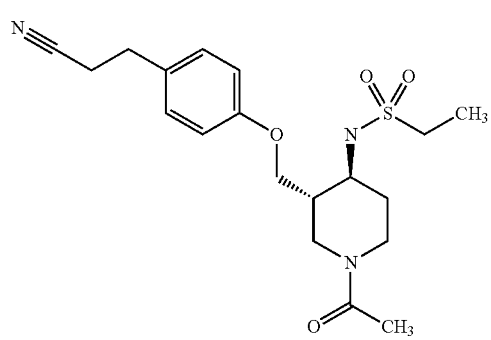 [SMILES: CCS(=O)(=O)N[C@H]1CCN(C(C)=O)C[C@@H]1COc1ccc(CCC#N)cc1] | | 394.4 |

TABLE 1-1-continued

| Ex. No. | IUPAC Name | Structure | Salt | MS |
|---|---|---|---|---|
| 3 | trans-N-[1-acetyl-3-{[4-(1H-pyrazol-1-yl)phenoxy]methyl}piperidin-4-yl]ethanesulfonamide | 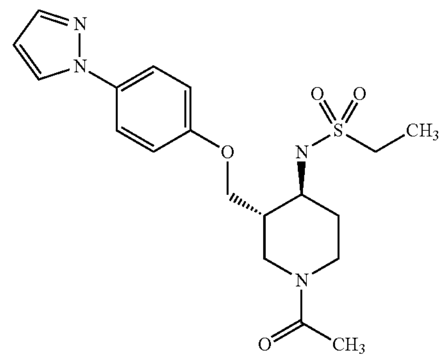 [SMILES: CCS(=O)(=O)N[C@H]1CCN(C(C)=O)C[C@@H]1COc1ccc(-n2cccn2)cc1] | | 407.3 |
| 4 | 1,5-anhydro-6-O-(4-cyclopropylphenyl)-2,3,4-trideoxy-4-[(ethylsulfonyl)amino]-DL-erythro-hexitol | 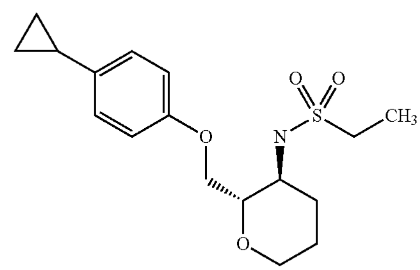 [SMILES: CCS(=O)(=O)N[C@H]1CCCO[C@@H]1COc1ccc(C2CC2)cc1] | | 340.1 |
| 5 | 1,5-anhydro-6-O-(4-cyclopropylphenyl)-2,3,4-trideoxy-4-[(methylsulfonyl)amino]-DL-erythro-hexitol | 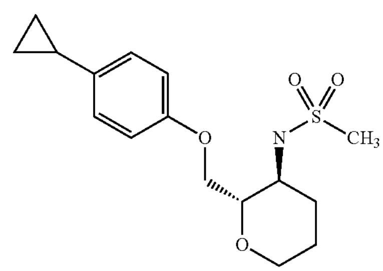 [SMILES: CS(=O)(=O)N[C@H]1CCCO[C@@H]1COc1ccc(C2CC2)cc1] | | 326.1 |
| 6 | optically active material of trans-N-[3-{[4-(1H-pyrazol-1-yl)phenoxy]methyl}tetrahydro-2H-pyran-4-yl]ethanesulfonamide | 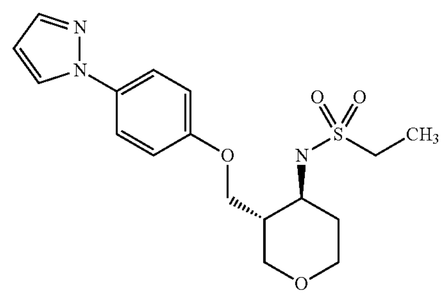 [SMILES: CCS(=O)(=O)N[C@H]1CCOC[C@@H]1COc1ccc(-n2cccn2)cc1] | | 366.4 |
| 7 | optically active material of trans-N-{3-[(4-cyclopropylphenoxy]methyl}tetrahydro-2H-pyran-4-yl}ethanesulfonamide | 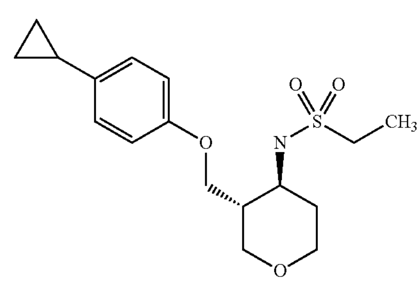 [SMILES: CCS(=O)(=O)N[C@H]1CCOC[C@@H]1COc1ccc(C2CC2)cc1] | | 338.2 |

TABLE 1-1-continued

| Ex. No. | IUPAC Name | Structure | Salt | MS |
|---|---|---|---|---|
| 8 | trans-N-[2-{[4-(1-methylethyl)phenoxy]methyl}cyclohexyl]ethanesulfonamide | 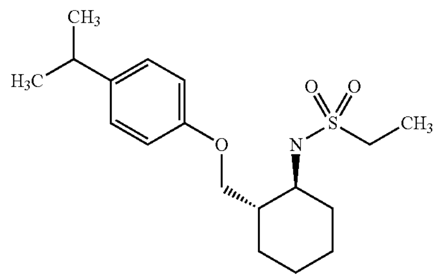 [SMILES: CCS(=O)(=O)N[C@H]1CCCC[C@@H]1COc1ccc(C(C)C)cc1] | | 340.1 |
| 9 | cis-N-[2-{[4-(1-methylethyl)phenoxy]methyl}cyclohexyl]ethanesulfonamide | 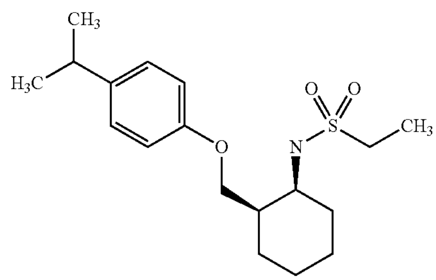 [SMILES: CCS(=O)(=O)N[C@H]1CCCC[C@H]1COc1ccc(C(C)C)cc1] | | 340.3 |
| 10 | cis-N-[2-{[4-(1-methylethyl)phenoxy]methyl}cyclopentyl]ethanesulfonamide | 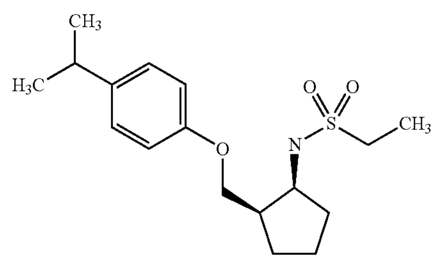 [SMILES: CCS(=O)(=O)N[C@H]1CCC[C@H]1COc1ccc(C(C)C)cc1] | | 326.3 |

TABLE 1-2

| Ex. No. | IUPAC Name | Structure | Salt | MS |
|---|---|---|---|---|
| 11 | trans-N-[2-{[4-(1-methylethyl)phenoxy]methyl}cyclohexyl]cyclopropanesulfonamide | 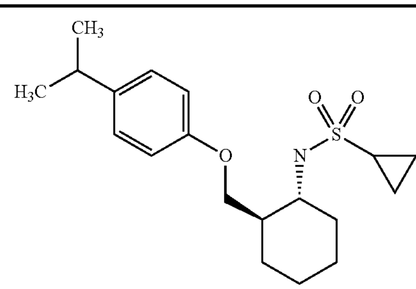 | | 352.4 |
| 12 | trans-N-{2-[(4-cycloproplphenoxy)methyl]cyclohexyl}cyclopropanesulfonamide | 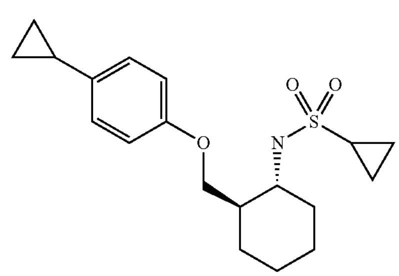 [SMILES: O=S(=O)(N[C@@H]1CCCC[C@H]1COc1ccc(C2CC2)cc1)C1CC1] | | 350.3 |

TABLE 1-2-continued

| Ex. No. | IUPAC Name | Structure | Salt | MS |
|---|---|---|---|---|
| 13 | N-[(1S,2S)-2-{[4-(1-methylethyl)phenoxy]methyl}cyclohexyl]ethanesulfonamide | 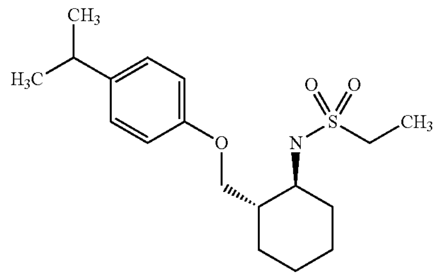 [SMILES: CCS(=O)(=O)N[C@H]1CCCC[C@@H]1COc1ccc(C(C)C)cc1] | | 340.3 |
| 14 | N-[(1R,2R)-2-{[4-(1-methylethyl)phenoxy]methyl}cyclohexyl]ethanesulfonamide | 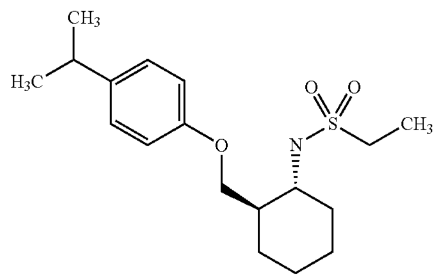 [SMILES: CCS(=O)(=O)N[C@@H]1CCCC[C@H]1COc1ccc(C(C)C)cc1] | | 340.3 |
| 15 | trans-N-[2-{[4-(1-methylethyl)phenoxy]methyl}cyclopentyl]ethanesulfonamide | 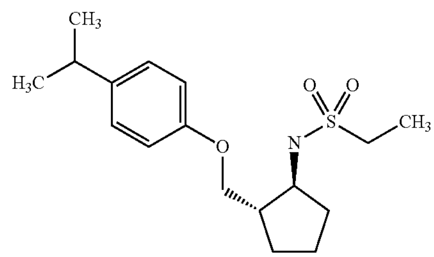 [SMILES: CCS(=O)(=O)N[C@H]1CCC[C@@H]1COc1ccc(C(C)C)cc1] | | 326.2 |
| 16 | trans-N-[2-{[4-(1-methylethyl)phenoxy]methyl}cyclopropyl]ethanesulfonamide | 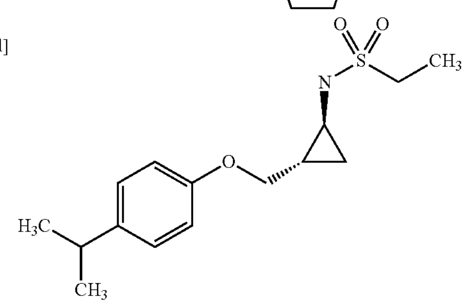 | | |

¹H NMR (300 MHz, DMSO-d₆) δ 0.68-0.78 (1H, m), 0.78-0.90 (1H, m), 1.08-1.25 (9H, m), 1.31-1.48 (1H, m), 2.41-2.52 (1H, m), 2.74-2.90 (1H, m), 3.08 (2H, q, J = 7.2 Hz), 3.71-3.81 (1H, m), 3.81-3.92 (1H, m), 6.76-6.86 (2H, m), 7.08-7.17 (2H, m), 7.40 (1H, d, J = 3.8 Hz).

| 17 | trans-N-{2-[(4-cyclopropylphenoxy)methyl]cyclobutyl}ethanesulfonamide | 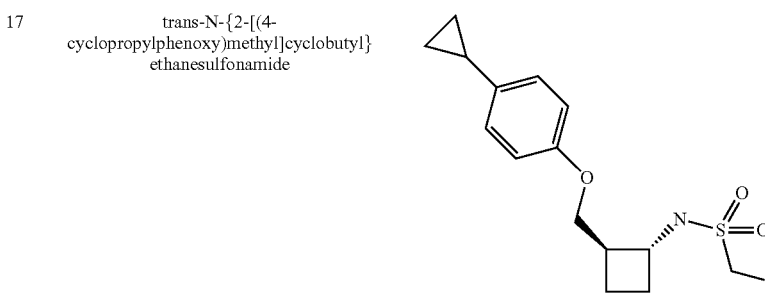 | | |

¹H NMR (300 MHz, CDCl₃) δ 0.56-0.64 (2H, m), 0.85-0.94 (2H, m), 1.35 (3H, t, J = 7.4 Hz), 1.53-1.68 (1H, m), 1.78-1.97 (3H, m), 2.30-2.44 (1H, m), 2.54-2.69 (1H, m), 2.93-3.12 (2H, m), 3.81 (1H, quin, J = 8.1 Hz), 3.90-4.01 (2H, m), 4.52 (1H, d, J = 8.3 Hz), 6.74-6.82 (2H, m), 6.96-7.03 (2H, m).

TABLE 1-2-continued

| Ex. No. | IUPAC Name | Structure | Salt | MS |
|---|---|---|---|---|
| 18 | cis-N-{2-[(4-cyclopropylphenoxy)methyl]cyclobutyl}ethanesulfonamide | 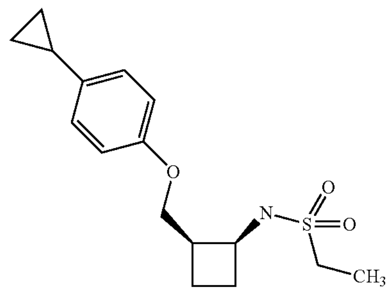 [SMILES: CCS(=O)(=O)N[C@H]1CC[C@H]1COc1ccc(C2CC2)cc1] | | |

$^1$H NMR (300 MHz, CDCl$_3$) δ 0.56-0.64 (2H, m), 0.85-0.94 (2H, m), 1.35 (3H, t, J = 7.4 Hz), 1.53-1.68 (1H, m), 1.78-1.97 (3H, m), 2.30-2.44 (1H, m), 2.54-2.69 (1H, m), 2.93-3.12 (2H, m), 3.81 (1H, quin, J = 8.1 Hz), 3.90-4.01 (2H, m), 4.52 (1H, d, J = 8.3 Hz), 6.74-6.82 (2H, m), 6.96-7.03 (2H, m).

TABLE 1-3

| Ex. No. | IUPAC Name | Structure | Salt | MS |
|---|---|---|---|---|
| 19 | cis-N-[4-{[4-(1-methylethyl)phenoxy]methyl}tetrahydrofuran-3-yl]ethanesulfonamide | 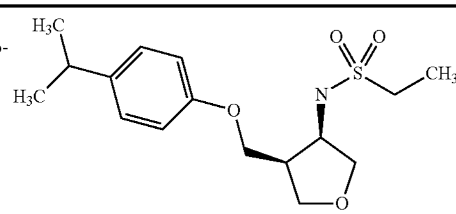 | | 328.3 |
| 20 | trans-N-[2-{[4-(1-methylethyl)phenoxy]methyl}cyclohexyl]propane-2-sulfonamide | 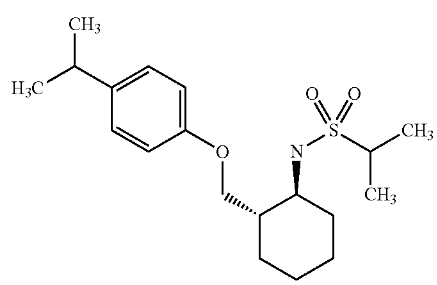 [SMILES: CC(C)c1ccc(OC[C@H]2CCCC[C@@H]2NS(=O)(=O)C(C)C)cc1] | | 354.2 |
| 21 | trans-N-{2-[(4-cyclopropylphenoxy)methyl]cyclohexyl}propane-2-sulfonamide | 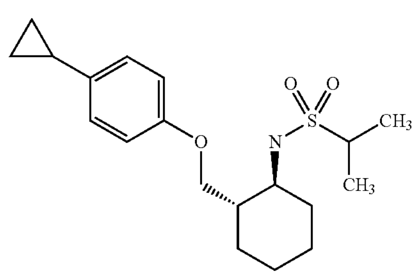 [SMILES: CC(C)S(=O)(=O)N[C@H]1CCCC[C@@H]1COc1ccc(C2CC2)cc1] | | 352.3 |
| 22 | trans-N-[4-{[4-(1-methylethyl)phenoxy]methyl}tetrahydrofuran-3-yl]ethanesulfonamide | 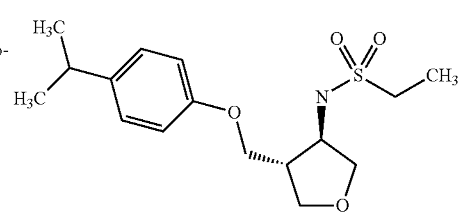 | | 326.5 |

TABLE 1-3-continued

| Ex. No. | IUPAC Name | Structure | Salt | MS |
|---|---|---|---|---|
| 23 | trans-N-[1-benzyl-3-{[4-(1-methylethyl)phenoxy]methyl}piperidin-4-yl]ethanesulfonamide | 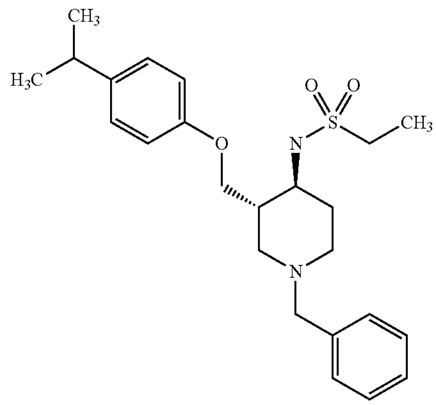 [SMILES: CCS(=O)(=O)N[C@H]1CCN(Cc2ccccc2)C[C@@H]1COc1ccc(C(C)C)cc1] | | 431.3 |
| 24 | cis-N-[1-benzyl-3-{[4-(1-methylethyl)phenoxy]methyl}piperidin-4-yl]ethanesulfonamide | 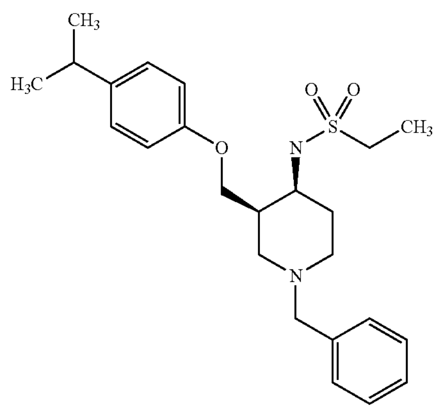 [SMILES: CCS(=O)(=O)N[C@H]1CCN(Cc2ccccc2)C[C@H]1COc1ccc(C(C)C)cc1] | | 431.3 |
| 25 | cis-N-[3-{[4-(1-methylethyl)phenoxy]methyl}piperidin-4-yl]ethanesulfonamide hydrochloride | 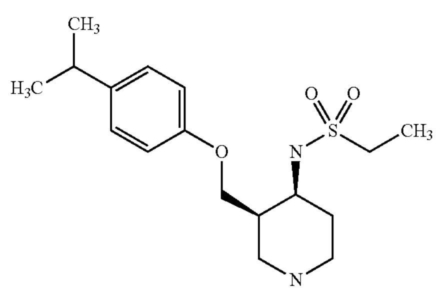 [SMILES: CCS(=O)(=O)N[C@H]1CCNC[C@H]1COc1ccc(C(C)C)cc1] | HCl | 341.3 |
| 26 | trans-2,2,2-trifluoro-N-[2-{[4-(1-methylethyl)phenoxy]methyl}cyclohexyl]ethanesulfonamide | 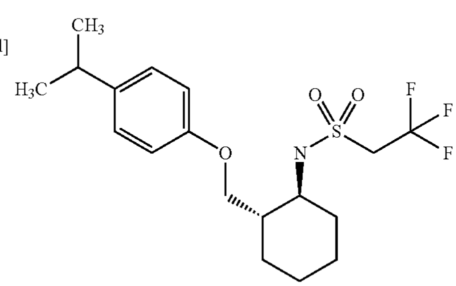 | | 392.3 |

TABLE 1-3-continued

| Ex. No. | IUPAC Name | Structure | Salt | MS |
|---|---|---|---|---|
| 27 | trans-N-{2-[(4-cyclopropylphenoxy)methyl]cyclohexyl}-2,2,2-trifluoroethanesulfonamide | 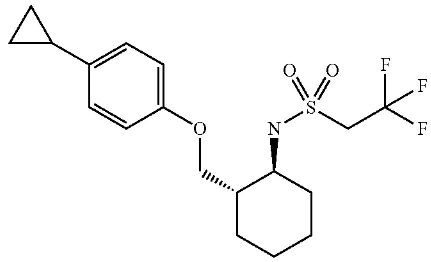 [SMILES: O=S(=O)(CC(F)(F)F)N[C@H]1CCCC[C@@H]1COc1ccc(C2CC2)cc1] | | 390.2 |
| 28 | N-[(1RS,2SR)-2-hydroxy-2-{[4-(1-methylethyl)phenoxy]methyl}cyclohexyl]ethanesulfonamide | 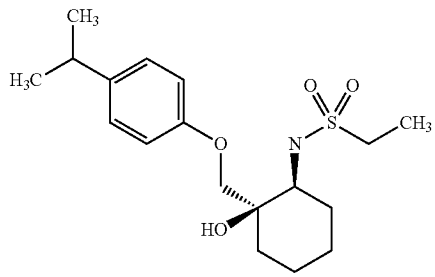 [SMILES: CCS(=O)(=O)N[C@H]1CCCC[C@]1(O)COc1ccc(C(C)C)cc1] | | 356.2 |
| 29 | trans-N-[3-{[4-(1-methylethyl)phenoxy]methyl}piperidin-4-yl]ethanesulfonamide hydrochloride | 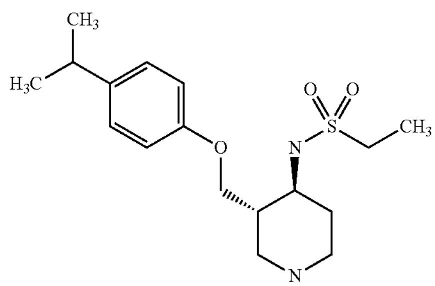 [SMILES: CCS(=O)(=O)N[C@H]1CCNC[C@@H]1COc1ccc(C(C)C)cc1] | HCl | 341.3 |

TABLE 1-4

| Ex. No. | IUPAC Name | Structure | Salt | MS |
|---|---|---|---|---|
| 30 | cis-N-[1-acetyl-3-{[4-(1-methylethyl)phenoxy]methyl}piperidin-4-yl]ethanesulfonamide | 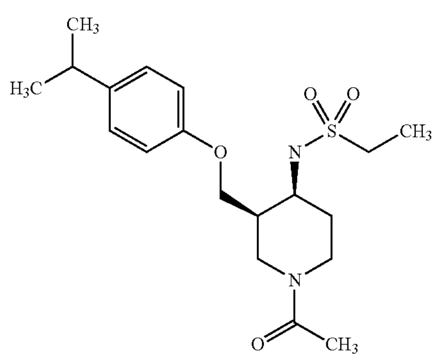 [SMILES: CCS(=O)(=O)N[C@H]1CCN(C(C)=O)C[C@H]1COc1ccc(C(C)C)cc1] | | 383.2 |

| Ex. No. | IUPAC Name | Structure | Salt | MS |
|---|---|---|---|---|
| 31 | trans-N-[1-acetyl-3-{[4-(1-methylethyl)phenoxy]methyl}piperidin-4-yl]ethanesulfonamide | 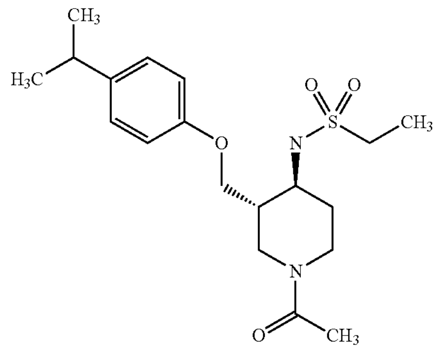 [SMILES: CCS(=O)(=O)N[C@H]1CCN(C(C)=O)C[C@@H]1COc1ccc(C(C)C)cc1] | | 383.2 |
| 32 | cis-N-[1-methyl-3-{[4-(1-methylethyl)phenoxy]methyl}piperidin-4-yl]ethanesulfonamide | 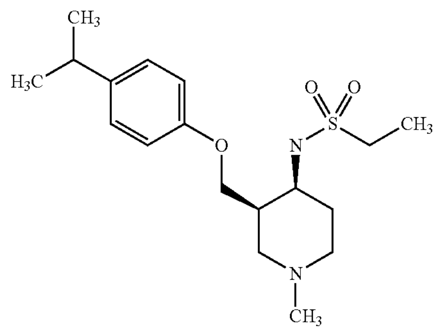 [SMILES: CCS(=O)(=O)N[C@H]1CCN(C)C[C@H]1COc1ccc(C(C)C)cc1] | | 355.3 |
| 33 | trans-N-[1-methyl-3-{[4-(1-methylethyl)phenoxy]methyl}piperidin-4-yl]ethanesulfonamide | 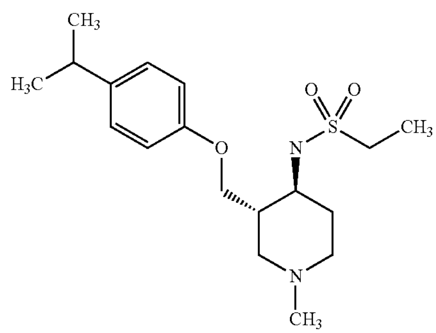 [SMILES: CCS(=O)(=O)N[C@H]1CCN(C)C[C@@H]1COc1ccc(C(C)C)cc1] | | 355.3 |
| 34 | trans-N-{3-[(4-isopropylphenoxy)methyl]tetrahydro-2H-pyran-4-yl}ethanesulfonamide | 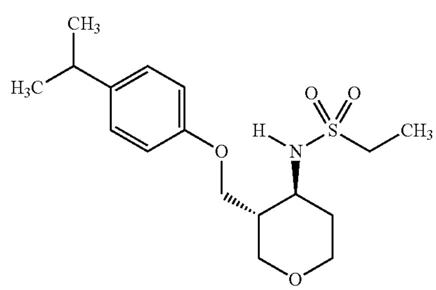 [SMILES: CCS(=O)(=O)N[C@H]1CCOC[C@@H]1COc1ccc(C(C)C)cc1] | | 342.3 |
| 35 | cis-N-{3-[(4-isopropylphenoxy)methyl]tetrahydro-2H-pyran-4-yl}ethanesulfonamide | 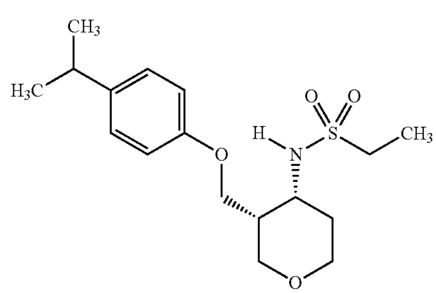 [SMILES: CCS(=O)(=O)N[C@@H]1CCOC[C@@H]1COc1ccc(C(C)C)cc1] | | 342.3 |

TABLE 1-4-continued

| Ex. No. | IUPAC Name | Structure | Salt | MS |
|---|---|---|---|---|
| 36 | cis-N-[2-{[4-(1-methylethyl)phenoxy]methyl}cyclopropyl]ethanesulfonamide | | | |

¹H NMR (300 MHz, DMSO-d₆) δ 0.56-0.69 (1H, m), 0.90-1.02 (1H, m), 1.09-1.41 (10H, m), 2.62-2.91 (2H, m), 3.08 (2H, q, J = 7.3 Hz), 3.87-4.08 (2H, m), 6.78-6.89 (2H, m), 7.08-7.20 (2H, m), 7.39 (1H, d, J = 2.3 Hz).

| Ex. No. | IUPAC Name | Structure | Salt | MS |
|---|---|---|---|---|
| 37 | N-[(1RS,2SR)-2-hydroxy-2-{[4-(1-methylethyl)phenoxy]methyl}cyclohexyl]ethanesulfonamide | 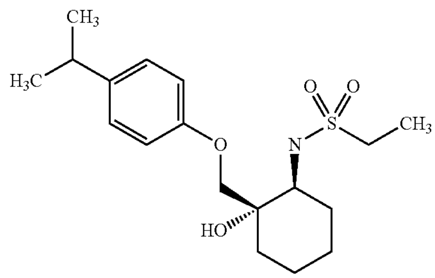 [SMILES: CCS(=O)(=O)N[C@H]1CCCC[C@@]1(O)COc1ccc(C(C)C)cc1] | | 354.4 |
| 39 | trans-N-[2-{[4-(1-methylethyl)phenoxy]methyl}-4-oxocyclohexyl]ethanesulfonamide | 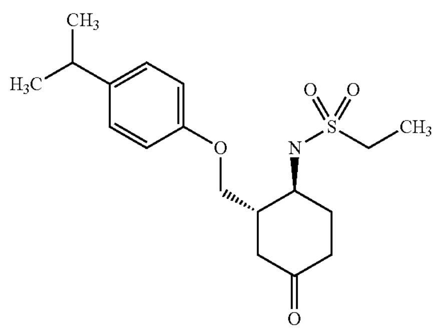 [SMILES: CCS(=O)(=O)N[C@H]1CCC(=O)C[C@@H]1COc1ccc(C(C)C)cc1] | | 352.4 |
| 42 | N-[(1RS,2SR)-2-hydroxy-2-{[4-(1-methylethyl)phenoxy]methyl}cyclopentyl]ethanesulfonamide | 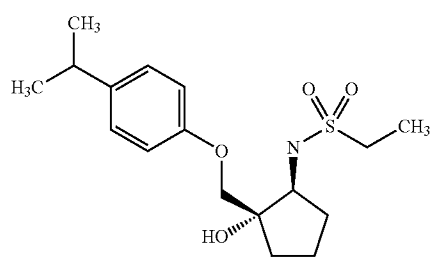 [SMILES: CCS(=O)(=O)N[C@H]1CCC[C@@]1(O)COc1ccc(C(C)C)cc1] | | 364.3 |

TABLE 1-5

| Ex. No. | IUPAC Name | Structure | Salt | MS |
|---|---|---|---|---|
| 43 | trans-N-{2-[(4-oxetan-3-ylphenoxy)methyl]cyclohexyl}ethanesulfonamide | 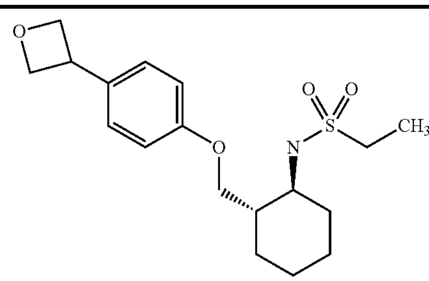 | | 352.3 |

TABLE 1-5-continued

| Ex. No. | IUPAC Name | Structure | Salt | MS |
|---|---|---|---|---|
| 44 | trans-N-{2-[(2-cyanophenoxy)methyl]cyclohexyl}ethanesulfonamide | 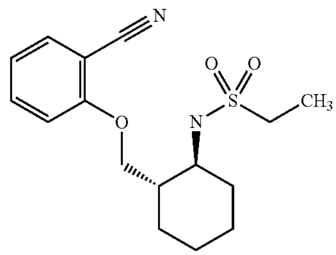 [SMILES: CCS(=O)(=O)N[C@H]1CCCC[C@@H]1COc1ccccc1C#N] | | 321.4 |
| 45 | trans-N-{2-[(2-fluorophenoxy)methyl]cyclohexyl}ethanesulfonamide | 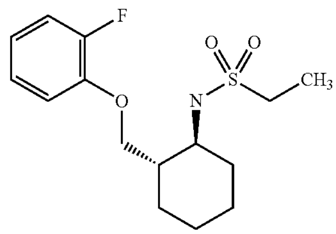 [SMILES: CCS(=O)(=O)N[C@H]1CCCC[C@@H]1COc1ccccc1F] | | 316.3 |
| 46 | cis-N-[1-methyl-{[4-(1-methylethyl)phenoxy]methyl}piperidin-3-yl]ethanesulfonamide | 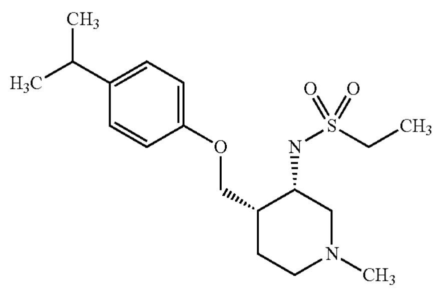 [SMILES: CCS(=O)(=O)N[C@@H]1CN(C)CC[C@@H]1COc1ccc(C(C)C)cc1] | | 355.3 |
| 47 | trans-N-[2-{[4-(trifluoromethyl)phenoxy]methyl}cyclohexyl]ethanesulfonamide | 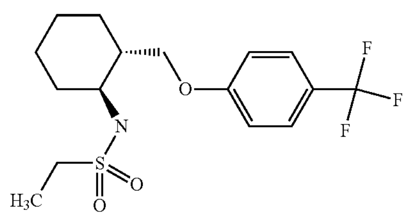 [SMILES: CCS(=O)(=O)N[C@H]1CCCC[C@@H]1COc1ccc(C(F)(F)F)cc1] | | 366.2 |
| 48 | trans-N-{2-[(4-tert-butylphenoxy)methyl]cyclohexyl}ethanesulfonamide | 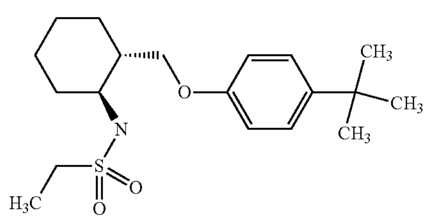 [SMILES: CCS(=O)(=O)N[C@H]1CCCC[C@@H]1COc1ccc(C(C)(C)C)cc1] | | 354.2 |
| 49 | trans-N-[2-{[4-(cyanomethyl)phenoxy]methyl}cyclohexyl]ethanesulfonamide | 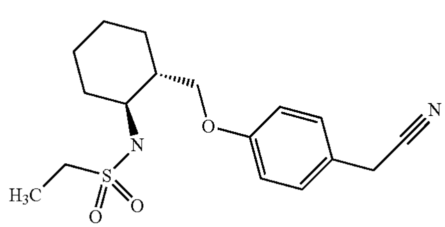 [SMILES: CCS(=O)(=O)N[C@H]1CCCC[C@@H]1COc1ccc(CC#N)cc1] | | 337.1 |

TABLE 1-5-continued

| Ex. No. | IUPAC Name | Structure | Salt | MS |
|---|---|---|---|---|
| 50 | trans-N-[2-{[4-(2-cyanoethyl)phenoxy]methyl}cyclohexyl]ethanesulfonamide | 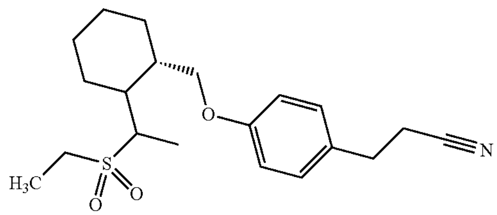 [SMILES: CCS(=O)(=O)C(C)C1CCCC[C@@H]1COc1ccc(CCC#N)cc1] | | 351.1 |
| 51 | trans-N-[2-{[4-(trifluoromethoxy)phenoxy]methyl}cyclohexyl]ethanesulfonamide | 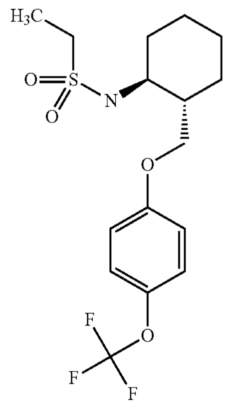 [SMILES: CCS(=O)(=O)N[C@H]1CCCC[C@@H]1COc1ccc(OC(F)(F)F)cc1] | | 382.1 |
| 52 | trans-N-[2-{[4-(difluoromethoxy)phenoxy]methyl}cyclohexyl]ethanesulfonamide | 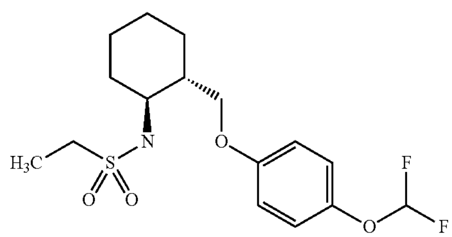 [SMILES: CCS(=O)(=O)N[C@H]1CCCC[C@@H]1COc1ccc(OC(F)F)cc1] | | 364.3 |
| 53 | trans-N-[2-({4-[(trifluoromethyl)sulfanyl]phenoxy}methyl)cyclohexyl]ethanesulfonamide | 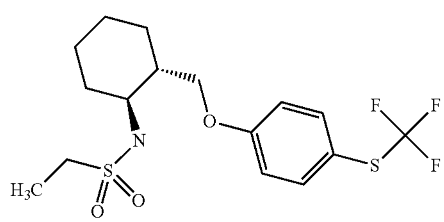 [SMILES: CCS(=O)(=O)N[C@H]1CCCC[C@@H]1COc1ccc(SC(F)(F)F)cc1] | | 398.1 |

TABLE 1-6

| Ex. No. | IUPAC Name | Structure | Salt | MS |
|---|---|---|---|---|
| 54 | trans-N-{2-[(4-fluorophenoxy)methyl]cyclohexyl}ethanesulfonamide | 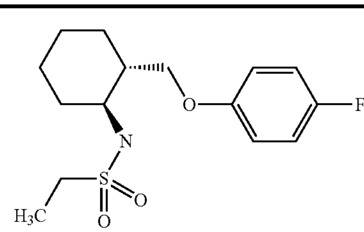 | | 316.1 |

TABLE 1-6-continued

| Ex. No. | IUPAC Name | Structure | Salt | MS |
|---|---|---|---|---|
| 55 | trans-N-{2-[(4-chlorophenoxy)methyl]cyclohexyl}ethanesulfonamide | 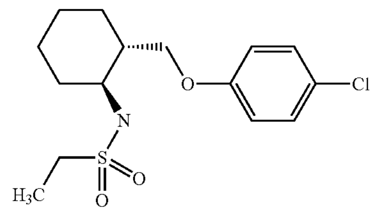 [SMILES: CCS(=O)(=O)N[C@H]1CCCC[C@@H]1COc1ccc(Cl)cc1] | | 332.1 |
| 56 | trans-N-{2-[(4-phenoxyphenoxy)methyl]cyclohexyl}ethanesulfonamide | 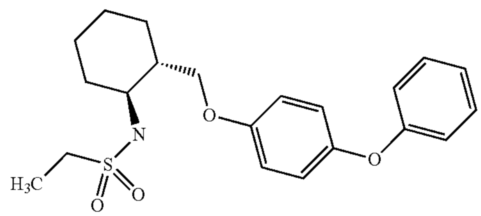 [SMILES: CCS(=O)(=O)N[C@H]1CCCC[C@@H]1COc1ccc(Oc2ccccc2)cc1] | | 390.2 |
| 57 | trans-N-[2-{[4-(phenylamino)phenoxy]methyl}cyclohexyl]ethanesulfonamide | 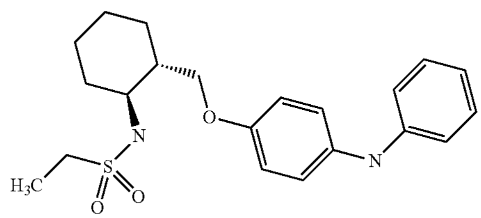 [SMILES: CCS(=O)(=O)N[C@H]1CCCC[C@@H]1COc1ccc(Nc2ccccc2)cc1] | | 389.2 |
| 58 | trans-N-{2-[(4-tricyclo[3.3.1.1~3,7~]dec-1-ylphenoxy)methyl]cyclohexyl}ethanesulfonamide | 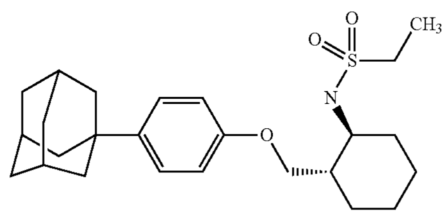 [SMILES: CCS(=O)(=O)N[C@H]1CCCC[C@@H]1COc1ccc(C23CC4CC(CC(C4)C2)C3)cc1] | | 432.2 |
| 59 | trans-N-{2-[(4-thiophen-3-ylphenoxy)methyl]cyclohexyl}ethanesulfonamide | 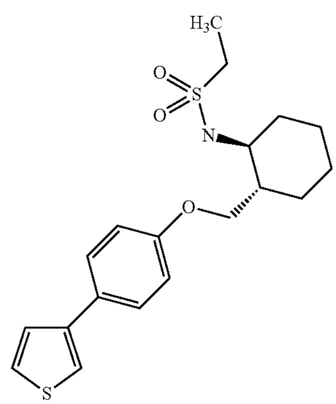 [SMILES: CCS(=O)(=O)N[C@H]1CCCC[C@@H]1COc1ccc(-c2ccsc2)cc1] | | 380.1 |
| 60 | trans-N-[2-{[4-(1H-pyrazol-1-yl)phenoxy]methyl}cyclohexyl]ethanesulfonamide | 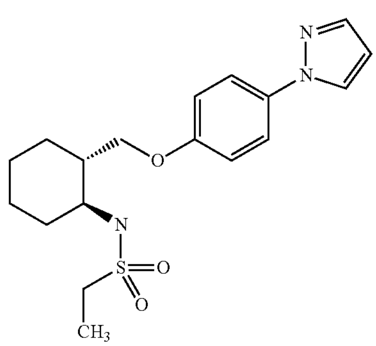 [SMILES: CCS(=O)(=O)N[C@H]1CCCC[C@@H]1COc1ccc(-n2cccn2)cc1] | | 364.1 |

TABLE 1-6-continued

| Ex. No. | IUPAC Name | Structure | Salt | MS |
|---|---|---|---|---|
| 61 | trans-N-[2-{[4-(1H-imidazol-1-yl)phenoxy]methyl}cyclohexyl]ethanesulfonamide | 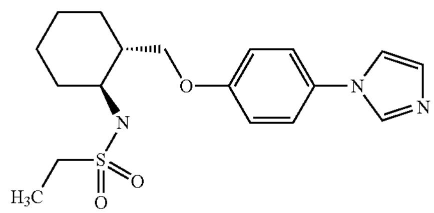 [SMILES: CCS(=O)(=O)N[C@H]1CCCC[C@@H]1COc1ccc(-n2ccnc2)cc1] | | 364.1 |
| 62 | trans-N-{2-[(biphenyl-4-yloxy)methyl]cyclohexyl}ethanesulfonamide | 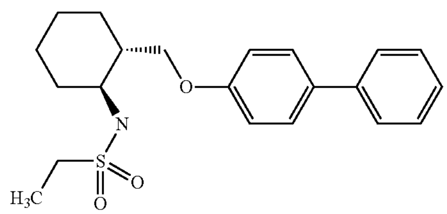 [SMILES: CCS(=O)(=O)N[C@H]1CCCC[C@@H]1COc1ccc(-c2ccccc2)cc1] | | 374.2 |
| 63 | trans-N-[2-{[3-(1-methylethyl)phenoxy]methyl}cyclohexyl]ethanesulfonamide | 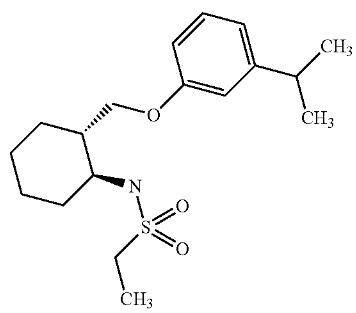 [SMILES: CCS(=O)(=O)N[C@H]1CCCC[C@@H]1COc1cccc(C(C)C)c1] | | 340.2 |
| 64 | trans-N-{2-[(3-methoxyphenoxy)methyl]cyclohexyl}ethanesulfonamide | 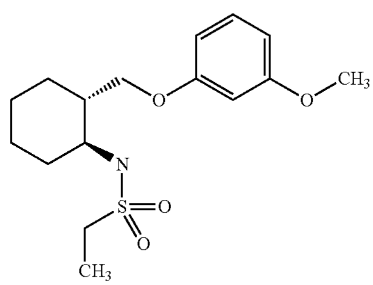 [SMILES: CCS(=O)(=O)N[C@H]1CCCC[C@@H]1COc1cccc(OC)c1] | | 328.1 |

TABLE 1-7

| Ex. No. | IUPAC Name | Structure | Salt | MS |
|---|---|---|---|---|
| 65 | trans-N-{2-[(3-phenoxyphenoxy)methyl]cyclohexyl}ethanesulfonamide | 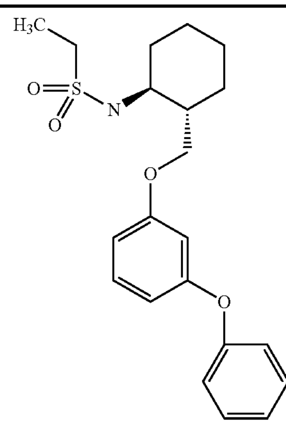 | | 390.1 |

TABLE 1-7-continued

| Ex. No. | IUPAC Name | Salt | MS |
|---|---|---|---|
| 66 | trans-N-{2-[(3-acetylphenoxy)methyl]cyclohexyl}ethanesulfonamide | | 340.1 |
| 67 | trans-N-[2-{[3-(dimethylamino)phenoxy]methyl}cyclohexyl]ethanesulfonamide | | 341.2 |
| 68 | trans-N-{2-[(3-morpholin-4-ylphenoxy)methyl]cyclohexyl}ethanesulfonamide | | 383.2 |
| 69 | trans-N-{2-[(3-fluorophenoxy)methyl]cyclohexyl}ethanesulfonamide | | 316.1 |
| 70 | trans-N-{2-[(3-chlorophenoxy)methyl]cyclohexyl}ethanesulfonamide | | 332.1 |

TABLE 1-7-continued

| Ex. No. | IUPAC Name | Structure | Salt | MS |
|---|---|---|---|---|
| 71 | trans-N-{2-[(3-cyanophenoxy)methyl]cyclohexyl}ethane-sulfonamide | 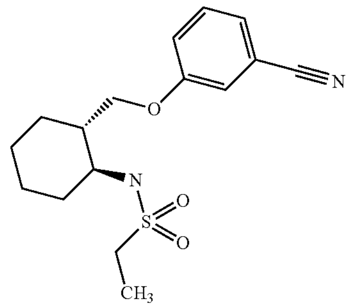 [SMILES: CCS(=O)(=O)N[C@H]1CCCC[C@@H]1COc1cccc(C#N)c1] | | 323.1 |
| 72 | trans-N-{2-[(4-acetyl-3-fluorophenoxy)methyl]cyclohexyl}ethane-sulfonamide | 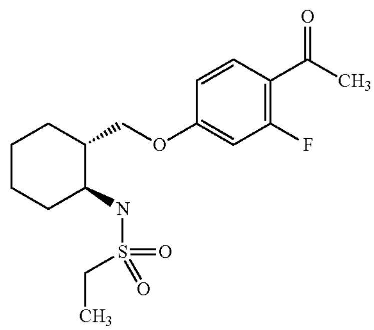 [SMILES: CCS(=O)(=O)N[C@H]1CCCC[C@@H]1COc1ccc(C(C)=O)c(F)c1] | | 358.1 |
| 73 | trans-N-{2-[(4-chloro-3-fluorophenoxy)methyl]cyclohexyl}ethane-sulfonamide | 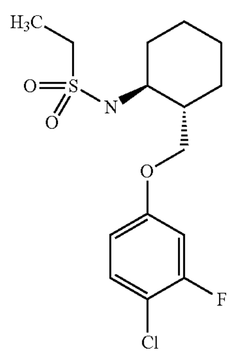 [SMILES: CCS(=O)(=O)N[C@H]1CCCC[C@@H]1COc1ccc(Cl)c(F)c1] | | 350.1 |
| 74 | trans-N-[2-({[2-oxo-4-(trifluoromethyl)-2H-chromen-7-yl]oxy}methyl)cyclohexyl]ethane-sulfonamide | 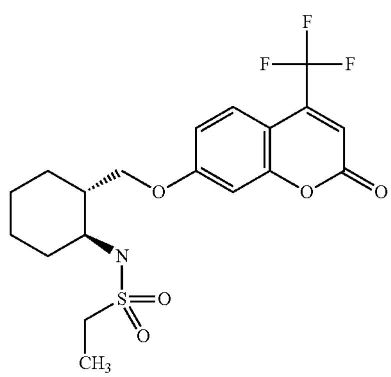 [SMILES: CCS(=O)(=O)N[C@H]1CCCC[C@@H]1COc1ccc2c(C(F)(F)F)cc(=O)oc2c1] | | 434.0 |

TABLE 1-7-continued

| Ex. No. | IUPAC Name | Structure | Salt | MS |
|---|---|---|---|---|
| 75 | trans-N-{2-[(1H-indol-6-yloxy)methyl]cyclohexyl}ethane-sulfonamide | 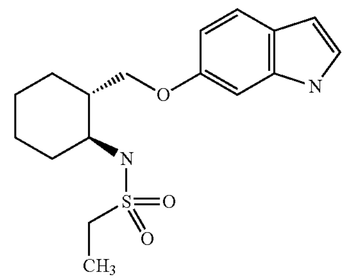 [SMILES: CCS(=O)(=O)N[C@H]1CCCC[C@@H]1COc1ccc2cc[nH]c2c1] | | 337.1 |

TABLE 1-8

| Ex. No. | IUPAC Name | Structure | Salt | MS |
|---|---|---|---|---|
| 76 | trans-N-{2-[(1,3-benzothiazol-6-yloxy)methyl]cyclohexyl}ethane-sulfonamide | 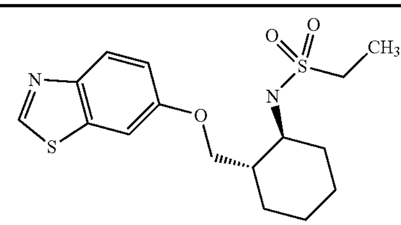 | | 355.1 |
| 77 | trans-N-{2-[(naphthalen-2-yloxy)methyl]cyclohexyl}ethane-sulfonamide | 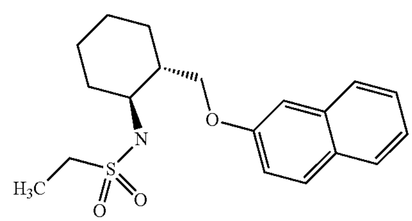 [SMILES: CCS(=O)(=O)N[C@H]1CCCC[C@@H]1COc1ccc2ccccc2c1] | | 348.1 |
| 78 | trans-N-[2-{[(6-methoxynaphthalen-2-yl)oxy]methyl}cyclohexyl]ethane-sulfonamide | 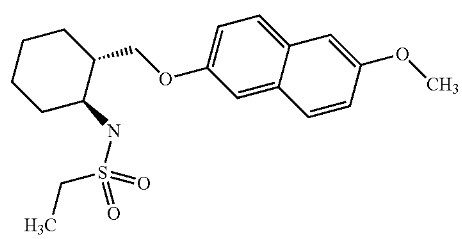 [SMILES: CCS(=O)(=O)N[C@H]1CCCC[C@@H]1COc1ccc2cc(OC)ccc2c1] | | 378.2 |
| 79 | trans-N-[2-{[(6-methylpyridin-3-yl)oxy]methyl}cyclohexyl]ethane-sulfonamide | 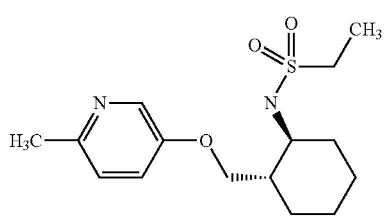 [SMILES: CCS(=O)(=O)N[C@H]1CCCC[C@@H]1COc1ccc(C)nc1] | | 313.1 |
| 80 | trans-N-{2-[(4-chloro-3-methylphenoxy)methyl]cyclohexyl}ethane-sulfonamide | 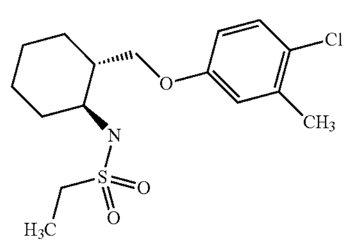 [SMILES: CCS(=O)(=O)N[C@H]1CCCC[C@@H]1COc1ccc(Cl)c(C)c1] | | 346.1 |

TABLE 1-8-continued

| Ex. No. | IUPAC Name | Structure | Salt | MS |
|---|---|---|---|---|
| 81 | trans-N-{2-[(3,4-dimethylphenoxy)methyl]cyclohexyl}ethane-sulfonamide | 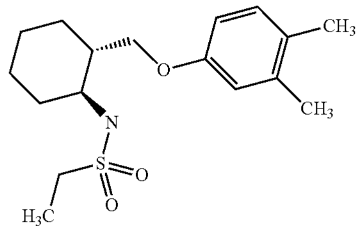 [SMILES: CCS(=O)(=O)N[C@H]1CCCC[C@@H]1COc1ccc(C)c(C)c1] | | 326.2 |
| 82 | trans-N-{2-[(3-chloro-5-fluorophenoxy)methyl]cyclohexyl}ethane-sulfonamide | 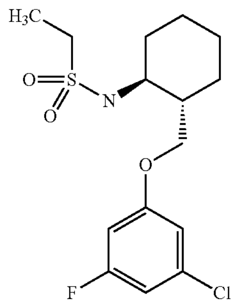 [SMILES: CCS(=O)(=O)N[C@H]1CCCC[C@@H]1COc1cc(F)cc(Cl)c1] | | 350.1 |
| 83 | trans-N-{2-[(3-chloro-4-fluorophenoxy)methyl]cyclohexyl}ethane-sulfonamide | 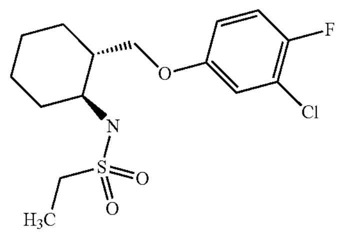 [SMILES: CCS(=O)(=O)N[C@H]1CCCC[C@@H]1COc1ccc(F)c(Cl)c1] | | 349.9 |
| 84 | trans-N-{2-[(3,4-difluorophenoxy)methyl]cyclohexyl}ethane-sulfonamide | 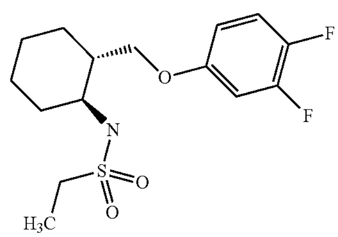 [SMILES: CCS(=O)(=O)N[C@H]1CCCC[C@@H]1COc1ccc(F)c(F)c1] | | 334.1 |
| 85 | trans-N-{2-[(3,5-difluorophenoxy)methyl]cyclohexyl}ethane-sulfonamide | 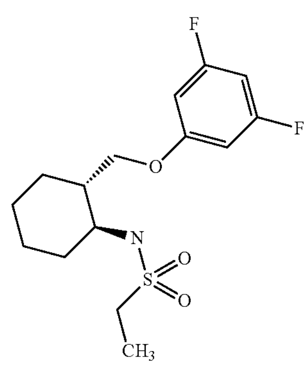 [SMILES: CCS(=O)(=O)N[C@H]1CCCC[C@@H]1COc1cc(F)cc(F)c1] | | 334.2 |
| 86 | trans-N-[2-{[(1-oxo-2,3-dihydro-1H-inden-5-yl)oxy]methyl}cyclohexyl]ethane-sulfonamide | 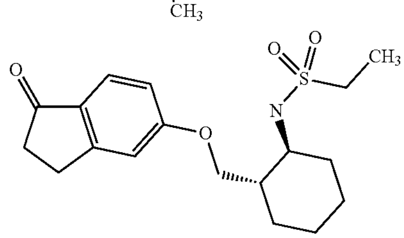 | | 352.1 |

TABLE 1-9

| Ex. No. | IUPAC Name | Structure | Salt | MS |
|---|---|---|---|---|
| 87 | trans-N-[2-{[(3-oxo-2,3-dihydro-1H-inden-5-yl)oxy]methyl}cyclohexyl]ethane-sulfonamide | 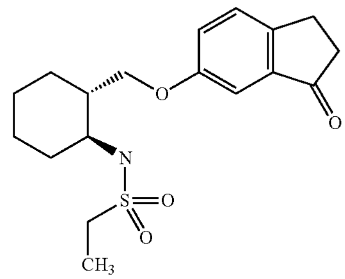 [SMILES: CCS(=O)(=O)N[C@H]1CCCC[C@@H]1COc1ccc2c(c1)C(=O)CC2] | | 352.1 |
| 88 | trans-N-{2-[(4-cyanophenoxy)methyl]cyclohexyl}ethane-sulfonamide | 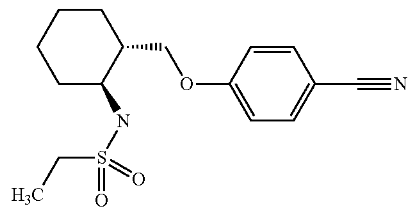 [SMILES: CCS(=O)(=O)N[C@H]1CCCC[C@@H]1COc1ccc(C#N)cc1] | | 323.1 |
| 89 | trans-N-{2-[(4-acetylphenoxy)methyl]cyclohexyl}ethane-sulfonamide | 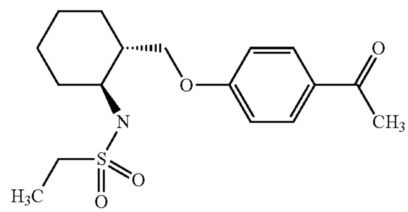 [SMILES: CCS(=O)(=O)N[C@H]1CCCC[C@@H]1COc1ccc(C(C)=O)cc1] | | 340.1 |
| 90 | trans-N-{2-[(4-cyano-3-fluorophenoxy)methyl]cyclohexyl}ethane-sulfonamide | 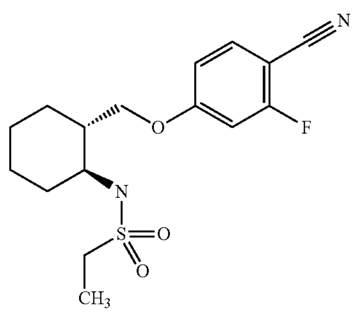 [SMILES: CCS(=O)(=O)N[C@H]1CCCC[C@@H]1COc1ccc(C#N)c(F)c1] | | 341.1 |
| 91 | trans-N-[2-{[(6-cyanonaphthalen-2-yl)oxy]methyl}cyclohexyl]ethane-sulfonamide | 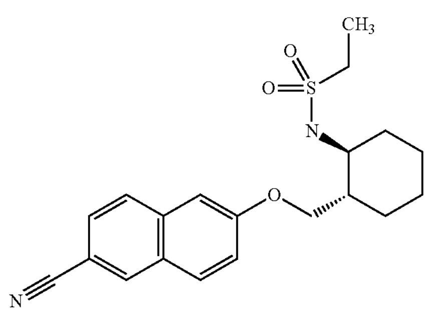 [SMILES: CCS(=O)(=O)N[C@H]1CCCC[C@@H]1COc1ccc2cc(C#N)ccc2c1] | | 373.2 |
| 92 | trans-N-[4-({2-[(ethylsulfonyl)amino]cyclohexyl}methoxy)phenyl]acetamide | 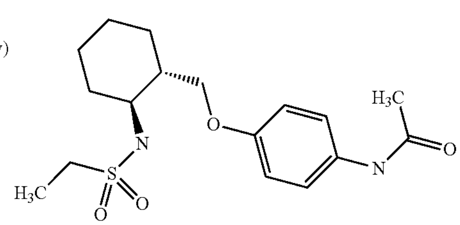 | | 355.0 |

TABLE 1-9-continued

| Ex. No. | IUPAC Name | Structure | Salt | MS |
|---|---|---|---|---|
| 93 | optically active material of trans-N-[1-acetyl-3-{[4-(1-methylethyl)phenoxy]methyl}piperidin-4-yl]ethanesulfonamide | 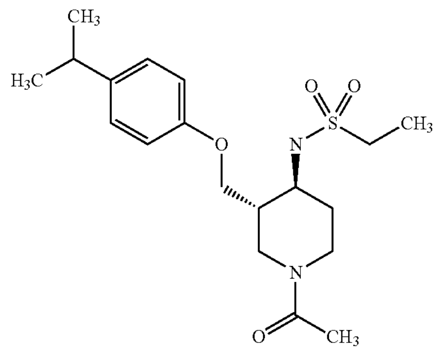 [SMILES: CCS(=O)(=O)N[C@H]1CCN(C(C)=O)C[C@@H]1COc1ccc(C(C)C)cc1] | | 383.3 |
| 94 | optically active material of trans-N-[1-acetyl-3-{[4-(1-methylethyl)phenoxy]methyl}piperidin-4-yl]ethanesulfonamide | 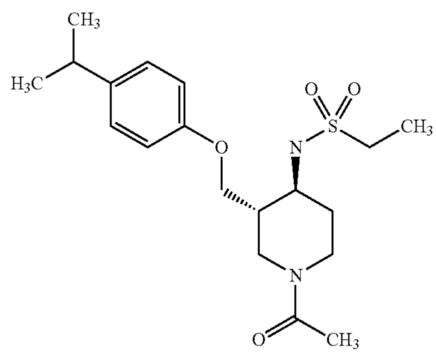 [SMILES: CCS(=O)(=O)N[C@H]1CCN(C(C)=O)C[C@@H]1COc1ccc(C(C)C)cc1] | | 383.3 |
| 95 | trans-N-[4-{[4-(1-methylethyl)phenoxy]methyl}tetrahydro-2H-pyran-3-yl]ethanesulfonamide | 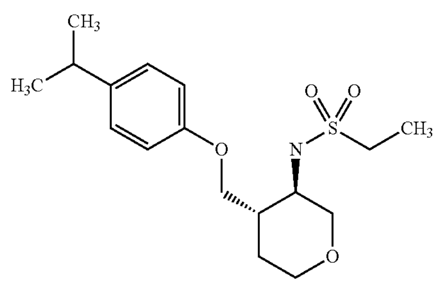 [SMILES: CCS(=O)(=O)N[C@H]1COCC[C@@H]1COc1ccc(C(C)C)cc1] | | |

¹H NMR (300 MHz, DMSO-d₆) δ 1.06 (3H, t, J = 7.2 Hz), 1.16 (6H, d, J = 6.8 Hz), 1.47-1.70 (1H, m), 1.72-1.94 (2H, m), 2.71-3.34 (6H, m), 3.75-4.12 (4H, m), 6.78-6.91 (2H, m), 7.08-7.20 (2H, m), 7.30 (1H, brs).

| 96 | trans-N-[1-ethyl-4-{[4-(1-methylethyl)phenoxy]methyl}piperidin-3-yl]ethanesulfonamide | | | 369.4 |

TABLE 1-10

| Ex. No. | IUPAC Name | Structure | Salt | MS |
|---|---|---|---|---|
| 97 | trans-N-[1-acetyl-4-{[4-(1-methylethyl)phenoxy]methyl}piperidin-3-yl]ethanesulfonamide | 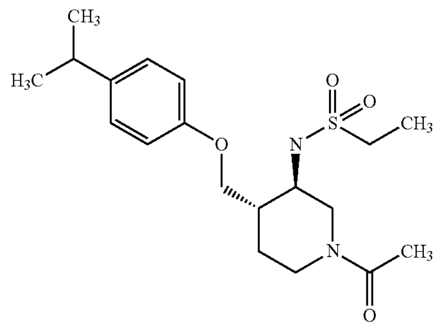 [SMILES: CCS(=O)(=O)N[C@H]1CN(C(C)=O)CC[C@@H]1COc1ccc(C(C)C)cc1] | | 383.2 |
| 98 | trans-N-[1-benzyl-3-{[4-(difluoromethoxy)phenoxy]methyl}piperidin-4-yl]ethanesulfonamide | 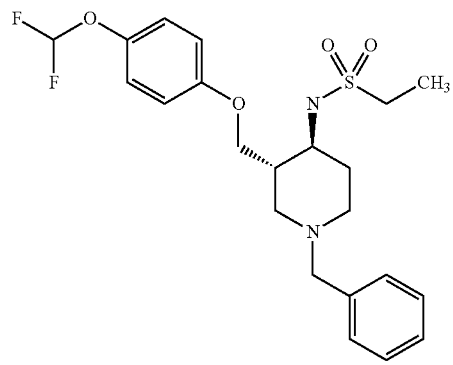 [SMILES: CCS(=O)(=O)N[C@H]1CCN(Cc2ccccc2)C[C@@H]1COc1ccc(OC(F)F)cc1] | | 455.2 |
| 99 | trans-N-[1-benzyl-3-{[4-(2-cyanoethyl)phenoxy]methyl}piperidin-4-yl]ethanesulfonamide | 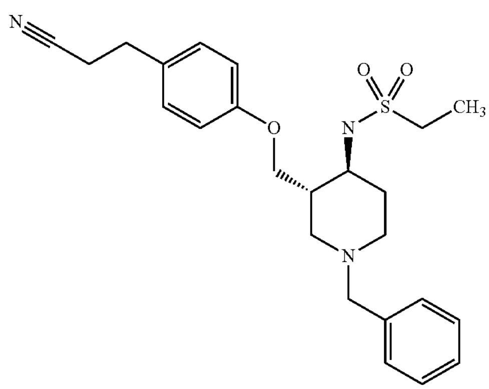 [SMILES: CCS(=O)(=O)N[C@H]1CCN(Cc2ccccc2)C[C@@H]1COc1ccc(CCC#N)cc1] | | 442.3 |
| 100 | optically active material of trans-N-[4,4-difluoro-2-{[4-(1-methylethyl)phenoxy]methyl}cyclohexyl]ethanesulfonamide | 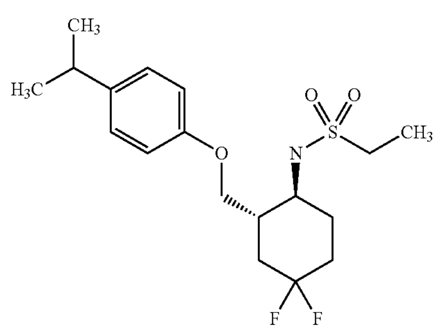 [SMILES: CCS(=O)(=O)N[C@H]1CCC(F)(F)C[C@@H]1COc1ccc(C(C)C)cc1] | | 374.2 |

TABLE 1-10-continued

| Ex. No. | IUPAC Name | Structure | Salt | MS |
|---|---|---|---|---|
| 101 | optically active material of trans-N-[4,4-difluoro-2-{[4-(1-methylethyl)phenoxy]methyl}cyclohexyl]ethanesulfonamide | 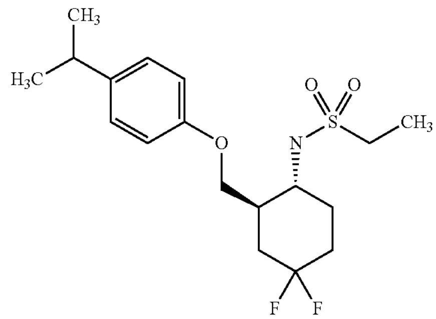 [SMILES: CCS(=O)(=O)N[C@@H]1CCC(F)(F)C[C@H]1COc1ccc(C(C)C)cc1] | | 374.2 |
| 102 | trans-N-[1-benzyl-3-{[4-(1H-pyrazol-1-yl)phenoxy]methyl}piperidin-4-yl]ethanesulfonamide | 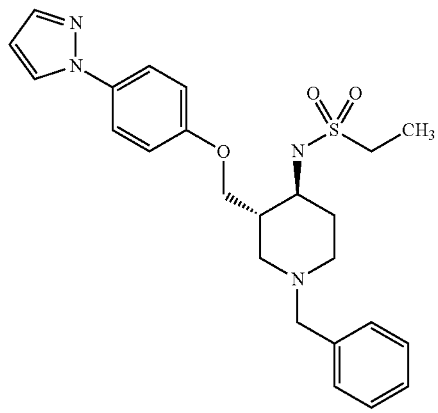 [SMILES: CCS(=O)(=O)N[C@H]1CCN(Cc2ccccc2)C[C@@H]1COc1ccc(-n2cccn2)cc1] | | 455.3 |
| 103 | 2,6-anhydro-3,4,5-trideoxy-3-[(ethylsulfonyl)amino]-1-O-[4-(1-methylethyl)phenyl]-DL-threo-hexitol | 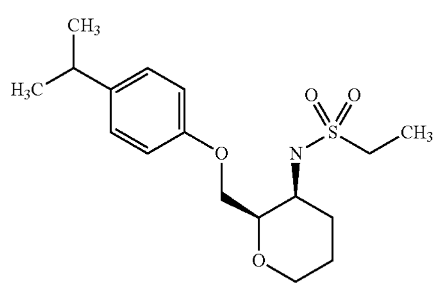 [SMILES: CCS(=O)(=O)N[C@H]1CCCO[C@H]1COc1ccc(C(C)C)cc1] | | 342.2 |
| 104 | 1,5-anhydro-2,3,4-trideoxy-4-[(ethylsulfonyl)amino]-6-O-[4-(1-methylethyl)phenyl]-DL-erythro-hexitol | 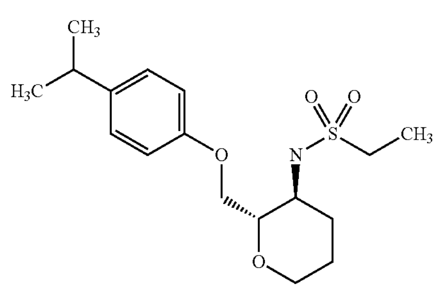 [SMILES: CCS(=O)(=O)N[C@H]1CCCO[C@@H]1COc1ccc(C(C)C)cc1] | | 342.2 |

TABLE 1-10-continued

| Ex. No. | IUPAC Name | Structure | Salt | MS |
|---|---|---|---|---|
| 105 | trans-N-{4-[(4-cyclopropylphenoxy)methyl]tetrahydro-2H-pyran-3-yl}ethanesulfonamide | 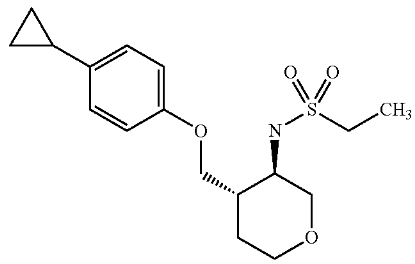 [SMILES: CCS(=O)(=O)N[C@H]1COCC[C@@H]1COc1ccc(C2CC2)cc1] | | |

$^1$H NMR (300 MHz, DMSO-$d_6$) δ 0.51-0.61 (2H, m), 0.81-0.92 (2H, m), 1.06 (3H, t, J = 7.4 Hz), 1.45-1.68 (1H, m), 1.73-1.93 (3H, m), 2.85-3.08 (3H, m), 3.10-3.32 (2H, m), 3.74-4.09 (4H, m), 6.76-6.86 (2H, m), 6.94-7.04 (2H, m), 7.30 (1H, d, J = 8.7 Hz).

TABLE 1-11

| Ex. No. | IUPAC Name | Structure | Salt | MS |
|---|---|---|---|---|
| 107 | trans-N-{2-[(4-isopropylphenoxy)methyl]piperidin-3-yl}ethanesulfonamide hydrochloride | 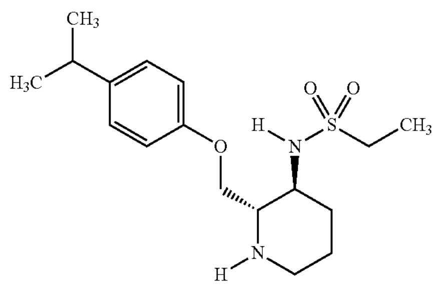 [SMILES: CCS(=O)(=O)N[C@H]1CCCN[C@@H]1COc1ccc(C(C)C)cc1] | HCl | 341.2 |
| 108 | trans-N-{1-acetyl-2-[(4-isopropylphenoxy)methyl]piperidin-3-yl}ethanesulfonamide | 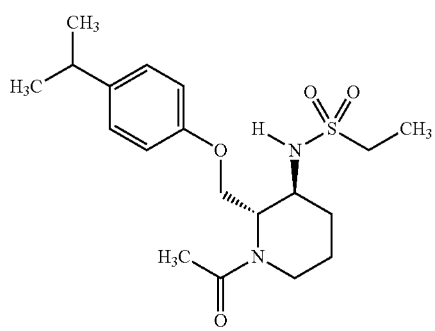 [SMILES: CCS(=O)(=O)N[C@H]1CCCN(C(C)=O)[C@@H]1COc1ccc(C(C)C)cc1] | | 383.2 |
| 109 | optically active material of trans-N-[4-{[4-(1-methylethyl)phenoxy]methyl}tetrahydro-2H-pyran-3-yl]ethanesulfonamide | 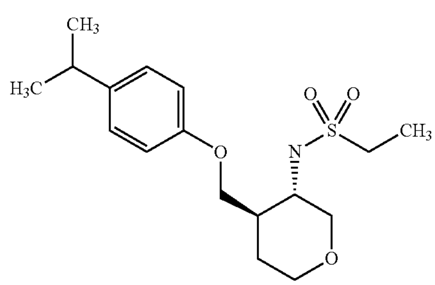 [SMILES: CCS(=O)(=O)N[C@@H]1COCC[C@H]1COc1ccc(C(C)C)cc1] | | |

$^1$H NMR (300 MHz, DMSO-$d_6$) δ 1.06 (3H, t, J = 7.2 Hz), 1.16 (6H, d, J = 6.8 Hz), 1.47-1.70 (1H, m), 1.72-1.94 (2H, m), 2.71-3.34 (6H, m), 3.75-4.12 (4H, m), 6.78-6.91 (2H, m), 7.08-7.20 (2H, m), 7.30 (1H, brs).

TABLE 1-11-continued

| Ex. No. | IUPAC Name | Structure | Salt | MS |
|---|---|---|---|---|
| 110 | optically active material of trans-N-[4-{[4-(1-methylethyl)phenoxy]methyl}tetrahydro-2H-pyran-3-yl]ethanesulfonamide | | | |

$^1$H NMR (300 MHz, DMSO-d$_6$) δ 1.06 (3H, t, J = 7.2 Hz), 1.16 (6H, d, J = 6.8 Hz), 1.47-1.70 (1H, m), 1.72-1.94 (2H, m), 2.71-3.34 (6H, m), 3.75-4.12 (4H, m), 6.78-6.91 (2H, m), 7.08-7.20 (2H, m), 7.30 (1H, brs).

| Ex. No. | IUPAC Name | Structure | Salt | MS |
|---|---|---|---|---|
| 111 | 2,6-anhydro-1-O-(4-cyclopropylphenyl)-3,4,5-trideoxy-3-[(ethylsulfonyl)amino]-DL-threo-hexitol | 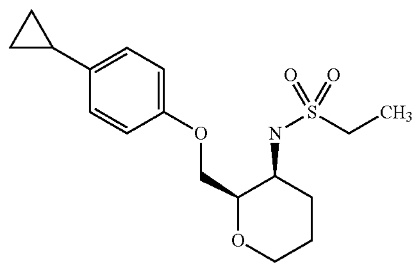 [SMILES: CCS(=O)(=O)N[C@H]1CCCO[C@H]1COc1ccc(C2CC2)cc1] | | 340.1 |
| 112 | 2,6-anhydro-1-O-(4-cyclopropylphenyl)-3,4,5-trideoxy-3-[(methylsulfonyl)amino]-DL-threo-hexitol | 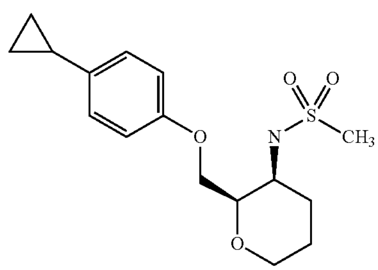 [SMILES: CS(=O)(=O)N[C@H]1CCCO[C@H]1COc1ccc(C2CC2)cc1] | | 326.1 |
| 113 | trans-N-[1-benzyl-4-{[4-(1-methylethyl)phenoxy]methyl}piperidin-3-yl]ethanesulfonamide | 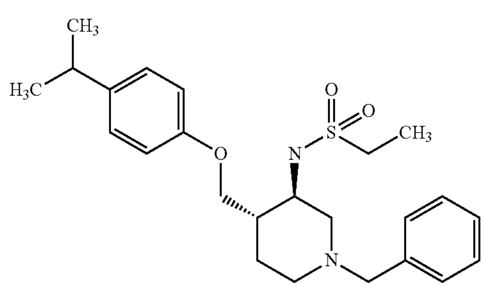 [SMILES: CCS(=O)(=O)N[C@H]1CN(Cc2ccccc2)CC[C@@H]1COc1ccc(C(C)C)cc1] | | 431.3 |
| 114 | trans-N-[4-{[4-(1-methylethyl)phenoxy]methyl}piperidin-3-yl]ethanesulfonamide | 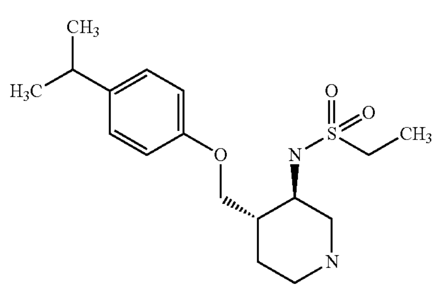 [SMILES: CCS(=O)(=O)N[C@H]1CNCC[C@@H]1COc1ccc(C(C)C)cc1] | | 341.1 |

TABLE 1-11-continued

| Ex. No. | IUPAC Name | Structure | Salt | MS |
|---|---|---|---|---|
| 115 | optically active material of trans-N-{3-[(4-cyclopropylphenoxy)methyl]tetrahydro-2H-pyran-4-yl}ethanesulfonamide | 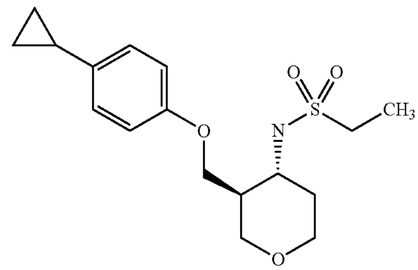 [SMILES: CCS(=O)(=O)N[C@@H]1CCOC[C@H]1COc1ccc(C2CC2)cc1] | | 338.2 |

TABLE 1-12

| Ex. No. | IUPAC Name | Structure | Salt | MS |
|---|---|---|---|---|
| 116 | trans-N-ethyl-3-[(ethylsulfonyl)amino]-4-{[4-(1-methylethyl)phenoxy]methyl}piperidine-1-carboxamide | 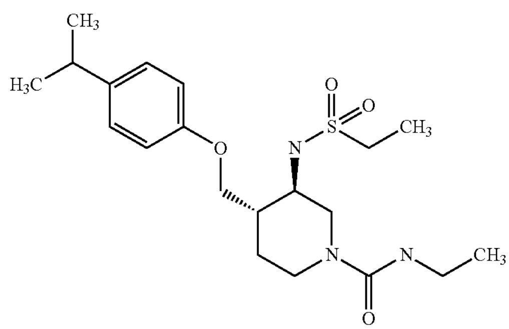 [SMILES: CCNC(=O)N1CC[C@H](COc2ccc(C(C)C)cc2)[C@@H](NS(=O)(=O)CC)C1] | | 412.3 |
| 117 | trans-N-[4-{[4-(1-methylethyl)phenoxy]methyl}-1-(methylsulfonyl)piperidin-3-yl]ethanesulfonamide | 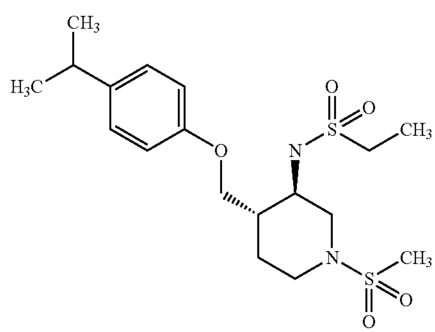 [SMILES: CCS(=O)(=O)N[C@H]1CN(S(C)(=O)=O)CC[C@@H]1COc1ccc(C(C)C)cc1] | | 419.3 |
| 118 | optically active material of trans-N-[1-acetyl-3-{[4-(1H-pyrazol-1-yl)phenoxy]methyl}piperidin-4-yl]ethanesulfonamide | 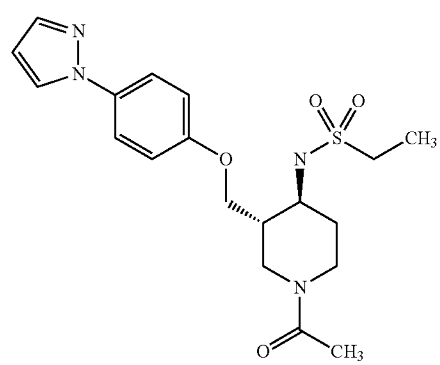 [SMILES: CCS(=O)(=O)N[C@H]1CCN(C(C)=O)C[C@@H]1COc1ccc(-n2cccn2)cc1] | | 407.0 |

TABLE 1-12-continued

| Ex. No. | IUPAC Name | Structure | Salt | MS |
|---|---|---|---|---|
| 119 | optically active material of trans-N-[1-acetyl-3-{[4-(1H-pyrazol-1-yl)phenoxy]methyl}piperidin-4-yl]ethanesulfonamide | 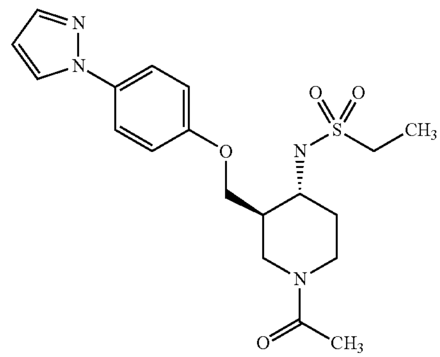 [SMILES: CCS(=O)(=O)N[C@@H]1CCN(C(C)=O)C[C@H]1COc1ccc(-n2cccn2)cc1] | | 407.0 |
| 120 | optically active material of trans-N-[3-{[4-(1H-pyrazol-1-yl)phenoxy]methyl}tetrahydro-2H-pyran-4-yl]ethanesulfonamide | 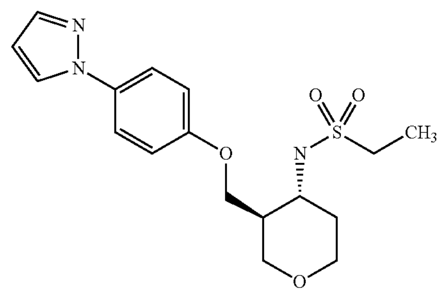 [SMILES: CCS(=O)(=O)N[C@@H]1CCOC[C@H]1COc1ccc(-n2cccn2)cc1] | | 366.4 |
| 121 | trans-N-[2-({[4-(1-methylethyl)phenyl]sulfanyl}methyl)cyclohexyl]ethanesulfonamide | 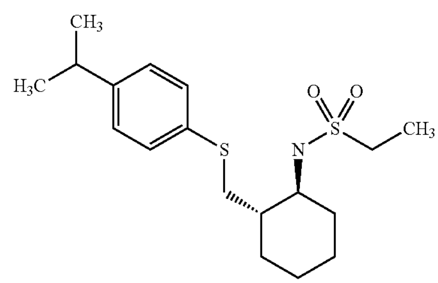 [SMILES: CCS(=O)(=O)N[C@H]1CCCC[C@@H]1CSc1ccc(C(C)C)cc1] | | 356.2 |
| 122 | optically active material of trans-N-[1-acetyl-3-{[4-(difluoromethoxy)phenoxy]methyl}piperidin-4-yl]ethanesulfonamide | 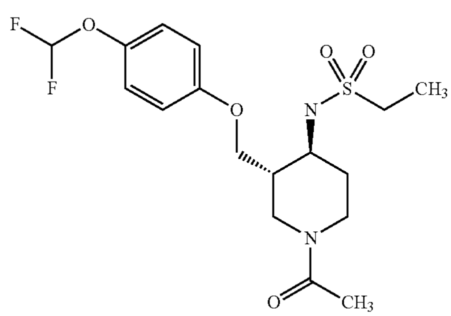 | | 406.9 |
| 123 | optically active material of trans-N-[1-acetyl-3-{[4-(difluoromethoxy)phenoxy]methyl}piperidin-4-yl]ethanesulfonamide | 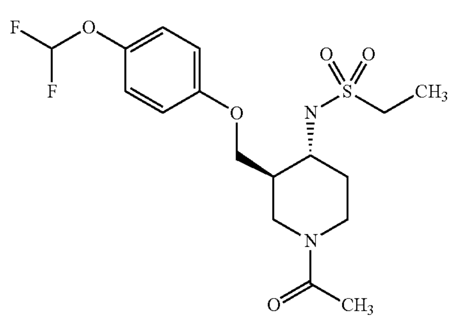 [SMILES: CCS(=O)(=O)N[C@@H]1CCN(C(C)=O)C[C@H]1COc1ccc(OC(F)F)cc1] | | 406.9 |

TABLE 1-12-continued

| Ex. No. | IUPAC Name | Structure | Salt | MS |
|---|---|---|---|---|
| 124 | optically active material of trans-N-[3-{[4-(difluoromethoxy)phenoxy]methyl}tetrahydro-2H-pyran-4-yl]ethanesulfonamide | 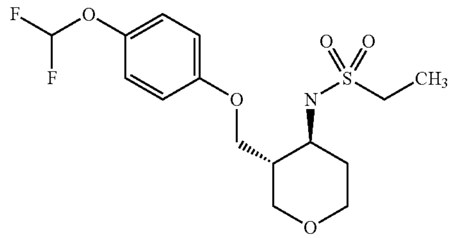 [SMILES: CCS(=O)(=O)N[C@H]1CCOC[C@@H]1COc1ccc(OC(F)F)cc1] | | 364.1 |
| Ref. Ex. 1 | N-[(1SR,2SR)-2-({[4-(1-methylethyl)phenyl]sulfinyl}methyl)cyclohexyl]ethanesulfonamide | 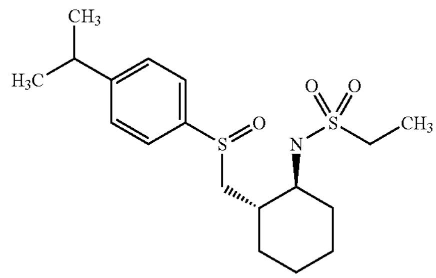 [SMILES: CCS(=O)(=O)N[C@H]1CCCC[C@@H]1CS(=O)c1ccc(C(C)C)cc1] | | 372.2 |
| Ref. Ex. 2 | N-[(1SR,2SR)-2-({[4-(1-methylethyl)phenyl]sulfonyl}methyl)cyclohexyl]ethanesulfonamide | 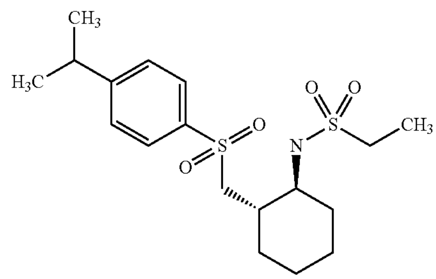 [SMILES: CCS(=O)(=O)N[C@H]1CCCC[C@@H]1CS(=O)(=O)c1ccc(C(C)C)cc1] | | 388.0 |

TABLE 1-13

| Ex. No. | IUPAC Name | Structure | Salt | MS |
|---|---|---|---|---|
| 127 | trans-N-[1-methyl-2-{[4-(1-methylethyl)phenoxy]methyl}-6-oxopiperidin-3-yl]ethanesulfonamide | 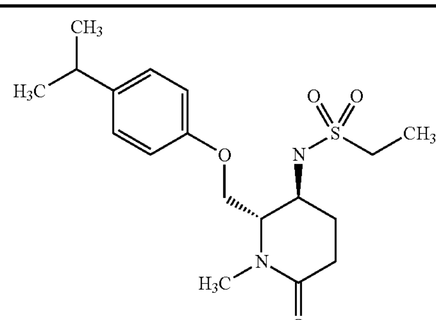 | | 369.1 |
| 128 | trans-N-(1-acetyl-3-[(4-cyclopropylphenoxy)methyl]piperidin-4-yl}ethanesulfonamide | 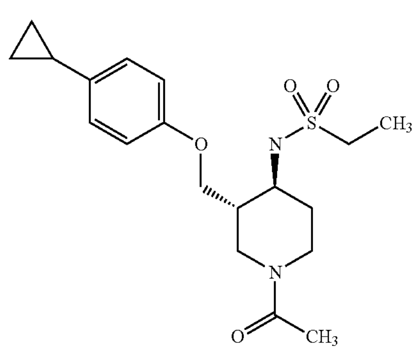 [SMILES: CCS(=O)(=O)N[C@H]1CCN(C(C)=O)C[C@@H]1COc1ccc(C2CC2)cc1] | | 381.4 |

TABLE 1-13-continued

| Ex. No. | IUPAC Name | Structure | Salt | MS |
|---|---|---|---|---|
| 129 | trans-N-[4-oxo-2-{[4-(1H-pyrazol-1-yl)phenoxy]methyl}cyclohexyl]ethanesulfonamide | 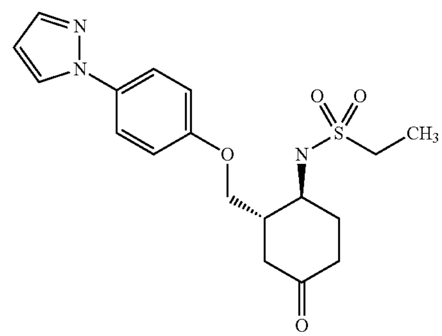 [SMILES: CCS(=O)(=O)N[C@H]1CCC(=O)C[C@@H]1COc1ccc(-n2cccn2)cc1] | | 378.1 |
| 130 | trans-N-[4,4-difluoro-2-{[4-(1H-pyrazol-1-yl)phenoxy]methyl}cyclohexyl]ethanesulfonamide | 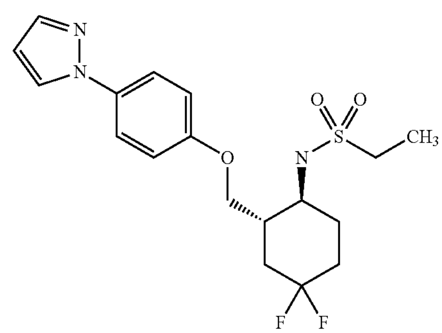 [SMILES: CCS(=O)(=O)N[C@H]1CCC(F)(F)C[C@@H]1COc1ccc(-n2cccn2)cc1] | | 400.3 |
| 131 | trans-N-{3-[(4-acetyl-3-fluorophenoxy)methyl]tetrahydro-2H-pyran-4-yl}ethanesulfonamide | 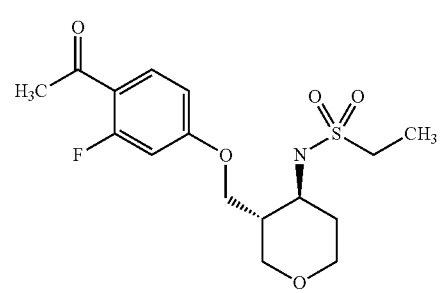 [SMILES: CCS(=O)(=O)N[C@H]1CCOC[C@@H]1COc1ccc(C(C)=O)c(F)c1] | | 360.1 |
| 132 | trans-N-[3-{[4-(3,5-dimethyl-1H-pyrazol-1-yl)phenoxy]methyl}tetrahydro-2H-pyran-4-yl]ethanesulfonamide | 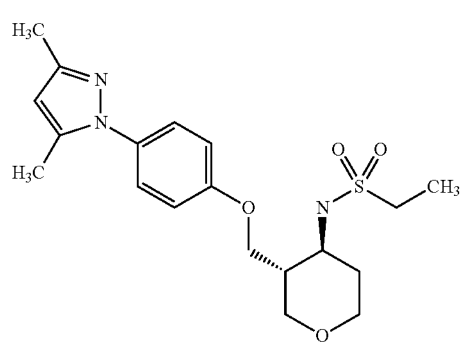 [SMILES: CCS(=O)(=O)N[C@H]1CCOC[C@@H]1COc1ccc(-n2nc(C)cc2C)cc1] | | 394.3 |

TABLE 1-13-continued

| Ex. No. | IUPAC Name | Structure | Salt | MS |
|---|---|---|---|---|
| 133 | trans-N-[3-({4-[3,5-bis(trifluoromethyl)-1H-pyrazol-1-yl]phenoxy}methyl)tetrahydro-2H-pyran-4-yl]ethanesulfonamide | 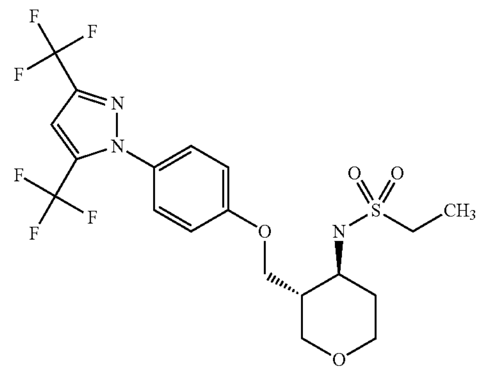 [SMILES: CCS(=O)(=O)N[C@H]1CCOC[C@@H]1COc1ccc(-n2nc(C(F)(F)F)cc2C(F)(F)F)cc1] | | 500.2 |
| 134 | trans-N-[3-{[4-(4-methyl-1H-pyrazol-1-yl)phenoxy]methyl}tetrahydro-2H-pyran-4-yl]ethanesulfonamide | 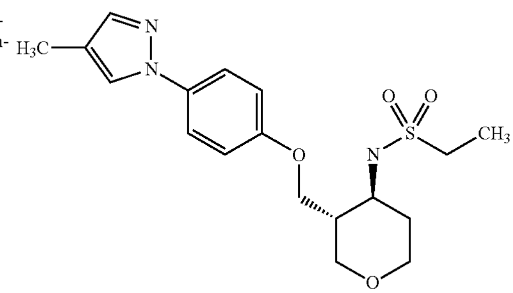 | | 380.2 |
| 135 | trans-N-{3-[(4-acetylphenoxy)methyl]tetrahydro-2H-pyran-4-yl}ethanesulfonamide | 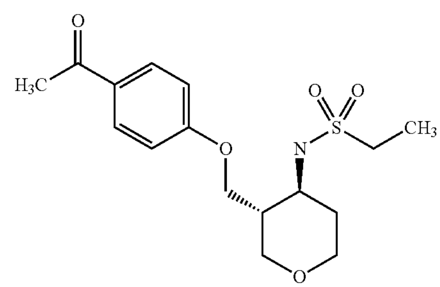 [SMILES: CCS(=O)(=O)N[C@H]1CCOC[C@@H]1COc1ccc(C(C)=O)cc1] | | 342.1 |
| 136 | trans-N-{3-[(4-acetyl-2-fluorophenoxy)methyl]tetrahydro-2H-pyran-4-yl}ethanesulfonamide | 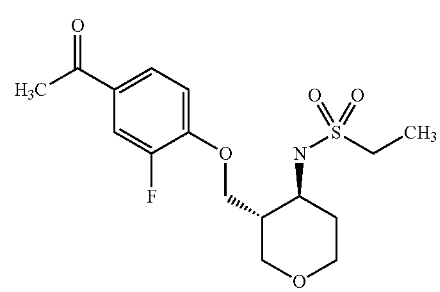 [SMILES: CCS(=O)(=O)N[C@H]1CCOC[C@@H]1COc1ccc(C(C)=O)cc1F] | | 360.1 |

TABLE 1-14

| Ex. No. | IUPAC Name | Structure | Salt | MS |
|---|---|---|---|---|
| 137 | trans-N-{3-[(4-pyridin-2-ylphenoxy)methyl]tetrahydro-2H-pyran-4-yl}ethanesulfonamide | 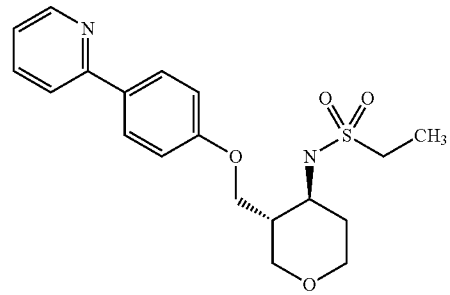 [SMILES: CCS(=O)(=O)N[C@H]1CCOC[C@@H]1COc1ccc(-c2ccccn2)cc1] | | 377.2 |
| 138 | trans-N-{3-[(4-pyridin-3-ylphenoxy)methyl]tetrahydro-2H-pyran-4-yl}ethanesulfonamide | 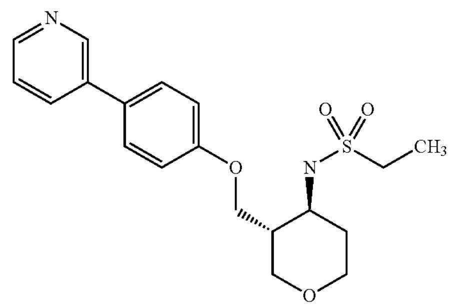 [SMILES: CCS(=O)(=O)N[C@H]1CCOC[C@@H]1COc1ccc(-c2cccnc2)cc1] | | 377.2 |
| 139 | trans-N-[3-{[4-(4-methyl-1H-imidazol-1-yl)phenoxy]methyl}tetrahydro-2H-pyran-4-yl]ethanesulfonamide | 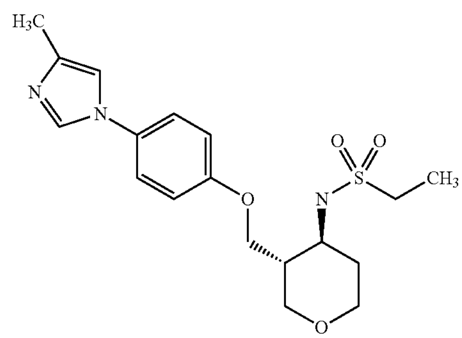 [SMILES: CCS(=O)(=O)N[C@H]1CCOC[C@@H]1COc1ccc(-n2cnc(C)c2)cc1] | | 380.2 |
| 140 | trans-N-[3-{[4-(4-chloro-1H-pyrazol-1-yl)phenoxy]methyl}tetrahydro-2H-pyran-4-yl]ethanesulfonamide | 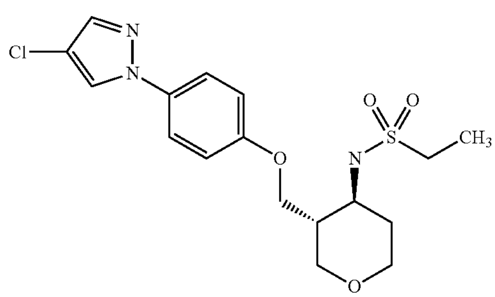 [SMILES: CCS(=O)(=O)N[C@H]1CCOC[C@@H]1COc1ccc(-n2cc(Cl)cn2)cc1] | | 400.1 |
| 141 | trans-N-[4,4-difluoro-2-{[4-(4-methyl-1H-pyrazol-1-yl)phenoxy]methyl}cyclohexyl]ethanesulfonamide | 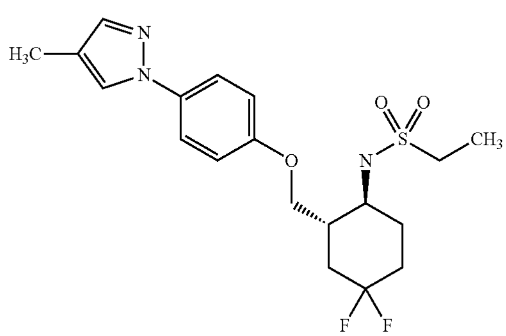 [SMILES: CCS(=O)(=O)N[C@H]1CCC(F)(F)C[C@@H]1COc1ccc(-n2cc(C)cn2)cc1] | | 414.1 |

TABLE 1-14-continued

| Ex. No. | IUPAC Name | Structure | Salt | MS |
|---|---|---|---|---|
| 142 | trans-N-[4,4-difluoro-2-{[4-(3-methyl-1H-pyrazol-1-yl)phenoxy]methyl}cyclohexyl]ethanesulfonamide | 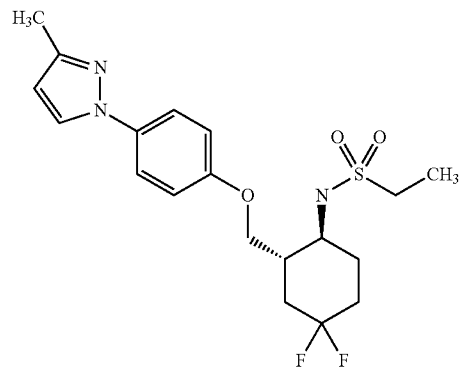 [SMILES: CCS(=O)(=O)N[C@H]1CCC(F)(F)C[C@@H]1COc1ccc(-n2ccc(C)n2)cc1] | | 414.1 |
| 143 | trans-N-[4,4-difluoro-2-{[4-(5-methyl-1H-pyrazol-1-yl)phenoxy]methyl}cyclohexyl]ethanesulfonamide | 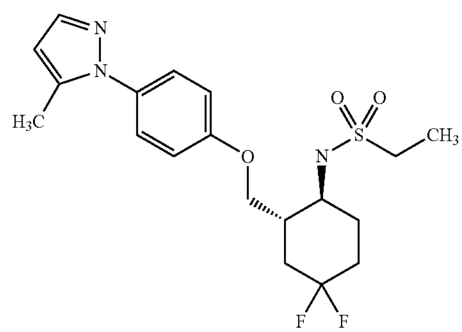 [SMILES: CCS(=O)(=O)N[C@H]1CCC(F)(F)C[C@@H]1COc1ccc(-n2nccc2C)cc1] | | 414.1 |

TABLE 1-15

| Ex. No. | IUPAC Name | Structure | Salt | MS |
|---|---|---|---|---|
| 144 | N-[(3R,4S)-4-{[4-(5-fluoropyridin-2-yl)phenoxy]methyl}tetrahydro-2H-pyran-3-yl]methanesulfonamide | 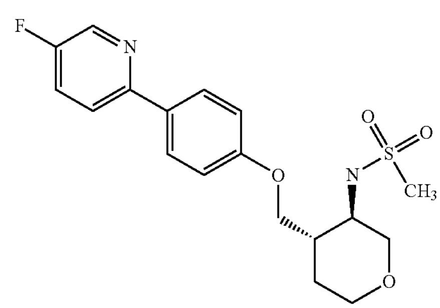 [SMILES: CS(=O)(=O)N[C@H]1COCC[C@@H]1COc1ccc(-c2ccc(F)cn2)cc1] | | 381.2 |
| 145 | N-[(3R,4S)-4-{[4-(5-cyanopyridin-2-yl)phenoxy]methyl}tetrahydro-2H-pyran-3-yl]methanesulfonamide | 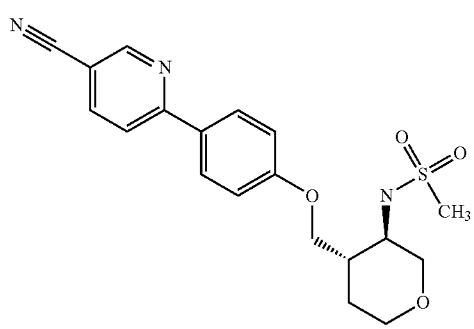 [SMILES: CS(=O)(=O)N[C@H]1COCC[C@@H]1COc1ccc(-c2ccc(C#N)cn2)cc1] | | 388.2 |

TABLE 1-15-continued

| Ex. No. | IUPAC Name | Structure | Salt | MS |
|---|---|---|---|---|
| 146 | N-[(3R,4S)-4-{[4-(4-methyl-1H-pyrazol-1-yl)phenoxy]methyl}tetrahydro-2H-pyran-3-yl]methanesulfonamide | 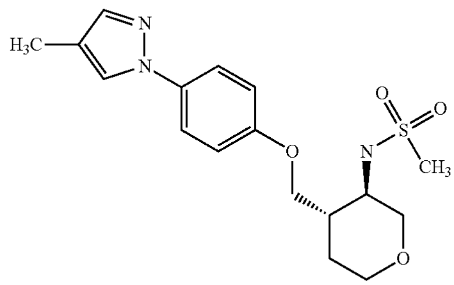 | | 366.2 |
| 147 | N-[(3R,4S)-4-{[2-fluoro-4-(4-methyl-1H-pyrazol-1-yl)phenoxy]methyl}tetrahydro-2H-pyran-3-yl]methanesulfonamide | 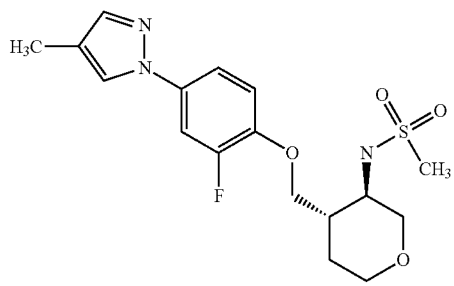 [SMILES: Cc1cnn(-c2ccc(OC[C@H]3CCOC[C@@H]3NS(C)(=O)=O)c(F)c2)c1] | | 384.2 |
| 148 | N-[(3R,4S)-4-({4-[4-(trifluoromethyl)-1H-pyrazol-1-yl]phenoxy}methyl)tetrahydro-2H-pyran-3-yl]methanesulfonamide | 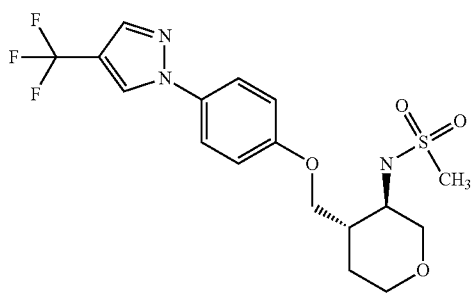 [SMILES: CS(=O)(=O)N[C@H]1COCC[C@@H]1COc1ccc(-n2cc(C(F)(F)F)cn2)cc1] | | 420.2 |
| 149 | N-[(3R,4S)-4-{[4-(2-methyl-1,3-oxazol-4-yl)phenoxy]methyl}tetrahydro-2H-pyran-3-yl]methanesulfonamide | 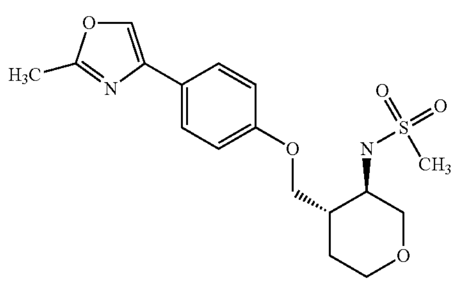 [SMILES: Cc1nc(-c2ccc(OC[C@H]3CCOC[C@@H]3NS(C)(=O)=O)cc2)co1] | | 367.3 |
| 150 | N-[(3R,4S)-4-{[4-(5-methyl-1,3-thiazol-2-yl)phenoxy]methyl}tetrahydro-2H-pyran-3-yl]methanesulfonamide | 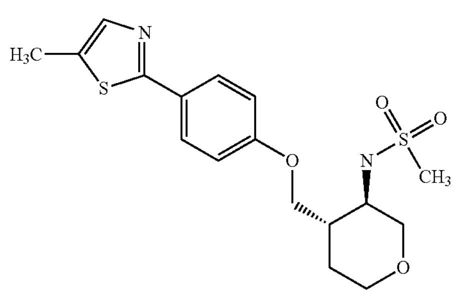 [SMILES: Cc1cnc(-c2ccc(OC[C@H]3CCOC[C@@H]3NS(C)(=O)=O)cc2)s1] | | 383.1 |

TABLE 1-15-continued

| Ex. No. | IUPAC Name | Structure | Salt | MS |
|---|---|---|---|---|
| 151 | N-[(3R,4S)-4-{[4-(2-methyl-1,3-thiazol-4-yl)phenoxy]methyl}tetrahydro-2H-pyran-3-yl]methanesulfonamide | 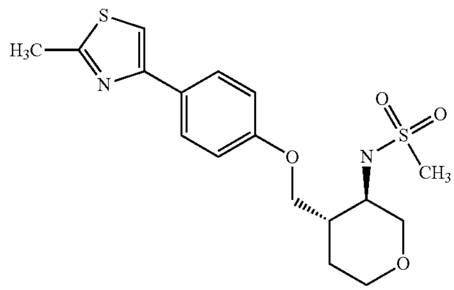 | | 383.2 |
| 152 | N-[(3R,4S)-4-{[4-(5-fluoropyridin-2-yl)phenoxy]methyl}tetrahydro-2H-pyran-3-yl]ethanesulfonamide | 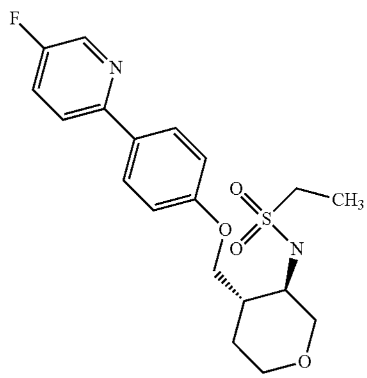 [SMILES: CCS(=O)(=O)N[C@H]1COCC[C@@H]1COc1ccc(-c2ccc(F)cn2)cc1] | | 395.2 |
| 153 | N-[(3R,4S)-4-{[4-(5-cyanopyridin-2-yl)phenoxy]methyl}tetrahydro-2H-pyran-3-yl]ethanesulfonamide | 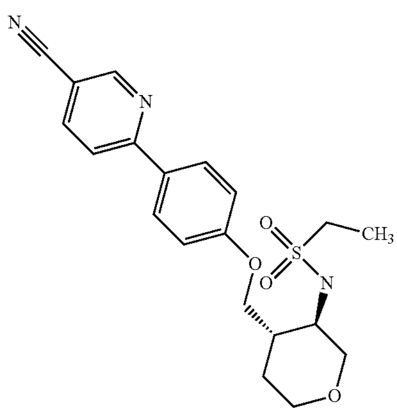 [SMILES: CCS(=O)(=O)N[C@H]1COCC[C@@H]1COc1ccc(-c2ccc(C#N)cn2)cc1] | | 402.2 |

TABLE 1-16

| Ex. No. | IUPAC Name | Structure | Salt | MS |
|---|---|---|---|---|
| 154 | N-[(3R,4S)-4-{[4-(4-methyl-1H-pyrazol-1-yl)phenoxy]methyl}tetrahydro-2H-pyran-3-yl]ethanesulfonamide | 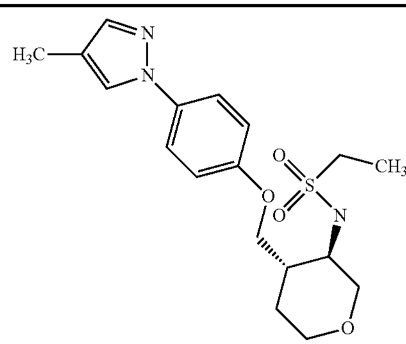 | | 380.3 |

TABLE 1-16-continued

| Ex. No. | IUPAC Name | Structure | Salt | MS |
|---|---|---|---|---|
| 155 | N-[(3R,4S)-4-{[4-(4-chloro-1H-pyrazol-1-yl)phenoxy]methyl}tetrahydro-2H-pyran-3-yl]ethanesulfonamide | 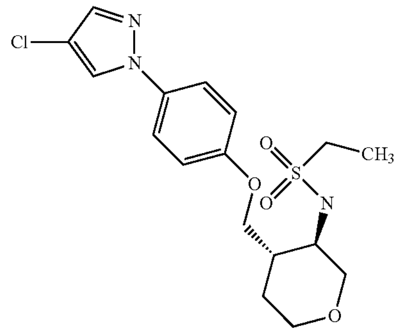 [SMILES: CCS(=O)(=O)N[C@H]1COCC[C@@H]1COc1ccc(-n2cc(Cl)cn2)cc1] | | 400.2 |
| 156 | N-[(3R,4S)-4-{[2-fluoro-4-(4-methyl-1H-pyrazol-1-yl)phenoxy]methyl}tetrahydro-2H-pyran-3-yl]ethanesulfonamide | 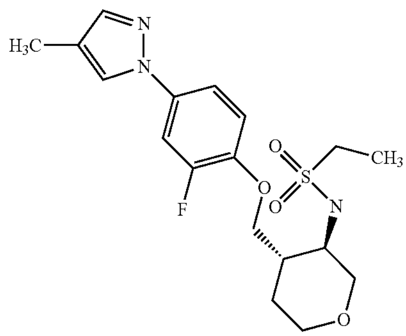 [SMILES: CCS(=O)(=O)N[C@H]1COCC[C@@H]1COc1ccc(-n2cc(C)cn2)cc1F] | | 398.2 |
| 157 | N-[(3R,4S)-4-{[4-(4-chloro-1H-pyrazol-1-yl)-2-fluorophenoxy]methyl}tetrahydro-2H-pyran-3-yl]ethanesulfonamide | 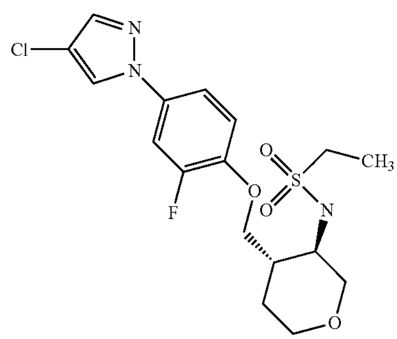 [SMILES: CCS(=O)(=O)N[C@H]1COCC[C@@H]1COc1ccc(-n2cc(Cl)cn2)cc1F] | | 418.1 |
| 158 | N-[(3R,4S)-4-({4-[4-(trifluoromethyl)-1H-pyrazol-1-yl]phenoxy}methyl)tetrahydro-2H-pyran-3-yl]ethanesulfonamide | 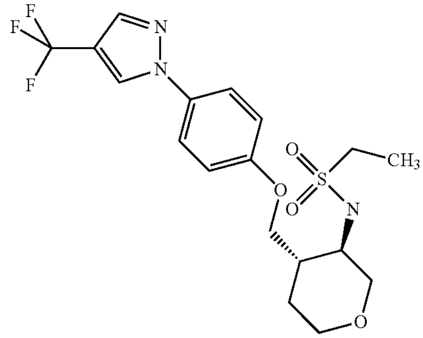 [SMILES: CCS(=O)(=O)N[C@H]1COCC[C@@H]1COc1ccc(-n2cc(C(F)(F)F)cn2)cc1] | | 434.2 |

TABLE 1-16-continued

| Ex. No. | IUPAC Name | Salt | MS |
|---|---|---|---|
| 159 | N-[(3R,4S)-4-{[4-(2-methyl-1,3-oxazol-4-yl)phenoxy]methyl}tetrahydro-2H-pyran-3-yl]ethanesulfonamide | | 381.2 |
| 160 | N-[(3R,4S)-4-{[4-(5-methyl-1,3-thiazol-2-yl)phenoxy]methyl}tetrahydro-2H-pyran-3-yl]ethanesulfonamide | | 397.2 |
| 161 | N-[(3R,4S)-4-{[4-(2-methyl-1,3-thiazol-4-yl)phenoxy]methyl}tetrahydro-2H-pyran-3-yl]ethanesulfonamide | | 397.2 |
| 162 | 1,5-anhydro-2,3,4-trideoxy-6-O-[4-(5-fluoropyridin-2-yl)phenyl]-4-[(methylsulfonyl)amino]-DL-erythro-hexitol | | 381.2 |
| 163 | 1,5-anhydro-6-O-[4-(5-chloropyridin-2-yl)phenyl]-2,3,4-trideoxy-4-[(methylsulfonyl)amino]-DL-erythro-hexitol | | 397.2 |

TABLE 1-17

| Ex. No. | IUPAC Name | Structure | Salt | MS |
|---|---|---|---|---|
| 164 | 1,5-anhydro-6-O-[4-(5-cyanopyridin-2-yl)phenyl]-2,3,4-trideoxy-4-[(methylsulfonyl)amino]-DL-erythro-hexitol | 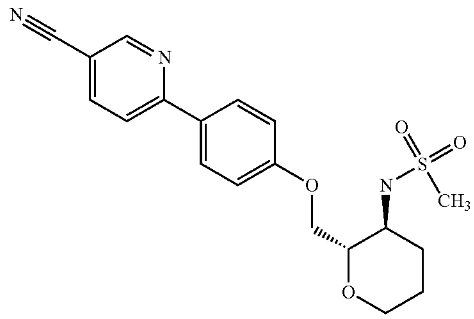 [SMILES: CS(=O)(=O)N[C@H]1CCCO[C@@H]1COc1ccc(-c2ccc(C#N)cn2)cc1] | | 388.3 |
| 165 | 1,5-anhydro-2,3,4-trideoxy-6-O-[4-(4-methyl-1H-pyrazol-1-yl)phenyl]-4-[(methylsulfonyl)amino]-DL-erythro-hexitol | 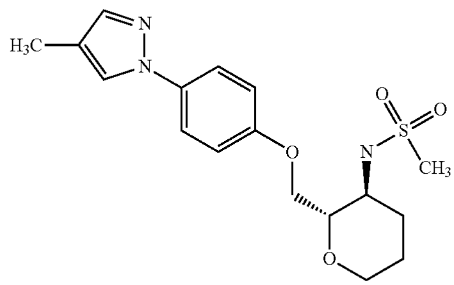 [SMILES: Cc1cnn(-c2ccc(OC[C@H]3OCCC[C@@H]3NS(C)(=O)=O)cc2)c1] | | 366.2 |
| 166 | 1,5-anhydro-6-O-[4-(4-chloro-1H-pyrazol-1-yl)phenyl]-2,3,4-trideoxy-4-[(methylsulfonyl)amino]-DL-erythro-hexitol | 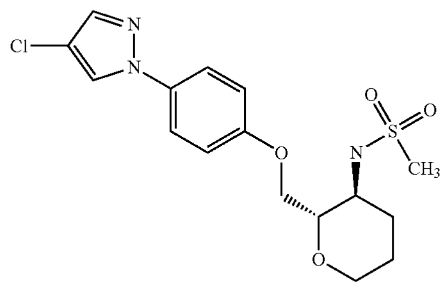 [SMILES: CS(=O)(=O)N[C@H]1CCCO[C@@H]1COc1ccc(-n2cc(Cl)cn2)cc1] | | 386.2 |
| 167 | 1,5-anhydro-2,3,4-trideoxy-6-O-[2-fluoro-4-(4-methyl-1H-pyrazol-1-yl)phenyl]-4-[(methylsulfonyl)amino]-DL-erythro-hexitol | 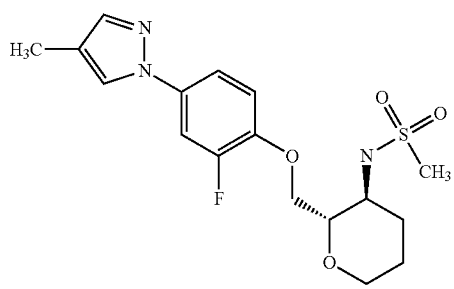 [SMILES: Cc1cnn(-c2ccc(OC[C@H]3OCCC[C@@H]3NS(C)(=O)=O)c(F)c2)c1] | | 384.2 |
| 168 | 1,5-anhydro-6-O-[4-(4-chloro-1H-pyrazol-1-yl)-2-fluorophenyl]-2,3,4-trideoxy-4-[(methylsulfonyl)amino]-DL-erythro-hexitol | 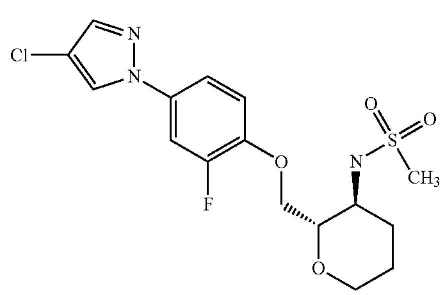 [SMILES: CS(=O)(=O)N[C@H]1CCCO[C@@H]1COc1ccc(-n2cc(Cl)cn2)cc1F] | | 404.2 |

TABLE 1-17-continued

| Ex. No. | IUPAC Name | Salt | MS |
|---|---|---|---|
| 169 | 1,5-anhydro-2,3,4-trideoxy-4-[(methylsulfonyl)amino]-6-O-{4-[4-(trifluoromethyl)-1H-pyrazol-1-yl]phenyl}-DL-erythro-hexitol | | 420.2 |
| 170 | 1,5-anhydro-2,3,4-trideoxy-6-O-[4-(5-methylisoxazol-3-yl)phenyl]-4-[(methylsulfonyl)amino]-DL-erythro-hexitol | | 367.2 |
| 171 | 1,5-anhydro-2,3,4-trideoxy-4-[(methylsulfonyl)amino]-6-O-[4-(5-methyl-1,3-thiazol-2-yl)phenyl]-DL-erythro-hexitol | | 383.2 |
| 172 | 1,5-anhydro-2,3,4-trideoxy-4-[(methylsulfonyl)amino]-6-O-[4-(2-methyl-1,3-thiazol-4-yl)phenyl]-DL-erythro-hexitol | | 383.2 |
| 173 | 1,5-anhydro-2,3,4-trideoxy-4-[(ethylsulfonyl)amino]-6-O-[4-(5-fluoropyridin-2-yl)phenyl]-DL-erythro-hexitol | | 395.3 |

TABLE 1-18

| Ex. No. | IUPAC Name | Structure | Salt | MS |
|---|---|---|---|---|
| 174 | 1,5-anhydro-6-O-[4-(5-chloropyridin-2-yl)phenyl]-2,3,4-trideoxy-4-[(ethylsulfonyl)amino]-DL-erythro-hexitol | 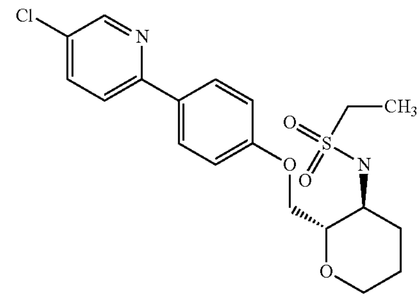 [SMILES: CCS(=O)(=O)N[C@H]1CCCO[C@@H]1COc1ccc(-c2ccc(Cl)cn2)cc1] | | 411.2 |
| 175 | 1,5-anhydro-6-O-[4-(5-cyanopyridin-2-yl)phenyl]-2,3,4-trideoxy-4-[(ethylsulfonyl)amino]-DL-erythro-hexitol | 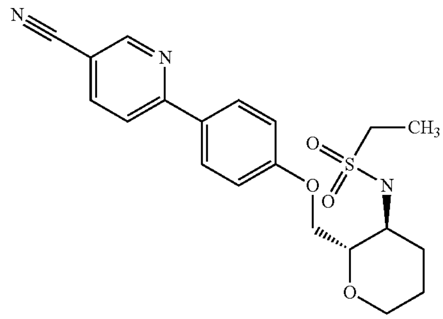 [SMILES: CCS(=O)(=O)N[C@H]1CCCO[C@@H]1COc1ccc(-c2ccc(C#N)cn2)cc1] | | 402.3 |
| 176 | 1,5-anhydro-2,3,4-trideoxy-4-[(ethylsulfonyl)amino]-6-O-[4-(4-methyl-1H-pyrazol-1-yl)phenyl]-DL-erythro-hexitol | 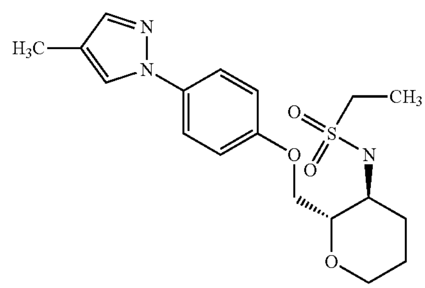 [SMILES: CCS(=O)(=O)N[C@H]1CCCO[C@@H]1COc1ccc(-n2cc(C)cn2)cc1] | | 380.3 |
| 177 | 1,5-anhydro-6-O-[4-(4-chloro-1H-pyrazol-1-yl)phenyl]-2,3,4-trideoxy-4-[(ethylsulfonyl)amino]-DL-erythro-hexitol | 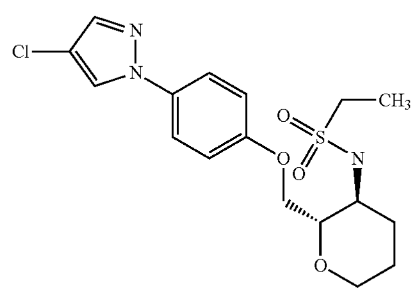 [SMILES: CCS(=O)(=O)N[C@H]1CCCO[C@@H]1COc1ccc(-n2cc(Cl)cn2)cc1] | | 400.1 |
| 178 | 1,5-anhydro-2,3,4-trideoxy-4-[(ethylsulfonyl)amino]-6-O-[2-fluoro-4-(4-methyl-1H-pyrazol-1-yl)phenyl]-DL-erythro-hexitol | 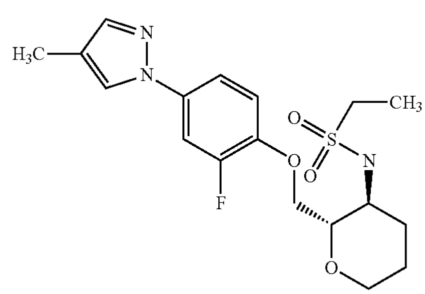 [SMILES: CCS(=O)(=O)N[C@H]1CCCO[C@@H]1COc1ccc(-n2cc(C)cn2)cc1F] | | 398.2 |

TABLE 1-18-continued

| Ex. No. | IUPAC Name | Structure | Salt | MS |
|---|---|---|---|---|
| 179 | 1,5-anhydro-6-O-[4-(4-chloro-1H-pyrazol-1-yl)-2-fluorophenyl]-2,3,4-trideoxy-4-[(ethylsulfonyl)amino]-DL-erythro-hexitol | 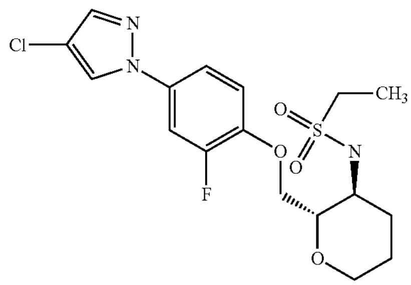 [SMILES: CCS(=O)(=O)N[C@H]1CCCO[C@@H]1COc1ccc(-n2cc(Cl)cn2)cc1F] | | 418.2 |
| 180 | 1,5-anhydro-2,3,4-trideoxy-4-[(ethylsulfonyl)amino]-6-O-[4-(5-methylisoxazol-3-yl)phenyl]-DL-erythro-hexitol | 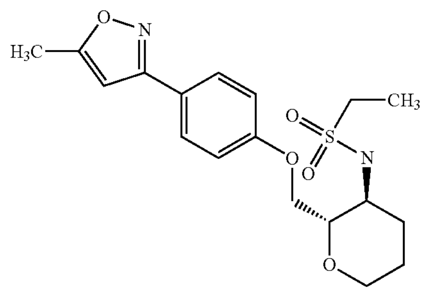 [SMILES: CCS(=O)(=O)N[C@H]1CCCO[C@@H]1COc1ccc(-c2cc(C)on2)cc1] | | 381.2 |
| 181 | 1,5-anhydro-2,3,4-trideoxy-4-[(ethylsulfonyl)amino]-6-O-[4-(5-methyl-1,3-thiazol-2-yl)phenyl]-DL-erythro-hexitol | 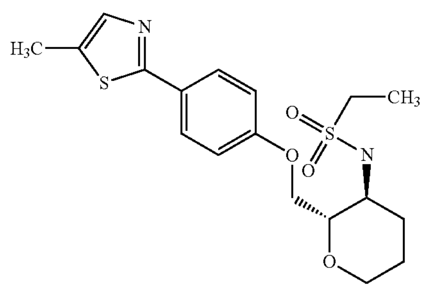 [SMILES: CCS(=O)(=O)N[C@H]1CCCO[C@@H]1COc1ccc(-c2ncc(C)s2)cc1] | | 397.2 |
| 182 | 1,5-anhydro-2,3,4-trideoxy-4-[(ethylsulfonyl)amino]-6-O-[4-(2-methyl-1,3-thiazol-4-yl)phenyl]-DL-erythro-hexitol | 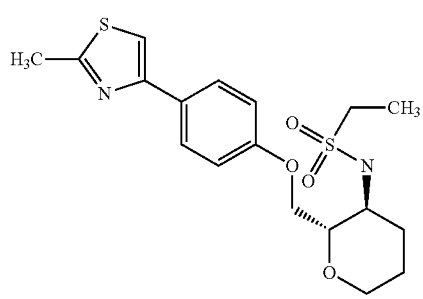 | | 397.2 |
| 183 | 1,5-anhydro-4-[(cyclopropylsulfonyl)amino]-2,3,4-trideoxy-6-O-[4-(5-fluoropyridin-2-yl)phenyl]-DL-erythro-hexitol | 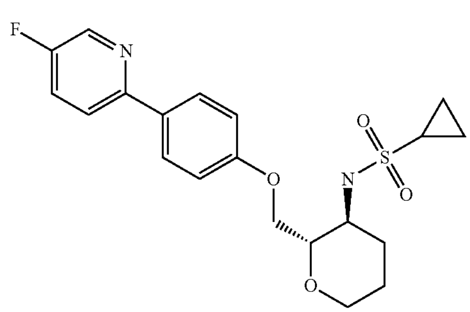 [SMILES: O=S(=O)(N[C@H]1CCCO[C@@H]1COc1ccc(-c2ccc(F)cn2)cc1)C1CC1] | | 407.2 |

TABLE 1-19

| Ex. No. | IUPAC Name | Structure | Salt | MS |
|---|---|---|---|---|
| 184 | 1,5-anhydro-6-O-[4-(5-chloropyridin-2-yl)phenyl]-4-[(cyclopropylsulfonyl)amino]-2,3,4-trideoxy-DL-erythro-hexitol | 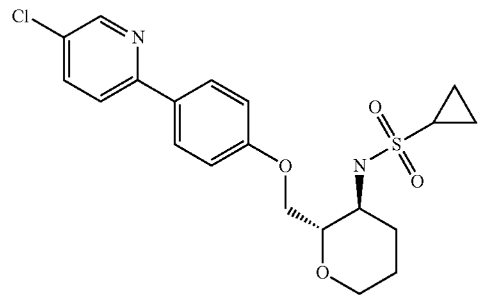 [SMILES: O=S(=O)(N[C@H]1CCCO[C@@H]1COc1ccc(-c2ccc(Cl)cn2)cc1)C1CC1] | | 423.2 |
| 185 | 1,5-anhydro-6-O-[4-(5-cyanopyridin-2-yl)phenyl]-4-[(cyclopropylsulfonyl)amino]-2,3,4-trideoxy-DL-erythro-hexitol | 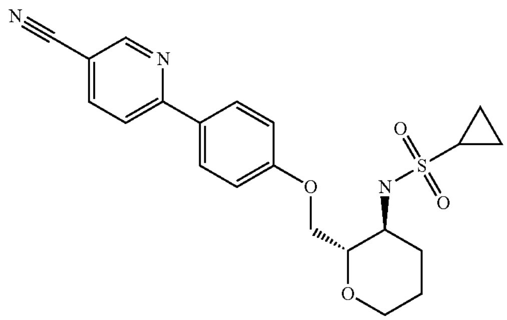 [SMILES: N#Cc1ccc(-c2ccc(OC[C@H]3OCCC[C@@H]3NS(=O)(=O)C3CC3)cc2)nc1] | | 414.2 |
| 186 | 1,5-anhydro-4-[(cyclopropylsulfonyl)amino]-2,3,4-trideoxy-6-O-[4-(4-methyl-1H-pyrazol-1-yl)phenyl]-DL-erythro-hexitol | 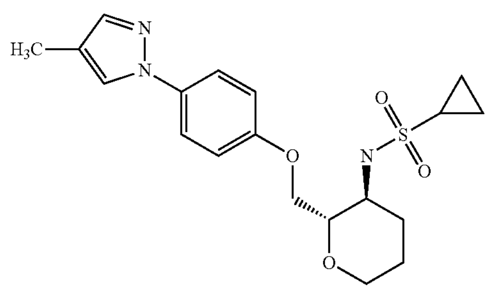 [SMILES: Cc1cnn(-c2ccc(OC[C@H]3OCCC[C@@H]3NS(=O)(=O)C3CC3)cc2)c1] | | 392.2 |
| 187 | 1,5-anhydro-6-O-[4-(4-chloro-1H-pyrazol-1-yl)phenyl]-4-[(cyclopropylsulfonyl)amino]-2,3,4-trideoxy-DL-erythro-hexitol | 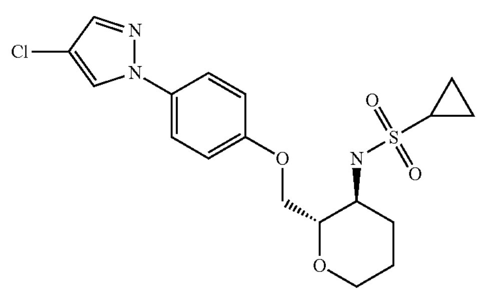 [SMILES: O=S(=O)(N[C@H]1CCCO[C@@H]1COc1ccc(-n2cc(Cl)cn2)cc1)C1CC1] | | 412.1 |
| 188 | 1,5-anhydro-4-[(cyclopropylsulfonyl)amino]-2,3,4-trideoxy-6-O-[2-fluoro-4-(4-methyl-1H-pyrazol-1-yl)phenyl]-DL-erythro-hexitol | 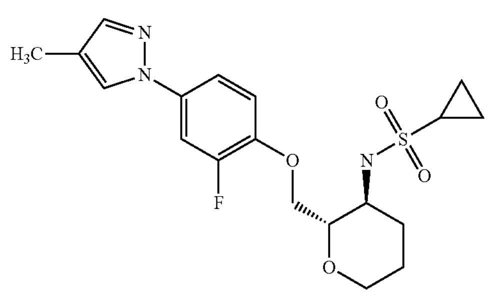 [SMILES: Cc1cnn(-c2ccc(OC[C@H]3OCCC[C@@H]3NS(=O)(=O)C3CC3)c(F)c2)c1] | | 410.2 |

TABLE 1-19-continued

| Ex. No. | IUPAC Name | Structure | Salt | MS |
|---|---|---|---|---|
| 189 | 1,5-anhydro-6-O-[4-(4-chloro-1H-pyrazol-1-yl)-2-fluorophenyl]-4-[(cyclopropylsulfonyl)amino]-2,3,4-trideoxy-DL-erythro-hexitol | 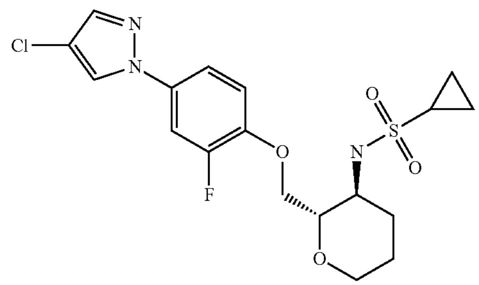 [SMILES: O=S(=O)(N[C@H]1CCCO[C@@H]1COc1ccc(-n2cc(Cl)cn2)cc1F)C1CC1] | | 430.1 |
| 190 | 1,5-anhydro-4-[(cyclopropylsulfonyl)amino]-2,3,4-trideoxy-6-O-[4-(5-methylisoxazol-3-yl)phenyl]-DL-erythro-hexitol | 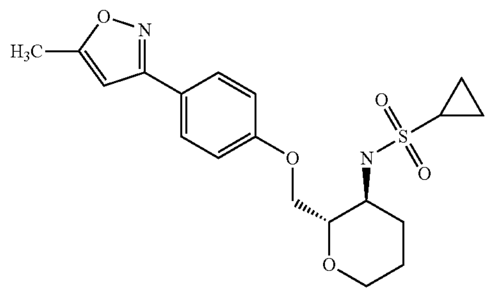 [SMILES: Cc1cc(-c2ccc(OC[C@H]3OCCC[C@@H]3NS(=O)(=O)C3CC3)cc2)no1] | | 393.2 |
| 191 | 1,5-anhydro-4-[(cyclopropylsulfonyl)amino]-2,3,4-trideoxy-6-O-[4-(2-methyl-1,3-oxazol-4-yl)phenyl]-DL-erythro-hexitol | 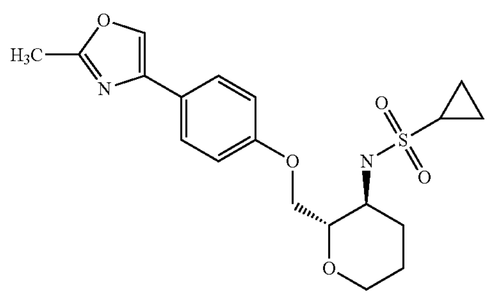 [SMILES: Cc1nc(-c2ccc(OC[C@H]3OCCC[C@@H]3NS(=O)(=O)C3CC3)cc2)co1] | | 393.2 |
| 192 | 1,5-anhydro-4-[(cyclopropylsulfonyl)amino]-2,3,4-trideoxy-6-O-[4-(5-methyl-1,3-thiazol-2-yl)phenyl]-DL-erythro-hexitol | 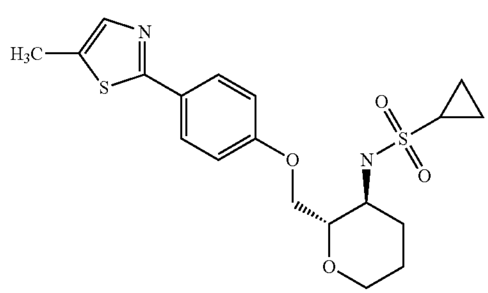 [SMILES: Cc1cnc(-c2ccc(OC[C@H]3OCCC[C@@H]3NS(=O)(=O)C3CC3)cc2)s1] | | 409.1 |
| 193 | 1,5-anhydro-4-[(cyclopropylsulfonyl)amino]-2,3,4-trideoxy-6-O-[4-(2-methyl-1,3-thiazol-4-yl)phenyl]-DL-erythro-hexitol | 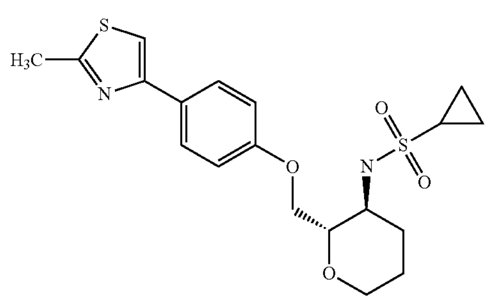 [SMILES: Cc1nc(-c2ccc(OC[C@H]3OCCC[C@@H]3NS(=O)(=O)C3CC3)cc2)cs1] | | 409.1 |

TABLE 1-20

| Ex. No. | IUPAC Name | Structure | Salt | MS |
|---|---|---|---|---|
| 194 | N-[(1S,2S)-4,4-difluoro-2-{[4-(5-methyl-1,3-thiazol-2-yl)phenoxy]methyl}cyclohexyl]methanesulfonamide | 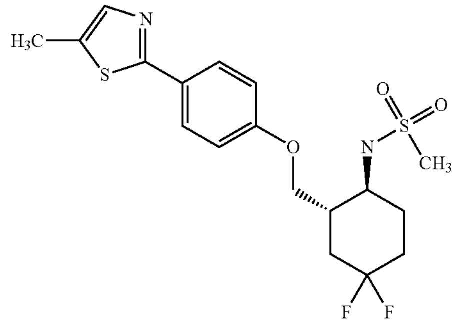 [SMILES: Cc1cnc(-c2ccc(OC[C@H]3CC(F)(F)CC[C@@H]3NS(C)(=O)=O)cc2)s1] | | 417.2 |
| 195 | N-[(1S,2S)-2-{[(2'-cyano-4'-fluorobiphenyl-4-yl)oxy]methyl}-4,4-difluorocyclohexyl]methanesulfonamide | 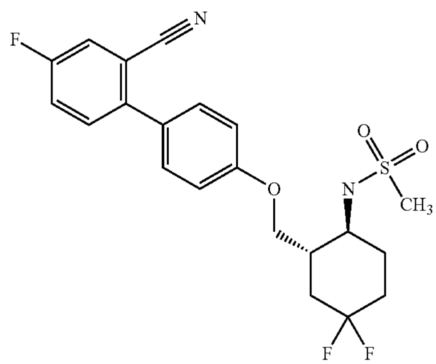 [SMILES: CS(=O)(=O)N[C@H]1CCC(F)(F)C[C@@H]1COc1ccc(-c2ccc(F)cc2C#N)cc1] | | 439.2 |
| 196 | N-[(1S,2S)-4,4-difluoro-2-{[4-(piperidin-1-ylcarbonyl)phenoxy]methyl}cyclohexyl]methanesulfonamide | 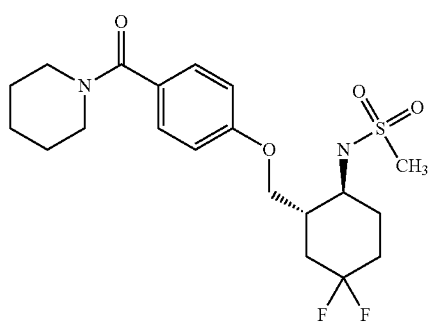 [SMILES: CS(=O)(=O)N[C@H]1CCC(F)(F)C[C@@H]1COc1ccc(C(=O)N2CCCCC2)cc1] | | 431.3 |
| 197 | 4-({(1S,2S)-5,5-difluoro-2-[(methylsulfonyl)amino]cyclohexyl}methoxy)-N,N-diethylbenzamide | 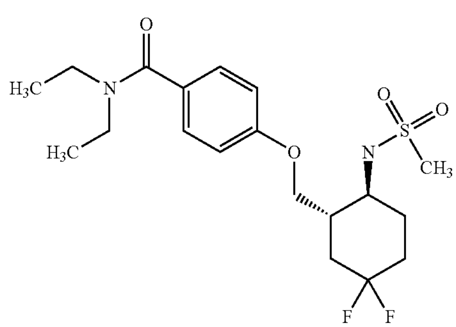 [SMILES: CCN(CC)C(=O)c1ccc(OC[C@H]2CC(F)(F)CC[C@@H]2NS(C)(=O)=O)cc1] | | 419.3 |

TABLE 1-20-continued

| Ex. No. | IUPAC Name | Structure | Salt | MS |
|---|---|---|---|---|
| 198 | N-[(1S,2S)-4,4-difluoro-2-{[4-(5-methyl-1,3-thiazol-2-yl)phenoxy]methyl}cyclohexyl]ethanesulfonamide | 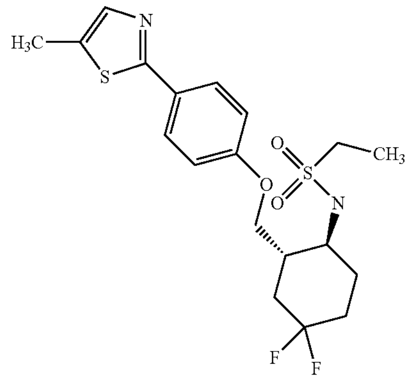 [SMILES: CCS(=O)(=O)N[C@H]1CCC(F)(F)C[C@@H]1COc1ccc(-c2ncc(C)s2)cc1] | | 431.1 |
| 199 | N-[(1S,2S)-2-{[(2'-cyano-4'-fluorobiphenyl-4-yl)oxy]methyl}-4,4-difluorocyclohexyl]ethanesulfonamide | 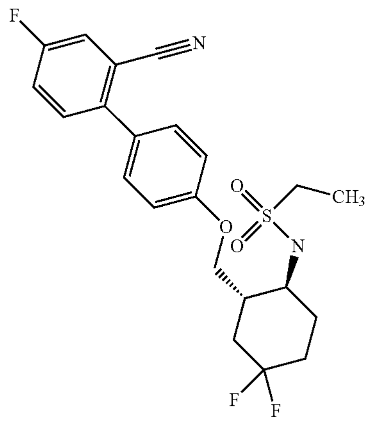 [SMILES: CCS(=O)(=O)N[C@H]1CCC(F)(F)C[C@@H]1COc1ccc(-c2ccc(F)cc2C#N)cc1] | | 453.3 |
| 200 | N-[(1S,2S)-4,4-difluoro-2-{[4-(piperidin-1-ylcarbonyl)phenoxy]methyl}cyclohexyl]ethanesulfonamide | 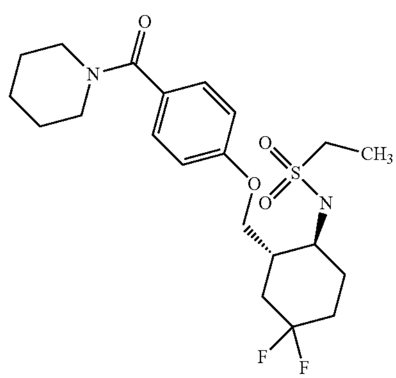 [SMILES: CCS(=O)(=O)N[C@H]1CCC(F)(F)C[C@@H]1COc1ccc(C(=O)N2CCCCC2)cc1] | | 445.3 |
| 201 | N,N-diethyl-4-({(1S,2S)-2-[(ethylsulfonyl)amino]-5,5-difluorocyclohexyl}methoxy)benzamide | 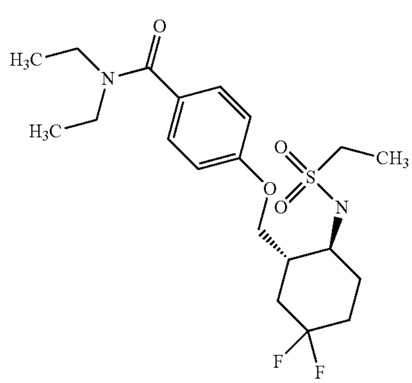 [SMILES: CCN(CC)C(=O)c1ccc(OC[C@H]2CC(F)(F)CC[C@@H]2NS(=O)(=O)CC)cc1] | | 433.3 |

TABLE 1-20-continued

| Ex. No. | IUPAC Name | Structure | Salt | MS |
|---|---|---|---|---|
| 202 | N-[(1S,2S)-4,4-difluoro-2-{[4-(5-methyl-1,3-thiazol-2-yl)phenoxy]methyl}cyclohexyl]cyclopropanesulfonamide | 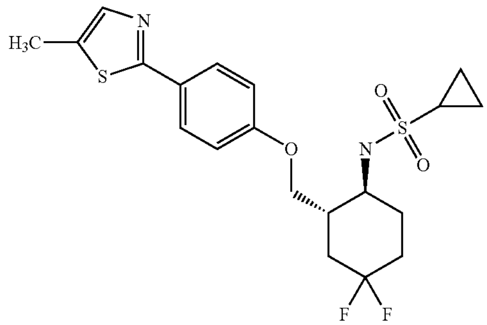 [SMILES: Cc1cnc(-c2ccc(OC[C@H]3CC(F)(F)CC[C@@H]3NS(=O)(=O)C3CC3)cc2)s1] | | 443.2 |
| 203 | N-[(1S,2S)-2-{[(2'-cyano-4'-fluorobiphenyl-4-yl)oxy]methyl}-4,4-difluorocyclohexyl]cyclopropanesulfonamide | 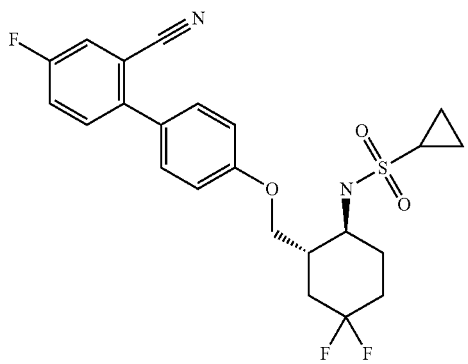 [SMILES: N#Cc1cc(F)ccc1-c1ccc(OC[C@H]2CC(F)(F)CC[C@@H]2NS(=O)(=O)C2CC2)cc1] | | 465.3 |

TABLE 1-21

| Ex. No. | IUPAC Name | Structure | Salt | MS |
|---|---|---|---|---|
| 204 | N-[(1S,2S)-4,4-difluoro-2-{[4-(piperidin-1-ylcarbonyl)phenoxy]methyl}cyclohexyl]cyclopropanesulfonamide | 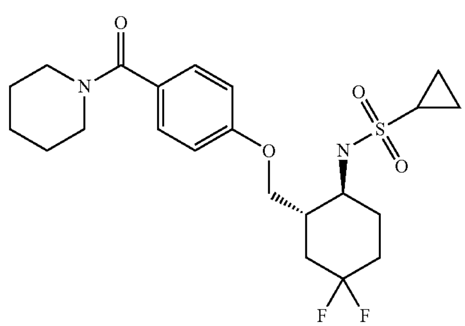 [SMILES: O=C(c1ccc(OC[C@H]2CC(F)(F)CC[C@@H]2NS(=O)(=O)C2CC2)cc1)N1CCCCC1] | | 457.3 |
| 205 | N-[(3R,4S)-4-{[4-(5-chloropyridin-2-yl)phenoxy]methyl}tetrahydro-2H-pyran-3-yl]methanesulfonamide | 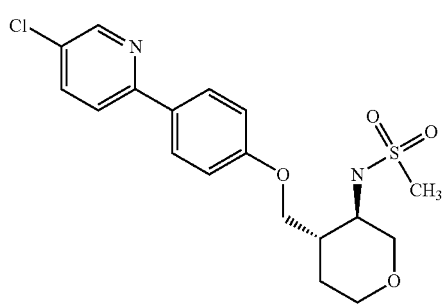 | | 397.2 |

TABLE 1-21-continued

| Ex. No. | IUPAC Name | Structure | Salt | MS |
|---|---|---|---|---|
| 206 | N-[(3R,4S)-4-{[4-(4-chloro-1H-pyrazol-1-yl)phenoxy]methyl}tetrahydro-2H-pyran-3-yl]methanesulfonamide | 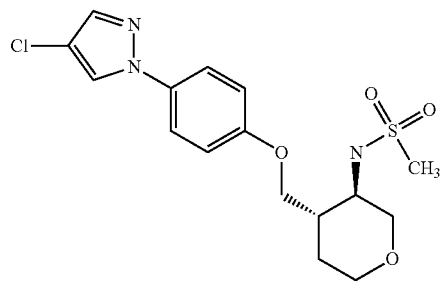 [SMILES: CS(=O)(=O)N[C@H]1COCC[C@@H]1COc1ccc(-n2cc(Cl)cn2)cc1] | | 386.2 |
| 207 | N-[(3R,4S)-4-{[4-(4-chloro-1H-pyrazol-1-yl)-2-fluorophenoxy]methyl}tetrahydro-2H-pyran-3-yl]methanesulfonamide | 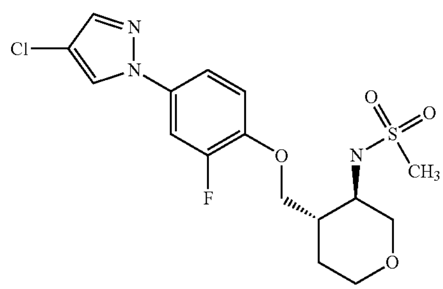 [SMILES: CS(=O)(=O)N[C@H]1COCC[C@@H]1COc1ccc(-n2cc(Cl)cn2)cc1F] | | 404.2 |
| 208 | N-[(3R,4S)-4-{[4-(5-methylisoxazol-3-yl)phenoxy]methyl}tetrahydro-2H-pyran-3-yl]methanesulfonamide | 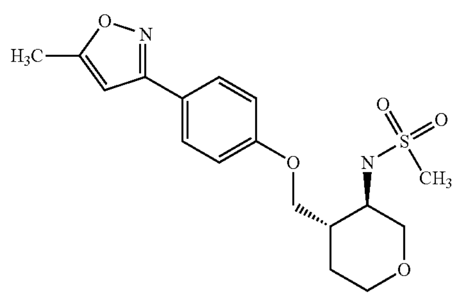 [SMILES: Cc1cc(-c2ccc(OC[C@H]3CCOC[C@@H]3NS(C)(=O)=O)cc2)no1] | | 367.2 |
| 209 | N-[(3R,4S)-4-{[4-(5-chloropyridin-2-yl)phenoxy]methyl}tetrahydro-2H-pyran-3-yl]ethanesulfonamide | 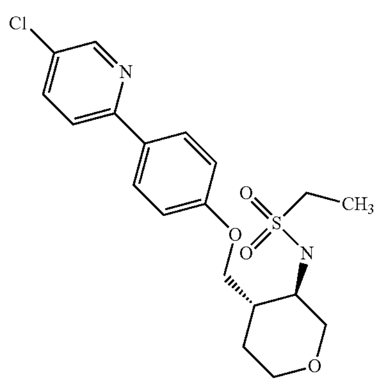 [SMILES: CCS(=O)(=O)N[C@H]1COCC[C@@H]1COc1ccc(-c2ccc(Cl)cn2)cc1] | | 411.2 |
| 210 | N-[(3R,4S)-4-{[4-(5-methylisoxazol-3-yl)phenoxy]methyl}tetrahydro-2H-pyran-3-yl]ethanesulfonamide | 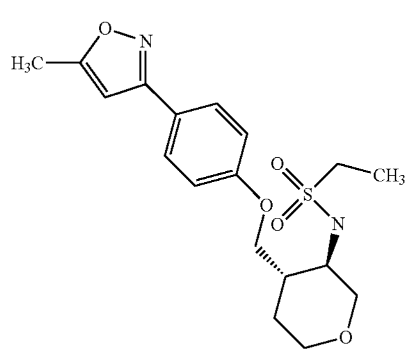 [SMILES: CCS(=O)(=O)N[C@H]1COCC[C@@H]1COc1ccc(-c2cc(C)on2)cc1] | | 381.2 |

TABLE 1-21-continued

| Ex. No. | IUPAC Name | Structure | Salt | MS |
|---|---|---|---|---|
| 211 | 1,5-anhydro-2,3,4-trideoxy-6-O-[4-(2-methyl-1,3-oxazol-4-yl)phenyl]-4-[(methylsulfonyl)amino]-DL-erythro-hexitol | 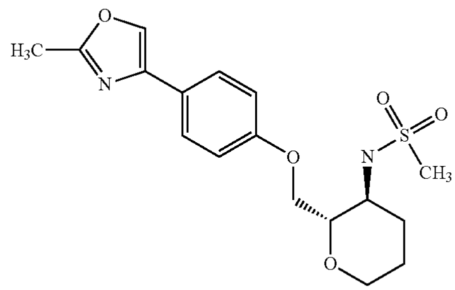 [SMILES: Cc1nc(-c2ccc(OC[C@H]3OCCC[C@@H]3NS(C)(=O)=O)cc2)co1] | | 367.3 |
| 212 | 1,5-anhydro-2,3,4-trideoxy-4-[(ethylsulfonyl)amino]-6-O-[4-(2-methyl-1,3-oxazol-4-yl)phenyl]-DL-erythro-hexitol | 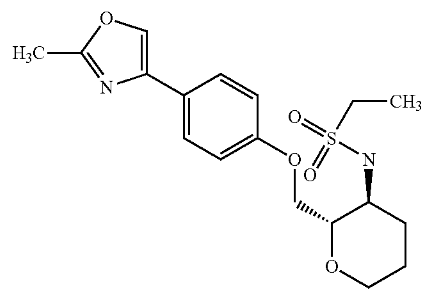 [SMILES: CCS(=O)(=O)N[C@H]1CCCO[C@@H]1COc1ccc(-c2coc(C)n2)cc1] | | 381.3 |
| 213 | N-[(1S,2S)-2-{[4-(4-cyano-1H-pyrazol-1-yl)phenoxy]methyl}-4,4-difluorocyclohexyl]methanesulfonamide | 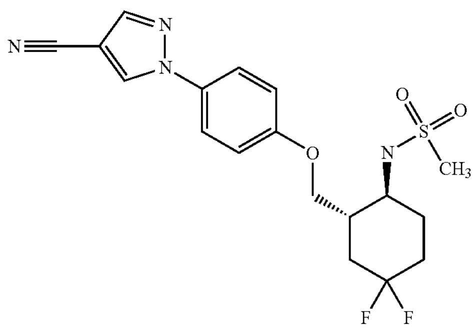 [SMILES: CS(=O)(=O)N[C@H]1CCC(F)(F)C[C@@H]1COc1ccc(-n2cc(C#N)cn2)cc1] | | 411.2 |

TABLE 1-22

| Ex. No. | IUPAC Name | Structure | Salt | MS |
|---|---|---|---|---|
| 214 | N-[(1S,2S)-2-{[4-(4-cyano-1H-pyrazol-1-yl)-2-fluorophenoxy]methyl}-4,4-difluorocyclohexyl]methanesulfonamide | 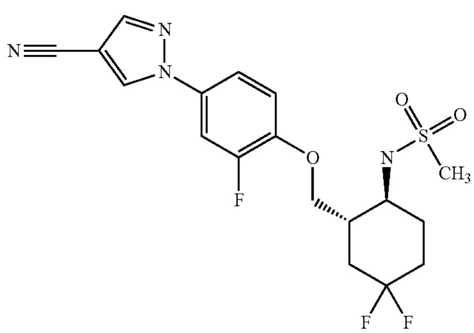 [SMILES: CS(=O)(=O)N[C@H]1CCC(F)(F)C[C@@H]1COc1ccc(-n2cc(C#N)cn2)cc1F] | | 429.2 |

TABLE 1-22-continued

| Ex. No. | IUPAC Name | Structure | Salt | MS |
|---|---|---|---|---|
| 215 | N-[(1S,2S)-2-{[4-(5-cyano-3-fluoropyridin-2-yl)phenoxy]methyl}-4,4-difluorocyclohexyl]methanesulfonamide | 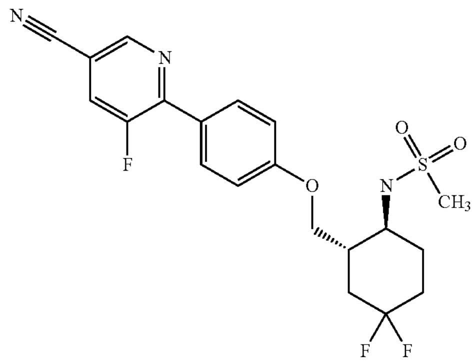 [SMILES: CS(=O)(=O)N[C@H]1CCC(F)(F)C[C@@H]1COc1ccc(-c2ncc(C#N)cc2F)cc1] | | 440.2 |
| 216 | N-[(1S,2S)-4,4-difluoro-2-{[4-(5-methylisoxazol-3-yl)phenoxy]methyl}cyclohexyl]methanesulfonamide | 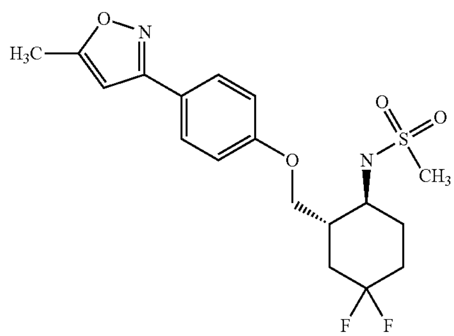 [SMILES: Cc1cc(-c2ccc(OC[C@H]3CC(F)(F)CC[C@@H]3NS(C)(=O)=O)cc2)no1] | | 401.2 |
| 217 | N-[(1S,2S)-4,4-difluoro-2-{[3-fluoro-4-(5-methylisoxazol-3-yl)phenoxy]methyl}cyclohexyl]methanesulfonamide | 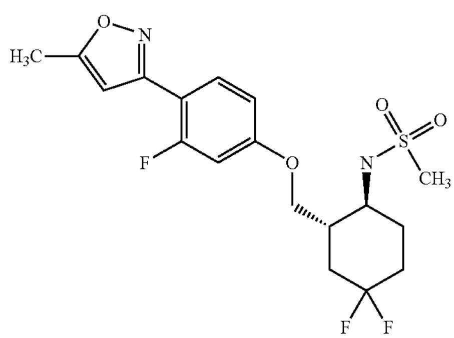 [SMILES: Cc1cc(-c2ccc(OC[C@H]3CC(F)(F)CC[C@@H]3NS(C)(=O)=O)cc2F)no1] | | 419.2 |
| 218 | N-[(1S,2S)-4,4-difluoro-2-{[2-fluoro-4-(5-methylisoxazol-3-yl)phenoxy]methyl}cyclohexyl]methanesulfonamide | 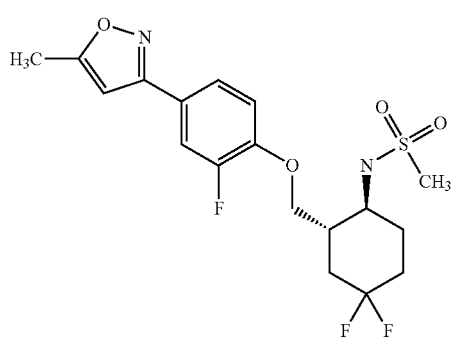 [SMILES: Cc1cc(-c2ccc(OC[C@H]3CC(F)(F)CC[C@@H]3NS(C)(=O)=O)c(F)c2)no1] | | 419.2 |

TABLE 1-22-continued

| Ex. No. | IUPAC Name | Structure | Salt | MS |
|---|---|---|---|---|
| 219 | N-[(1S,2S)-2-{[4-(4-cyano-1H-pyrazol-1-yl)phenoxy]methyl}-4,4-difluorocyclohexyl]ethanesulfonamide | 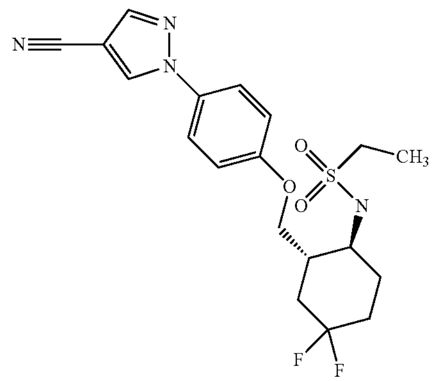 [SMILES: CCS(=O)(=O)N[C@H]1CCC(F)(F)C[C@@H]1COc1ccc(-n2cc(C#N)cn2)cc1] | | 425.2 |
| 220 | N-[(1S,2S)-2-{[4-(4-cyano-1H-pyrazol-1-yl)-2-fluorophenoxy]methyl}-4,4-difluorocyclohexyl]ethanesulfonamide | 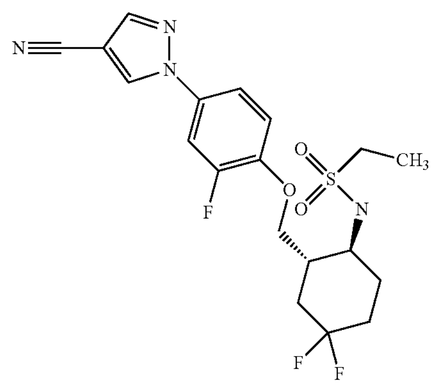 [SMILES: CCS(=O)(=O)N[C@H]1CCC(F)(F)C[C@@H]1COc1ccc(-n2cc(C#N)cn2)cc1F] | | 443.2 |
| 221 | N-[(1S,2S)-2-{[4-(5-cyanopyridin-2-yl)phenoxy]methyl}-4,4-difluorocyclohexyl]ethanesulfonamide | 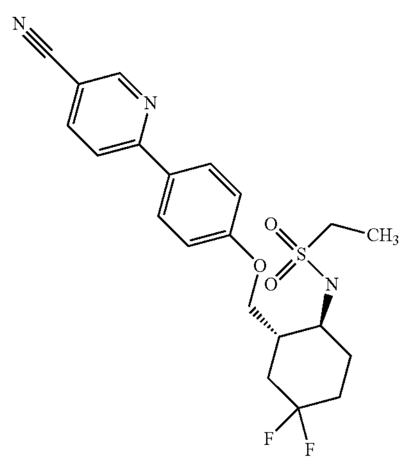 [SMILES: CCS(=O)(=O)N[C@H]1CCC(F)(F)C[C@@H]1COc1ccc(-c2ccc(C#N)cn2)cc1] | | 436.2 |

TABLE 1-22-continued

| Ex. No. | IUPAC Name | Structure | Salt | MS |
|---|---|---|---|---|
| 222 | N-[(1S,2S)-2-{[4-(5-cyano-3-fluoropyridin-2-yl)phenoxy]methyl}-4,4-difluorocyclohexyl]ethanesulfonamide | 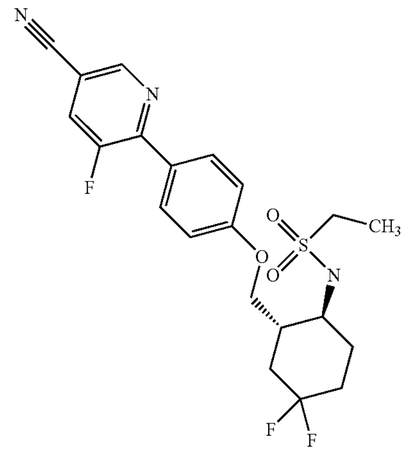 [SMILES: CCS(=O)(=O)N[C@H]1CCC(F)(F)C[C@@H]1COc1ccc(-c2ncc(C#N)cc2F)cc1] | | 454.2 |
| 223 | N-[(1S,2S)-4,4-difluoro-2-{[4-(5-methylisoxazol-3-yl)phenoxy]methyl}cyclohexyl]ethanesulfonamide | 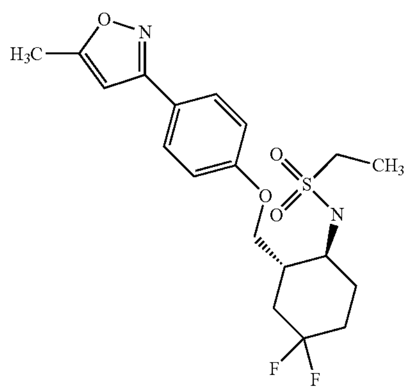 [SMILES: CCS(=O)(=O)N[C@H]1CCC(F)(F)C[C@@H]1COc1ccc(-c2cc(C)on2)cc1] | | 415.2 |

TABLE 1-23

| Ex. No. | IUPAC Name | Structure | Salt | MS |
|---|---|---|---|---|
| 224 | N-[(1S,2S)-4,4-difluoro-2-{[3-fluoro-4-(5-methylisoxazol-3-yl)phenoxy]methyl}cyclohexyl]ethanesulfonamide | 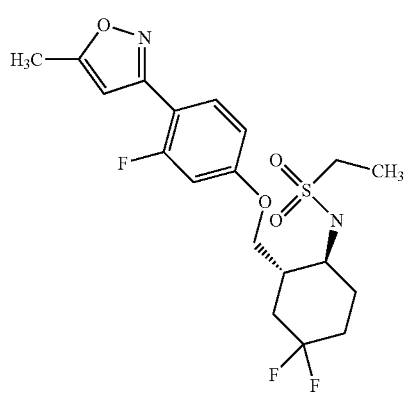 [SMILES: CCS(=O)(=O)N[C@H]1CCC(F)(F)C[C@@H]1COc1ccc(-c2cc(C)on2)c(F)c1] | | 433.2 |

| Ex. No. | IUPAC Name | Structure | Salt | MS |
|---|---|---|---|---|
| 225 | N-[(1S,2S)-4,4-difluoro-2-{[2-fluoro-4-(5-methylisoxazol-3-yl)phenoxy]methyl}cyclohexyl]ethanesulfonamide | 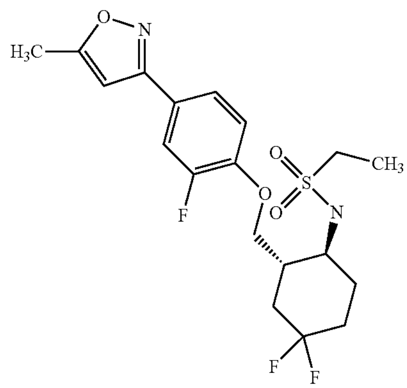 [SMILES: CCS(=O)(=O)N[C@H]1CCC(F)(F)C[C@@H]1COc1ccc(-c2cc(C)on2)cc1F] | | 433.2 |
| 226 | N-[(1S,2S)-2-{[4-(4-cyano-1H-pyrazol-1-yl)phenoxy]methyl}-4,4-difluorocyclohexyl]cyclopropanesulfonamide | 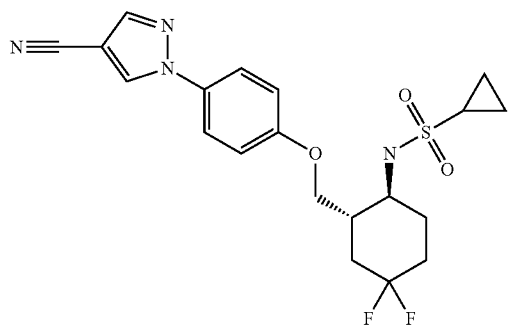 [SMILES: N#Cc1cnn(-c2ccc(OC[C@H]3CC(F)(F)CC[C@@H]3NS(=O)(=O)C3CC3)cc2)c1] | | 437.3 |
| 227 | N-[(1S,2S)-2-{[4-(4-cyano-1H-pyrazol-1-yl)-2-fluorophenoxy]methyl}-4,4-difluorocyclohexyl]cyclopropanesulfonamide | 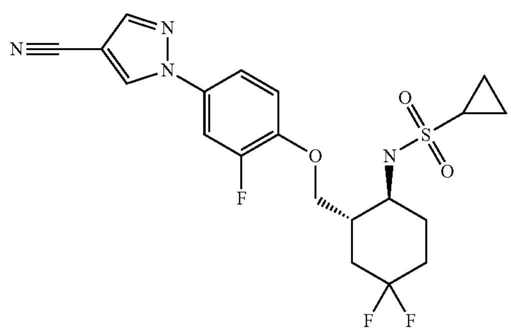 [SMILES: N#Cc1cnn(-c2ccc(OC[C@H]3CC(F)(F)CC[C@@H]3NS(=O)(=O)C3CC3)c(F)c2)c1] | | 455.2 |
| 228 | N-[(1S,2S)-2-{[4-(5-cyanopyridin-2-yl)phenoxy]methyl}-4,4-difluorocyclohexyl]cyclopropanesulfonamide | 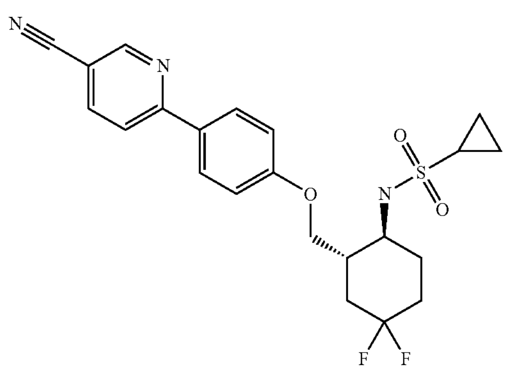 [SMILES: N#Cc1ccc(-c2ccc(OC[C@H]3CC(F)(F)CC[C@@H]3NS(=O)(=O)C3CC3)cc2)nc1] | | 448.3 |

TABLE 1-23-continued

| Ex. No. | IUPAC Name | Structure | Salt | MS |
|---|---|---|---|---|
| 229 | N-[(1S,2S)-2-{[4-(5-cyano-3-fluoropyridin-2-yl)phenoxy]methyl}-4,4-difluorocyclohexyl]cyclopropane-sulfonamide | 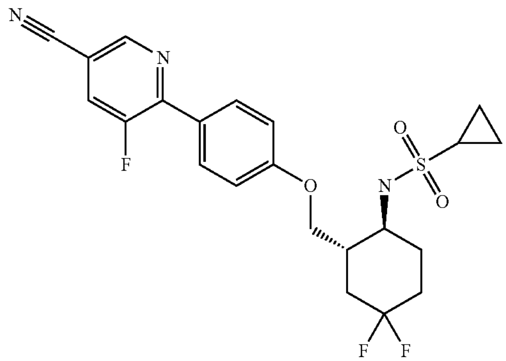 [SMILES: N#Cc1cnc(-c2ccc(OC[C@H]3CC(F)(F)CC[C@@H]3NS(=O)(=O)C3CC3)cc2)c(F)c1] | | 466.3 |
| 230 | N-[(1S,2S)-4,4-difluoro-2-{[4-(5-methylisoxazol-3-yl)phenoxy]methyl}cyclohexyl]cyclopropanesulfonamide | 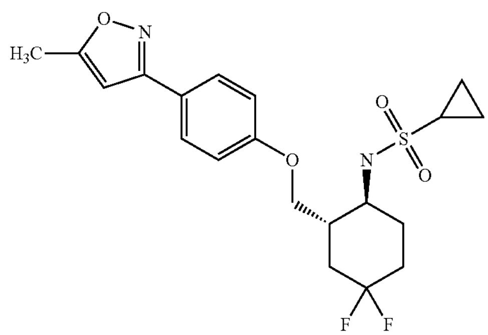 [SMILES: Cc1cc(-c2ccc(OC[C@H]3CC(F)(F)CC[C@@H]3NS(=O)(=O)C3CC3)cc2)no1] | | 427.3 |
| 231 | N-[(1S,2S)-4,4-difluoro-2-{[3-fluoro-4-(5-methylisoxazol-3-yl)phenoxy]methyl}cyclohexyl]cyclopropanesulfonamide | 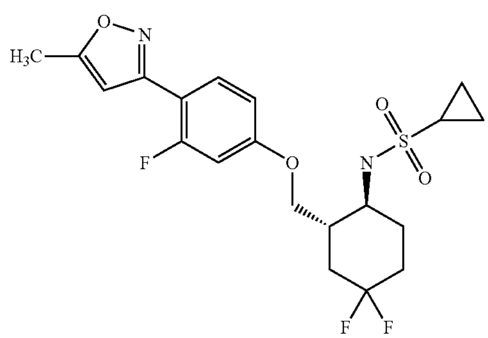 [SMILES: Cc1cc(-c2ccc(OC[C@H]3CC(F)(F)CC[C@@H]3NS(=O)(=O)C3CC3)cc2F)no1] | | 445.3 |
| 232 | N-[(1S,2S)-4,4-difluoro-2-{[2-fluoro-4-(5-methylisoxazol-3-yl)phenoxy]methyl}cyclohexyl]cyclopropanesulfonamide | 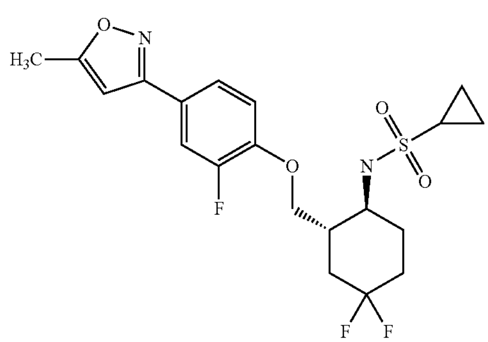 [SMILES: Cc1cc(-c2ccc(OC[C@H]3CC(F)(F)CC[C@@H]3NS(=O)(=O)C3CC3)c(F)c2)no1] | | 445.3 |

TABLE 1-23-continued

| Ex. No. | IUPAC Name | Structure | Salt | MS |
|---|---|---|---|---|
| 233 | N-[(3R,4S)-4-{[4-(5-chloropyridin-2-yl)phenoxy]methyl}tetrahydro-2H-pyran-3-yl]methanesulfonamide | 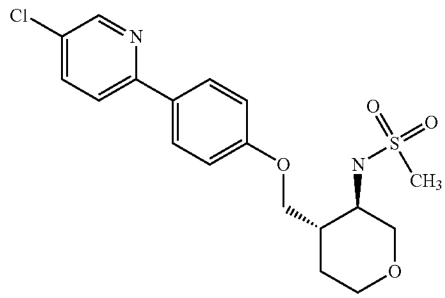 [SMILES: CS(=O)(=O)N[C@H]1COCC[C@@H]1COc1ccc(-c2ccc(Cl)cn2)cc1] | | 397.1 |

TABLE 1-24

| Ex. No. | IUPAC Name | Structure | Salt | MS |
|---|---|---|---|---|
| 234 | N-[(3R,4S)-4-{[4-(4-chloro-1H-pyrazol-1-yl)phenoxy]methyl}tetrahydro-2H-pyran-3-yl]methanesulfonamide | 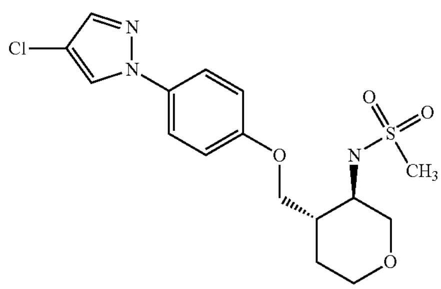 [SMILES: CS(=O)(=O)N[C@H]1COCC[C@@H]1COc1ccc(-n2cc(Cl)cn2)cc1] | | 386.0 |
| 235 | N-[(3R,4S)-4-{[4-(4-chloro-1H-pyrazol-1-yl)-2-fluorophenoxy]methyl}tetrahydro-2H-pyran-3-yl]methanesulfonamide | 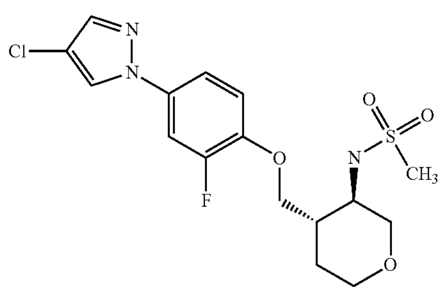 [SMILES: CS(=O)(=O)N[C@H]1COCC[C@@H]1COc1ccc(-n2cc(Cl)cn2)cc1F] | | 401.9 |
| 236 | N-[(3R,4S)-4-{[4-(5-chloropyridin-2-yl)phenoxy]methyl}tetrahydro-2H-pyran-3-yl]ethanesulfonamide | 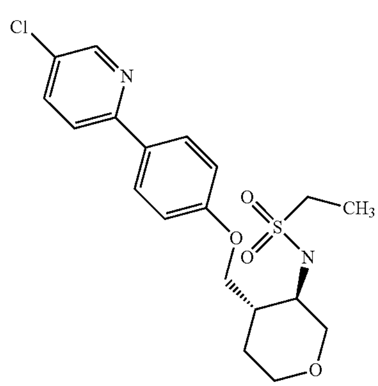 [SMILES: CCS(=O)(=O)N[C@H]1COCC[C@@H]1COc1ccc(-c2ccc(Cl)cn2)cc1] | | 411.2 |

TABLE 1-24-continued

| Ex. No. | IUPAC Name | Structure | Salt | MS |
|---|---|---|---|---|
| 237 | N-[(1S,2S)-2-{[4-(5-cyano-3-fluoropyridin-2-yl)phenoxy]methyl}4,4-difluorocyclohexyl]methanesulfonamide | 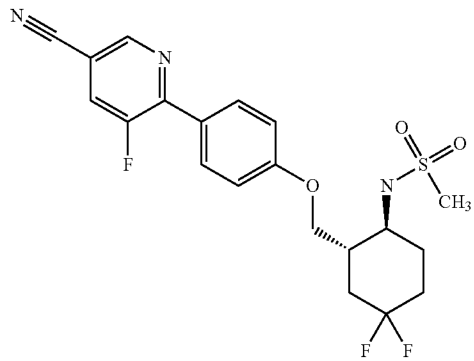 [SMILES: CS(=O)(=O)N[C@H]1CCC(F)(F)C[C@@H]1COc1ccc(-c2ncc(C#N)cc2F)cc1] | | 440.2 |
| 238 | N-[(1S,2S)-2-{[4-(5-cyano-3-fluoropyridin-2-yl)phenoxy]methyl}-4,4-difluorocyclohexyl]ethanesulfonamide | 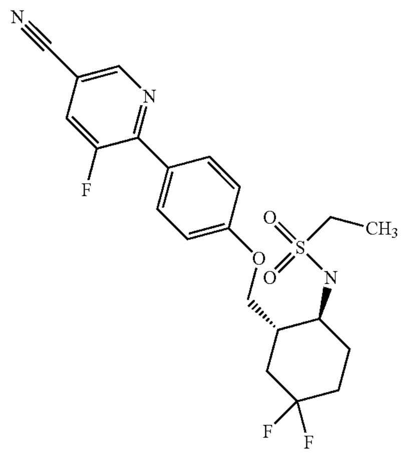 [SMILES: CCS(=O)(=O)N[C@H]1CCC(F)(F)C[C@@H]1COc1ccc(-c2ncc(C#N)cc2F)cc1] | | 454.1 |
| 239 | N-[(3RS,4SR)-3-{[4-(5-chloropyridin-2-yl)phenoxy]methyl}tetrahydro-2H-pyran-4-yl]methanesulfonamide | 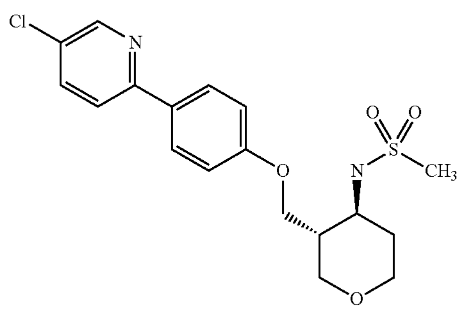 [SMILES: CS(=O)(=O)N[C@H]1CCOC[C@@H]1COc1ccc(-c2ccc(Cl)cn2)cc1] | | 397.1 |
| 240 | N-[(3RS,4SR)-3-{[4-(5-fluoropyridin-2-yl)phenoxy]methyl}tetrahydro-2H-pyran-4-yl]ethanesulfonamide | 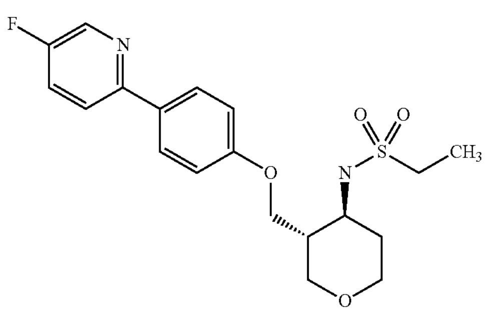 [SMILES: CCS(=O)(=O)N[C@H]1CCOC[C@@H]1COc1ccc(-c2ccc(F)cn2)cc1] | | 395.2 |

TABLE 1-24-continued

| Ex. No. | IUPAC Name | Structure | Salt | MS |
|---|---|---|---|---|
| 241 | N-[(3RS,4SR)-3-{[4-(5-fluoropyridin-2-yl)phenoxy]methyl}tetrahydro-2H-pyran-4-yl]cyclopropanesulfonamide | 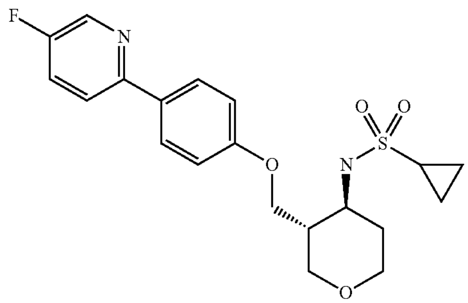 [SMILES: O=S(=O)(N[C@H]1CCOC[C@@H]1COc1ccc(-c2ccc(F)cn2)cc1)C1CC1] | | 407.2 |
| 242 | N-[(3RS,4SR)-3-{[4-(5-methyl-1,3-thiazol-2-yl)phenoxy]methyl}tetrahydro-2H-pyran-4-yl]cyclopropanesulfonamide | 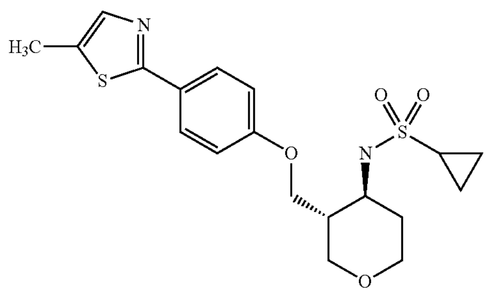 [SMILES: Cc1cnc(-c2ccc(OC[C@H]3COCC[C@@H]3NS(=O)(=O)C3CC3)cc2)s1] | | 409.1 |
| 243 | N-[(3RS,4SR)-3-{[3-fluoro-4-(5-fluoropyridin-2-yl)phenoxy]methyl}tetrahydro-2H-pyran-4-yl]cyclopropanesulfonamide | 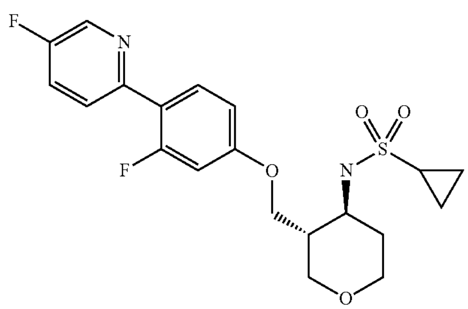 [SMILES: O=S(=O)(N[C@H]1CCOC[C@@H]1COc1ccc(-c2ccc(F)cn2)c(F)c1)C1CC1] | | 425.2 |

TABLE 1-25

| Ex. No. | IUPAC Name | Structure | Salt | MS |
|---|---|---|---|---|
| 244 | N-[(3RS,4SR)-3-{[4-(5-chloropyridin-2-yl)-3-fluorophenoxy]methyl}tetrahydro-2H-pyran-4-yl]methanesulfonamide | 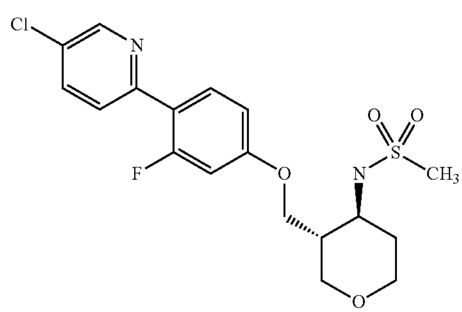 [SMILES: CS(=O)(=O)N[C@H]1CCOC[C@@H]1COc1ccc(-c2ccc(Cl)cn2)c(F)c1] | | 415.1 |

TABLE 1-25-continued

| Ex. No. | IUPAC Name | Structure | Salt | MS |
|---|---|---|---|---|
| 245 | N-[(3RS,4SR)-3-{[4-(5-chloropyridin-2-yl)-2-fluorophenoxy]methyl}tetrahydro-2H-pyran-4-yl]methanesulfonamide | 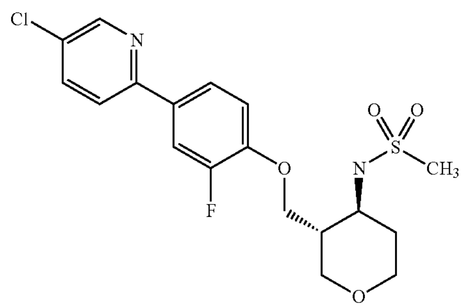 [SMILES: CS(=O)(=O)N[C@H]1CCOC[C@@H]1COc1ccc(-c2ccc(Cl)cn2)cc1F] | | 415.1 |
| 246 | N-[(3R,4S)-3-{[4-(5-cyanopyridin-2-yl)phenoxy]methyl}tetrahydro-2H-pyran-4-yl]cyclopropanesulfonamide | 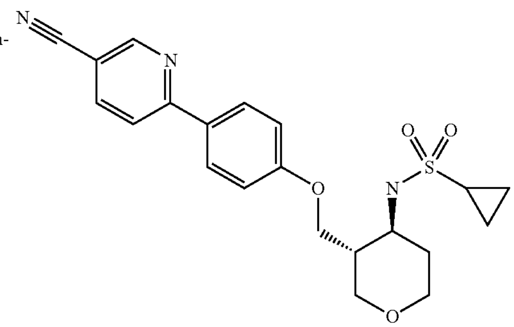 | | 414.2 |
| 247 | N-[(3R,4S)-3-{[3-fluoro-4-(5-methylisoxazol-3-yl)phenoxy]methyl}tetrahydro-2H-pyran-4-yl]methanesulfonamide | 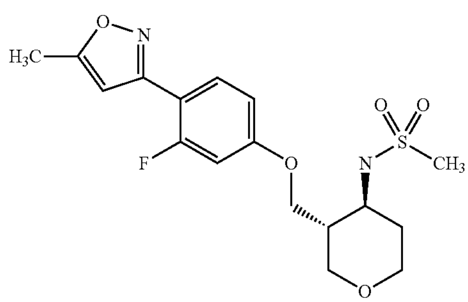 | | 385.1 |
| 248 | N-[(3R,4S)-3-{[3-fluoro-4-(5-methylisoxazol-3-yl)phenoxy]methyl}tetrahydro-2H-pyran-4-yl]ethanesulfonamide | 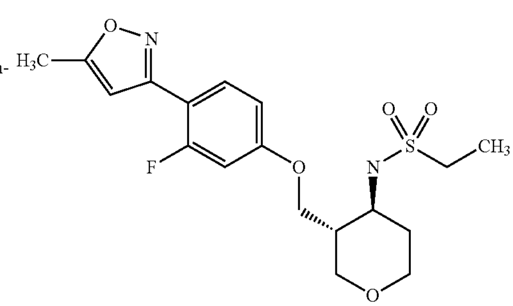 | | 399.1 |
| 249 | N-[(3R,4S)-3-{[3-fluoro-4-(5-methylisoxazol-3-yl)phenoxy]methyl}tetrahydro-2H-pyran-4-yl]cyclopropanesulfonamide | 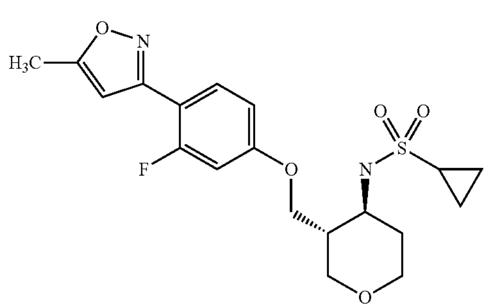 [SMILES: Cc1cc(-c2ccc(OC[C@H]3COCC[C@@H]3NS(=O)(=O)C3CC3)cc2F)no1] | | 411.1 |

TABLE 1-25-continued

| Ex. No. | IUPAC Name | Structure | Salt | MS |
|---|---|---|---|---|
| 250 | N-[(3R,4S)-3-{[2,3-difluoro-4-(5-fluoropyridin-2-yl)phenoxy]methyl}tetrahydro-2H-pyran-4-yl]ethanesulfonamide | 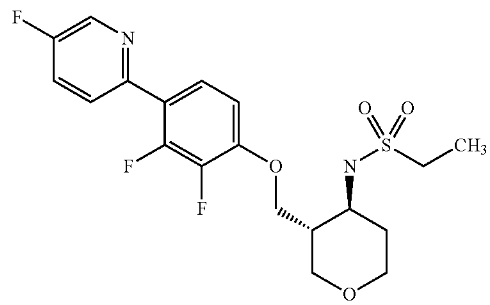 [SMILES: CCS(=O)(=O)N[C@H]1CCOC[C@@H]1COc1ccc(-c2ccc(F)cn2)c(F)c1F] | | 431.1 |
| 251 | N-[(3R,4S)-4-{[4-(3,5-difluoropyridin-2-yl)phenoxy]methyl}tetrahydro-2H-pyran-3-yl]ethanesulfonamide | 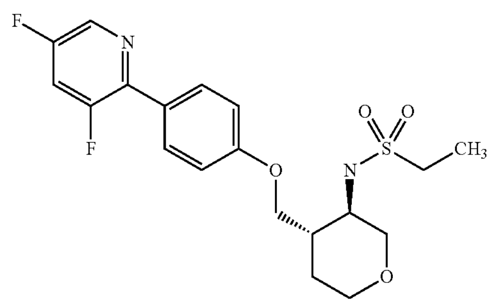 [SMILES: CCS(=O)(=O)N[C@H]1COCC[C@@H]1COc1ccc(-c2ncc(F)cc2F)cc1] | | 413.1 |
| 252 | N-[(3R,4S)-3-{[4-(5-fluoropyrimidin-2-yl)phenoxy]methyl}tetrahydro-2H-pyran-4-yl]ethanesulfonamide | 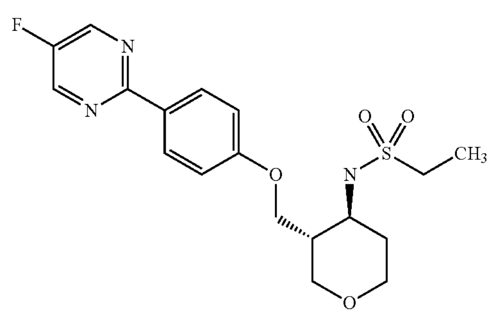 | | 396.2 |
| 253 | N-[(3R,4S)-3-{[4-(5-chloropyrimidin-2-yl)phenoxy]methyl}tetrahydro-2H-pyran-4-yl]ethanesulfonamide | 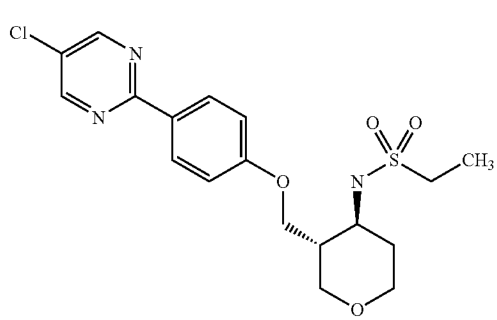 [SMILES: CCS(=O)(=O)N[C@H]1CCOC[C@@H]1COc1ccc(-c2ncc(Cl)cn2)cc1] | | 412.1 |

TABLE 1-26

| Ex. No. | IUPAC Name | Structure | Salt | MS |
|---|---|---|---|---|
| 254 | N-[(3R,4S)-3-{[4-(5-chloropyridin-2-yl)phenoxy]methyl}tetrahydro-2H-pyran-4-yl]methanesulfonamide | 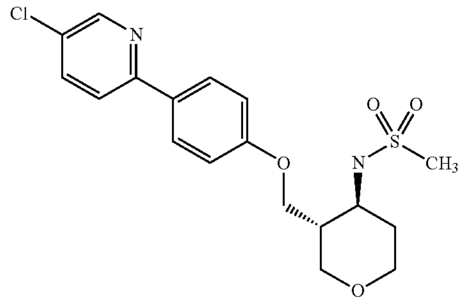 [SMILES: CS(=O)(=O)N[C@H]1CCOC[C@@H]1COc1ccc(-c2ccc(Cl)cn2)cc1] | | 397.1 |
| 255 | N-[(3R,4S)-3-{[4-(5-chloropyridin-2-yl)-3-fluorophenoxy]methyl}tetrahydro-2H-pyran-4-yl]methanesulfonamide or N-[(3S,4R)-3-{[4-(5-chloropyridin-2-yl)-3-fluorophenoxy]methyl}tetrahydro-2H-pyran-4-yl]methanesulfonamide | 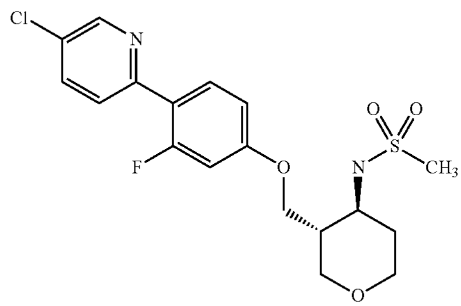 [SMILES: CS(=O)(=O)N[C@H]1CCOC[C@@H]1COc1ccc(-c2ccc(Cl)cn2)c(F)c1] | | 414.9 |
| 256 | N-[(3R,4S)-3-{[4-(5-chloro-3-fluoropyridin-2-yl)phenoxy]methyl}tetrahydro-2H-pyran-4-yl]cyclopropanesulfonamide | 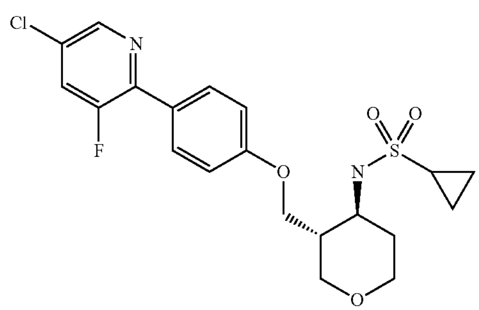 [SMILES: O=S(=O)(N[C@H]1CCOC[C@@H]1COc1ccc(-c2ncc(Cl)cc2F)cc1)C1CC1] | | 441.1 |
| 257 | N-[(3R,4S)-3-{[4-(5-chloro-1,3-thiazol-2-yl)phenoxy]methyl}tetrahydro-2H-pyran-4-yl]ethanesulfonamide | 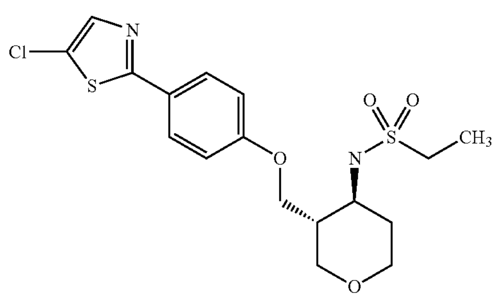 [SMILES: CCS(=O)(=O)N[C@H]1CCOC[C@@H]1COc1ccc(-c2ncc(Cl)s2)cc1] | | 417.1 |
| 258 | 1,5-anhydro-2,3,4-trideoxy-4-[(ethylsulfonyl)amino]-6-O-[4-(5-methyl-1,3-thiazol-2-yl)phenyl]-D-erythro-hexitol | 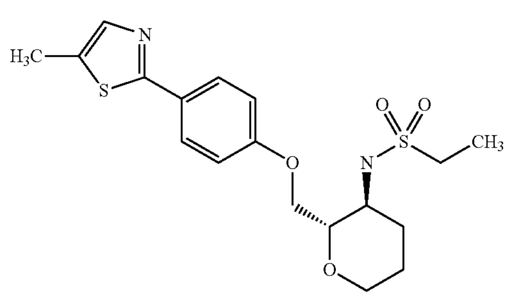 [SMILES: CCS(=O)(=O)N[C@H]1CCCO[C@@H]1COc1ccc(-c2ncc(C)s2)cc1] | | 397.1 |

TABLE 1-26-continued

| Ex. No. | IUPAC Name | Structure | Salt | MS |
|---|---|---|---|---|
| 259 | N-[(1S,2S)-2-{[4-(5-cyanopyrimidin-2-yl)phenoxy]methyl}-4,4-difluorocyclohexyl]methanesulfonamide | 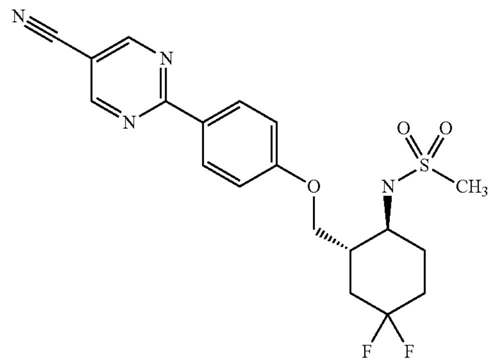 [SMILES: CS(=O)(=O)N[C@H]1CCC(F)(F)C[C@@H]1COc1ccc(-c2ncc(C#N)cn2)cc1] | | 422.8 |
| 260 | N-[(1SR,2SR)-2-{[4-(5-cyanopyridin-2-yl)phenoxy]methyl}-4,4-difluorocyclohexyl]methanesulfonamide | 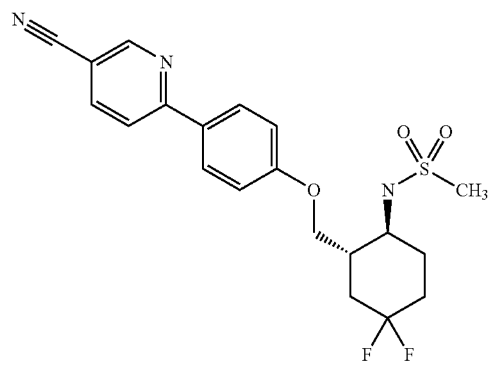 [SMILES: CS(=O)(=O)N[C@H]1CCC(F)(F)C[C@@H]1COc1ccc(-c2ccc(C#N)cn2)cc1] | | 422.2 |
| 261 | N-[(3RS,4SR)-3-{[4-(5-chloro-1,3-thiazol-2-yl)phenoxy]methyl}tetrahydro-2H-pyran-4-yl]ethanesulfonamide | 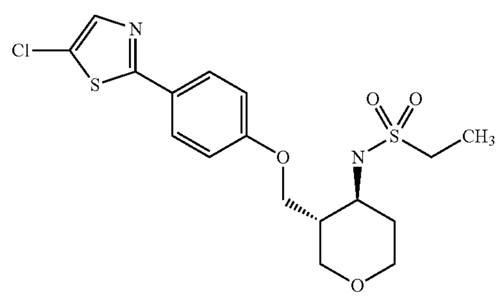 [SMILES: CCS(=O)(=O)N[C@H]1CCOC[C@@H]1COc1ccc(-c2ncc(Cl)s2)cc1] | | 417.1 |
| 262 | N-[(3RS,4SR)-3-{[4-(5-chloro-3-fluoropyridin-2-yl)phenoxy]methyl}tetrahydro-2H-pyran-4-yl]cyclopropanesulfonamide | 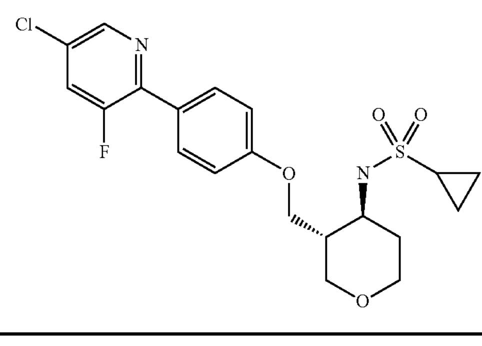 | | 441.1 |

TABLE 1-27

| Ex. No. | IUPAC Name | Structure | Salt | MS |
|---|---|---|---|---|
| 263 | N-[(3RS,4SR)-3-{[4-(2-methyl-1,3-thiazol-4-yl)phenoxy]methyl}tetrahydro-2H-pyran-4-yl]methanesulfonamide | 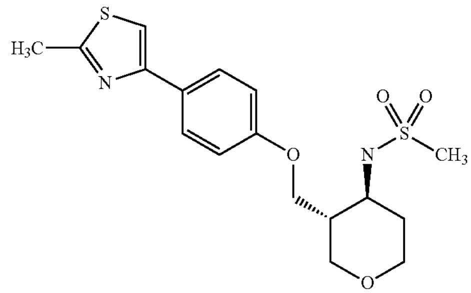 | | 383.1 |
| 264 | N-[(3R,4S)-4-{[2-fluoro-4-(5-fluoropyridin-2-yl)phenoxy]methyl}tetrahydro-2H-pyran-3-yl]cyclopropanesulfonamide | 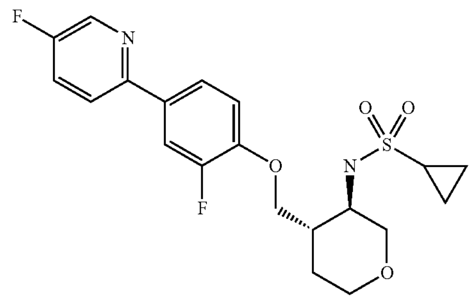 [SMILES: O=S(=O)(N[C@H]1COCC[C@@H]1COc1ccc(-c2ccc(F)cn2)cc1F)C1CC1] | | 425.1 |
| 265 | N-[(3R,4S)-3-({4-[4-(trifluoromethyl)-1H-pyrazol-1-yl]phenoxy}methyl)tetrahydro-2H-pyran-4-yl]methanesulfonamide | 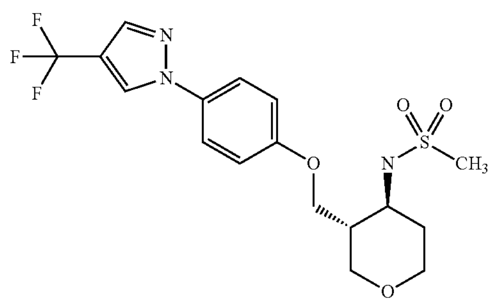 [SMILES: CS(=O)(=O)N[C@H]1CCOC[C@@H]1COc1ccc(-n2cc(C(F)(F)F)cn2)cc1] | | 420.1 |
| 266 | N-[(3S,4R)-3-{[4-(5-chloropyridin-2-yl)-2-fluorophenoxy]methyl}tetrahydro-2H-pyran-4-yl]methanesulfonamide or N-[(3R,4S)-3-{[4-(5-chloropyridin-2-yl)-2-fluorophenoxy]methyl}tetrahydro-2H-pyran-4-yl]methanesulfonamide | 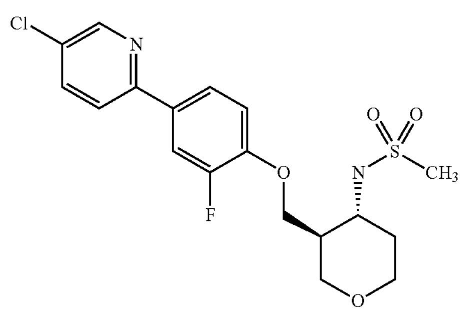 [SMILES: CS(=O)(=O)N[C@@H]1CCOC[C@H]1COc1ccc(-c2ccc(Cl)cn2)cc1F] | | 414.9 |
| 267 | N-[(1S,2S)-4,4-difluoro-2-{[4-(1-methyl-2-oxo-1,2-dihydropyridin-3-yl)phenoxy]methyl}cyclohexyl]ethanesulfonamide | 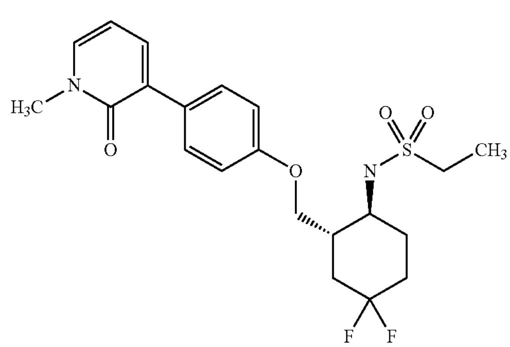 [SMILES: CCS(=O)(=O)N[C@H]1CCC(F)(F)C[C@@H]1COc1ccc(-c2cccn(C)c2=O)cc1] | | 441.1 |

TABLE 1-27-continued

| Ex. No. | IUPAC Name | Structure | Salt | MS |
|---|---|---|---|---|
| 268 | N-[(1S,2S)-2-{[4-(5-cyanopyridin-2-yl)phenoxy]methyl}-4,4-difluorocyclohexyl]methanesulfonamide | 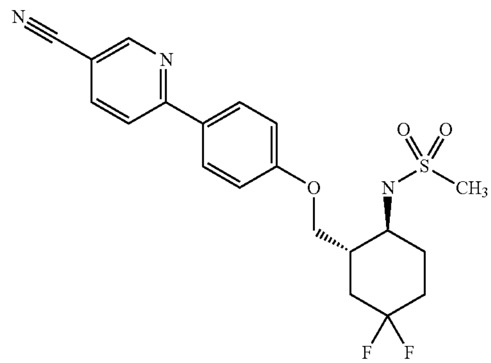 [SMILES: CS(=O)(=O)N[C@H]1CCC(F)(F)C[C@@H]1COc1ccc(-c2ccc(C#N)cn2)cc1] | | 421.9 |
| 269 | N-[(3R,4S)-3-{[4-(4-chloro-1H-pyrazol-1-yl)phenoxy]methyl}tetrahydro-2H-pyran-4-yl]methanesulfonamide | 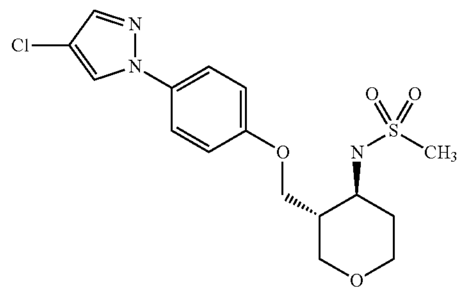 [SMILES: CS(=O)(=O)N[C@H]1CCOC[C@@H]1COc1ccc(-n2cc(Cl)cn2)cc1] | | 386.1 |
| 270 | N-[(3RS,4SR)-3-{[4-(4-chloro-1H-pyrazol-1-yl)phenoxy]methyl}tetrahydro-2H-pyran-4-yl]methanesulfonamide | 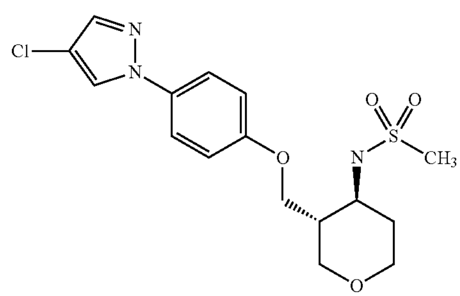 [SMILES: CS(=O)(=O)N[C@H]1CCOC[C@@H]1COc1ccc(-n2cc(Cl)cn2)cc1] | | 386.0 |
| 271 | N-[(3RS,4SR)-3-{[4-(4-chloro-1H-pyrazol-1-yl)phenoxy]methyl}tetrahydro-2H-pyran-4-yl]cyclopropanesulfonamide | 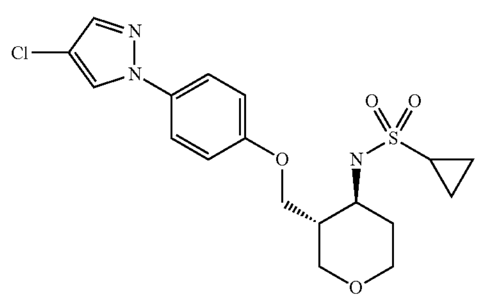 [SMILES: O=S(=O)(N[C@H]1CCOC[C@@H]1COc1ccc(-n2cc(Cl)cn2)cc1)C1CC1] | | 412.1 |

TABLE 1-28

| Ex. No. | IUPAC Name | Structure | Salt | MS |
|---|---|---|---|---|
| 272 | N-[(3RS,4SR)-3-{[4-(4-methyl-1H-pyrazol-1-yl)phenoxy]methyl}tetrahydro-2H-pyran-4-yl]cyclopropanesulfonamide | 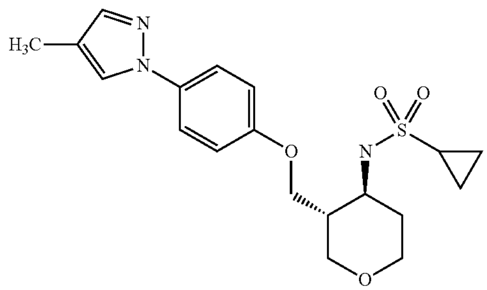 [SMILES: Cc1cnn(-c2ccc(OC[C@H]3COCC[C@@H]3NS(=O)(=O)C3CC3)cc2)c1] | | 392.2 |
| 273 | N-[(3RS,4SR)-3-[(4-acetylphenoxy)methyl]tetrahydro-2H-pyran-4-yl}methanesulfonamide | 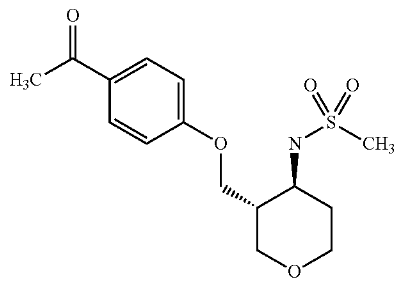 [SMILES: CC(=O)c1ccc(OC[C@H]2COCC[C@@H]2NS(C)(=O)=O)cc1] | | 328.1 |
| 274 | N-{(3RS,4SR)-3-[(4-acetylphenoxy)methyl]tetrahydro-2H-pyran-4-yl}-2,2,2-trifluoromethanesulfonamide | 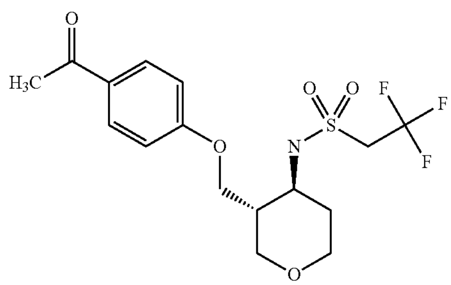 [SMILES: CC(=O)c1ccc(OC[C@H]2COCC[C@@H]2NS(=O)(=O)CC(F)(F)F)cc1] | | 396.1 |
| 275 | N-[(3S,4R)-3-{[4-(5-chloropyridin-2-yl)phenoxy]methyl}tetrahydro-2H-pyran-4-yl]ethanesulfonamide or N-[(3R,4S)-3-{[4-(5-chloropyridin-2-yl)phenoxy]methyl}tetrahydro-2H-pyran-4-yl]ethanesulfonamide | 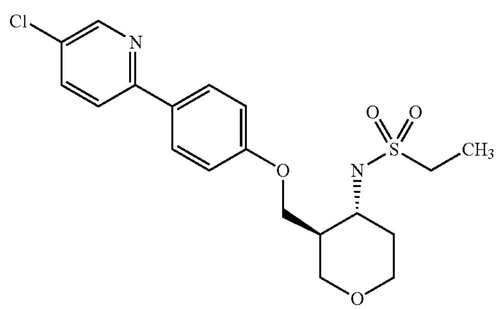 [SMILES: CCS(=O)(=O)N[C@@H]1CCOC[C@H]1COc1ccc(-c2ccc(Cl)cn2)cc1] | | 411.1 |
| 276 | N-[(1S,2S)-4,4-difluoro-2-{[4-(4-methyl-1H-pyrazol-1-yl)phenoxy]methyl}cyclohexyl]methanesulfonamide | 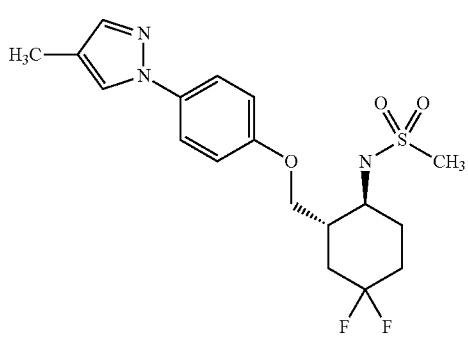 | | 400.3 |

TABLE 1-28-continued

| Ex. No. | IUPAC Name | Salt | MS |
|---|---|---|---|
| 277 | N-[(3R,4S)-3-{[4-(4-chloro-1H-pyrazol-1-yl)phenoxy]methyl}tetrahydro-2H-pyran-4-yl]cyclopropanesulfonamide | | 412.1 |
| 278 | N-[(3R,4S)-3-{[(2'-fluorobiphenyl-4-yl}oxy]methyl}tetrahydro-2H-pyran-4-yl]methanesulfonamide | | 378.1 |
| 279 | N'-[(3RS,4SR)-3-{[4-(4-chloro-1H-pyrazol-1-yl)phenoxy]methyl}tetrahydro-2H-pyran-4-yl]-N,N-dimethylsulfamide | | 415.1 |
| 280 | 1,1,1-trifluoro-N-[(3RS,4SR)-3-{[4-(4-methyl-1H-pyrazol-1-yl)phenoxy]methyl}tetrahydro-2H-pyran-4-yl]methanesulfonamide | | 420.1 |

TABLE 1-29

| Ex. No. | IUPAC Name | Salt | MS |
|---|---|---|---|
| 281 | N-[(3RS.4SR)-3-{[4-(1,5-dimethyl-1H-pyrazol-3-yl)phenoxy]methyl}tetrahydro-2H-pyran-4-yl]methanesulfonamide | | 380.2 |

TABLE 1-29-continued

| Ex. No. | IUPAC Name | Salt | MS |
|---|---|---|---|
| 282 | 1,5-anhydro-4-[(cyclopropylsulfonyl)amino]-2,3,4-trideoxy-6-O-[4-(5-fluoropyridin-2-yl)phenyl]-D-erythro-hexitol | | 407.2 |
| 283 | N-[(3R,4S)-4-{[4-(5-fluoropyrimidin-2-yl)phenoxy]methyl}tetrahydro-2H-pyran-3-yl]methanesulfonamide | | 382.1 |
| 284 | N-[(3R,4S)-4-{[4-(5-chloropyrimidin-2-yl)phenoxy]methyl}tetrahydro-2H-pyran-3-yl]methanesulfonamide | | 398.1 |
| 285 | N-[(3RS,4SR)-3-{[4-(4-chloro-1H-pyrazol-1-yl)-2-fluorophenoxy]methyl}tetrahydro-2H-pyran-4-yl]ethanesulfonamide | | 418.1 |
| 286 | N-[(3RS,4SR)-3-{[2-fluoro-4-(4-methyl-1H-pyrazol-1-yl)phenoxy]methyl}tetrahydro-2H-pyran-4-yl]ethanesulfonamide | | 399.0 |

TABLE 1-29-continued

| Ex. No. | IUPAC Name | Structure | Salt | MS |
|---|---|---|---|---|
| 287 | N-[(3RS,4SR)-3-{[3-fluoro-4-(4-methyl-1H-pyrazol-1-yl)phenoxy]methyl}tetrahydro-2H-pyran-4-yl]ethanesulfonamide | 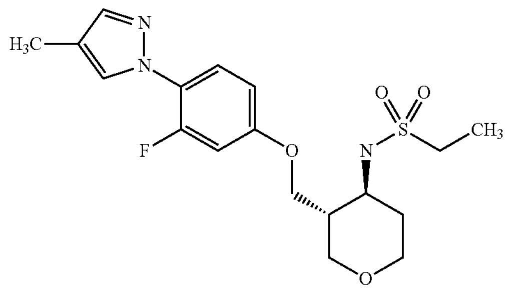 [SMILES: CCS(=O)(=O)N[C@H]1CCOC[C@@H]1COc1ccc(-n2cc(C)cn2)c(F)c1] | | 394.0 |
| 288 | N-[(3R,4S)-3-{[4-(4-chloro-1H-pyrazol-1-yl)-3-fluorophenoxy]methyl}tetrahydro-2H-pyran-4-yl]methanesulfonamide | 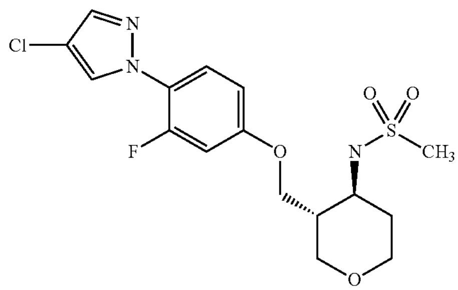 [SMILES: CS(=O)(=O)N[C@H]1CCOC[C@@H]1COc1ccc(-n2cc(Cl)cn2)c(F)c1] | | 404.1 |
| 289 | N-[(3R,4S)-3-{[4-(4-chloro-1H-pyrazol-1-yl)-2,5-difluorophenoxy]methyl}tetrahydro-2H-pyran-4-yl]ethanesulfonamide | 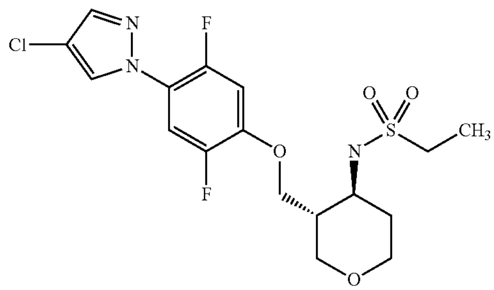 [SMILES: CCS(=O)(=O)N[C@H]1CCOC[C@@H]1COc1cc(F)c(-n2cc(Cl)cn2)cc1F] | | 436.1 |
| 290 | N-[(3R,4S)-3-{[4-(4-chloro-1H-pyrazol-1-yl)-3,5-difluorophenoxy]methyl}tetrahydro-2H-pyran-4-yl]methanesulfonamide | 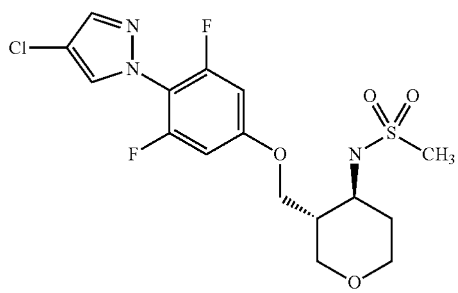 [SMILES: CS(=O)(=O)N[C@H]1CCOC[C@@H]1COc1cc(F)c(-n2cc(Cl)cn2)c(F)c1] | | 422.1 |

TABLE 1-30

| Ex. No. | IUPAC Name | Structure | Salt | MS |
|---|---|---|---|---|
| 291 | N-[(3R,4S)-3-{[4-(4-chloro-1H-pyrazol-1-yl)-2-fluorophenoxy]methyl}tetrahydro-2H-pyran-4-yl]methanesulfonamide | 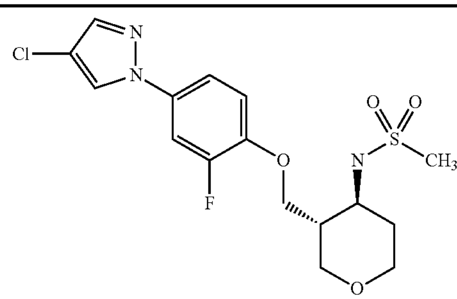 | | 404.2 |

TABLE 1-30-continued

| Ex. No. | IUPAC Name | Structure | Salt | MS |
|---|---|---|---|---|
| 292 | N-[(3RS,4SR)-3-{[4-(1,3-thiazol-2-yl)phenoxy]methyl}tetrahydro-2H-pyran-4-yl]ethanesulfonamide | 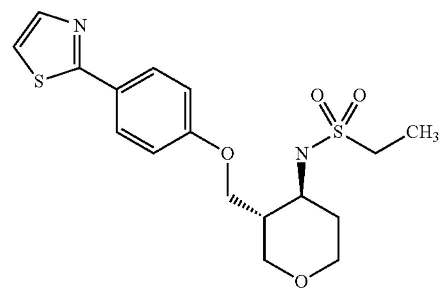 [SMILES: CCS(=O)(=O)N[C@H]1CCOC[C@@H]1COc1ccc(-c2nccs2)cc1] | | 383.1 |
| 293 | N-[(3RS,4SR)-3-{[4-(6-chloropyridin-3-yl)phenoxy]methyl}tetrahydro-2H-pyran-4-yl]ethanesulfonamide | 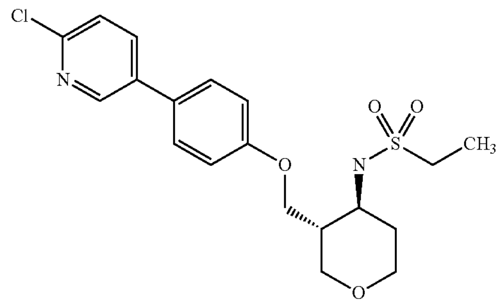 [SMILES: CCS(=O)(=O)N[C@H]1CCOC[C@@H]1COc1ccc(-c2ccc(Cl)nc2)cc1] | | 411.1 |
| 294 | N-[(3RS,4SR)-3-{[4-(5-methylpyridin-2-yl)phenoxy]methyl}tetrahydro-2H-pyran-4-yl]ethanesulfonamide | 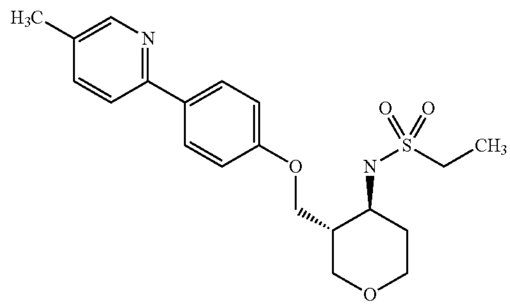 [SMILES: CCS(=O)(=O)N[C@H]1CCOC[C@@H]1COc1ccc(-c2ccc(C)cn2)cc1] | | 391.1 |
| 295 | N-[(3RS,4SR)-3-{[4-(2-methyl-1,3-thiazol-5-yl)phenoxy]methyl}tetrahydro-2H-pyran-4-yl]ethanesulfonamide | 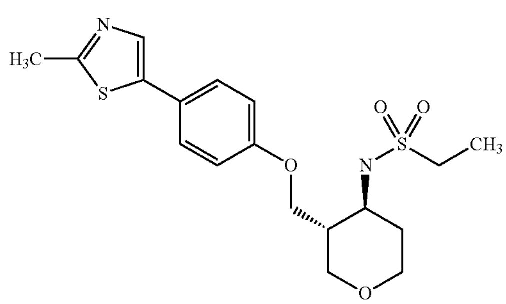 [SMILES: CCS(=O)(=O)N[C@H]1CCOC[C@@H]1COc1ccc(-c2cnc(C)s2)cc1] | | 397.1 |
| 296 | N-[(3RS,4SR)-3-{[4-(5-chloropyridin-2-yl)-3-fluorophenoxy)methyl}tetrahydro-2H-pyran-4-yl]ethanesulfonamide | 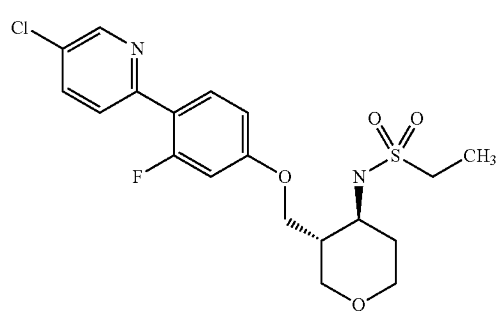 [SMILES: CCS(=O)(=O)N[C@H]1CCOC[C@@H]1COc1ccc(-c2ccc(Cl)cn2)c(F)c1] | | 429.1 |

TABLE 1-30-continued

| Ex. No. | IUPAC Name | Structure | Salt | MS |
|---|---|---|---|---|
| 297 | N-[(3R,4S)-3-{[4-(5-cyanopyridin-2-yl)phenoxy]methyl}tetrahydro-2H-pyran-4-yl]ethanesulfonamide | 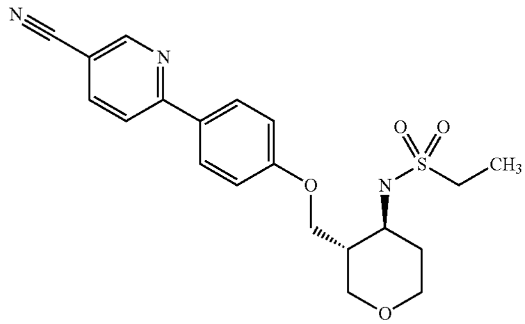 [SMILES: CCS(=O)(=O)N[C@H]1CCOC[C@@H]1COc1ccc(-c2ccc(C#N)cn2)cc1] | | 402.1 |
| 298 | N-[(3R,4S)-3-{[2,3-difluoro-4-(5-fluoropyridin-2-yl)phenoxy]methyl}tetrahydro-2H-pyran-4-yl]methanesulfonamide | 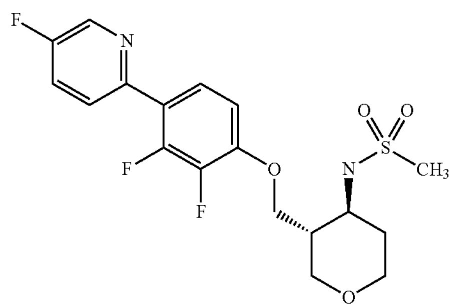 [SMILES: CS(=O)(=O)N[C@H]1CCOC[C@@H]1COc1ccc(-c2ccc(F)cn2)c(F)c1F] | | 417.1 |
| 299 | N-[(3R,4S)-4-{[4-(5-chloro-3-fluoropyridin-2-yl)phenoxy]methyl}tetrahydro-2H-pyran-3-yl]ethanesulfonamide | 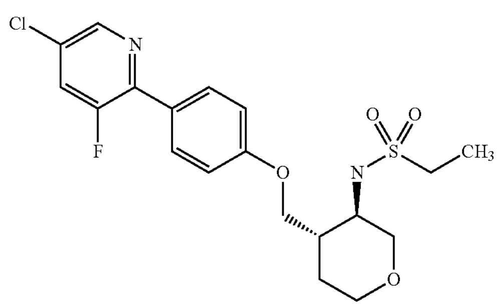 [SMILES: CCS(=O)(=O)N[C@H]1COCC[C@@H]1COc1ccc(-c2ncc(Cl)cc2F)cc1] | | 429.1 |
| 300 | N-[(3R,4S)-3-{[4-(tetrahydro-2H-pyran-4-yl)phenoxy]methyl}tetrahydro-2H-pyran-4-yl]methanesulfonamide | 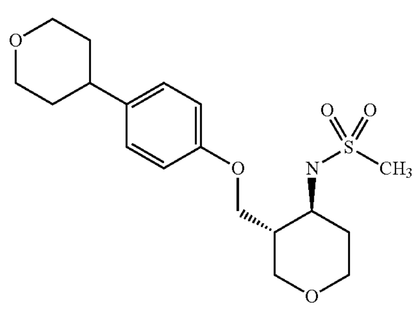 | | 369.9 |

TABLE 1-31

| Ex. No. | IUPAC Name | Structure | Salt | MS |
|---|---|---|---|---|
| 301 | N-[(3R,4S)-3-{[4-(5-chloropyridin-2-yl)-2-fluorophenoxy]methyl}tetrahydro-2H-pyran-4-yl]methanesulfonamide or N-[(3S,4R)-3-{[4-(5-chloropyridin-2-yl)-2-fluorophenoxy]methyl}tetrahydro-2H-pyran-4-yl]methanesulfonamide | 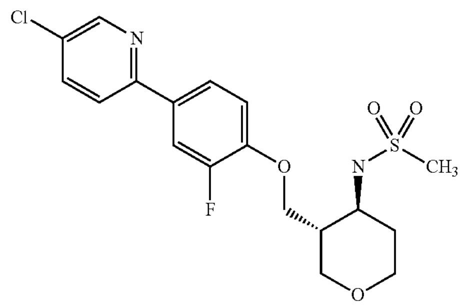 [SMILES: CS(=O)(=O)N[C@H]1CCOC[C@@H]1COc1ccc(-c2ccc(Cl)cn2)cc1F] | | 414.9 |
| 302 | N-[(3RS,4SR)-3-{[4-(4-ethyl-1H-pyrazol-1-yl)phenoxy]methyl}tetrahydro-2H-pyran-4-yl]ethanesulfonamide | 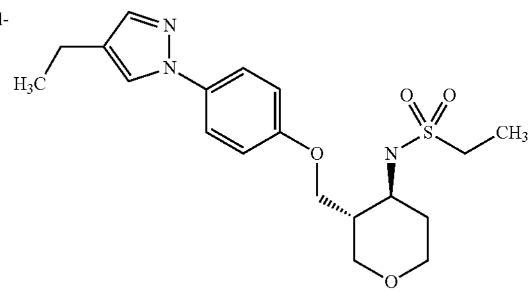 | | 394.2 |
| 303 | N-[(3RS,4SR)-3-{[4-(3,5-difluoropyridin-2-yl)phenoxy]methyl}tetrahydro-2H-pyran-4-yl]methanesulfonamide | 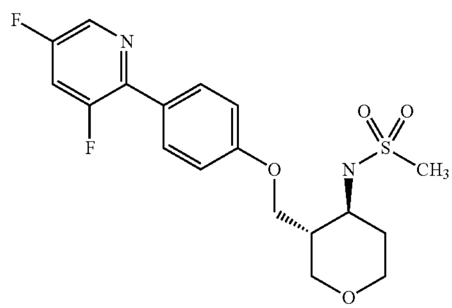 [SMILES: CS(=O)(=O)N[C@H]1CCOC[C@@H]1COc1ccc(-c2ncc(F)cc2F)cc1] | | 399.2 |
| 304 | N-[(3RS,4SR)-3-{[4-(3,5-difluoropyridin-2-yl)phenoxy]methyl}tetrahydro-2H-pyran-4-yl]ethanesulfonamide | 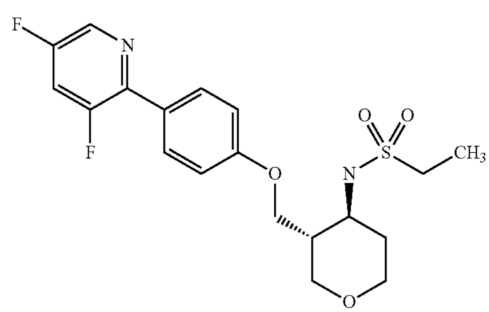 [SMILES: CCS(=O)(=O)N[C@H]1CCOC[C@@H]1COc1ccc(-c2ncc(F)cc2F)cc1] | | 413.2 |
| 305 | N-[(3RS,4SR)-3-{[2-fluoro-4-(5-fluoropyridin-2-yl)phenoxy]methyl}tetrahydro-2H-pyran-4-yl]methanesulfonamide | 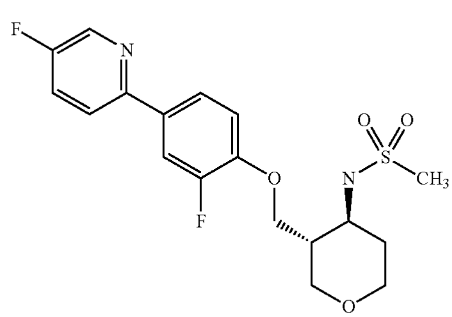 [SMILES: CS(=O)(=O)N[C@H]1CCOC[C@@H]1COc1ccc(-c2ccc(F)cn2)cc1F] | | 399.1 |

TABLE 1-31-continued

| Ex. No. | IUPAC Name | Structure | Salt | MS |
|---|---|---|---|---|
| 306 | N-[(3RS,4SR)-3-{[2-fluoro-4-(5-fluoropyridin-2-yl)phenoxy]methyl}tetrahydro-2H-pyran-3-yl]ethanesulfonamide | 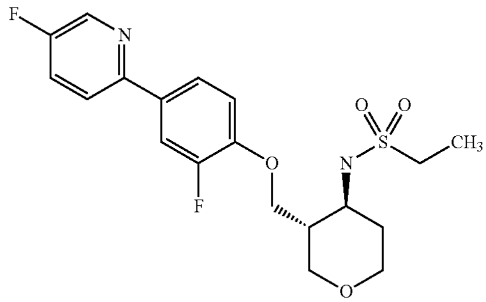 [SMILES: CCS(=O)(=O)N[C@H]1CCOC[C@@H]1COc1ccc(-c2ccc(F)cn2)cc1F] | | 413.1 |
| 307 | N-[(3RS,4SR)-3-{[2-fluoro-4-(5-fluoropyridin-2-yl)phenoxy]methyl}tetrahydro-2H-pyran-4-yl]cyclopropanesulfonamide | 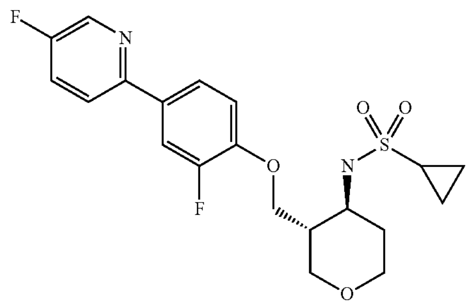 [SMILES: O=S(=O)(N[C@H]1CCOC[C@@H]1COc1ccc(-c2ccc(F)cn2)cc1F)C1CC1] | | 425.1 |
| 308 | N-[(3RS,4SR)-3-{[4-(5-chloro-1,3-thiazol-2-yl)phenoxy]methyl}tetrahydro-2H-pyran-4-yl]methanesulfonamide | 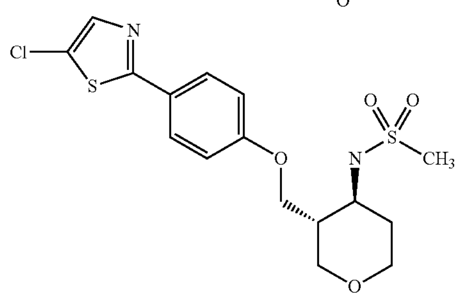 | | 403.1 |
| 309 | N-[(3RS,4SR)-3-{[3-fluoro-4-(5-fluoropyridin-2-yl)phenoxy]methyl}tetrahydro-2H-pyran-4-yl]methanesulfonamide | 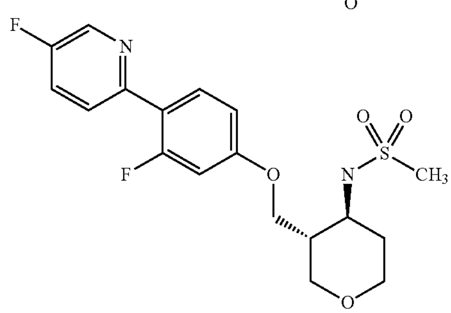 | | 399.1 |

TABLE 1-32

| Ex. No. | IUPAC Name | Structure | Salt | MS |
|---|---|---|---|---|
| 310 | N-[(3RS,4SR)-3-{[3-fluoro-4-(5-fluoropyridin-2-yl)phenoxy]methyl}tetrahydro-2H-pyran-4-yl]ethanesulfonamide | 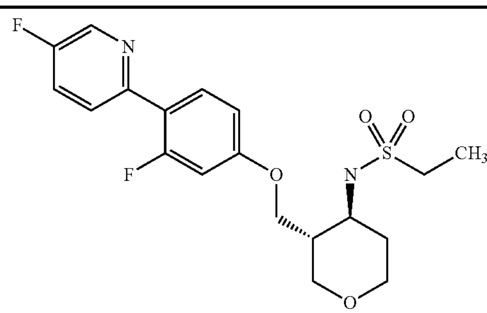 | | 413.1 |

TABLE 1-32-continued

| Ex. No. | IUPAC Name | Salt | MS |
|---|---|---|---|
| 311 | N-[(3RS,4SR)-3-{[4-(5-chloro-3-fluoropyridin-2-yl)phenoxy]methyl}tetrahydro-2H-pyran-4-yl]methanesulfonamide | | 415.1 |
| 312 | N-[(3R,4S)-3-{[4-(5-chloro-1,3-thiazol-2-yl)phenoxy]methyl}tetrahydro-2H-pyran-4-yl]cyclopropanesulfonamide | | 429.1 |
| 313 | N-[(3R,4S)-3-{[3-fluoro-4-(5-fluoropyridin-2-yl)phenoxy]methyl}tetrahydro-2H-pyran-4-yl]ethanesulfonamide or N-[(3S,4R)-3-{[3-fluoro-4-(5-fluoropyridin-2-yl)phenoxy]methyl}tetrahydro-2H-pyran-4-yl]ethanesulfonamide | | 413.0 |
| 314 | N-[(3R,4S)-3-{[4-(5-chloro-3-fluoropyridin-2-yl)phenoxy]methyl}tetrahydro-2H-pyran-4-yl]ethanesulfonamide or N-[(3S,4R)-3-{[4-(5-chloro-3-fluoropyridin-2-yl)phenoxy]methyl}tetrahydro-2H-pyran-4-yl]ethanesulfonamide | | 429.0 |
| 315 | N-[(3RS,4SR)-3-[(4-pyridin-3-ylphenoxy)methyl]tetrahydro-2H-pyran-4-yl}propane-1-sulfonamide | | 391.2 |

TABLE 1-32-continued

| Ex. No. | IUPAC Name | Structure | Salt | MS |
|---|---|---|---|---|
| 316 | N-[(3RS,4SR)-3-{[4-(1,3-thiazol-5-yl)phenoxy]methyl}tetrahydro-2H-pyran-4-yl]propane-1-sulfonamide | 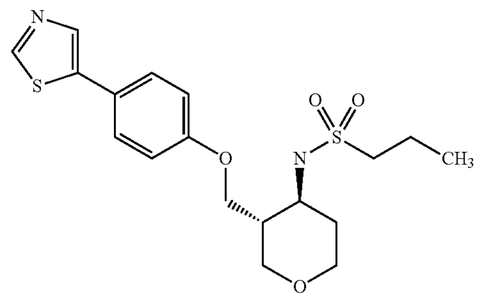 [SMILES: CCCS(=O)(=O)N[C@H]1CCOC[C@@H]1COc1ccc(-c2cncs2)cc1] | | 397.1 |
| 317 | N-[(3RS,4SR)-3-{[4-(1,3-thiazol-4-yl)phenoxy]methyl}tetrahydro-2H-pyran-4-yl]ethanesulfonamide | 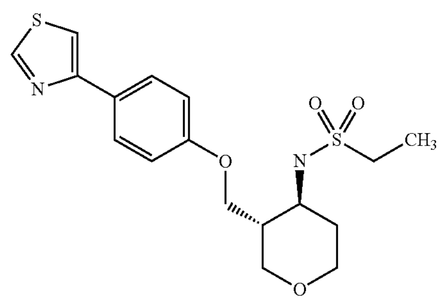 [SMILES: CCS(=O)(=O)N[C@H]1CCOC[C@@H]1COc1ccc(-c2cscn2)cc1] | | 383.1 |

TABLE 1-33

| Ex. No. | IUPAC Name | Structure | Salt | MS |
|---|---|---|---|---|
| 318 | N-{(3RS,4SR)-3-[(4-pyridin-2-ylphenoxy)methyl]tetrahydro-2H-pyran-4-yl}propane-1-sulfonamide | 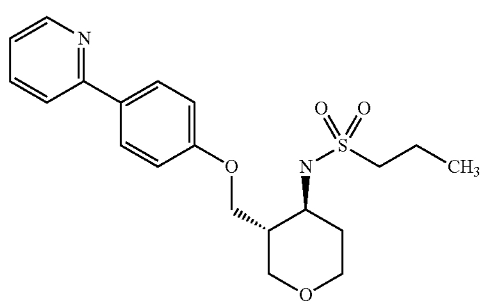 [SMILES: CCCS(=O)(=O)N[C@H]1CCOC[C@@H]1COc1ccc(-c2ccccn2)cc1] | | 391.2 |
| 319 | N-[(3RS,4SR)-3-({4-[6-(trifluoromethyl)pyridin-3-yl]phenoxy}methyl)tetrahydro-2H-pyran-4-yl]ethanesulfonamide | 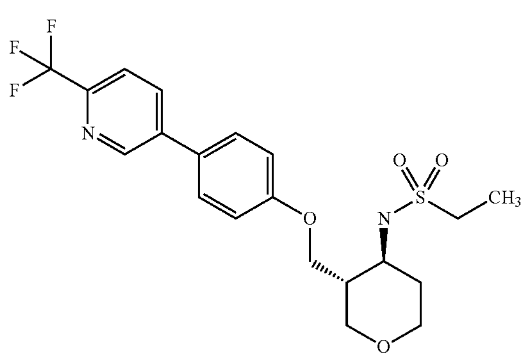 [SMILES: CCS(=O)(=O)N[C@H]1CCOC[C@@H]1COc1ccc(-c2ccc(C(F)(F)F)nc2)cc1] | | 445.1 |

| Ex. No. | IUPAC Name | Structure | Salt | MS |
|---|---|---|---|---|
| 320 | N-[(3RS,4SR)-3-({4-[4-(trifluoromethyl)pyridin-2-yl]phenoxy}methyl)tetrahydro-2H-pyran-4-yl]ethanesulfonamide | 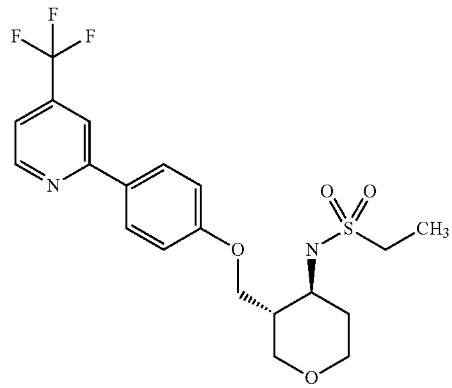 [SMILES: CCS(=O)(=O)N[C@H]1CCOC[C@@H]1COc1ccc(-c2cc(C(F)(F)F)ccn2)cc1] | | 445.2 |
| 321 | N-[(3RS,4SR)-3-{[4-(6-methylpyridin-3-yl)phenoxy]methyl}tetrahydro-2H-pyran-4-yl]ethanesulfonamide | 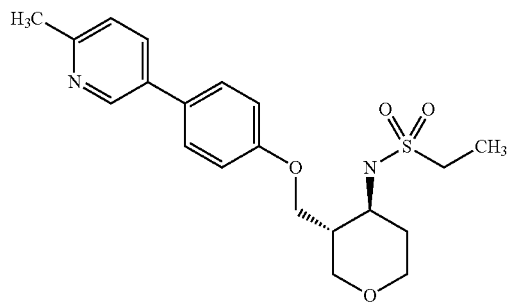 [SMILES: CCS(=O)(=O)N[C@H]1CCOC[C@@H]1COc1ccc(-c2ccc(C)nc2)cc1] | | 391.2 |
| 322 | N-[(3RS,4SR)-3-{[4-(2-methylpyridin-3-yl)phenoxy]methyl}tetrahydro-2H-pyran-4-yl]ethanesulfonamide | 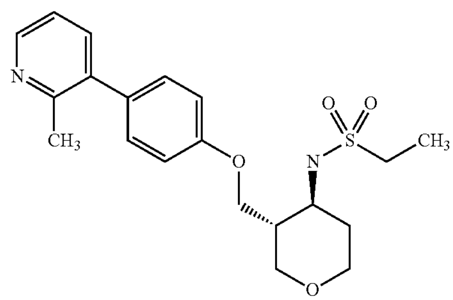 [SMILES: CCS(=O)(=O)N[C@H]1CCOC[C@@H]1COc1ccc(-c2cccnc2C)cc1] | | 390.9 |
| 323 | N-[(3RS,4SR)-3-{[4-(2-methyl-1,3-thiazol-4-yl)phenoxy]methyl}tetrahydro-2H-pyran-4-yl]ethanesulfonamide | 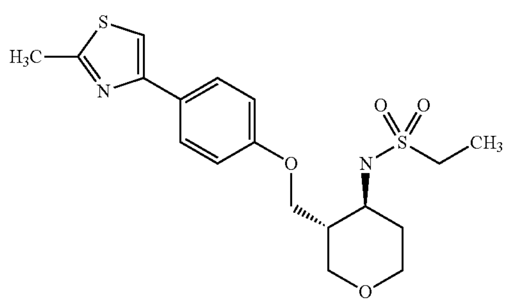 [SMILES: CCS(=O)(=O)N[C@H]1CCOC[C@@H]1COc1ccc(-c2csc(C)n2)cc1] | | 397.1 |
| 324 | N-[(3RS,4SR)-3-({4-[4-(1-methylethyl)-1H-pyrazol-1-yl]phenoxy}methyl)tetrahydro-2H-pyran-4-yl]ethanesulfonamide | 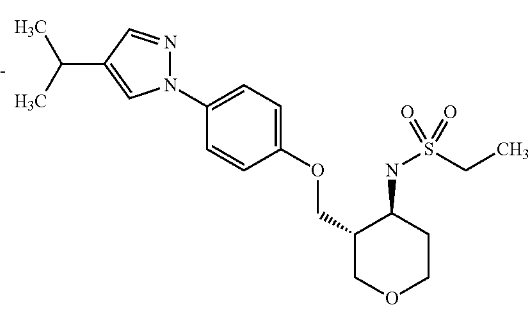 | | 408.2 |

TABLE 1-33-continued

| Ex. No. | IUPAC Name | Structure | Salt | MS |
|---|---|---|---|---|
| 325 | N-[(3RS,4SR)-3-({4-[4-(trifluoromethyl)-1H-pyrazol-1-yl]phenoxy}methyl)tetrahydro-2H-pyran-4-yl]ethanesulfonamide | 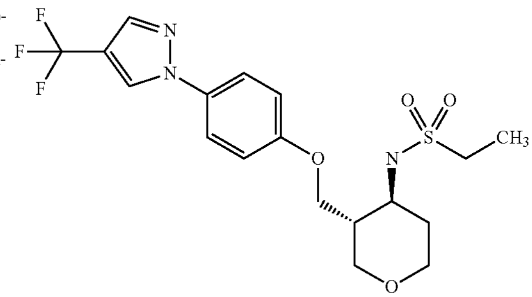 | | 434.1 |
| 326 | N-[(3RS,4SR)-3-{[4-(5-chloropyridin-2-yl)phenoxy]methyl}tetrahydro-2H-pyran-4-yl]ethanesulfonamide | 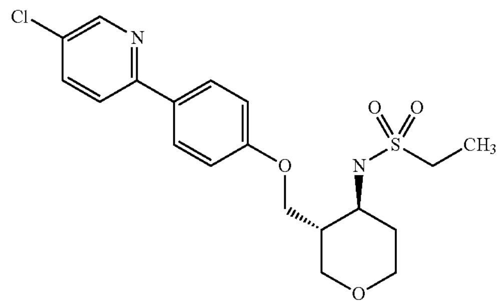 [SMILES: CCS(=O)(=O)N[C@H]1CCOC[C@@H]1COc1ccc(-c2ccc(Cl)cn2)cc1] | | 411.1 |
| 327 | N-[(3RS,4SR)-3-{[4-(4-methylpyridin-2-yl)phenoxy]methyl}tetrahydro-2H-pyran-4-yl]ethanesulfonamide | 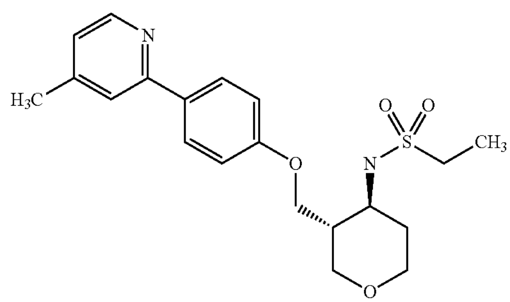 [SMILES: CCS(=O)(=O)N[C@H]1CCOC[C@@H]1COc1ccc(-c2cc(C)ccn2)cc1] | | 391.1 |

TABLE 1-34

| Ex. No. | IUPAC Name | Structure | Salt | MS |
|---|---|---|---|---|
| 328 | N-[(1SR,2SR)-2-{[4-(4-cyano-1H-pyrazol-1-yl)phenoxy]methyl}-4,4-difluorocyclohexyl]ethanesulfonamide | 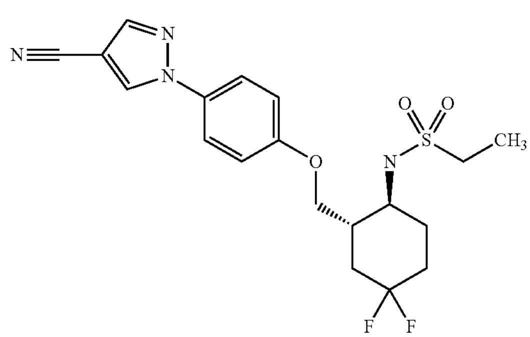 [SMILES: CCS(=O)(=O)N[C@H]1CCC(F)(F)C[C@@H]1COc1ccc(-n2cc(C#N)cn2)cc1] | | 425.1 |

TABLE 1-34-continued

| Ex. No. | IUPAC Name | Structure | Salt | MS |
|---|---|---|---|---|
| 329 | N-[(3RS,4SR)-3-{[4-(4-cyano-1H-pyrazol-1-yl)phenoxy]methyl}tetrahydro-2H-pyran-4-yl]ethanesulfonamide | 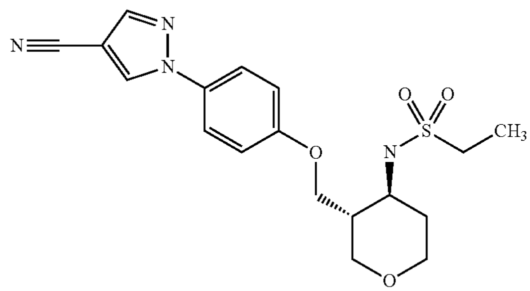 [SMILES: CCS(=O)(=O)N[C@H]1CCOC[C@@H]1COc1ccc(-n2cc(C#N)cn2)cc1] | | 391.1 |
| 330 | N-[(3RS,4SR)-3-{[4-(5-methyl-1,3-thiazol-2-yl))phenoxy]methyl}tetrahydro-2H-pyran-4-yl]ethanesulfonamide | 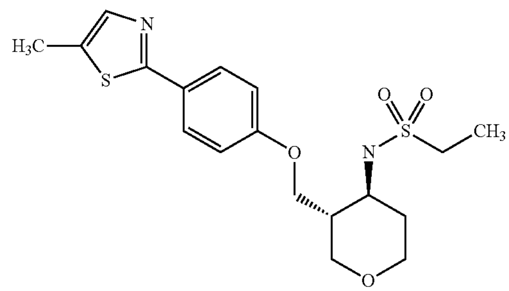 | | 397.2 |
| 331 | N-[(3RS,4SR)-3-{[4-(4-methyl-1,3-thiazol-2-yl)phenoxy]methyl}tetrahydro-2H-pyran-4-yl]ethanesulfonamide | 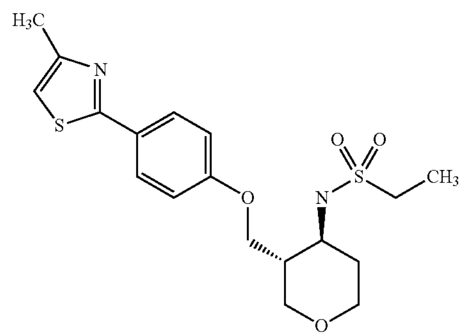 [SMILES: CCS(=O)(=O)N[C@H]1CCOC[C@@H]1COc1ccc(-c2nc(C)cs2)cc1] | | 397.1 |
| 332 | N-[(3RS,4SR)-3-{[4-(1-methyl-1H-pyrazol-4-yl)phenoxy]methyl}tetrahydro-2H-pyran-4-yl]ethanesulfonamide | 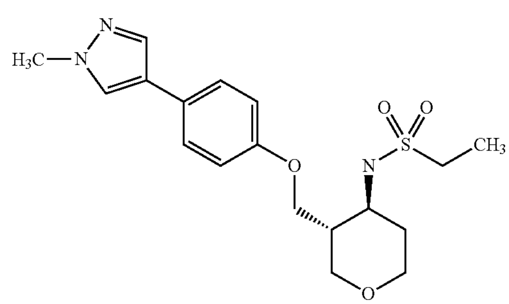 [SMILES: CCS(=O)(=O)N[C@H]1CCOC[C@@H]1COc1ccc(-c2cnn(C)c2)cc1] | | 380.2 |
| 333 | N-[(3RS,4SR)-3-{[4-(5-methyl-1,3-thiazol-2-yl)phenoxy]methyl}tetrahydro-2H-pyran-4-yl]methanesulfonamide | 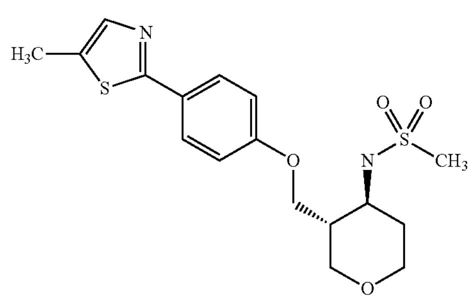 | | 383.1 |

TABLE 1-34-continued

| Ex. No. | IUPAC Name | Structure | Salt | MS |
|---|---|---|---|---|
| 334 | N-[(1SR,2SR)-2-{[4-(5-cyanopyridin-2-yl)phenoxy]methyl}-4,4-difluorocyclohexyl]ethanesulfonamide | 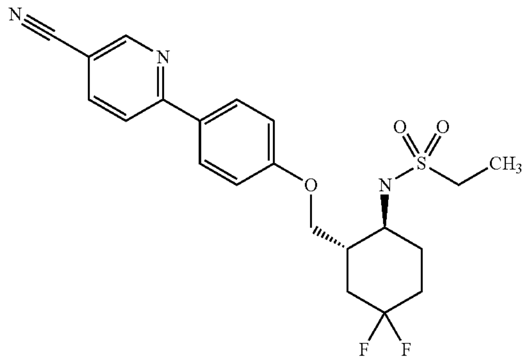 [SMILES: CCS(=O)(=O)N[C@H]1CCC(F)(F)C[C@@H]1COc1ccc(-c2ccc(C#N)cn2)cc1] | | 436.2 |
| 335 | N-[(3RS,4SR)-3-{[4-(5-fluoropyridin-2-yl)phenoxy]methyl}tetrahydro-2H-pyran-4-yl]methanesulfonamide | 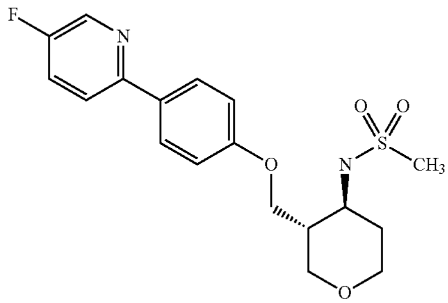 [SMILES: CS(=O)(=O)N[C@H]1CCOC[C@@H]1COc1ccc(-c2ccc(F)cn2)cc1] | | 381.2 |
| 336 | N-[(3RS,4SR)-3-{[4-(2-methyl-1,3-oxazol-4-yl)phenoxy]methyl}tetrahydro-2H-pyran-4-yl]ethanesulfonamide | 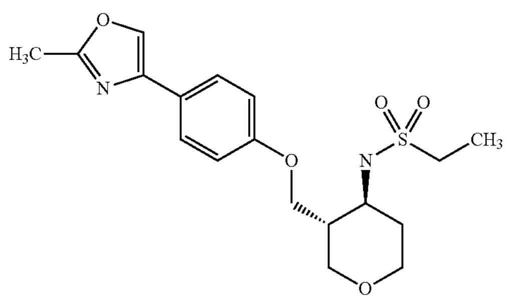 [SMILES: CCS(=O)(=O)N[C@H]1CCOC[C@@H]1COc1ccc(-c2coc(C)n2)cc1] | | 381.2 |
| 337 | N-[(3RS,4SR)-3-{[4-(2-methyl-1,3-oxazol-4-yl)phenoxy]methyl}tetrahydro-2H-pyran-4-yl]propane-1-sulfonamide | 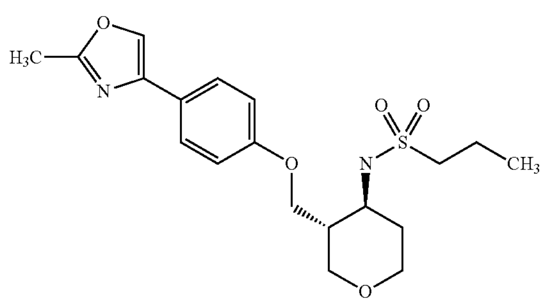 [SMILES: CCCS(=O)(=O)N[C@H]1CCOC[C@@H]1COc1ccc(-c2coc(C)n2)cc1] | | 395.2 |

TABLE 1-35

| Ex. No. | IUPAC Name | Structure | Salt | MS |
|---|---|---|---|---|
| 338 | 2,2,2-trifluoro-N-[(3RS,4SR)-3-{[4-(2-methyl-1,3-oxazol-4-yl)phenoxy]methyl}tetrahydro-2H-pyran-4-yl]ethanesulfonamide | 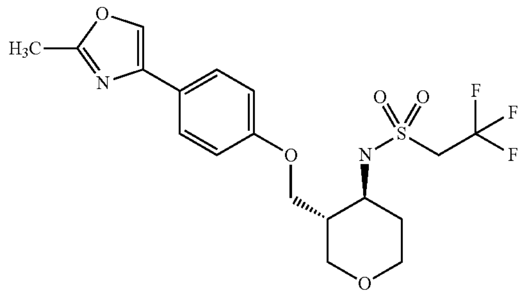 [SMILES: Cc1nc(-c2ccc(OC[C@H]3COCC[C@@H]3NS(=O)(=O)CC(F)(F)F)cc2)co1] | | 435.2 |
| 339 | N-[(3RS,4SR)-3-{[4-(5-methyl-1,3-oxazol-2-yl)phenoxy]methyl}tetrahydro-2H-pyran-4-yl]ethanesulfonamide | 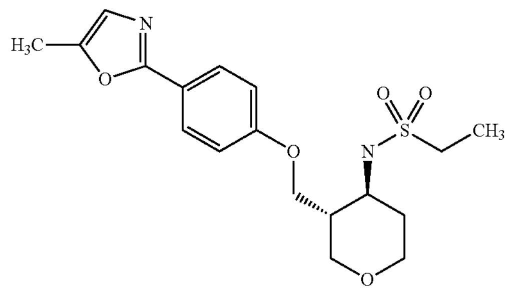 [SMILES: CCS(=O)(=O)N[C@H]1CCOC[C@@H]1COc1ccc(-c2ncc(C)o2)cc1] | | 381.2 |
| 340 | N-[(3RS,4SR)-3-{[4-(5-methyl-1,3-oxazol-2-yl)phenoxy]methyl}tetrahydro-2H-pyran-4-yl]propane-1-sulfonamide | 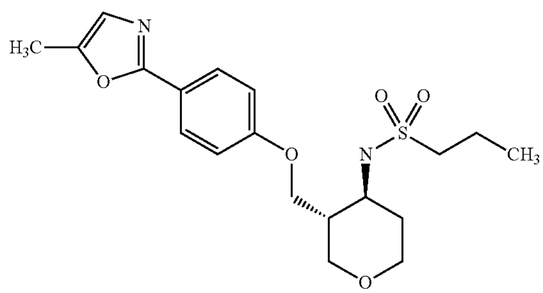 [SMILES: CCCS(=O)(=O)N[C@H]1CCOC[C@@H]1COc1ccc(-c2ncc(C)o2)cc1] | | 395.2 |
| 341 | N-[(3R,4S)-3-{[4-(4-ethyl-1H-pyrazol-1-yl)phenoxy]methyl}tetrahydro-2H-pyran-4-yl]ethanesulfonamide or N-[(3S,4R)-3-{[4-(4-ethyl-1H-pyrazol-1-yl)phenoxy]methyl}tetrahydro-2H-pyran-4-yl]ethanesulfonamide | 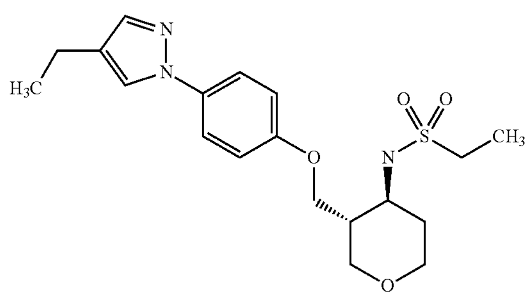 [SMILES: CCc1cnn(-c2ccc(OC[C@H]3COCC[C@@H]3NS(=O)(=O)CC)cc2)c1] | | 394.2 |
| 342 | N-[(3RS,4SR)-3-{[4-(4-ethyl-1H-pyrazol-1-yl)phenoxy]methyl}tetrahydro-2H-pyran-4-yl]methanesulfonamide | 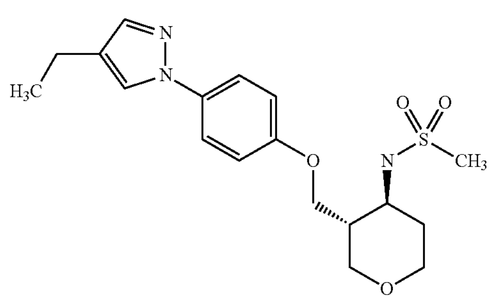 [SMILES: CCc1cnn(-c2ccc(OC[C@H]3COCC[C@@H]3NS(C)(=O)=O)cc2)c1] | | 380.2 |

TABLE 1-35-continued

| Ex. No. | IUPAC Name | Structure | Salt | MS |
|---|---|---|---|---|
| 343 | N-[(3RS,4SR)-3-{[4-(5-methylisoxazol-3-yl)phenoxy]methyl}tetrahydro-2H-pyran-4-yl]methanesulfonamide | 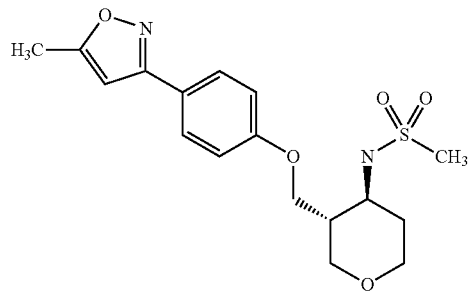 | | 367.2 |
| 344 | N-[(3RS,4SR)-3-{[4-(5-methylisoxazol-3-yl)phenoxy]methyl}tetrahydro-2H-pyran-4-yl]ethanesulfonamide | 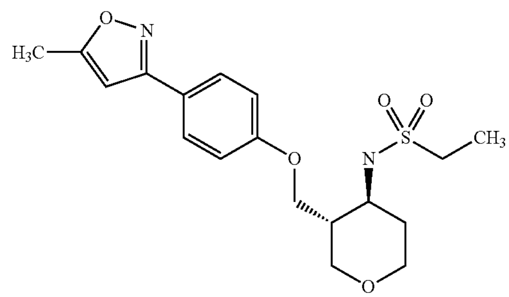 [SMILES: CCS(=O)(=O)N[C@H]1CCOC[C@@H]1COc1ccc(-c2cc(C)on2)cc1] | | 381.2 |
| 345 | N-[(3RS,4SR)-3-{[4-(5-methylisoxazol-3-yl)phenoxy]methyl}tetrahydro-2H-pyran-4-yl]cyclopropanesulfonamide | 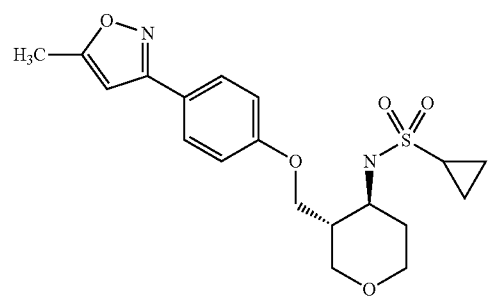 [SMILES: Cc1cc(-c2ccc(OC[C@H]3COCC[C@@H]3NS(=O)(=O)C3CC3)cc2)no1] | | 393.2 |
| 346 | N-[(3RS,4SR)-3-{[4-(4-ethyl-1H-pyrazol-1-yl)phenoxy]methyl}tetrahydro-2H-pyran-4-yl]cyclopropanesulfonamide | 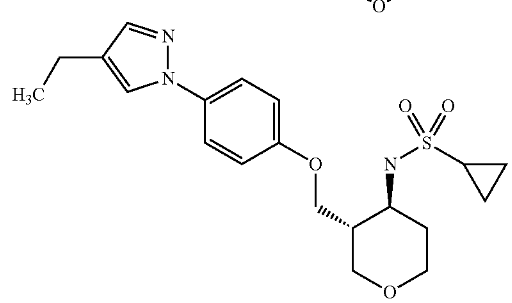 | | 406.2 |

TABLE 1-36

| Ex. No. | IUPAC Name | Structure | Salt | MS |
|---|---|---|---|---|
| 347 | N-[(3RS,4SR)-3-{[4-(1,3-dimethyl-1H-pyrazol-5-yl)phenoxy]methyl}tetrahydro-2H-pyran-4-yl]ethanesulfonamide | 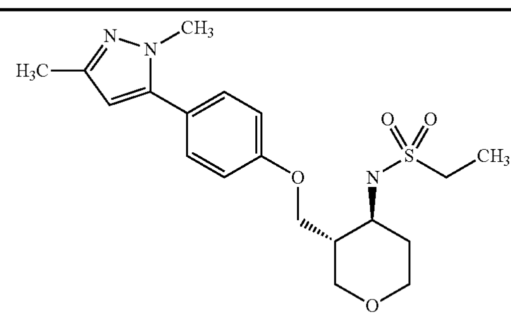 | | 394.2 |

TABLE 1-36-continued

| Ex. No. | IUPAC Name | Structure | Salt | MS |
|---|---|---|---|---|
| 348 | N-[(3RS,4SR)-3-({4-[6-(trifluoromethyl)pyridin-3-yl]phenoxy}methyl)tetrahydro-2H-pyran-4-yl]methanesulfonamide | 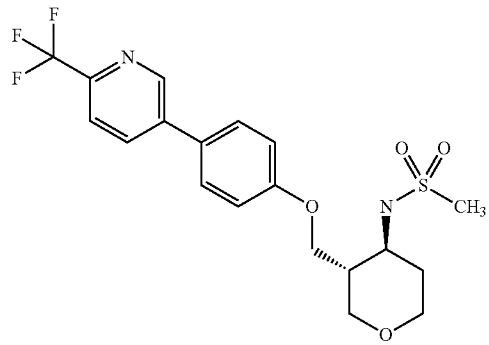 [SMILES: CS(=O)(=O)N[C@H]1CCOC[C@@H]1COc1ccc(-c2ccc(C(F)(F)F)nc2)cc1] | | 431.2 |
| 349 | N-[(3RS,4SR)-3-({4-[6-(trifluoromethyl)pyridin-3-yl]phenoxy}methyl)tetrahydro-2H-pyran-4-yl]cyclopropanesulfonamide | 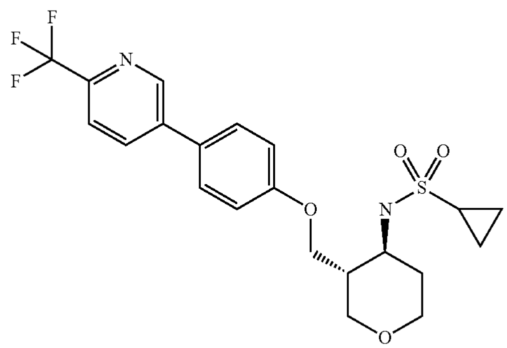 [SMILES: O=S(=O)(N[C@H]1CCOC[C@@H]1COc1ccc(-c2ccc(C(F)(F)F)nc2)cc1)C1CC1] | | 457.2 |
| 350 | N-[(3RS,4SR)-3-({4-[5-(trifluoromethyl)pyridin-2-yl]phenoxy}methyl)tetrahydro-2H-pyran-4-yl]methanesulfonamide | 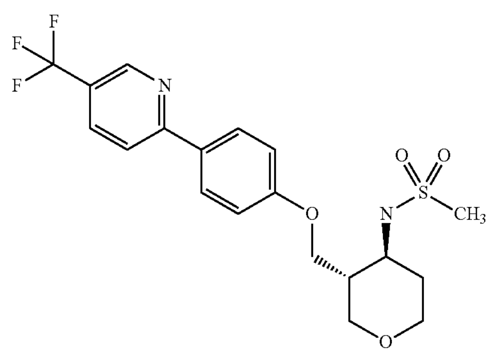 [SMILES: CS(=O)(=O)N[C@H]1CCOC[C@@H]1COc1ccc(-c2ccc(C(F)(F)F)cn2)cc1] | | 431.2 |
| 351 | N-[(3RS,4SR)-3-({4-[5-(trifluoromethyl)pyridin-2-yl]phenoxy}methyl)tetrahydro-2H-pyran-4-yl]ethanesulfonamide | 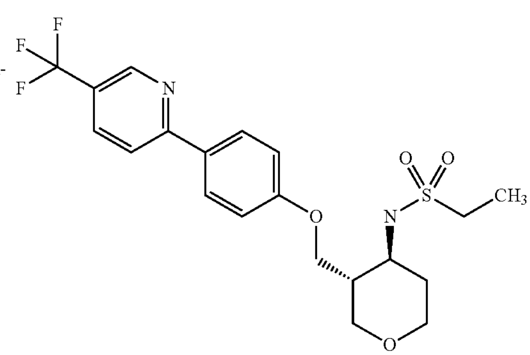 | | 445.2 |

TABLE 1-36-continued

| Ex. No. | IUPAC Name | Structure | Salt | MS |
|---|---|---|---|---|
| 352 | N-[(3RS,4SR)-3-({4-[2-(trifluoromethyl)-1,3-oxazol-4-yl]phenoxy}methyl)tetrahydro-2H-pyran-4-yl]methanesulfonamide | 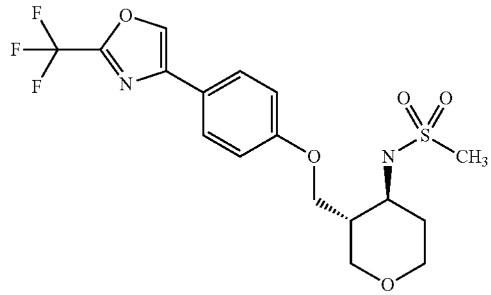 [SMILES: CS(=O)(=O)N[C@H]1CCOC[C@@H]1COc1ccc(-c2coc(C(F)(F)F)n2)cc1] | | ND |
| 353 | N-[(3RS,4SR)-3-({4-[2-(trifluoromethyl)-1,3-oxazol-4-yl]phenoxy}methyl)tetrahydro-2H-pyran-4-yl]ethanesulfonamide | 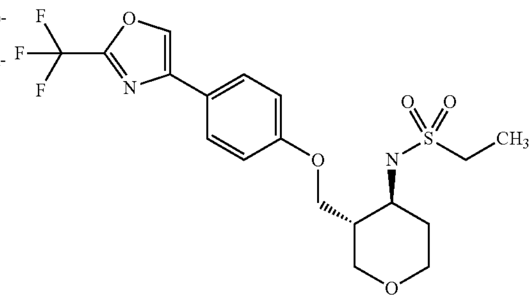 | | ND |
| 354 | N-[(3RS,4SR)-3-({4-[4-(trifluoromethyl)-1H-pyrazol-1-yl]phenoxy}methyl)tetrahydro-2H-pyran-4-yl]methanesulfonamide | 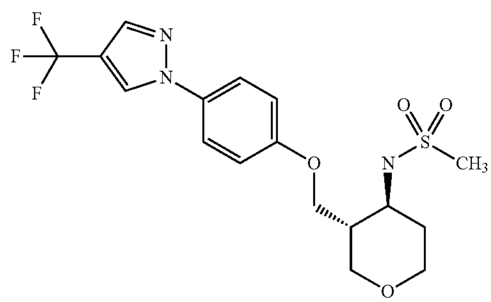 [SMILES: CS(=O)(=O)N[C@H]1CCOC[C@@H]1COc1ccc(-n2cc(C(F)(F)F)cn2)cc1] | | 420.2 |
| 355 | N-[(3RS,4SR)-3-({4-[4-(trifluoromethyl)-1H-pyrazol-1-yl]phenoxy}methyl)tetrahydro-2H-pyran-4-yl]cyclopropanesulfonamide | 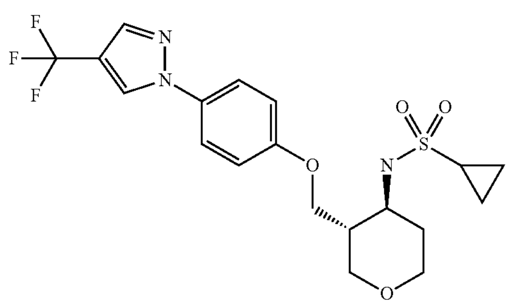 [SMILES: O=S(=O)(N[C@H]1CCOC[C@@H]1COc1ccc(-n2cc(C(F)(F)F)cn2)cc1)C1CC1] | | 446.2 |
| 356 | N-[(3RS,4SR)-3-{[4-(5-fluoro-3-methylpyridin-2-yl)phenoxy]methyl}tetrahydro-2H-pyran-4-yl]methanesulfonamide | 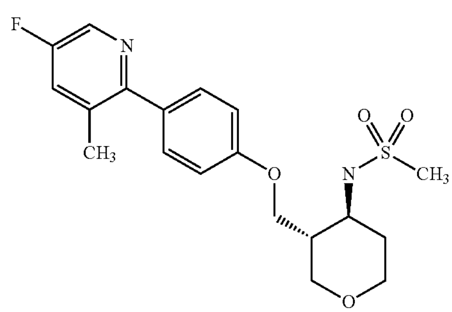 [SMILES: Cc1cc(F)cnc1-c1ccc(OC[C@H]2COCC[C@@H]2NS(C)(=O)=O)cc1] | | 395.1 |

TABLE 1-37

| Ex. No. | IUPAC Name | Structure | Salt | MS |
|---|---|---|---|---|
| 357 | N-[(3RS,4SR)-3-{[4-(5-fluoro-3-methylpyridin-2-yl)phenoxy]methyl}tetrahydro-2H-pyran-4-yl]ethanesulfonamide | 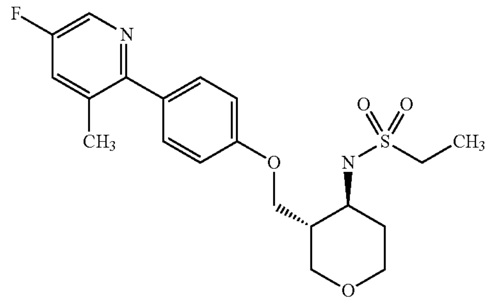 [SMILES: CCS(=O)(=O)N[C@H]1CCOC[C@@H]1COc1ccc(-c2ncc(F)cc2C)cc1] | | 409.1 |
| 358 | N-[(3RS,4SR)-3-{[4-(5-fluoro-3-methylpyridin-2-yl)phenoxy]methyl}tetrahydro-2H-pyran-4-yl]cyclopropanesulfonamide | 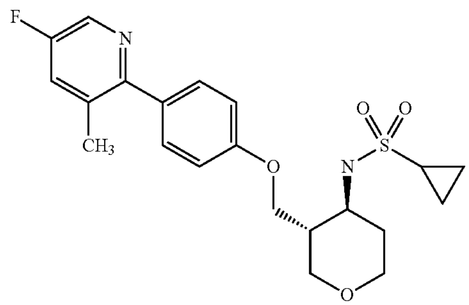 [SMILES: Cc1cc(F)cnc1-c1ccc(OC[C@H]2COCC[C@@H]2NS(=O)(=O)C2CC2)cc1] | | 421.1 |
| 359 | N-[(3RS,4SR)-3-({4-[2-(trifluoromethyl)-1,3-thiazol-4-yl]phenoxy}methyl)tetrahydro-2H-pyran-4-yl]methanesulfonamide | 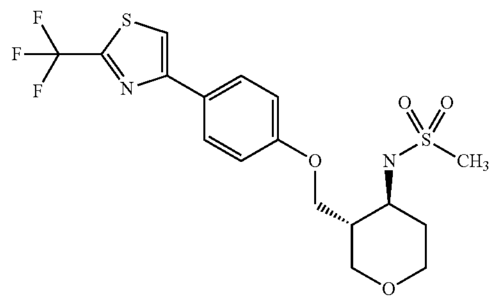 [SMILES: CS(=O)(=O)N[C@H]1CCOC[C@@H]1COc1ccc(-c2csc(C(F)(F)F)n2)cc1] | | 437.1 |
| 360 | N-[(3RS,4SR)-3-({4-[2-(trifluoromethyl)-1,3-thiazol-4-yl]phenoxy}methyl)tetrahydro-2H-pyran-4-yl]ethanesulfonamide | 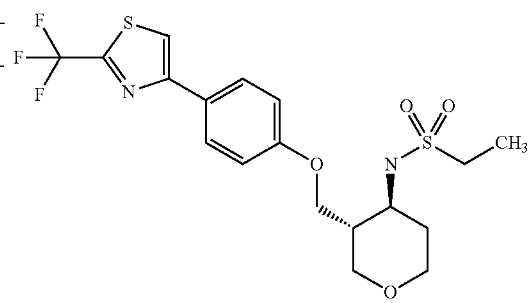 | | 451.1 |
| 361 | N-[(3RS,4SR)-3-({4-[2-(trifluoromethyl)-1,3-thiazol-4-yl]phenoxy}methyl)tetrahydro-2H-pyran-4-yl]cyclopropanesulfonamide | 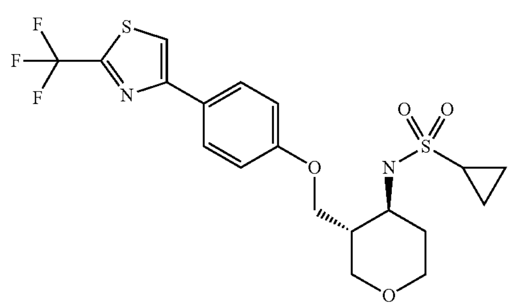 [SMILES: O=S(=O)(N[C@H]1CCOC[C@@H]1COc1ccc(-c2csc(C(F)(F)F)n2)cc1)C1CC1] | | 463.1 |

TABLE 1-37-continued

| Ex. No. | IUPAC Name | Structure | Salt | MS |
|---|---|---|---|---|
| 362 | N-[(3RS,4SR)-3-{[4-(3,5-difluoropyridin-2-yl)phenoxy]methyl}tetrahydro-2H-pyran-4-yl]cyclopropanesulfonamide | 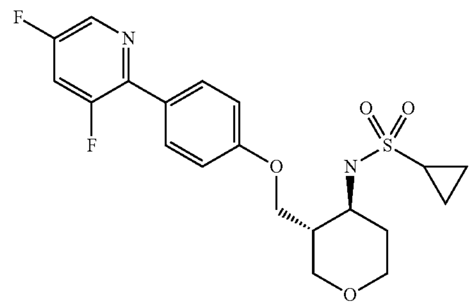 [SMILES: O=S(=O)(N[C@H]1CCOC[C@@H]1COc1ccc(-c2ncc(F)cc2F)cc1)C1CC1] | | 425.1 |
| 363 | N-[(3RS,4SR)-3-{[4-(5-chloro-1,3-thiazol-2-yl)phenoxy]methyl}tetrahydro-2H-pyran-4-yl]cyclopropanesulfonamide | 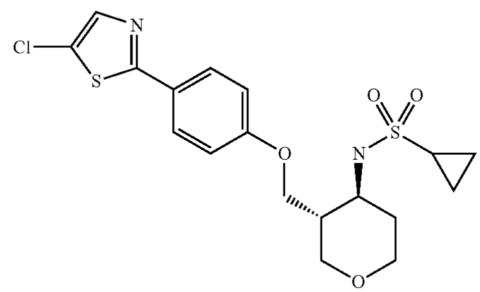 [SMILES: O=S(=O)(N[C@H]1CCOC[C@@H]1COc1ccc(-c2ncc(Cl)s2)cc1)C1CC1] | | 429.1 |
| 364 | N-[(3RS,4SR)-3-{[4-(5-chloropyridin-2-yl)-3-fluorophenoxy]methyl}tetrahydro-2H-pyran-4-yl]cyclopropanesulfonamide | 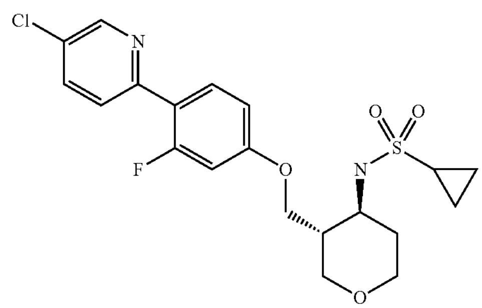 [SMILES: O=S(=O)(N[C@H]1CCOC[C@@H]1COc1ccc(-c2ccc(Cl)cn2)c(F)c1)C1CC1] | | 441.1 |
| 365 | N-[(3RS,4SR)-3-{[4-(5-chloropyridin-2-yl)-2-fluorophenoxy]methyl}tetrahydro-2H-pyran-4-yl]ethanesulfonamide | 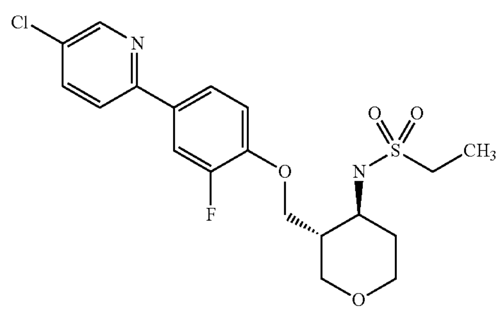 [SMILES: CCS(=O)(=O)N[C@H]1CCOC[C@@H]1COc1ccc(-c2ccc(Cl)cn2)cc1F] | | 429.1 |
| 366 | N-[(3RS,4SR)-3-{[4-(5-chloropyridin-2-yl)-2-fluorophenoxy]methyl}tetrahydro-2H-pyran-4-yl]cyclopropanesulfonamide | 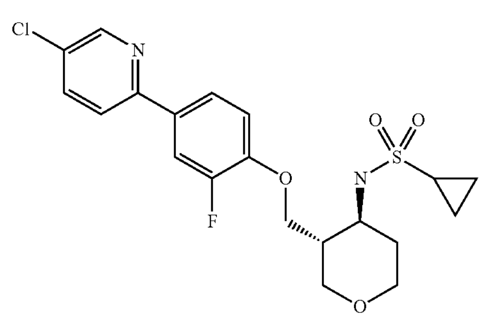 [SMILES: O=S(=O)(N[C@H]1CCOC[C@@H]1COc1ccc(-c2ccc(Cl)cn2)cc1F)C1CC1] | | 441.1 |

TABLE 1-38

| Ex. No. | IUPAC Name | Structure | Salt | MS |
|---|---|---|---|---|
| 367 | N-[(3RS,4SR)-3-{[(2'-cyano-4'-fluorobiphenyl-4-yl)oxy]methyl}tetrahydro-2H-pyran-4-yl]methanesulfonamide | 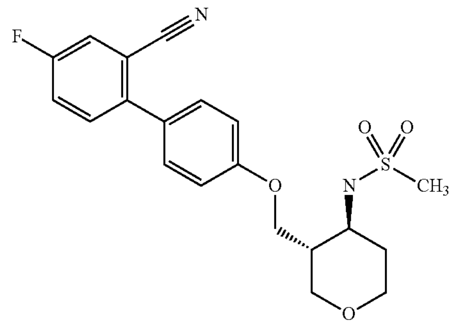 [SMILES: CS(=O)(=O)N[C@H]1CCOC[C@@H]1COc1ccc(-c2ccc(F)cc2C#N)cc1] | | 403.1 neg |
| 368 | N-[(3RS,4SR)-3-{[(2'-cyano-4'-fluorobiphenyl-4-yl)oxy]methyl}tetrahydro-2H-pyran-4-yl]ethanesulfonamide | 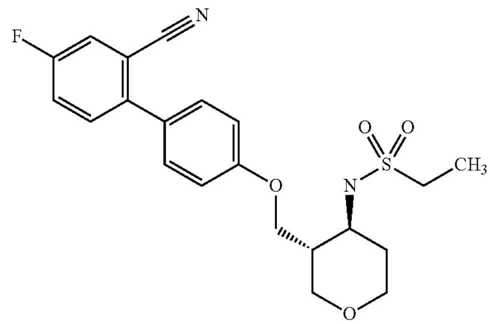 [SMILES: CCS(=O)(=O)N[C@H]1CCOC[C@@H]1COc1ccc(-c2ccc(F)cc2C#N)cc1] | | 417.1 neg |
| 369 | N-[(3RS,4SR)-3-{[(2'-cyano-4'-fluorobiphenyl-4-yl)oxy]methyl}tetrahydro-2H-pyran-4-yl]cyclopropanesulfonamide | 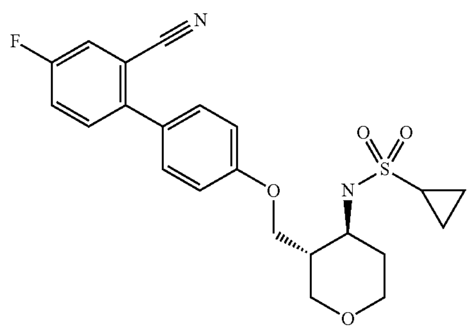 [SMILES: N#Cc1cc(F)ccc1-c1ccc(OC[C@H]2COCC[C@@H]2NS(=O)(=O)C2CC2)cc1] | | ND |
| 370 | N-[(3RS,4SR)-3-{[4-(5-chloro-3-fluoropyridin-2-yl)phenoxy]methyl}tetrahydro-2H-pyran-4-yl]ethanesulfonamide | 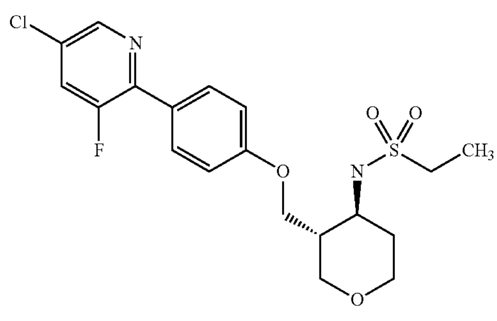 [SMILES: CCS(=O)(=O)N[C@H]1CCOC[C@@H]1COc1ccc(-c2ncc(Cl)cc2F)cc1] | | 429.1 |
| 371 | N-[(3R,4S)-3-{[4-(5-cyanopyridin-2-yl)phenoxy]methyl}tetrahydro-2H-pyran-4-yl]methanesulfonamide | 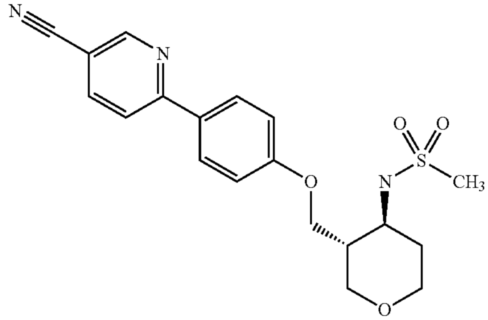 [SMILES: CS(=O)(=O)N[C@H]1CCOC[C@@H]1COc1ccc(-c2ccc(C#N)cn2)cc1] | | 388.1 |

TABLE 1-38-continued

| Ex. No. | IUPAC Name | Structure | Salt | MS |
|---|---|---|---|---|
| 372 | N-[(3R,4S)-4-{[2-fluoro-4-(5-fluoropyridin-2-yl)phenoxy]methyl}tetrahydro-2H-pyran-3-yl]methanesulfonamide | 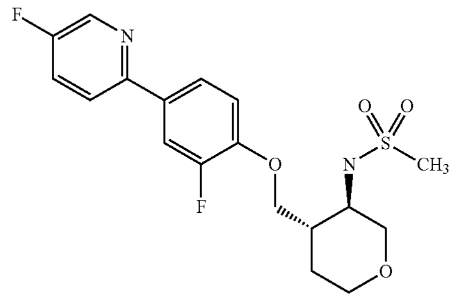 [SMILES: CS(=O)(=O)N[C@H]1COCC[C@@H]1COc1ccc(-c2ccc(F)cn2)cc1F] | | 399.1 |
| 373 | N-[(3R,4S)-4-{[2-fluoro-4-(5-fluoropyridin-2-yl)phenoxy]methyl}tetrahydro-2H-pyran-3-yl]ethanesulfonamide | 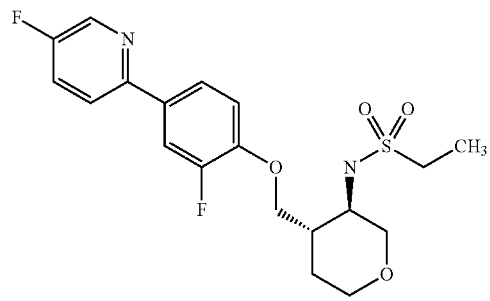 [SMILES: CCS(=O)(=O)N[C@H]1COCC[C@@H]1COc1ccc(-c2ccc(F)cn2)cc1F] | | 413.1 |
| 374 | N-[(3R,4S)-4-{[4-(3,5-difluoropyridin-2-yl)phenoxy]methyl}tetrahydro-2H-pyran-3-yl]methanesulfonamide | 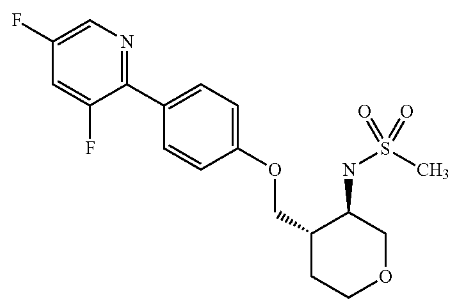 [SMILES: CS(=O)(=O)N[C@H]1COCC[C@@H]1COc1ccc(-c2ncc(F)cc2F)cc1] | | 399.1 |
| 375 | N-[(3R,4S)-4-{[4-(5-chloro-3-fluoropyridin-2-yl)phenoxy]methyl}tetrahydro-2H-pyran-3-yl]methanesulfonamide | 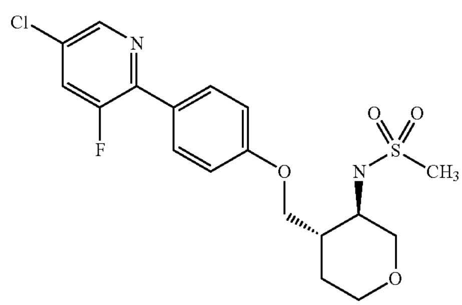 [SMILES: CS(=O)(=O)N[C@H]1COCC[C@@H]1COc1ccc(-c2ncc(Cl)cc2F)cc1] | | 415.1 |
| 376 | N-[(3R,4S)-3-{[4-(5-fluoropyrimidin-2-yl)phenoxy]methyl}tetrahydro-2H-pyran-4-yl]methanesulfonamide | 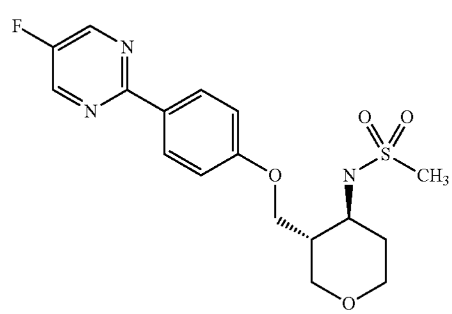 [SMILES: CS(=O)(=O)N[C@H]1CCOC[C@@H]1COc1ccc(-c2ncc(F)cn2)cc1] | | 382.1 |

TABLE 1-39

| Ex. No. | IUPAC Name | Structure | Salt | MS |
|---|---|---|---|---|
| 377 | N-[(3R,4S)-3-{[4-(5-chloropyrimidin-2-yl)phenoxy]methyl}tetrahydro-2H-pyran-4-yl]methanesulfonamide | 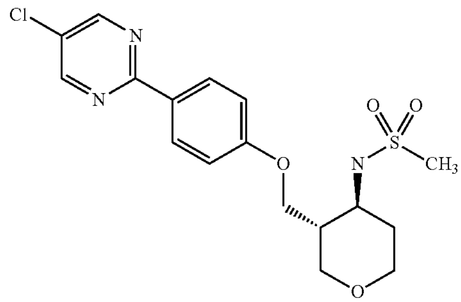 [SMILES: CS(=O)(=O)N[C@H]1CCOC[C@@H]1COc1ccc(-c2ncc(Cl)cn2)cc1] | | 398.1 |
| 378 | N-[(3R,4S)-3-{[4-(3,5-difluoropyridin-2-yl)phenoxy]methyl}tetrahydro-2H-pyran-4-yl]methanesulfonamide or N-[(3S,4R)-3-{[4-(3,5-difluoropyridin-2-yl)phenoxy]methyl}tetrahydro-2H-pyran-4-yl]methanesulfonamide | 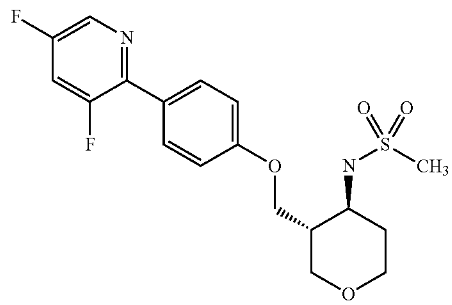 [SMILES: CS(=O)(=O)N[C@H]1CCOC[C@@H]1COc1ccc(-c2ncc(F)cc2F)cc1] | | 399.0 |
| 379 | N-[(3R,4S)-3-{[4-(3,5-difluoropyridin-2-yl)phenoxy]methyl}tetrahydro-2H-pyran-4-yl]methanesulfonamide or N-[(3R,4S)-3-{[4-(3,5-difluoropyridin-2-yl)phenoxy]methyl}tetrahydro-2H-pyran-4-yl]methanesulfonamide | 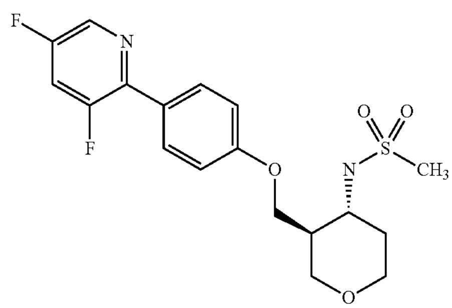 [SMILES: CS(=O)(=O)N[C@@H]1CCOC[C@H]1COc1ccc(-c2ncc(F)cc2F)cc1] | | 399.0 |
| 380 | N-[(3S,4R)-3-{[4-(5-chloropyridin-2-yl)-3-fluorophenoxy]methyl}tetrahydro-2H-pyran-4-yl]methanesulfonamide or N-[(3R,4S)-3-{[4-(5-chloropyridin-2-yl)-3-fluorophenoxy]methyl}tetrahydro-2H-pyran-4-yl]methanesulfonamide | 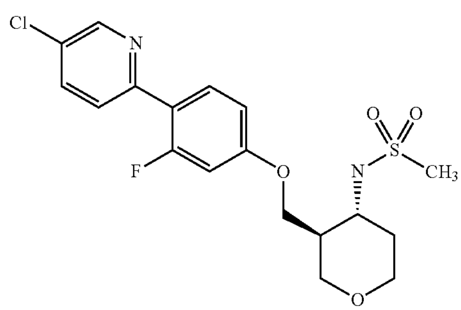 [SMILES: CS(=O)(=O)N[C@@H]1CCOC[C@H]1COc1ccc(-c2ccc(Cl)cn2)c(F)c1] | | 414.9 |
| 381 | N-[(3R,4S)-3-{[4-(5-chloro-3-fluoropyridin-2-yl)phenoxy]methyl}tetrahydro-2H-pyran-4-yl]methanesulfonamide or N-[(3S,4R)-3-{[4-(5-chloro-3-fluoropyridin-2-yl)phenoxy]methyl}tetrahydro-2H-pyran-4-yl]methanesulfonamide | 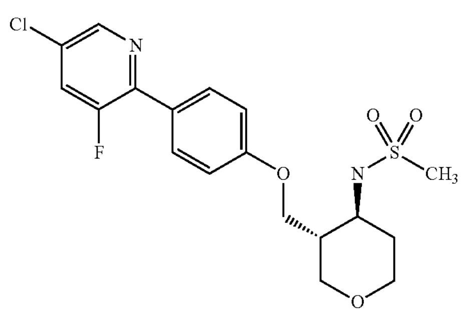 [SMILES: CS(=O)(=O)N[C@H]1CCOC[C@@H]1COc1ccc(-c2ncc(Cl)cc2F)cc1] | | 414.9 |

TABLE 1-39-continued

| Ex. No. | IUPAC Name | Structure | Salt | MS |
|---|---|---|---|---|
| 382 | N-[(3S,4R)-3-{[4-(5-chloro-3-fluoropyridin-2-yl)phenoxy]methyl}tetrahydro-2H-pyran-4-yl]methanesulfonamide or N-[(3R,4S)-3-{[4-(5-chloro-3-fluoropyridin-2-yl)phenoxy]methyl}tetrahydro-2H-pyran-4-yl]methanesulfonamide | 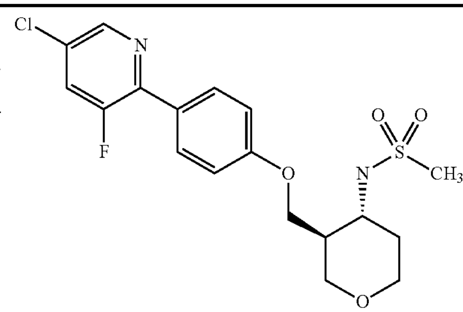 | | 414.9 |

TABLE 1-40

| Ex. No. | IUPAC Name | Structure | Salt | MS |
|---|---|---|---|---|
| 383 | N-[(3R,4S)-4-{[4-(5-chloro-3-fluoropyridin-2-yl)phenoxy]methyl}tetrahydro-2H-pyran-3-yl]cyclopropanesulfonamide | 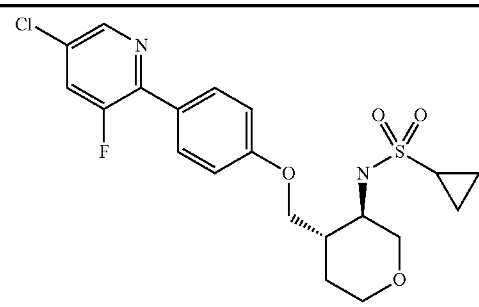 | | 441.1 |
| 384 | N-[(3R,4S)-4-{[2-fluoro-4-(5-methylisoxazol-3-yl)phenoxy]methyl}tetrahydro-2H-pyran-3-yl]ethanesulfonamide | 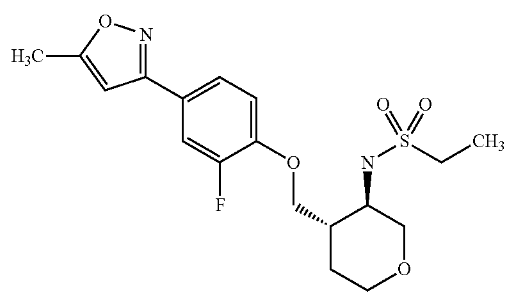 [SMILES: CCS(=O)(=O)N[C@H]1COCC[C@@H]1COc1ccc(-c2cc(C)on2)cc1F] | | 399.0 |
| 385 | 1,1,1-trifluoro-N-[(3R,4S)-3-{[3-fluoro-4-(5-methylisoxazol-3-yl)phenoxy]methyl}tetrahydro-2H-pyran-4-yl]methanesulfonamide | 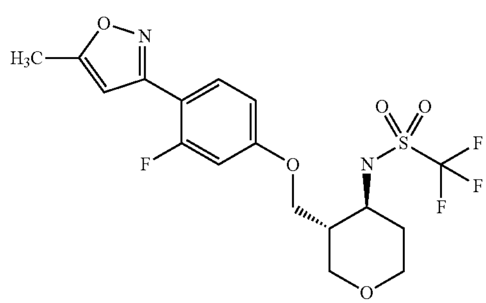 [SMILES: Cc1cc(-c2ccc(OC[C@H]3COCC[C@@H]3NS(=O)(=O)C(F)(F)F)cc2F)no1] | | 439.1 |
| 386 | N-[(3R,4S)-3-{[4-(5-chloro-1,3-thiazol-2-yl)phenoxy]methyl}tetrahydro-2H-pyran-4-yl]methanesulfonamide | 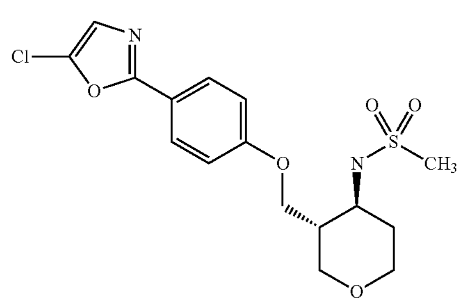 [SMILES: CS(=O)(=O)N[C@H]1CCOC[C@@H]1COc1ccc(-c2ncc(Cl)o2)cc1] | | 403.1 |

TABLE 1-40-continued

| Ex. No. | IUPAC Name | Structure | Salt | MS |
|---|---|---|---|---|
| 387 | N-[(3R,4S)-3-{[2-fluoro-4-(5-methylisoxazol-3-yl)phenoxy]methyl}tetrahydro-2H-pyran-4-yl]methanesulfonamide | 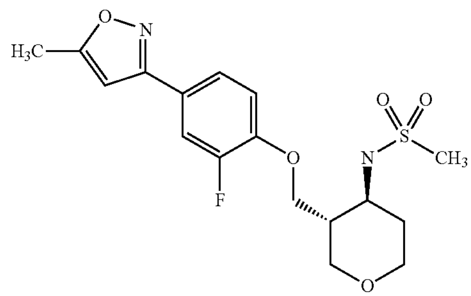 | | 385.1 |
| 388 | N-[(3R,4S)-3-{[2-fluoro-4-(5-methylisoxazol-3-yl)phenoxy]methyl}tetrahydro-2H-pyran-4-yl]ethanesulfonamide | 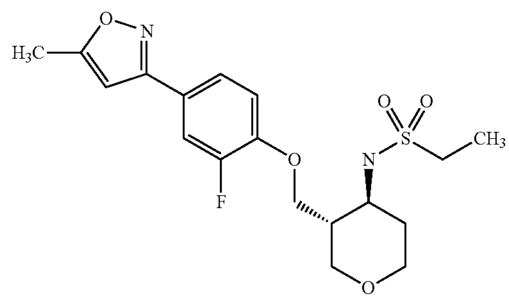 [SMILES: CCS(=O)(=O)N[C@H]1CCOC[C@@H]1COc1ccc(-c2cc(C)on2)cc1F] | | 399.0 |
| 389 | N-[(3R,4S)-4-{[2-fluoro-4-(5-methylisoxazol-3-yl)phenoxy]methyl}tetrahydro-2H-pyran-3-yl]methanesulfonamide | 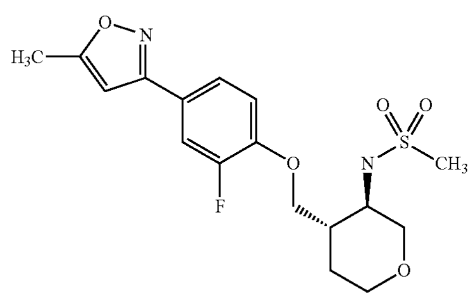 | | 385.0 |
| 390 | N-[(3R,4S)-3-{[2-fluoro-4-(5-methylisoxazol-3-yl)phenoxy]methyl}tetrahydro-2H-pyran-4-yl]cyclopropanesulfonamide | 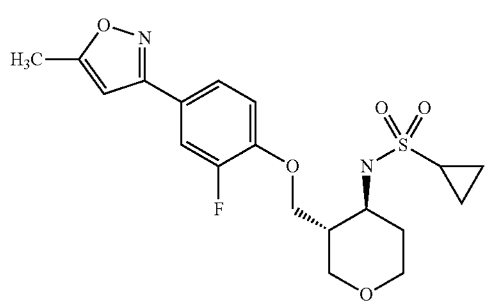 [SMILES: Cc1cc(-c2ccc(OC[C@H]3COCC[C@@H]3NS(=O)(=O)C3CC3)c(F)c2)no1] | | 411.0 |
| 391 | N-[(3R,4S)-4-{[2-fluoro-4-(5-methylisoxazol-3-yl)phenoxy]methyl}tetrahydro-2H-pyran-3-yl]cyclopropanesulfonamide | 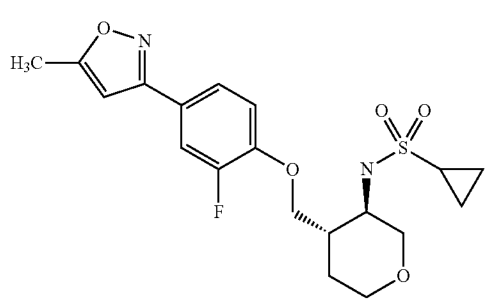 [SMILES: Cc1cc(-c2ccc(OC[C@H]3CCOC[C@@H]3NS(=O)(=O)C3CC3)c(F)c2)no1] | | 411.2 |

TABLE 1-40-continued

| Ex. No. | IUPAC Name | Structure | Salt | MS |
|---|---|---|---|---|
| 392 | 1,5-anhydro-6-O-[4-(5-chloro-3-fluoropyridin-2-yl)phenyl]-2,3,4-trideoxy-4-[(methylsulfonyl)amino]-D-erythro-hexitol | 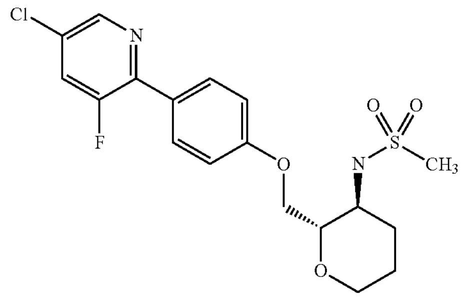 [SMILES: CS(=O)(=O)N[C@H]1CCCO[C@@H]1COc1ccc(-c2ncc(Cl)cc2F)cc1] | | 415.1 |

TABLE 1-41

| Ex. No. | IUPAC Name | Structure | Salt | MS |
|---|---|---|---|---|
| 393 | 1,5-anhydro-6-O-[4-(5-chloro-3-fluoropyridin-2-yl)phenyl]-2,3,4-trideoxy-4-[(ethylsulfonyl)amino]-D-erythro-hexitol | 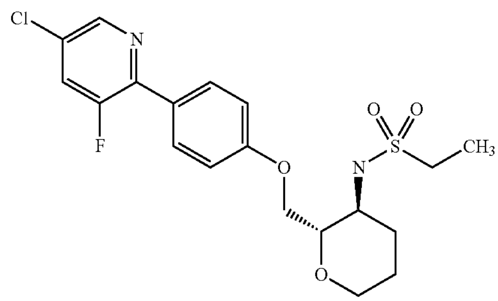 [SMILES: CCS(=O)(=O)N[C@H]1CCCO[C@@H]1COc1ccc(-c2ncc(Cl)cc2F)cc1] | | 429.1 |
| 394 | 1,5-anhydro-6-O-[4-(5-chloropyrimidin-2-yl)phenyl]-2,3,4-trideoxy-4-[(methylsulfonyl)amino]-D-erythro-hexitol | 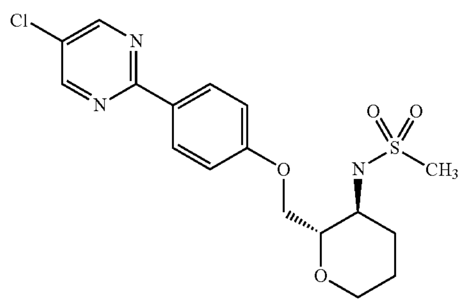 [SMILES: CS(=O)(=O)N[C@H]1CCCO[C@@H]1COc1ccc(-c2ncc(Cl)cn2)cc1] | | 398.1 |
| 395 | 1,5-anhydro-6-O-[4-(5-chloropyrimidin-2-yl)phenyl]-2,3,4-trideoxy-4-[(ethylsulfonyl)amino]-D-erythro-hexitol | 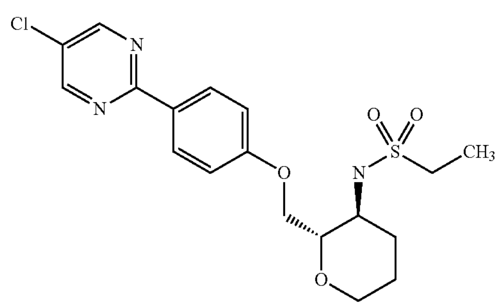 [SMILES: CCS(=O)(=O)N[C@H]1CCCO[C@@H]1COc1ccc(-c2ncc(Cl)cn2)cc1] | | 412.1 |

| Ex. No. | IUPAC Name | Structure | Salt | MS |
|---|---|---|---|---|
| 396 | 1,5-anhydro-6-O-[4-(5-chloropyridin-2-yl)phenyl]-2,3,4-trideoxy-4-[(methylsulfonyl)amino]-D-erythro-hexitol | 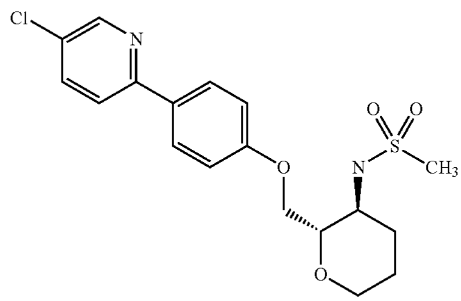 [SMILES: CS(=O)(=O)N[C@H]1CCCO[C@@H]1COc1ccc(-c2ccc(Cl)cn2)cc1] | | 397.1 |
| 397 | 1,5-anhydro-6-O-[4-(5-chloropyridin-2-yl)phenyl]-2,3,4-trideoxy-4-[(ethylsulfonyl)amino]-D-erythro-hexitol | 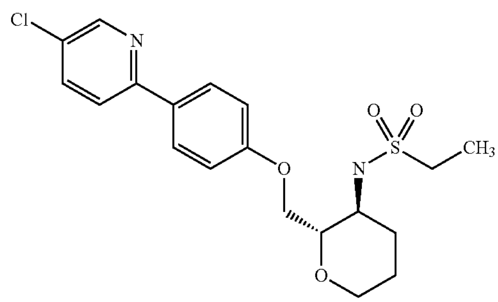 [SMILES: CCS(=O)(=O)N[C@H]1CCCO[C@@H]1COc1ccc(-c2ccc(Cl)cn2)cc1] | | 411.1 |
| 398 | 1,5-anhydro-2,3,4-trideoxy-6-O-[4-(5-fluoropyrimidin-2-yl)phenyl]-4-[(methylsulfonyl)amino]-D-erythro-hexitol | 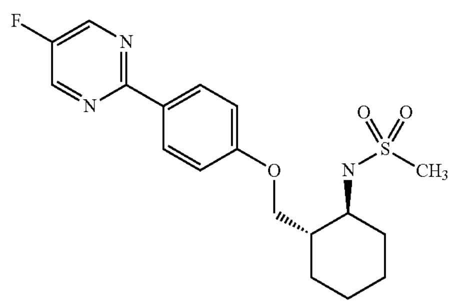 [SMILES: CS(=O)(=O)N[C@H]1CCCC[C@@H]1COc1ccc(-c2ncc(F)cn2)cc1] | | 382.1 |
| 399 | 1,5-anhydro-2,3,4-trideoxy-4-[(ethylsulfonyl)amino]-6-O-[4-(5-fluoropyrimidin-2-yl)phenyl]-D-erythro-hexitol | 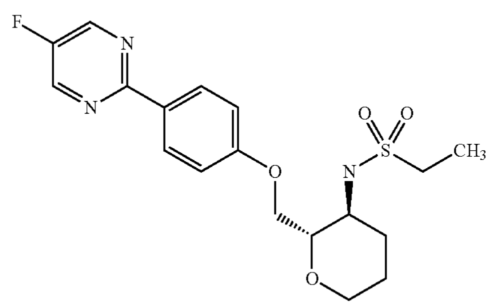 [SMILES: CCS(=O)(=O)N[C@H]1CCCO[C@@H]1COc1ccc(-c2ncc(F)cn2)cc1] | | 396.2 |
| 400 | 1,5-anhydro-4-[(cyclopropylsulfonyl)amino]-2,3,4-trideoxy-6-O-[4-(5-fluoropyrimidin-2-yl)phenyl]-D-erythro-hexitol | 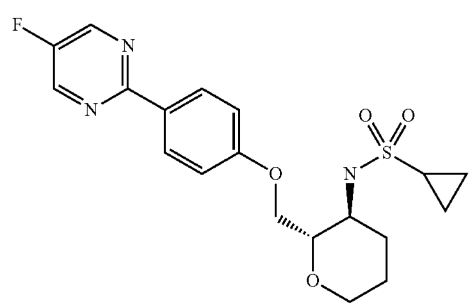 [SMILES: O=S(=O)(N[C@H]1CCCO[C@@H]1COc1ccc(-c2ncc(F)cn2)cc1)C1CC1] | | 408.1 |

TABLE 1-41-continued

| Ex. No. | IUPAC Name | Structure | Salt | MS |
|---|---|---|---|---|
| 401 | N-[(3S,4R)-3-{[3-fluoro-4-(5-fluoropyridin-2-yl)phenoxy]methyl}tetrahydro-2H-pyran-4-yl]ethanesulfonamide or N-[(3R,4S)-3-{[3-fluoro-4-(5-fluoropyridin-2-yl)phenoxy]methyl}tetrahydro-2H-pyran-4-yl]ethanesulfonamide | 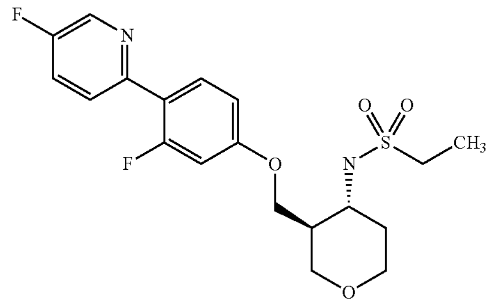 [SMILES: CCS(=O)(=O)N[C@@H]1CCOC[C@H]1COc1ccc(-c2ccc(F)cn2)c(F)c1] | | 413.0 |

TABLE 1-42

| Ex. No. | IUPAC Name | Structure | Salt | MS |
|---|---|---|---|---|
| 402 | N-[(3R,4S)-3-{[4-(5-chloropyridin-2-yl)-2-fluorophenoxy]methyl}tetrahydro-2H-pyran-4-yl]ethanesulfonamide or N-[(3S,4R)-3-{[4-(5-chloropyridin-2-yl)-2-fluorophenoxy]methyl}tetrahydro-2H-pyran-4-yl]ethanesulfonamide | 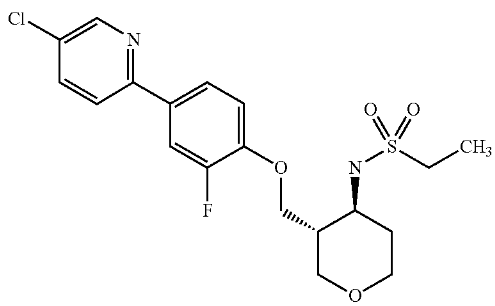 [SMILES: CCS(=O)(=O)N[C@H]1CCOC[C@@H]1COc1ccc(-c2ccc(Cl)cn2)cc1F] | | 429.0 |
| 403 | N-[(3S,4R)-3-{[4-(5-chloropyridin-2-yl)-2-fluorophenoxy]methyl}tetrahydro-2H-pyran-4-yl]ethanesulfonamide or N-[(3R,4S)-{[4-(5-chloropyridin-2-yl)-2-fluorophenoxy]methyl}tetrahydro-2H-pyran-4-yl]ethanesulfonamide | 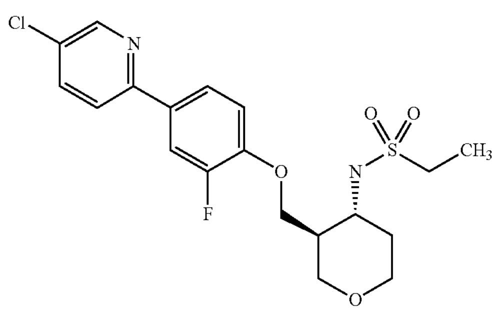 | | 428.9 |
| 404 | N-[(3R,4S)-3-{[4-(5-chloropyridin-2-yl)-3-fluorophenoxy]methyl}tetrahydro-2H-pyran-4-yl]cyclopropanesulfonamide or N-[(3S,4R)-3-{[4-{5-chloropyridin-2-yl)-3-fluorophenoxy]methyl}tetrahydro-2H-pyran-4-yl]cyclopropanesulfonamide | 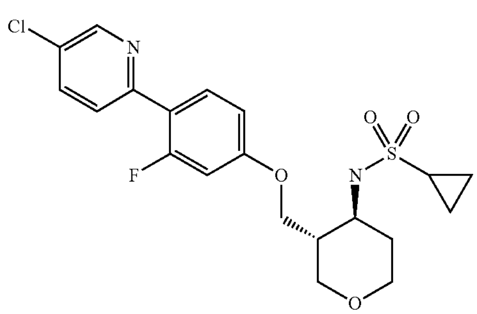 [SMILES: O=S(=O)(N[C@H]1CCOC[C@@H]1COc1ccc(-c2ccc(Cl)cn2)c(F)c1)C1CC1] | | 440.9 |

TABLE 1-42-continued

| Ex. No. | IUPAC Name | Structure | Salt | MS |
|---|---|---|---|---|
| 405 | N-[(3S,4R)-3-{[4-(5-chloro-3-fluoropyridin-2-yl)phenoxy]methyl}tetrahydro-2H-pyran-4-yl]ethanesulfonamide or N-[(3R,4S)-3-{[4-(5-chloro-3-fluoropyridin-2-yl)phenoxy]methyl}tetrahydro-2H-pyran-4-yl]ethanesulfonamide | 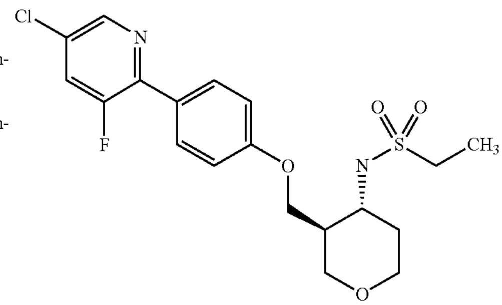 | | 429.0 |
| 406 | N-[(3R,4S)-3-{[4-(5-chloropyridin-2-yl)-2-fluorophenoxy]methyl}tetrahydro-2H-pyran-4-yl]cyclopropanesulfonamide or N-[(3S,4R)-3{[4-(5-chloropyridin-2-yl)-2-fluorophenoxy]methyl}tetrahydro-2H-pyran-4-yl]cyclopropanesulfonamide | 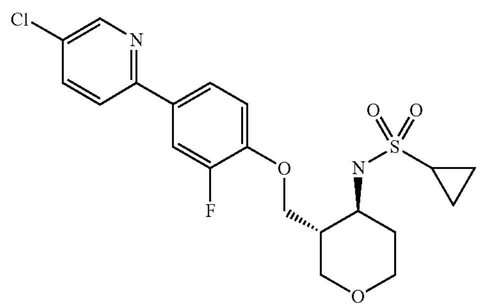 [SMILES: O=S(=O)(N[C@H]1CCOC[C@@H]1COc1ccc(-c2ccc(Cl)cn2)cc1F)C1CC1] | | 441.0 |

TABLE 1-43

| Ex. No. | IUPAC Name | Structure | Salt | MS |
|---|---|---|---|---|
| 407 | N-[(1S,2S)-2-{[4-(5-cyanopyrimidin-2-yl)phenoxy]methyl}-4,4-difluorocyclohexyl]ethanesulfonamide | 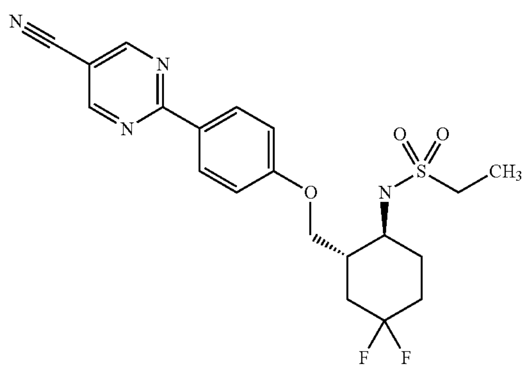 | | 437.0 |
| 408 | N-[(3R,4S)-3-{[4-(5-cyanothiophen-2-yl)phenoxy]methyl}tetrahydro-2H-pyran-4-yl]methanesulfonamide | 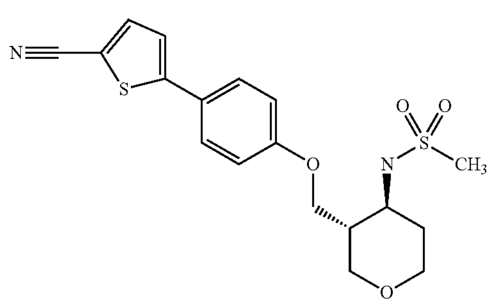 [SMILES: CS(=O)(=O)N[C@H]1CCOC[C@@H]1COc1ccc(-c2ccc(C#N)s2)cc1] | | ND |

TABLE 1-43-continued

| Ex. No. | IUPAC Name | Structure | Salt | MS |
|---|---|---|---|---|
| 409 | N-[(3R,4S)-3-{[4-(5-cyanothiophen-2-yl)phenoxy]methyl}tetrahydro-2H-pyran-4-yl]ethanesulfonamide | 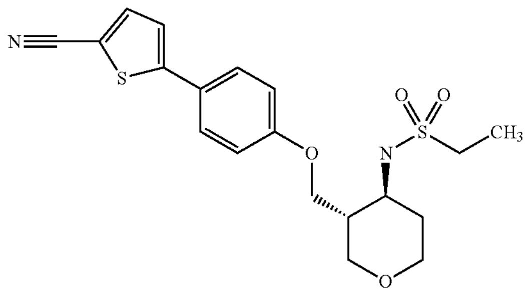 [SMILES: CCS(=O)(=O)N[C@H]1CCOC[C@@H]1COc1ccc(-c2ccc(C#N)s2)cc1] | | ND |
| 410 | N-[(3R,4S)-3-{[4-(5-cyanothiophen-2-yl)phenoxy]methyl}tetrahydro-2H-pyran-4-yl]cyclopropanesulfonamide | 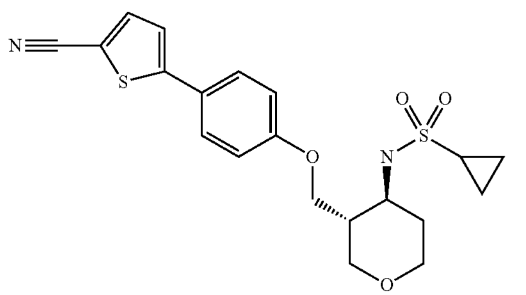 [SMILES: N#Cc1ccc(-c2ccc(OC[C@H]3COCC[C@@H]3NS(=O)(=O)C3CC3)cc2)s1] | | 419.0 |
| 411 | N-[(3R,4S)-4-{[4-(5-cyanothiophen-2-yl)phenoxy]methyl}tetrahydro-2H-pyran-3-yl]methanesulfonamide | 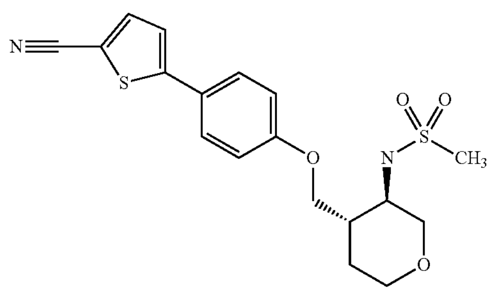 [SMILES: CS(=O)(=O)N[C@H]1COCC[C@@H]1COc1ccc(-c2ccc(C#N)s2)cc1] | | ND |
| 412 | N-[(3R,4S)-4-{[4-(5-cyanothiophen-2-yl)phenoxy]methyl}tetrahydro-2H-pyran-3-yl]ethanesulfonamide | 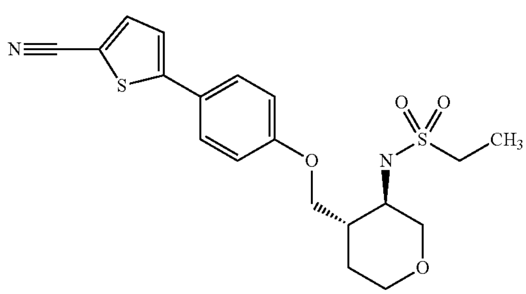 [SMILES: CCS(=O)(=O)N[C@H]1COCC[C@@H]1COc1ccc(-c2ccc(C#N)s2)cc1] | | ND |
| 413 | N-[(3R,4S)-3-{[4-(tetrahydro-2H-pyran-4-yl)phenoxy]methyl}tetrahydro-2H-pyran-4-yl]ethanesulfonamide | 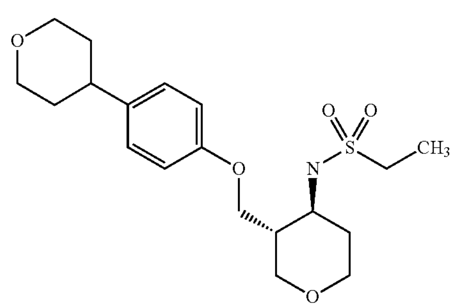 | | 384.0 |

TABLE 1-43-continued

| Ex. No. | IUPAC Name | Structure | Salt | MS |
|---|---|---|---|---|
| 414 | N-[(3R,4S)-3-{[4-(tetrahydro-2H-pyran-4-yl)phenoxy)methyl}tetrahydro-2H-pyran-4-yl]cyclopropanesulfonamide | 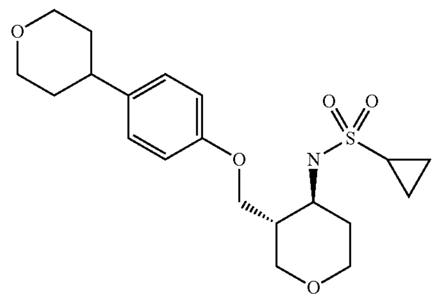 [SMILES: O=S(=O)(N[C@H]1CCOC[C@@H]1COc1ccc(C2CCOCC2)cc1)C1CC1] | | 396.1 |
| 415 | N-[(3R,4S)-3-({4-[(4-chloro-1H-pyrazol-1-yl)methyl]phenoxy}methyl)tetrahydro-2H-pyran-4-yl]methanesulfonamide | 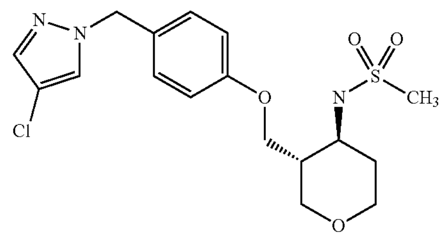 [SMILES: CS(=O)(=O)N[C@H]1CCOC[C@@H]1COc1ccc(Cn2cc(Cl)cn2)cc1] | | 400.1 |
| 416 | N-[(1S,2S)-4,4-difluoro-2-{[4-(1-methyl-2-oxo-1,2-dihydropyridin-3-yl)phenoxy]methyl}cyclohexyl]methanesulfonamide | 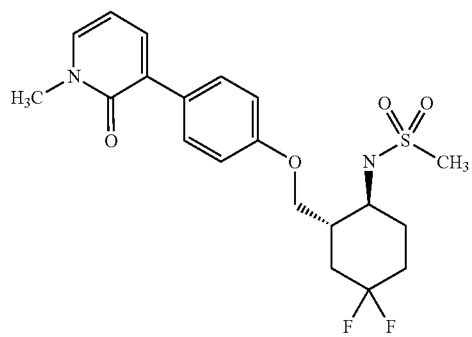 | | 427.1 |

TABLE 1-44

| Ex. No. | IUPAC Name | Structure | Salt | MS |
|---|---|---|---|---|
| 417 | N-[(1S,2S)-4,4-difluoro-2-{[4-(1-methyl-2-oxo-1,2-dihydropyridin-4-yl)phenoxy]methyl}cyclohexyl]methanesulfonamide | 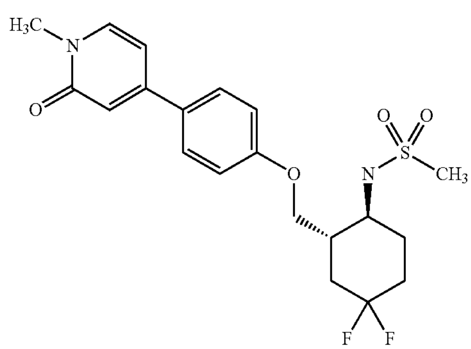 [SMILES: Cn1ccc(-c2ccc(OC[C@H]3CC(F)(F)CC[C@@H]3NS(C)(=O)=O)cc2)cc1=O] | | 427.2 |

TABLE 1-44-continued

| Ex. No. | IUPAC Name | Salt | MS |
|---|---|---|---|
| 418 | N-[(1S,2S)-4,4-difluoro-2-{[4-(1-methyl-2-oxo-1,2-dihydropyridin-4-yl)phenoxy]methyl}cyclohexyl]ethanesulfonamide | | 441.2 |
| 419 | N-[(3R,4S)-4-{[4-(tetrahydro-2H-pyran-4-yl)phenoxy]methyl}tetrahydro-2H-pyran-3-yl]methanesulfonamide | | 368.3 neg |
| 420 | N-[(3R,4S)-4-{[4-(tetrahydro-2H-pyran-4-yl)phenoxy]methyl}tetrahydro-2H-pyran-3-yl]ethanesulfonamide | | 382.2 neg |
| 421 | N-[(1S,2S)-4,4-difluoro-2-{[4-(tetrahydro-2H-pyran-4-yl)phenoxy]methyl}cyclohexyl]methanesulfonamide | | 402.2 neg |
| 422 | N-[(1S,2S)-4,4-difluoro-2-{[4-(tetrahydro-2H-pyran-4-yl)phenoxy]methyl}cyclohexyl]ethanesulfonamide | | 416.2 neg |

TABLE 1-44-continued

| Ex. No. | IUPAC Name | Salt | MS |
|---|---|---|---|
| 423 | N-[(1S,2S)-2-({4-[1-(2,2-difluoroethyl)-2-oxopiperidin-3-yl]phenoxy}methyl)-4,4-difluorocyclohexyl]methanesulfonamide | | 481.2 |
| 424 | N-[(1S,2S)-2-({4-[1-(2,2-difluoroethyl)-2-oxopiperidin-3-yl]phenoxy}methyl)-4,4-difluorocyclohexyl]ethanesulfonamide | | 495.1 |
| 425 | N-[(3R,4S)-3-{[2,3-difluoro-4-(1H-pyrazol-1-yl)phenoxy]methyl}tetrahydro-2H-pyran-4-yl]methanesulfonamide hydrochloride | HCl | 388.1 |

TABLE 1-45

| Ex. No. | IUPAC Name | Salt | MS |
|---|---|---|---|
| 426 | N-[(3R,4S)-3-{[2-fluoro-4-(5-fluoropyridin-2-yl)phenoxy]methyl}tetrahydro-2H-pyran-4-yl]ethanesulfonamide or N-[(3S,4R)-3-{[2-fluoro-4-(5-fluoropyridin-2-yl)phenoxy]methyl}tetrahydro-2H-pyran-4-yl]ethanesulfonamide | | 412.9 |

TABLE 1-45-continued

| Ex. No. | IUPAC Name | Structure | Salt | MS |
|---|---|---|---|---|
| 427 | N-[(3R,4S)-3-{[4-(3,5-difluoropyridin-2-yl)phenoxy]methyl}tetrahydro-2H-pyran-4-yl]ethanesulfonamide or N-[(3S,4R)-3-{[4-(3,5-difluoropyridin-2-yl)phenoxy]methyl}tetrahydro-2H-pyran-4-yl]ethanesulfonamide | 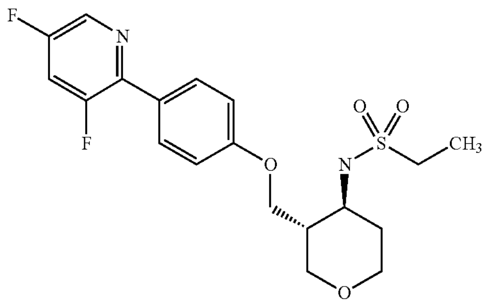 [SMILES: CCS(=O)(=O)N[C@H]1CCOC[C@@H]1COc1ccc(-c2ncc(F)cc2F)cc1] | | 413.0 |
| 428 | N-[(3R,4S)-3-{[3-fluoro-4-(5-fluoropyridin-2-yl)phenoxy]methyl}tetrahydro-2H-pyran-4-yl]methanesulfonamide or N-[(3S,4R)-3-{[3-fluoro-4-(5-fluoropyridin-2-yl)phenoxy]methyl}tetrahydro-2H-pyran-4-yl]methanesulfonamide | 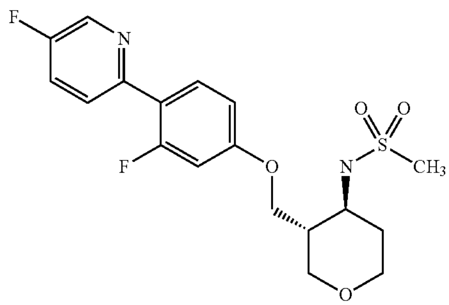 [SMILES: CS(=O)(=O)N[C@H]1CCOC[C@@H]1COc1ccc(-c2ccc(F)cn2)c(F)c1] | | 399.0 |
| 429 | N-[(3RS,4SR)-3-{[4-(trifluoroacetyl)phenoxy]methyl}tetrahydro-2H-pyran-4-yl]ethanesulfonamide | 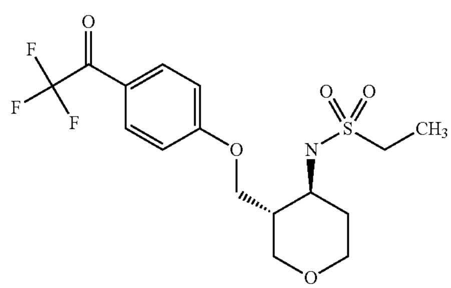 [SMILES: CCS(=O)(=O)N[C@H]1CCOC[C@@H]1COc1ccc(C(=O)C(F)(F)F)cc1] | | 394.0 |
| 430 | N-[(3RS,4SR)-3-{[4-(3-methyl-1H-pyrazol-1-yl)phenoxy]methyl}tetrahydro-2H-pyran-4-yl]ethanesulfonamide | 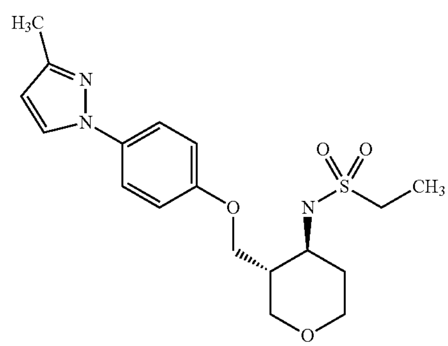 [SMILES: CCS(=O)(=O)N[C@H]1CCOC[C@@H]1COc1ccc(-n2ccc(C)n2)cc1] | | 380.2 |
| 431 | N-[(3RS,4SR)-3-{[4-(5-methyl-1H-pyrazol-1-yl)phenoxy]methyl}tetrahydro-2H-pyran-4-yl]ethanesulfonamide | 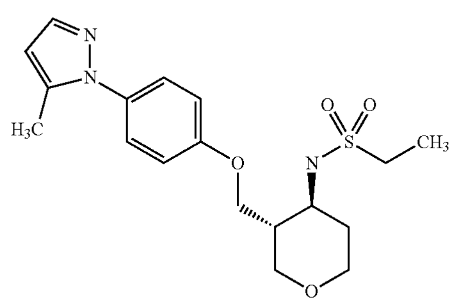 [SMILES: CCS(=O)(=O)N[C@H]1CCOC[C@@H]1COc1ccc(-n2nccc2C)cc1] | | 380.2 |

TABLE 1-45-continued

| Ex. No. | IUPAC Name | Structure | Salt | MS |
|---|---|---|---|---|
| 432 | N-[(3RS,4SR)-3-({4-[3-(trifluoromethyl)-1H-pyrazol-1-yl]phenoxy}methyl)tetrahydro-2H-pyran-4-yl]ethanesulfonamide | 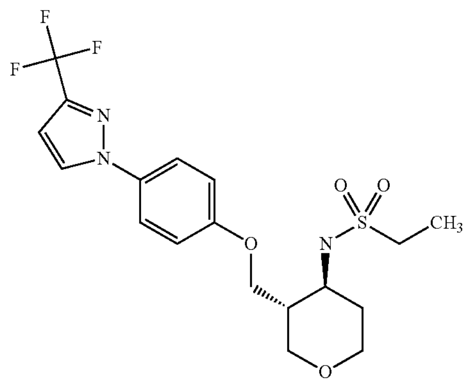 [SMILES: CCS(=O)(=O)N[C@H]1CCOC[C@@H]1COc1ccc(-n2ccc(C(F)(F)F)n2)cc1] | | 432.1 |

TABLE 1-46

| Ex. No. | IUPAC Name | Structure | Salt | MS |
|---|---|---|---|---|
| 433 | N-[(3S,4R)-3-{[4-(4-chloro-1H-pyrazol-1-yl)phenoxy]methyl}tetrahydro-2H-pyran-4-yl]ethanesulfonamide or N-[(3R,4S)-3-{[4-(4-chloro-1H-pyrazol-1-yl)phenoxy]methyl}tetrahydro-2H-pyran-4-yl]ethanesulfonamide | 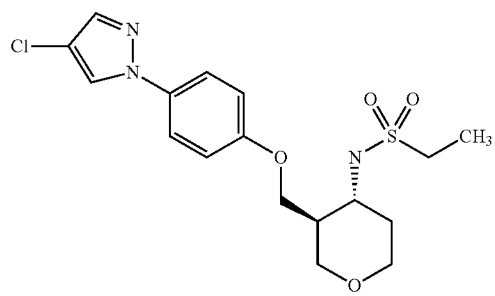 [SMILES: CCS(=O)(=O)N[C@@H]1CCOC[C@H]1COc1ccc(-n2cc(Cl)cn2)cc1] | | 440.2 |
| 434 | N-[(1SR,2SR)-2-{[4-(4-chloro-1H-pyrazol-1-yl)phenoxy]methyl}-4,4-difluorocyclohexyl]ethanesulfonamide | 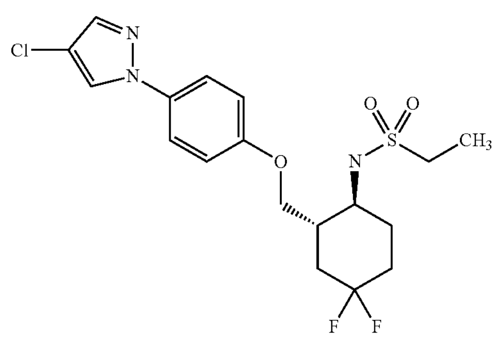 [SMILES: CCS(=O)(=O)N[C@H]1CCC(F)(F)C[C@@H]1COc1ccc(-n2cc(Cl)cn2)cc1] | | 434.0 |
| 435 | N-[(1S,2S)-4,4-difluoro-2-{[4-(1H-pyrazol-1-yl)phenoxy]methyl}cyclohexyl]ethanesulfonamide or N-[(1R,2R)-4,4-difluoro-2-{[4-(1H-pyrazol-1-yl)phenoxy]methyl}cyclohexyl]ethanesulfonamide | 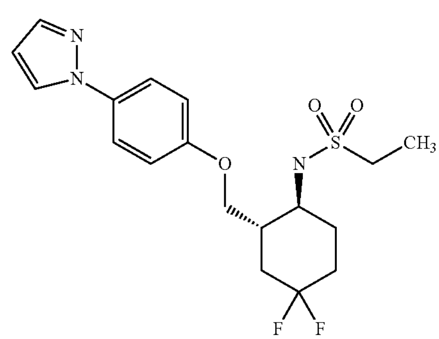 [SMILES: CCS(=O)(=O)N[C@H]1CCC(F)(F)C[C@@H]1COc1ccc(-n2cccn2)cc1] | | 400.2 |

TABLE 1-46-continued

| Ex. No. | IUPAC Name | Structure | Salt | MS |
|---|---|---|---|---|
| 436 | N-{(1SR,2SR)-4,4-difluoro-2-[(4-pyridin-2-ylphenoxy)methyl]cyclohexyl}ethanesulfonamide | 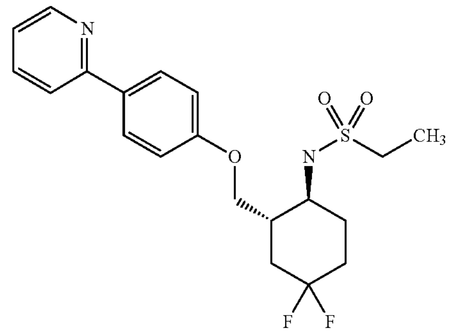 [SMILES: CCS(=O)(=O)N[C@H]1CCC(F)(F)C[C@@H]1COc1ccc(-c2ccccn2)cc1] | | 411.2 |
| 437 | N-{(1SR,2SR)-4,4-difluoro-2-{(4-pyridin-2-ylphenoxy)methyl]cyclohexyl}methanesulfonamide | 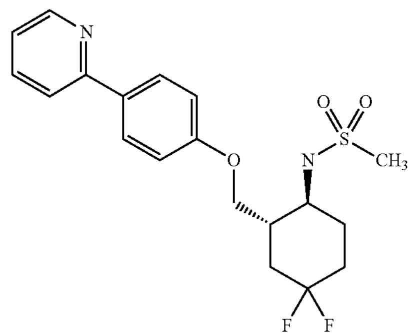 [SMILES: CS(=O)(=O)N[C@H]1CCC(F)(F)C[C@@H]1COc1ccc(-c2ccccn2)cc1] | | 397.1 |
| 438 | N-[(3RS,4SR)-3-{[4-(4-chloro-1H-pyrazol-1-yl)phenoxy]methyl}tetrahydro-2H-pyran-4-yl]-2,2,2-trifluoroethanesulfonamide | 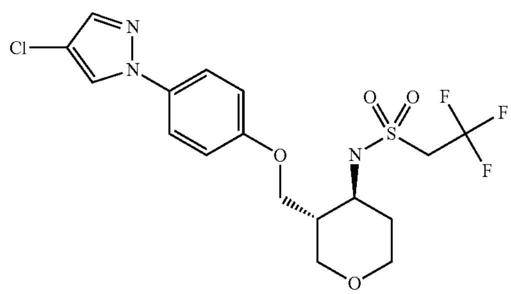 [SMILES: O=S(=O)(CC(F)(F)F)N[C@H]1CCOC[C@@H]1COc1ccc(-n2cc(Cl)cn2)cc1] | | 454.0 |
| 439 | N-[(3RS,4SR)-3-{[4-(4-chloro-1H-pyrazol-1-yl)phenoxy]methyl}tetrahydro-2H-pyran-4-yl]-2-methoxyethanesulfonamide | 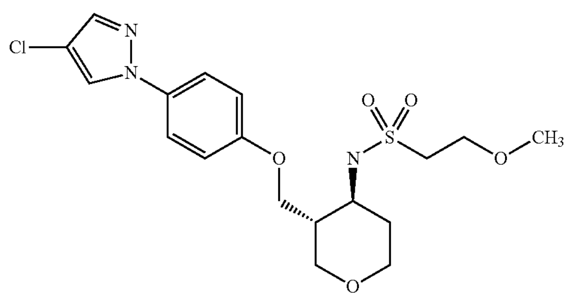 [SMILES: COCCS(=O)(=O)N[C@H]1CCOC[C@@H]1COc1ccc(-n2cc(Cl)cn2)cc1] | | 430.1 |
| 440 | N-[(3R,4S)-3-{[4-(4-methyl-1H-pyrazol-1-yl)phenoxy]methyl}tetrahydro-2H-pyran-4-yl]ethanesulfonamide or N-[(3S,4R)-3-{[4-(4-methyl-1H-pyrazol-1-yl)phenoxy]methyl}tetrahydro-2H-pyran-4-yl]ethanesulfonamide | 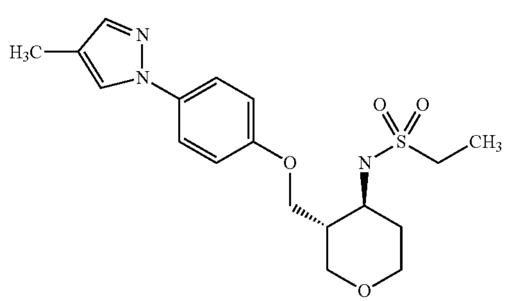 [SMILES: CCS(=O)(=O)N[C@H]1CCOC[C@@H]1COc1ccc(-n2cc(C)cn2)cc1] | | 380.2 |

TABLE 1-47

| Ex. No. | IUPAC Name | Structure | Salt | MS |
|---|---|---|---|---|
| 441 | N-[(3RS,4SR)-3-{[4-(1,3-oxazol-5-yl)phenoxy]methyl}tetrahydro-2H-pyran-4-yl]ethanesulfonamide | 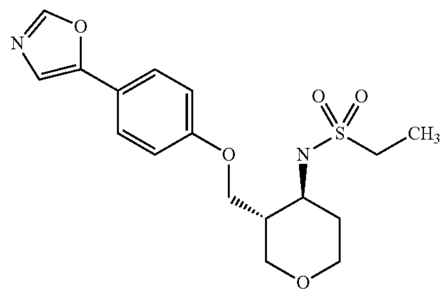 [SMILES: CCS(=O)(=O)N[C@H]1CCOC[C@@H]1COc1ccc(-c2cnco2)cc1] | | 367.1 |
| 442 | 1-chloro-N-[(3RS,4SR)-3-{[4-(4-chloro-1H-pyrazol-1-yl)phenoxy]methyl}tetrahydro-2H-pyran-4-yl]methanesulfonamide | 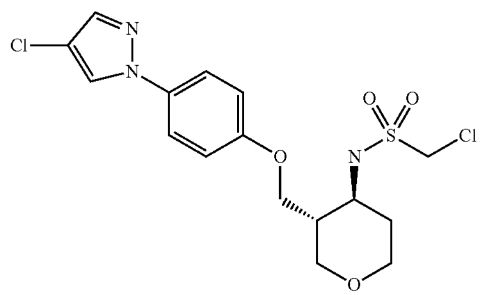 [SMILES: O=S(=O)(CCl)N[C@H]1CCOC[C@@H]1COc1ccc(-n2cc(Cl)cn2)cc1] | | |
| 443 | N-[(1SR,2SR)-4,4-difluoro-2-{[4-(4-methyl-1H-pyrazol-1-yl)phenoxy]methyl}cyclohexyl]cyclopropanesulfonamide | 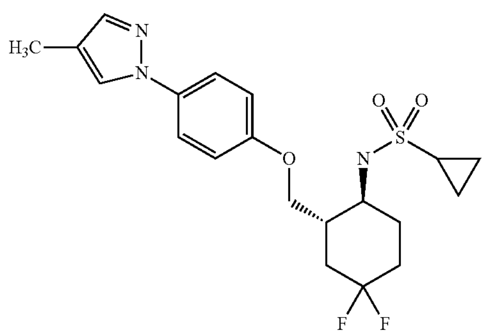 [SMILES: Cc1cnn(-c2ccc(OC[C@H]3CC(F)(F)CC[C@@H]3NS(=O)(=O)C3CC3)cc2)c1] | | 426.1 |
| 444 | N'-[(1SR,2SR)-4,4-difluoro-2-{[4-(4-methyl-1H-pyrazol-1-yl)phenoxy]methyl}cyclohexyl]-N,N-dimethylsulfamide | 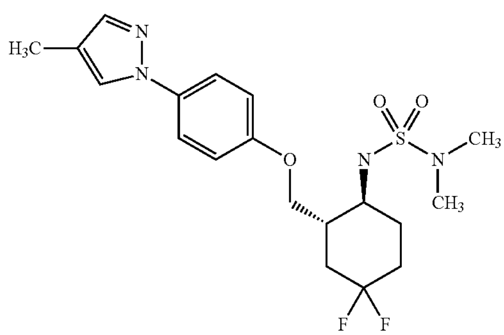 | | 429.2 |
| 445 | N-[(3SR,4SR)-1-acetyl-3-{[4-(4-chloro-1H-pyrazol-1-yl)phenoxy]methyl}piperidin-4-yl]ethanesulfonamide | 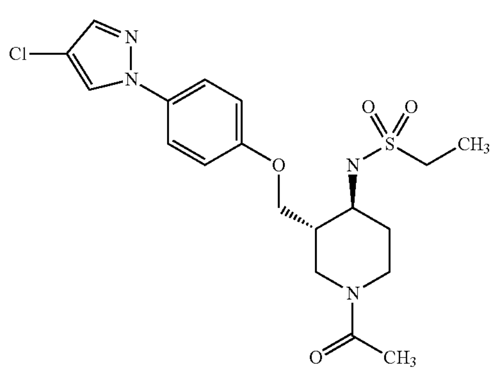 [SMILES: CCS(=O)(=O)N[C@H]1CCN(C(C)=O)C[C@@H]1COc1ccc(-n2cc(Cl)cn2)cc1] | | 441.1 |

TABLE 1-47-continued

| Ex. No. | IUPAC Name | Structure | Salt | MS |
|---|---|---|---|---|
| 446 | N-{(3RS,4SR)-3-[(4-acetylphenoxy)methyl]tetrahydro-2H-pyran-4-yl}-1,1,1-trifluoromethanesulfonamide | 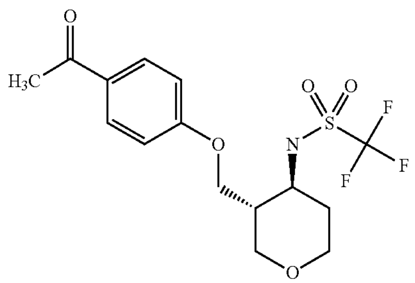 [SMILES: CC(=O)c1ccc(OC[C@H]2COCC[C@@H]2NS(=O)(=O)C(F)(F)F)cc1] | | 380.2 |
| 447 | N-[(3RS,4SR)-3-{[4-(1-cyano-1-methylethyl)-2-fluorophenoxy]methyl}tetrahydro-2H-pyran-4-yl]cyclopropanesulfonamide | 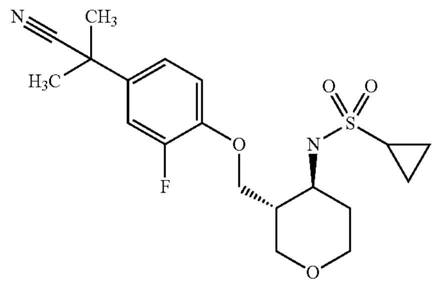 [SMILES: CC(C)(C#N)c1ccc(OC[C@H]2COCC[C@@H]2NS(=O)(=O)C2CC2)c(F)c1] | | 395.2 |
| 448 | N-[(3S,4R)-3-{[4-(4-chloro-1H-pyrazol-1-yl)phenoxy]methyl}tetrahydro-2H-pyran-4-yl]methanesulfonamide | 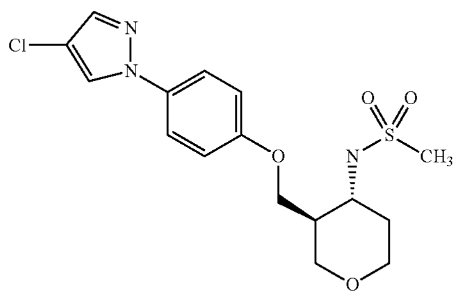 [SMILES: CS(=O)(=O)N[C@@H]1CCOC[C@H]1COc1ccc(-n2cc(Cl)cn2)cc1] | | 386.0 |
| 449 | N-[(3RS,4SR)-3-{[4-(1,3-dimethyl-1H-pyrazol-5-yl)phenoxy]methyl}tetrahydro-2H-pyran-4-yl]methanesulfonamide | 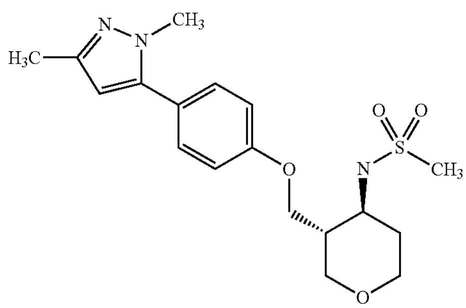 | | 380.2 |
| 450 | N-[(3RS,4SR)-3-{[4-(1,5-dimethyl-1H-pyrazol-3-yl)phenoxy]methyl}tetrahydro-2H-pyran-4-yl]ethanesulfonamide | 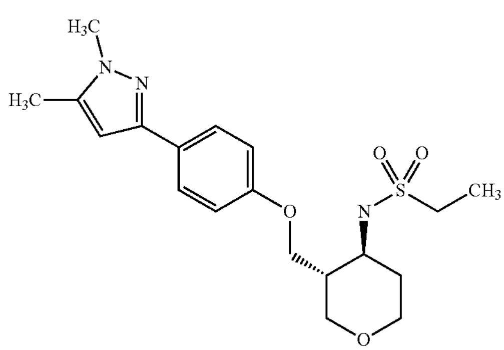 [SMILES: CCS(=O)(=O)N[C@H]1CCOC[C@@H]1COc1ccc(-c2cc(C)n(C)n2)cc1] | | 394.1 |

TABLE 1-48

| Ex. No. | IUPAC Name | Structure | Salt | MS |
|---|---|---|---|---|
| 451 | N'-[(3RS,4SR)-3-{[4-(1,5-dimethyl-1H-pyrazol-3-yl)phenoxy]methyl}tetrahydro-2H-pyran-4-yl]-N,N-dimethylsulfamide | 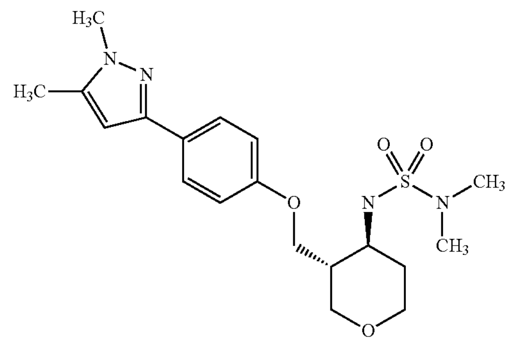 | | 409.1 |
| 452 | N'-[(3RS,4SR)-3-{[4-(1,3-dimethyl-1H-pyrazol-5-yl)phenoxy]methyl}tetrahydro-2H-pyran-4-yl]-N,N-dimethylsulfamide | 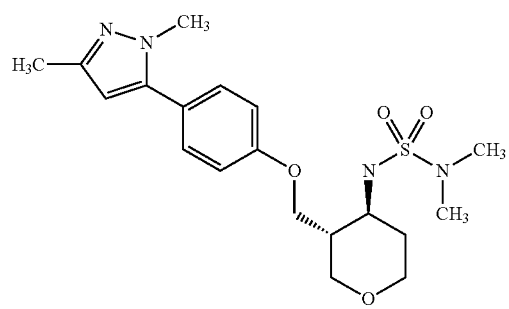 | | 409.1 |
| 453 | N-[(3R,4S)-3-{[4-(4-methoxy-1H-pyrazol-1-yl)phenoxy]methyl}tetrahydro-2H-pyran-4-yl]ethanesulfonamide | 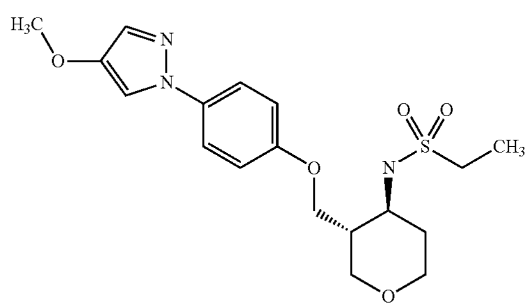 [SMILES: CCS(=O)(=O)N[C@H]1CCOC[C@@H]1COc1ccc(-n2cc(OC)cn2)cc1] | | 396.2 |
| 454 | N-[(3R,4S)-3-{[4-(4-chloro-1H-pyrazol-1-yl)-2-fluorophenoxy]methyl}tetrahydro-2H-pyran-4-yl]ethanesulfonamide | 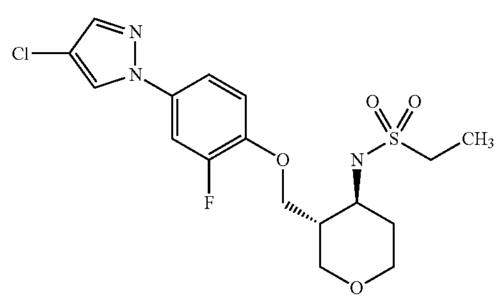 [SMILES: CCS(=O)(=O)N[C@H]1CCOC[C@@H]1COc1ccc(-n2cc(Cl)cn2)cc1F] | | 418.1 |
| 455 | N'-[(1S,2S)-4,4-difluoro-2-{[4-(4-methyl-1H-pyrazol-1-yl)phenoxy]methyl}cyclohexyl]-N,N-dimethylsulfamide | 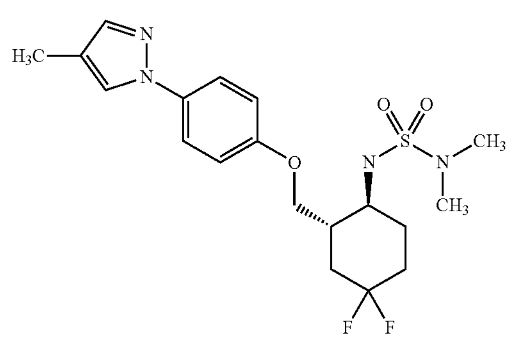 | | 429.2 |

TABLE 1-48-continued

| Ex. No. | IUPAC Name | Structure | Salt | MS |
|---|---|---|---|---|
| 456 | N-[(3RS,4SR)-3-{[4-(4-chloro-1H-pyrazol-1-yl)phenoxy]methyl}tetrahydro-2H-pyran-4-yl]-1,1,1-trifluoromethanesulfonamide | 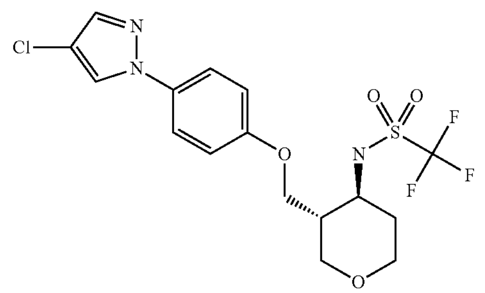 [SMILES: O=S(=O)(N[C@H]1CCOC[C@@H]1COc1ccc(-n2cc(Cl)cn2)cc1)C(F)(F)F] | | 440.0 |
| 457 | ethyl 4-({(1S,2S)-2-[(ethylsulfonyl)amino]-5,5-difluorocyclohexyl}methoxy)benzoate | 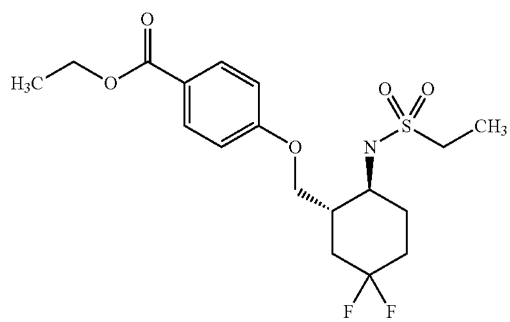 [SMILES: CCOC(=O)c1ccc(OC[C@H]2CC(F)(F)CC[C@@H]2NS(=O)(=O)CC)cc1] | | 404.2 |
| 458 | N-[(1S,2S)-4,4-difluoro-2-{[4-(4-methyl-1H-pyrazol-1-yl)phenoxy]methyl}cyclohexyl]ethanesulfonamide | 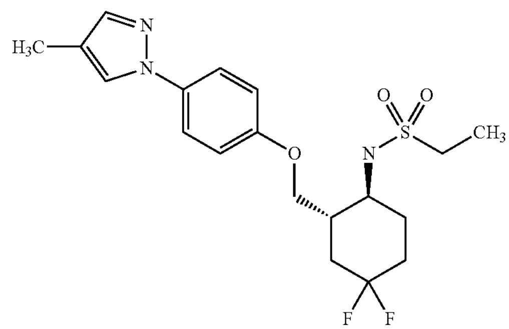 [SMILES: CCS(=O)(=O)N[C@H]1CCC(F)(F)C[C@@H]1COc1ccc(-n2cc(C)cn2)cc1] | | 414.2 |
| 459 | N'-[(3R,4S)-3-{[2-fluoro-4-(4-methyl-1H-pyrazol-1-yl)phenoxy]methyl}tetrahydro-2H-pyran-4-yl]-N,N-dimethylsulfamide | 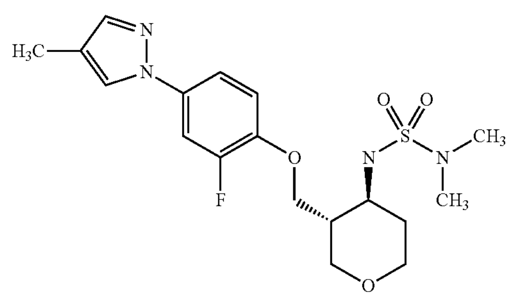 | | 413.2 |
| 460 | N-[(3R,4S)-4-{[4-(4-chloro-1H-pyrazol-1-yl)phenoxy]methyl}tetrahydro-2H-pyran-3-yl]cyclopropanesulfonamide | 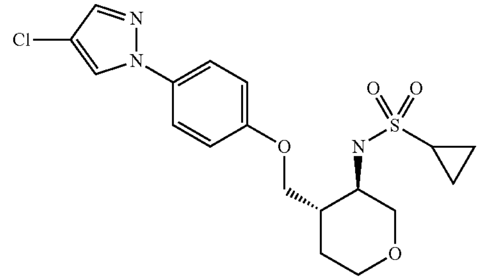 [SMILES: O=S(=O)(N[C@H]1COCC[C@@H]1COc1ccc(-n2cc(Cl)cn2)cc1)C1CC1] | | 412.1 |

TABLE 1-49

| Ex. No. | IUPAC Name | Structure | Salt | MS |
|---|---|---|---|---|
| 461 | N-[(3R,4S)-4-{[4-(4-chloro-1H-pyrazol-1-yl)-2-fluorophenoxy]methyl}tetrahydro-2H-pyran-3-yl]cyclopropanesulfonamide | 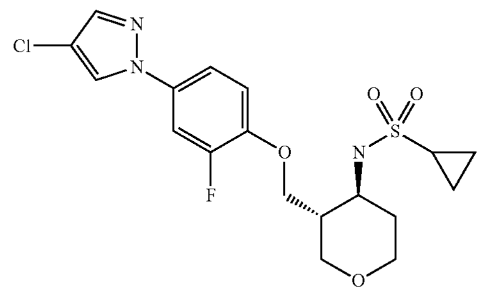 [SMILES: O=S(=O)(N[C@H]1CCOC[C@@H]1COc1ccc(-n2cc(Cl)cn2)cc1F)C1CC1] | | 430.1 |
| 462 | N-[(3R,4S)-3-{[4-(4-chloro-1H-pyrazol-1-yl)-2,3-difluorophenoxy]methyl}tetrahydro-2H-pyran-4-yl]methanesulfonamide | 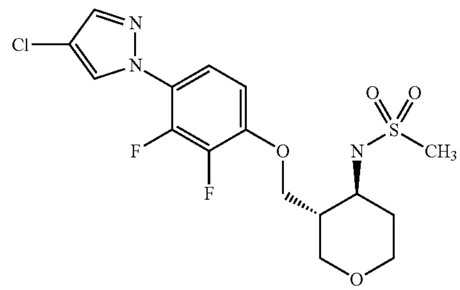 [SMILES: CS(=O)(=O)N[C@H]1CCOC[C@@H]1COc1ccc(-n2cc(Cl)cn2)c(F)c1F] | | 422.0 |
| 463 | N-[(3R,4S)-3-({4-[4-(difluoromethoxy)-1H-pyrazol-1-yl]phenoxy}methyl)tetrahydro-2H-pyran-4-yl]methanesulfonamide | 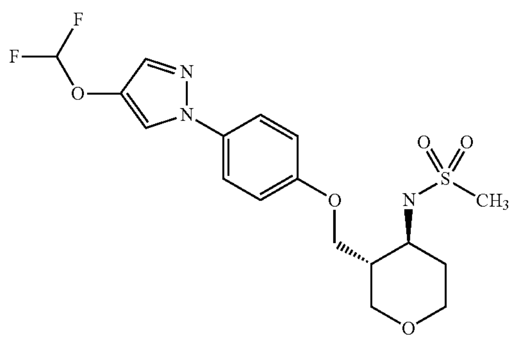 [SMILES: CS(=O)(=O)N[C@H]1CCOC[C@@H]1COc1ccc(-n2cc(OC(F)F)cn2)cc1] | | 418.1 |
| 464 | N-[(3R,4S)-3-({4-[4-(difluoromethoxy)-1H-pyrazol-1-yl]phenoxy}methyl)tetrahydro-2H-pyran-4-yl]cyclopropanesulfonamide | 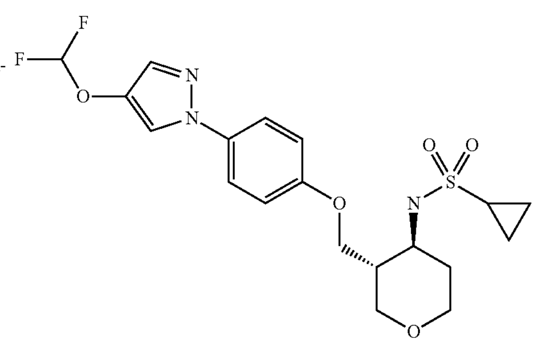 | | 444.1 |
| 465 | 1,5-anhydro-2,3,4-trideoxy-4-[(ethylsulfonyl)amino]-6-O-[4-(5-fluoropyridin-2-yl)phenyl]-D-erythro-hexitol | 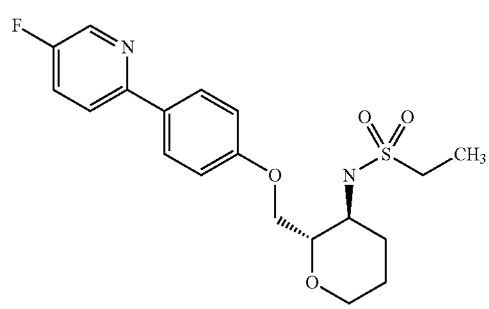 [SMILES: CCS(=O)(=O)N[C@H]1CCCO[C@@H]1COc1ccc(-c2ccc(F)cn2)cc1] | | 395.2 |

TABLE 1-49-continued

| Ex. No. | IUPAC Name | Structure | Salt | MS |
|---|---|---|---|---|
| 466 | N-[(3R,4S)-3-{[4-(4-chloro-3-methyl-1H-pyrazol-1-yl)phenoxy]methyl}tetrahydro-2H-pyran-4-yl]methanesulfonamide | 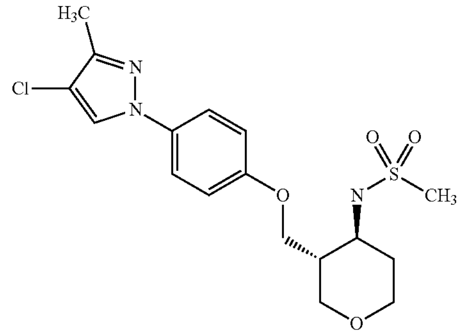 [SMILES: Cc1nn(-c2ccc(OC[C@H]3COCC[C@@H]3NS(C)(=O)=O)cc2)cc1Cl] | | |
| 467 | N-[(3R,4S)-3-({[6-(4-chloro-1H-pyrazol-1-yl)pyridin-3-yl]oxy}methyl)tetrahydro-2H-pyran-4-yl]cyclopropanesulfonamide | 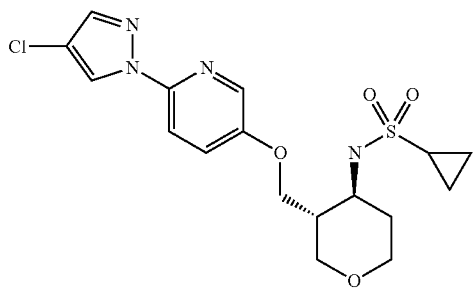 [SMILES: O=S(=O)(N[C@H]1CCOC[C@@H]1COc1ccc(-n2cc(Cl)cn2)nc1)C1CC1] | | 413.2 |
| 468 | N-[(1S,2S)-2-({[6-(4-chloro-1H-pyrazol-1-yl)pyridin-3-yl]oxy}methyl)-4,4-difluorocyclohexyl]methanesulfonamide | 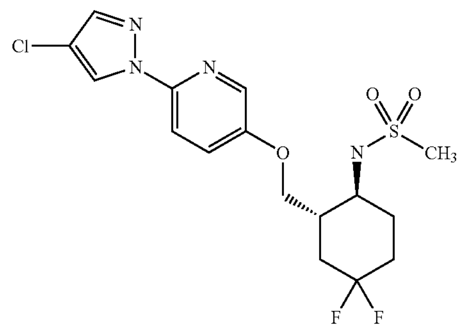 [SMILES: CS(=O)(=O)N[C@H]1CCC(F)(F)C[C@@H]1COc1ccc(-n2cc(Cl)cn2)nc1] | | 421.1 |
| 469 | 1,5-anhydro-2,3,4-trideoxy-6-O-[4-(5-fluoropyridin-2-yl)phenyl]-4-[(methylsulfonyl)amino]-D-erythro-hexitol | 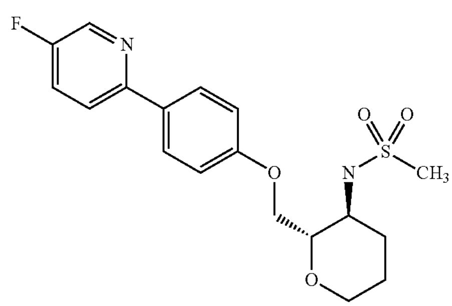 [SMILES: CS(=O)(=O)N[C@H]1CCCO[C@@H]1COc1ccc(-c2ccc(F)cn2)cc1] | | 381.2 |
| 470 | N'-[(3R,4S)-3-{[4-(4-chloro-1H-pyrazol-1-yl)phenoxy]methyl}tetrahydro-2H-pyran-4-yl]-N,N-dimethylsulfamide | 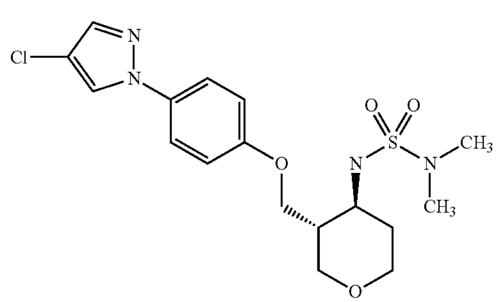 [SMILES: CN(C)S(=O)(=O)N[C@H]1CCOC[C@@H]1COc1ccc(-n2cc(Cl)cn2)cc1] | | 415.1 |

TABLE 1-50

| Ex. No. | IUPAC Name | Structure | Salt | MS |
|---|---|---|---|---|
| 471 | N-[(3R,4S)-3-{[2-fluoro-4-(5-fluoropyridin-2-yl)phenoxy]methyl}tetrahydro-2H-pyran-4-yl]ethanesulfonamide or N-[(3S,4R)-3-{[2-fluoro-4-(5-fluoropyridin-2-yl)phenoxy]methyl}tetrahydro-2H-pyran-4-yl]ethanesulfonamide | 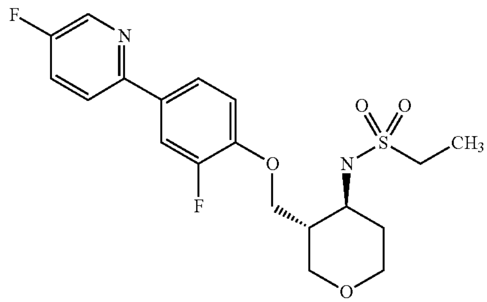 [SMILES: CCS(=O)(=O)N[C@H]1CCOC[C@@H]1COc1ccc(-c2ccc(F)cn2)cc1F] | | 412.9 |
| 472 | N-[(3R,4S)-3-{[4-(3,5-difluoropyridin-2-yl)phenoxy]methyl}tetrahydro-2H-pyran-4-yl]ethanesulfonamide or N-[(3S,4R)-3-{[4-(3,5-difluoropyridin-2-yl)phenoxy]methyl}tetrahydro-2H-pyran-4-yl]ethanesulfonamide | 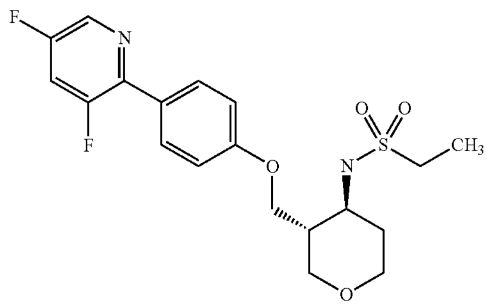 [SMILES: CCS(=O)(=O)N[C@H]1CCOC[C@@H]1COc1ccc(-c2ncc(F)cc2F)cc1] | | 413.0 |
| 473 | N-[(3R,4S)-3-{[2-fluoro-4-(5-fluoropyridin-2-yl)phenoxy]methyl}tetrahydro-2H-pyran-4-yl]cyclopropanesulfonamide or N-[(3S,4R)-3-{[2-fluoro-4-(5-fluoropyridin-2-yl)phenoxy]methyl}tetrahydro-2H-pyran-4-yl]cyclopropanesulfonamide | 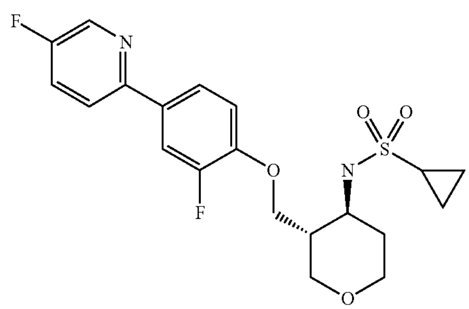 | | 425.0 |
| 474 | N-[(3R,4S)-3-{[2-fluoro-4-(5-fluoropyridin-2-yl)phenoxy]methyl}tetrahydro-2H-pyran-4-yl]cyclopropanesulfonamide or N-[(3S,4R)-3-{[2-fluoro-4-(5-fluoropyridin-2-yl)phenoxy]methyl}tetrahydro-2H-pyran-4-yl]cyclopropanesulfonamide | 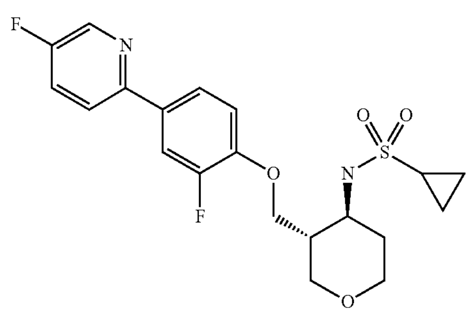 [SMILES: O=S(=O)(N[C@H]1CCOC[C@@H]1COc1ccc(-c2ccc(F)cn2)cc1F)C1CC1] | | 424.9 |
| 475 | N-[(3R,4S)-3-{[2-fluoro-4-(5-fluoropyridin-2-yl)phenoxy]methyl}tetrahydro-2H-pyran-4-yl]methanesulfonamide or N-[(3S,4R)-3-{[2-fluoro-4-(5-fluoropyridin-2-yl)phenoxy]methyl}tetrahydro-2H-pyran-4-yl]methanesulfonamide | 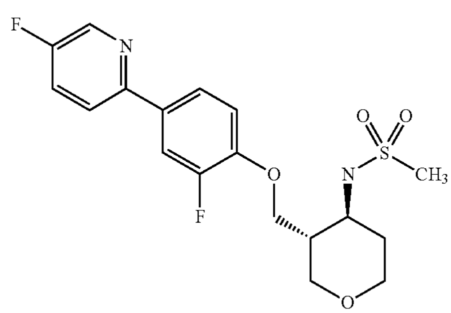 [SMILES: CS(=O)(=O)N[C@H]1CCOC[C@@H]1COc1ccc(-c2ccc(F)cn2)cc1F] | | 399.0 |

TABLE 1-51

| Ex. No. | IUPAC Name | Structure | Salt | MS |
|---|---|---|---|---|
| 476 | N-[(3R,4S)-3-{[2-fluoro-4-(5-fluoropyridin-2-yl)phenoxy]methyl}tetrahydro-2H-pyran-4-yl]methanesulfonamide or N-[(3S,4R)-3-{[2-fluoro-4-(5-fluoropyridin-2-yl)phenoxy]methyl}tetrahydro-2H-pyran-4-yl]methanesulfonamide | 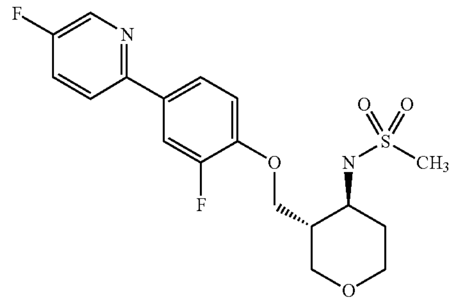 [SMILES: CS(=O)(=O)N[C@H]1CCOC[C@@H]1COc1ccc(-c2ccc(F)cn2)cc1F] | | 399.0 |
| 477 | N-[(3R,4S)-3-{[3-fluoro-4-(5-fluoropyridin-2-yl)phenoxy]methyl}tetrahydro-2H-pyran-4-yl]methanesulfonamide or N-[(3S,4R)-3-{[3-fluoro-4-(5-fluoropyridin-2-yl)phenoxy]methyl}tetrahydro-2H-pyran-4-yl]methanesulfonamide | 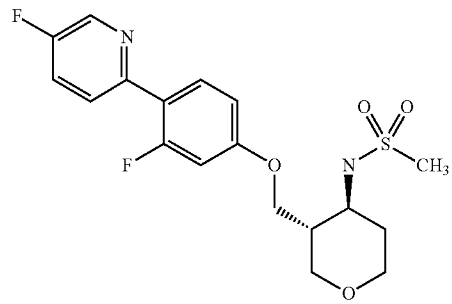 [SMILES: CS(=O)(=O)N[C@H]1CCOC[C@@H]1COc1ccc(-c2ccc(F)cn2)c(F)c1] | | 399.0 |
| 478 | 1,1,1-trifluoro-N-[(3R,4S)-3-{[4-(4-methyl-1H-pyrazol-1-yl)phenoxy]methyl}tetrahydro-2H-pyran-4-yl]methanesulfonamide | 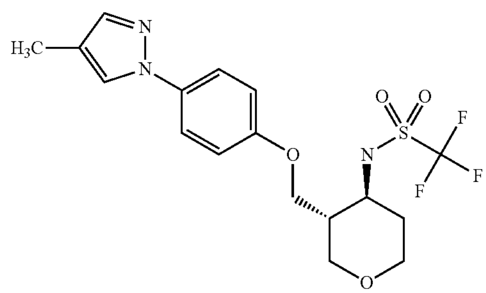 [SMILES: Cc1cnn(-c2ccc(OC[C@H]3COCC[C@@H]3NS(=O)(=O)C(F)(F)F)cc2)c1] | | 420.0 |
| 479 | N-[(3R,4S)-3-{[4-(4-methoxy-1H-pyrazol-1-yl)phenoxy]methyl}tetrahydro-2H-pyran-4-yl]methanesulfonamide | 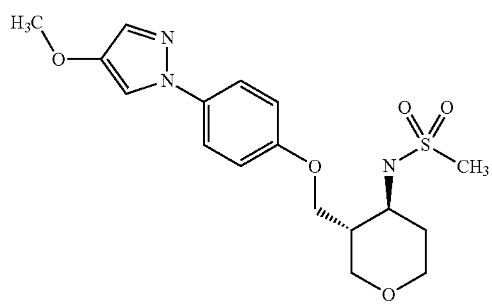 | | 381.9 |
| 480 | N-[(3R,4S)-3-{[4-(4-methoxy-1H-pyrazol-1-yl)phenoxy]methyl}tetrahydro-2H-pyran-4-yl]cyclopropanesulfonamide | 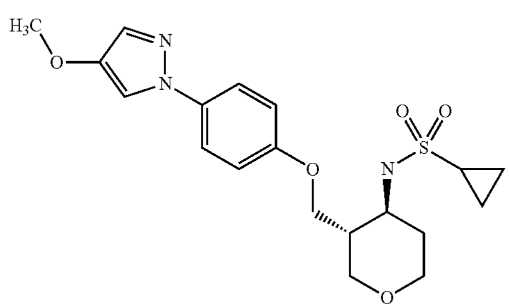 [SMILES: COc1cnn(-c2ccc(OC[C@H]3COCC[C@@H]3NS(=O)(=O)C3CC3)cc2)c1] | | ND |

TABLE 1-51-continued

| Ex. No. | IUPAC Name | Structure | Salt | MS |
|---|---|---|---|---|
| 481 | N-[(1S,2S)-4,4-difluoro-2-{[4-(2-oxopyrrolidin-1-yl)phenoxy]methyl}cyclohexyl]methanesulfonamide | 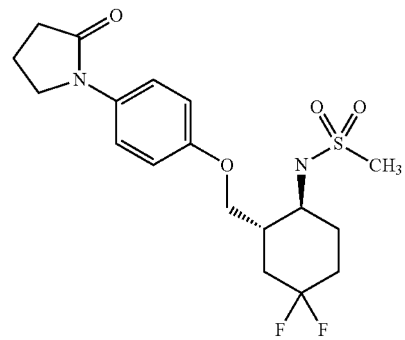 [SMILES: CS(=O)(=O)N[C@H]1CCC(F)(F)C[C@@H]1COc1ccc(N2CCCC2=O)cc1] | | 403.2 |
| 482 | N-[(1S,2S)-4,4-difluoro-2-{[4-(2-oxopyrrolidin-1-yl)phenoxy]methyl}cyclohexyl]ethanesulfonamide | 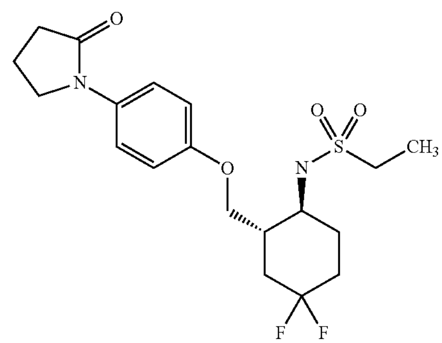 [SMILES: CCS(=O)(=O)N[C@H]1CCC(F)(F)C[C@@H]1COc1ccc(N2CCCC2=O)cc1] | | 417.1 |
| 483 | N-[(1S,2S)-4,4-difluoro-2-{[4-(2-oxopyrrolidin-1-yl)phenoxy]methyl}cyclohexyl]cyclopropanesulfonamide | 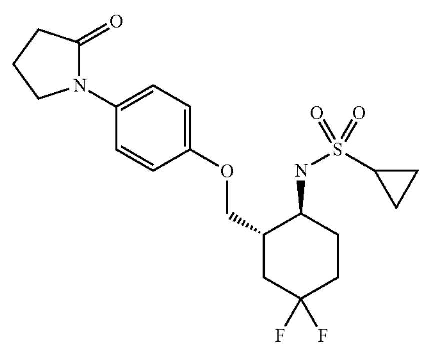 [SMILES: O=C1CCCN1c1ccc(OC[C@H]2CC(F)(F)CC[C@@H]2NS(=O)(=O)C2CC2)cc1] | | 429.2 |

TABLE 1-52

| Ex. No. | IUPAC Name | Structure | Salt | MS |
|---|---|---|---|---|
| 484 | N-[(1S,2S)-2-{[4-(5-cyanopyridin-2-yl)-2-fluorophenoxy]methyl}-4,4-difluorocyclohexyl]methanesulfonamide | 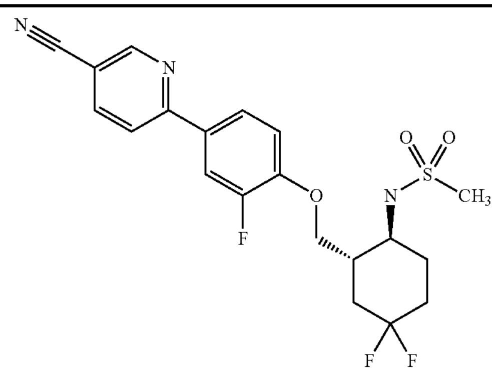 | | 440.1 |

| Ex. No. | IUPAC Name | Structure | Salt | MS |
|---|---|---|---|---|
| 485 | N-[(1S,2S)-2-{[4-(5-cyano-3-fluoropyridin-2-yl)-2-fluorophenoxy]methyl}-4,4-difluorocyclohexyl]methanesulfonamide | 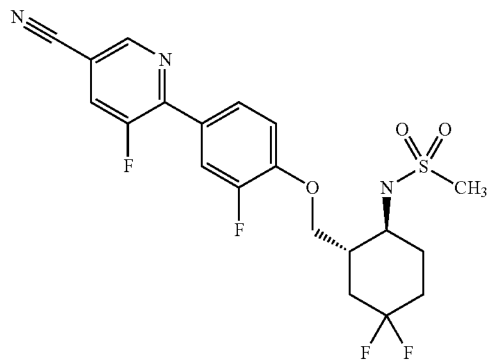 [SMILES: CS(=O)(=O)N[C@H]1CCC(F)(F)C[C@@H]1COc1ccc(-c2ncc(C#N)cc2F)cc1F] | | 458.2 |
| 486 | N-[(1S,2S)-2-{[4-(5-cyano-3-fluoropyridin-2-yl)-2-fluorophenoxy]methyl}-4,4-difluorocyclohexyl]ethanesulfonamide | 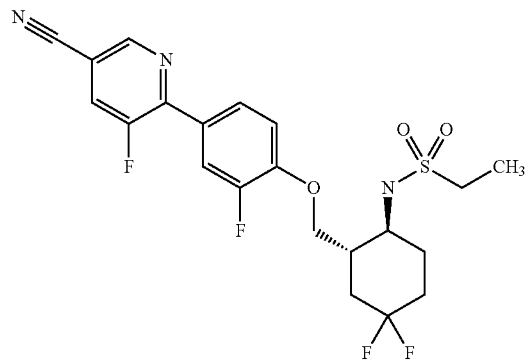 [SMILES: CCS(=O)(=O)N[C@H]1CCC(F)(F)C[C@@H]1COc1ccc(-c2ncc(C#N)cc2F)cc1F] | | 472.2 |
| 487 | N-[(1S,2S)-4,4-difluoro-2-{[4-(1-methyl-6-oxo-1,4,5,6-tetrahydropyridazin-3-yl)phenoxy]methyl}cyclohexyl]methanesulfonamide | 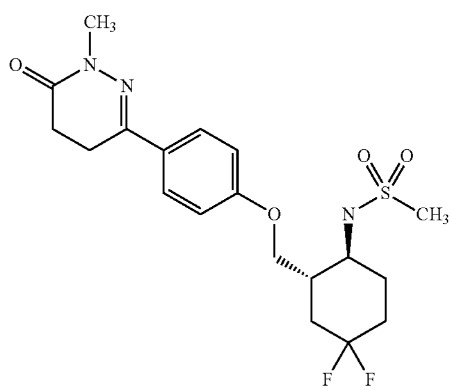 [SMILES: CN1N=C(c2ccc(OC[C@H]3CC(F)(F)CC[C@@H]3NS(C)(=O)=O)cc2)CCC1=O] | | 430.1 |
| 488 | N-[(1S,2S)-2-{[4-(3,3-difluoro-2-oxopyrrolidin-1-yl)phenoxy]methyl}-4,4-difluorocyclohexyl]methanesulfonamide | 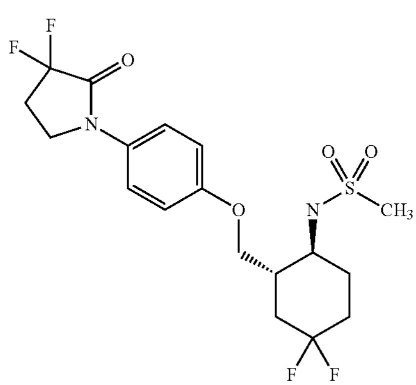 [SMILES: CS(=O)(=O)N[C@H]1CCC(F)(F)C[C@@H]1COc1ccc(N2CCC(F)(F)C2=O)cc1] | | 439.1 |

US 9,527,807 B2

TABLE 1-52-continued

| Ex. No. | IUPAC Name | Structure | Salt | MS |
|---|---|---|---|---|
| 489 | N-[(3RS,4SR)-3-{[4-(4-chloro-1H-pyrazol-1-yl)-3-fluorophenoxy]methyl}tetrahydro-2H-pyran-4-yl]ethanesulfonamide | 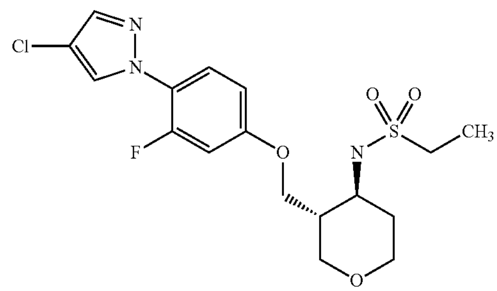 [SMILES: CCS(=O)(=O)N[C@H]1CCOC[C@@H]1COc1ccc(-n2cc(Cl)cn2)c(F)c1] | | 418.1 |
| 490 | N-[(3RS,4SR)-3-{[2-fluoro-4-(1H-pyrazol-1-yl)phenoxy]methyl}tetrahydro-2H-pyran-4-yl]ethanesulfonamide | 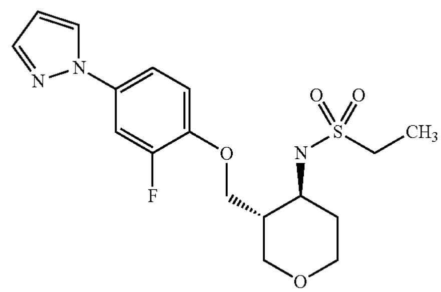 [SMILES: CCS(=O)(=O)N[C@H]1CCOC[C@@H]1COc1ccc(-n2cccn2)cc1F] | | 384.1 |
| 491 | N-[(1SR,2SR)-4,4-difluoro-2-{[2-fluoro-4-(1H-pyrazol-1-yl)phenoxy]methyl}cyclohexyl]ethanesulfonamide | 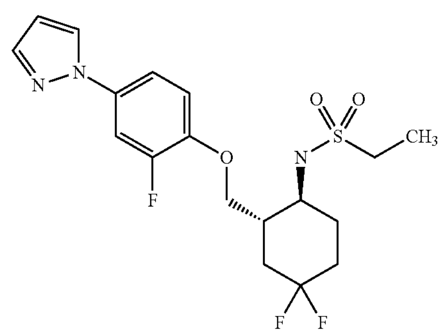 [SMILES: CCS(=O)(=O)N[C@H]1CCC(F)(F)C[C@@H]1COc1ccc(-n2cccn2)cc1F] | | 418.1 |
| 492 | N-[(3RS,4SR)-3-{[3-chloro-4-(1H-pyrazol-1-yl)phenoxy]methyl)tetrahydro-2H-pyran-4-yl]ethanesulfonamide | 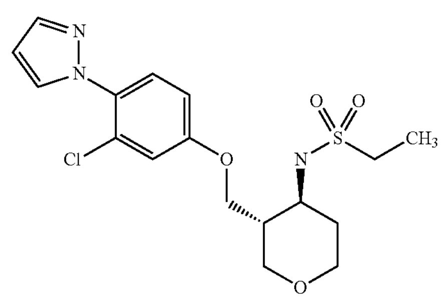 [SMILES: CCS(=O)(=O)N[C@H]1CCOC[C@@H]1COc1ccc(-n2cccn2)c(Cl)c1] | | 400.2 |
| 493 | N-[(3RS,4SR)-3-{[3-fluoro-4-(1H-pyrazol-1-yl)phenoxy]methyl}tetrahydro-2H-pyran-4-yl]ethanesulfonamide | 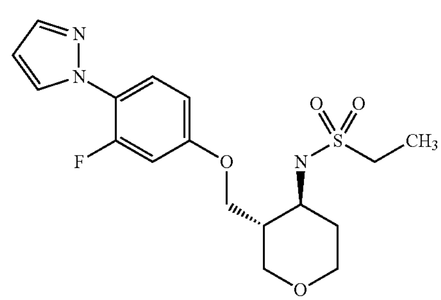 [SMILES: CCS(=O)(=O)N[C@H]1CCOC[C@@H]1COc1ccc(-n2cccn2)c(F)c1] | | 384.2 |

TABLE 1-53

| Ex. No. | IUPAC Name | Structure | Salt | MS |
|---|---|---|---|---|
| 494 | N-[(3RS,4SR)-3-{[3-methyl-4-(1H-pyrazol-1-yl)phenoxy]methyl}tetrahydro-2H-pyran-4-yl]ethanesulfonamide | 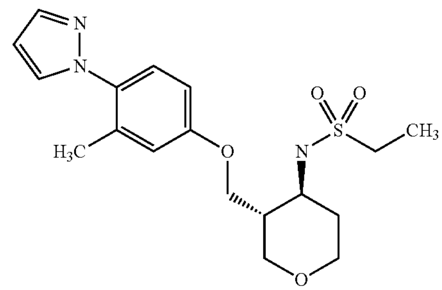 [SMILES: CCS(=O)(=O)N[C@H]1CCOC[C@@H]1COc1ccc(-n2cccn2)c(C)c1] | | 380.2 |
| 495 | N-[(3RS,4SR)-3-{[3-chloro-4-(4-chloro-1H-pyrazol-1-yl)phenoxy]methyl}tetrahydro-2H-pyran-4-yl]ethanesulfonamide | 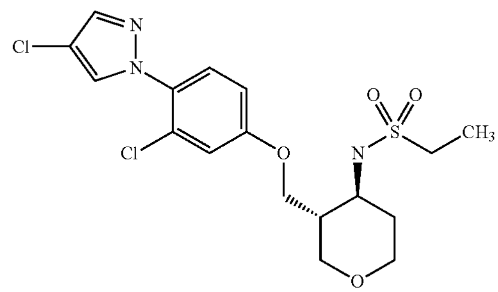 [SMILES: CCS(=O)(=O)N[C@H]1CCOC[C@@H]1COc1ccc(-n2cc(Cl)cn2)c(Cl)c1] | | 434.1 |
| 496 | N-[(3R,4S)-3-{[2-fluoro-4-(4-methyl-1H-pyrazol-1-yl)phenoxy]methyl}tetrahydro-2H-pyran-4-yl]methanesulfonamide | 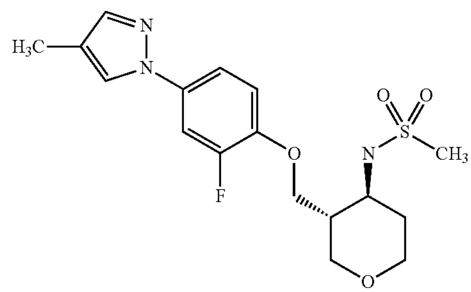 | | 384.1 |
| 497 | N-[(3RS,4SR)-3-{[3-chloro-4-(4-methyl-1H-pyrazol-1-yl)phenoxy]methyl}tetrahydro-2H-pyran-4-yl]ethanesulfonamide | 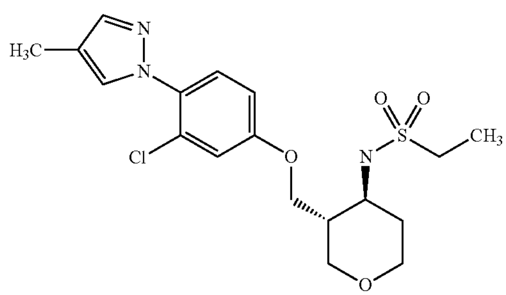 [SMILES: CCS(=O)(=O)N[C@H]1CCOC[C@@H]1COc1ccc(-n2cc(C)cn2)c(Cl)c1] | | 414.1 |
| 498 | N-[(3R,4S)-4-{[4-(4-chloro-1H-pyrazol-1-yl)-3-fluorophenoxy]methyl}tetrahydro-2H-pyran-3-yl]methanesulfonamide | 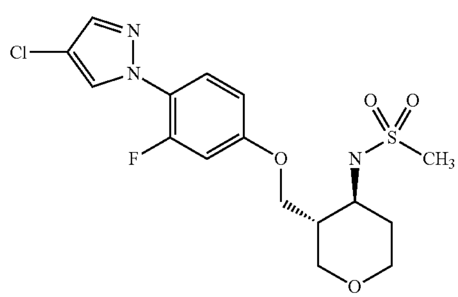 [SMILES: CS(=O)(=O)N[C@H]1CCOC[C@@H]1COc1ccc(-n2cc(Cl)cn2)c(F)c1] | | 404.1 |

TABLE 1-53-continued

| Ex. No. | IUPAC Name | Structure | Salt | MS |
|---|---|---|---|---|
| 499 | N-[(3R,4S)-{[4-(4-chloro-1H-pyrazol-1-yl)-3-fluorophenoxy]methyl}tetrahydro-2H-pyran-3-yl]ethanesulfonamide | 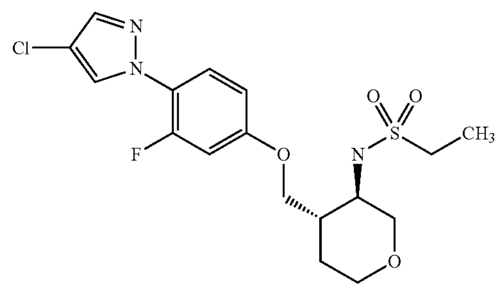 [SMILES: CCS(=O)(=O)N[C@H]1COCC[C@@H]1COc1ccc(-n2cc(Cl)cn2)c(F)c1] | | 419.1 |
| 500 | N-[(3R,4S)-3-{[4-(4-chloro-1H-pyrazol-1-yl)-2,5-difluorophenoxy]methyl}tetrahydro-2H-pyran-4-yl]methanesulfonamide | 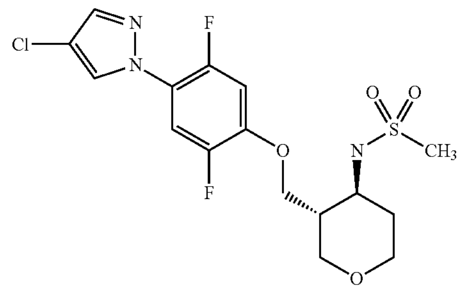 [SMILES: CS(=O)(=O)N[C@H]1CCOC[C@@H]1COc1cc(F)c(-n2cc(Cl)cn2)cc1F] | | 422.1 |
| 501 | 1,5-anhydro-6-O-[4-(5-cyanopyridin-2-yl)phenyl]-2,3,4-trideoxy-4-[(methylsulfonyl)amino]-D-erythro-hexitol | 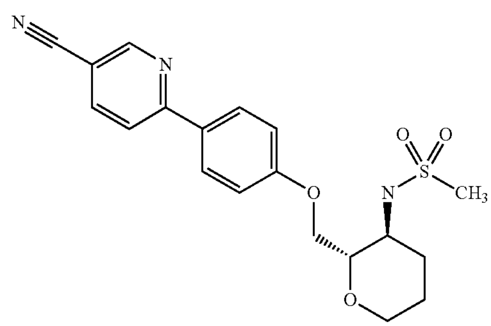 [SMILES: CS(=O)(=O)N[C@H]1CCCO[C@@H]1COc1ccc(-c2ccc(C#N)cn2)cc1] | | 388.1 |
| 502 | 1,5-anhydro-6-O-[4-(5-cyanopyridin-2-yl)phenyl]-2,3,4-trideoxy-4-[(ethylsulfonyl)amino]-D-erythro-hexitol | 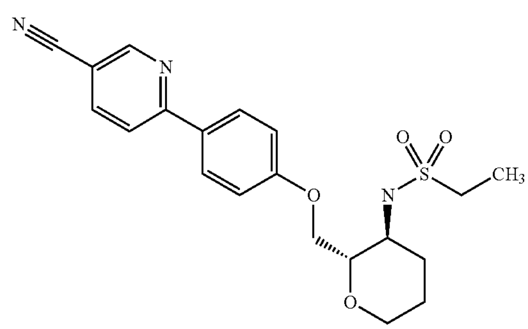 [SMILES: CCS(=O)(=O)N[C@H]1CCCO[C@@H]1COc1ccc(-c2ccc(C#N)cn2)cc1] | | 402.2 |
| 503 | N-[(3R,4S)-3-{[4-(4-chloro-1H-pyrazol-1-yl)-3-fluorophenoxy]methyl}tetrahydro-2H-pyran-4-yl]ethanesulfonamide | 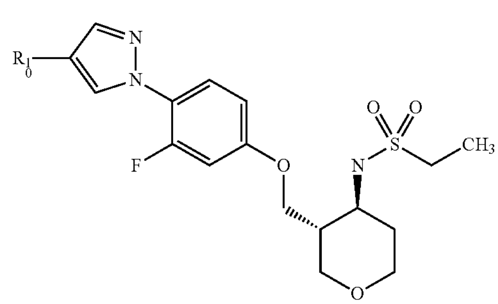 | | 418.1 |

TABLE 1-54

| Ex. No. | IUPAC Name | Structure | Salt | MS |
|---|---|---|---|---|
| 504 | N-[(3R,4S)-3-({[5-(2-cyanophenyl)pyridin-2-yl]oxy}methyl)tetrahydro-2H-pyran-4-yl]methanesulfonamide | 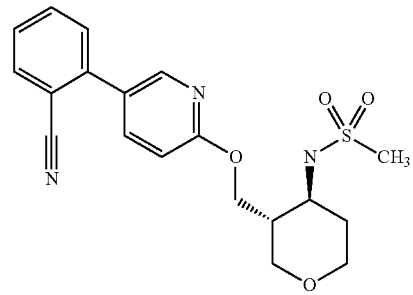 [SMILES: CS(=O)(=O)N[C@H]1CCOC[C@@H]1COc1ccc(-c2ccccc2C#N)cn1] | | 388.1 |
| 508 | N-((1S,2SR,3SR,5R)-2-((4-(5-cyanopyridin-2-yl)phenoxy)methyl)-8-oxabicyclo[3.2.1]oct-3-yl)methanesulfonamide | 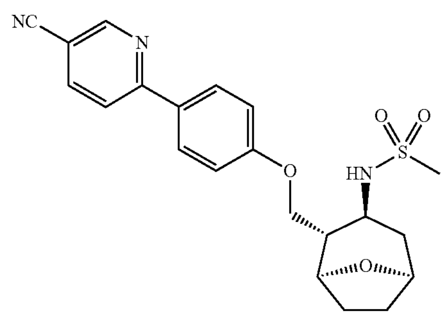 [SMILES: CS(=O)(=O)N[C@H]1C[C@H]2CC[C@H](O2)[C@@H]1COc1ccc(-c2ccc(C#N)cn2)cc1] | | |
| 509 | N-((3S,4S)-3-((4-(4-methyl-1H-pyrazol-1-yl)phenoxy)methyl)tetrahydro-2H-thiopyran-4-yl)methanesulfonamide | 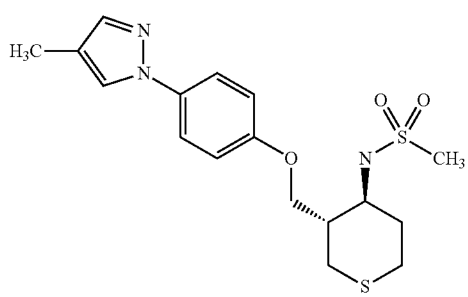 | | 381.9 |
| 510 | N-((3S,4S)-3-((4-(4-chloro-1H-pyrazol-1-yl)phenoxy)methyl)tetrahydro-2H-thiopyran-4-yl)methanesulfonamide | 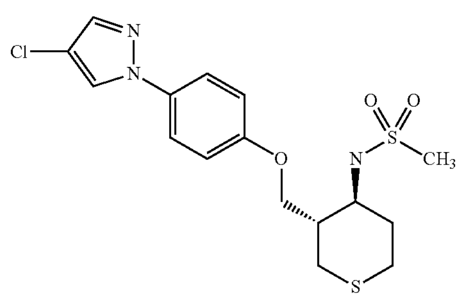 [SMILES: CS(=O)(=O)N[C@H]1CCSC[C@@H]1COc1ccc(-n2cc(Cl)cn2)cc1] | | 401.9 |
| 511 | N-((3S,4S)-3-((4-(4-cyano-1H-pyrazol-1-yl)phenoxy)methyl)tetrahydro-2H-thiopyran-4-yl)methanesulfonamide | 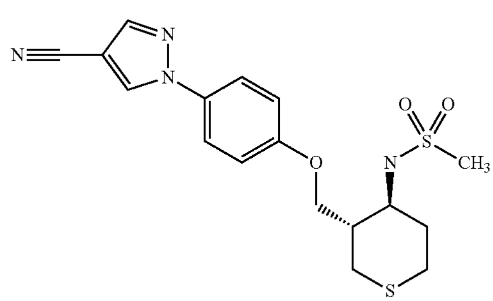 [SMILES: CS(=O)(=O)N[C@H]1CCSC[C@@H]1COc1ccc(-n2cc(C#N)cn2)cc1] | | 392.9 |

TABLE 1-54-continued

| Ex. No. | IUPAC Name | Structure | Salt | MS |
|---|---|---|---|---|
| 512 | N-((3S,4S)-3-((4-(4-cyano-1H-pyrazol-1-yl)-2-fluorophenoxy)methyl)tetrahydro-2H-thiopyran-4-yl)methanesulfonamide | 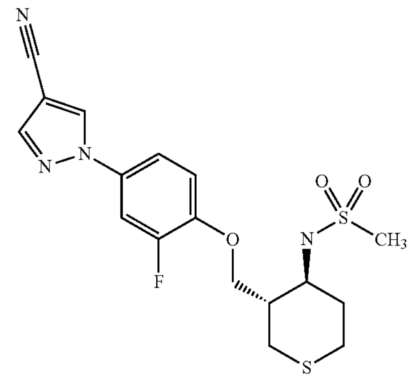 [SMILES: CS(=O)(=O)N[C@H]1CCSC[C@@H]1COc1ccc(-n2cc(C#N)cn2)cc1F] | | 410.9 |
| 513 | N-((3S,4S)-3-((4-(5-chloropyridin-2-yl)-2-fluorophenoxy)methyl)tetrahydro-2H-thiopyran-4-yl)methanesulfonamide | 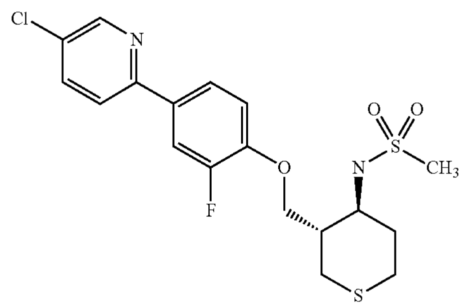 | | 430.9 |
| 514 | N-((3S,4S)-3-((4-(3,5-difluoropyridin-2-yl)phenoxy)methyl)tetrahydro-2H-thiopyran-4-yl)methanesulfonamide | 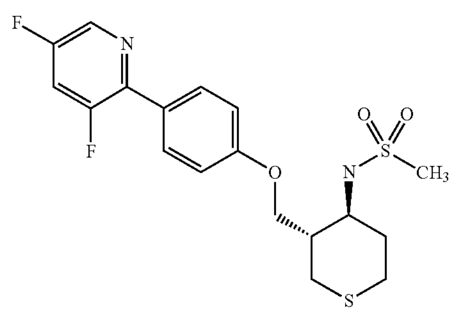 | | 414.9 |
| 515 | N-((3S,4S)-3-((4-(5-chloro-3-fluoropyridin-2-yl)phenoxy)methyl)tetrahydro-2H-thiopyran-4-yl)methanesulfonamide | 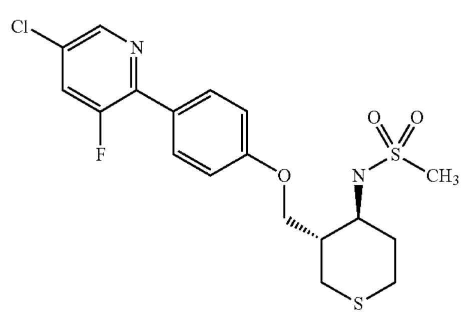 | | 430.9 |

TABLE 1-54-continued

| Ex. No. | IUPAC Name | Structure | Salt | MS |
|---|---|---|---|---|
| 516 | N-((3S,4S)-3-((4-(5-cyanopyridin-2-yl)phenoxy)methyl)tetrahydro-2H-thiopyran-4-yl)methanesulfonamide | 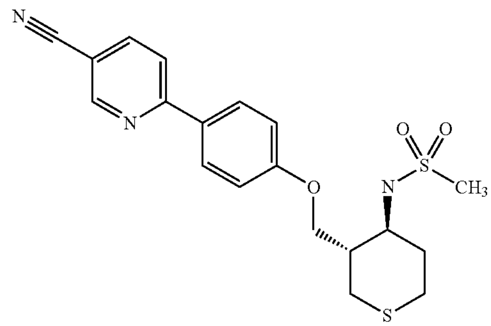 [SMILES: CS(=O)(=O)N[C@H]1CCSC[C@@H]1COc1ccc(-c2ccc(C#N)cn2)cc1] | | 403.9 |

TABLE 1-55

| Ex. No. | IUPAC Name | Structure | Salt | MS |
|---|---|---|---|---|
| 517 | N-((3S,4S)-3-((4-(5-methyl-1,3-thiazol-2-yl)phenoxy)methyl)tetrahydro-2H-thiopyran-4-yl)methanesulfonamide | 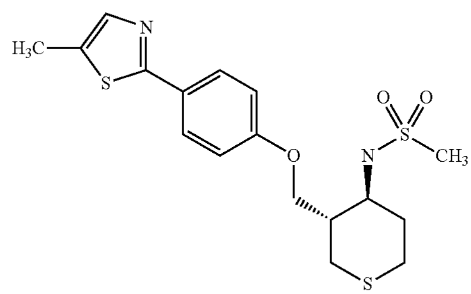 | | 398.9 |
| 518 | N-((3S,4S)-3-((4-(1-methyl-2-oxo-1,2-dihydropyridin-3-yl)phenoxy)methyl)tetrahydro-2H-thiopyran-4-yl)methanesulfonamide | 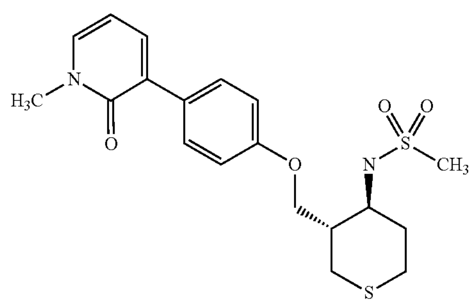 | | 408.9 |
| 519 | N-((3S,4S)-3-((4-(tetrahydro-2H-pyran-4-yl)phenoxy)methyl)tetrahydro-2H-thiopyran-4-yl)methanesulfonamide | 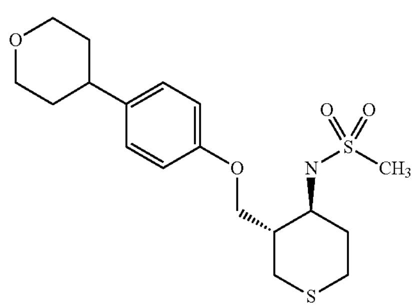 [SMILES: CS(=O)(=O)N[C@H]1CCSC[C@@H]1COc1ccc(C2CCOCC2)cc1] | | 386 |

TABLE 1-55-continued

| Ex. No. | IUPAC Name | Structure | Salt | MS |
|---|---|---|---|---|
| 520 | N-((3S,4S)-3-((4-(4-methyl-1H-pyrazol-1-yl)phenoxy)methyl)tetrahydro-2H-thiopyran-4-yl)ethanesulfonamide | 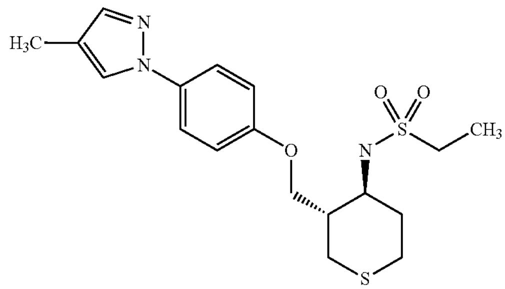 [SMILES: CCS(=O)(=O)N[C@H]1CCSC[C@@H]1COc1ccc(-n2cc(C)cn2)cc1] | | 395.9 |
| 521 | N-((3S,4S)-3-((4-(4-chloro-1H-pyrazol-1-yl)phenoxy)methyl)tetrahydro-2H-thiopyran-4-yl)ethanesulfonamide | 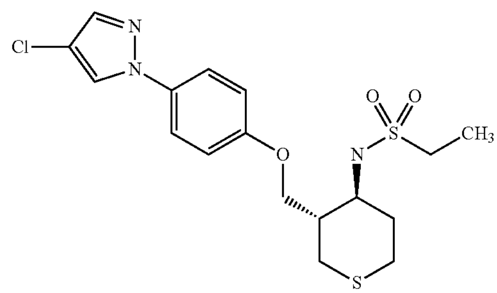 [SMILES: CCS(=O)(=O)N[C@H]1CCSC[C@@H]1COc1ccc(-n2cc(Cl)cn2)cc1] | | 415.9 |
| 522 | N-((3S,4S)-3-((4-(4-cyano-1H-pyrazol-1-yl)phenoxy)methyl)tetrahydro-2H-thiopyran-4-yl)ethanesulfonamide | 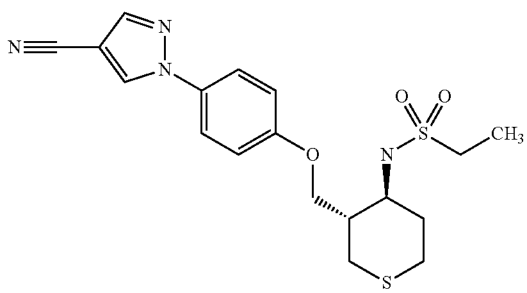 [SMILES: CCS(=O)(=O)N[C@H]1CCSC[C@@H]1COc1ccc(-n2cc(C#N)cn2)cc1] | | 406.9 |
| 523 | N-((3S,4S)-3-((4-(4-cyano-1H-pyrazol-1-yl)-2-fluorophenoxy)methyl)tetrahydro-2H-thiopyran-4-yl)ethanesulfonamide | 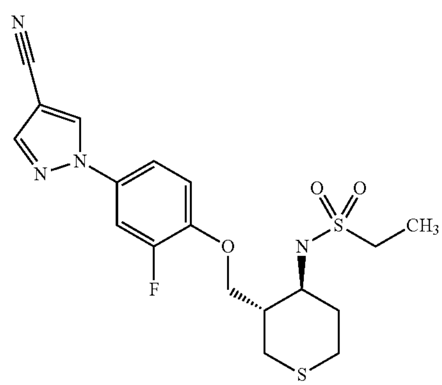 [SMILES: CCS(=O)(=O)N[C@H]1CCSC[C@@H]1COc1ccc(-n2cc(C#N)cn2)cc1F] | | 424.9 |
| 524 | N-((3S,4S)-3-((4-(3,5-difluoropyridin-2-yl)phenoxy)methyl)tetrahydro-2H-thiopyran-4-yl)ethanesulfonamide | 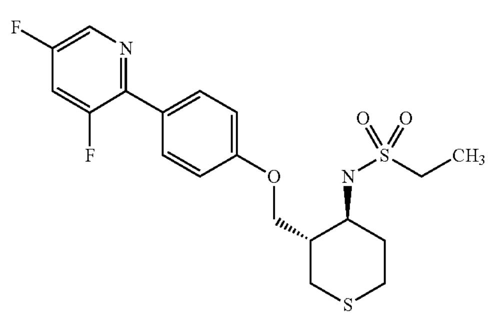 | | 428.9 |

TABLE 1-55-continued

| Ex. No. | IUPAC Name | Structure | Salt | MS |
|---|---|---|---|---|
| 525 | N-((3S,4S)-3-((4-(5-chloro-3-fluoropyridin-2-yl)phenoxy)methyl)tetrahydro-2H-thiopyran-4-yl)ethanesulfonamide | 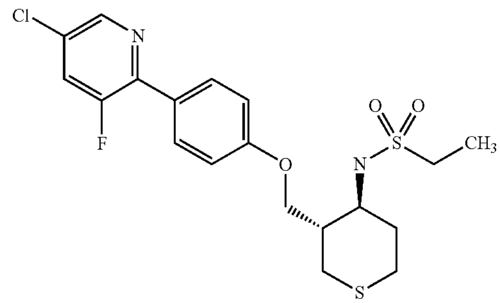 | | 444.9 |
| 526 | N-((3S,4S)-3-((4-(5-cyanopyridin-2-yl)phenoxy)methyl)tetrahydro-2H-thiopyran-4-yl)ethanesulfonamide | 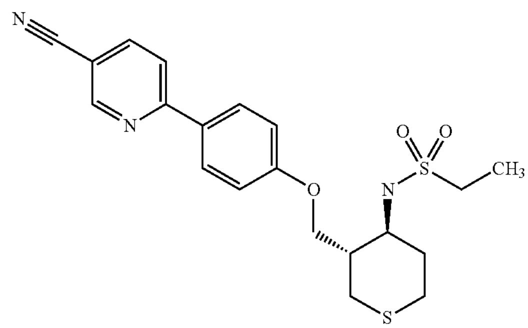 [SMILES: CCS(=O)(=O)N[C@H]1CCSC[C@@H]1COc1ccc(-c2ccc(C#N)cn2)cc1] | | 417.9 |

TABLE 1-56

| Ex. No. | IUPAC Name | Structure | Salt | MS |
|---|---|---|---|---|
| 527 | N-((3S,4S)-3-((4-(5-methyl-1,3-thiazol-2-yl)phenoxy)methyl)tetrahydro-2H-thiopyran-4-yl)ethanesulfonamide | 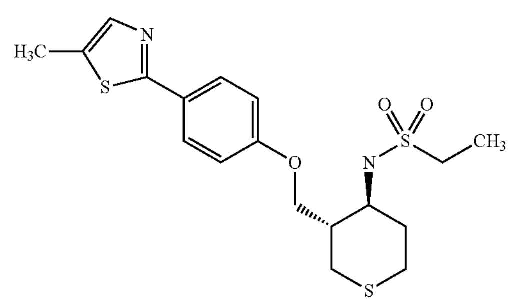 [SMILES: CCS(=O)(=O)N[C@H]1CCSC[C@@H]1COc1ccc(-c2ncc(C)s2)cc1] | | 412.9 |
| 528 | N-((3S,4S)-3-((4-(1-methyl-2-oxo-1,2-dihydropyridin-3-yl)phenoxy)methyl)tetrahydro-2H-thiopyran-4-yl)ethanesulfonamide | 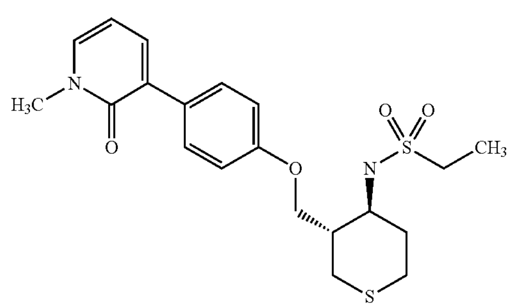 [SMILES: CCS(=O)(=O)N[C@H]1CCSC[C@@H]1COc1ccc(-c2cccn(C)c2=O)cc1] | | 422.9 |

TABLE 1-56-continued

| Ex. No. | IUPAC Name | Structure | Salt | MS |
|---|---|---|---|---|
| 529 | N-((3S,4S)-3-((4-(tetrahydro-2H-pyran-4-yl)phenoxy)methyl)tetrahydro-2H-thiopyran-4-yl)ethanesulfonamide | 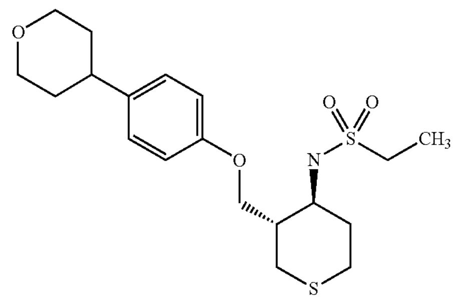 [SMILES: CCS(=O)(=O)N[C@H]1CCSC[C@@H]1COc1ccc(C2CCOCC2)cc1] | | 399.9 |

Preparation Example 1

A medicament containing the compound of the present invention as an active ingredient can be produced, for example, in the following formulation.

1. Capsule

| | |
|---|---|
| (1) compound obtained in Example 1 | 40 mg |
| (2) lactose | 70 mg |
| (3) microcrystalline cellulose | 9 mg |
| (4) magnesium stearate | 1 mg |
| 1 capsule | 120 mg |

(1), (2), (3) and ½ of (4) are blended and granulated. Thereto is added the remaining (4) and the whole is sealed in a gelatin capsule.

2. Tablet

| | |
|---|---|
| (1) compound obtained in Example 1 | 40 mg |
| (2) lactose | 58 mg |
| (3) cornstarch | 18 mg |
| (4) microcrystalline cellulose | 3.5 mg |
| (5) magnesium stearate | 0.5 mg |
| 1 tablet | 120 mg |

(1), (2), (3), ⅔ of (4) and ½ of (5) are blended and granulated. Thereto is added the remaining (4) and (5) and the mixture is compression formed into a tablet.

Preparation Example 2

The compound obtained in Example 1 (50 mg) is dissolved in the Japanese Pharmacopoeia distilled water for injection (50 mL), and the Japanese Pharmacopoeia distilled water for injection is added to 100 mL. The solution is filtered under sterilization conditions, the solution (1 mL) is taken and filled in a vial for injection under sterilization conditions, and the vial is freeze-dried and sealed.

Experimental Example 1

(1) Construction of Expression Gene

Human GluR1 flip cDNA was amplified by PCR using forward primer ACTGAATTCGCCACCATGCAGCA-CATTTTTGCCTTCTTCTGC (SEQ ID NO: 1) and reverse primer CCGCGGCCGCTTACAATCCCGTGGCTC-CCAAG (SEQ ID NO: 2) artificially synthesized using human brain-derived cDNA (BD Bio science) as a template. The amplified product was digested with restriction enzymes EcoRI, NotI (TAKARA SHUZO CO. LTD.), and incorporated into the same site of pcDNA3.1(+) (Invitrogen) to construct pcDNA3.1(+)/human GluR1 flip gene. Human stargazin cDNA was amplified by PCR using forward primer GGTCTCGAGGCCACCATGGGGCTGTTTGATCGAG-GTGTTCA (SEQ ID NO: 3) and reverse primer. GTTG-GATCCTTATACGGGGGTGGTCCGGCGGTTGGCT-GTG (SEQ ID NO: 4) artificially synthesized using human hippocampus cDNA as a template. The amplified product was digested with restriction enzymes XhoI, BamHI (TAKARA SHUZO CO. LTD.), and incorporated into the same site of pcDNA3.1(−) (Invitrogen) to construct pcDNA3.1 Zeo(−)/human stargazin gene.

(2) Construction of GluR1 Flip/Stargazin Expressing Cell

CHO-K1 cells passaged in a culture medium (Ham's F12 medium (Invitrogen) added with 10% inactivated fetal bovine serum (Morgate) and penicillin, streptomycin (Invitrogen)) were detached with 0.05% trypsin, 0.53 mM EDTA (Invitrogen) diluted with D-PBS(−). The detached cells were suspended in a culture medium, and recovered by a centrifugation operation at 1,000 rpm. The recovered cells were suspended again in D-PBS(−), and added to a 0.4 cm electroporation cuvette (BioRad). pcDNA3.1(+)/human GluR1 flip gene (5 µg) and pcDNA3.1 Zeo(−)/human stargazin gene (15 µg) were added, and the mixture was introduced into CHO-K1 cells using Gene Pulser II (BioRad) under the conditions of 950 µFd, 250 mV. The introduced cells were cultured overnight in a culture medium and, the next day, plated in a 96 well plate at 250 cells/well using a selection medium (culture medium added with Zeocin (Invitrogen) to 250 µg/mL). Clones showing drug resistance were selected, and GluR1 flip/stargazin expressing clones were selected by an assay method using calcium influx as an index as shown below.

(3) Measurement Method of AMPA Receptor Function Enhancing Activity of Compound Using Calcium Influx as Index CHO-K1/GluR1 flip/stargazin expressing cells were plated on a 384 well black transparent bottom plate (FMAT4307723) at $0.5 \times 10^4$ cells/well, and cultured in a 37° C., $CO_2$ incubator (SANYO Electric Co., Ltd.) for 2 days. The medium in the cell plate was removed, and a calcium indicator (Calcium 4 Assay Kit, Molecular. Devices) containing 1.25 mM probenecid (Invitrogen) was added at 25 µL/well and the well was left standing in 37° C., $CO_2$ incubator for 1 hr. The cell plate was set in FLITRtetra (Molecular Devices), a mixture (12.5 µL) of 9 mM glutamic acid diluted with assay buffer B (HBSS (Invitrogen), 0.1% BSA, 10 mM HEPES) and a test compound was added, and the amount of change in fluorescence level in 3 min was measured. In the definition here, the amount of change in fluorescence level of well added with glutamic acid at final concentration 3 mM and 300 μM cyclothiazide (TOCRIS) is 100%, the amount of change in fluorescence level of well added only with glutamic acid at final concentration 3 mM is 0%, and the compound activity was calculated according to the following formula.

$$\text{activity }(\%) = (X-C)/(T-C) \times 100$$

T: amount of change in fluorescence level of well added with glutamic acid at final concentration 3 mM and 300 μM cyclothiazide
C: amount of change in fluorescence level of well added only with glutamic acid at final concentration 3 mM
X: amount of change in fluorescence level of well added with to test compound The results are shown in the following Table.

TABLE 2

| Example No. | activity (%) |
|---|---|
| 1 | 46 |
| 2 | 38 |
| 3 | 57 |
| 4 | 86 |
| 5 | 78 |
| 6 | 82 |
| 7 | 91 |
| 8 | 79 |
| 12 | 72 |
| 13 | 81 |
| 15 | 88 |
| 21 | 82 |
| 34 | 77 |
| 39 | 81 |
| 43 | 86 |
| 50 | 78 |
| 52 | 69 |
| 60 | 80 |
| 89 | 75 |
| 94 | 70 |
| 95 | 73 |
| 110 | 88 |
| 124 | 81 |
| 130 | 90 |
| 131 | 89 |
| 134 | 92 |
| 135 | 88 |
| 136 | 85 |
| 137 | 91 |
| 138 | 95 |
| 139 | 97 |
| 140 | 90 |
| 141 | 78 |
| 142 | 54 |
| 143 | 42 |
| 164 | 76 |
| 181 | 77 |
| 192 | 74 |
| 205 | 65 |
| 206 | 74 |
| 207 | 74 |
| 209 | 85 |
| 215 | 101 |
| 222 | 89 |
| 243 | 96 |
| 244 | 96 |
| 247 | 87 |
| 248 | 87 |
| 256 | 91 |
| 260 | 82 |
| 261 | 92 |
| 262 | 89 |
| 263 | 66 |
| 264 | 104 |

TABLE 2-continued

| Example No. | activity (%) |
|---|---|
| 265 | 78 |
| 266 | 92 |
| 267 | 93 |
| 268 | 101 |
| 269 | 93 |
| 270 | 74 |
| 277 | 90 |
| 279 | 79 |
| 280 | 108 |
| 281 | 64 |
| 282 | 96 |
| 283 | 98 |
| 284 | 92 |
| 297 | 95 |
| 312 | 91 |
| 313 | 99 |
| 322 | 91 |
| 333 | 93 |
| 351 | 70 |
| 362 | 96 |
| 382 | 59 |
| 383 | 60 |
| 399 | 94 |
| 425 | 96 |
| 431 | 66 |
| 454 | 89 |
| 477 | 68 |
| 482 | 99 |
| 489 | 99 |
| 508 | 38 |
| 518 | 95 |
| 519 | 88 |
| 522 | 95 |
| 529 | 89 |

Experimental Example 2

(1) Animals

Male ICR mice were supplied by CLEA Japan, Inc (Japan). After arrival to the vivarium, animals were allowed a minimum of 1 week for acclimation. They were housed under a 12:12-h light/dark cycle in a temperature- and humidity-controlled laboratory and allowed food and water ad libitum.

(2) Drug Administration

A test compound was suspended in 0.5% methylcellulose in distilled water and orally administered (p.o.). Methamphetamine (Dainippon Sumitomo Pharma Co., Ltd.) was dissolved in saline and subcutaneously administered (s.c.). All drugs were dosed in a volume of 10 mL/kg body weight for mice.

(3) Inhibition of Methamphetamine (MAP)-Induced Hyperlocomotion

The widely used animal models of psychosis have been the measurement of the extent of hyperlocomotion induced by psychostimulants (e.g., amphetamine, cocaine, methamphetamine, MK-801 and phencyclidine) in rodents (Psychopharmacology 1999, vol. 145: 237-250). 2 compounds (A and B) were tested for its ability to antagonize MAP-induced hyperlocomotion in mice. Male ICR mice were habituated in the locomotor chambers with infrared sensors (BrainScienceIdea Co., Ltd. Japan) to the experiment. After the habituation, animals were treated with either vehicle or the compounds (10 mg/kg, p.o.), and MAP (2 mg/kg, s.c.)

was administered 60 min later. Locomotion activities were measured, and accumulated counts (120 min after administration of MAP) were calculated in each treatment group. All data were represented as means plus the standard errors of the means (n=3-8) and analyzed using Welch's t-test with significance set at $^{\$}P<0.05$, $^{\$\$}P<0.01$ and $^{\$\$\$}P<0.001$.

Compound A is N-[(3R,4S)-3-{[4-(4-chloro-1H-pyrazol-1-yl)phenoxy]methyl}tetrahydro-2H-pyran-4-yl]methanesulfonamide, and compound B is N-[(3R,4S)-3-{[4-(4-chloro-1H-pyrazol-1-yl)-2-fluorophenoxy]methyl}tetrahydro-2H-pyran-4-yl]ethanesulfonamide.

The graphs of FIG. 1 show inhibition of methamphetamine (MAP)-induced hyperlocomotion by compound A and B. By administered 60 min before MAP (2 mg/kg, s.c.) treatment, compound A and B produced significant inhibition of MAP-induced hyperlocomotion (0-120 min).

INDUSTRIAL APPLICABILITY

The compound of the present invention is useful as a prophylactic or therapeutic drug for depression, Alzheimer's disease, schizophrenia, attention deficit hyperactivity disorder (ADHD) and the like.

This application is based on patent application No. 2011-084100 filed in Japan, the contents of which are incorporated in full herein.

The invention claimed is:
1. A compound represented by the formula (I)

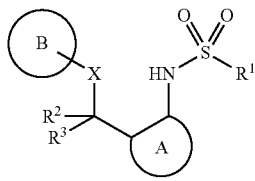

wherein
R¹ is
a $C_{1-6}$ alkyl group optionally substituted by 1 to 3 substituent(s) selected from a halogen atom and a $C_{1-3}$ alkoxy group;
a $C_{3-6}$ cycloalkyl group; or
an amino group substituted by a $C_{1-6}$ alkyl group,
R² and R³ are hydrogen atoms,
X is —O—,
ring A is selected from
$C_{3-6}$ cycloalkane;
a tetrahydrofuran ring;
a tetrahydropyran ring;
a piperidine ring;
a tetrahydrothiopyran ring; and
a 8-oxabicyclo[3.2.1]octane ring, each optionally substituted by 1 to 3 substituents selected from
(1) 1 to 3 halogen atoms;
(2) a $C_{1-6}$ alkyl group optionally substituted by one phenyl group;
(3) a carbamoyl group substituted by a $C_{1-6}$ alkyl group;
(4) a $C_{1-6}$ alkyl-carbonyl group;
(5) a $C_{1-6}$ alkoxy-carbonyl group;
(6) an oxo group;
(7) a hydroxyl group; and
(8) a $C_{1-6}$ alkylsulfonyl group, and
ring B is selected from
a benzene ring;
$C_{3-6}$ cycloalkane;
a dihydroindene ring;
a naphthalene ring;
a pyridine ring;
a chromene ring;
an indole ring; and
a benzothiazole ring, each optionally having 1 to 3 substituent(s) selected from
(1) a halogen atom;
(2) a cyano group;
(3) a $C_{1-6}$ alkyl group optionally substituted by 1 to 3 substituents selected from a halogen atom and a cyano group;
(4) a hydroxyl group optionally substituted by a $C_{1-6}$ alkyl group optionally substituted by 1 to 3 halogen atoms or a phenyl group;
(5) an amino group optionally substituted by 1 or 2 substituents selected from a $C_{1-6}$ alkyl group, a $C_{1-6}$ alkyl-carbonyl and a phenyl group;
(6) a $C_{3-6}$ cycloalkyl group;
(7) a tricyclo[3.3.1.1.3.7]decyl group;
(8) phenyl optionally substituted by 1 to 3 substituents selected from a halogen atom and a cyano group;
(9) pyridyl optionally substituted by 1 to 3 substituents selected from a halogen atom, a cyano group and a $C_{1-6}$ alkyl group optionally substituted by 1 to 3 halogen atoms;
(10) pyrazolyl optionally substituted by 1 to 3 substituents selected from a halogen atom, a cyano group, a $C_{1-6}$ alkyl group optionally substituted by 1 to 3 halogen atoms and a $C_{1-6}$ alkoxy group optionally substituted by 1 to 3 halogen atoms;
(11) imidazolyl optionally substituted by a $C_{1-6}$ alkyl group;
(12) thienyl optionally substituted by a cyano group;
(13) pyrimidinyl optionally substituted by 1 to 3 substituents selected from a halogen atom and a cyano group;
(14) isoxazolyl substituted by a $C_{1-6}$ alkyl group;
(15) oxazolyl optionally substituted by a $C_{1-6}$ alkyl group optionally substituted by 1 to 3 halogen atoms;
(16) thiazolyl optionally substituted by 1 to 3 substituents selected from a halogen atom and a $C_{1-6}$ alkyl group optionally substituted by 1 to 3 halogen atoms;
(17) piperidyl optionally substituted by 1 to 3 substituents selected from a $C_{1-6}$ alkyl group optionally substituted by 1 to 3 halogen atoms and an oxo group;
(18) pyrrolidyl optionally substituted by 1 to 3 substituents selected from a halogen atom and an oxo group;
(19) dihydropyridyl optionally substituted by 1 to 3 substituents selected from a $C_{1-6}$ alkyl group and an oxo group;
(20) tetrahydropyridazinyl optionally substituted by 1 to 3 substituents selected from a $C_{1-6}$ alkyl group and an oxo group;
(21) oxetanyl;
(22) morpholinyl;
(23) tetrahydropyranyl;
(24) a sulfanyl group optionally substituted by a $C_{1-6}$ alkyl group substituted by 1 to 3 halogen atoms;
(25) a $C_{1-6}$ alkyl-carbonyl group;
(26) a $C_{1-6}$ alkoxy-carbonyl group; and
(27) an oxo group,
or a salt thereof.
2. The compound according to claim 1, wherein R¹ is
a $C_{1-6}$ alkyl group optionally substituted by 1 to 3 halogen atoms;
a $C_{3-6}$ cycloalkyl group; or
an amino group substituted by a $C_{1-6}$ alkyl group,
R² and R³ are hydrogen atoms,
X is —O—,
ring A is
$C_{3-6}$ cycloalkane,
a tetrahydropyran ring,
a piperidine ring,
a tetrahydrothiopyran ring or
a 8-oxabicyclo[3.2.1]octane ring, each optionally substituted by 1 to 3 substituents selected from
(1) 1 to 3 halogen atoms,
(2) a $C_{1-6}$ alkyl-carbonyl group and
(3) an oxo group, and
ring B is a benzene ring optionally having 1 to 3 substituent(s) selected from
(1) a halogen atom;
(2) a $C_{1-6}$ alkyl group optionally substituted by one cyano group;
(3) a hydroxyl group substituted by a $C_{1-6}$ alkyl group substituted by 1 to 3 halogen atoms;
(4) a $C_{3-6}$ cycloalkyl group;
(5) pyridyl optionally substituted by 1 to 3 substituents selected from a halogen atom, a cyano group and a $C_{1-6}$ alkyl group optionally substituted by 1 to 3 halogen atoms;

(6) pyrazolyl optionally substituted by 1 to 3 substituents selected from a halogen atom, a cyano group and a $C_{1-6}$ alkyl group optionally substituted by 1 to 3 halogen atoms;
(7) imidazolyl substituted by 1 to 3 $C_{1-6}$ alkyl groups;
(8) pyrimidinyl substituted by 1 to 3 halogen atoms;
(9) isoxazolyl substituted by one $C_{1-6}$ alkyl group;
(10) thiazolyl optionally substituted by 1 to 3 substituents selected from a halogen atom and a $C_{1-6}$ alkyl group;
(11) pyrrolidyl substituted by one oxo group;
(12) dihydropyridyl optionally substituted by 1 to 3 substituents selected from a $C_{1-6}$ alkyl group and an oxo group;
(13) oxetanyl;
(14) tetrahydropyranyl; and
(15) a $C_{1-6}$ alkyl-carbonyl group,
or a salt thereof.

3. N-[(3R,4S)-3-{[4-(4-chloro-1H-pyrazol-1-yl)phenoxy]methyl}tetrahydro-2H-pyran-4-yl]methanesulfonamide or a salt thereof.

4. N-[(3RS,4SR)-3-({4-[5-(trifluoromethyl)pyridin-2-yl]phenoxy}methyl)tetrahydro-2H-pyran-4-yl]ethanesulfonamide or a salt thereof.

5. N-[(3R,4S)-4-{[4-(5-chloro-3-fluoropyridin-2-yl)phenoxy]methyl}tetrahydro-2H-pyran-3-yl]cyclopropanesulfonamide or a salt thereof.

6. A pharmaceutical composition comprising the compound according to claim 1, or a salt thereof, and a pharmaceutically acceptable carrier.

7. The pharmaceutical composition according to claim 6, which is an AMPA receptor function enhancer.

8. The pharmaceutical composition according to claim 6, which is a therapeutic drug for depression, Alzheimer's disease, schizophrenia or attention deficit hyperactivity disorder.

9. A method of enhancing AMPA receptor function of a mammal, comprising administering an effective amount of the compound according to claim 1 or a salt thereof to the mammal.

10. A method of treating depression, Alzheimer's disease, schizophrenia or attention deficit hyperactivity disorder in a mammal, comprising administering an effective amount of the compound according to claim 1 or a salt thereof to the mammal.

11. The compound according to claim 1 or a salt thereof, suitable for the treatment of depression, Alzheimer's disease, schizophrenia or attention deficit hyperactivity disorder.

* * * * *

SEQUENCE LISTING

<160> NUMBER OF SEQ ID NOS: 4

<210> SEQ ID NO 1
<211> LENGTH: 42
<212> TYPE: DNA
<213> ORGANISM: Artificial
<220> FEATURE:
<223> OTHER INFORMATION: Forward primer for GluR1 flip cDNA

<400> SEQUENCE: 1
actgaattcg ccaccatgca gcacattttt gccttcttct gc                42

<210> SEQ ID NO 2
<211> LENGTH: 32
<212> TYPE: DNA
<213> ORGANISM: Artificial
<220> FEATURE:
<223> OTHER INFORMATION: Reverse primer for GluR1 flip cDNA

<400> SEQUENCE: 2
ccgcggccgc ttacaatccc gtggctccca ag                          32

<210> SEQ ID NO 3
<211> LENGTH: 41
<212> TYPE: DNA
<213> ORGANISM: Artificial
<220> FEATURE:
<223> OTHER INFORMATION: Forward primer for stargazin cDNA

<400> SEQUENCE: 3
ggtctcgagg ccaccatggg gctgtttgat cgaggtgttc a                41

<210> SEQ ID NO 4
<211> LENGTH: 40
<212> TYPE: DNA
<213> ORGANISM: Artificial
<220> FEATURE:
<223> OTHER INFORMATION: Reverse primer for stargazin cDNA

<400> SEQUENCE: 4
gttggatcct tatacggggg tggtccggcg gttggctgtg                  40